(12) United States Patent
Beigelman et al.

(10) Patent No.: US 9,657,294 B2
(45) Date of Patent: May 23, 2017

(54) RNA INTERFERENCE MEDIATED INHIBITION OF GENE EXPRESSION USING CHEMICALLY MODIFIED SHORT INTERFERING NUCLEIC ACID (SINA)

(71) Applicant: SIRNA THERAPEUTICS, INC., Cambridge, MA (US)

(72) Inventors: Leonid Beigelman, San Mateo, CA (US); James McSwiggen, Arlington, MA (US); Chandra Vargeese, Schwenksville, PA (US)

(73) Assignee: SIRNA THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 14/861,805

(22) Filed: Sep. 22, 2015

(65) Prior Publication Data

US 2016/0053269 A1    Feb. 25, 2016

Related U.S. Application Data

(63) Continuation-in-part of application No. 14/514,112, filed on Oct. 14, 2014, now Pat. No. 9,181,551, which is a continuation of application No. 14/083,525, filed on Nov. 19, 2013, now abandoned, which is a continuation of application No. 13/480,655, filed on May 25, 2012, now Pat. No. 8,618,277, which is a continuation of application No. 10/720,448, filed on Nov. 24, 2003, now Pat. No. 8,273,866, which is a continuation-in-part of application No. 10/693,059, filed on Oct. 23, 2003, now abandoned, which is a continuation-in-part of application No. 10/444,853, filed on May 23, 2003, now Pat. No. 8,202,979, and a continuation-in-part of application No. 10/652,791, filed on Aug. 29, 2003, now abandoned, and a continuation-in-part of application No. PCT/US03/05346, filed on Feb. 20, 2003, and a continuation-in-part of application No. PCT/US03/05028, filed on Feb. 20, 2003, and a continuation-in-part of application No. 10/427,160, filed on Apr. 30, 2003, now Pat. No. 7,833,992.

(60) Provisional application No. 60/440,129, filed on Jan. 15, 2003, provisional application No. 60/409,293, filed on Sep. 9, 2002, provisional application No. 60/408,378, filed on Sep. 5, 2002, provisional application No. 60/406,784, filed on Aug. 29, 2002, provisional application No. 60/386,782, filed on Jun. 6, 2002, provisional application No. 60/363,124, filed on Mar. 11, 2002, provisional application No. 60/358,580, filed on Feb. 20, 2002.

(51) Int. Cl.
C07H 21/02 (2006.01)
C07H 21/04 (2006.01)
C12N 15/113 (2010.01)

(52) U.S. Cl.
CPC ........ *C12N 15/113* (2013.01); *C12N 15/1137* (2013.01); *C12Y 304/21021* (2013.01); *C12N 2310/14* (2013.01); *C12N 2310/315* (2013.01); *C12N 2310/322* (2013.01); *C12N 2310/3231* (2013.01); *C12N 2310/346* (2013.01); *C12N 2310/351* (2013.01); *C12N 2320/32* (2013.01)

(58) Field of Classification Search
CPC .......................... C12N 15/113; C12N 2310/11
See application file for complete search history.

(56) References Cited

U.S. PATENT DOCUMENTS

| | | | |
|---|---|---|---|
| 4,501,729 A | 2/1985 | Boucher et al. |
| 4,987,071 A | 1/1991 | Cech et al. |
| 5,108,921 A | 4/1992 | Low et al. |
| 5,138,045 A | 8/1992 | Cook et al. |
| 5,214,136 A | 5/1993 | Lin et al. |
| 5,334,711 A | 8/1994 | Sproat et al. |
| 5,413,908 A | 5/1995 | Jeffreys |
| 5,416,016 A | 5/1995 | Low et al. |
| 5,421,818 A | 6/1995 | Arenberg |
| 5,444,650 A | 8/1995 | Abe et al. |
| 5,474,529 A | 12/1995 | Arenberg |
| 5,476,446 A | 12/1995 | Arenburg |
| 5,572,594 A | 11/1996 | Devoe et al. |

(Continued)

FOREIGN PATENT DOCUMENTS

| | | |
|---|---|---|
| CA | 2359180 A1 | 8/2000 |
| DE | 19925052 A1 | 12/2000 |

(Continued)

OTHER PUBLICATIONS

Jen et al. (Stem Cells, 2000, 18, 307-319).*
Hu et al., "Inhibition of Retroviral Pathogenesis by RNA Interference", 2002, Current Biology, vol. 12, pp. 1301-1311.
Hunziker et al., "Nucleic Acid Analogues: Synthesis and Properties, in Modern Synthetic Methods," VCH, 331-417 (1995).
Hutvagner and Zamore, "A MicroRNA in a Multiple-Turnover RNAi Enzyme Complex," Science 297:2056-2060 (2002).

(Continued)

*Primary Examiner* — Amy Bowman
(74) *Attorney, Agent, or Firm* — Lando & Anastasi, LLP

(57) ABSTRACT

The present invention concerns methods and reagents useful in modulating gene expression in a variety of applications, including use in therapeutic, diagnostic, target validation, and genomic discovery applications. Specifically, the invention relates to synthetic chemically modified small nucleic acid molecules, such as short interfering nucleic acid (siNA), short interfering RNA (siRNA), double-stranded RNA (dsRNA), micro-RNA (miRNA), and short hairpin RNA (shRNA) molecules capable of mediating RNA interference (RNAi) against target nucleic acid sequences. The small nucleic acid molecules are useful in the treatment of any disease or condition that responds to modulation of gene expression or activity in a cell, tissue, or organism.

23 Claims, 95 Drawing Sheets

(56) References Cited

U.S. PATENT DOCUMENTS

| | | |
|---|---|---|
| 5,587,471 A | 12/1996 | Cook et al. |
| 5,589,332 A | 12/1996 | Shih et al. |
| 5,624,803 A | 4/1997 | Noonberg et al. |
| 5,627,053 A | 5/1997 | Usman et al. |
| 5,631,359 A | 5/1997 | Chowrira et al. |
| 5,631,360 A | 5/1997 | Usman et al. |
| 5,670,633 A | 9/1997 | Cook et al. |
| 5,672,695 A | 9/1997 | Eckstein et al. |
| 5,716,824 A | 2/1998 | Beigelman et al. |
| 5,741,679 A | 4/1998 | George et al. |
| 5,792,847 A | 8/1998 | Buhr et al. |
| 5,804,683 A | 9/1998 | Usman et al. |
| 5,814,620 A | 9/1998 | Robinson et al. |
| 5,831,071 A | 11/1998 | Usman et al. |
| 5,834,186 A | 11/1998 | George et al. |
| 5,849,902 A | 12/1998 | Arrow et al. |
| 5,854,038 A | 12/1998 | Sullenger et al. |
| 5,871,914 A | 2/1999 | Nathan |
| 5,877,309 A | 3/1999 | McKay et al. |
| 5,885,968 A | 3/1999 | Biessen et al. |
| 5,889,136 A | 3/1999 | Scaringe et al. |
| 5,891,468 A | 4/1999 | Martin et al. |
| 5,898,031 A | 4/1999 | Crooke |
| 5,902,880 A | 5/1999 | Thompson |
| 5,932,580 A | 8/1999 | Levitzki et al. |
| 5,968,909 A | 10/1999 | Agrawal et al. |
| 5,985,558 A | 11/1999 | Dean et al. |
| 5,989,912 A | 11/1999 | Arrow et al. |
| 5,990,090 A | 11/1999 | Nabel |
| 5,994,517 A | 11/1999 | Ts'o et al. |
| 5,998,148 A | 12/1999 | Bennett et al. |
| 5,998,203 A | 12/1999 | Matulic-Adamic et al. |
| 5,998,206 A | 12/1999 | Cowsert |
| 6,001,311 A | 12/1999 | Brennan |
| 6,005,087 A | 12/1999 | Cook et al. |
| 6,008,400 A | 12/1999 | Scaringe et al. |
| 6,040,181 A | 3/2000 | Reed |
| 6,041,181 A | 3/2000 | Ju et al. |
| 6,045,528 A | 4/2000 | Arenberg et al. |
| 6,046,175 A | 4/2000 | Lori et al. |
| 6,054,576 A | 4/2000 | Bellon et al. |
| 6,057,156 A | 5/2000 | Akhtar et al. |
| 6,060,456 A | 5/2000 | Arnold, Jr. et al. |
| 6,069,008 A | 5/2000 | Bennett et al. |
| 6,093,702 A | 7/2000 | Malley et al. |
| 6,107,062 A | 8/2000 | Hu et al. |
| 6,107,094 A | 8/2000 | Crooke |
| 6,111,086 A | 8/2000 | Scaringe |
| 6,117,657 A | 9/2000 | Usman et al. |
| 6,120,484 A | 9/2000 | Silverstein |
| 6,133,242 A | 10/2000 | Zalewski et al. |
| 6,146,886 A | 11/2000 | Thompson |
| 6,153,737 A | 11/2000 | Manoharan et al. |
| 6,162,909 A | 12/2000 | Bellon et al. |
| 6,168,778 B1 | 1/2001 | Janjic et al. |
| 6,180,613 B1 | 1/2001 | Kaplitt et al. |
| 6,194,151 B1 | 2/2001 | Busfield |
| 6,214,805 B1 | 4/2001 | Torrence et al. |
| 6,235,310 B1 | 5/2001 | Wang et al. |
| 6,235,886 B1 | 5/2001 | Manoharan et al. |
| 6,248,878 B1 | 6/2001 | Matulic-Adamic et al. |
| 6,261,840 B1 | 7/2001 | Cowsert et al. |
| 6,300,074 B1 | 10/2001 | Gold et al. |
| 6,300,131 B1 | 10/2001 | Greider et al. |
| 6,303,773 B1 | 10/2001 | Bellon et al. |
| 6,323,184 B1 | 11/2001 | Zalewski et al. |
| 6,335,434 B1 | 1/2002 | Guzaev et al. |
| 6,346,398 B1 | 2/2002 | Pavco et al. |
| 6,348,312 B1 | 2/2002 | Peyman et al. |
| 6,350,934 B1 | 2/2002 | Zwick et al. |
| 6,353,098 B1 | 3/2002 | Usman et al. |
| 6,362,323 B1 | 3/2002 | Usman et al. |
| 6,372,427 B1 | 4/2002 | Kandimalla et al. |
| 6,387,366 B1* | 5/2002 | Hurwitz .............. A61K 38/37 424/130.1 |
| 6,395,492 B1 | 5/2002 | Manoharan et al. |
| 6,395,713 B1 | 5/2002 | Beigelman et al. |
| 6,414,134 B1 | 7/2002 | Reed |
| 6,437,117 B1 | 8/2002 | Usman et al. |
| 6,440,102 B1 | 8/2002 | Arenberg et al. |
| 6,447,796 B1 | 9/2002 | Vook et al. |
| 6,469,158 B1 | 10/2002 | Usman et al. |
| 6,476,205 B1 | 11/2002 | Buhr et al. |
| 6,503,533 B1 | 1/2003 | Korba et al. |
| 6,506,559 B1 | 1/2003 | Fire et al. |
| 6,518,268 B1 | 2/2003 | Chin et al. |
| 6,528,631 B1 | 3/2003 | Cook et al. |
| 6,565,885 B1 | 5/2003 | Tarara et al. |
| 6,568,524 B1 | 5/2003 | Cornell et al. |
| 6,573,099 B2 | 6/2003 | Graham |
| 6,582,728 B1 | 6/2003 | Platz et al. |
| 6,586,524 B2 | 7/2003 | Sagara |
| 6,592,904 B2 | 7/2003 | Platz et al. |
| 6,617,156 B1 | 9/2003 | Doucette-Stamm et al. |
| 6,656,559 B2 | 12/2003 | Mizushima et al. |
| 6,685,967 B1 | 2/2004 | Patton et al. |
| 6,733,627 B2 | 5/2004 | Krukonis et al. |
| 6,824,972 B2 | 11/2004 | Kenwrick et al. |
| 6,906,182 B2 | 6/2005 | Ts'o et al. |
| 7,022,828 B2 | 4/2006 | McSwiggen |
| 7,056,704 B2 | 6/2006 | Tuschl et al. |
| 7,078,196 B2 | 7/2006 | Tuschl et al. |
| 7,109,165 B2 | 9/2006 | Matulic-Adamic et al. |
| 7,262,177 B2 | 8/2007 | Ts'O et al. |
| 7,491,805 B2 | 2/2009 | Vargeese et al. |
| 7,833,992 B2 | 11/2010 | Vargeese et al. |
| 7,858,625 B2 | 12/2010 | Matulic-Adamic et al. |
| 7,858,769 B2 | 12/2010 | Jadhav et al. |
| 7,923,547 B2 | 4/2011 | McSwiggen et al. |
| 7,935,812 B2 | 5/2011 | McSwiggen et al. |
| 7,956,176 B2 | 6/2011 | McSwiggen et al. |
| 7,964,578 B2 | 6/2011 | Vargeese et al. |
| 7,989,612 B2 | 8/2011 | McSwiggen et al. |
| 8,106,022 B2 | 1/2012 | Manoharan et al. |
| 8,188,247 B2 | 5/2012 | Beigelman et al. |
| 8,202,979 B2 | 6/2012 | McSwiggen et al. |
| 8,232,383 B2 | 7/2012 | McSwiggen et al. |
| 8,236,944 B2 | 8/2012 | Beigelman et al. |
| 8,242,257 B2 | 8/2012 | Beigelman et al. |
| 8,263,760 B2 | 9/2012 | de Kimpe et al. |
| 8,268,986 B2 | 9/2012 | Beigelman et al. |
| 8,273,866 B2 | 9/2012 | McSwiggen et al. |
| 8,314,227 B2 | 11/2012 | Wengel |
| 8,329,463 B2 | 12/2012 | Tuschl et al. |
| 8,349,809 B2 | 1/2013 | Brown |
| 8,362,231 B2 | 1/2013 | Tuschl et al. |
| 8,372,968 B2 | 2/2013 | Tuschl et al. |
| 8,394,628 B2 | 3/2013 | Tuschl et al. |
| 8,420,391 B2 | 4/2013 | Tuschl et al. |
| 8,445,237 B2 | 5/2013 | Tuschl et al. |
| 8,450,467 B2 | 5/2013 | Manoharan et al. |
| 8,461,313 B2 | 6/2013 | Matulic-Adamic et al. |
| 8,507,455 B2 | 8/2013 | Manoharan et al. |
| 8,513,207 B2 | 8/2013 | Brown |
| 8,552,171 B2 | 10/2013 | Tuschl et al. |
| 8,618,277 B2 | 12/2013 | Beigelman et al. |
| 8,632,997 B2 | 1/2014 | Tuschl et al. |
| 8,648,185 B2 | 2/2014 | McSwigen et al. |
| 8,742,092 B2 | 6/2014 | Tuschl et al. |
| 8,765,930 B2 | 7/2014 | Tuschl et al. |
| 8,778,902 B2 | 7/2014 | Tuschl et al. |
| 8,790,922 B2 | 7/2014 | Tuschl et al. |
| 8,796,016 B2 | 8/2014 | Tuschl et al. |
| 8,846,894 B2 | 9/2014 | McSwiggen et al. |
| 8,927,705 B2 | 1/2015 | Brown |
| 2001/0007666 A1 | 7/2001 | Hoffman et al. |
| 2001/0034333 A1* | 10/2001 | Kosak ................ A61K 9/1075 514/44 A |
| 2002/0037866 A1 | 3/2002 | Schlingensiepen et al. |
| 2002/0086356 A1 | 7/2002 | Tuschl et al. |
| 2002/0130430 A1 | 9/2002 | Castor |
| 2002/0137210 A1 | 9/2002 | Churikov |
| 2002/0151693 A1 | 10/2002 | Breaker et al. |
| 2003/0059944 A1 | 3/2003 | Lois-Caballe et al. |

(56) References Cited

U.S. PATENT DOCUMENTS

| | | | |
|---|---|---|---|
| 2003/0064945 A1 | 4/2003 | Akhtar et al. |
| 2003/0077829 A1 | 4/2003 | MacLachlan |
| 2003/0083294 A1 | 5/2003 | Sullenger et al. |
| 2003/0087855 A1 | 5/2003 | Ward et al. |
| 2003/0119017 A1 | 6/2003 | McSwiggen |
| 2003/0119724 A1* | 6/2003 | Ts'o et al. ........ A61K 47/48092 |
| | | | 530/391.9 |
| 2003/0124513 A1 | 7/2003 | McSwiggen |
| 2003/0130186 A1 | 7/2003 | Vargeese et al. |
| 2003/0143732 A1 | 7/2003 | Fosnaugh et al. |
| 2003/0190635 A1 | 10/2003 | McSwiggen |
| 2003/0206887 A1 | 11/2003 | Morrissey et al. |
| 2004/0019001 A1 | 1/2004 | McSwiggen |
| 2004/0037780 A1 | 2/2004 | Parsons et al. |
| 2004/0110296 A1 | 6/2004 | Vargeese et al. |
| 2004/0161844 A1 | 8/2004 | Baker et al. |
| 2004/0171033 A1* | 9/2004 | Baker ..................... C12N 9/22 |
| | | | 435/6.11 |
| 2004/0180351 A1 | 9/2004 | Giese et al. |
| 2004/0192626 A1 | 9/2004 | McSwiggen et al. |
| 2004/0219671 A1 | 11/2004 | McSwiggen et al. |
| 2004/0259247 A1 | 12/2004 | Tuschl et al. |
| 2005/0020521 A1 | 1/2005 | Rana |
| 2005/0020525 A1 | 1/2005 | McSwiggen et al. |
| 2005/0032733 A1 | 2/2005 | McSwiggen et al. |
| 2005/0048529 A1 | 3/2005 | McSwiggen |
| 2005/0079610 A1 | 4/2005 | Polisky et al. |
| 2005/0080246 A1 | 4/2005 | Allerson et al. |
| 2005/0106726 A1 | 5/2005 | McSwiggen et al. |
| 2005/0137155 A1 | 6/2005 | McSwiggen et al. |
| 2005/0176665 A1 | 8/2005 | McSwiggen |
| 2005/0182005 A1 | 8/2005 | Tuschl et al. |
| 2005/0209180 A1 | 9/2005 | Jadhav et al. |
| 2005/0227256 A1 | 10/2005 | Hutvagner et al. |
| 2005/0233329 A1 | 10/2005 | McSwiggen et al. |
| 2005/0266422 A1 | 12/2005 | Vagle et al. |
| 2005/0282188 A1 | 12/2005 | Haeberli et al. |
| 2006/0217331 A1 | 9/2006 | Vargeese et al. |
| 2006/0217332 A1 | 9/2006 | Vargeese et al. |
| 2006/0217334 A1 | 9/2006 | McSwiggen et al. |
| 2006/0217335 A1 | 9/2006 | McSwiggen et al. |
| 2006/0217336 A1 | 9/2006 | McSwiggen et al. |
| 2006/0217337 A1 | 9/2006 | McSwiggen et al. |
| 2006/0247428 A1 | 11/2006 | McSwiggen et al. |
| 2006/0247429 A1 | 11/2006 | McSwiggen et al. |
| 2006/0275903 A1 | 12/2006 | McSwiggen et al. |
| 2006/0276635 A1 | 12/2006 | McSwiggen et al. |
| 2006/0281175 A1 | 12/2006 | McSwiggen et al. |
| 2006/0287266 A1 | 12/2006 | McSwiggen et al. |
| 2006/0292691 A1 | 12/2006 | McSwiggen et al. |
| 2006/0293271 A1 | 12/2006 | McSwiggen et al. |
| 2006/0293272 A1 | 12/2006 | McSwiggen et al. |
| 2007/0004663 A1 | 1/2007 | McSwiggen et al. |
| 2007/0004664 A1 | 1/2007 | McSwiggen et al. |
| 2007/0004665 A1 | 1/2007 | McSwiggen et al. |
| 2007/0004667 A1 | 1/2007 | McSwiggen et al. |
| 2007/0032441 A1 | 2/2007 | McSwiggen et al. |
| 2007/0042983 A1 | 2/2007 | Haeberli et al. |
| 2007/0160980 A1 | 7/2007 | Haeberli et al. |
| 2007/0167393 A1 | 7/2007 | McSwiggen et al. |
| 2007/0270579 A1 | 11/2007 | Jadhav et al. |
| 2008/0039412 A1 | 2/2008 | Jadhav et al. |
| 2008/0039414 A1 | 2/2008 | McSwiggen et al. |
| 2008/0161256 A1 | 7/2008 | Morrisey et al. |
| 2008/0249294 A1 | 10/2008 | Haeberli et al. |
| 2009/0023675 A1 | 1/2009 | McSwiggen et al. |
| 2009/0137500 A1 | 5/2009 | McSwiggen et al. |
| 2009/0176725 A1 | 7/2009 | Morrissey et al. |
| 2009/0247608 A1 | 10/2009 | Manoharan et al. |
| 2009/0306184 A1 | 12/2009 | Mcswiggen et al. |
| 2010/0145038 A1 | 6/2010 | McSwiggen et al. |
| 2010/0240730 A1 | 9/2010 | Beigelman et al. |
| 2011/0014123 A1 | 1/2011 | Tuschl et al. |
| 2011/0020234 A1 | 1/2011 | Tuschl et al. |
| 2011/0065773 A1 | 3/2011 | Tuschl et al. |
| 2011/0112283 A1 | 5/2011 | Tuschl et al. |
| 2011/0118335 A1 | 5/2011 | Jadhav et al. |
| 2011/0124853 A1 | 5/2011 | Chen et al. |
| 2011/0263683 A1 | 10/2011 | Beigelman et al. |
| 2011/0301219 A1 | 12/2011 | Beigelman et al. |
| 2011/0301220 A1 | 12/2011 | Beigelman et al. |
| 2012/0015042 A1 | 1/2012 | Tuschl et al. |
| 2012/0122111 A1 | 5/2012 | Tuschl et al. |
| 2013/0012567 A1 | 1/2013 | McSwigen et al. |
| 2013/0018082 A1 | 1/2013 | McSwigen et al. |
| 2013/0096290 A1 | 4/2013 | Brown |
| 2013/0123342 A1 | 5/2013 | Brown |
| 2013/0125259 A1 | 5/2013 | Tuschl et al. |
| 2013/0171242 A1 | 7/2013 | Lim et al. |
| 2013/0178512 A1 | 7/2013 | Manoharan et al. |
| 2013/0198875 A1 | 8/2013 | Tuschl et al. |
| 2013/0217756 A1 | 8/2013 | Cancilla et al. |
| 2013/0225652 A1 | 8/2013 | Chorn et al. |
| 2014/0045919 A1 | 2/2014 | Manoharan et al. |
| 2014/0134399 A1 | 5/2014 | Kirby et al. |
| 2014/0179761 A1 | 6/2014 | Manoharan et al. |
| 2014/0221454 A1 | 8/2014 | Brown |
| 2014/0288148 A1 | 9/2014 | Beigelman et al. |
| 2014/0348857 A1 | 11/2014 | Chang et al. |
| 2014/0377767 A1 | 12/2014 | Gong et al. |
| 2015/0038554 A1 | 2/2015 | Brown |
| 2015/0038555 A1 | 2/2015 | Brown |
| 2015/0105445 A1 | 4/2015 | McSwiggen et al. |
| 2015/0148530 A1 | 5/2015 | McSwiggen et al. |
| 2015/0267200 A1 | 9/2015 | McSwiggen et al. |
| 2016/0017336 A1 | 1/2016 | de Fougerolles et al. |
| 2016/0244760 A1 | 8/2016 | Beigelman et al. |

FOREIGN PATENT DOCUMENTS

| | | |
|---|---|---|
| EP | 0653439 A2 | 5/1995 |
| EP | 0808898 A1 | 11/1997 |
| EP | 1212416 A2 | 6/2002 |
| EP | 1389637 A1 | 2/2004 |
| EP | 1445312 A1 | 8/2004 |
| EP | 1458741 A2 | 9/2004 |
| EP | 1572067 A2 | 9/2005 |
| EP | 1622572 A2 | 2/2006 |
| EP | 1627061 A2 | 2/2006 |
| EP | 1675948 A2 | 7/2006 |
| EP | 1682661 A2 | 7/2006 |
| EP | 1710307 A2 | 10/2006 |
| EP | 1713915 A2 | 10/2006 |
| EP | 1931781 A2 | 6/2008 |
| EP | 2042510 A2 | 4/2009 |
| EP | 1423406 B1 | 9/2010 |
| EP | 2278004 A1 | 1/2011 |
| EP | 2287305 A1 | 2/2011 |
| EP | 2287306 A1 | 2/2011 |
| EP | 2415486 A2 | 2/2012 |
| JP | 08208687 | 8/1996 |
| JP | 2001355896 A | 12/2001 |
| WO | 88/09810 A1 | 12/1988 |
| WO | 8902439 A1 | 3/1989 |
| WO | 9012096 A1 | 10/1990 |
| WO | 9014090 A1 | 11/1990 |
| WO | 9103162 A1 | 3/1991 |
| WO | 9115580 A1 | 10/1991 |
| WO | 9207065 A1 | 4/1992 |
| WO | 9315187 A1 | 8/1993 |
| WO | 9323569 A1 | 11/1993 |
| WO | 9401550 A1 | 1/1994 |
| WO | 9402595 A1 | 2/1994 |
| WO | 9504142 A2 | 2/1995 |
| WO | 9506731 A2 | 3/1995 |
| WO | 9509236 A1 | 4/1995 |
| WO | 9511304 A1 | 4/1995 |
| WO | 9511910 A1 | 5/1995 |
| WO | 9532986 A1 | 12/1995 |
| WO | 9610390 A1 | 4/1996 |
| WO | 9610391 A1 | 4/1996 |
| WO | 9610392 A1 | 4/1996 |
| WO | 9618736 A2 | 6/1996 |
| WO | 9622689 A1 | 8/1996 |

(56) References Cited

FOREIGN PATENT DOCUMENTS

| | | |
|---|---|---|
| WO | 9718312 A1 | 5/1997 |
| WO | 9721808 A1 | 6/1997 |
| WO | 9726270 A2 | 7/1997 |
| WO | 9813526 A1 | 4/1998 |
| WO | 9827104 A1 | 6/1998 |
| WO | 9828317 A2 | 7/1998 |
| WO | 9843993 A2 | 10/1998 |
| WO | 9858058 A1 | 12/1998 |
| WO | 9903819 A1 | 1/1999 |
| WO | 9904819 A1 | 2/1999 |
| WO | 9905094 A1 | 2/1999 |
| WO | 9906540 A2 | 2/1999 |
| WO | 9907409 A1 | 2/1999 |
| WO | 9913886 A1 | 3/1999 |
| WO | 9914226 A2 | 3/1999 |
| WO | WO 99/13886 * 3/1999 ........... C12N 15/113 | |
| WO | WO 99/14226 * 3/1999 ........... C12N 15/113 | |
| WO | 9916871 A2 | 4/1999 |
| WO | 9917120 A1 | 4/1999 |
| WO | 9929350 A1 | 6/1999 |
| WO | 9929842 A1 | 6/1999 |
| WO | 9931262 A2 | 6/1999 |
| WO | 9932619 A1 | 7/1999 |
| WO | 9949029 A1 | 9/1999 |
| WO | 9953050 A1 | 10/1999 |
| WO | 9954459 A2 | 10/1999 |
| WO | 9955857 A2 | 11/1999 |
| WO | 9961631 A1 | 12/1999 |
| WO | 9966063 A2 | 12/1999 |
| WO | 0001846 A2 | 1/2000 |
| WO | 0003683 A2 | 1/2000 |
| WO | 0017369 A2 | 3/2000 |
| WO | 0021560 A1 | 4/2000 |
| WO | 0024931 A2 | 5/2000 |
| WO | 0026226 A1 | 5/2000 |
| WO | 0044895 A1 | 8/2000 |
| WO | 0044914 A1 | 8/2000 |
| WO | 0049035 A1 | 8/2000 |
| WO | 0053722 A2 | 9/2000 |
| WO | 0063364 A2 | 10/2000 |
| WO | 0066604 A2 | 11/2000 |
| WO | 0078431 A1 | 12/2000 |
| WO | 0104313 A1 | 1/2001 |
| WO | 0111023 A1 | 2/2001 |
| WO | 0116312 A2 | 3/2001 |
| WO | 0129058 A1 | 4/2001 |
| WO | 0136646 A1 | 5/2001 |
| WO | 0138551 A1 | 5/2001 |
| WO | 0142443 A1 | 6/2001 |
| WO | 0149844 A1 | 7/2001 |
| WO | 0153475 A2 | 7/2001 |
| WO | 0153528 A1 | 7/2001 |
| WO | 0161030 A2 | 8/2001 |
| WO | 0168836 A2 | 9/2001 |
| WO | 0170944 A2 | 9/2001 |
| WO | 0170949 A1 | 9/2001 |
| WO | 0172774 A2 | 10/2001 |
| WO | 0174136 A2 | 10/2001 |
| WO | 0175164 A2 | 10/2001 |
| WO | 0183740 A2 | 11/2001 |
| WO | 0192513 A1 | 12/2001 |
| WO | 0196388 A2 | 12/2001 |
| WO | 0196584 A2 | 12/2001 |
| WO | 0197850 A2 | 12/2001 |
| WO | 0207747 A1 | 1/2002 |
| WO | 0210374 A2 | 2/2002 |
| WO | 0210378 A2 | 2/2002 |
| WO | 0215876 A2 | 2/2002 |
| WO | 0216620 A2 | 2/2002 |
| WO | 0222636 A1 | 3/2002 |
| WO | 0238805 A2 | 5/2002 |
| WO | 0244321 A2 | 6/2002 |
| WO | 02055692 A3 | 7/2002 |
| WO | 02055693 A2 | 7/2002 |
| WO | 02081494 A1 | 10/2002 |
| WO | 02094185 A2 | 11/2002 |
| WO | 02096927 A2 | 12/2002 |
| WO | 03005028 A1 | 1/2003 |
| WO | 03005346 A1 | 1/2003 |
| WO | 03016572 A1 | 2/2003 |
| WO | 03024420 A1 | 3/2003 |
| WO | 03030989 A2 | 4/2003 |
| WO | 03034985 A2 | 5/2003 |
| WO | 03043689 A1 | 5/2003 |
| WO | 03044188 A1 | 5/2003 |
| WO | 03046185 A1 | 6/2003 |
| WO | 03047518 A2 | 6/2003 |
| WO | 03064621 A2 | 8/2003 |
| WO | 03064625 A2 | 8/2003 |
| WO | 03064626 A2 | 8/2003 |
| WO | 03068797 A1 | 8/2003 |
| WO | 03070193 A2 | 8/2003 |
| WO | 03070197 A2 | 8/2003 |
| WO | 03070742 A1 | 8/2003 |
| WO | 03070743 A1 | 8/2003 |
| WO | 03070744 A1 | 8/2003 |
| WO | 03070750 A2 | 8/2003 |
| WO | 03070881 A2 | 8/2003 |
| WO | 03070884 A2 | 8/2003 |
| WO | 03070886 A2 | 8/2003 |
| WO | 03070887 A2 | 8/2003 |
| WO | 03070888 A2 | 8/2003 |
| WO | 03070895 A2 | 8/2003 |
| WO | 03070896 A2 | 8/2003 |
| WO | 03070897 A2 | 8/2003 |
| WO | 03070903 A2 | 8/2003 |
| WO | 03070910 A2 | 8/2003 |
| WO | 03070911 A2 | 8/2003 |
| WO | 03070912 A2 | 8/2003 |
| WO | 03070914 A2 | 8/2003 |
| WO | 03070917 A2 | 8/2003 |
| WO | 03070918 A2 | 8/2003 |
| WO | 03070966 A2 | 8/2003 |
| WO | 03070968 A2 | 8/2003 |
| WO | 03070969 A2 | 8/2003 |
| WO | 03070970 A2 | 8/2003 |
| WO | 03070972 A2 | 8/2003 |
| WO | 03070983 A1 | 8/2003 |
| WO | 03072590 A1 | 9/2003 |
| WO | 03072704 A2 | 9/2003 |
| WO | 03072705 A2 | 9/2003 |
| WO | 03074654 A2 | 9/2003 |
| WO | 03080638 A2 | 10/2003 |
| WO | 03099298 A1 | 12/2003 |
| WO | 03104456 A1 | 12/2003 |
| WO | 03106476 A1 | 12/2003 |
| WO | 2004009769 A2 | 1/2004 |
| WO | 2004009794 A2 | 1/2004 |
| WO | 2004013280 A2 | 2/2004 |
| WO | 2004015107 A2 | 2/2004 |
| WO | 2004029212 A2 | 4/2004 |
| WO | 2004043977 A2 | 5/2004 |
| WO | 2004048566 A1 | 6/2004 |
| WO | 2004072261 A2 | 8/2004 |
| WO | 2004090105 A2 | 10/2004 |
| WO | 2004097020 A2 | 11/2004 |
| WO | 2005014859 A1 | 2/2005 |
| WO | 2005019453 A2 | 3/2005 |
| WO | 2005028649 A1 | 3/2005 |
| WO | 2005028650 A2 | 3/2005 |
| WO | 2005041859 A2 | 5/2005 |
| WO | 2005044981 A2 | 5/2005 |
| WO | 2005045034 A2 | 5/2005 |
| WO | 2005049821 A1 | 6/2005 |
| WO | 2005078097 A2 | 8/2005 |
| WO | 2007022369 A2 | 2/2007 |
| WO | 2008147824 A2 | 12/2008 |
| WO | 2009073809 A2 | 6/2009 |
| WO | 2009076400 A2 | 6/2009 |
| WO | 2009082606 A2 | 7/2009 |
| WO | 2009082607 A2 | 7/2009 |
| WO | 2011088058 A1 | 7/2011 |
| WO | 2012068187 A1 | 5/2012 |

(56) References Cited

FOREIGN PATENT DOCUMENTS

| WO | 2013074974 A2 | 5/2013 |
|---|---|---|
| WO | 2013165816 A2 | 11/2013 |
| WO | 2015003113 A2 | 1/2015 |

OTHER PUBLICATIONS

Hutvagner et al., "A Cellular Function for the RNA-Interference Enzyme Dicer in the Maturation of the let-7 Small Temporal RNA," Science 293:834-838 (2001).
International Search Report for PCT/US02/15876 mailed Apr. 4, 2007.
International Search Report for PCT/US03/02510 mailed May 30, 2003.
International Search Report for PCT/US03/03473 mailed Aug. 19, 2003.
International Search Report for PCT/US03/03662 mailed Sep. 5, 2003.
International Search Report for PCT/US03/04034 mailed Aug. 5, 2003.
International Search Report for PCT/US03/04088 mailed Jul. 11, 2003.
International Search Report for PCT/US03/04123 mailed Jun. 22, 2004.
International Search Report for PCT/US03/04250 mailed Dec. 19, 2003.
International Search Report for PCT/US03/04347 mailed Oct. 30, 2003.
International Search Report for PCT/US03/04397 mailed Jun. 2, 2003.
International Search Report for PCT/US03/04402 mailed Nov. 20, 2003.
International Search Report for PCT/US03/04448 mailed Dec. 22, 2003.
International Search Report for PCT/US03/04464 mailed Jan. 13, 2004.
International Search Report for PCT/US03/04566 mailed May 27, 2003.
International Search Report for PCT/US03/04710 mailed Nov. 18, 2003.
International Search Report for PCT/US03/04738 mailed Dec. 10, 2003.
International Search Report for PCT/US03/04741 mailed Jul. 16, 2004.
International Search Report for PCT/US03/04907 mailed Dec. 11, 2003.
International Search Report for PCT/US03/04908 mailed Oct. 20, 2003.
International Search Report for PCT/US03/04909 mailed Mar. 18, 2005.
International Search Report for PCT/US03/04951 mailed Feb. 19, 2004.
International Search Report for PCT/US03/05022 mailed Jan. 6, 2005.
International Search Report for PCT/US03/05028 mailed Oct. 17, 2003.
International Search Report for PCT/US03/05043 mailed Jan. 16, 2004.
International Search Report for PCT/US03/05044 mailed Jul. 2, 2004.
International Search Report for PCT/US03/05045 mailed Sep. 14, 2004.
International Search Report for PCT/US03/05162 mailed Sep. 17, 2003.
International Search Report for PCT/US03/05190 mailed Nov. 4, 2003.
International Search Report for PCT/US03/05234 mailed Apr. 8, 2004.
International Search Report for PCT/US03/05326 mailed Nov. 14, 2003.
International Search Report for PCT/US03/05346 mailed Oct. 17, 2003.
International Search Report for PCT/US03/07273 mailed Oct. 27, 2003.
International Search Report for PCT/US03/18911 mailed Nov. 19, 2003.
International Search Report for PCT/US04/16390 mailed on Mar. 31, 2005, 2 pages.
International Search Report for PCT/US2004/012517 mailed Sep. 28, 2005.
International Search Report for PCT/US2004/016390 mailed Mar. 31, 2005.
International Search Report for PCT/US2004/030488 mailed Jan. 12, 2005.
International Search Report for PCT/US2006/032168 mailed Jun. 6, 2007.
Ishiwata et al., "Physical-Chemistry Characteristics and Biodistribution of Poly(ethylene glycoi)-Coated Liposomes Using Poly(oxyethylene) Cholesteryl Ether," Chem. Pharm. Bull. 43:1005-1011 (1995) (mistakenly referred to as Ishiwataet).
Izant and Weintraub, "Constitutive and Conditional Suppression of Exogenous and Endogeneous Genes by Anti-Sense RNA," Science 229:345-352 (1985).
Jacque et al., "Modulation of HIV-1 replication by RNA interference." Nature 418: 435-438 (2002).
Janowski et al, "Inhibitng gene expression at transcription start sites inchromosomal DNA with antigene RNAs", Nature Chemical Biology, 1, 216-222 (2005).
Jaschke et al., "Automated Incorporation of Polyethylene Glycol into Synthetic Oligonucleotides," Tetrahedron Letters 34:301-304 (1993) (sometimes mistakenly referred as to Jschke).
Jaschke et al., "Synthesis and Properties of Oligodeoxyribonuclotide-polyethylene Glycol Conjugates," Nucleic Acids Research 22:4810-4817 (1994).
Jaschke, "Oligonucleotide-Poly(ethylene glycol) Conjugates: Synthesis, Properties, and Application," American Chemical Society 680:265-283 (1997).
Jayasena, "Aptamers: An Emerging Class of Molecules that Rival Antibodies in Diagnostics," Clinical Chemistry 45:1628-1650 (1999).
Stein et al., "A Specificity Comparison of Four Antisense Types: Morpholino, 2'-0-Methyl RNA, DNA, and Phosphorothioate DNA," Antisense & Nucleic Acid Drug Development 7:151-157 (1997).
Strauss, Evelyn, "Molecular Biology: Candidate 'Gene Silencers' Found," Molecular Biology, vol. 286, No. 5441, p. 886 (1999) (sometimes mistakenly referred to as being published in Science].
Strobel and Dervan, "Site-Specific Cleavage of a Yeast Chromosome by Oligonucleotide-Directed Triple-Helix Formation," Science 249:73-75 (1990).
Sullenger et al., "Overexpression of TAR Sequences Renders Cells Resistant to Human Immunodeficiency Virus Replication," Cell 63:601-608 (1990).
Svoboda et al., "Selective reduction of dormant maternal mRNAs in mouse oocytes by RNA interference," Development, 127,4147-4156 (2000).
Szostak, "In Vitro Genetics," TIBS 17:89-93 (1992).
Table 1 of application as submitted in US proceedings for European Application EP1423406 (May 31, 2011).
Takagi et al., "Mechanism of action of hammerhead ribozymes and their applications in vivo: rapid identification of functional genes in the post-genome era by novel hybrid ribozyme libraries," Biochemical Society Transactions, 30, 1145-1149 (2002) [abstract only].
Tang et al., "Examination of the catalytic fitness of the hammerhead ribozyme by in vitro selection," RNA 3:914-925 (1997).
Tari et al., "Growth Inhibition of breast cancer cells by Grb2 downregulation is correlated with inactivation of mitogen-activated protein kinase in EGFR, but not in ErbB2, cells." Oncogene 18:1325-1332 (1999).
Tari et al., "Inhibition of Grb2 and Crkl Proteins Results in Growth Inhibition of Philadelphia Chromosome Positive Leukemic Cells." Biochem and Biophys Research Comm 235: 383-388 (1997).

(56) References Cited

OTHER PUBLICATIONS

Tavernarakis et al, "Heritable and inducible genetic interference by double-stranded RNA encoded by transgenes," Nature Genetics 24, 180-183 (2000).
Thomas et al., "Enhancing polyethylenimine's delivery of plasmid DNA into mammalian cells," PNAS, 99, 14640-14645 (2002).
Thomson et al., "Activity of hammerhead ribozymes containing non-nucleotidic linkers," Nucleic Acids Research 21:5600-5603 (1993) (May Be Referred to As Thompson).
Tuschl et al., "Small Interfering RNAs: A Revolutionary Tool for Analysis of Gene Function and Gene Therapy," Molecular Interventions, 2, 3, 158-167 (2002).
Tuschl et al., "Targeted mRNA Degradation by Double-Stranded RNA In Vitro," Genes & Development 3191-3197 (1999).
Tuschl, "RNA Interference and Small Interfering RNAs," Chembiochem 2:239-245 (2001).
Tyler et al., "Peptide nucleic acids targeted to the neurotensin receptor and administered i.p. cross the blood-brain barrier and specifically reduce gene expression," Proc. Natl. Acad. Sci. USA 96:7053-7058 (1999).
Tyler et al., "Specific gene blockade shows that peptide nucleic acids readily enter neuronal cells in vivo," FEBS Letters 421:280-284 (1998).
U.S. Appl. No. 14/458,578, filed Aug. 13, 2014.
Uhlmann and Peyman, "Antisense Oligonucleotides: A New Therapeutic Principle," Chemical Reviews 90:544-584 (1990).
Ui-Tei et al., "Guidelines for the selection of highly effective siRNA sequences for mammalian and chick RNA interference," Nucleic Acids Research, 32, 3, 936-948 (2004) [also referred to as doi:1 0.1 093/nar/gkh247].
Ullrich et al., "Insulin-like growth factor I receptor primary structure: comparison with insulin receptor suggests structural determinants that define functional specificity," The EMBO Journal, 5:10, 2503-2512 (1986).
Usman and Cedergren, "Exploiting the chemical synthesis of RNA," TIBS 17:334-339 (1992).
Usman et al., "Automated Chemical Synthesis of Long Oligoribonucleotides Using 2'-O-Silylated Ribonucleoside 3'-O-Phosphoramidites on a Controlled-Pore Glass Support: Synthesis of a 43-Nucleotide Sequence Similar to the 3'-Half Molecule of an*Escherichia coli* Formylmethoionine tRNA," J. Am. Chem. Soc. 109:7845-7854 (1987).
Usman et al., "Hammerhead ribozyme engineering," Current Opinion in Structural Biology 6: 527-533 (1996).
Vaish et al., "Isolation of Hammerhead Ribozymes with Altered Core Sequences by in Vitro Selection," Biochemistry 36:6495-6501 (1997).
Vaughn and Martienssen, "It's a Small RNA World, After All," Science, 309, 1525-1526 (2005).
Verdel et al., "RNAi-Mediated Targeting ofHeterochromatin by the RITS Complex," Science, 303, 672-676 (2004).
Verma and Eckstein, "Modified Oligonucleotides: Synthesis and Strategy for Users," Annu. Rev. Biochem. 67:99-134 (1998).
Vickers et al., "Efficient Reduction of Target RNAs by Small Interfering RNA and RNase H-dependent Antisense Agents," Journal of Biological Chemistry, 278, 7108-7118 (2003).
Volpe et al., "Regulation of Heterochromatic Silencing and Histone H3 Lysine-9 Methylation by RNAi " Science 297:1833-1837 (2002).
Wang et al., "Delivery of Antisense Oligodeoxyribonucleotides Against the Human Epidermal Growth Factor Receptor into Cultured KB Cells with Liposomes Conjugated to Folate via Polyethylene Glycol," Proc. Natl. Acad. Sci. USA 92:3318-3322 (1995).
Wang et al., "Small Hairpin RNAs Efficiently Inhibit Hepatitis C IRES-Mediated Gene Expression in Human Tissue Culture Cells and a Mouse Model," 2005, Molecular Therapy, vol. 12, No. 3, pp. 562-568.
Waterhouse et al., "Virus resistance and gene silencing in plants can be induced by simultaneous expression of sense and antisense RNA," Proc. Natl. Acad. Sci. USA, 95, 13959-13964 (1998).

Wen et al., "Preparation and property analysis of a hepatocyte targeting pH-sensitive liposome," World J Gastroenterology, 10(2):244-249 (2004).
Werner and Uhlenbeck, "The effect of base mismatches in the substrate recognition helices of hammerhead ribozymes on binding and catalysis," Nucleic Acids Research 23:2092-2096 (1995).
Wianny and Zernicka-Goetz et al., "Specific Interference with Gene Function by Double-Stranded RNA in Early Mouse Development," Nature Cell Biology 2:70-75 (2000).
Wilda et al., "Killing of leukemic cells with a BCRIABL fusion gene by RNA interference (RNAi)," Oncogene, 21, 5716-5724 (2002).
Wincott et al., "A Practical Method for the Production of RNA and Ribozymes," Methods in Molecular Biology 74:59-69 (1997).
Wincott et al., "Synthesis, deprotection, analysis and purification of RNA and ribozymes," Nucleic Acids Research 23 (14):2677-2684 (1995).
Withdrawal of an opposition (dated Mar. 10, 2014, from European Application EP1458741).
Woolf et al., "Specificity of Antisense Oligonucleotides in vivo," Proc. Natl. Acad. Sci. USA 89:7305-7309 (1992).
Wraight et al., "Anitsense oligonucleotides in cutaneous therapy," Pharmacology & Therapeutics, 90, 89-104 (2001).
Written submission by Patentee during examination proceedings for European application EP1423406 dated Oct. 13, 2009.
Wu and Kaufman, "A Model for the Double-stranded RNA (dsRNA)-dependent Dimerization and Activation of the dsRNA-activated Protein Kinase PKR ," The Journal of Biological Chemistry, 272:2, 1291-1296 (1997).
Wu and Wu, "Receptor-mediated in Vitro Gene Transformation by a Soluble DNA Carrier System," The Journ. of Biol. Chem. 262:4429-4432 (1987).
Wu et al., "Small Interfering RNA-induced Suppression of MDR1 (P-Giycoprotein) Restores Sensitiviy to Multidrug-resistant Cancer Cells," Cancer Research, 63, 1515-1519 (2003).
Wu-Pong et al., "Nucleic Acid Drug Delivery, Part 2; Delivery to the Brain," 38 (1999) BioPharm 32-38 (1999).
Yamada et al., "Nanoparticles for the delivery of genes and drugs to human hepatocytes," Nature Biotechnology, Published online: Jun. 29, 2003, doi:10.1038/nbt843 (Aug. 2003 vol. 21 No. 8 pp. 885-890) (2003).
Yang et al., "Hydrodynamic injection of viral DNA: A mouse model of acute hepatitis B virus infection," PNAS, 99, 21, 13825-13830 (2002).
Ying et al., "Intron-derived microRNAs-fine tuning of gene functions", Gene, 342, 25-28 (2004).
Yu et al., "A Hairpin Ribozyme Inhibits Expression of Diverse Strains of Human Immunodeficiency Virus Type 1 ," Proc. Natl. Acad. Sci. USA 90:6340-6344 (1993).
Yu et al., "Antisense inhibition of Chk2/hCds1 expression attenuates DNA damage-induced S and G2 checkpoints and enhances apoptotic activity in HEK-293 cells," FEBS Letters, 505,7-12 (2001).
Zamore and Haley, "Ribo-gnome: The Big World of Small RNAs," Science, 309, 1519-1524 (2005).
Zamore et al., "RNAi: Double-Stranded RNA Directs the ATP-Dependent Cleavage of mRNA at 21 to 23 Nucleotide Intervals," Cell 101:25-33 (2000).
Zhang et al., "Single Processing Center Models for Human Dicer and Bacterial RNase III," Cell, 118:57-68 (2004).
Zhou et al., "Probing of the secondary structure of maxizymes," Nucleic Acids Symposium Series No. 42, 219-220 (1999).
Zhou et al., "Synthesis of Functional mRNA in Mammalian Cells by Bacteriophage T3 RNA Polymerase," Mol. Cell. Biol. 10:4529-4537 (1990).
Zimmerly et al., "A Group II Intron RNA is a Catalytic Component of a DNA Endonuclease Involved in Intron Mobility," Cell 83:529-538 (1995).
Bauer et al., "Discrimination Between Sialic Acid-Containing Receptors and Pseudoreceptors Regulates Polyomavirus Spread in the Mouse", Journal of Virology, vol. 73, No. 7, p. 5826-5832, Jul. 1999

(56) References Cited

OTHER PUBLICATIONS

Bauer et al., "Discrimination Between Sialic Acid-Containing Receptors and Pseudoreceptors Regulates Polyomavirus Spread in the Mouse", Journal of Virology, vol. 73, No. 7, p. 5826-5832, Jul. 1999.
Communication to the Parties Concerning Termination of Opposition Proceedings in EP 1458741 filed Jul. 31, 2015.
Decision to Maintain the European Patent in Amended Form in EP 1423406 dated Oct. 29, 2015.
Declaration of Sharon Avkin-Nachum filed in EP2287305 on Oct. 6, 2015.
Declaration under 37 CFR §1.132 of Dr. Hagit Ashush filed in EP2287305 on Oct. 6, 2015.
Geisbert, T.W. et al. "Treatment of Ebola Virus Infection with a Recombinant Inhibitor of Factor VIIa/Tissue Factor: A Study in Rhesus Monkeys", Lancet 2003; 362:1953-58.
Hornung, V. et al., "Sequence-Specific Potent Induction of IFN-a by Short Interfering RNA in Plasmacytoid Dendritic cells Through TLR7", Nature Medicine, vol. 11, No. 3, pp. 263-270, Mar. 2005.
Information about the Result of Oral Proceedings in Application No. 10008930.9 filed Nov. 25, 2015.
Interlocutory Decision in Opposition Proceedings filed in EP1423406 on Apr. 16, 2015.
Interlocutory Decision in Opposition Proceedings in EP2287306 filed on Feb. 17, 2016.
Minutes of the Oral Proceedings in EP2287306 filed on Jan. 28, 2016.
Notice of Opposition by Quark Pharmaceuticals, Inc. against EP2287305 filed on Oct. 6, 2015.
Notice of Opposition filed by Quark Pharmaceuticals, Inc. in EP2287306 on May 22, 2013.
Notice of Opposition filed in EP2287306 by Sima Therapeutics, Inc. and D9 (Annex A) Cited Therein on May 21, 2013.
Reply filed in EP2287305 by Sima Therapeutics, Inc. on Feb. 2, 2016.
Reply filed in EP2287306 by Sima Therapeutics, Inc. on Dec. 24, 2013.
Summons to Attend Oral Proceedings in EP2287306 by Sima Therapeutics, Inc. on Jan. 23, 2015.
Termination of Opposition Proceedings of Patent No. 1458741 with Maintenance of the Patent filed Jul. 28, 2015.
Termination of Opposition Proceedings of Patent No. EP 1423406 with Maintenance of the Patent filed Oct. 23, 2015.
U.S. Appl. No. 60/358,580, filed Feb. 20, 2002 by Beigelman et al.
Volkov et al, "Selective Protection of Nuclease-Sensitive Sites in siRNA Prolongs Silencing Effect", Oligonucleotides, vol. 19, No. 2, Feb. 21, 2009.
Wallin, R. et al., "Enhanced Synthesis of Functional Recombinant Factors IX and VII by BHK Cells Engineered to Overexpress VKORC1 Combined with siRNA Silencing of the g-Carboxylation Inhibitor Calumenin", Blood, (ASH Annual Meeting Abstracts) 2006 108 Abstract 1707.
Weil, D. et al. "Targeting the Kinesin Eg5 to Monitor siRNA Transfection in Mammalian Cells", BioTechniques 33:1244-1248 (Dec. 2002).
Withdrawal of Opposition by Sima Therapeutics, Inc. in EP2287306 filed on Mar. 10, 2014.
Written Submission in EP2287306 filed by Quark Pharmaceuticals, Inc. on Sep. 25, 2015.
Zimmermann, T.S. et al., "RNAi-Mediated Gene Silencing in Non-Human Primates", Nature, vol. 441 No. 4, May 2006, pp. 111-114.
Jen et al., "Suppression of gene Expression by Targeted Disruption of Messenger RNA: Available Options and Current Strategies," Stem Cells, 18:307-319(2000).
Jenuwein, "An RNA-Guided Pathway for the Epigenome," Science 297:2215-2218 (2002).
Jolliet-Riant and Tillement, "Drug transfer across the blood-brain barrier and improvement of brain delivery," Fundam. Clin. Pharmacol. 13:16-26 (1999).

Judge et al., "Sequence-dependent stimulation of the mammalian innate immune response by synthetic siRNA," Nature Biotechnology, 23(4):457-462 (2005).
Kanikkannan, "Iontophoresis-Based Transdermal Delivery Systems," Biodrugs, 16(5):339-347 (2002).
Kapadia et al., "Interference of hepatitis C virus RNA replication by short interfering RNAs," Proceedings of the National Academy of Sciences of USA, National Academy of Science, Washington, US, 100(4):2014-2018 (2003).
Karle et al., "Differential Changes in Induced Seizures After Hippocampal Treatment of Rats with an Antisense Oligodeoxynucleotide to the GABAA Receptor .gamma.2 Subunit," Euro. Jour. of Pharmacology 340:153-160 (1997).
Karpeisky et al, "Highly Efficient Synthesis of 2'-0-Amino Nucleosides and Their Incorporation in Hammerhead Ribozymes," Tetrahedron Letters 39:1131-1134 (1998).
Kawasaki et al., "siRNAs generated by recombinant human Dicer induce specific and significant but target site-independent gene silencing in human cells," Nucleic Acids Research, 31 (3 ):981-987 (2003).
Kawasaki et al., "Uniformly Modified 2'-Modified 2'-Deoxy-2'-fluoro Phosphorothioate Oligonucleotides as Nuclease-Resistant Antisense Compounds with High Affinity and Specificity for RNA Targets," J. Med. Chem., 36, 831-841 (1993).
Kennerdell et al., "Heritable gene silencing in Drosophila using double-stranded RNA," Nature Biotech 18: 896-898 (2000).
Kim et al., "A Conserved p38 MAP Kinase Pathway in Caenorhabditis elegans Innate Immunity," Science, 297, 623-626 (2002).
Kraynack et al, "Small interfering RNAs containing full 2'-O-methylribonucleotide-modified sense strands display Argonaute2/eIF2C2-dependent activity," RNA 12: 163-176 (2006).
Kronenwett et al., "Oligodeoxyribonucleotide Uptake in Primary Human Hematopoietic Cells is Enhanced by Cationic Lipids and Depends on the Hematopoietic Cell Subset," Blood 91:852-862 (1998).
Kunath et al., "The structure of PEG-modified poly(ethylene imines) influences biodistribution and pharmacokinetics of their complexes with NF-kappaB decoy in mice.," Medline (Pharm Res.) 19(6): 810-817 (Jun. 1, 2002).
Kurreck et al., Design of antisense oligonucleotides stabilized by locked nucleic acids, 2002, Nucleic Acids Research, vol. 30, No. 9, pp. 1911-1918.
Kusser, "Chemically modified nucleic acid aptamers for in vitro selections: evolving evolution," Reviews in Molecular Biotechnology 74:27-38 (2000).
Kuwabara et al., "Activities of tRNA-embedded dimeric minizymes," Nucleic Acids Symposium Series No. 37, 307-308 (1997).
L'Huillier et al., "Cytoplasmic Delivery of Ribozymes Leads to Efficient Reduction in a-Lactalbumin mRNA Levels in C1271 Mouse," EMBO J. 11:4411-4418 (1992).
Laible et al., "Mammalian homologues of the Polycomb-group gene Enhancer of zeste mediate gene silencing in Drosophila heterochromatin and at S. cervisiae telomeres," The EMBO Journal, 16, 3219-3232 (1997).
Lasic and Needham "The 'Stealth' Liposome: A Prototypical Biomaterial," Chemical Reviews 95:2601-2627 (1995).
Lasic and Papahadjopoulos, "Liposomes Revisited," Science 267:1275-1276 ( 1995).
Lee and Larson, "Modified Liposome Formulations for Cytosolic Delivery of Macromolecules," ACS Symposium Series 752:184-192 (2000).
Lee and Lee, "Preparation of Cluster Glycosides of N-Acetylgalactosamine That Have Subnanomolar Binding Constants Towards the Mammalian Hepatic Gal/GalNAc-specific Receptor," Glyconjugates J, 4.317-328 (1987).
Lee et al., "Enhancing the Catalytic Repertoire of Nucleic Acids: A Systematic Study of Linker Length and Rigidity," Nucleic Acids Research 29:1565-1573 (2001).
Lee et al., "Expression of Small Interfering RNA's Targeted Against HIV-1 rev Transcripts in Human Cells," Nature Biotechnology 19:500-505 (2002).

(56) References Cited

OTHER PUBLICATIONS

Leirdal et al., "Gene silencing in mammalian cells by preformed small RNA duplexes," Biochemical and Biophysical Research Communications, 295: 744-748 (2002).
Letter regarding the opposition procedure (no time limit) (dated Jan. 29, 2014, from European Application EP1423406).
Letter regarding the opposition procedure (no time limit) (dated Jan. 31, 2014, from European Application EP1423406).
Letter regarding the opposition procedure (no time limit) (dated Sep. 10, 2013, from European Application EP1423406).
Li and Altman, "Cleavage by RNase P of gene N mRNA reduces bacteriophage 'A burst size," Nucleic Acids Research 24:835-842 (1996).
Lichner et al., "Double-stranded RNA-binding proteins could suppress RNA interference-mediated antiviral defences," Journal of General Virology, 84, 975-980 (2003).
Limbach et al., "Summary: the modified nucleosides of RNA," Nucleic Acids Research 22(12):2183-2196 (1994).
Lin et al., "A Novel mRNA-cRNA Interference Phenomenon for Silencing bcl-2 Expression in Human LNCaP Cells," Biochemical and Biophysical Research Communications, 281, 639-644 (2001).
Lin et al., "Policing rogue genes," Nature, 402, 128-129 (1999).
Lisziewicz et al., "Inhibition of Human Immunodeficiency Virus Type 1 Replication by Regulated Expression of a Polymeric Tat Activation Response RNA Decoy as a Strategy for Gene Therapy in AIDS," Proc. Natl. Acad. Sci. U.S.A. 90:8000-8004 (1993).
Liu et al., "Cationic Liposome-mediated Intravenous Gene Delivery," J. Biol. Chem. 70(42):24864-24870 (1995).
Liu et al., "Hydrodynamics-based transfection in animals by systemic administration of plasmid DNA," Gene Therapy, 6, 1258-1266 (1999).
Liu et al., "Poly( cationic lipid)-mediated in vivo gene delivery to mouse liver," Gene Therapy, 10:180-187 (2003).
Loakes, "The Applications of Universal DNA Base Analogues," Nucleic Acids Research 29:2437-2447 (2001).
Lu et al., "Tumor Inhibition by RNAi-Mediated VEGF an VEGFR2 Down Regulation in Xenograft Models," Cancer Gene Therapy, 10, SuppL 1, S4-S5 (2003).
Luo et al., "Blocking CHK1 Expression Induces Apoptosis and Abrogates the G2 Checkpoint Mechanism," Neoplasia, 3:5,411-419 (2001).
Ma and Wei, "Enhanced Delivery of Synthetic Oligonucleotides to Human Leukaemic Cells by Liposomes and Immunoliposomes," Leukemia Research 20:925-930 (1996).
Ma et al., "Design and Synthesis of RNA Miniduplexes via a Synthetic Linker Approach," Biochemistry 32:1751-1758 (1993).
Ma et al., "Design and Synthesis of RNA Miniduplexes via a Synthetic Linker Approach. 2. Generation of Covalently Closed, Double-Stranded Cyclic HIV-1 TAR RNA Analogs with High Tat-Binding Affinity," Nucleic Acids Research 21:2585-2589 (1993).
Martinez et al., "Single-Stranded Antisense siRNAs Guide Target RNA Cleavage in RNAi," Cell 110:563-574 (2002).
Matranga et al., "Passenger-Strand Cleavage Facilitates Assembly of siRNA into Agog-Containing RNAi Enzyme Complexes," Cell, 123:1-114 (2005).
Matsuno et al., "Hepatocyte growth factor gene transfer into the liver via the portal vein using electroporation attenuates rat liver cirrhosis," Gene Therapy 10:1559-1566 (2003).
Maurer et al., "Lipid-based systems for the intracellular delivery of genetic drugs," Molecular Membrane Biology 16:129-140 (1999).
McCaffrey et al., "RNA interference in adult mice," Nature, 418, 38-39 (2002).
Ponpipom et al., "Cell-Specific Ligands for Selective Drug Delivery to Tissues and Organs," J. Med. Chem. 24:1388-1395 (1981).
Prakash et al., "Positional Effect of Chemical Modifications on Short Interference RNA Activity in Mammalian Cells," J. Med. Chem. 48: 4247-4253 (2005).

Praseuth et al., "Triple helix formation and the antigene for sequence-specific control of gene expression," Biochimica et Biophysica Acta 1489:181-206 (1999).
Preat et al., "Topical delivery of nucleic acids in the skin," S.T.P. Pharma Sciences, 11(1): 57-68 (2001).
Puttaraju et al., "A circular trans-acting hepatitis delta virus ribozyme," Nucleic Acids Research 21:4253-4258 (1993).
Qu et al., "Selective Inhibition of IL-2 Gene Expression by IL-2 Antisense Oligonucleotides Blocks Heart Allograft Rejection," Transplantation, 72, 5, 915-923 (2001).
Rajakumar et al., "Effects of Intrastriatal Infusion of D2 Receptor Antisense Oligonucleotide on Apomorphine-Induced Behaviors in the Rat," Synapse 26:199-208 (1997).
Rand et al., "Argonaute2 Cleaves the Anti-Guide Strand of siRNA during RISC Activation," Cell, 123:621-629 (2005).
Randall et al., "Clearance of replicating hepatitis C virus by small interfering RNAs," Proceedings of the National Academy of Sciences of USA, 1 00(1) Abstract only (2003).
Ray et al., "Common Signaling Themes," Science, 306, 1505 (2004).
Regnier et al., "Parameters Controlling Topical Delivery of Oligonucleotides by Electroporation," Journal of Drug Targeting, 5(4 ), 275-289 (1998).
Reinhart and Bartel, "Small RNAs Correspond to Centromer Heterochromatic Repeats," Science 297:1831 (2002).
Reinhart et al., "MicroRNAs in Plants," Genes & Development 16:1616-1626 (2002).
Reply of the patent proprietor to the notice(s) of opposition (dated Mar. 19, 2014, from European Application EP1458741).
Reply of the patent proprietor to the notice(s) of opposition (dated Nov. 9, 2011, from European Apllication EP1423406).
Reply of the patent proprietor to the notice(s) of opposition (dated Nov. 9, 2011, from European Application EP1423406).
Reynolds et al., "Rational siRNA designe for RNA intereference," Nature Biotechnology, 22, 3, 326-330 (2004) [also referred to as 1 Feb. 4, 2004, doi: 10.1 038/nbt936].
Richardson and Schepartz, "Tethered Oligonucleotide Probes. A Strategy for the Recognition of Structured RNA," J. Am. Chem. Soc. 113:5109-5111 (1991).
Robertson et al., "Purification and Properties of a Specific *Escherichia coli* Riobnuclease which Cleaves a Tyrosine Transfer Ribonucleic Acid Precursor," J. Biol. Chern. 247:5243-5251 (1972).
Rossi et al., "Ribozymes as Anti-HIV-1 Therapeutic Agents: Principles, Applications, an Problems," Aids Research and Human Retroviruses 8:183-189 (1992).
Salo et al., "Aminooxy Functionalized Oligonucleotides: Preparation, On-Support Derivatization, and Postsynthetic Attachment to Polymer Support," Bioconjugate Chem. 10:815-823 (1999).
Sanghvi et al., "Improved Process for the Preparation of Nucleosidic Phosphoramidites Using a Safer and Cheaper Activator," Organic Process Res. & Dev. 4:175-181 (2000).
Santoro and Joyce, "A general purpose RNA-cleaving DNA enzyme," Proc. Natl. Acad. Sci. USA 94:4262-4266 (1997).
Santoro et al., "Mechanism and Utility of an RNA-Cleaving DNA Enzyme," Biochemistry 37:13330-13342 (1998).
Santoro et al., "RNA Cleavage by a DNA Enzyme with Extended Chemical Functionality," J. Am. Chem. Soc. 122:2433-2439 (2000).
Sarver et al., "Ribozymes as Potential Anti-HIV-1 Therapeutic Agents" Science 247:1222-1225 (1990).
Saville and Collins, "A Site-Specific Self-Cleavage Reaction Performed by a Novel RNA in Neurospora Mitochondria," Cell 61:685-696 (1990).
Saville and Collins, "RNA-Mediated Ligation of Self-Cleavage Products of a Neurospora Mitochondrial Plasmid Transcript," Proc. Natl. Acad. Sci. USA 88:8826-8830 (1991).
Scanlon et al., "Ribozyme-Mediated Cleavage of c-fos mRNA Reduces Gene Expression of DNA Synthesis Enzymes and Metallothionein," Proc. Natl. Acad. Sci. USA 88:10591-10595 (1991).
Scanlon, "Antigenes: siRNA, Ribozymes and Antisense", Current Pharmaceutical Biotechnology, vol. 5:415-420, (2004).

(56) References Cited

OTHER PUBLICATIONS

Scaringe et al., "Chemical synthesis of biologically active oligoribonucleotides using .beta.-cyanoethyl protected ribonucleoside phosphoramidites," Nucl Acids Res. 18:5433-5441 (1990).
Scherr et al., "Specific inhibition of bcr-abl gene expression by small interfering RNA," Blood, 1 01 :4, 1566-1569 (2003).
Schmajuk et al., "Antisense Oligonucleotides with Different Backbones," The Journal of Biological Chemistry 274:21783-21789 (1999).
Schmidt et al., "Base and sugar requirements for RNA cleavage of essential nucleoside residues in internal loop B of the hairpin ribozyme: implications for secondary structure," Nucleic Acids Research 24:573-581 (1996).
Schroeder et al., "Diffusion Enhancement of Drugs by Loaded Nanoparticles in Vitro," Prog. Neuro-Psychopharmacol. & Biol. Psychiat. 23:941-949 (1999) [sometimes cited by RPI as Prog Neuropsychopharmacol Biol Psychiatry 23:941-949, 1999].
Schwarz et al., "Asymmetry in the Assembly of the RNAi Enzyme Complex," Cell, 1115, 199-208 (2003).
Schwarz et al., "Evidence that siRNA's Function as Guides, Not Primers, in the Drosophila and Human RNAi Pathways," Molecular Cell 10: 537-548 (2002).
Scott et al., "The crystal structure of an All-RNA hammerhead ribozyme: A proposed mechanism for RNA catalytic cleavage," Cell 81: 991-1002 (1995).
Seela and Kaiser, "Oligodeoxyribonucleotides containing 1,3-propanediol as nucleoside substitute," Nucleic Acids Research 15:3113-3129 (1987).
Segarra et al., "Molecular Characterization of the Enterococcus faecalis Cytolysin Activator", Infection and Immunity, vol. 59, No. 4, p. 1239-1246, (1991).
Semizarov, et al., "siRNA-mediated gene silencing: a global genome view," Nucleic Acids research, 32(13): 3836-3845 (2004).
Sethupathy et al., "TarBase: A comprehensive database of experimentally supported animal microRNA targets," RNA, 12:192-197 (2006).
Shabarova et al., "Chemical ligation of DNA: The first non-enyzmatic assembly of a biologically active gene," Nucleic Acids Research 19:4247-4251 (1991).
Sharp, "RNAi and double-strand RNA," Genes & Development, 13:139-141 (1999).
Sheehan et al., "Biochemical properties of phosphonoacetate and thiophosphonoacetate oligodeoxyribonucleotides," Nucleic Acids Research, 31 (14), 4109-4118 (2003).
Silverman et al., "Selective RNA Cleavage by Isolated RNase L Activated with 2-5A Antisense Chimeric Oligonucleotides," Methods in Enzymology 313:522-533 (1999).
Simantov et al., "Dopamine-Induced Apoptosis in Human Neuronal Cells: Inhibition by Nucleic Acids Antisense to the Dopamine Transporter," Neuroscience 74(1):39-50 (1996).
Sirois et al., "Anitsense Oligonucleotide Inhibition of PDGFR-p Receptor Subunit Expression Directs Suppression of Intimal Thickening," Circulation, 95:669-676 (1997).
Sommer et al., "The Spread and Uptake Pattern of Intracerebrally Administered Oligonucleotides in Nerve and Glial Cell Populations of the Rat Brain," Antisense & Nucleic Acid Drug Development 8:75-85 (1998).
Stein and Cheng, "Antisense Oligonucleotides as Therapeutic Agents—Is the Bullet Really Magical?" Science 261:1004-1288 (1993).
Abramovitz et al., "Catalytic Role of 2'-Hydroxyl Groups Within a Group II Intron Active Site," Science 271:1410-1413 (1996).
Adah et al., "Chemistry and Biochemistry of 2, 5 -Oligoadenylate-Based Antisense Strategy," Current Medicinal Chemistry, 8, 1189-1212 (2001).
Agrawal, "Importance of Nucleotide Sequence and Chemical Modifications of Antisense Oligonucleotides", Biochimica et Biophysica Acta, vol. 1489:53-68, (1999).

Akhtar and Juliano, "Cellular Uptake and Intracellular Fate of AntiSense Oligonucleotides," Trends Cell Biol. 2:139-144 (1992).
Aldrian-Herrada et al., "A peptide nucleic acid (PNA) is more rapidly internalized in cultured neurons when coupled to a retro-inverso delivery peptide. The antisense activity depresses the target mRNA and protein in magnocellular oxytocin neurons,"Nucleic Acids Research 26:4910-4916 (1998).
Alexeev et al., "Localized in vivo genotypic and phentypic correction of the albino mutation in skin by RNA-DNA oligonucleotide," Nature Biotechnology, 18:43-47 (2000).
Allerson et al., "Fully 2'-Modified Oligonucleotide Duplexes with Improved in Vitro Potency and Stability Compared to Unmodified Small Interfering RNA," J. Med. Chem., 48:901-904 (2005).
Allshire, "RNAi and Heterochromatin—A Hushed-up Affair," Science 297:1818-1819 (2002).
Almendral et al., "Cloning and Sequence of the Human Nuclear Protein Cyclin: Homology with DNA-binding Protein," Proc. Natl. Acad. Sci., 84:1575-1579 (1987).
Amarzguioui et al. "Tolerance for mutations and chemical modifications in a siRNA," Nucl. Acids. Res. 31:589-595 (2003).
Anderson et al., "Bispecific short hairpin siRNA constructs targeted to CD4 CXCR4, and CCR5 confer HIV-1 resistance," Oligonucleuotides, vol. 13, No. 5, pp. 303-312 (2003).
Andrews and Faller, "A rapid micropreparation technique for extraction of DNA-binding proteins from limiting numbers of mammalian cells," Nucleic Acids Research 19:2499 (1991).
Annex to the communication—opposition (dated Oct. 7, 2013, from European Application EP1423406).
Antopolsky et al., "Peptide-Oligonucleotide Phosphorothioate Conjugates with Membrane Translocation and Nuclear Localization Properties," Bioconjugate Chem. 10:598-606 (1999).
Arap et al., "Cancer Treatment by Targeted Drug Delivery to Tumor Vasculature in a Mouse Model," Science 279:377-380 (1998).
Baenziger and Fiete, "Galactose and N-Acetylgalactosamine-Specific Endocytosis of Glycopeptides by Isolated Rat Hepatocytes," Cell 22:611-620 (1980).
Bahramian et al., "Transcriptional and Posttranscriptional Silencing of Rodent a1(I) Collagen by a Homologous Transcriptionally Self-Silenced Transgene," Molecular and Cellular Biology, vol. 19 No. 1, pp. 274-283 (1999).
Bannai et al., "Effect of Injection of Antisense Oligodeoxynucleotides of GAD Isozymes into Rat Ventromedial Hypothalamus on Food Intake and Locomotor Activity," Brain Research 784:305-315 (1998).
Bannai et al., "Water-absorbent Polymer as a Carrier for a Discrete Deposit of Antisense Oligodeoxynucleotides in the Central Nervous System," Brain Research Protocols 3:83-87 (1998).
Basi et al., "Antagonistic Effects of b-Site Amyloid Precursor Prtein-cleaving Enzymes 1 and 2 on b-Amyloid Peptide Production in Cells," The Journal of Biological Chemistry, 278, 31512-31520 (2003).
Bass et al., "RNA interference: The short answer," Nature 411: 428-429 (2001).
Bass, "Double-Stranded RNA as a Template for Gene Silencing," Cell, 101, 235-238 (2000).
Bass, "RNA editing and hypermutation by adenosine deamination," TIBS 22(5): 157-162 (1997).
Bayard et al., "Increased stability and antiviral activity of 2'-0-phosphoglyceryl derivatives of (2'-5')oligo(adenylate)," Eur. J. Biochem., 142(29):291-298 (1984).
Beaucage and Iyer, "The Functionalization of Oligonucleotides Via Phosphoramidite Derivatives," Tetrahedron 49:1925-1963 (1993).
Beigelman et al., "Chemical Modification of Hammerhead Ribozymes," The Journal of Biological Chemistry 270:25702-25708 (1995).
Bellon et al., "4-Thio-oligo-.beta.-D-ribonucleotides: synthesis of .beta.-4'-thio-oligouridylates, nuclease resistance, base pairing properties, and interaction with HIV-1 reverse transcriptase," Nucleic Acids Research, 21(7):1587-1593 (1993).
Bernstein et al., "Role for a Bidentate Ribonuclease in the Initiation Step of RNA Interference," Nature 409:363-366 (2001).
Bernstein et al., "The rest is silence," RNA, 7:1509-1521 (2001).

(56) References Cited

OTHER PUBLICATIONS

Bertrand et al., "Comparison of antisense oligonucleotides and siRNAs in cell culture and in vivo", BBRC, vol. 296, pp. 1000-1004 (2002).
Berzai-Herranz et al., "Essential nucleotide sequences and secondary structure elements of the hairpin ribozyme," EMBO J. 12:2567-2574 (1993).
Bettinger et al., "Size Reduction of Galactosylated PEI/DNA Complexes Improves Lectin-Mediated Gene Transfer into Hepatocytes," Bioconjugate Chem., 10, 558-561 (1999).
Bitko et al., "Phenotypic silencing of cytoplasmic genes using sequence-specific double-stranded short interfering RNA and its application in the reverse genetics of wild type negative-strand RNA viruses," BMC Microbiology, 1:34 (2001).
Boado et al., "Drug Delivery of Antisense Molecules to the Brain for Treatment of Alzheimer's Disease and Cerebral Aids," Journal of Pharmaceutical Sciences 87:1308-1315 (1998).
Boado, "Antisense drug delivery through the blood-brain barrier," Advanced Drug Delivery Reviews 15:73-107 (1995).
Bongartz et al., "Improved biological activity of antisense oligonucleotides conjugated to a fusogenic peptide," Nucleic Acids Research 22:4681-4688 (1994).
Bonora et al, "Biological Properties of Antisense Oligonucleotides Conjugated to Different High-Molecular Mass Poly (ethylen glycols)," Nucleosides & Nucleotides 18:1723-1725 (1999).
Bonora et al., "Synthesis and Characterization of High-Molecular Mass Polyethylene Glycol-Conjugated Oligonucleotides," Bioconjugate Chern. 8:793-797 (1997).
Braasch et al., "Novel antisense and peptide nucleic acid strategies for controlling gene expression", Biochem. 41(14): 4503-4510 (2002).
Braasch et al., "RNA Inteference in Mammalian Cells by Chemically-Modified RNA," Biochemistry, 42, 7967-7975 (2003).
Brand, "Topical and transdermal delivery of antisense oligonucleotides," Curr. Opin. Mol. Ther., 3(3):244-248 (2001) [Abstract Only].
Breaker et al., "A DNA enzyme with Mg2+-dependent RNA phosphoesterase activity," Chemistry & Biology 2 (10):655-660 (1995).
Breaker, "Are engineered proteins getting competition from RNA?" Current Opinion in Biotechnology 7:442-448 (1996).
Broaddus et al., "Distribution and stability of antisense phosphorothioate oligonucleotides in rodent brain following direct intraparenchymal controlled-rate infusion," J Neurosurg 88:734-742 (1998).
Brody and Gold, "Aptamers as therapeutic and diagnostic agents," Reviews in Molecular Biotechnology 74:5-13 (2000).
Brummelkamp et al. "A System for Stable Expression of Short Interfering RNAs in Mammalian Cells," (2002) Science 296:550-553.
Buckwold et al., "Effects of a Naturally Occuring Mutation in the Hepatitis B Virus Basal Core Promoter on Precore Gene Expression and Viral Replication," Journal of Virology, vol. 70(9), 5845-5851 (1996).
Caplen et al., "Specific inhibition of gene expression by small double-stranded RNAs in invertebrate and vertebrate systems", Proc. Natl. Acad. Sci., vol. 98, pp. 9742-9747 (2001).
Caplen, "RNAi as a gene therapy approach," Expert Opin. Biol. Ther., 3(4):575-586 (2003).
Cardoso et al., "The human EZH2 gene: genomic organisation and revised mapping in 7q35 within the critical region for malignant myeloid disorders," European Journal of Human Genetics, 8, 174-180 (2000).
McCurdy et al., "Deoxyoligonucleotides with Inverted Polarity: Synthesis and Use in Triple-Helix Formation" Nucleosides & Nucleotides 10:287-290 (1991).
McGarry and Lindquist, "Inhibition of heat shock protein synthesis by heat-inducible antisense RNA," Proc. Natl. Acad. Sci. USA 83:399-403 (1986).
McManus et al., "Gene Silencing Using Micro-RNA Designed Hairpins," RNA 8:842-850 (2002).
Mesmaeker et al, "Novel Backbone Replacements for Oligonucleotides," American Chemical Society, pp. 24-39 (1994).
Miller et al., "Targeting Alzheimer's disease genes with RNA interference: An efficient strategy for silencing mutant alleles," Nucleic Acids Research, 32(2):661-668 (2004).
Milner et al., "Selecting effective antisense reagents on combinatorial oligonucleotide arrays," Nature Biotechnology 15:537-541 (1997).
Minutes of the oral proceedings (Opposition Division)—conclusion of the proceedings (Dated Apr. 25, 2014, from European application EP1423406).
Miyagishi and Taira, "U6 Promoter-driven siRNAs with Four Uridine 3' Overhangs Efficiently Suppress Targeted Gene Expression in Mammalian Cells," Nature Biotechnology 20:497-500 (2002).
Miyagishi et al., "Strategies for generation of an siRNA expression library directed against the human genome," Oligonucleotides, 13(5):325-333 (2003).
Monia et al., "Evaluation of 2'-Modified Oligonucleotides Containing 2'-Deoxy Gaps as Antisense Inhibitors of Gene Expression," J. Biol. Chem. 268:14514-14522 (1993).
Moore and Sharp, "Site-Specific Modification of Pre-mRNA: The 2'-Hydroxyl Groups at the Splice Sites," Science 256:992-996 (1992).
Morris et al., "A New Peptide Vector for Efficient Delivery of Oligonucleotides into Mammalian Cells," Nucleic Acids Research 25:2730-2736 (1997).
Morris et al., "Glycolysis modulates trypanosome glycoprotein expression as revealed by an RNAi library," The EMBO Journal, 21:17,4429-4438 (2002).
Morvan et al., "Comparative Evaluation of Seven Oligonucleotide Analogues as Potential Antisense Agents," J. Med. Chem., 36, 280-287 (1993).
Murao et al., "Targeting Efficiency of Galactosylated Liposomes to Hepatocytes in Vivo: Effect of Lipid Composition," Pharmaceutical Research, 19(12):1808-1814 (2002).
Nemunaitis et al., "Phase I evaluation of CGP 64128A, an antisense inhibitor of protein kinase C-a (PKCa), in patients with refractory cancer," Proc. Ann. Meet Am. A-Soc Clin. Oncol., vol. 16 #870 (1997).
Neureitter et al., "Growth inhibition of pancreatic cancer in nude mice by targeting bc12-suppression with specific short interfering RNA molecules," Pathology Research and Practice, 199(4):257 (2003) Abstract only.
Nieth et al., "Modulation of the classical multidrug resistance (MDR) phenotype by RNA interference (RNAi)", 2003.
Noiseux et al., "A Bolus Endovascular Treatment with a PDGFR-P Antisense is Sufficient to Suppress Intimal Thickening in a Rat Carotid Injury Model," Circulation, 100(18) Supplement 1-816 (1999).
Nomura et al., "Development of an Efficient Intermediate, a-[2-(Trimethylsilyl) ethoxy]-2-N-[2-trimethylsilyl) ethoxycarbonyl]folic Acid, for the Synthesis of Folate (y)-Conjugates, and Its Application to the Synthesis of Folate-Nucleoside Conjugates," J. Org. Chem. 65:5016-5021 (2000).
Noonberg et al., "In vivo generation of highly abundant sequence-specific oligonucleotides for antisense and triplex gene regulation," Nucleic Acids Research 22(14):2830-2836 (1994).
Notice of Opposition by Alcon Research to European Application EP1423406, dated Jun. 1, 2011.
Notice of Opposition by Alnylam Pharmaceuticals, Inc. to European Application EP1423406 dated May 31, 2011.
Notice of Opposition by Alnylam Pharmaceuticals, Inc. to European Application EP1458741, dated Jul. 16, 2013.
Notice of Opposition by Dharmacon, Inc. to European Application EP1423406, dated May 31, 2011.
Notice of Opposition by Novartis to European Application EP1423406, dated May 26, 2011.
Notice of Opposition by Sanofi to European Application EP1423406, dated May 18, 2011.

(56) References Cited

OTHER PUBLICATIONS

Novina et al., "siRNA-directed inhibition of HIV-1 infection," Nature Medicine, 8, 681-686 (2002).
Nykanen et al., "ATP Requirements and Small Interfering RNA Structure in the RNA Interference Pathway," Cell 107:309-321 (2001).
Ogris et al., "DNA/polyethylenimine transfection particles: Influence of ligands, polymer size, and PEGylation on internalization and gene expression," AAPS PharmSci., 3 (3) article 21 (http://www.pharmsci.org) p. 1-11 (2001).
Ohkawa et al., "Activities of HIV-RNA Targeted Ribozymes Transcribed From a 'Shot-Gun' Type Ribozyme-trimming Plasmid," Nucleic Acids Symp. Ser. 27:15-16 (1992).
Ojwang et al., "Inhibition of Human Immunodeficiency Virus Type 1 Expression by a Hairpin Ribozyme," Proc. Natl. Acad. Sci. USA 89:10802-10806 (1992).
Oku et al., "Real-time analysis of liposomal trafficking in tumor-bearing mice by use of positron emission tomography," Biochimica et Biophysica Acta 1238:86-90 (1995).
Olie et al., "Analysis of ribosyl-modified, mixed backbone analogs of a bcl-2/bcl-xL antisense oligonucleotide", Biochim. Biophys. Acta, vol. 1576, pp. 101-109 (2002).
Ono et al., "DNA Triplex Formation of Oligonucleotide Analogues Consisting of Linker Groups and Octamer Segments That Have Opposite Sugar-Phosphate Backbone Polarities," Biochemistry 30:9914-9921 (1991).
Opalinska et al., "A Rational Approach to Nucleic Acid Based Targeting of RNA Molecules Using Self-Quenching Reporter Molecules," Blood, 100(11):193a (2002) Abstract only.
Opalinska et al., "Nucleic-Acid Therapeutics: Basic Principles and Recent Applications," Nature Reviews Drug Discovery, (1 ):503-514 (2002).
Opponents' Briefs Filed in Opposition to European Patent App. 03743684.7 dated Jul. 6, 2011.
Pal-Bhadra et al., "Heterochromatic Silencing and HP1 Localizatin in Drosophila Are Dependent on the RNAi Machinery," Science, 303, 669-672 (2004).
Pan et al., "Probing of tertiary interactions in RNA: 2'-Hydroxyl-base contacts between the Rnase P And pre-tRNA," Proc. Natl. Acad. Sci. USA 92:12510-12514 (1995).
Pardridge et al., "Vector-mediated delivery of a polyamide ("peptide") nucleic acid analogue through the blood-brain barrier in vivo," Proc. Natl. Acad. Sci. USA 92:5592-5596 (1995).
Parrish et al., "Functional Anatomy of a dsRNA Trigger: Differential Requirement for the Two Trigger Strands in RNA Interference," Molecular Cell 6: 1077-1087 (2000).
Patentee's Briefs Filed in Opposition to European Patent App. 03743684.7 (Nov. 9, 2011).
Paul et al., "Effective Expression of Small Interfering RNA in Human Cells," Nature Biotechnology 20:505-508 (2002).
Perreault et al., "Mixed Deoxyribo- and Ribo-Oligonucleotides with Catalytic Activity," Nature 344:565-567 (1990) (often mistakenly listed as Perrault).
Perrotta and Been, "A pseudoknot-like structure required for efficeint self-cleavage of hepatitis delta virus RNA," Nature 350:434-436 (1991).
Perrotta and Been, "Cleavage of Oligoribonucleotides by a Ribozyme Derived from the Hepatitis 8 Virus RNA Sequence," Biochemistry 31:16-21 (1992).
Petersen et al., "Polyethylenimine-graft-Poly(ethylene glycol) Copolymers: Influence of Copolymer Block Structure on DNA Complexation and Biological Activities as Gene Delivery System," Bioconjugate Chem., 13, 845-854 (2002).
Pilone, "D-Amino acid oxidase: new findings," Cellular and Molecular Life Sciences, vol. 57, 1732-1747 (2000).
Player and Torrence, "The 2-5A System: Modulation of Viral and Cellular Processes Through Acceleration of RNA Degradation," Pharmacal Ther. 78:55-113 (1998).
Carmichael et al., "Silencing viruses with RNA," Nature, 418, 379-380 (2002).
Caruthers et al., "Chemical Synthesis of Deoxyoligonucleotides and Deoxyoligonucleotide Analogs," Methods in Enzymology 211:3-19 (1992).
Chaloin et al., "Design of Carrier Peptide-Oligonucleotide Conjugates With Rapid Membrane Translocation and Nuclear Localization Properties," BBRC 243:601-608 (1998).
Chen et al., "Cloning of a Human Homolog of the Drosophilia Enhancer of zeste Gene (EZH2) That Maps to Chromosome 21 q22.2," Genomics, 38, 30-37 (1996).
Chernolovskaya et al., "Interaction of LNA Oliognucleotides with MDR1 Promoter," Nucleosides, Nucleotides & Nucleic Acids, 20, No. 4-7, 847-850 (2001).
Chiu et al, "RNAi in Human Cells: Basic Structural and Functional Features of Small Interfering RNA," Molecular Cell 10, 549-561 (2002).
Chiu et al., "siRNA function in RNAi: A chemical modification analysis," RNA 9: 1034-1048 (2003).
Choi et al., "Effect of Poly(ethylene glycol) Grafting on Polyethylenimine as a Gene Transfer Vector in vitro," Bull. Korean Chem. Soc., 22, 46-52 (2001).
Chowrira et al., "In Vitro and in Vivo Comparison of Hammerhead, Hairpin, and Hepatitis Delta Virus Self-Processing Ribozyme Cassettes," J. Biol. Chem. 269:25856-25864 (1994).
Chumakov et al., "Genetic and Physiological Data Implicating the New Human Gene G72 and the Gene for D-amino Acid Oxidase in Schizophrenia," PNAS 99:13675-13680 (2002).
Chun et al., "Effect of infusion of vasoactive intestinal peptide (VI P)-antisense oligodeoxynucleotide into the third cerebral ventricle above the hypothalamic cuprachiasmatic nucleus on the hyperglycemia caused by intracranial injection of 2-deoxy-D-glucose in rats," Neuroscience Letters 257:135-138 (1998).
Cioca et al., "RNA interference is a functional pathway with therapeutic potential in human myeloid leukemia cell lines," Cancer Gene Therapy, 10, 125-133 (2003).
Claverie, Jean-Michel, "Fewer Genes, More Noncoding RNA," Science, 309, 1529-1530 (2005).
Clemens et al., "The Double-Stranded RNA-Dependent Protein Kinase PKR: Structure and Function," Journal of Interferon and Cytokine Research, 17:503-524 (1997).
Clemens et al., "Use of double-stranded RNA Interference in Drosophila cell lines to dissect signal transduction pathways," PNAS, 97, 12, 6499-6503 (2000).
Cload and Schepartz, "Polyether Tethered Oligonucleotide Probes," J. Am. Chem. Soc. 113:6324-6326 (1991).
Cole et al., "Activation of RNase L by 2',5'-0iigoadenylates," The Journal of Biological Chemistry, 272:31,19187-19192 (1997).
Connolly et al., "Binding and Endocytosis of Cluster Glycosides by Rabbit Hepatocytes," The Journ. of Biol. Chem. 257:939-945 (1982).
Crooke et al., "Kinetic characteristics of *Escherichia coli* RNase H1: cleavage of various antisense oligonucleotide-RNA duplexes," (1995), Biochem. J., 312, pp. 599-608.
Crooke, "Advances in Understanding the Pharmacological Properties of Antisense Oligonucleotides," Advances in Pharmacology 40:1-49 (1997).
Crooke, "Antisense Therapeutics," Biotechnology and Genetic Engineering Reviews 15:121-157 (1998).
Crooke, "Progress in Antisense Technology: The End of the Beginning," Methods in Enzymology 313:3-45 (1999).
Cullen, Bryan R., "Derivation and function of small interfering RNAs and microRNAs," Virus Research, 102, 3-9 (2004).
Czauderna et al., "Structural variations and stabilising modifications of synthetic siRNAs in mammalian cells," Nucleic Acids Research 31(11): 2705-2716 (2003).
Czech, Michael P., "MicroRNAs as Therapeutic Targets," The New England Journal of Medicine, 354, 1194-1195 (2006).
D'Aldin et al., "Antisense oligonucleotides to the GluR2 AMPA receptor subunit modify excitatory synaptic transmission in vivo," Molecular Brain Research 55:151-164 (1998).
Decision of the Opposition Division and Instruction in EP1423406 dated Apr. 16, 2015.
Decision to Discontinue the Opposition Proceedings in EP1458741 dated Apr. 16, 2015.

(56) References Cited

OTHER PUBLICATIONS

Defrancq and Lhomme, "Use of an Aminooxy Linker for the Functionalization of Oligodeoxyribonucleotides," Bioorganic & Medicinal Chem. Lett. 11:931-933 (2001).
Delihas et al., "Natural antisense RNA/target RNA interactions: Possible models for antisense oligonucleotide drug design," Nature Biotechnology 15:751-753 (1997).
Diebold et al., "Mannose Polyethylenimine Conjugates for Targeted DNA Delivery into Dendritic Cells," The Journal of Biological Chemistry, 274, 19087-19094 (1999).
Dryden et al., "The lack of specificity of neuropeptide Y (NPY) antisense oligodeoxynucleotides administered intracerebroventricularly in inhibiting food intake and NPY gene expression in the rat hypothalamus," Journal of Endocrinology 157:169-175(1998).
Durand et al., "Circular Dichroism Studies of an Oligodeoxyribonucleotide Containing a Hairpin Loop Made of a Hexaethylene Glycol Chain: Conformation and Stability," Nucleic Acids Research 18:6353-6359 (1990) [sometimes referred to as Seela and Kaiser].
Duval-Valentin, "Specific inhibition of transcription by triple helix-forming oligonucleotides," Proc. Natl. Acad. Sci. USA 89:504-508 (1992).
Earnshaw et al., "Modified Oligoribonucleotides as Site-Specific Probes of RNA Structure and Function," Biopolymers 48:39-55 (1998).
Egholm et al., "PNA hybridizes to complementary oligonucleotides obeying the Watson-Crick hydrogen-bonding rules," Nature 365:566-568 (1993).
Elbashir et al. "Functional anatomy of siRNAs for mediating efficient RNAi in Drosophila melanogaster embryo lysate," EMBO J. 20(23):6877-6888 (2001).
Elbashir et al., "Analysis of gene function in somatic mammalian cells using small interfering RNAs," Methods, 26:199-213 (2002).
Elbashir et al., "Duplexes of 21-nucleotide RNAs mediate RNA interference in cultured mammalian cells" Nature 411: 494-498 (2001).
Elbashir et al., "Functional anatomy of siRNAs for mediating efficienct RNAi in *Drosophila melanogaster* embryo lysate", The EMBO Journal 20(23): 6877-6888 (2001).
Elbashir et al., "RNA interference is mediated by 21- and 22-nucleotide RNAs" Genes & Development 15: 188-200 (2001).
Emerich et al., "Biocompatability of Poly (DL-Lactide-co-Glycolide) Microshperes Implanted Into the Brain," Cell Transplantation 8:47-58 (1999).
EP Appl. No. 02017601.2, filed Aug. 5, 2002, Klippel et al.
Epa et al., "Downregulation of the p75 Neurotrophin Receptor in Tissue Culture and In Vivo, Using .beta.-Cyclodextrin-Adamantane-Oligonucleotide Conjugates," Antisense and Nucleic Acid Drug Dev. 10:469-478 (2000).
Erbacher et al., Transfection and physical properties of various sacccharide, poly(ethylene glycol), and antibody-derivatized polyethylenimines (PEI), The Journal of Gene Medicine, 1, 210-222 (1999) [sometimes incorrectly cited as pp. 1-18].
European Search Report for EP App. 03 71 6126 mailed Jul. 15, 2005.
European Search Report for EP App. 10 00 8929 mailed Dec. 20, 2010.
Extended European Search Report from European Application No. 14195627.6 dated Jul. 6, 2015.
Falke et al., "Selective gene regulation with designed transcription factors: Implications for therapy," Current Opinion in Molecular Therapeutics, 5(2):161-166 (2003).
Feldstein et al., "Two sequences participating in the autolytic processing of satellite tobacco ringspot virus complementary RNA," Gene 82:53-61 (1989).
Ferentz and Verdine, "Disulfied Cross-Linked Oligonucleotides," J. Am. Chem. Soc. 113:4000-4002 (1991).

Filion and Phillips, "Toxicity and immunomodulatory activity of liposomal vectors formulated with cationic lipids toward immune effector cells," Biochimica et Biophysica Acta 1329:345-356 (1997).
Findeis, "Stepwise Synthesis of a GaINAc-containing Cluster Glycoside Ligand of the Asialoglycoprotein Receptor," Int. J. Peptide Protein Res. 43:477-485 (1994).
Fire et al., "Potent and Specific Genetic Interference by Double-Stranded RNA in Caenorhabditis Elegans," Nature 391 :806-811(1998).
Fire, "RNA-triggered Gene Silencing," TIG 15:358-363(1999).
Forster and Altman, "External Guide Sequences for an RNA Enzyme," Science 249:783-786 (1990).
Fox, "Targeting DNA with Triplexes," Current Medicinal Chemistry 7:17-37 (2000).
Fraser et al., "Functional genomic analysis of C. elegans chromosome I by systematic RNA interference," Nature, 408, 325-330 (2000).
Freier et al., "Improved free-energy parameters for predictions of RNA duplex stability," Proc. Natl. Acad. Sci. USA 83:9373-9377 (1986) [sometimes referred to as Frier].
Freier et al., "The ups and downs of nucleic acid duplex stability: structure-stability studies on chemically-modified DNA:RNA duplexes", Nucl. Acids Res. 25: 4429-4443 (1997).
Furgeson et al., "Modified Linear Polyethylenimine—Cholesterol Conjugates for DNA Complexation," Bioconjugate Chem., 14, 840-847 (2003).
Furuno et al., "Expression polymorphism of the blood-brain barrier component P-glycoprotein (MDR1) in relation to Parkinson's disease," Pharmacogenetics, 12, 7, 529-534 (2002).
Futami et al., "Induction of Apoptosis in HeLa Cells with siRNA Expression Vector Targeted Against bcl-2," Nucleic Acids Research Supplement 2:251-252 (2002).
Gao and Huang, "Cytoplasmic Expression of a Reporter Gene by Co-Delivery of T7 RNA Polymerase and T7 Promoter Sequence with Cationic Liposomes," Nucleic Acids Research 21:2867-2872 (1993).
Ghirnikar et al., "Chemokine inhibition in rat stab would brain injury using antisense oligodeoxynucleotides," Neuroscience Letters 247:21-24 (1998).
Godbey et al., "Poly(ethylenimine) and its role in gene delivery," Journal of Controlled Release, 60, 149-160 (1999).
Godbey et al., "Tracking the intracellular path of poly(ethylenimine)/DNA complexes for gene delivery," Proc. Natl. Acad. Sci. USA, 96, 5177-5181 (1999).
Godwin et al., "The Synthesis of Biologically Active Pteroyloligo-y-L-Giutamates (Folic Acid Conjugates)," The Journal of Biolooical Chemistry 247:2266-2271 (1972).
Gold et al., "Diversity of Oligonucleotide Functions," Annu. Rev. Biochem. 64:763-797 (1995).
Gonczy et al., "Functional genomic analysis of cell division in C. e/egans using RNAi of genes in chromosome III," Nature, 408, 331-336 (2000).
Gonzalez et al., "New Class of Polymers for the Delivery of Macromolecular Therapeutics," Bioconjugate Chem., 10, 1068-1074 (1999).
Good et al., "Expression of small, therapuetic RNAs in human nuclei," Gene Therapy 4:45-54 (1997).
Grasby et al., "Purine Functional Groups in Essential Residues of the Hairpin Ribozyme Required for Catalytic Cleavage of RNA," Biochemistry 34:4068-4076 (1995).
Griffin et al., "Group II intron ribozymes that cleave DNA and RNA linkages with similar efficiency, and lack contacts with substrate 2'-hydroxyl groups," Chemistry & Biology 2:761-770 (1995).
Guerrier-Takada et al., "The RNA Moiety of Ribonuclease P Is the Catalytic Subunit of the Enzyme," Cell 35:849-857 (1983).
Guo and Collins, "Efficient trans-cleavage of a stem-loop RNA substrate by a ribozyme derived from NeurosporaVS RNA," EMBO J. 14:368-376 (1995).
Habus et al., "A Mild and Efficient Solid-Support Synthesis of Novel Oligonucleotide Conjugates," Bioconjugate Chem. 9:283-291 (1998).

(56) References Cited

OTHER PUBLICATIONS

Hamasaki et al., "Short interfering RNA-directed inhibition of hepatitis B virus replication," FEBS Letters, 543:51-54 (2003).
Hamilton, et al., "A Species of Small Antisense RNA in Post-transcriptional Gene Silencing in Plants," Science, 286, 950-952 (1999)).
Hammann et al., "Length Variation of Helix III in a Hammerhead Ribozyme and Its Influence on Cleavage Activity," Antisense & Nucleic Acid Drug Development 9:25-31 (1999).
Hammond et al., "An RNA-Directed Nuclease Mediates Post-Transcriptional Gene Silencing in Drosophila Cells," Nature 404:293-296 (2000).
Hammond et al., "Post-Transcriptional Gene Silencing by Double-Stranded RNA," Nature Reviews Genetics, 2:110-119 (2001).
Hampel and Tritz, "RNA Catalytic Properties of the Minimum (-)sTRSV Sequence," Biochemistry 28:4929-4933 (1989).
Hampel et al., "'Hairpin' Catalytic RNA Model: Evidence for Helices and Sequence Requirement for Substrate RNA," Nucleic Acids Research 18:299-304 (1990).
Harborth et al., "Identification of essential genes in cultured mammalian cells using small interfering RNAs" Journal of Cell Science 114: 4557-4565 (2001).
Harborth et al., "Sequence, Chemical, and Structural Variation of Small Interfering RNAs and Short Hairpin RNAs and the Effect on Mammalian Gene Silencing," Antisense and Nucleic Acid Drug Development, 13:83-105 (2003).
Harris et al., "Identification of phosphates involved in catalysis by the ribozyme RNase P RNA," RNA 1:210-218 (1995).
Hartmann et al., "Spontaneous and Cationic Lipid-Mediated Uptake of Antisense Oligonucleotides in Human Monocytes and Lymphocytes," The Journal of Pharmacology and Experimental Therapeutics 285:920-928 (1998).
Haseloff and Gerlach, "Sequences required for self-catalysed cleavage of the satellite RNA of tobacco ringspot virus," Gene 82:43-52 (1989).
He et al., "MicroRNAs: Small RNAs with a Big Role in Gene Regulation," Nat. Rev. Genet., 5, 522-531 (2004).
Hegg et al., "Kinetics and Thermodynamics of Intermolecular Catalysis by Hairpin Ribozymes," Biochemistry 34:15813-15828 (1995}.
Hermann and Patel, "Adaptive Recognition by Nucleic Acid Aptamers," Science 287:820-825 (2000).
Herrmann et al., "Comparative analysis of adenoviral transgene delivery via tail or portal vein into rat liver," Arch Virol149:1611-1617 (2004).
Hertel et al., "A Kinetic Thermodynamic Framework for the Hammerhead Ribozyme Reaction," Biochemistry 33:3374-3385 (1994).
Hirotsune et al., "An expressed Pseudogene regulates the messenger-RNA stability of its homologous coding gene," Nature, 423, 91-96 (2003).
Hofland and Huang, "Formulation and Delivery of Nucleic Acids," Handbook of Exp. Pharmacol. 137:165-192 (1999).
Hohjoh et al., "RNA interference (RNAi) induction with various types of synthetic oligonucleotides duplexes in cultured human cells," FEBS Letters 521: 195-199 (2002).
Holen et al., "Positional effects of short interfering RNAs targeting the human coagulation trigger Tissue Factor," Nucleic Acids Research, 30:8, 1757-1766 (2002).
Hong et al., "pH-sensivite, serum-stable and long-circulating liposomes as a new drug delivery system," Journal of Pharmacy and Pharmacology, 54:51-58 (2002).
Hornung et al., "Sequence-specific potent induction of IFN-.alpha. by short interfering Rna in plasmacytoid dendritic cells through TLR7," Nature Medicine, 11, 263-270 (2005).
Annex to a Communication in Opposition Proceedings in EP2287305 dated Sep. 26, 2016.
Decision to maintain the European Patent in Amended Form in Opposition in EP2287306 dated Sep. 15, 2016.
Termination of opposition proceedings in EP2287306, European Patent Office, Sep. 9, 2016.

\* cited by examiner

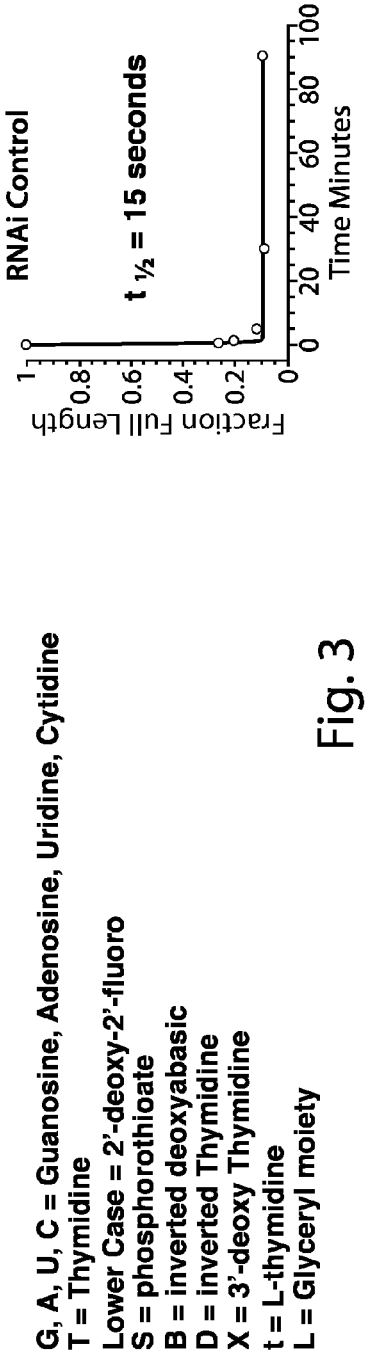

5'-CGUACGCGGGAAUACUUCGATT (SEQ ID NO: 394)
3'-TTGCAUGCGCCCUUAUGAAGCU (SEQ ID NO: 395)
T ½ = 15 seconds (control)

5'-B cAAccAcAAAAuAcAAcAATT B (SEQ ID NO: 396)
3'-TXGuuGGuGuuuuAuGuuGuu (SEQ ID NO: 397)
T ½ = 138 min 5'-B cAAccAcAAAAuAcAAcAATT B (SEQ ID NO: 396)
3'-TDGuuGGuGuuuuAuGuuGuu (SEQ ID NO: 398)
T ½ = 3.7 days 5'-B cAAccAcAAAAuAcAAcAATT B (SEQ ID NO: 396)
3'-XTGuuGGuGuuuuAuGuuGuu (SEQ ID NO: 399)
T ½ = 72 minutes 5'-B cAAccAcAAAAuAcAAcAATT B (SEQ ID NO: 396)
3'-LTGuuGGuGuuuuAuGuuGuu (SEQ ID NO: 400)
T ½ = 40 days 5'-B cAAccAcAAAAuAcAAcAATT B (SEQ ID NO: 396)
3'-tTGuuGGuGuuuuAuGuuGuu (SEQ ID NO: 401)
T ½ = 32 days G, A, U, C = Guanosine, Adenosine, Uridine, Cytidine
T = Thymidine
Lower Case = 2'-deoxy-2'-fluoro
S = phosphorothioate
B = inverted deoxyabasic
D = inverted Thymidine
X = 3'-deoxy Thymidine
t = L-thymidine
L = Glyceryl moiety

Fig. 3

Fig. 18A
{
SENSE STRAND
ALL PYRIMIDINES = 2'-O-ME OR 2'-FLUORO EXCEPT POSITIONS (N N)
5'-    $N_S$ $N_S$ $N_S$ $N_S$ N N N N N N N N N N $NN_S N_S N_S (N_S N)$    -3'
3'- L-$(N_S N)$ N N N N N N N N N N N N N $N_S$ $N_S$ $N_S$ $N_S$ N    -5'
ANTISENSE STRAND
ALL PYRIMIDINES = 2'-FLUORO EXCEPT POSITIONS (N N)
}

Fig. 18B
{
SENSE STRAND
ALL PYRIMIDINES = 2'-O-ME OR 2'-FLUORO EXCEPT POSITIONS (N N)
5'-    N N N N N N N N N N N N N N N N $(N_S N)$    -3'
3'- L-(N N) N N N N N N N N N N N N N N N N N    -5'
ANTISENSE STRAND (SEQ ID NO 474)
ALL PYRIMIDINES = 2'-FLUORO EXCEPT POSITIONS (N N)
}

Fig. 18C
{
SENSE STRAND
ALL PYRIMIDINES = 2'-O-ME OR 2'-FLUORO EXCEPT POSITIONS (N N)
5'-    B- N N N N N N N N N N N N N N N N (N N) -B    -3'
3'- L-$(N_S N)$ N N N N N N N N N N N N N N N N    -5'
ANTISENSE STRAND
ALL PYRIMIDINES = 2'-FLUORO EXCEPT POSITIONS (N N)
}

Fig. 18D
{
SENSE STRAND
ALL PYRIMIDINES = 2'-FLUORO EXCEPT POSITIONS (N N) AND PURINES = 2'-DEOXY
5'-    B- N N N N N N N N N N N N N N N N (N N) -B    -3'
3'- L-$(N_S N)$ N N N N N N N N N N N N N N N N    -5'
ANTISENSE STRAND
ALL PYRIMIDINES = 2'-FLUORO AND ALL PURINES = 2'-O-ME EXCEPT POSITIONS (N N)
}

Fig. 18E
{
SENSE STRAND
ALL PYRIMIDINES = 2'-FLUORO EXCEPT POSITIONS (N N)
5'-    B- N N N N N N N N N N N N N N N N (N N) -B    -3'
3'-L-$(N_S N)$ N N N N N N N N N N N N N N N N    -5'
ANTISENSE STRAND
ALL PYRIMIDINES = 2'-FLUORO AND ALL PURINES = 2'-O-ME EXCEPT POSITIONS (N N)
}

Fig. 18F
{
SENSE STRAND
ALL PYRIMIDINES = 2'-FLUORO EXCEPT POSITIONS (N N) AND PURINES = 2'-DEOXY
5'-    B- N N N N N N N N N N N N N N N N (N N) -B    -3'
3'- L-$(N_S N)$ N N N N N N N N N N N N N N N N    -5'
ANTISENSE STRAND
ALL PYRIMIDINES = 2'-FLUORO EXCEPT POSITIONS (N N) AND ALL PURINES = 2'-DEOXY
}

POSITIONS (NN) CAN COMPRISE ANY NUCLEOTIDE, SUCH AS DEOXYNUCLEOTIDES
(eg. THYMIDINE) OR UNIVERSAL BASES
B = ABASIC, INVERTED ABASIC, INVERTED NUCLEOTIDE OR OTHER TERMINAL CAP
    THAT IS OPTIONALLY PRESENT
L = GLYCERYL MOIETY THAT IS OPTIONALLY PRESENT
S = PHOSPHOROTHIOATE OR PHOSPHOROSITHIOATE

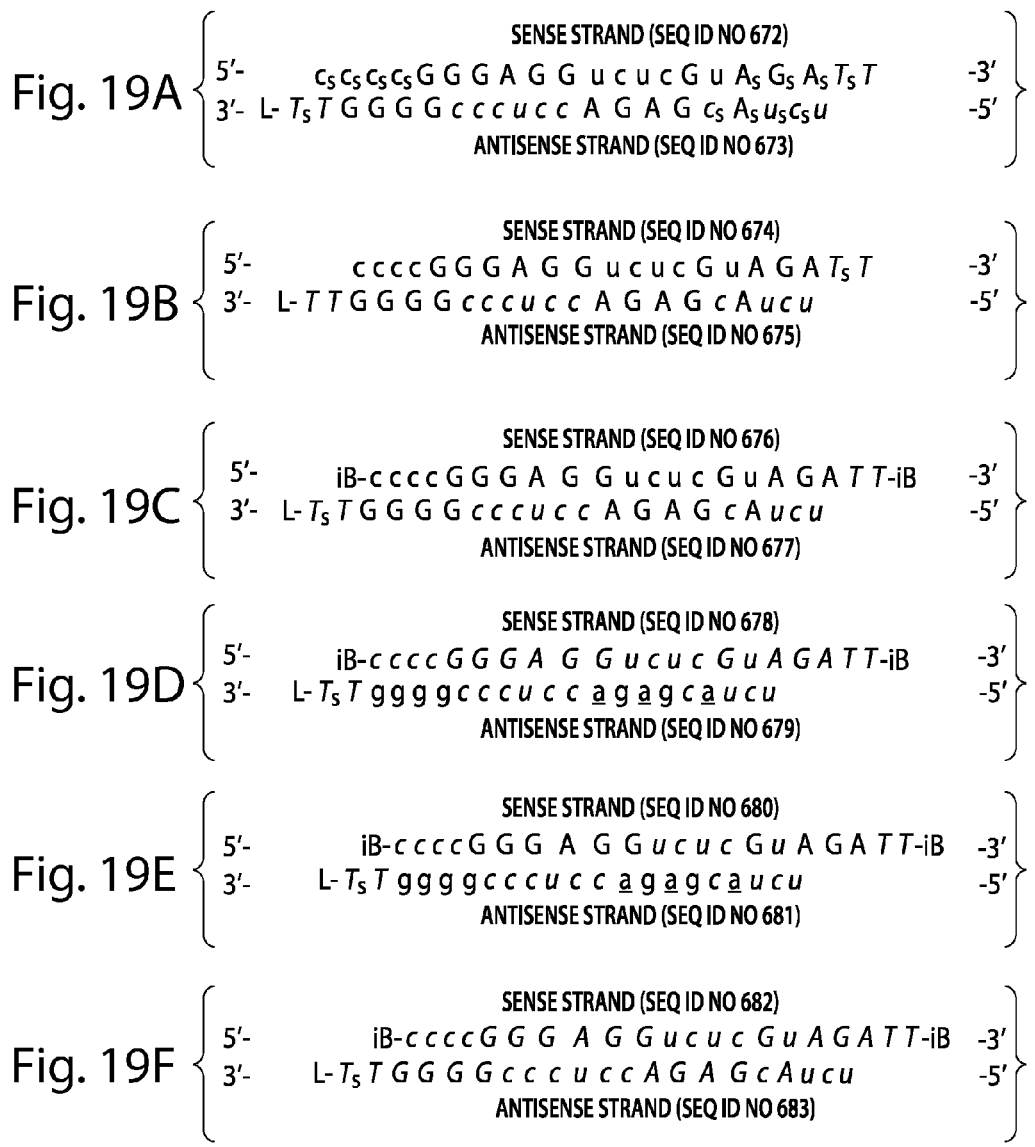

Target site Selection using siRNA

Synthesize oligos encoding siRNA
against Target RNA sequence

⇩

Transfect cells

⇩

Select cells exhibiting desired phenotype

⇩

Identify efficacious target sites
based on siRNA sequence from
Positional analysis

Fig. 34

Chemically Modified siRNAs targeting HCV chimera

Chemically Modified siRNAs targeting HCV chimera

HCV/PV#280-siRNA to HCV-Luc site 325/345

Fig. 37

Conjugation of targeting ligands to the 5'-end of a siNA molecule

N-acetyl-D-galactosamine conjugate

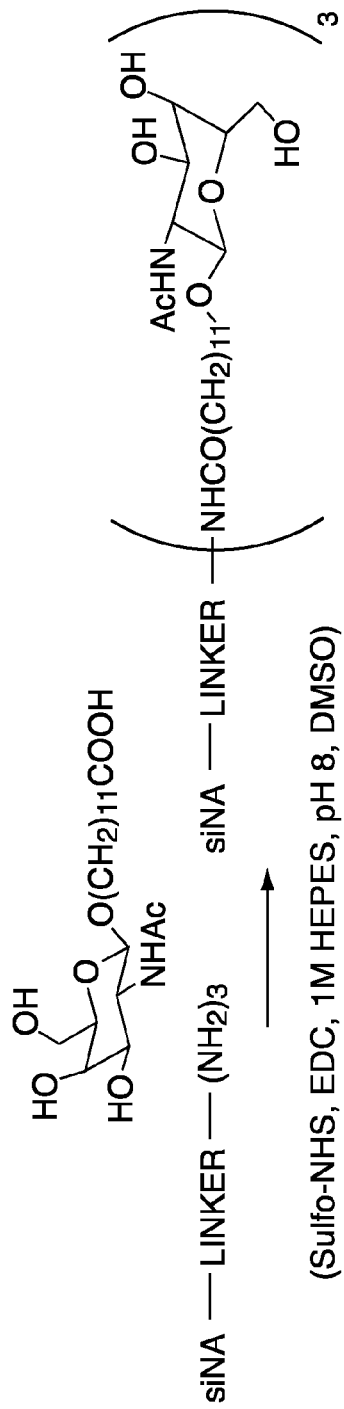
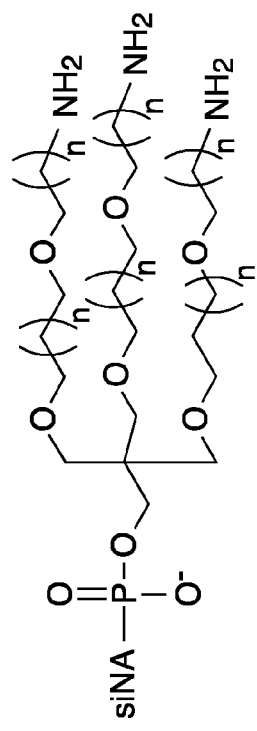
Fig. 53

CL = CLEAVABLE LINKER, E.G. ADENOSINE-THYMIDINE DIMER THAT IS OPTIONALLY PRESENT siNA Lipid Conjugates
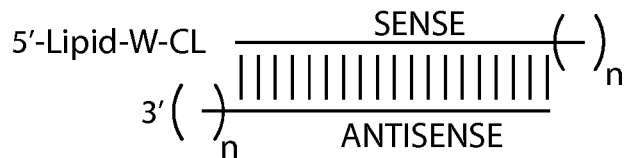
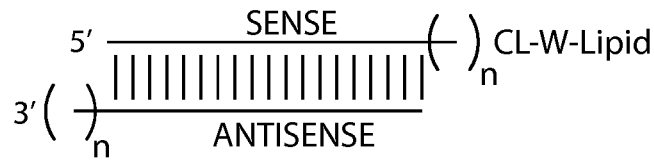
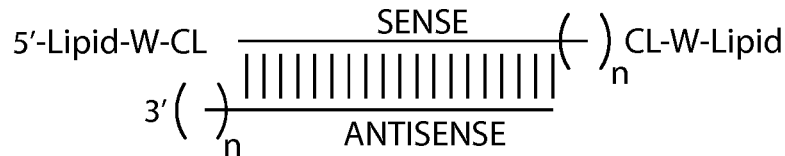
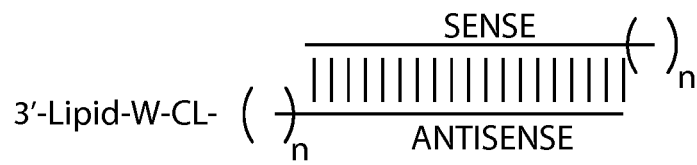
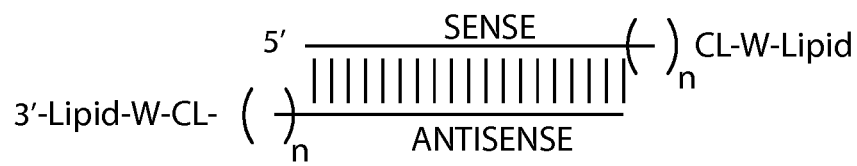
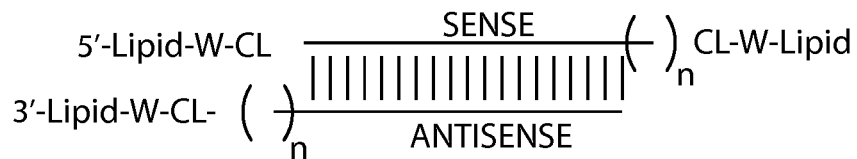
CL=cleavable linker (e.g. A-dT, C-dT) that is optionally present
Lipid=Straight chain or branched alkyl or fatty acid, e.g. $C_{18}H_{37}$
W=linker molecule (see for example Formulae 48, 49, 64, or 65)
n = interger, e.g. 1, 2, or 3
Fig. 61

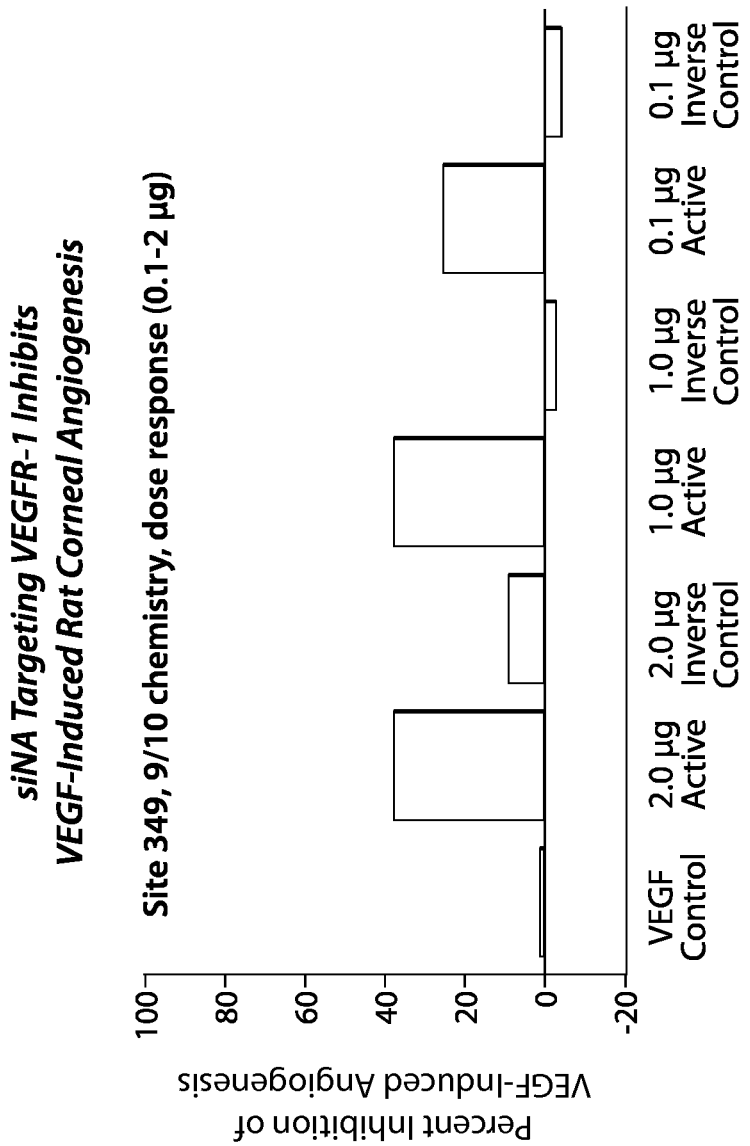

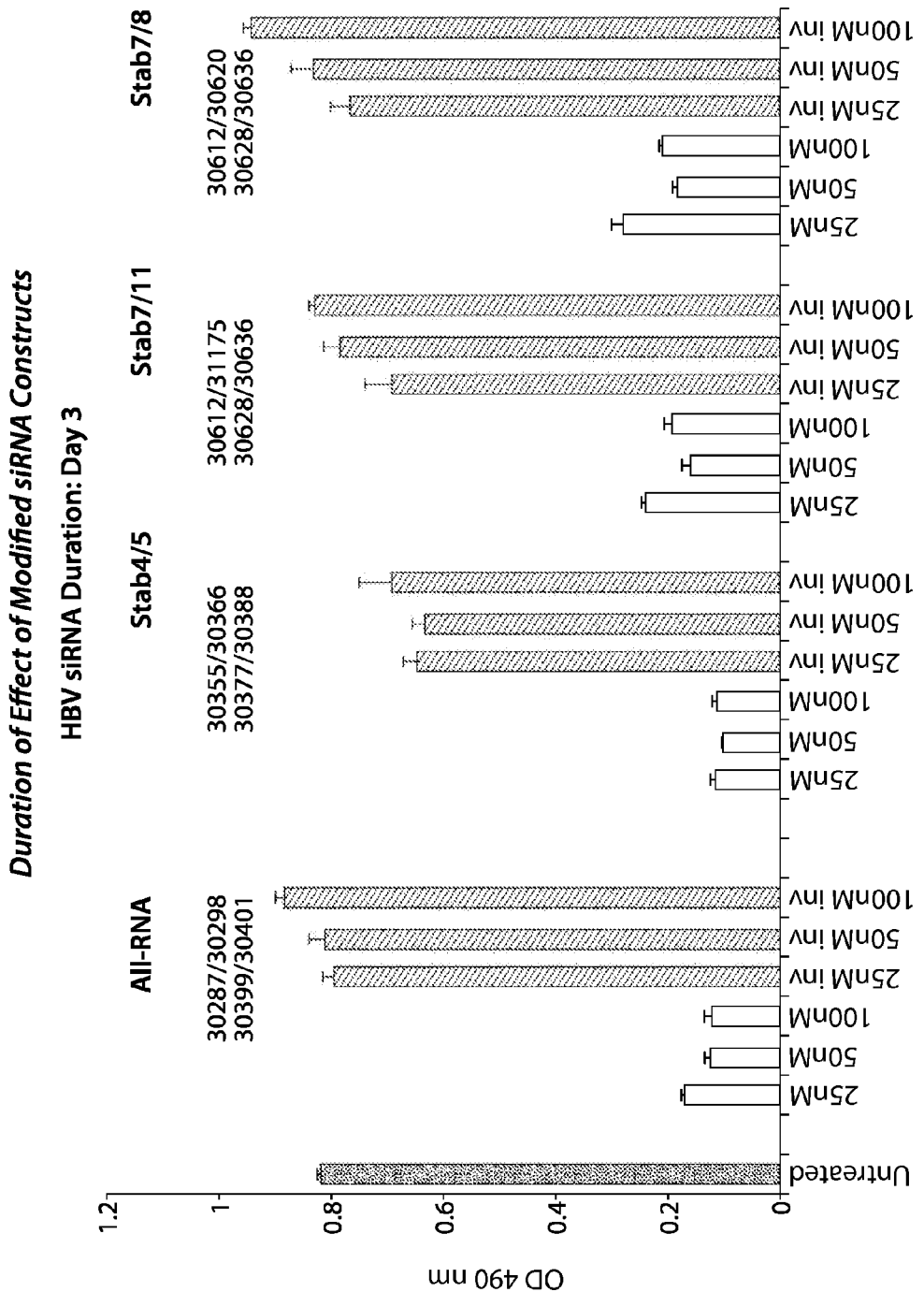

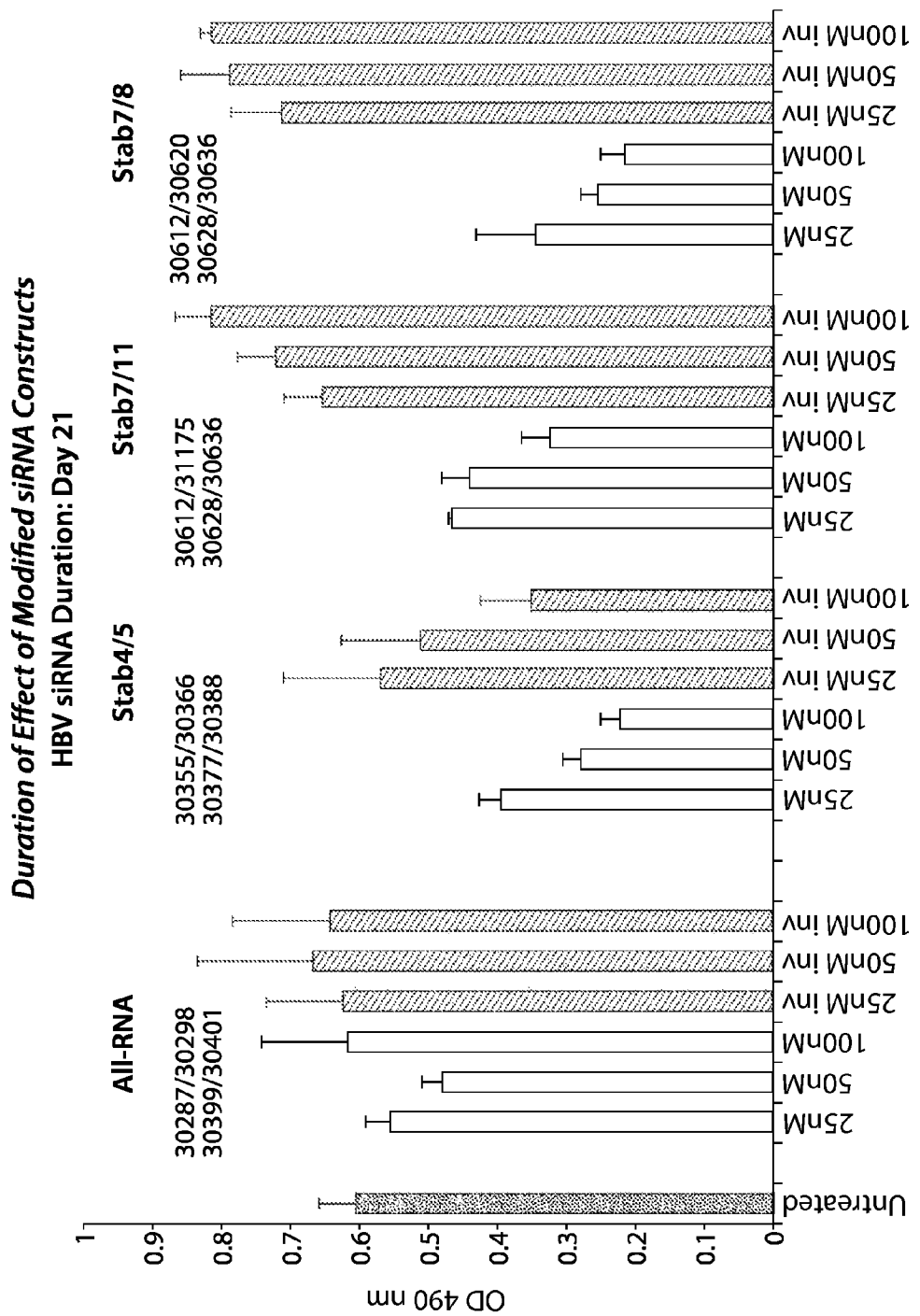

SEQUENCE LISTING

<160> NUMBER OF SEQ ID NOS: 685

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
uaaccucgua cuggugccuc c                                              21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 2
ggaggcacca guacgagguu a                                            21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
aaacuccaag auccccaauc a                                            21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ugauugggga ucuuggaguu u                                            21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
guuggagucu guaggacuug g                                            21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ccaaguccua cagacuccaa c                                            21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gcaaaaaccc ugugauuucc u                                            21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 8
aggaaaucac aggguuuuug c                                        21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
uuggucaguu ucuggcaguu c                                        21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
gaacugccag aaacugacca a                                        21

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gguccuuucu uggaucaacc c                                        21

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ggguugaucc aagaaaggac c                                        21

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
uggacuucuc ucaauuuucu a                                        21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
uagaaaauug agagaagucc a					21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
uuuuucaccu cugccuaauc a					21

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ugauuaggca gaggugaaaa a					21

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
caagccucca agcugugccu u					21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
aaggcacagc uuggaggcuu g					21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
uccauggugc ucacugcggc u					21

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20

```
agccgcagug agcaccaugg a                                          21
```

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21

```
agguaccacg agugacgccg a                                          21
```

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22

```
ucggcgucac ucgugguacc u                                          21
```

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23

```
ccuccguggu caugcuccaa u                                          21
```

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24

```
auuggagcau gaccacggag g                                          21
```

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25

```
cccaacuagg uucuuuccug g                                          21
```

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26

```
ccaggaaaga accuaguugg g                                          21
```

<210> SEQ ID NO 27
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 27
uaaccucgua cuggugccuc cuu                                              23

<210> SEQ ID NO 28
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 28
ggaggcacca guacgagguu auu                                              23

<210> SEQ ID NO 29
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 29
aaacuccaag auccccaauc auu                                              23

<210> SEQ ID NO 30
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 30
uaaccucgua cuggugccuc cuu                                              23

<210> SEQ ID NO 31
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 31
ggaggcacca guacgagguu auu                                              23

<210> SEQ ID NO 32
<211> LENGTH: 23
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 32
aaacuccaag auccccaauc auu                                              23

<210> SEQ ID NO 33
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33 ugauuggga ucuuggaguu uuu                                              23

<210> SEQ ID NO 34
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
guuggagucu guaggacuug guu                                             23

<210> SEQ ID NO 35
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
ccaaguccua cagacuccaa cuu                                             23

<210> SEQ ID NO 36
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
ugauugggga ucuuggaguu uuu                                             23

<210> SEQ ID NO 37
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
guuggagucu guaggacuug guu                                             23

<210> SEQ ID NO 38
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ccaaguccua cagacuccaa cuu                                             23

-continued

```
<210> SEQ ID NO 39
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
gcaaaaaccc ugugauuucc uuu                                              23

<210> SEQ ID NO 40
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
aggaaaucac aggguuuuug cuu                                              23

<210> SEQ ID NO 41
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
uuggucaguu ucuggcaguu cuu                                              23

<210> SEQ ID NO 42
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
gcaaaaaccc ugugauuucc uuu                                              23

<210> SEQ ID NO 43
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
aggaaaucac aggguuuuug cuu                                              23

<210> SEQ ID NO 44
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
uuggucaguu ucuggcaguu cuu                                              23

<210> SEQ ID NO 45
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
gaacugccag aaacugacca auu                                            23

<210> SEQ ID NO 46
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
gguccuuucu uggaucaacc cuu                                            23

<210> SEQ ID NO 47
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
ggguugaucc aagaaaggac cuu                                            23

<210> SEQ ID NO 48
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
gaacugccag aaacugacca auu                                            23

<210> SEQ ID NO 49
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
gguccuuucu uggaucaacc cuu                                            23

<210> SEQ ID NO 50
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
ggguugaucc aagaaaggac cuu                                            23

<210> SEQ ID NO 51
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
uggacuucuc ucaauuuucu auu                                           23

<210> SEQ ID NO 52
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
uagaaaauug agagaagucc auu                                           23

<210> SEQ ID NO 53
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
uuuuucaccu cugccuaauc auu                                           23

<210> SEQ ID NO 54
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
uggacuucuc ucaauuuucu auu                                           23

<210> SEQ ID NO 55
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
uagaaaauug agagaagucc auu                                           23

<210> SEQ ID NO 56
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
uuuuucaccu cugccuaauc auu                                           23

<210> SEQ ID NO 57
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 57
ugauuaggca gaggugaaaa auu                                              23

<210> SEQ ID NO 58
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
caagccucca agcugugccu uuu                                              23

<210> SEQ ID NO 59
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
aaggcacagc uuggaggcuu guu                                              23

<210> SEQ ID NO 60
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
ugauuaggca gaggugaaaa auu                                              23

<210> SEQ ID NO 61
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
caagccucca agcugugccu uuu                                              23

<210> SEQ ID NO 62
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
aaggcacagc uuggaggcuu guu                                              23

<210> SEQ ID NO 63
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 63
uccauggugc ucacugcggc uuu                                                23

<210> SEQ ID NO 64
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
agccgcagug agcaccaugg auu                                                23

<210> SEQ ID NO 65
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
uccauggugc ucacugcggc uuu                                                23

<210> SEQ ID NO 66
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
agccgcagug agcaccaugg auu                                                23

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 67
cguacgcgga auacuucgat t                                                  21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 68
ucgaaguauu ccgcguacgt t                                                  21
```

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 69
agcuucauaa ggcgcaugct t                                              21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 70
gcaugcgccu uaugaagcut t                                              21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 71
cguacgcgga auacuucgat t                                              21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 72
cguacgcgga auacuucgat t                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 73
cguacgcgga auacuucgat t                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 74
cguacgcgga auacuucgat t                                         21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 75
cguacgcgga auacuucgat t                                         21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 76
ucgaaguauu ccgcguacgt t                                         21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 77
ucgaaguauu ccgcguacgt t                                         21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 78
ucgaaguauu ccgcguacgt t                                                   21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 79
ucgaaguauu ccgcguacgt t                                                   21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 80
ucgaaguauu ccgcguacgt t                                                   21

<210> SEQ ID NO 81
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81 cguacg                                                                     6

<210> SEQ ID NO 82
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 82
cggaauacuu cgatt                                                          15

<210> SEQ ID NO 83
<211> LENGTH: 8
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83 ucgaagua                                                                   8

<210> SEQ ID NO 84
<211> LENGTH: 13

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 84
uuccgcguac gtt                                                         13

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 85
cguacgcgga auacuucgat t                                                21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 86
ucgaaguauu ccgcguacgt t                                                21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 87
ucgaaguauu ccgcguacgt t                                                21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 88 ugggguccguc aaagacguut t                                               21

<210> SEQ ID NO 89
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 89
aacgucuuug acgaccccat t                                           21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 90
uugcagaaac ugcuggggut t                                           21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 91
accccagcag uuucugcaat t                                           21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 92
ggugcuugga ucuggcgcut t                                           21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 93
agcgccagau ccaagcacct t                                           21
```

```
<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 94
ucgcggucua gguucguggt t                                                  21

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 95
ccacgaaccu agaccgcgat t                                                  21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 96
gaucuuuggg agccuggcat t                                                  21

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 97
ugccaggcuc ccaaagauct t                                                  21

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 98
acgguccgag gguuucuagt t                                                  21
```

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 99
cuagaaaccc ucggaccgut t                                              21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 100
agcuucauaa ggcgcaugct t                                              21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 101
agcuucauaa ggcgcaugct t                                              21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 102
gcaugcgccu uaugaagcut t                                              21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 103
gcaugcgccu uaugaagcut t                                              21

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 104
gcaugcgccu uaugaagcut t                                              21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 105
gcaugcgccu uaugaagcut t                                              21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 106
gcaugcgccu uaugaagcut t                                              21

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 107
cagcacagac ccagcugugt t                                              21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 108
cacagcuggg ucugugcugt t                                              21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 109
gugucgaccc agacacgact t                                              21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 110
gucgugucug ggucgacact t                                              21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 111
gcaggcugga gguaaggcct t                                              21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 112
ggccuuaccu ccagccugct t                                              21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 113

```
ccggaaugga ggucggacgt t                                              21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 114
cguccgaccu ccauuccggt t                                              21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 115
gacuucuccu ccauugcggt t                                              21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 116
ccgcaaugga ggagaaguct t                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 117
ggcguuaccu ccucuucagt t                                              21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 118
cugaagagga gguaacgcct t                                              21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 119
cacugccgag cucaagauct t                                              21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 120
gaucuugagc ucggcagugt t                                              21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 121
cuagaacucg agccgucact t                                              21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 122
gugacggcuc gaguucuagt t                                              21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 123
ggaguuccuc augugcaagt t                                              21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 124
cuugcacaug aggaacucct t                                              21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 125
gaacguguac uccuugaggt t                                              21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 126
ccucaaggag uacacguuct t                                              21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 127
ucaagagcuc cgagaugcct t                                              21

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 128
ggcaucucgg agcucuugat t          21

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 129
ccguagagcc ucgagaacut t          21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 130
aguucucgag gcucuacggt t          21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 131
gcagauggcu gaggacaagt t          21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 132
cuuguccuca gccaucugct t          21

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 133
gaacaggagu cgguagacgt t                                              21

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 134
cgucuaccga cuccuguuct t                                              21

<210> SEQ ID NO 135
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
aacguacgcg gaauacuucg auuaaaagua aucgaaguau uccgcguacg uu            52

<210> SEQ ID NO 136
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
cguacgcgga auacuucgau uaaaaguaau cgaaguauuc cgcguacguu               50

<210> SEQ ID NO 137
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
aacguacgcg gaauacuucg auuaaagaau cgaaguauuc cgcguacguu               50

<210> SEQ ID NO 138
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
cguacgcgga auacuucgau uaaagaaucg aaguauuccg cguacguu                 48

<210> SEQ ID NO 139
<211> LENGTH: 47
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 139
cguacgcgga auacuucgau uguuaaucga aguauccgc guacguu                  47

<210> SEQ ID NO 140
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
aacguacgcg gaauacuucg auuguuaauc gaaguauucc gcguacguu               49

<210> SEQ ID NO 141
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
aacguacgcg gaauacuucg auuaguuuaa ucgaaguauu ccgcguacgu u            51

<210> SEQ ID NO 142
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
cguacgcgga auacuucgau uaguuuaauc gaaguauucc gcguacguu               49

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 143
ccccgggagg ucucguagat t                                             21

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 144
cggaaccggu gaguacacct t                                             21
```

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 145
gccccgggag gucucguagt t                                              21

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 146
ggaaccggug aguacaccgt t                                              21

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 147
gugguacugc cugauagggt t                                              21

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 148
ugugguacug ccugauaggt t                                              21

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 149
uugugguacu gccugauagt t                                              21

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 150
ucuacgagac cuccegggggt t                                             21

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 151
gguguacuca ccgguuccgt t                                              21

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 152
cuacgagacc ucccggggct t                                              21

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 153
cgguguacuc accgguucct t                                              21

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 154
cccuaucagg caguaccact t                                                21

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 155
ccuaucaggc aguaccacat t                                                21

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 156
cuaucaggca guaccacaat t                                                21

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 157
ttagaugcuc uggagggccc c                                                21

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 158
ttccacauga guggccaagg c                                                21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 159
ttgaugcucu ggagggcccc g                                              21

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 160
ttgccacaug aguggccaag g                                              21

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 161
ttgggauagu ccgucauggu g                                              21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 162
ttggauaguc cgucauggug u                                              21

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 163
ttgauagucc gucauggugu u                                              21

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 164
ttggggcccu ccagagcauc u                                              21

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 165
ttgccuuggc cacucaugug g                                              21

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 166
ttcggggccc uccagagcau c                                              21

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 167
ttccuuggcc acucaugugg c                                              21

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 168
ttcaccauga cggacuaucc c                                              21

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 169
ttacaccaug acggacuauc c         21

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 170
ttaacaccau gacggacuau c         21

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 171
agcuucauaa ggcgcaugct t         21

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 172
gcaugcgccu uaugaagcut t         21

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 173
cguacgcgga auacuucgat t         21

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 174
ucgaaguauu ccgcguacgt t                                              21

<210> SEQ ID NO 175
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 175
cguacgcgga auacuucgat tucgaaguau uccgcguacg tt                        42

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 176
gucuagacuc gugguggact t                                              21

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 177
ccugcugcua ugccucauct t                                              21

<210> SEQ ID NO 178
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 178
caagccucca agcugugcct t                                              21

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 179
agcugugccu uggguggcut t                                              21

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 180
guccaccacg agucuagact t                                              21

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 181
gaugaggcau agcagcaggt t                                              21

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 182
ggcacagcuu ggaggcuugt t                                              21

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 183
agccacccaa ggcacagcut t                                              21

<210> SEQ ID NO 184
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 184 caggguggugc ucagaucugt t                                              21

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 185
cuacuccgua ucgucgucct t                                               21

<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 186
ccgugucgaa ccuccgaact t                                               21

<210> SEQ ID NO 187
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 187
ucgguggguu ccgugucgat t                                               21

<210> SEQ ID NO 188
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 188
cagaucugag caccaccugt t                                               21

<210> SEQ ID NO 189
<211> LENGTH: 21
<212> TYPE: DNA
<213> ORGANISM: Artificial Sequence
<220> FEATURE:

```
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 189
ggacgacgau acggaguagt t                                             21

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 190
guucggaggu ucgacacggt t                                             21

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 191
ucgacacgga acccaccgat t                                             21

<210> SEQ ID NO 192
<211> LENGTH: 21
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 192
cggaaccggu gaguacaccg g                                             21

<210> SEQ ID NO 193
<211> LENGTH: 21
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 193
ggaaccggug aguacaccgg a                                             21

<210> SEQ ID NO 194
<211> LENGTH: 21
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 194
```
uugugguacu gccugauagg g         21

<210> SEQ ID NO 195
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
ugugguacug ccugauaggg u         21

<210> SEQ ID NO 196
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
gugguacugc cugauagggu g         21

<210> SEQ ID NO 197
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
gccccgggag gucucguaga c         21

<210> SEQ ID NO 198
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
ccccgggagg ucucguagac c         21

<210> SEQ ID NO 199
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
gguguacuca ccgguuccgc a         21

<210> SEQ ID NO 200
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
cgguguacuc accgguuccg c         21

<210> SEQ ID NO 201
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
cuaucaggca guaccacaag g                                              21

<210> SEQ ID NO 202
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
ccuaucaggc aguaccacaa g                                              21

<210> SEQ ID NO 203
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
cccuaucagg caguaccaca a                                              21

<210> SEQ ID NO 204
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
cuacgagacc ucccggggca c                                              21

<210> SEQ ID NO 205
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
ucuacgagac cucccggggc a                                              21

<210> SEQ ID NO 206
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
ggccacauga guggccaagg c                                              21

<210> SEQ ID NO 207
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
aggccacaug aguggccaag g                                              21

<210> SEQ ID NO 208
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
gggauagucc gucauggugu u                                              21

<210> SEQ ID NO 209
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
ugggauaguc cgucauggug u                                              21

<210> SEQ ID NO 210
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
gugggauagu ccgucauggu g                                              21

<210> SEQ ID NO 211
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
cagaugcucu ggagggcccc g                                              21

<210> SEQ ID NO 212
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
ccagaugcuc uggagggccc c                                              21

```
<210> SEQ ID NO 213
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
acgccuuggc cacucaugug g                                              21

<210> SEQ ID NO 214
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
cgccuuggcc acucaugugg c                                              21

<210> SEQ ID NO 215
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
ggaacaccau gacggacuau c                                              21

<210> SEQ ID NO 216
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
gaacaccaug acggacuauc c                                              21

<210> SEQ ID NO 217
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
aacaccauga cggacuaucc c                                              21

<210> SEQ ID NO 218
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
cacggggccc uccagagcau c                                              21

<210> SEQ ID NO 219
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
acggggcccu ccagagcauc u                                            21

<210> SEQ ID NO 220
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
cagaugcaca uaucgaggug a                                            21

<210> SEQ ID NO 221
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
cagaugcaca uaucgaggug g                                            21

<210> SEQ ID NO 222
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 222
cagaugcaca uaucgaggut t                                            21

<210> SEQ ID NO 223
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
accucgauau gugcaucugu a                                            21

<210> SEQ ID NO 224
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 224
```

-continued

```
accucgauau gugcaucugt t                                              21

<210> SEQ ID NO 225
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
uacuucgaaa uguccguucg g                                              21

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 226
uacuucgaaa uguccguuct t                                              21

<210> SEQ ID NO 227
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
gaacggacau uucgaaguau u                                              21

<210> SEQ ID NO 228
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
gaacggacau uucgaaguac u                                              21

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 229
gaacggacau uucgaaguat t                                              21

<210> SEQ ID NO 230
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 230
acuucgaaau guccguucgg u                                              21

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 231
acuucgaaau guccguucgt t                                              21

<210> SEQ ID NO 232
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
cgaacggaca uuucgaagua u                                              21

<210> SEQ ID NO 233
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
cgaacggaca uuucgaagua c                                              21

<210> SEQ ID NO 234
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 234
cgaacggaca uuucgaagut t                                              21

<210> SEQ ID NO 235
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
agauucucgc augccagaga u                                              21
```

<210> SEQ ID NO 236
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 236
agauucucgc augccagagt t                                          21

<210> SEQ ID NO 237
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
cucuggcaug cgagaaucug a                                          21

<210> SEQ ID NO 238
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
cucuggcaug cgagaaucuc a                                          21

<210> SEQ ID NO 239
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 239
cucuggcaug cgagaaucut t                                          21

<210> SEQ ID NO 240
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
gauucucgca ugccagagau c                                          21

<210> SEQ ID NO 241
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 241
gauucucgca ugccagagat t                                              21

<210> SEQ ID NO 242
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
ucucuggcau gcgagaaucu g                                              21

<210> SEQ ID NO 243
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
ucucuggcau gcgagaaucu c                                              21

<210> SEQ ID NO 244
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 244
ucucuggcau gcgagaauct t                                              21

<210> SEQ ID NO 245
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
uucuucgcca aaagcacucu g                                              21

<210> SEQ ID NO 246
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 246
uucuucgcca aaagcacuct t                                              21
```

<210> SEQ ID NO 247
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
gagugcuuuu ggcgaagaau g                                              21

<210> SEQ ID NO 248
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
gagugcuuuu ggcgaagaag g                                              21

<210> SEQ ID NO 249
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 249
gagugcuuuu ggcgaagaat t                                              21

<210> SEQ ID NO 250
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
caaggauaug ggcucacuga g                                              21

<210> SEQ ID NO 251
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 251
caaggauaug ggcucacugt t                                              21

<210> SEQ ID NO 252
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 252
cagugagccc auauccuugu c                                              21

<210> SEQ ID NO 253
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
cagugagccc auauccuugc c                                              21

<210> SEQ ID NO 254
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 254
cagugagccc auauccuugt t                                              21

<210> SEQ ID NO 255
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
aaacgcuggg cguuaaucag a                                              21

<210> SEQ ID NO 256
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
aaacgcuggg cguuaaucaa a                                              21

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 257
aaacgcuggg cguuaaucat t                                              21

<210> SEQ ID NO 258
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
ugauuaacgc ccagcguuuu c                                              21

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 259
ugauuaacgc ccagcguuut t                                              21

<210> SEQ ID NO 260
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
aagacgaaca cuucuucaua g                                              21

<210> SEQ ID NO 261
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
aagacgaaca cuucuucauc g                                              21

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 262
aagacgaaca cuucuucaut t                                              21

<210> SEQ ID NO 263
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
```

```
augaagaagu guucgucuuc g                                      21
```

<210> SEQ ID NO 264
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 264

```
augaagaagu guucgucuut t                                      21
```

<210> SEQ ID NO 265
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265

```
aagagaucgu ggauuacgug g                                      21
```

<210> SEQ ID NO 266
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266

```
aagagaucgu ggauuacguc g                                      21
```

<210> SEQ ID NO 267
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 267

```
aagagaucgu ggauuacgut t                                      21
```

<210> SEQ ID NO 268
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268

```
acguaaucca cgaucucuuu u                                      21
```

<210> SEQ ID NO 269
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 269
acguaaucca cgaucucuut t                                              21

<210> SEQ ID NO 270
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
aggccaagaa gggcggaaag u                                              21

<210> SEQ ID NO 271
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
aggccaagaa gggcggaaag a                                              21

<210> SEQ ID NO 272
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 272
aggccaagaa gggcggaaat t                                              21

<210> SEQ ID NO 273
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
uuuccgcccu ucuuggccuu u                                              21

<210> SEQ ID NO 274
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 274
uuuccgcccu ucuuggccut t                                        21

<210> SEQ ID NO 275
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
ggccaagaag ggcggaaagu c                                        21

<210> SEQ ID NO 276
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
ggccaagaag ggcggaaaga u                                        21

<210> SEQ ID NO 277
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 277
ggccaagaag ggcggaaagt t                                        21

<210> SEQ ID NO 278
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
cuuuccgccc uucuuggccu u                                        21

<210> SEQ ID NO 279
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 279
cuuuccgccc uucuuggcct t                                        21

<210> SEQ ID NO 280
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 280
ucgaaguauu ccgcguacgu t                                             21

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 281
cguacgcgga auacuucgau t                                             21

<210> SEQ ID NO 282
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 282
cguacgcgga auacuucgau t                                             21

<210> SEQ ID NO 283
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 283
ucgaaguauu ccgcguacgu t                                             21

<210> SEQ ID NO 284
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 284
cguacgcgga auacuucgat t                                             21

<210> SEQ ID NO 285
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 285
cguacgcgga auacuucgat t                                                    21

<210> SEQ ID NO 286
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 286
cguacgcgga auacuucgat t                                                    21

<210> SEQ ID NO 287
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 287
ucgaaguauu ccgcguacgt t                                                    21

<210> SEQ ID NO 288
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 288
ucgaaguauu ccgcguacgt t                                                    21

<210> SEQ ID NO 289
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 289
ucgaaguauu ccgcguacgt t                                                    21

<210> SEQ ID NO 290
<211> LENGTH: 42
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 290
ucgaaguauu ccgcguacgt tcguacgcgg aauacuucga tt                     42

<210> SEQ ID NO 291
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291 cguacg                                                              6

<210> SEQ ID NO 292
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 292
cggaauacuu cgatt                                                   15

<210> SEQ ID NO 293
<211> LENGTH: 8
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293 ucgaagua                                                            8

<210> SEQ ID NO 294
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 294
uuccgcguac gtt                                                     13

<210> SEQ ID NO 295
<211> LENGTH: 8
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 295 ucgaagua                                                                  8

<210> SEQ ID NO 296
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 296
uuccgcguac gtt                                                           13

<210> SEQ ID NO 297
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 297
cugaguuuaa aaggcaccct t                                                  21

<210> SEQ ID NO 298
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 298
caaccacaaa auacaacaat t                                                  21

<210> SEQ ID NO 299
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 299
ccuggaaaga aucaaaacct t                                                  21

<210> SEQ ID NO 300
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 300
gcaaggaggg ccucugaugt t          21

<210> SEQ ID NO 301
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 301
gggugccuuu uaaacucagt t          21

<210> SEQ ID NO 302
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 302
uuguuguauu uugugguugt t          21

<210> SEQ ID NO 303
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 303
gguuuugauu cuuuccaggt t          21

<210> SEQ ID NO 304
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 304
caucagaggc ccuccuugct t          21

<210> SEQ ID NO 305
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 305
gggugccuuu uaaacucagt t                                              21

<210> SEQ ID NO 306
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 306
uuguuguauu uugugguugt t                                              21

<210> SEQ ID NO 307
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 307
gguuuugauu cuuuccaggt t                                              21

<210> SEQ ID NO 308
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 308
caucagaggc ccuccuugct t                                              21

<210> SEQ ID NO 309
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
ggcauuggcc aacguacgcg gaauacuucg auucgguuac gaa                      43

<210> SEQ ID NO 310
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
cguacgcgga auacuucgau u                                              21

<210> SEQ ID NO 311
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 311
cguacgcgga auacuucgat t                                              21

<210> SEQ ID NO 312
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 312
cguacgcgga auacuucgat t                                              21

<210> SEQ ID NO 313
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 313
cguacgcgga auacuucgat t                                              21

<210> SEQ ID NO 314
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
ucgaaguauu ccgcguacgu u                                              21

<210> SEQ ID NO 315
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
ucgaaguauu ccgcguacgu u                                              21

<210> SEQ ID NO 316
<211> LENGTH: 21
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 316
ucgaaguauu ccgcguacgt t                                              21

<210> SEQ ID NO 317
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 317
ucgaaguauu ccgcguacgt t                                              21

<210> SEQ ID NO 318
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 318
ucgaaguauu ccgcguacgt t                                              21

<210> SEQ ID NO 319
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 319
cguacgcgga auacuucgat t                                              21

<210> SEQ ID NO 320
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
cguacgcgga auacuucgau u                                              21

<210> SEQ ID NO 321
<211> LENGTH: 21
<212> TYPE: DNA
<213> ORGANISM: Artificial Sequence
<220> FEATURE:
```

<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 321
cguacgcgga auacuucgat t                                              21

<210> SEQ ID NO 322
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 322
ucgaaguauu ccgcguacgt t                                              21

<210> SEQ ID NO 323
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide
<220> FEATURE:
<221> NAME/KEY: modified_base
<222> LOCATION: (20)..(21)
<223> OTHER INFORMATION: 5-nitroindole universal base

<400> SEQUENCE: 323
cguacgcgga auacuucgan n                                              21

<210> SEQ ID NO 324
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide
<220> FEATURE:
<221> NAME/KEY: modified_base
<222> LOCATION: (20)..(21)
<223> OTHER INFORMATION: 3-nitropyrrole universal base

<400> SEQUENCE: 324
cguacgcgga auacuucgan n                                              21

<210> SEQ ID NO 325
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide
<220> FEATURE:
<221> NAME/KEY: modified_base
<222> LOCATION: (20)..(21)
<223> OTHER INFORMATION: 5-nitroindole universal base

<400> SEQUENCE: 325
ucgaaguauu ccgcguacgn n                                              21

<210> SEQ ID NO 326
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 5-nitroindole universal base

<400> SEQUENCE: 326
ucgaaguauu ccgcguacgn n                                              21

<210> SEQ ID NO 327
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327 cguacg                                                                6

<210> SEQ ID NO 328
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 328
cggaauacuu cgatt                                                     15

<210> SEQ ID NO 329
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 329
cguacgcgga auacuucgat t                                              21

<210> SEQ ID NO 330
<211> LENGTH: 8
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 330 ucgaagua                                                                    8

<210> SEQ ID NO 331
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 331
uuccgcguac gtt                                                             13

<210> SEQ ID NO 332
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 332
ucgaaguauu ccgcguacgt t                                                    21

<210> SEQ ID NO 333
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333 cguacg                                                                      6

<210> SEQ ID NO 334
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 334
cggaauacuu cgatt                                                           15

<210> SEQ ID NO 335
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

<400> SEQUENCE: 335
cguacgcgga auacuucgat t                                              21

<210> SEQ ID NO 336
<211> LENGTH: 8
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336 ucgaagua                                                              8

<210> SEQ ID NO 337
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 337
uuccgcguac gtt                                                       13

<210> SEQ ID NO 338
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 338
ucgaaguauu ccgcguacgt t                                              21

<210> SEQ ID NO 339
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 339
agcuucauaa ggcgcaugct t                                              21

<210> SEQ ID NO 340
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 340

```
gcaugcgccu uaugaagcut t                                           21
```

<210> SEQ ID NO 341
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 341

```
agcuucauaa ggcgcaugct t                                           21
```

<210> SEQ ID NO 342
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 342

```
gcaugcgccu uaugaagcut t                                           21
```

<210> SEQ ID NO 343
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 343

```
cguacgcgga auacuucgat t                                           21
```

<210> SEQ ID NO 344
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 344

```
ucgaaguauu ccgcguacgt t                                           21
```

<210> SEQ ID NO 345
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 345
cugaguuuaa aaggcaccct t          21

<210> SEQ ID NO 346
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 346
caaccacaaa auacaacaat t          21

<210> SEQ ID NO 347
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 347
ccuggaaaga aucaaaacct t          21

<210> SEQ ID NO 348
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 348
gcaaggaggg ccucugaugt t          21

<210> SEQ ID NO 349
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 349
cguacgcgga auacuucgat t          21

<210> SEQ ID NO 350
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 350
ucgaaguauu ccgcguacgt t                                           21

<210> SEQ ID NO 351
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 351
cguacgcgga auacuucgau t                                           21

<210> SEQ ID NO 352
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 352
ucgaaguauu ccgcguacgu t                                           21

<210> SEQ ID NO 353
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 5-nitroindole universal base

<400> SEQUENCE: 353
ccccgggagg ucucguagan n                                           21

<210> SEQ ID NO 354
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 5-nitroindole universal base

<400> SEQUENCE: 354
agaugcucug gagggccccn n                                           21

<210> SEQ ID NO 355
<211> LENGTH: 21

-continued

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 5-nitroindole universal base

<400> SEQUENCE: 355
ucuacgagac cucccggggn n                                              21

<210> SEQ ID NO 356
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 5-nitroindole universal base

<400> SEQUENCE: 356
ggggcccucc agagcaucun n                                              21

<210> SEQ ID NO 357
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 5-nitroindole universal base

<400> SEQUENCE: 357
ccccgggagg ucucguagan n                                              21

<210> SEQ ID NO 358
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 5-nitroindole universal base

<400> SEQUENCE: 358
agaugcucug gagggcccn n                                               21

<210> SEQ ID NO 359
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 5-nitroindole universal base

<400> SEQUENCE: 359
ucuacgagac cucccggggn n                                              21

<210> SEQ ID NO 360
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 5-nitroindole universal base

<400> SEQUENCE: 360
ggggcccucc agagcaucun n                                              21

<210> SEQ ID NO 361
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 5-nitroindole universal base

<400> SEQUENCE: 361
ccccgggagg ucucguagan n                                              21

<210> SEQ ID NO 362
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 5-nitroindole universal base

<400> SEQUENCE: 362
agaugcucug gagggccccn n                                              21
```

```
<210> SEQ ID NO 363
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 5-nitroindole universal base

<400> SEQUENCE: 363
ccccgggagg ucucguagan n                                              21

<210> SEQ ID NO 364
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 5-nitroindole universal base

<400> SEQUENCE: 364
agaugcucug gagggccccn n                                              21

<210> SEQ ID NO 365
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 5-nitroindole universal base

<400> SEQUENCE: 365
ucuacgagac cucccggggn n                                              21

<210> SEQ ID NO 366
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
ucuacgagac cucccgggg                                                 19

<210> SEQ ID NO 367
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 367
ggggcccucc agagcaucu                                                19

<210> SEQ ID NO 368
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 5-nitroindole universal base

<400> SEQUENCE: 368
ucuacgagac cucccggggn n                                             21

<210> SEQ ID NO 369
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 5-nitroindole universal base

<400> SEQUENCE: 369
ggggcccucc agagcaucun n                                             21

<210> SEQ ID NO 370
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 5-nitroindole universal base

<400> SEQUENCE: 370
ucuacgagac cucccggggn n                                             21

<210> SEQ ID NO 371
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (20)..(21)
<223> OTHER INFORMATION: 5-nitroindole universal base

<400> SEQUENCE: 371
ccccgggagg ucucguagan n                                              21

<210> SEQ ID NO 372
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 372
cguacgcgga auacuucgat t                                              21

<210> SEQ ID NO 373
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 373
cguacgcgga auacuucgat t                                              21

<210> SEQ ID NO 374
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 374
ucgaaguauu ccgcguacgt t                                              21

<210> SEQ ID NO 375
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 375
ucgaaguauu ccgcguacgt t                                              21

<210> SEQ ID NO 376
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 376
cguacgcgga auacuucgat t                                                    21

<210> SEQ ID NO 377
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 377
cguacgcgga auacuucgat t                                                    21

<210> SEQ ID NO 378
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 378
ucgaaguauu ccgcguacgt t                                                    21

<210> SEQ ID NO 379
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 379
ucgaaguauu ccgcguacgt                                                      20

<210> SEQ ID NO 380
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 380
ucgaaguauu ccgcguacgt t                                                    21

<210> SEQ ID NO 381
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
                         oligonucleotide
<220> FEATURE:
<223> OTHER INFORMATION: Description of Combined DNA/RNA Molecule:
      Synthetic oligonucleotide

<400> SEQUENCE: 381
agcuucauaa ggcgcaugct t                                              21

<210> SEQ ID NO 382
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 382
agcuucauaa ggcgcaugct t                                              21

<210> SEQ ID NO 383
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 383
gcaugcgccu uaugaagcut t                                              21

<210> SEQ ID NO 384
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 384
cguacgcgga auacuucgat t                                              21

<210> SEQ ID NO 385
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 385
cguacgcgga auacuucgat t                                              21

<210> SEQ ID NO 386
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 386
ucgaaguauu ccgcguacgt                                                   20

<210> SEQ ID NO 387
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 387
ucgaaguauu ccgcguacgt c                                                 21

<210> SEQ ID NO 388
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 388
ucgaaguauu ccgcguacgt                                                   20

<210> SEQ ID NO 389
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 389
ucgaaguauu ccgcguacgt t                                                 21

<210> SEQ ID NO 390
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 390
taugugcacu ucgcuucacc utt                                               23

<210> SEQ ID NO 391
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 391
aggugaagcg aagugcacat t                                              21

<210> SEQ ID NO 392
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 392
taugugcacu ucgcuucacc utt                                            23

<210> SEQ ID NO 393
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 393
augugcacuu cgcuucaccu tt                                             22

<210> SEQ ID NO 394
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 394
cguacgcgga auacuucgat t                                              21

<210> SEQ ID NO 395
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 395
ucgaaguauu ccgcguacgt t                                              21

<210> SEQ ID NO 396
<211> LENGTH: 21
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 396
caaccacaaa auacaacaat t                                              21

<210> SEQ ID NO 397
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 397
uuguuguauu uugugguugt t                                              21

<210> SEQ ID NO 398
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 398
uuguuguauu uugugguugt t                                              21

<210> SEQ ID NO 399
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 399
uuguuguauu uugugguugt t                                              21

<210> SEQ ID NO 400
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 400
uuguuguauu uugugguugt                                                20

<210> SEQ ID NO 401
<211> LENGTH: 21
```

<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 401
uuguuguauu uugugguugt t                                          21

<210> SEQ ID NO 402

<400> SEQUENCE: 402

000

<210> SEQ ID NO 403

<400> SEQUENCE: 403

000

<210> SEQ ID NO 404

<400> SEQUENCE: 404

000

<210> SEQ ID NO 405

<400> SEQUENCE: 405

000

<210> SEQ ID NO 406

<400> SEQUENCE: 406

000

<210> SEQ ID NO 407

<400> SEQUENCE: 407

000

<210> SEQ ID NO 408

<400> SEQUENCE: 408

000

<210> SEQ ID NO 409

<400> SEQUENCE: 409

000

<210> SEQ ID NO 410

<400> SEQUENCE: 410

000

<210> SEQ ID NO 411

```
<400> SEQUENCE: 411

000

<210> SEQ ID NO 412
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 412
cguacgcgga auacuucgat t                                            21

<210> SEQ ID NO 413
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 413
ucgaaguauu ccgcguacgt t                                            21

<210> SEQ ID NO 414
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 414
uuguuguauu ugugguugt t                                             21

<210> SEQ ID NO 415
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 415
uuguuguauu ugugguugt t                                             21

<210> SEQ ID NO 416
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 416
uuguuguauu uugugguugt t                                              21

<210> SEQ ID NO 417
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 417
uuguuguauu uugugguugt t                                              21

<210> SEQ ID NO 418
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 418
uuguuguauu uugugguugt t                                              21

<210> SEQ ID NO 419
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 419
caaccacaaa auacaacaat t                                              21

<210> SEQ ID NO 420
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 420
uuguuguauu uugugguugt t                                              21

<210> SEQ ID NO 421
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 421
gaugaggcau agcagcaggt t                                              21

<210> SEQ ID NO 422
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 422
ccugcugcua ugccucauct t                                              21

<210> SEQ ID NO 423
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 423
ggacgacgau acggaguagt t                                              21

<210> SEQ ID NO 424
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 424
cuacuccgua ucgucgucct t                                              21

<210> SEQ ID NO 425
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
uggacuucuc ucaauuuucu a                                              21

<210> SEQ ID NO 426
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 426
gaaaauugag agaaguccat t					21

<210> SEQ ID NO 427
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
aucuuuuaac ucucuucagg u					21

<210> SEQ ID NO 428
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 428
accugaagag aguuaaaagt t					21

<210> SEQ ID NO 429
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
ugugucugcg gcguuuuauc a					21

<210> SEQ ID NO 430
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 430
auaaaacgcc gcagacacat t					21

<210> SEQ ID NO 431
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
acuauuuugc ggcgucugug u					21

<210> SEQ ID NO 432
<211> LENGTH: 21
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 432
acacagacgc cgcaaaauat t                                             21

<210> SEQ ID NO 433
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
uccugcugcu augccucauc u                                             21

<210> SEQ ID NO 434
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 434
augaggcaua gcagcaggat t                                             21

<210> SEQ ID NO 435
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
ucuacuccgu aucgucgucc u                                             21

<210> SEQ ID NO 436
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 436
aggacgacga uacggaguat t                                             21

<210> SEQ ID NO 437
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 437
uauguugccc guuuguccuc u                                             21

<210> SEQ ID NO 438
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 438
aggacaaacg ggcaacauat t                                             21

<210> SEQ ID NO 439
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 439
ucuccuguuu gcccguugua u                                             21

<210> SEQ ID NO 440
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 440
auacaacggg caaacaggat t                                             21

<210> SEQ ID NO 441
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 441
ugugcacuuc gcuucaccuc u                                             21

<210> SEQ ID NO 442
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 442
aggugaagcg aagugcacat t                                             21
```

```
<210> SEQ ID NO 443
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 443
ucuccacuuc gcuucacgug u                                                   21

<210> SEQ ID NO 444
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 444
acacgugaag cgaaguggat t                                                   21

<210> SEQ ID NO 445
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
cuucgcuuca ccucugcacg u                                                   21

<210> SEQ ID NO 446
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 446
gugcagaggu gaagcgaagt t                                                   21

<210> SEQ ID NO 447
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 447
ugcacgucuc cacuucgcuu c                                                   21

<210> SEQ ID NO 448
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide

<400> SEQUENCE: 448
gaagcgaagu ggagacgugt t                                             21

<210> SEQ ID NO 449
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
aggcuguagg cauaaauugg u                                             21

<210> SEQ ID NO 450
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 450
caauuuaugc cuacagccut t                                             21

<210> SEQ ID NO 451
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
ugguuaaaua cggaugucgg a                                             21

<210> SEQ ID NO 452
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 452
uccgacaucc guauuuaact t                                             21

<210> SEQ ID NO 453
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 453
```
ugugcacuuc gcuucaccut t                                              21

<210> SEQ ID NO 454
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 454
aggugaagcg aagugcacat t                                              21

<210> SEQ ID NO 455
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 455
ucuccacuuc gcuucacgut t                                              21

<210> SEQ ID NO 456
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 456
gcacacguga agcgaagugt t                                              21

<210> SEQ ID NO 457
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 457
ugugcacuuc gcuucaccut t                                              21

<210> SEQ ID NO 458
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 458

```
aggugaagcg aagugcacat t                                              21

<210> SEQ ID NO 459
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 459
ugugcacuuc gcuucaccut t                                              21

<210> SEQ ID NO 460
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 460
gcacacguga agcgaagugt t                                              21

<210> SEQ ID NO 461
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461
ugugcacuuc gcuucaccuc u                                              21

<210> SEQ ID NO 462
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 462
aggugaagcg aagugcacac g                                              21

<210> SEQ ID NO 463
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 463
ugugcacuuc gcuucaccuc u                                              21

<210> SEQ ID NO 464
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 464
aggugaagcg aagugcacat t                                              21

<210> SEQ ID NO 465
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 465
ugugcacuuc gcuucaccut t                                              21

<210> SEQ ID NO 466
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 466
aggugaagcg aagugcacat t                                              21

<210> SEQ ID NO 467
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 467
ugugcacuuc gcuucaccut t                                              21

<210> SEQ ID NO 468
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 468
aggugaagcg aagugcacat t                                              21

<210> SEQ ID NO 469
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 469
ugugcacuuc gcuucaccut t                                                21

<210> SEQ ID NO 470
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 470
aggugaagcg aagugcacat t                                                21

<210> SEQ ID NO 471
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 471
cuugugguac ugccugauat t                                                21

<210> SEQ ID NO 472
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 472
uaucaggcag uaccacaagt t                                                21

<210> SEQ ID NO 473
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 473
auaguccguc augguguuct t                                                21

<210> SEQ ID NO 474
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 474
gaacaccaug acggacuaut t                                              21

<210> SEQ ID NO 475
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 475
cugccugaua gggugcuugt t                                              21

<210> SEQ ID NO 476
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 476
caagcacccu aucaggcagt t                                              21

<210> SEQ ID NO 477
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 477
guucguggga uaguccguct t                                              21

<210> SEQ ID NO 478
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 478
gacggacuau cccacgaact t                                              21

<210> SEQ ID NO 479
```

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 479
ccugauaggg ugcuugcgat t                                              21

<210> SEQ ID NO 480
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 480
ucgcaagcac ccuaucaggt t                                              21

<210> SEQ ID NO 481
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 481
agcguucgug ggauagucct t                                              21

<210> SEQ ID NO 482
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 482
ggacuauccc acgaacgcut t                                              21

<210> SEQ ID NO 483
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 483
ccccgggagg ucucguagat t                                              21
```

-continued

```
<210> SEQ ID NO 484
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 484
ucuacgagac cucccggggt t                                              21

<210> SEQ ID NO 485
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 485
agaugcucug gagggcccct t                                              21

<210> SEQ ID NO 486
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 486
ggggcccucc agagcaucut t                                              21

<210> SEQ ID NO 487
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 487
cccgggaggu cucguagact t                                              21

<210> SEQ ID NO 488
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 488
gucuacgaga ccucccgggt t                                              21
```

<210> SEQ ID NO 489
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 489
cagaugcucu ggagggccct t                                              21

<210> SEQ ID NO 490
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 490
gggcccucca gagcaucugt t                                              21

<210> SEQ ID NO 491
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 491
ccgggagguc ucguagacct t                                              21

<210> SEQ ID NO 492
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 492
ggucuacgag accucccggt t                                              21

<210> SEQ ID NO 493
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 493
ccagaugcuc uggagggcct t                                              21

<210> SEQ ID NO 494
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 494
ggcccuccag agcaucuggt t                                          21

<210> SEQ ID NO 495
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 495
cgggaggucu cguagaccgt t                                          21

<210> SEQ ID NO 496
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 496
cggucuacga gaccucccgt t                                          21

<210> SEQ ID NO 497
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 497
gccagaugcu cuggagggct t                                          21

<210> SEQ ID NO 498
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 498
gcccuccaga gcaucuggct t                            21

<210> SEQ ID NO 499
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 499
gggaggucuc guagaccgut t                            21

<210> SEQ ID NO 500
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 500
acggucuacg agaccuccct t                            21

<210> SEQ ID NO 501
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 501
ugccagaugc ucuggagggt t                            21

<210> SEQ ID NO 502
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 502
cccuccagag caucuggcat t                            21

<210> SEQ ID NO 503
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 503

```
ccgggagguc ucguagacct t                                              21

<210> SEQ ID NO 504
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 504
ggucuacgag accucccggt t                                              21

<210> SEQ ID NO 505
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 505
ccagaugcuc uggagggcct t                                              21

<210> SEQ ID NO 506
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 506
ggcccuccag agcaucuggt t                                              21

<210> SEQ ID NO 507
<211> LENGTH: 16
<212> TYPE: PRT
<213> ORGANISM: Drosophila sp.

<400> SEQUENCE: 507

Arg Gln Ile Lys Ile Trp Phe Gln Asn Arg Arg Met Lys Trp Lys Lys
1               5                   10                  15

<210> SEQ ID NO 508
<211> LENGTH: 26
<212> TYPE: PRT
<213> ORGANISM: Unknown
<220> FEATURE:
<223> OTHER INFORMATION: Description of Unknown: Conjugating peptide
      derived from Kaposi fibroblast growth factor

<400> SEQUENCE: 508

Ala Ala Val Ala Leu Leu Pro Ala Val Leu Leu Ala Leu Leu Ala Pro
1               5                   10                  15

Val Gln Arg Lys Arg Gln Lys Leu Met Pro
            20                  25
```

<210> SEQ ID NO 509
<211> LENGTH: 17
<212> TYPE: PRT
<213> ORGANISM: Caiman crocodilus

<400> SEQUENCE: 509

Met Gly Leu Gly Leu His Leu Leu Val Leu Ala Ala Ala Leu Gln Gly
1               5                   10                  15

Ala

<210> SEQ ID NO 510
<211> LENGTH: 23
<212> TYPE: PRT
<213> ORGANISM: Human immunodeficiency virus

<400> SEQUENCE: 510

Gly Ala Leu Phe Leu Gly Phe Leu Gly Ala Ala Gly Ser Thr Met Gly
1               5                   10                  15

Ala Pro Lys Ser Lys Arg Lys
            20

<210> SEQ ID NO 511
<211> LENGTH: 9
<212> TYPE: PRT
<213> ORGANISM: Human immunodeficiency virus

<400> SEQUENCE: 511

Arg Lys Lys Arg Arg Gln Arg Arg Arg
1               5

<210> SEQ ID NO 512
<211> LENGTH: 24
<212> TYPE: PRT
<213> ORGANISM: Unknown
<220> FEATURE:
<223> OTHER INFORMATION: Description of Unknown: Conjugating peptide
      derived from Influenza hemagglutinin envelope glycoprotein

<400> SEQUENCE: 512

Gly Leu Phe Glu Ala Ile Ala Gly Phe Ile Glu Asn Gly Trp Glu Gly
1               5                   10                  15

Met Ile Asp Gly Gly Gly Tyr Cys
            20

<210> SEQ ID NO 513
<211> LENGTH: 5
<212> TYPE: PRT
<213> ORGANISM: Unknown
<220> FEATURE:
<223> OTHER INFORMATION: Description of Unknown: Conjugating peptide
      derived from RGD peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 513

Xaa Arg Gly Asp Xaa
1               5

<210> SEQ ID NO 514

```
<211> LENGTH: 27
<212> TYPE: PRT
<213> ORGANISM: Unknown
<220> FEATURE:
<223> OTHER INFORMATION: Description of Unknown: Conjugating peptide
      derived from transportan A

<400> SEQUENCE: 514

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 515
<211> LENGTH: 9
<212> TYPE: PRT
<213> ORGANISM: Unknown
<220> FEATURE:
<223> OTHER INFORMATION: Description of Unknown: Conjugating peptide
      derived from Somatostatin (tyr-3-octreotate)
<220> FEATURE:
<221> NAME/KEY: misc_feature
<222> LOCATION: (1)..(1)
<223> OTHER INFORMATION: May or may not be present
<220> FEATURE:
<221> NAME/KEY: MOD_RES
<222> LOCATION: (2)..(2)
<223> OTHER INFORMATION: D- or L- configured amino acid
<220> FEATURE:
<221> NAME/KEY: MOD_RES
<222> LOCATION: (5)..(5)
<223> OTHER INFORMATION: D- or L- configured amino acid

<400> SEQUENCE: 515

Ser Phe Cys Tyr Trp Lys Thr Cys Thr
1               5

<210> SEQ ID NO 516
<211> LENGTH: 9
<212> TYPE: PRT
<213> ORGANISM: Unknown
<220> FEATURE:
<223> OTHER INFORMATION: Description of Unknown: Conjugating peptide
      derived from Pre-S-peptide
<220> FEATURE:
<221> NAME/KEY: misc_feature
<222> LOCATION: (1)..(1)
<223> OTHER INFORMATION: May or may not be present

<400> SEQUENCE: 516

Ser Asp His Gln Leu Asn Pro Ala Phe
1               5

<210> SEQ ID NO 517

<400> SEQUENCE: 517

000

<210> SEQ ID NO 518

<400> SEQUENCE: 518

000

<210> SEQ ID NO 519

<400> SEQUENCE: 519

000
```

```
<210> SEQ ID NO 520

<400> SEQUENCE: 520

000

<210> SEQ ID NO 521
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: a, c, t, g, unknown or other

<400> SEQUENCE: 521
nnnnnnnnnn nnnnnnnnnn n                                              21

<210> SEQ ID NO 522
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: a, c, t, g, unknown or other

<400> SEQUENCE: 522
nnnnnnnnnn nnnnnnnnnn n                                              21

<210> SEQ ID NO 523
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: a, c, t, g, unknown or other

<400> SEQUENCE: 523
nnnnnnnnnn nnnnnnnnnn n                                              21

<210> SEQ ID NO 524
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: a, c, t, g, unknown or other

<400> SEQUENCE: 524
nnnnnnnnnn nnnnnnnnnn n                                              21

<210> SEQ ID NO 525
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: a, c, t, g, unknown or other

<400> SEQUENCE: 525
nnnnnnnnnn nnnnnnnnnn n                                              21

<210> SEQ ID NO 526
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: a, c, t, g, unknown or other

<400> SEQUENCE: 526
nnnnnnnnnn nnnnnnnnnn n                                              21

<210> SEQ ID NO 527
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: a, c, t, g, unknown or other

<400> SEQUENCE: 527
nnnnnnnnnn nnnnnnnnnn n                                              21

<210> SEQ ID NO 528
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: a, c, t, g, unknown or other

<400> SEQUENCE: 528
nnnnnnnnnn nnnnnnnnnn n                                              21

<210> SEQ ID NO 529
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: a, c, t, g, unknown or other

<400> SEQUENCE: 529
```
nnnnnnnnnn nnnnnnnnnn n                                          21

<210> SEQ ID NO 530
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: a, c, t, g, unknown or other

<400> SEQUENCE: 530
nnnnnnnnnn nnnnnnnnnn n                                          21

<210> SEQ ID NO 531

<400> SEQUENCE: 531

000

<210> SEQ ID NO 532
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 532
ccccgggagg ucucguagat t                                          21

<210> SEQ ID NO 533
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 533
ucuacgagac cucccggggt t                                          21

<210> SEQ ID NO 534
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 534
ccccgggagg ucucguagat t                                          21

<210> SEQ ID NO 535
<211> LENGTH: 21
<212> TYPE: DNA

-continued

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 535
ucuacgagac cucccggggt t                                           21

<210> SEQ ID NO 536
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 536
ccccgggagg ucucguagat t                                           21

<210> SEQ ID NO 537
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 537
ucuacgagac cucccggggt t                                           21

<210> SEQ ID NO 538
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 538
ccccgggagg ucucguagat t                                           21

<210> SEQ ID NO 539
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 539
ucuacgagac cucccggggt t                                           21

<210> SEQ ID NO 540
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 540
ccccgggagg ucucguagat t                                          21

<210> SEQ ID NO 541
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 541
ucuacgagac cucccggggt t                                          21

<210> SEQ ID NO 542
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 542
ucuacgagac cucccggggt t                                          21

<210> SEQ ID NO 543
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 543
ccccgggagg ucucguagac cgu                                        23

<210> SEQ ID NO 544
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 544
ucucguagac cuuggucuac gagaccuccc ggtt                            34

<210> SEQ ID NO 545
<211> LENGTH: 32
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 545
ucguagaccu uggucuacga gaccucccgg tt                                     32

<210> SEQ ID NO 546
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 546
guagaccuug gucuacgaga ccucccggtt                                        30

<210> SEQ ID NO 547
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 547
agaccuuggu cuacgagacc ucccggtt                                          28

<210> SEQ ID NO 548
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 548
ggucuacgag accucccggu uccgggaggu cu                                     32

<210> SEQ ID NO 549
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 549
ggucuacgag accucccggu uccgggaggu                                        30

<210> SEQ ID NO 550
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 550
```
ggucuacgag accucccggu uccgggag        28

<210> SEQ ID NO 551
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 551
ggucuacgag accucccggu uccggg        26

<210> SEQ ID NO 552
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 552
cucguagacc gaaaggucua cgagaccucc cggtt        35

<210> SEQ ID NO 553
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 553
cguagaccga aaggucuacg agaccucccg gtt        33

<210> SEQ ID NO 554
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 554
uagaccgaaa ggucuacgag accucccggt t        31

<210> SEQ ID NO 555
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 555
gaccgaaagg ucuacgagac cucccggtt        29

<210> SEQ ID NO 556
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 556
ggucuacgag accucccggu ugaaaccggg agguc                                35

<210> SEQ ID NO 557
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 557
ggucuacgag accucccggu ugaaaccggg agg                                  33

<210> SEQ ID NO 558
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 558
ggucuacgag accucccggu ugaaaccggg a                                    31

<210> SEQ ID NO 559
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 559
ggucuacgag accucccggu ugaaaccgg                                       29

<210> SEQ ID NO 560
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 560
cguagaccuu uuuguguagg gucuacgaga ccucccggtt                           40

<210> SEQ ID NO 561
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 561
uagaccuuuu uguguagggu cuacgagacc ucccggtt                38

<210> SEQ ID NO 562
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 562
gaccuuuuug uguagggucu acgagaccuc ccggtt                  36

<210> SEQ ID NO 563
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 563
ccuuuuugug uagggucuac gagaccuccc ggtt                    34

<210> SEQ ID NO 564
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 564
ggucuacgag accucccggu uuuuguguag ccgggagguc              40

<210> SEQ ID NO 565
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 565
ggucuacgag accucccggu uuuuguguag ccgggagg                38

<210> SEQ ID NO 566
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 566
ggucuacgag accucccggu uuuuguguag ccggga                  36

<210> SEQ ID NO 567

```
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 567
ggucuacgag accucccggu uuuuguguag ccgg                                    34

<210> SEQ ID NO 568
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 568
ucucguagac cuuggucuac gagaccuccc ggtt                                    34

<210> SEQ ID NO 569
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 569
ucguagaccu uggucuacga gaccucccgg tt                                      32

<210> SEQ ID NO 570
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 570
guagaccuug gucuacgaga ccucccggtt                                         30

<210> SEQ ID NO 571
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 571
agaccuuggu cuacgagacc ucccggtt                                           28

<210> SEQ ID NO 572
<211> LENGTH: 32
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 572
ggucuacgag accucccggu uccgggaggu cu                                    32

<210> SEQ ID NO 573
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 573
ggucuacgag accucccggu uccgggaggu                                       30

<210> SEQ ID NO 574
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 574
ggucuacgag accucccggu uccgggag                                         28

<210> SEQ ID NO 575
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 575
ggucuacgag accucccggu uccggg                                           26

<210> SEQ ID NO 576
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 576
cucguagacc gaaaggucua cgagaccucc cggtt                                 35

<210> SEQ ID NO 577
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 577
cguagaccga aaggucuacg agaccucccg gtt                                   33
```

<210> SEQ ID NO 578
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 578
uagaccgaaa ggucuacgag accucccggt t                                31

<210> SEQ ID NO 579
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 579
gaccgaaagg ucuacgagac cucccggtt                                   29

<210> SEQ ID NO 580
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 580
ggucuacgag accucccggu ugaaaccggg agguc                            35

<210> SEQ ID NO 581
<211> LENGTH: 33
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 581
ggucuacgag accucccggu ugaaaccggg agg                              33

<210> SEQ ID NO 582
<211> LENGTH: 31
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 582
ggucuacgag accucccggu ugaaaccggg a                                31

<210> SEQ ID NO 583
<211> LENGTH: 29
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 583
ggucuacgag accucccggu ugaaaccgg                                          29

<210> SEQ ID NO 584
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 584
cguagaccuu uuuguguagg gucuacgaga ccucccggtt                              40

<210> SEQ ID NO 585
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 585
uagaccuuuu uguguagggu cuacgagacc ucccggtt                                38

<210> SEQ ID NO 586
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 586
gaccuuuuug uguagggucu acgagaccuc ccggtt                                  36

<210> SEQ ID NO 587
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 587
ccuuuuugug uagggucuac gagaccuccc ggtt                                    34

<210> SEQ ID NO 588
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 588
ggucuacgag accucccggu uuuuguguag ccgggagguc                    40

<210> SEQ ID NO 589
<211> LENGTH: 38
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 589
ggucuacgag accucccggu uuuuguguag ccgggagg                      38

<210> SEQ ID NO 590
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 590
ggucuacgag accucccggu uuuuguguag ccggga                        36

<210> SEQ ID NO 591
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 591
ggucuacgag accucccggu uuuuguguag ccgg                          34

<210> SEQ ID NO 592
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 592
acggucuacg agaccucccg gtt                                      23

<210> SEQ ID NO 593
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 593
cggucuacga gaccucccgg tt                                       22

<210> SEQ ID NO 594
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 594
ggucuacgag accucccggt t                                              21

<210> SEQ ID NO 595
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 595
gucuacgaga ccucccggtt                                                20

<210> SEQ ID NO 596
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 596
ucuacgagac cucccggtt                                                 19

<210> SEQ ID NO 597
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 597
cuacgagacc ucccggtt                                                  18

<210> SEQ ID NO 598
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 598
uacgagaccu cccggtt                                                   17

<210> SEQ ID NO 599
<211> LENGTH: 16
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 599
acgagaccuc ccggtt                                                       16

<210> SEQ ID NO 600
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 600
cgagaccucc cggtt                                                        15

<210> SEQ ID NO 601
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 601
ggucuacgag accucccggg g                                                 21

<210> SEQ ID NO 602
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 602
ggucuacgag accucccggg                                                   20

<210> SEQ ID NO 603
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 603
ggucuacgag accucccggt                                                   20

<210> SEQ ID NO 604
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 604
ggucuacgag accucccgg                                                        19

<210> SEQ ID NO 605
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 605
ggucuacgag accucccg                                                         18

<210> SEQ ID NO 606
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 606
ggucuacgag accuccc                                                          17

<210> SEQ ID NO 607
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 607
ggucuacgag accucc                                                           16

<210> SEQ ID NO 608
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 608
ggucuacgag accuc                                                            15

<210> SEQ ID NO 609
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 609
ccgggagguc ucguagacct t                                                     21

<210> SEQ ID NO 610
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 610
ccgggagguc ucguagaccg t                                           21

<210> SEQ ID NO 611
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 611
cgggaggucu cguagacctt                                             20

<210> SEQ ID NO 612
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 612
gggaggucuc guagacctt                                              19

<210> SEQ ID NO 613
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 613
ggaggucucg uagacctt                                               18

<210> SEQ ID NO 614
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 614
gaggucucgu agacctt                                                17

<210> SEQ ID NO 615
<211> LENGTH: 16
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 615
aggucucgua gacctt                                                       16

<210> SEQ ID NO 616
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 616
ccgggagguc ucguagacct                                                   20

<210> SEQ ID NO 617
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 617
ccgggagguc ucguagacc                                                    19

<210> SEQ ID NO 618
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 618
ccgggagguc ucguagac                                                     18

<210> SEQ ID NO 619
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 619
ccgggagguc ucguaga                                                      17

<210> SEQ ID NO 620
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 620
ccgggagguc ucguag                                                       16
```

<210> SEQ ID NO 621
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 621
cugaguuuaa aaggcaccct t                                              21

<210> SEQ ID NO 622
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 622
gggugccuuu uaaacucagt t                                              21

<210> SEQ ID NO 623
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 623
cccacggaaa auuugaguct t                                              21

<210> SEQ ID NO 624
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 624
gacucaaauu uuccgugggt t                                              21

<210> SEQ ID NO 625
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 625
aggugaagcg aagugcacau u                                              21

<210> SEQ ID NO 626

<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 626
ugugcacuuc gcuucaccuc u                                              21

<210> SEQ ID NO 627
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 627
uccacuucgc uucacgugut t                                              21

<210> SEQ ID NO 628

<400> SEQUENCE: 628

000

<210> SEQ ID NO 629
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 629
acacgugaag cgaaguggat t                                              21

<210> SEQ ID NO 630
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 630
auaaggcuau gaagagauat t                                              21

<210> SEQ ID NO 631
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 631
uaucucuuca uagccuuaut t                                              21

<210> SEQ ID NO 632
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 632
cguaugcagu gaaaacucut t                                              21

<210> SEQ ID NO 633
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 633
agaguuuuca cugcauacgt t                                              21

<210> SEQ ID NO 634
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 634
ugacggaaaa agagaucgut t                                              21

<210> SEQ ID NO 635
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 635
acgaucucuu uuuccgucat t                                              21

<210> SEQ ID NO 636
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 636
gaguuguguu uuggacgat t                                                    21

<210> SEQ ID NO 637
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 637
ucguccacaa acacaacuct t                                                   21

<210> SEQ ID NO 638
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 638
gagagauccu cauaaaggct t                                                   21

<210> SEQ ID NO 639
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 639
gccuuuauga ggaucucuct t                                                   21

<210> SEQ ID NO 640
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 640
gcgaaaggcc uuguggguact t                                                  21

<210> SEQ ID NO 641
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

<400> SEQUENCE: 641
guaccacaag gccuuucgct t                                              21

<210> SEQ ID NO 642
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 642
cgaaaggccu ugugguacut t                                              21

<210> SEQ ID NO 643
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 643
aguaccacaa ggccuuucgt t                                              21

<210> SEQ ID NO 644
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 644
gccuuguggu acugccugat t                                              21

<210> SEQ ID NO 645
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 645
ucaggcagua ccacaaggct t                                              21

<210> SEQ ID NO 646
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 646
cugauagggu gcuugcgagt t                                          21

<210> SEQ ID NO 647
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 647
ggcaguacca caaggccuut t                                          21

<210> SEQ ID NO 648
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 648
ugauagggug cuugcgagut t                                          21

<210> SEQ ID NO 649
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 649
acucgcaagc acccuaucat t                                          21

<210> SEQ ID NO 650
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 650
auagggugcu ugcgagugct t                                          21

<210> SEQ ID NO 651
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 651
gcacucgcaa gcacccuaut t                                            21

<210> SEQ ID NO 652
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 652
ugcgagugcc ccgggaggut t                                            21

<210> SEQ ID NO 653
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 653
aagcacccua ucaggcagut t                                            21

<210> SEQ ID NO 654
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 654
gugguggacu ucucucaaut t                                            21

<210> SEQ ID NO 655
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 655
auugagagaa guccaccact t                                            21

<210> SEQ ID NO 656
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 656
gguggacuuc ucucaauuut t                                              21

<210> SEQ ID NO 657
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 657
aaauugagag aaguccacct t                                              21

<210> SEQ ID NO 658
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 658
ggacuucucu caauuuucut t                                              21

<210> SEQ ID NO 659
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 659
agaaaauuga gagaagucct t                                              21

<210> SEQ ID NO 660
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 660
gcacuucgcu ucaccucugt t                                              21

<210> SEQ ID NO 661
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<223> OTHER INFORMATION: Description of Combined DNA/RNA Molecule:
      Synthetic oligonucleotide

<400> SEQUENCE: 661
cagaggugaa gcgaagugct t                                              21

<210> SEQ ID NO 662
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 662
acuucgcuuc accucugcat t                                              21

<210> SEQ ID NO 663
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 663
ugcagaggug aagcgaagut t                                              21

<210> SEQ ID NO 664
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 664
ugugcacuuc gcuucaccut t                                              21

<210> SEQ ID NO 665
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 665
uccacuucgc uucacgugut t                                              21

<210> SEQ ID NO 666
<211> LENGTH: 21
<212> TYPE: DNA
<213> ORGANISM: Artificial Sequence
<220> FEATURE:
```

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 666
ugugcacuuc gcuucaccut t                                              21

<210> SEQ ID NO 667
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 667
uccacuucgc uucacgugut t                                              21

<210> SEQ ID NO 668
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 668
ugugcacuuc gcuucaccut t                                              21

<210> SEQ ID NO 669
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 669
uccacuucgc uucacgugut t                                              21

<210> SEQ ID NO 670
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 670
uuguuguauu uugugguug                                                 19

<210> SEQ ID NO 671
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

```
<220> FEATURE:
<223> OTHER INFORMATION: Description of Combined DNA/RNA Molecule:
      Synthetic oligonucleotide

<400> SEQUENCE: 671
caaccacaaa auacaacaat t                                              21

<210> SEQ ID NO 672
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 672
ccccgggagg ucucguagat t                                              21

<210> SEQ ID NO 673
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 673
ucuacgagac cucccggggt t                                              21

<210> SEQ ID NO 674
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 674
ccccgggagg ucucguagat t                                              21

<210> SEQ ID NO 675
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 675
ucuacgagac cucccggggt t                                              21

<210> SEQ ID NO 676
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
             oligonucleotide
<220> FEATURE:
<223> OTHER INFORMATION: Description of Combined DNA/RNA Molecule:
      Synthetic oligonucleotide

<400> SEQUENCE: 676
ccccgggagg ucucguagat t                                              21

<210> SEQ ID NO 677
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 677
ucuacgagac cucccggggt t                                              21

<210> SEQ ID NO 678
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 678
ccccgggagg ucucguagat t                                              21

<210> SEQ ID NO 679
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 679
ucuacgagac cucccggggt t                                              21

<210> SEQ ID NO 680
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 680
ccccgggagg ucucguagat t                                              21

<210> SEQ ID NO 681
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 681
ucuacgagac cucccggggt t                                              21

<210> SEQ ID NO 682
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 682
ccccgggagg ucucguagat t                                              21

<210> SEQ ID NO 683
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 683
ucuacgagac cucccggggt t                                              21

<210> SEQ ID NO 684
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 684

Ser Gly Ala Cys Arg Gly Asp Cys Leu Gly Ala
1               5                   10

<210> SEQ ID NO 685
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 685

Gly Ala Cys Arg Gly Asp Cys Leu Gly Ala
1               5                   10
```

RNA INTERFERENCE MEDIATED INHIBITION OF GENE EXPRESSION USING CHEMICALLY MODIFIED SHORT INTERFERING NUCLEIC ACID (SINA)

This application is a continuation of U.S. patent application Ser. No. 14/514,112, filed Oct. 14, 2014, which is a continuation of U.S. patent application Ser. No. 14/083,525, filed Nov. 19, 2013, which is a continuation of U.S. patent application Ser. No. 13/480,655 filed May 25, 2012 (now issued as U.S. Pat. No. 8,618,277), which is a continuation of U.S. patent application Ser. No. 10/720,448 filed Nov. 24, 2003 (now issued as U.S. Pat. No. 8,273,866), which is a continuation-in-part of U.S. patent application Ser. No. 10/693,059, filed Oct. 23, 2003 (now abandoned), which is a continuation-in-part of U.S. patent application Ser. No. 10/444,853, filed May 23, 2003 (now issued as U.S. Pat. No. 8,202,979) and a continuation-in-part of Ser. No. 10/652,791, filed Aug. 29, 2003 (now abandoned). The Ser. No. 10/693,059 application is also a continuation-in-part of International Patent Application No. PCT/US03/05346, filed Feb. 20, 2003, and a continuation-in-part of International Patent Application No. PCT/US03/05028, filed Feb. 20, 2003, both of which claim the benefit of U.S. Provisional Application No. 60/358,580 filed Feb. 20, 2002, U.S. Provisional Application No. 60/363,124 filed Mar. 11, 2002, U.S. Provisional Application No. 60/386,782 filed Jun. 6, 2002, U.S. Provisional Application No. 60/406,784 filed Aug. 29, 2002, U.S. Provisional Application No. 60/408,378 filed Sep. 5, 2002, U.S. Provisional Application No. 60/409,293 filed Sep. 9, 2002, and U.S. Provisional Application No. 60/440,129 filed Jan. 15, 2003. The Ser. No. 10/693,059 application is also a continuation-in-part of U.S. patent application Ser. No. 10/427,160, filed Apr. 30, 2003 (now issued as U.S. Pat. No. 7,833,992). The instant application claims the benefit of all the listed applications, which are hereby incorporated by reference herein in their entireties, including the drawings.

FIELD OF THE INVENTION

The present invention concerns methods and reagents useful in modulating gene expression in a variety of applications, including use in therapeutic, diagnostic, target validation, and genomic discovery applications. Specifically, the invention relates to synthetic small nucleic acid molecules, such as short interfering nucleic acid (siNA), short interfering RNA (siRNA), double-stranded RNA (dsRNA), microRNA (miRNA), and short hairpin RNA (shRNA) molecules capable of mediating RNA interference (RNAi).

SEQUENCE LISTING

The instant application contains a Sequence Listing which has been submitted electronically in ASCII format and is hereby incorporated by reference in its entirety. Said ASCII copy, created in Jun. 4, 2014, is named A2038-720624_SL.txt and is 203,137 bytes in size.

BACKGROUND OF THE INVENTION

The following is a discussion of relevant art pertaining to RNAi. The discussion is provided only for understanding of the invention that follows. The summary is not an admission that any of the work described below is prior art to the claimed invention. Applicant demonstrates herein that chemically modified short interfering nucleic acids possess the same capacity to mediate RNAi as do siRNA molecules and are expected to possess improved stability and activity in vivo; therefore, this discussion is not meant to be limiting only to siRNA and can be applied to siNA as a whole.

RNA interference refers to the process of sequence-specific post-transcriptional gene silencing in animals mediated by short interfering RNAs (siRNAs) (Zamore et al., 2000, Cell, 101, 25-33; Fire et al., 1998, Nature, 391, 806; Hamilton et al., 1999, Science, 286, 950-951). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., 1999, Trends Genet., 15, 358). Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA. The presence of dsRNA in cells triggers the RNAi response though a mechanism that has yet to be fully characterized. This mechanism appears to be different from the interferon response that results from dsRNA-mediated activation of protein kinase PKR and 2',5'-oligoadenylate synthetase resulting in non-specific cleavage of mRNA by ribonuclease L.

The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Hamilton et al., supra; Zamore et al., 2000, Cell, 101, 25-33; Berstein et al., 2001, Nature, 409, 363). Short interfering RNAs derived from dicer activity are typically about 21 to about 23 nucleotides in length and comprise about 19 base pair duplexes (Hamilton et al., supra; Elbashir et al., 2001, Genes Dev., 15, 188). Dicer has also been implicated in the excision of 21- and 22-nucleotide small temporal RNAs (stRNAs) from precursor RNA of conserved structure that are implicated in translational control (Hutvagner et al., 2001, Science, 293, 834). The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex (Elbashir et al., 2001, Genes Dev., 15, 188).

RNAi has been studied in a variety of systems. Fire et al., 1998, Nature, 391, 806, were the first to observe RNAi in C. elegans. Bahramian and Zarbl, 1999, Molecular and Cellular Biology, 19, 274-283 and Wianny and Goetz, 1999, Nature Cell Biol., 2, 70, describe RNAi mediated by dsRNA in mammalian systems. Hammond et al., 2000, Nature, 404, 293, describe RNAi in Drosophila cells transfected with dsRNA. Elbashir et al., 2001, Nature, 411, 494, describe RNAi induced by introduction of duplexes of synthetic 21-nucleotide RNAs in cultured mammalian cells including human embryonic kidney and HeLa cells. Recent work in Drosophila embryonic lysates (Elbashir et al., 2001, EMBO J., 20, 6877) has revealed certain requirements for siRNA length, structure, chemical composition, and sequence that are essential to mediate efficient RNAi activity. These studies have shown that 21-nucleotide siRNA duplexes are most active when containing 3'-terminal dinucleotide overhangs.

Furthermore, complete substitution of one or both siRNA strands with 2'-deoxy (2'-H) or 2'-O-methyl nucleotides abolishes RNAi activity, whereas substitution of the 3'-terminal siRNA overhang nucleotides with 2'-deoxy nucleotides (2'-H) was shown to be tolerated. Single mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end of the guide sequence (Elbashir et al., 2001, *EMBO J.,* 20, 6877). Other studies have indicated that a 5'-phosphate on the target-complementary strand of a siRNA duplex is required for siRNA activity and that ATP is utilized to maintain the 5'-phosphate moiety on the siRNA (Nykanen et al., 2001, *Cell,* 107, 309).

Studies have shown that replacing the 3'-terminal nucleotide overhanging segments of a 21-mer siRNA duplex having two-nucleotide 3'-overhangs with deoxyribonucleotides does not have an adverse effect on RNAi activity. Replacing up to four nucleotides on each end of the siRNA with deoxyribonucleotides has been reported to be well tolerated, whereas complete substitution with deoxyribonucleotides results in no RNAi activity (Elbashir et al., 2001, *EMBO J.,* 20, 6877). In addition, Elbashir et al., supra, also report that substitution of siRNA with 2'-O-methyl nucleotides completely abolishes RNAi activity. Li et al., International PCT Publication No. WO 00/44914, and Beach et al., International PCT Publication No. WO 01/68836 preliminarily suggest that siRNA may include modifications to either the phosphate-sugar backbone or the nucleoside to include at least one of a nitrogen or sulfur heteroatom, however, neither application postulates to what extent such modifications would be tolerated in siRNA molecules, nor provides any further guidance or examples of such modified siRNA. Kreutzer et al., Canadian Patent Application No. 2,359,180, also describe certain chemical modifications for use in dsRNA constructs in order to counteract activation of double-stranded RNA-dependent protein kinase PKR, specifically 2'-amino or 2'-O-methyl nucleotides, and nucleotides containing a 2'-O or 4'-C methylene bridge. However, Kreutzer et al. similarly fails to provide examples or guidance as to what extent these modifications would be tolerated in siRNA molecules.

Parrish et al., 2000, *Molecular Cell,* 6, 1077-1087, tested certain chemical modifications targeting the unc-22 gene in *C. elegans* using long (>25 nt) siRNA transcripts. The authors describe the introduction of thiophosphate residues into these siRNA transcripts by incorporating thiophosphate nucleotide analogs with T7 and T3 RNA polymerase and observed that RNAs with two phosphorothioate modified bases also had substantial decreases in effectiveness as RNAi. Further, Parrish et al. reported that phosphorothioate modification of more than two residues greatly destabilized the RNAs in vitro such that interference activities could not be assayed. Id. at 1081. The authors also tested certain modifications at the 2'-position of the nucleotide sugar in the long siRNA transcripts and found that substituting deoxynucleotides for ribonucleotides produced a substantial decrease in interference activity, especially in the case of Uridine to Thymidine and/or Cytidine to deoxy-Cytidine substitutions. Id. In addition, the authors tested certain base modifications, including substituting, in sense and antisense strands of the siRNA, 4-thiouracil, 5-bromouracil, 5-iodouracil, and 3-(aminoallyl)uracil for uracil, and inosine for guanosine. Whereas 4-thiouracil and 5-bromouracil substitution appeared to be tolerated, Parrish reported that inosine produced a substantial decrease in interference activity when incorporated in either strand. Parrish also reported that incorporation of 5-iodouracil and 3-(aminoallyl)uracil in the antisense strand resulted in a substantial decrease in RNAi activity as well.

The use of longer dsRNA has been described. For example, Beach et al., International PCT Publication No. WO 01/68836, describes specific methods for attenuating gene expression using endogenously-derived dsRNA. Tuschl et al., International PCT Publication No. WO 01/75164, describe a *Drosophila* in vitro RNAi system and the use of specific siRNA molecules for certain functional genomic and certain therapeutic applications; although Tuschl, 2001, *Chem. Biochem.,* 2, 239-245, doubts that RNAi can be used to cure genetic diseases or viral infection due to the danger of activating interferon response. Li et al., International PCT Publication No. WO 00/44914, describe the use of specific dsRNAs for attenuating the expression of certain target genes. Zernicka-Goetz et al., International PCT Publication No. WO 01/36646, describe certain methods for inhibiting the expression of particular genes in mammalian cells using certain dsRNA molecules. Fire et al., International PCT Publication No. WO 99/32619, describe particular methods for introducing certain dsRNA molecules into cells for use in inhibiting gene expression. Plaetinck et al., International PCT Publication No. WO 00/01846, describe certain methods for identifying specific genes responsible for conferring a particular phenotype in a cell using specific dsRNA molecules. Mello et al., International PCT Publication No. WO 01/29058, describe the identification of specific genes involved in dsRNA-mediated RNAi. Deschamps Depaillette et al., International PCT Publication No. WO 99/07409, describe specific compositions consisting of particular dsRNA molecules combined with certain anti-viral agents. Waterhouse et al., International PCT Publication No. 99/53050, describe certain methods for decreasing the phenotypic expression of a nucleic acid in plant cells using certain dsRNAs. Driscoll et al., International PCT Publication No. WO 01/49844, describe specific DNA constructs for use in facilitating gene silencing in targeted organisms.

Others have reported on various RNAi and gene-silencing systems. For example, Parrish et al., 2000, *Molecular Cell,* 6, 1077-1087, describe specific chemically-modified siRNA constructs targeting the unc-22 gene of *C. elegans*. Grossniklaus, International PCT Publication No. WO 01/38551, describes certain methods for regulating polycomb gene expression in plants using certain dsRNAs. Churikov et al., International PCT Publication No. WO 01/42443, describe certain methods for modifying genetic characteristics of an organism using certain dsRNAs. Cogoni et al., International PCT Publication No. WO 01/53475, describe certain methods for isolating a *Neurospora* silencing gene and uses thereof. Reed et al., International PCT Publication No. WO 01/68836, describe certain methods for gene silencing in plants. Honer et al., International PCT Publication No. WO 01/70944, describe certain methods of drug screening using transgenic nematodes as Parkinson's Disease models using certain dsRNAs. Deak et al., International PCT Publication No. WO 01/72774, describe certain *Drosophila*-derived gene products that may be related to RNAi in *Drosophila*. Arndt et al., International PCT Publication No. WO 01/92513 describe certain methods for mediating gene suppression by using factors that enhance RNAi. Tuschl et al., International PCT Publication No. WO 02/44321, describe certain synthetic siRNA constructs. Pachuk et al., International PCT Publication No. WO 00/63364, and Satishchandran et al., International PCT Publication No. WO 01/04313, describe certain methods and compositions for inhibiting the function of certain polynucleotide sequences using certain dsRNAs. Echeverri et al., International PCT Publication No. WO 02/38805, describe certain C. elegans genes identified via RNAi. Kreutzer et al., International PCT Publications Nos. WO 02/055692, WO 02/055693, and EP 1144623 B1 describes certain methods for inhibiting gene expression using RNAi. Graham et al., International PCT Publications Nos. WO 99/49029 and WO 01/70949, and AU 4037501 describe certain vector expressed siRNA molecules. Fire et al., U.S. Pat. No. 6,506,559, describe certain methods for inhibiting gene expression in vitro using certain long dsRNA (greater than 25 nucleotide) constructs that mediate RNAi.

SUMMARY OF THE INVENTION

This invention relates to compounds, compositions, and methods useful for modulating RNA function and/or gene expression in a cell. Specifically, the instant invention features synthetic small nucleic acid molecules, such as short interfering nucleic acid (siNA), short interfering RNA (siRNA), double-stranded RNA (dsRNA), micro-RNA (miRNA), and short hairpin RNA (shRNA) molecules capable of modulating gene expression in cells by RNA inference (RNAi). The siNA molecules of the invention can be chemically modified. The use of chemically modified siNA can improve various properties of native siRNA molecules through increased resistance to nuclease degradation in vivo and/or improved cellular uptake. The chemically modified siNA molecules of the instant invention provide useful reagents and methods for a variety of therapeutic, diagnostic, agricultural, target validation, genomic discovery, genetic engineering and pharmacogenomic applications.

In a non-limiting example, the introduction of chemically modified nucleotides into nucleic acid molecules provides a powerful tool in overcoming potential limitations of in vivo stability and bioavailability inherent to native RNA molecules that are delivered exogenously. For example, the use of chemically modified nucleic acid molecules can enable a lower dose of a particular nucleic acid molecule for a given therapeutic effect since chemically modified nucleic acid molecules tend to have a longer half-life in serum. Furthermore, certain chemical modifications can improve the bioavailability of nucleic acid molecules by targeting particular cells or tissues and/or improving cellular uptake of the nucleic acid molecule. Therefore, even if the activity of a chemically modified nucleic acid molecule is reduced as compared to a native nucleic acid molecule, for example when compared to an all RNA nucleic acid molecule, the overall activity of the modified nucleic acid molecule can be greater than the native molecule due to improved stability and/or delivery of the molecule. Unlike native unmodified siRNA, chemically modified siNA can also minimize the possibility of activating interferon activity in humans.

In one embodiment, the nucleic acid molecules of the invention that act as mediators of the RNA interference gene silencing response are chemically modified double stranded nucleic acid molecules. As in their native double stranded RNA counterparts, these siNA molecules typically consist of duplexes containing about 19 base pairs between oligonucleotides comprising about 19 to about 25 nucleotides. The most active siRNA molecules are thought to have such duplexes with overhanging ends of 1-3 nucleotides, for example 21 nucleotide duplexes with 19 base pairs and 2 nucleotide 3'-overhangs. These overhanging segments are readily hydrolyzed by endonucleases in vivo. Studies have shown that replacing the 3'-overhanging segments of a 21-mer siRNA duplex having 2 nucleotide 3' overhangs with deoxyribonucleotides does not have an adverse effect on RNAi activity. Replacing up to 4 nucleotides on each end of the siRNA with deoxyribonucleotides has been reported to be well tolerated whereas complete substitution with deoxyribonucleotides results in no RNAi activity (Elbashir et al., 2001, EMBO J., 20, 6877). In addition, Elbashir et al, supra, also report that substitution of siRNA with 2'-O-methyl nucleotides completely abolishes RNAi activity. Li et al., International PCT Publication No. WO 00/44914, and Beach et al., International PCT Publication No. WO 01/68836 both suggest that siRNA may include modifications to either the phosphate-sugar back bone or the nucleoside to include at least one of a nitrogen or sulfur heteroatom, however neither application teaches to what extent these modifications are tolerated in siRNA molecules nor provide any examples of such modified siRNA. Kreutzer and Limmer, Canadian Patent Application No. 2,359,180, also describe certain chemical modifications for use in dsRNA constructs in order to counteract activation of double stranded-RNA-dependent protein kinase PKR, specifically 2'-amino or 2'-O-methyl nucleotides, and nucleotides containing a 2'-O or 4'-C methylene bridge. However, Kreutzer and Limmer similarly fail to show to what extent these modifications are tolerated in siRNA molecules nor provide any examples of such modified siRNA.

In one embodiment, the invention features chemically modified siNA constructs having specificity for target nucleic acid molecules in a cell. Non-limiting examples of such chemical modifications include without limitation phosphorothioate internucleotide linkages, 2'-O-methyl ribonucleotides, 2'-deoxy-2'-fluoro ribonucleotides, 2'-deoxy ribonucleotides, "universal base" nucleotides, 5-C-methyl nucleotides, and inverted deoxyabasic residue incorporation. These chemical modifications, when used in various siNA constructs, are shown to preserve RNAi activity in cells while at the same time, dramatically increasing the serum stability of these compounds. Furthermore, contrary to the data published by Parrish et al., supra, applicant demonstrates that multiple (greater than one) phosphorothioate substitutions are well-tolerated and confer substantial increases in serum stability for modified siNA constructs.

In one embodiment, the chemically-modified siNA molecules of the invention comprise a duplex having two strands, one or both of which can be chemically-modified, wherein each strand is about 19 to about 29 (e.g., about 19, 20, 21, 22, 23, 24, 25, 26, 27, 28, or 29) (e.g., about 19, 20, 21, 22, 23, 24, 25, 26, 27, 28, or 29) nucleotides. In one embodiment, the chemically-modified siNA molecules of the invention comprise a duplex having two strands, one or both of which can be chemically-modified, wherein each strand is about 19 to about 23 (e.g., about 19, 20, 21, 22, or 23) nucleotides. In one embodiment, a siNA molecule of the invention comprises modified nucleotides while maintaining the ability to mediate RNAi. The modified nucleotides can be used to improve in vitro or in vivo characteristics such as stability, activity, and/or bioavailability. For example, a siNA molecule of the invention can comprise modified nucleotides as a percentage of the total number of nucleotides present in the siNA molecule. As such, a siNA molecule of the invention can generally comprise modified nucleotides from about 5 to about 100% of the nucleotide positions (e.g., 5%, 10%, 15%, 20%, 25%, 30%, 35%, 40%, 45%, 50%, 55%, 60%, 65%, 70%, 75%, 80%, 85%, 90%, 95% or 100% of the nucleotide positions). The actual percentage of modified nucleotides present in a given siNA molecule depends on the total number of nucleotides present in the siNA. If the siNA molecule is single stranded, the percent modification can be based upon the total number of nucleotides present in the single stranded siNA molecules. Likewise, if the siNA molecule is double stranded, the percent modification can be based upon the total number of nucleotides present in the sense strand, antisense strand, or both the sense and antisense strands. In addition, the actual percentage of modified nucleotides present in a given siNA molecule can also depend on the total number of purine and pyrimidine nucleotides present in the siNA, for example, wherein all pyrimidine nucleotides and/or all purine nucleotides present in the siNA molecule are modified.

The antisense region of a siNA molecule of the invention can comprise a phosphorothioate internucleotide linkage at the 3'-end of said antisense region. The antisense region can comprise about one to about five phosphorothioate internucleotide linkages at the 5'-end of said antisense region. The 3'-terminal nucleotide overhangs of a siNA molecule of the invention can comprise ribonucleotides or deoxyribonucleotides that are chemically-modified at a nucleic acid sugar, base, or backbone. The 3'-terminal nucleotide overhangs can comprise one or more universal base ribonucleotides. The 3'-terminal nucleotide overhangs can comprise one or more acyclic nucleotides.

In one embodiment, a siNA molecule of the invention comprises blunt ends, i.e., the ends do not include any overhanging nucleotides. For example, a siNA molecule of the invention comprising modifications described herein (e.g., comprising nucleotides having Formulae I-VII or siNA constructs comprising Stab1-Stab18 or any combination thereof) and/or any length described herein can comprise blunt ends or ends with no overhanging nucleotides.

In one embodiment, any siNA molecule of the invention can comprise one or more blunt ends, i.e. where a blunt end does not have any overhanging nucleotides. In a non-limiting example, a blunt ended siNA molecule has a number of base pairs equal to the number of nucleotides present in each strand of the siNA molecule. In another example, a siNA molecule comprises one blunt end, for example wherein the 5'-end of the antisense strand and the 3'-end of the sense strand do not have any overhanging nucleotides. In another example, a siNA molecule comprises one blunt end, for example wherein the 3'-end of the antisense strand and the 5'-end of the sense strand do not have any overhanging nucleotides. In another example, a siNA molecule comprises two blunt ends, for example wherein the 3'-end of the antisense strand and the 5'-end of the sense strand as well as the 5'-end of the antisense strand and 3'-end of the sense strand do not have any overhanging nucleotides. A blunt ended siNA molecule can comprise, for example, from about 18 to about 30 nucleotides (e.g., about 18, 19, 20, 21, 22, 23, 24, 25, 26, 27, 28, 29, or 30 nucleotides). Other nucleotides present in a blunt ended siNA molecule can comprise mismatches, bulges, loops, or wobble base pairs, for example, to modulate the activity of the siNA molecule to mediate RNA interference.

By "blunt ends" is meant symmetric termini or termini of a double stranded siNA molecule having no overhainging nucleotides. The two strands of a double stranded siNA molecule align with each other without over-hanging nucleotides at the termini. For example, a blunt ended siNA construct comprises terminal nucleotides that are complimentary between the sense and antisense regions of the siNA molecule.

In one embodiment, the invention features the use of a double-stranded short interfering nucleic acid (siNA) molecule to down-regulate expression of a target gene, wherein the siNA molecule comprises one or more chemical modifications and each strand of the double-stranded siNA is about 19 to about 23 nucleotides (e.g., about 19, 20, 21, 22, or 23 nucleotides) long.

In one embodiment, the invention features a double-stranded short interfering nucleic acid (siNA) molecule that down-regulates expression of a target gene, wherein the siNA molecule comprises no ribonucleotides and each strand of the double-stranded siNA comprises about 19 to about 23 nucleotides.

In one embodiment, one of the strands of a double-stranded siNA molecule of the invention comprises a nucleotide sequence that is complementary to a nucleotide sequence or a portion thereof of a target gene, and wherein the second strand of a double-stranded siNA molecule comprises a nucleotide sequence substantially similar to the nucleotide sequence or a portion thereof of the target gene.

In one embodiment, a siNA molecule of the invention comprises about 19 to about 23 nucleotides, and each strand comprises at least about 19 nucleotides that are complementary to the nucleotides of the other strand.

In one embodiment, a siNA molecule of the invention comprises an antisense region comprising a nucleotide sequence that is complementary to a nucleotide sequence or a portion thereof of a target gene, and the siNA further comprises a sense region, wherein the sense region comprises a nucleotide sequence substantially similar to the nucleotide sequence or a portion thereof of the target gene. The antisense region and the sense region each comprise about 19 to about 23 nucleotides, and the antisense region comprises at least about 19 nucleotides that are complementary to nucleotides of the sense region.

In one embodiment, a siNA molecule of the invention comprises a sense region and an antisense region, wherein the antisense region comprises a nucleotide sequence that is complementary to a nucleotide sequence or a portion thereof of RNA encoded by a target gene and the sense region comprises a nucleotide sequence that is complementary to the antisense region.

In one embodiment, a siNA molecule of the invention is assembled from two separate oligonucleotide fragments wherein one fragment comprises the sense region and the second fragment comprises the antisense region of the siNA molecule. In another embodiment, the sense region is connected to the antisense region via a linker molecule, which can be a polynucleotide linker or a non-nucleotide linker.

In one embodiment, a siNA molecule of the invention comprises a sense region and antisense region, wherein pyrimidine nucleotides in the sense region comprises 2'-O-methyl pyrimidine nucleotides and purine nucleotides in the sense region comprise 2'-deoxy purine nucleotides. In one embodiment, a siNA molecule of the invention comprises a sense region and antisense region, wherein pyrimidine nucleotides present in the sense region comprise 2'-deoxy-2'-fluoro pyrimidine nucleotides and wherein purine nucleotides present in the sense region comprise 2'-deoxy purine nucleotides.

In one embodiment, a siNA molecule of the invention comprises a sense region and antisense region, wherein the pyrimidine nucleotides when present in said antisense region are 2'-deoxy-2'-fluoro pyrimidine nucleotides and the purine nucleotides when present in said antisense region are 2'-O-methyl purine nucleotides.

In one embodiment, a siNA molecule of the invention comprises a sense region and antisense region, wherein the pyrimidine nucleotides when present in said antisense region are 2'-deoxy-2'-fluoro pyrimidine nucleotides and wherein the purine nucleotides when present in said antisense region comprise 2'-deoxy-purine nucleotides.

In one embodiment, a siNA molecule of the invention comprises a sense region and antisense region, wherein the sense region includes a terminal cap moiety at the 5'-end, the 3'-end, or both of the 5' and 3' ends of the sense region. In another embodiment, the terminal cap moiety is an inverted deoxy abasic moiety.

In one embodiment, a siNA molecule of the invention has RNAi activity that modulates expression of RNA encoded by a gene. Because many genes can share some degree of sequence homology with each other, siNA molecules can be designed to target a class of genes (and associated receptor or ligand genes) or alternately specific genes by selecting sequences that are either shared amongst different gene targets or alternatively that are unique for a specific gene target. Therefore, in one embodiment, the siNA molecule can be designed to target conserved regions of a RNA sequence having homology between several genes so as to target several genes or gene families (e.g., different gene isoforms, splice variants, mutant genes etc.) with one siNA molecule. In another embodiment, the siNA molecule can be designed to target a sequence that is unique to a specific RNA sequence of a specific gene due to the high degree of specificity that the siNA molecule requires to mediate RNAi activity.

In one embodiment, nucleic acid molecules of the invention that act as mediators of the RNA interference gene silencing response are double-stranded nucleic acid molecules. In another embodiment, the siNA molecules of the invention consist of duplexes containing about 19 base pairs between oligonucleotides comprising about 19 to about 25 (e.g., about 19, 20, 21, 22, 23, 24 or 25) nucleotides. In yet another embodiment, siNA molecules of the invention comprise duplexes with overhanging ends of about 1 to about 3 (e.g., about 1, 2, or 3) nucleotides, for example, about 21-nucleotide duplexes with about 19 base pairs and 3'-terminal mononucleotide, dinucleotide, or trinucleotide overhangs.

In one embodiment, the invention features one or more chemically-modified siNA constructs having specificity for nucleic acid molecules that express or encode a protein sequence, such as RNA or DNA encoding a protein sequence. Non-limiting examples of such chemical modifications include without limitation phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy abasic residue incorporation. These chemical modifications, when used in various siNA constructs, are shown to preserve RNAi activity in cells while at the same time, dramatically increasing the serum stability of these compounds.

In one embodiment, a siNA molecule of the invention does not contain any ribonucleotides. In another embodiment, a siNA molecule of the invention comprises one or more ribonucleotides.

In one embodiment, the invention features the use of compounds or compositions that inhibit the activity of double stranded RNA binding proteins (dsRBPs, see for example Silhavy et al., 2003, *Journal of General Virology*, 84, 975-980). Non-limiting examples of compounds and compositions that can be used to inhibit the activity of dsRBPs include but are not limited to small molecules and nucleic acid aptamers that bind to or interact with the dsRBPs and consequently reduce dsRBP activity and/or siNA molecules that target nucleic acid sequences encoding dsRBPs. The use of such compounds and compositions is expected to improve the activity of siNA molecules in biological systems in which dsRBPs can abrogate or suppress the efficacy of siNA mediated RNA interference, such as where dsRBPs are expressed during viral infection of a cell to escape RNAi surveillance. Therefore, the use of agents that inhibit dsRBP activity is preferred in those instances where RNA interference activity can be improved via the abrogation or suppression of dsRBP activity. Such anti-dsRBP agents can be administered alone or can be co-administered with siNA molecules of the invention, or can be used to pretreat cells or a subject before siNA administration. In another embodiment, anti-dsRBP agents are used to treat viral infection, such as HCV, HBV, or HIV infection with or without siNA molecules of the invention.

In one embodiment, the invention features a double-stranded short interfering nucleic acid (siNA) molecule that down-regulates expression of a gene, wherein one of the strands of the double-stranded siNA molecule comprises a nucleotide sequence that is complementary to a nucleotide sequence of the gene or RNA encoded by the gene or a portion thereof, and wherein the second strand of the double-stranded siNA molecule comprises a nucleotide sequence substantially similar to the nucleotide sequence of the gene or RNA encoded by the gene or a portion thereof.

In one embodiment, the invention features a double-stranded short interfering nucleic acid (siNA) molecule that down-regulates expression of a gene, wherein each strand of the siNA molecule comprises about 19 to about 23 nucleotides, and wherein each strand comprises at least about 19 nucleotides that are complementary to the nucleotides of the other strand.

In one embodiment, the invention features a double-stranded short interfering nucleic acid (siNA) molecule that down-regulates expression of a gene, wherein the siNA molecule comprises an antisense region comprising a nucleotide sequence that is complementary to a nucleotide sequence of the gene or RNA encoded by the gene or a portion thereof, and wherein the siNA further comprises a sense region, wherein the sense region comprises a nucleotide sequence substantially similar to the nucleotide sequence of the gene or RNA encoded by the gene or a portion thereof.

In one embodiment, the invention features a double-stranded short interfering nucleic acid (siNA) molecule that inhibits the expression of a target gene by mediating RNA interference (RNAi) process, wherein the siNA molecule comprises no ribonucleotides and wherein each strand of the double-stranded siNA molecule comprises about 21 nucleotides.

In one embodiment, the invention features a double-stranded short interfering nucleic acid (siNA) molecule that inhibits the replication of a virus (e.g, as mammalian virus, plant virus, hepatitis C virus, human immunodeficiency virus, hepatitis B virus, herpes simplex virus, cytomegalovirus, human papilloma virus, respiratory syncytial virus, or influenza virus), wherein the siNA molecule does not require the presence of a ribonucleotide within the siNA molecule for the inhibition of replication of the virus and each strand of the double-stranded siNA molecule comprises about 21 nucleotides.

In one embodiment, the invention features a double-stranded short interfering nucleic acid (siNA) molecule that down-regulates expression of a gene, wherein the siNA molecule comprises a sense region and an antisense region and wherein the antisense region comprises a nucleotide sequence that is complementary to a nucleotide sequence or a portion thereof of RNA encoded by the gene and the sense region comprises a nucleotide sequence that is complementary to the antisense region or a portion thereof, and wherein the purine nucleotides present in the antisense region comprise 2'-deoxy-purine nucleotides. In another embodiment, the purine nucleotides present in the antisense region comprise 2'-O-methyl purine nucleotides. In either of the above embodiments, the antisense region comprises a phosphorothioate internucleotide linkage at the 3' end of the antisense region. In an alternative embodiment, the antisense region comprises a glyceryl modification at the 3' end of the antisense region. In another embodiment of any of the above described siNA molecules, any nucleotides present in a non-complementary region of the antisense strand (e.g. overhang region) are 2'-deoxy nucleotides.

In one embodiment, the invention features a double-stranded short interfering nucleic acid (siNA) molecule that down-regulates expression of a gene, wherein the siNA molecule is assembled from two separate oligonucleotide fragments each comprising 21 nucleotides, wherein one fragment comprises the sense region and the second fragment comprises the antisense region of the siNA molecule, and wherein about 19 nucleotides of each fragment of the siNA molecule are base-paired to the complementary nucleotides of the other fragment of the siNA molecule and wherein at least two 3' terminal nucleotides of each fragment of the siNA molecule are not base-paired to the nucleotides of the other fragment of the siNA molecule. In one embodiment, each of the two 3' terminal nucleotides of each fragment of the siNA molecule is a 2'-deoxy-pyrimidine nucleotide, such as 2'-deoxy-thymidine. In another embodiment, all 21 nucleotides of each fragment of the siNA molecule are base-paired to the complementary nucleotides of the other fragment of the siNA molecule. In another embodiment, about 19 nucleotides of the antisense region are base-paired to the nucleotide sequence or a portion thereof of the RNA encoded by the gene. In another embodiment, 21 nucleotides of the antisense region are base-paired to the nucleotide sequence or a portion thereof of the RNA encoded by the gene. In any of the above embodiments, the 5'-end of the fragment comprising said antisense region can optionally include a phosphate group.

In one embodiment, the invention features a double-stranded short interfering nucleic acid (siNA) molecule that inhibits the expression of a RNA sequence (e.g., wherein said target RNA sequence is encoded by a gene or a gene involved in a pathway of gene expression), wherein the siNA molecule does not contain any ribonucleotides and wherein each strand of the double-stranded siNA molecule is about 21 nucleotides long.

In one embodiment, the invention features a medicament comprising a siNA molecule of the invention.

In one embodiment, the invention features an active ingredient comprising a siNA molecule of the invention.

In one embodiment, the invention features the use of a double-stranded short interfering nucleic acid (siNA) molecule to down-regulate expression of a target gene, wherein the siNA molecule comprises one or more chemical modifications and each strand of the double-stranded siNA is about 21 nucleotides long.

The invention features a double-stranded short interfering nucleic acid (siNA) molecule that inhibits expression of a gene, wherein one of the strands of the double-stranded siNA molecule is an antisense strand which comprises nucleotide sequence that is complementary to nucleotide sequence of a RNA encoded by the gene or a portion thereof, the other strand is a sense strand which comprises nucleotide sequence that is complementary to a nucleotide sequence of the antisense strand and wherein a majority of the pyrimidine nucleotides present in the double-stranded siNA molecule comprises a sugar modification. In one embodiment, the nucleotide sequence of the antisense strand of the double-stranded siNA molecule is complementary to the nucleotide sequence of a RNA which encodes a protein or a portion thereof. In one embodiment, each strand of the siNA molecule comprises about 19 to about 29 (e.g., about 19, 20, 21, 22, 23, 24, 25, 26, 27, 28, or 29) nucleotides, and each strand comprises at least about 19 nucleotides that are complementary to the nucleotides of the other strand. In one embodiment, the siNA molecule is assembled from two oligonucleotide fragments, wherein one fragment comprises the nucleotide sequence of the antisense strand of the siNA molecule and a second fragment comprises nucleotide sequence of the sense region of the siNA molecule. In another embodiment, the sense strand is connected to the antisense strand via a linker molecule, such as a polynucleotide linker or a non-nucleotide linker. In one embodiment, the pyrimidine nucleotides present in the sense strand are 2'-deoxy-2'-fluoro pyrimidine nucleotides and the purine nucleotides present in the sense region are 2'-deoxy purine nucleotides. In another embodiment, the pyrimidine nucleotides present in the sense strand are 2'-deoxy-2'-fluoro pyrimidine nucleotides and the purine nucleotides present in the sense region are 2'-O-methyl purine nucleotides. In one embodiment, the sense strand comprises a 3'-end and a 5'-end, wherein a terminal cap moiety (e.g., an inverted deoxy abasic moiety) is present at the 5'-end, the 3'-end, or both of the 5' and 3' ends of the sense strand. In one embodiment, the antisense strand comprises one or more 2'-deoxy-2'-fluoro pyrimidine nucleotides and one or more 2'-O-methyl purine nucleotides. In one embodiment, the pyrimidine nucleotides present in the antisense strand are 2'-deoxy-2'-fluoro pyrimidine nucleotides and any purine nucleotides present in the antisense strand are 2'-O-methyl purine nucleotides. In one embodiment, the antisense strand comprises a phosphorothioate internucleotide linkage at the 3' end of the antisense strand. In another embodiment, the antisense strand comprises a glyceryl modification at the 3' end. In another embodiment, the 5'-end of the antisense strand optionally includes a phosphate group. In one embodiment, the invention features a double-stranded short interfering nucleic acid (siNA) molecule that down-regulates expression of a gene, wherein one of the strands of the double-stranded siNA molecule is an antisense strand which comprises nucleotide sequence that is complementary to nucleotide sequence of RNA encoded by a gene or a portion thereof, the other strand is a sense strand which comprises nucleotide sequence that is complementary to a nucleotide sequence of the antisense strand and wherein a majority of the pyrimidine nucleotides present in the double-stranded siNA molecule comprises a sugar modification, and wherein the nucleotide sequence of the antisense strand is complementary to a nucleotide sequence of the 5'-untranslated region or a portion thereof of the RNA. In another embodiment, the nucleotide sequence of the antisense strand is complementary to a nucleotide sequence of the RNA or a portion thereof.

In one embodiment, the invention features a double-stranded short interfering nucleic acid (siNA) molecule that inhibits expression of a gene, wherein one of the strands of the double-stranded siNA molecule is an antisense strand which comprises nucleotide sequence that is complementary to nucleotide sequence of a RNA or a portion thereof, the other strand is a sense strand which comprises nucleotide sequence that is complementary to a nucleotide sequence of the antisense strand and wherein a majority of the pyrimidine nucleotides present in the double-stranded siNA molecule comprises a sugar modification, and wherein each of the two strands of the siNA molecule comprises 21 nucleotides. In one embodiment, about 19 nucleotides of each strand of the siNA molecule are base-paired to the complementary nucleotides of the other strand of the siNA molecule and at least two 3' terminal nucleotides of each strand of the siNA molecule are not base-paired to the nucleotides of the other strand of the siNA molecule. In one embodiment, each of the two 3' terminal nucleotides of each fragment of the siNA molecule are 2'-deoxy-pyrimidines, such as 2'-deoxythymidine. In another embodiment, each strand of the siNA molecule is base-paired to the complementary nucleotides of the other strand of the siNA molecule. In one embodiment, about 19 nucleotides of the antisense strand are base-paired to the nucleotide sequence of the RNA or a portion thereof. In another embodiment, 21 nucleotides of the antisense strand are base-paired to the nucleotide sequence of the RNA or a portion thereof.

In one embodiment, the invention features a composition comprising a siNA molecule of the invention and a pharmaceutically acceptable carrier or diluent.

In one embodiment, the invention features a method of increasing the stability of a siNA molecule against cleavage by ribonucleases comprising introducing at least one modified nucleotide into the siNA molecule, wherein the modified nucleotide is a 2'-deoxy-2'-fluoro nucleotide. In another embodiment, all pyrimidine nucleotides present in the siNA are 2'-deoxy-2'-fluoro pyrimidine nucleotides. In another embodiment, the modified nucleotides in the siNA include at least one 2'-deoxy-2'-fluoro cytidine or 2'-deoxy-2'-fluoro uridine nucleotide. In another embodiment, the modified nucleotides in the siNA include at least one 2'-fluoro cytidine and at least one 2'-deoxy-2'-fluoro uridine nucleotides. In another embodiment, all uridine nucleotides present in the siNA are 2'-deoxy-2'-fluoro uridine nucleotides. In another embodiment, all cytidine nucleotides present in the siNA are 2'-deoxy-2'-fluoro cytidine nucleotides. In another embodiment, all adenosine nucleotides present in the siNA are 2'-deoxy-2'-fluoro adenosine nucleotides. In another embodiment, all guanosine nucleotides present in the siNA are 2'-deoxy-2'-fluoro guanosine nucleotides. The siNA can further comprise at least one modified internucleotidic linkage, such as phosphorothioate linkage. In another embodiment, the 2'-deoxy-2'-fluoronucleotides are present at specifically selected locations in the siNA that are sensitive to cleavage by ribonucleases, such as locations having pyrimidine nucleotides.

In one embodiment, the invention features the use of a double-stranded short interfering nucleic acid (siNA) molecule that inhibits expression of a gene, wherein one of the strands of the double-stranded siNA molecule is an antisense strand which comprises nucleotide sequence that is complementary to nucleotide sequence of a RNA or a portion thereof, the other strand is a sense strand which comprises nucleotide sequence that is complementary to a nucleotide sequence of the antisense strand and wherein a majority of the pyrimidine nucleotides present in the double-stranded siNA molecule comprises a sugar modification.

In one embodiment, the invention features a short interfering nucleic acid (siNA) molecule comprising a double-stranded structure that down-regulates expression of a target nucleic acid, wherein the siNA molecule does not require a 2'-hydroxyl group containing ribonucleotide, each strand of the double-stranded structure of the siNA molecule comprises about 21 nucleotides and the siNA molecule comprises nucleotide sequence having complementarity to nucleotide sequence of the target nucleic acid or a portion thereof. The target nucleic acid can be an endogenous gene, an exogenous gene, a viral nucleic acid, or a RNA, such as a mammalian gene, plant gene, viral gene, fungal gene, bacterial gene, plant viral gene, or mammalian viral gene. Examples of mammalian viral gene include hepatitis C virus, human immunodeficiency virus, hepatitis B virus, herpes simplex virus, cytomegalovirus, human papilloma virus, respiratory syncytial virus, influenza virus, and severe acute respiratory syndrome virus (SARS).

In one embodiment, a siNA molecule of the invention comprises a sense region and an antisense region wherein the antisense region comprises the nucleotide sequence that is complementary to a nucleotide sequence or a portion thereof of the target nucleic acid and the sense region comprises a nucleotide sequence that is complementary to nucleotide sequence of the antisense region or a portion thereof.

In one embodiment, a siNA molecule of the invention is assembled from two separate oligonucleotide fragments wherein one fragment comprises the sense region and the second fragment comprises the antisense region of the siNA molecule. The sense region can be connected to the antisense region via a linker molecule, such as a polynucleotide linker or non-nucleotide linker. In another embodiment, each sense region and antisense region comprise about 21 nucleotides in length. In another embodiment, about 19 nucleotides of each fragment of the siNA molecule are base-paired to the complementary nucleotides of the other fragment of the siNA molecule and at least two 3' terminal nucleotides of each fragment of the siNA molecule are not base-paired to the nucleotides of the other fragment of the siNA molecule. In another embodiment, each of the two 3' terminal nucleotides of each fragment of the siNA molecule are 2'-deoxy-pyrimidines, such as the thymidine. In another embodiment, all 21 nucleotides of each fragment of the siNA molecule are base-paired to the complementary nucleotides of the other fragment of the siNA molecule. In another embodiment, about 19 nucleotides of the antisense region of the siNA molecule are base-paired to the nucleotide sequence or a portion thereof of the the target nucleic acid. In another embodiment, 21 nucleotides of the antisense region of the siNA molecule are base-paired to the nucleotide sequence or a portion thereof of the target nucleic acid. In another embodiment, the 5'-end of the fragment comprising the antisense region optionally includes a phosphate group.

In one embodiment, a siNA molecule of the invention comprises nucleotide sequence having complementarity to nucleotide sequence of RNA or a portion thereof encoded by the target nucleic acid or a portion thereof.

In one embodiment, a siNA molecule of the invention comprises a sense region and an antisense region, wherein the pyrimidine nucleotides when present in the sense region are 2'-O-methyl pyrimidine nucleotides and wherein the purine nucleotides when present in the sense region are 2'-deoxy purine nucleotides.

In one embodiment, a siNA molecule of the invention comprises a sense region and an antisense region, wherein the pyrimidine nucleotides when present in the sense region are 2'-deoxy-2'-fluoro pyrimidine nucleotides and wherein the purine nucleotides when present in the sense region are 2'-deoxy purine nucleotides.

In one embodiment, a siNA molecule of the invention comprises a sense region and an antisense region, wherein the sense region includes a terminal cap moiety at the 5'-end, the 3'-end, or both of the 5' and 3' ends. The cap moiety can be an inverted deoxy abasic moiety, an inverted deoxy thymidine moiety, or a thymidine moiety.

In one embodiment, a siNA molecule of the invention comprises a sense region and an antisense region, wherein the pyrimidine nucleotides when present in the antisense region are 2'-deoxy-2'-fluoro pyrimidine nucleotides and the purine nucleotides when present in the antisense region are 2'-O-methyl purine nucleotides.

In one embodiment, a siNA molecule of the invention comprises a sense region and an antisense region, wherein the pyrimidine nucleotides when present in the antisense region are 2'-deoxy-2'-fluoro pyrimidine nucleotides and wherein the purine nucleotides when present in the antisense region comprise 2'-deoxy-purine nucleotides.

In one embodiment, a siNA molecule of the invention comprises a sense region and an antisense region, wherein the antisense region comprises a phosphate backbone modification at the 3' end of the antisense region. The phosphate backbone modification can be a phosphorothioate.

In one embodiment, a siNA molecule of the invention comprises a sense region and an antisense region, wherein the antisense region comprises a glyceryl modification at the 3' end of the antisense region.

In one embodiment, a siNA molecule of the invention comprises a sense region and an antisense region, wherein each of sense and the antisense regions of the siNA molecule comprise about 21 nucleotides.

In a non-limiting example, the introduction of chemically-modified nucleotides into nucleic acid molecules provides a powerful tool in overcoming potential limitations of in vivo stability and bioavailability inherent to native RNA molecules that are delivered exogenously. For example, the use of chemically-modified nucleic acid molecules can enable a lower dose of a particular nucleic acid molecule for a given therapeutic effect since chemically-modified nucleic acid molecules tend to have a longer half-life in serum. Furthermore, certain chemical modifications can improve the bioavailability of nucleic acid molecules by targeting particular cells or tissues and/or improving cellular uptake of the nucleic acid molecule. Therefore, even if the activity of a chemically-modified nucleic acid molecule is reduced as compared to a native nucleic acid molecule, for example, when compared to an all-RNA nucleic acid molecule, the overall activity of the modified nucleic acid molecule can be greater than that of the native molecule due to improved stability and/or delivery of the molecule. Unlike native unmodified siNA, chemically-modified siNA can also minimize the possibility of activating interferon activity in humans.

In any of the embodiments of siNA molecules described herein, the antisense region of a siNA molecule of the invention can comprise a phosphorothioate internucleotide linkage at the 3'-end of said antisense region. In any of the embodiments of siNA molecules described herein, the antisense region can comprise about one to about five phosphorothioate internucleotide linkages at the 5'-end of said antisense region. In any of the embodiments of siNA molecules described herein, the 3'-terminal nucleotide overhangs of a siNA molecule of the invention can comprise ribonucleotides or deoxyribonucleotides that are chemically-modified at a nucleic acid sugar, base, or backbone. In any of the embodiments of siNA molecules described herein, the 3'-terminal nucleotide overhangs can comprise one or more universal base ribonucleotides. In any of the embodiments of siNA molecules described herein, the 3'-terminal nucleotide overhangs can comprise one or more acyclic nucleotides.

One embodiment of the invention provides an expression vector comprising a nucleic acid sequence encoding at least one siNA molecule of the invention in a manner that allows expression of the nucleic acid molecule. Another embodiment of the invention provides a mammalian cell comprising such an expression vector. The mammalian cell can be a human cell. The siNA molecule of the expression vector can comprise a sense region and an antisense region. The antisense region can comprise sequence complementary to an RNA or DNA sequence encoding a protein or polypeptide and the sense region can comprise sequence complementary to the antisense region. The siNA molecule can comprise two distinct strands having complementary sense and antisense regions. The siNA molecule can comprise a single strand having complementary sense and antisense regions.

In one embodiment, the invention features a chemically-modified short interfering nucleic acid (siNA) molecule capable of mediating RNA interference (RNAi) inside a cell or reconstituted in vitro system, wherein the chemical modification comprises one or more (e.g., about 1, 2, 3, 4, 5, 6, 7, 8, 9, 10, or more) nucleotides comprising a backbone modified internucleotide linkage having Formula I:

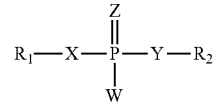

wherein each R1 and R2 is independently any nucleotide, non-nucleotide, or polynucleotide which can be naturally-occurring or chemically-modified, each X and Y is independently O, S, N, alkyl, or substituted alkyl, each Z and W is independently O, S, N, alkyl, substituted alkyl, O-alkyl, S-alkyl, alkaryl, or aralkyl, and wherein W, X, Y, and Z are optionally not all O. In another embodiment, a backbone modification of the invention comprises a phosphonoacetate and/or thiophosphonoacetate internucleotide linkage (see for example Sheehan et al., 2003, Nucleic Acids Research, 31, 4109-4118).

The chemically-modified internucleotide linkages having Formula I, for example, wherein any Z, W, X, and/or Y independently comprises a sulphur atom, can be present in one or both oligonucleotide strands of the siNA duplex, for example, in the sense strand, the antisense strand, or both strands. The siNA molecules of the invention can comprise one or more (e.g., about 1, 2, 3, 4, 5, 6, 7, 8, 9, 10, or more) chemically-modified internucleotide linkages having Formula I at the 3'-end, the 5'-end, or both of the 3' and 5'-ends of the sense strand, the antisense strand, or both strands. For example, an exemplary siNA molecule of the invention can comprise about 1 to about 5 or more (e.g., about 1, 2, 3, 4, 5, or more) chemically-modified internucleotide linkages having Formula I at the 5'-end of the sense strand, the antisense strand, or both strands. In another non-limiting example, an exemplary siNA molecule of the invention can comprise one or more (e.g., about 1, 2, 3, 4, 5, 6, 7, 8, 9, 10, or more) pyrimidine nucleotides with chemically-modified internucleotide linkages having Formula I in the sense strand, the antisense strand, or both strands. In yet another non-limiting example, an exemplary siNA molecule of the invention can comprise one or more (e.g., about 1, 2, 3, 4, 5, 6, 7, 8, 9, 10, or more) purine nucleotides with chemically-modified internucleotide linkages having Formula I in the sense strand, the antisense strand, or both strands. In another embodiment, a siNA molecule of the invention having internucleotide linkage(s) of Formula I also comprises a chemically-modified nucleotide or non-nucleotide having any of Formulae I-VII.

In one embodiment, the invention features a chemically-modified short interfering nucleic acid (siNA) molecule capable of mediating RNA interference (RNAi) inside a cell or reconstituted in vitro system, wherein the chemical modification comprises one or more (e.g., about 1, 2, 3, 4, 5, 6, 7, 8, 9, 10, or more) nucleotides or non-nucleotides having Formula II:

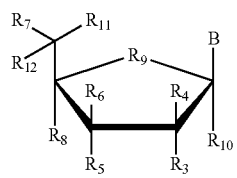

wherein each R3, R4, R5, R6, R7, R8, R10, R11 and R12 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-S-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or group having Formula I or II; R9 is O, S, CH2, S=O, CHF, or CF2, and B is a nucleosidic base such as adenine, guanine, uracil, cytosine, thymine, 2-aminoadenosine, 5-methylcytosine, 2,6-diaminopurine, or any other non-naturally occurring base that can be complementary or non-complementary to target RNA or a non-nucleosidic base such as phenyl, naphthyl, 3-nitropyrrole, 5-nitroindole, nebularine, pyridone, pyridinone, or any other non-naturally occurring universal base that can be complementary or non-complementary to target RNA.

The chemically-modified nucleotide or non-nucleotide of Formula II can be present in one or both oligonucleotide strands of the siNA duplex, for example in the sense strand, the antisense strand, or both strands. The siNA molecules of the invention can comprise one or more chemically-modified nucleotide or non-nucleotide of Formula II at the 3'-end, the 5'-end, or both of the 3' and 5'-ends of the sense strand, the antisense strand, or both strands. For example, an exemplary siNA molecule of the invention can comprise about 1 to about 5 or more (e.g., about 1, 2, 3, 4, 5, or more) chemically-modified nucleotides or non-nucleotides of Formula II at the 5'-end of the sense strand, the antisense strand, or both strands. In anther non-limiting example, an exemplary siNA molecule of the invention can comprise about 1 to about 5 or more (e.g., about 1, 2, 3, 4, 5, or more) chemically-modified nucleotides or non-nucleotides of Formula II at the 3'-end of the sense strand, the antisense strand, or both strands.

In one embodiment, the invention features a chemically-modified short interfering nucleic acid (siNA) molecule capable of mediating RNA interference (RNAi) inside a cell or reconstituted in vitro system, wherein the chemical modification comprises one or more (e.g., about 1, 2, 3, 4, 5, 6, 7, 8, 9, 10, or more) nucleotides or non-nucleotides having Formula III:

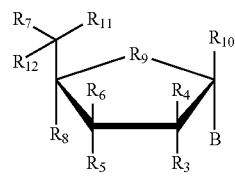

wherein each R3, R4, R5, R6, R7, R8, R10, R11 and R12 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-S-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or group having Formula I or II; R9 is O, S, CH2, S=O, CHF, or CF2, and B is a nucleosidic base such as adenine, guanine, uracil, cytosine, thymine, 2-aminoadenosine, 5-methylcytosine, 2,6-diaminopurine, or any other non-naturally occurring base that can be employed to be complementary or non-complementary to target RNA or a non-nucleosidic base such as phenyl, naphthyl, 3-nitropyrrole, 5-nitroindole, nebularine, pyridone, pyridinone, or any other non-naturally occurring universal base that can be complementary or non-complementary to target RNA.

The chemically-modified nucleotide or non-nucleotide of Formula III can be present in one or both oligonucleotide strands of the siNA duplex, for example, in the sense strand, the antisense strand, or both strands. The siNA molecules of the invention can comprise one or more chemically-modified nucleotide or non-nucleotide of Formula III at the 3'-end, the 5'-end, or both of the 3' and 5'-ends of the sense strand, the antisense strand, or both strands. For example, an exemplary siNA molecule of the invention can comprise about 1 to about 5 or more (e.g., about 1, 2, 3, 4, 5, or more) chemically-modified nucleotide(s) or non-nucleotide(s) of Formula III at the 5'-end of the sense strand, the antisense strand, or both strands. In anther non-limiting example, an exemplary siNA molecule of the invention can comprise about 1 to about 5 or more (e.g., about 1, 2, 3, 4, 5, or more) chemically-modified nucleotide or non-nucleotide of Formula III at the 3'-end of the sense strand, the antisense strand, or both strands.

In another embodiment, a siNA molecule of the invention comprises a nucleotide having Formula II or III, wherein the nucleotide having Formula II or III is in an inverted configuration. For example, the nucleotide having Formula II or III is connected to the siNA construct in a 3'-3', 3'-2', 2'-3', or 5'-5' configuration, such as at the 3'-end, the 5'-end, or both of the 3' and 5'-ends of one or both siNA strands.

In one embodiment, the invention features a chemically-modified short interfering nucleic acid (siNA) molecule capable of mediating RNA interference (RNAi) inside a cell or reconstituted in vitro system, wherein the chemical modification comprises a 5'-terminal phosphate group having Formula IV:

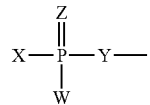

wherein each X and Y is independently O, S, N, alkyl, substituted alkyl, or alkylhalo; wherein each Z and W is independently O, S, N, alkyl, substituted alkyl, O-alkyl, S-alkyl, alkaryl, aralkyl, or alkylhalo or acetyl; and/or wherein W, X, Y and Z are not all O.

In one embodiment, the invention features a siNA molecule having a 5'-terminal phosphate group having Formula IV on the target-complementary strand, for example, a strand complementary to a target RNA, wherein the siNA molecule comprises an all RNA siNA molecule. In another embodiment, the invention features a siNA molecule having a 5'-terminal phosphate group having Formula IV on the target-complementary strand wherein the siNA molecule also comprises about 1 to about 3 (e.g., about 1, 2, or 3) nucleotide 3'-terminal nucleotide overhangs having about 1 to about 4 (e.g., about 1, 2, 3, or 4) deoxyribonucleotides on the 3'-end of one or both strands. In another embodiment, a 5'-terminal phosphate group having Formula IV is present on the target-complementary strand of a siNA molecule of the invention, for example a siNA molecule having chemical modifications having any of Formulae I-VII.

In one embodiment, the invention features a chemically-modified short interfering nucleic acid (siNA) molecule capable of mediating RNA interference (RNAi) inside a cell or reconstituted in vitro system, wherein the chemical modification comprises one or more phosphorothioate, phosphonoacetate, and/or thiophosphonoacetate internucleotide linkages. For example, in a non-limiting example, the invention features a chemically-modified short interfering nucleic acid (siNA) having about 1, 2, 3, 4, 5, 6, 7, 8 or more phosphorothioate internucleotide linkages in one siNA strand. In yet another embodiment, the invention features a chemically-modified short interfering nucleic acid (siNA) individually having about 1, 2, 3, 4, 5, 6, 7, 8 or more phosphorothioate internucleotide linkages in both siNA strands. The phosphorothioate internucleotide linkages can be present in one or both oligonucleotide strands of the siNA duplex, for example in the sense strand, the antisense strand, or both strands. The siNA molecules of the invention can comprise one or more phosphorothioate, phosphonoacetate, and/or thiophosphonoacetate internucleotide linkages at the 3'-end, the 5'-end, or both of the 3'- and 5'-ends of the sense strand, the antisense strand, or both strands. For example, an exemplary siNA molecule of the invention can comprise about 1 to about 5 or more (e.g., about 1, 2, 3, 4, 5, or more) consecutive phosphorothioate internucleotide linkages at the 5'-end of the sense strand, the antisense strand, or both strands. In another non-limiting example, an exemplary siNA molecule of the invention can comprise one or more (e.g., about 1, 2, 3, 4, 5, 6, 7, 8, 9, 10, or more) pyrimidine phosphorothioate internucleotide linkages in the sense strand, the antisense strand, or both strands. In yet another non-limiting example, an exemplary siNA molecule of the invention can comprise one or more (e.g., about 1, 2, 3, 4, 5, 6, 7, 8, 9, 10, or more) purine phosphorothioate internucleotide linkages in the sense strand, the antisense strand, or both strands.

In one embodiment, the invention features a siNA molecule, wherein the sense strand comprises one or more, for example, about 1, 2, 3, 4, 5, 6, 7, 8, 9, 10, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or about one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises about 1 to about 10 or more, specifically about 1, 2, 3, 4, 5, 6, 7, 8, 9, 10, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In another embodiment, one or more, for example about 1, 2, 3, 4, 5, 6, 7, 8, 9, 10, or more, pyrimidine nucleotides of the sense and/or antisense siNA strand are chemically-modified with 2'-deoxy, 2'-O-methyl and/or 2'-deoxy-2'-fluoro nucleotides, with or without one or more, for example about 1, 2, 3, 4, 5, 6, 7, 8, 9, 10, or more, phosphorothioate internucleotide linkages and/or a terminal cap molecule at the 3'-end, the 5'-end, or both of the 3'- and 5'-ends, being present in the same or different strand.

In another embodiment, the invention features a siNA molecule, wherein the sense strand comprises about 1 to about 5, specifically about 1, 2, 3, 4, or 5 phosphorothioate internucleotide linkages, and/or one or more (e.g., about 1, 2, 3, 4, 5, or more) 2'-deoxy, 2'-O-methyl, 2'-deoxy-2'-fluoro, and/or one or more (e.g., about 1, 2, 3, 4, 5, or more) universal base modified nucleotides, and optionally a terminal cap molecule at the 3-end, the 5'-end, or both of the 3'- and 5'-ends of the sense strand; and wherein the antisense strand comprises about 1 to about 5 or more, specifically about 1, 2, 3, 4, 5, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In another embodiment, one or more, for example about 1, 2, 3, 4, 5, 6, 7, 8, 9, 10, or more, pyrimidine nucleotides of the sense and/or antisense siNA strand are chemically-modified with 2'-deoxy, 2'-O-methyl and/or 2'-deoxy-2'-fluoro nucleotides, with or without about 1 to about 5 or more, for example about 1, 2, 3, 4, 5, or more phosphorothioate internucleotide linkages and/or a terminal cap molecule at the 3'-end, the 5'-end, or both of the 3'- and 5'-ends, being present in the same or different strand.

In one embodiment, the invention features a siNA molecule, wherein the antisense strand comprises one or more, for example, about 1, 2, 3, 4, 5, 6, 7, 8, 9, 10, or more phosphorothioate internucleotide linkages, and/or about one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises about 1 to about 10 or more, specifically about 1, 2, 3, 4, 5, 6, 7, 8, 9, 10 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In another embodiment, one or more, for example about 1, 2, 3, 4, 5, 6, 7, 8, 9, 10 or more pyrimidine nucleotides of the sense and/or antisense siNA strand are chemically-modified with 2'-deoxy, 2'-O-methyl and/or 2'-deoxy-2'-fluoro nucleotides, with or without one or more, for example, about 1, 2, 3, 4, 5, 6, 7, 8, 9, 10 or more phosphorothioate internucleotide linkages and/or a terminal cap molecule at the 3'-end, the 5'-end, or both of the 3' and 5'-ends, being present in the same or different strand.

In another embodiment, the invention features a siNA molecule, wherein the antisense strand comprises about 1 to about 5 or more, specifically about 1, 2, 3, 4, 5 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the sense strand; and wherein the antisense strand comprises about 1 to about 5 or more, specifically about 1, 2, 3, 4, 5 or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. In another embodiment, one or more, for example about 1, 2, 3, 4, 5, 6, 7, 8, 9, 10 or more pyrimidine nucleotides of the sense and/or antisense siNA strand are chemically-modified with 2'-deoxy, 2'-O-methyl and/or 2'-deoxy-2'-fluoro nucleotides, with or without about 1 to about 5, for example about 1, 2, 3, 4, 5 or more phosphorothioate internucleotide linkages and/or a terminal cap molecule at the 3'-end, the 5'-end, or both of the 3'- and 5'-ends, being present in the same or different strand.

In one embodiment, the invention features a chemically-modified short interfering nucleic acid (siNA) molecule having about 1 to about 5, specifically about 1, 2, 3, 4, 5 or more phosphorothioate internucleotide linkages in each strand of the siNA molecule.

In another embodiment, the invention features a siNA molecule comprising 2'-5' internucleotide linkages. The 2'-5' internucleotide linkage(s) can be at the 3'-end, the 5'-end, or both of the 3'- and 5'-ends of one or both siNA sequence strands. In addition, the 2'-5' internucleotide linkage(s) can be present at various other positions within one or both siNA sequence strands, for example, about 1, 2, 3, 4, 5, 6, 7, 8, 9, 10, or more including every internucleotide linkage of a pyrimidine nucleotide in one or both strands of the siNA molecule can comprise a 2'-5' internucleotide linkage, or about 1, 2, 3, 4, 5, 6, 7, 8, 9, 10, or more including every internucleotide linkage of a purine nucleotide in one or both strands of the siNA molecule can comprise a 2'-5' internucleotide linkage.

In another embodiment, a chemically-modified siNA molecule of the invention comprises a duplex having two strands, one or both of which can be chemically-modified, wherein each strand is about 18 to about 27 (e.g., about 18, 19, 20, 21, 22, 23, 24, 25, 26, or 27) nucleotides in length, wherein the duplex has about 18 to about 23 (e.g., about 18, 19, 20, 21, 22, or 23) base pairs, and wherein the chemical modification comprises a structure having any of Formulae I-VII. For example, an exemplary chemically-modified siNA molecule of the invention comprises a duplex having two strands, one or both of which can be chemically-modified with a chemical modification having any of Formulae I-VII or any combination thereof, wherein each strand consists of about 21 nucleotides, each having a 2-nucleotide 3'-terminal nucleotide overhang, and wherein the duplex has about 19 base pairs. In another embodiment, a siNA molecule of the invention comprises a single stranded hairpin structure, wherein the siNA is about 36 to about 70 (e.g., about 36, 40, 45, 50, 55, 60, 65, or 70) nucleotides in length having about 18 to about 23 (e.g., about 18, 19, 20, 21, 22, or 23) base pairs, and wherein the siNA can include a chemical modification comprising a structure having any of Formulae I-VII or any combination thereof. For example, an exemplary chemically-modified siNA molecule of the invention comprises a linear oligonucleotide having about 42 to about 50 (e.g., about 42, 43, 44, 45, 46, 47, 48, 49, or 50) nucleotides that is chemically-modified with a chemical modification having any of Formulae I-VII or any combination thereof, wherein the linear oligonucleotide forms a hairpin structure having about 19 base pairs and a 2-nucleotide 3'-terminal nucleotide overhang. In another embodiment, a linear hairpin siNA molecule of the invention contains a stem loop motif, wherein the loop portion of the siNA molecule is biodegradable. For example, a linear hairpin siNA molecule of the invention is designed such that degradation of the loop portion of the siNA molecule in vivo can generate a double-stranded siNA molecule with 3'-terminal overhangs, such as 3'-terminal nucleotide overhangs comprising about 2 nucleotides.

In another embodiment, a siNA molecule of the invention comprises a hairpin structure, wherein the siNA is about 25 to about 50 (e.g., about 25, 26, 27, 28, 29, 30, 31, 32, 33, 34, 35, 36, 37, 38, 39, 40, 41, 42, 43, 44, 45, 46, 47, 48, 49, or 50) nucleotides in length having about 3 to about 25 (e.g., about 3, 4, 5, 6, 7, 8, 9, 10, 11, 12, 13, 14, 15, 16, 17, 18, 19, 20, 21, 22, 23, 24, or 25) base pairs, and wherein the siNA can include one or more chemical modifications comprising a structure having any of Formulae I-VII or any combination thereof. For example, an exemplary chemically-modified siNA molecule of the invention comprises a linear oligonucleotide having about 25 to about 35 (e.g., about 25, 26, 27, 28, 29, 30, 31, 32, 33, 34, or 35) nucleotides that is chemically-modified with one or more chemical modifications having any of Formulae I-VII or any combination thereof, wherein the linear oligonucleotide forms a hairpin structure having about 3 to about 23 (e.g., about 3, 4, 5, 6, 7, 8, 9, 10, 11, 12, 13, 14, 15, 16, 17, 18, 19, 20, 21, 22, or 23) base pairs and a 5'-terminal phosphate group that can be chemically modified as described herein (for example a 5'-terminal phosphate group having Formula IV). In another embodiment, a linear hairpin siNA molecule of the invention contains a stem loop motif, wherein the loop portion of the siNA molecule is biodegradable. In another embodiment, a linear hairpin siNA molecule of the invention comprises a loop portion comprising a non-nucleotide linker.

In another embodiment, a siNA molecule of the invention comprises an asymmetric hairpin structure, wherein the siNA is about 25 to about 50 (e.g., about 25, 26, 27, 28, 29, 30, 31, 32, 33, 34, 35, 36, 37, 38, 39, 40, 41, 42, 43, 44, 45, 46, 47, 48, 49, or 50) nucleotides in length having about 3 to about 20 (e.g., about 3, 4, 5, 6, 7, 8, 9, 10, 11, 12, 13, 14, 15, 16, 17, 18, 19, or 20) base pairs, and wherein the siNA can include one or more chemical modifications comprising a structure having any of Formulae I-VII or any combination thereof. For example, an exemplary chemically-modified siNA molecule of the invention comprises a linear oligonucleotide having about 25 to about 35 (e.g., about 25, 26, 27, 28, 29, 30, 31, 32, 33, 34, or 35) nucleotides that is chemically-modified with one or more chemical modifications having any of Formulae I-VII or any combination thereof, wherein the linear oligonucleotide forms an asymmetric hairpin structure having about 3 to about 18 (e.g., about 3, 4, 5, 6, 7, 8, 9, 10, 11, 12, 13, 14, 15, 16, 17 or 18) base pairs and a 5'-terminal phosphate group that can be chemically modified as described herein (for example a 5'-terminal phosphate group having Formula IV). In another embodiment, an asymmetric hairpin siNA molecule of the invention contains a stem loop motif, wherein the loop portion of the siNA molecule is biodegradable. In another embodiment, an asymmetric hairpin siNA molecule of the invention comprises a loop portion comprising a non-nucleotide linker.

In another embodiment, a siNA molecule of the invention comprises an asymmetric double stranded structure having separate polynucleotide strands comprising sense and antisense regions, wherein the antisense region is about 16 to about 25 (e.g., about 16, 17, 18, 19, 20, 21, 22, 23, 24, or 25) nucleotides in length, wherein the sense region is about 3 to about 18 (e.g., about 3, 4, 5, 6, 7, 8, 9, 10, 11, 12, 13, 14, 15, 16, 17, or 18) nucleotides in length, wherein the sense region the antisense region have at least 3 complementary nucleotides, and wherein the siNA can include one or more chemical modifications comprising a structure having any of Formulae I-VII or any combination thereof. For example, an exemplary chemically-modified siNA molecule of the invention comprises an asymmetric double stranded structure having separate polynucleotide strands comprising sense and antisense regions, wherein the antisense region is about 18 to about 22 (e.g., about 18, 19, 20, 21, or 22) nucleotides in length and wherein the sense region is about 3 to about 15 (e.g., about 3, 4, 5, 6, 7, 8, 9, 10, 11, 12, 13, 14, or 15) nucleotides in length, wherein the sense region the antisense region have at least 3 complementary nucleotides, and wherein the siNA can include one or more chemical modifications comprising a structure having any of Formulae I-VII or any combination thereof. In another embodiment, the asymmetic double stranded siNA molecule can also have a 5'-terminal phosphate group that can be chemically modified as described herein (for example a 5'-terminal phosphate group having Formula IV).

In another embodiment, a siNA molecule of the invention comprises a circular nucleic acid molecule, wherein the siNA is about 38 to about 70 (e.g., about 38, 40, 45, 50, 55, 60, 65, or 70) nucleotides in length having about 18 to about 23 (e.g., about 18, 19, 20, 21, 22, or 23) base pairs, and wherein the siNA can include a chemical modification, which comprises a structure having any of Formulae I-VII or any combination thereof. For example, an exemplary chemically-modified siNA molecule of the invention comprises a circular oligonucleotide having about 42 to about 50 (e.g., about 42, 43, 44, 45, 46, 47, 48, 49, or 50) nucleotides that is chemically-modified with a chemical modification having any of Formulae I-VII or any combination thereof, wherein the circular oligonucleotide forms a dumbbell shaped structure having about 19 base pairs and 2 loops.

In another embodiment, a circular siNA molecule of the invention contains two loop motifs, wherein one or both loop portions of the siNA molecule is biodegradable. For example, a circular siNA molecule of the invention is designed such that degradation of the loop portions of the siNA molecule in vivo can generate a double-stranded siNA molecule with 3'-terminal overhangs, such as 3'-terminal nucleotide overhangs comprising about 2 nucleotides.

In one embodiment, a siNA molecule of the invention comprises at least one (e.g., about 1, 2, 3, 4, 5, 6, 7, 8, 9, 10, or more) abasic moiety, for example a compound having Formula V:

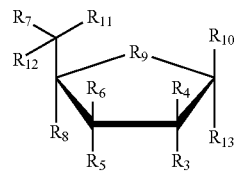

wherein each R3, R4, R5, R6, R7, R8, R10, R11, R12, and R13 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-S-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or group having Formula I or II; R9 is O, S, CH2, S=O, CHF, or CF2.

In one embodiment, a siNA molecule of the invention comprises at least one (e.g., about 1, 2, 3, 4, 5, 6, 7, 8, 9, 10, or more) inverted abasic moiety, for example a compound having Formula VI:

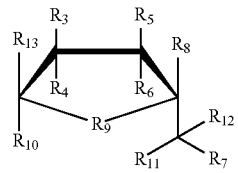

wherein each R3, R4, R5, R6, R7, R8, R10, R11, R12, and R13 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-S-alkyl, alkyl-O-alkyl, ONO2, NO2, N3, NH2, aminoalkyl, aminoacid, aminoacyl, ONH2, O-aminoalkyl, O-aminoacid, O-aminoacyl, heterocycloalkyl, heterocycloalkaryl, aminoalkylamino, polyalklylamino, substituted silyl, or group having Formula I or II; R9 is O, S, CH2, S=O, CHF, or CF2, and either R3, R5, R8 or R13 serve as points of attachment to the siNA molecule of the invention.

In another embodiment, a siNA molecule of the invention comprises at least one (e.g., about 1, 2, 3, 4, 5, 6, 7, 8, 9, 10, or more) substituted polyalkyl moieties, for example a compound having Formula VII:

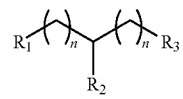

wherein each n is independently an integer from 1 to 12, each R1, R2 and R3 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-S-alkyl, alkyl-O-alkyl, ONO2, NO2, N3, NH2, aminoalkyl, aminoacid, aminoacyl, ONH2, O-aminoalkyl, O-aminoacid, O-amino-acyl, heterocycloalkyl, heterocycloalkaryl, aminoalkylamino, polyalklylamino, substituted silyl, or a group having Formula I, and R1, R2 or R3 serves as points of attachment to the siNA molecule of the invention.

In another embodiment, the invention features a compound having Formula VII, wherein R1 and R2 are hydroxyl (OH) groups, n=1, and R3 comprises O and is the point of attachment to the 3'-end, the 5'-end, or both of the 3' and 5'-ends of one or both strands of a double-stranded siNA molecule of the invention or to a single-stranded siNA molecule of the invention. This modification is referred to herein as "glyceryl" (for example modification 6 in FIG. 22).

In another embodiment, a moiety having any of Formula V, VI or VII of the invention is at the 3'-end, the 5'-end, or both of the 3' and 5'-ends of a siNA molecule of the invention. For example, a moiety having Formula V, VI or VII can be present at the 3'-end, the 5'-end, or both of the 3' and 5'-ends of the antisense strand, the sense strand, or both antisense and sense strands of the siNA molecule. In addition, a moiety having Formula VII can be present at the 3'-end or the 5'-end of a hairpin siNA molecule as described herein.

In another embodiment, a siNA molecule of the invention comprises an abasic residue having Formula V or VI, wherein the abasic residue having Formula V or VI is connected to the siNA construct in a 3-3', 3-2', 2-3', or 5-5' configuration, such as at the 3'-end, the 5'-end, or both of the 3' and 5'-ends of one or both siNA strands.

In one embodiment, a siNA molecule of the invention comprises one or more (e.g., about 1, 2, 3, 4, 5, 6, 7, 8, 9, 10, or more) locked nucleic acid (LNA) nucleotides, for example at the 5'-end, the 3'-end, both of the 5' and 3'-ends, or any combination thereof, of the siNA molecule.

In another embodiment, a siNA molecule of the invention comprises one or more (e.g., about 1, 2, 3, 4, 5, 6, 7, 8, 9, 10, or more) acyclic nucleotides, for example at the 5'-end, the 3'-end, both of the 5' and 3'-ends, or any combination thereof, of the siNA molecule.

In one embodiment, the sense strand of a double stranded siNA molecule of the invention comprises a terminal cap moiety, (see for example FIG. 22) such as an inverted deoxyabasic moiety or inverted nucleotide, at the 3'-end, 5'-end, or both 3' and 5'-ends of the sense strand.

In one embodiment, the invention features a chemically-modified short interfering nucleic acid (siNA) molecule of the invention, wherein the chemically-modified siNA comprises a sense region, where any (e.g., one or more or all) pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and where any (e.g., one or more or all) purine nucleotides present in the sense region are 2'-deoxy purine nucleotides (e.g., wherein all purine nucleotides are 2'-deoxy purine nucleotides or alternately a plurality of purine nucleotides are 2'-deoxy purine nucleotides).

In one embodiment, the invention features a chemically-modified short interfering nucleic acid (siNA) molecule of the invention, wherein the chemically-modified siNA comprises a sense region, where any (e.g., one or more or all) pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and where any (e.g., one or more or all) purine nucleotides present in the sense region are 2'-deoxy purine nucleotides (e.g., wherein all purine nucleotides are 2'-deoxy purine nucleotides or alternately a plurality of purine nucleotides are 2'-deoxy purine nucleotides), wherein any nucleotides comprising a 3'-terminal nucleotide overhang that are present in said sense region are 2'-deoxy nucleotides.

In one embodiment, the invention features a chemically-modified short interfering nucleic acid (siNA) molecule of the invention, wherein the chemically-modified siNA comprises a sense region, where any (e.g., one or more or all) pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and where any (e.g., one or more or all) purine nucleotides present in the sense region are 2'-O-methyl purine nucleotides (e.g., wherein all purine nucleotides are 2'-O-methyl purine nucleotides or alternately a plurality of purine nucleotides are 2'-O-methyl purine nucleotides).

In one embodiment, the invention features a chemically-modified short interfering nucleic acid (siNA) molecule of the invention, wherein the chemically-modified siNA comprises a sense region, where any (e.g., one or more or all) pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and where any (e.g., one or more or all) purine nucleotides present in the sense region are 2'-O-methyl purine nucleotides (e.g., wherein all purine nucleotides are 2'-O-methyl purine nucleotides or alternately a plurality of purine nucleotides are 2'-O-methyl purine nucleotides), wherein any nucleotides comprising a 3'-terminal nucleotide overhang that are present in said sense region are 2'-deoxy nucleotides.

In one embodiment, the invention features a chemically-modified short interfering nucleic acid (siNA) molecule of the invention, wherein the chemically-modified siNA comprises an antisense region, where any (e.g., one or more or all) pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides).

In one embodiment, the invention features a chemically-modified short interfering nucleic acid (siNA) molecule of the invention, wherein the chemically-modified siNA comprises an antisense region, where any (e.g., one or more or all) pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides), wherein any nucleotides comprising a 3'-terminal nucleotide overhang that are present in said antisense region are 2'-deoxy nucleotides.

In one embodiment, the invention features a chemically-modified short interfering nucleic acid (siNA) molecule of the invention, wherein the chemically-modified siNA comprises an antisense region, where any (e.g., one or more or all) pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and where any (e.g., one or more or all) purine nucleotides present in the antisense region are 2'-deoxy purine nucleotides (e.g., wherein all purine nucleotides are 2'-deoxy purine nucleotides or alternately a plurality of purine nucleotides are 2'-deoxy purine nucleotides).

In one embodiment, the invention features a chemically-modified short interfering nucleic acid (siNA) molecule of the invention capable of mediating RNA interference (RNAi) inside a cell or reconstituted in vitro system comprising a sense region and an antisense region. In one embodiment, the sense region comprises one or more 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and one or more 2'-deoxy purine nucleotides (e.g., wherein all purine nucleotides are 2'-deoxy purine nucleotides or alternately a plurality of purine nucleotides are 2'-deoxy purine nucleotides). The sense region can comprise inverted deoxy abasic modifications that are optionally present at the 3'-end, the 5'-end, or both of the 3' and 5'-ends of the sense region. The sense region can optionally further comprise a 3'-terminal overhang having about 1 to about 4 (e.g., about 1, 2, 3, or 4) 2'-deoxyribonucleotides. The antisense region comprises one or more 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and one or more 2'-O-methyl purine nucleotides (e.g., wherein all purine nucleotides are 2'-O-methyl purine nucleotides or alternately a plurality of purine nucleotides are 2'-O-methyl purine nucleotides). The antisense region can comprise a terminal cap modification, such as any modification described herein or shown in FIG. 22, that is optionally present at the 3'-end, the 5'-end, or both of the 3' and 5'-ends of the antisense sequence. The antisense region optionally further comprises a 3'-terminal nucleotide overhang having about 1 to about 4 (e.g., about 1, 2, 3, or 4) 2'-deoxynucleotides, wherein the overhang nucleotides can further comprise one or more (e.g., 1, 2, 3, or 4) phosphorothioate internucleotide linkages. Non-limiting examples of these chemically-modified siNAs are shown in FIGS. 18A-18F and 19A-19F and Table IV herein.

In another embodiment of the chemically-modified short interfering nucleic acid comprising a sense region and an antisense region, the sense region comprises one or more 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and one or more purine ribonucleotides (e.g., wherein all purine nucleotides are purine ribonucleotides or alternately a plurality of purine nucleotides are purine ribonucleotides). The sense region can also comprise inverted deoxy abasic modifications that are optionally present at the 3'-end, the 5'-end, or both of the 3' and 5'-ends of the sense region. The sense region optionally further comprises a 3'-terminal overhang having about 1 to about 4 (e.g., about 1, 2, 3, or 4) 2'-deoxyribonucleotides. The antisense region comprises one or more 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and one or more 2'-O-methyl purine nucleotides (e.g., wherein all purine nucleotides are 2'-O-methyl purine nucleotides or alternately a plurality of purine nucleotides are 2'-O-methyl purine nucleotides). The antisense region can also comprise a terminal cap modification, such as any modification described herein or shown in FIG. 22, that is optionally present at the 3'-end, the 5'-end, or both of the 3' and 5'-ends of the antisense sequence. The antisense region optionally further comprises a 3'-terminal nucleotide overhang having about 1 to about 4 (e.g., about 1, 2, 3, or 4) 2'-deoxynucleotides, wherein the overhang nucleotides can further comprise one or more (e.g., 1, 2, 3, or 4) phosphorothioate internucleotide linkages. Non-limiting examples of these chemically-modified siNAs are shown in FIGS. 18A-18F and 19A-19F and Table IV herein.

In another embodiment of the chemically-modified short interfering nucleic acid comprising a sense region and an antisense region, the sense region comprises one or more 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and one or more purine nucleotides selected from the group consisting of 2'-deoxy nucleotides, locked nucleic acid (LNA) nucleotides, 2'-methoxyethyl nucleotides, 4'-thionucleotides, and 2'-O-methyl nucleotides (e.g., wherein all purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides or alternately a plurality of purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides). The sense region can comprise inverted deoxy abasic modifications that are optionally present at the 3'-end, the 5'-end, or both of the 3' and 5'-ends of the sense region. The sense region can optionally further comprise a 3'-terminal overhang having about 1 to about 4 (e.g., about 1, 2, 3, or 4) 2'-deoxyribonucleotides. The antisense region comprises one or more 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and one or more purine nucleotides selected from the group consisting of 2'-deoxy nucleotides, locked nucleic acid (LNA) nucleotides, 2'-methoxyethyl nucleotides, 4'-thionucleotides, and 2'-O-methyl nucleotides (e.g., wherein all purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides or alternately a plurality of purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides). The antisense can also comprise a terminal cap modification, such as any modification described herein or shown in FIG. 22, that is optionally present at the 3'-end, the 5'-end, or both of the 3' and 5'-ends of the antisense sequence. The antisense region optionally further comprises a 3'-terminal nucleotide overhang having about 1 to about 4 (e.g., about 1, 2, 3, or 4) 2'-deoxynucleotides, wherein the overhang nucleotides can further comprise one or more (e.g., 1, 2, 3, or 4) phosphorothioate internucleotide linkages.

In another embodiment, any modified nucleotides present in the siNA molecules of the invention, preferably in the antisense strand of the siNA molecules of the invention, but also optionally in the sense and/or both antisense and sense strands, comprise modified nucleotides having properties or characteristics similar to naturally occurring ribonucleotides. For example, the invention features siNA molecules including modified nucleotides having a Northern conformation (e.g., Northern pseudorotation cycle, see for example Saenger, *Principles of Nucleic Acid Structure*, Springer-Verlag ed., 1984). As such, chemically modified nucleotides present in the siNA molecules of the invention, preferably in the antisense strand of the siNA molecules of the invention, but also optionally in the sense and/or both antisense and sense strands, are resistant to nuclease degradation while at the same time maintaining the capacity to mediate RNAi. Non-limiting examples of nucleotides having a northern configuration include locked nucleic acid (LNA) nucleotides (e.g., 2'-0,4'-C-methylene-(D-ribofuranosyl) nucleotides); 2'-methoxyethoxy (MOE) nucleotides; 2'-methyl-thio-ethyl, 2'-deoxy-2'-fluoro nucleotides, 2'-deoxy-2'-chloro nucleotides, 2'-azido nucleotides, and 2'-O-methyl nucleotides.

In one embodiment, the invention features a chemically-modified short interfering nucleic acid molecule (siNA) capable of mediating RNA interference (RNAi) inside a cell or reconstituted in vitro system, wherein the chemical modification comprises a conjugate attached to the chemically-modified siNA molecule. The conjugate can be attached to the chemically-modified siNA molecule via a covalent attachment. In one embodiment, the conjugate is attached to the chemically-modified siNA molecule via a biodegradable linker. In one embodiment, the conjugate molecule is attached at the 3'-end of either the sense strand, the antisense strand, or both strands of the chemically-modified siNA molecule. In another embodiment, the conjugate molecule is attached at the 5'-end of either the sense strand, the antisense strand, or both strands of the chemically-modified siNA molecule. In yet another embodiment, the conjugate molecule is attached both the 3'-end and 5'-end of either the sense strand, the antisense strand, or both strands of the chemically-modified siNA molecule, or any combination thereof. In one embodiment, the conjugate molecule of the invention comprises a molecule that facilitates delivery of a chemically-modified siNA molecule into a biological system, such as a cell. In another embodiment, the conjugate molecule attached to the chemically-modified siNA molecule is a poly ethylene glycol, human serum albumin, or a ligand for a cellular receptor that can mediate cellular uptake. Examples of specific conjugate molecules contemplated by the instant invention that can be attached to chemically-modified siNA molecules are described in Vargeese et al., U.S. Ser. No. 10/201,394, incorporated by reference herein. The type of conjugates used and the extent of conjugation of siNA molecules of the invention can be evaluated for improved pharmacokinetic profiles, bioavailability, and/or stability of siNA constructs while at the same time maintaining the ability of the siNA to mediate RNAi activity. As such, one skilled in the art can screen siNA constructs that are modified with various conjugates to determine whether the siNA conjugate complex possesses improved properties while maintaining the ability to mediate RNAi, for example in animal models as are generally known in the art.

In one embodiment, the invention features a chemically-modified short interfering nucleic acid (siNA) molecule of the invention capable of mediating RNA interference (RNAi) inside a cell or reconstituted in vitro system, wherein the chemically-modified siNA comprises a sense region, where one or more pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and where one or more purine nucleotides present in the sense region are 2'-deoxy purine nucleotides (e.g., wherein all purine nucleotides are 2'-deoxy purine nucleotides or alternately a plurality of purine nucleotides are 2'-deoxy purine nucleotides), and inverted deoxy abasic modifications that are optionally present at the 3'-end, the 5'-end, or both of the 3' and 5'-ends of the sense region, the sense region optionally further comprising a 3'-terminal overhang having about 1 to about 4 (e.g., about 1, 2, 3, or 4) 2'-deoxyribonucleotides; and wherein the chemically-modified short interfering nucleic acid molecule comprises an antisense region, where one or more pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein one or more purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides), and a terminal cap modification, such as any modification described herein or shown in FIG. 22, that is optionally present at the 3'-end, the 5'-end, or both of the 3' and 5'-ends of the antisense sequence, the antisense region optionally further comprising a 3'-terminal nucleotide overhang having about 1 to about 4 (e.g., about 1, 2, 3, or 4) 2'-deoxynucleotides, wherein the overhang nucleotides can further comprise one or more (e.g., 1, 2, 3, or 4) phosphorothioate internucleotide linkages. Non-limiting examples of these chemically-modified siNAs are shown in FIGS. 18A-18F and 19A-19F and Table IV herein.

In one embodiment, the invention features a chemically-modified short interfering nucleic acid (siNA) molecule of the invention capable of mediating RNA interference (RNAi) inside a cell or reconstituted in vitro system, wherein the chemically-modified siNA comprises a sense region, where one or more pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and where one or more purine nucleotides present in the sense region are 2'-O-methyl purine nucleotides (e.g., wherein all purine nucleotides are 2'-O-methyl purine nucleotides or alternately a plurality of purine nucleotides are 2'-O-methyl purine nucleotides), and inverted deoxy abasic modifications that are optionally present at the 3'-end, the 5'-end, or both of the 3' and 5'-ends of the sense region, the sense region optionally further comprising a 3'-terminal overhang having about 1 to about 4 (e.g., about 1, 2, 3, or 4) 2'-deoxyribonucleotides; and wherein the chemically-modified short interfering nucleic acid molecule comprises an antisense region, where one or more pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein one or more purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides), and a terminal cap modification, such as any modification described herein or shown in FIG. 22, that is optionally present at the 3'-end, the 5'-end, or both of the 3' and 5'-ends of the antisense sequence, the antisense region optionally further comprising a 3'-terminal nucleotide overhang having about 1 to about 4 (e.g., about 1, 2, 3, or 4) 2'-deoxynucleotides, wherein the overhang nucleotides can further comprise one or more (e.g., 1, 2, 3, or 4) phosphorothioate internucleotide linkages. Non-limiting examples of these chemically-modified siNAs are shown in FIGS. 18A-18F and 19A-19F and Table IV herein.

In one embodiment, the invention features a chemically-modified short interfering nucleic acid (siNA) molecule of the invention capable of mediating RNA interference (RNAi) inside a cell or reconstituted in vitro system, wherein the siNA comprises a sense region, where one or more pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and where one or more purine nucleotides present in the sense region are purine ribonucleotides (e.g., wherein all purine nucleotides are purine ribonucleotides or alternately a plurality of purine nucleotides are purine ribonucleotides), and inverted deoxy abasic modifications that are optionally present at the 3'-end, the 5'-end, or both of the 3' and 5'-ends of the sense region, the sense region optionally further comprising a 3'-terminal overhang having about 1 to about 4 (e.g., about 1, 2, 3, or 4) 2'-deoxyribonucleotides; and wherein the siNA comprises an antisense region, where one or more pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides), and a terminal cap modification, such as any modification described herein or shown in FIG. 22, that is optionally present at the 3'-end, the 5'-end, or both of the 3' and 5'-ends of the antisense sequence, the antisense region optionally further comprising a 3'-terminal nucleotide overhang having about 1 to about 4 (e.g., about 1, 2, 3, or 4) 2'-deoxynucleotides, wherein the overhang nucleotides can further comprise one or more (e.g., 1, 2, 3, or 4) phosphorothioate internucleotide linkages. Non-limiting examples of these chemically-modified siNAs are shown in FIGS. 18A-18F and 19A-19F and Table IV herein.

In one embodiment, the invention features a chemically-modified short interfering nucleic acid (siNA) molecule of the invention capable of mediating RNA interference (RNAi) inside a cell or reconstituted in vitro system, wherein the chemically-modified siNA comprises a sense region, where one or more pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and for example where one or more purine nucleotides present in the sense region are selected from the group consisting of 2'-deoxy nucleotides, locked nucleic acid (LNA) nucleotides, 2'-methoxyethyl nucleotides, 4'-thionucleotides, and 2'-O-methyl nucleotides (e.g., wherein all purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides or alternately a plurality of purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides), and wherein inverted deoxy abasic modifications are optionally present at the 3'-end, the 5'-end, or both of the 3' and 5'-ends of the sense region, the sense region optionally further comprising a 3'-terminal overhang having about 1 to about 4 (e.g., about 1, 2, 3, or 4) 2'-deoxyribonucleotides; and wherein the chemically-modified short interfering nucleic acid molecule comprises an antisense region, where one or more pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein one or more purine nucleotides present in the antisense region are selected from the group consisting of 2'-deoxy nucleotides, locked nucleic acid (LNA) nucleotides, 2'-methoxyethyl nucleotides, 4'-thionucleotides, and 2'-O-methyl nucleotides (e.g., wherein all purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides or alternately a plurality of purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides), and a terminal cap modification, such as any modification described herein or shown in FIG. 22, that is optionally present at the 3'-end, the 5'-end, or both of the 3' and 5'-ends of the antisense sequence, the antisense region optionally further comprising a 3'-terminal nucleotide overhang having about 1 to about 4 (e.g., about 1, 2, 3, or 4) 2'-deoxynucleotides, wherein the overhang nucleotides can further comprise one or more (e.g., 1, 2, 3, or 4) phosphorothioate internucleotide linkages.

In one embodiment, the invention features a short interfering nucleic acid (siNA) molecule of the invention, wherein the siNA further comprises a nucleotide, non-nucleotide, or mixed nucleotide/non-nucleotide linker that joins the sense region of the siNA to the antisense region of the siNA. In one embodiment, a nucleotide linker of the invention can be a linker of ≥2 nucleotides in length, for example 3, 4, 5, 6, 7, 8, 9, or 10 nucleotides in length. In another embodiment, the nucleotide linker can be a nucleic acid aptamer. By "aptamer" or "nucleic acid aptamer" as used herein is meant a nucleic acid molecule that binds specifically to a target molecule wherein the nucleic acid molecule has sequence that comprises a sequence recognized by the target molecule in its natural setting. Alternately, an aptamer can be a nucleic acid molecule that binds to a target molecule where the target molecule does not naturally bind to a nucleic acid. The target molecule can be any molecule of interest. For example, the aptamer can be used to bind to a ligand-binding domain of a protein, thereby preventing interaction of the naturally occurring ligand with the protein. This is a non-limiting example and those in the art will recognize that other embodiments can be readily generated using techniques generally known in the art (see, for example, Gold et al., 1995, *Annu. Rev. Biochem.*, 64, 763; Brody and Gold, 2000, *J. Biotechnol.*, 74, 5; Sun, 2000, *Curr. Opin. Mol. Ther.*, 2, 100; Kusser, 2000, *J. Biotechnol.*, 74, 27; Hermann and Patel, 2000, *Science*, 287, 820; and Jayasena, 1999, *Clinical Chemistry*, 45, 1628.)

In yet another embodiment, a non-nucleotide linker of the invention comprises abasic nucleotide, polyether, polyamine, polyamide, peptide, carbohydrate, lipid, polyhydrocarbon, or other polymeric compounds (e.g. polyethylene glycols such as those having between 2 and 100 ethylene glycol units). Specific examples include those described by Seela and Kaiser, *Nucleic Acids Res.* 1990, 18:6353 and *Nucleic Acids Res.* 1987, 15:3113; Cload and Schepartz, *J. Am. Chem. Soc.* 1991, 113:6324; Richardson and Schepartz, *J. Am. Chem. Soc.* 1991, 113:5109; Ma et al., *Nucleic Acids Res.* 1993, 21:2585 and *Biochemistry* 1993, 32:1751; Durand et al., *Nucleic Acids Res.* 1990, 18:6353; McCurdy et al., *Nucleosides & Nucleotides* 1991, 10:287; Jschke et al., *Tetrahedron Lett.* 1993, 34:301; Ono et al., *Biochemistry* 1991, 30:9914; Arnold et al., International Publication No. WO 89/02439; Usman et al., International Publication No. WO 95/06731; Dudycz et al., International Publication No. WO 95/11910 and Ferentz and Verdine, *J. Am. Chem. Soc.* 1991, 113:4000, all hereby incorporated by reference herein. A "non-nucleotide" further means any group or compound that can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymine, for example at the C1 position of the sugar.

In one embodiment, the invention features a chemically-modified short interfering nucleic acid molecule (siNA) capable of mediating RNA interference (RNAi) against a target gene inside a cell or reconstituted in vitro system, wherein the chemical modification comprises a conjugate covalently attached to the chemically-modified siNA molecule. Non-limiting examples of conjugates contemplated by the invention include conjugates and ligands described in Vargeese et al., U.S. Ser. No. 10/427,160, filed Apr. 30, 2003, incorporated by reference herein in its entirety, including the drawings. In another embodiment, the conjugate is covalently attached to the chemically-modified siNA molecule via a biodegradable linker. In one embodiment, the conjugate molecule is attached at the 3'-end of either the sense strand, the antisense strand, or both strands of the chemically-modified siNA molecule. In another embodiment, the conjugate molecule is attached at the 5'-end of either the sense strand, the antisense strand, or both strands of the chemically-modified siNA molecule. In yet another embodiment, the conjugate molecule is attached both the 3'-end and 5'-end of either the sense strand, the antisense strand, or both strands of the chemically-modified siNA molecule, or any combination thereof. In one embodiment, a conjugate molecule of the invention comprises a molecule that facilitates delivery of a chemically-modified siNA molecule into a biological system, such as a cell. In another embodiment, the conjugate molecule attached to the chemically-modified siNA molecule is a polyethylene glycol, human serum albumin, or a ligand for a cellular receptor that can mediate cellular uptake. Examples of specific conjugate molecules contemplated by the instant invention that can be attached to chemically-modified siNA molecules are described in Vargeese et al., U.S. Ser. No. 10/201,394, incorporated by reference herein. The type of conjugates used and the extent of conjugation of siNA molecules of the invention can be evaluated for improved pharmacokinetic profiles, bioavailability, and/or stability of siNA constructs while at the same time maintaining the ability of the siNA to mediate RNAi activity. As such, one skilled in the art can screen siNA constructs that are modified with various conjugates to determine whether the siNA conjugate complex possesses improved properties while maintaining the ability to mediate RNAi, for example in animal models as are generally known in the art.

In one embodiment, the invention features a short interfering nucleic acid (siNA) molecule capable of mediating RNA interference (RNAi) inside a cell or reconstituted in vitro system, wherein one or both strands of the siNA molecule that are assembled from two separate oligonucleotides do not comprise any ribonucleotides. For example, a siNA molecule can be assembled from a single oligonculeotide where the sense and antisense regions of the siNA comprise separate oligonucleotides that do not have any ribonucleotides (e.g., nucleotides having a 2'-OH group) present in the oligonucleotides. In another example, a siNA molecule can be assembled from a single oligonculeotide where the sense and antisense regions of the siNA are linked or circularized by a nucleotide or non-nucleotide linker as described herein, wherein the oligonucleotide does not have any ribonucleotides (e.g., nucleotides having a 2'-OH group) present in the oligonucleotide. Applicant has surprisingly found that the presense of ribonucleotides (e.g., nucleotides having a 2'-hydroxyl group) within the siNA molecule is not required or essential to support RNAi activity. As such, in one embodiment, all positions within the siNA can include chemically modified nucleotides and/or non-nucleotides such as nucleotides and or non-nucleotides having Formula I, II, III, IV, V, VI, or VII or any combination thereof to the extent that the ability of the siNA molecule to support RNAi activity in a cell is maintained.

In one embodiment, the invention features a siNA molecule that does not require the presence of a 2'-OH group (ribonucleotide) to be present with the siNA molecule to support RNA interference.

In one embodiment, a siNA molecule of the invention is a single stranded siNA molecule that mediates RNAi activity in a cell or reconstituted in vitro system, wherein the siNA molecule comprises a single stranded polynucleotide having complementarity to a target nucleic acid sequence. In another embodiment, the single stranded siNA molecule of the invention comprises a 5'-terminal phosphate group. In another embodiment, the single stranded siNA molecule of the invention comprises a 5'-terminal phosphate group and a 3'-terminal phosphate group (e.g., a 2',3'-cyclic phosphate). In another embodiment, the single stranded siNA molecule of the invention comprises about 19 to about 29 (e.g., about 19, 20, 21, 22, 23, 24, 25, 26, 27, 28, or 29) nucleotides. In yet another embodiment, the single stranded siNA molecule of the invention comprises one or more chemically modified nucleotides or non-nucleotides described herein. For example, all the positions within the siNA molecule can include chemically-modified nucleotides such as nucleotides having any of Formulae I-VII, or any combination thereof to the extent that the ability of the siNA molecule to support RNAi activity in a cell is maintained.

In one embodiment, the single stranded siNA molecule having complementarity to a target nucleic acid sequence comprises one or more 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and one or more 2'-O-methyl purine nucleotides (e.g., wherein all purine nucleotides are 2'-O-methyl purine nucleotides or alternately a plurality of purine nucleotides are 2'-O-methyl purine nucleotides). In another embodiment, the single stranded siNA molecule comprises one or more 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and one or more 2'-deoxy purine nucleotides (e.g., wherein all purine nucleotides are 2'-deoxy purine nucleotides or alternately a plurality of purine nucleotides are 2'-deoxy purine nucleotides). In another embodiment, the single stranded siNA molecule comprises one or more 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), wherein any purine nucleotides present in the antisense region are locked nucleic acid (LNA) nucleotides (e.g., wherein all purine nucleotides are LNA nucleotides or alternately a plurality of purine nucleotides are LNA nucleotides). In another embodiment, the single stranded siNA molecule comprises one or more 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and one or more 2'-methoxyethyl purine nucleotides (e.g., wherein all purine nucleotides are 2'-methoxyethyl purine nucleotides or alternately a plurality of purine nucleotides are 2'-methoxyethyl purine nucleotides), the single stranded siNA can comprise a terminal cap modification, such as any modification described herein or shown in FIG. 22, that is optionally present at the 3'-end, the 5'-end, or both of the 3' and 5'-ends of the antisense sequence. The single stranded siNA optionally further comprises about 1 to about 4 (e.g., about 1, 2, 3, or 4) terminal 2'-deoxynucleotides at the 3'-end of the siNA molecule, wherein the terminal nucleotides can further comprise one or more (e.g., 1, 2, 3, or 4) phosphorothioate internucleotide linkages. The single stranded siNA optionally further comprises a terminal phosphate group, such as a 5'-terminal phosphate group.

In one embodiment, a siNA molecule of the invention is a single stranded siNA molecule that mediates RNAi activity in a cell or reconstituted in vitro system, wherein the siNA molecule comprises a single stranded polynucleotide having complementarity to a target nucleic acid sequence, and wherein one or more pyrimidine nucleotides present in the siNA are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides), and a terminal cap modification, such as any modification described herein or shown in FIG. 22, that is optionally present at the 3'-end, the 5'-end, or both of the 3' and 5'-ends of the antisense sequence. The siNA optionally further comprises about 1 to about 4 or more (e.g., about 1, 2, 3, 4 or more) terminal 2'-deoxynucleotides at the 3'-end of the siNA molecule, wherein the terminal nucleotides can further comprise one or more (e.g., 1, 2, 3, 4 or more) phosphorothioate, phosphonoacetate, and/or thiophosphonoacetate internucleotide linkages, and wherein the siNA optionally further comprises a terminal phosphate group, such as a 5'-terminal phosphate group. In any of these embodiments, any purine nucleotides present in the antisense region are alternatively 2'-deoxy purine nucleotides (e.g., wherein all purine nucleotides are 2'-deoxy purine nucleotides or alternately a plurality of purine nucleotides are 2'-deoxy purine nucleotides). Also, in any of these embodiments, any purine nucleotides present in the siNA (i.e., purine nucleotides present in the sense and/or antisense region) can alternatively be locked nucleic acid (LNA) nucleotides (e.g., wherein all purine nucleotides are LNA nucleotides or alternately a plurality of purine nucleotides are LNA nucleotides). Also, in any of these embodiments, any purine nucleotides present in the siNA are alternatively 2'-methoxyethyl purine nucleotides (e.g., wherein all purine nucleotides are 2'-methoxyethyl purine nucleotides or alternately a plurality of purine nucleotides are 2'-methoxyethyl purine nucleotides). In another embodiment, any modified nucleotides present in the single stranded siNA molecules of the invention comprise modified nucleotides having properties or characteristics similar to naturally occurring ribonucleotides. For example, the invention features siNA molecules including modified nucleotides having a Northern conformation (e.g., Northern pseudorotation cycle, see for example Saenger, *Principles of Nucleic Acid Structure*, Springer-Verlag ed., 1984). As such, chemically modified nucleotides present in the single stranded siNA molecules of the invention are preferably resistant to nuclease degradation while at the same time maintaining the capacity to mediate RNAi In one embodiment, a siNA molecule of the invention is a single stranded siNA molecule that mediates RNAi activity in a cell or reconstituted in vitro system, wherein the siNA molecule comprises a single stranded polynucleotide having complementarity to a target nucleic acid sequence, and wherein one or more pyrimidine nucleotides present in the siNA are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any purine nucleotides present in the siNA are 2'-O-methyl purine nucleotides (e.g., wherein all purine nucleotides are 2'-O-methyl purine nucleotides or alternately a plurality of purine nucleotides are 2'-O-methyl purine nucleotides), and a terminal cap modification, such as any modification described herein or shown in FIG. 22, that is optionally present at the 3'-end, the 5'-end, or both of the 3' and 5'-ends of the antisense sequence, the siNA optionally further comprising about 1 to about 4 (e.g., about 1, 2, 3, or 4) terminal 2'-deoxynucleotides at the 3'-end of the siNA molecule, wherein the terminal nucleotides can further comprise one or more (e.g., 1, 2, 3, or 4) phosphorothioate internucleotide linkages, and wherein the siNA optionally further comprises a terminal phosphate group, such as a 5'-terminal phosphate group.

In one embodiment, a siNA molecule of the invention is a single stranded siNA molecule that mediates RNAi activity in a cell or reconstituted in vitro system, wherein the siNA molecule comprises a single stranded polynucleotide having complementarity to a target nucleic acid sequence, and wherein one or more pyrimidine nucleotides present in the siNA are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any purine nucleotides present in the siNA are 2'-deoxy purine nucleotides (e.g., wherein all purine nucleotides are 2'-deoxy purine nucleotides or alternately a plurality of purine nucleotides are 2'-deoxy purine nucleotides), and a terminal cap modification, such as any modification described herein or shown in FIG. 22, that is optionally present at the 3'-end, the 5'-end, or both of the 3' and 5'-ends of the antisense sequence, the siNA optionally further comprising about 1 to about 4 (e.g., about 1, 2, 3, or 4) terminal 2'-deoxynucleotides at the 3'-end of the siNA molecule, wherein the terminal nucleotides can further comprise one or more (e.g., 1, 2, 3, or 4) phosphorothioate internucleotide linkages, and wherein the siNA optionally further comprises a terminal phosphate group, such as a 5'-terminal phosphate group.

In one embodiment, a siNA molecule of the invention is a single stranded siNA molecule that mediates RNAi activity in a cell or reconstituted in vitro system, wherein the siNA molecule comprises a single stranded polynucleotide having complementarity to a target nucleic acid sequence, and wherein one or more pyrimidine nucleotides present in the siNA are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any purine nucleotides present in the siNA are locked nucleic acid (LNA) nucleotides (e.g., wherein all purine nucleotides are LNA nucleotides or alternately a plurality of purine nucleotides are LNA nucleotides), and a terminal cap modification, such as any modification described herein or shown in FIG. 22, that is optionally present at the 3'-end, the 5'-end, or both of the 3' and 5'-ends of the antisense sequence, the siNA optionally further comprising about 1 to about 4 (e.g., about 1, 2, 3, or 4) terminal 2'-deoxynucleotides at the 3'-end of the siNA molecule, wherein the terminal nucleotides can further comprise one or more (e.g., 1, 2, 3, or 4) phosphorothioate internucleotide linkages, and wherein the siNA optionally further comprises a terminal phosphate group, such as a 5'-terminal phosphate group.

In one embodiment, a siNA molecule of the invention is a single stranded siNA molecule that mediates RNAi activity in a cell or reconstituted in vitro system, wherein the siNA molecule comprises a single stranded polynucleotide having complementarity to a target nucleic acid sequence, and wherein one or more pyrimidine nucleotides present in the siNA are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any purine nucleotides present in the siNA are 2'-methoxyethyl purine nucleotides (e.g., wherein all purine nucleotides are 2'-methoxyethyl purine nucleotides or alternately a plurality of purine nucleotides are 2'-methoxyethyl purine nucleotides), and a terminal cap modification, such as any modification described herein or shown in FIG. 22, that is optionally present at the 3'-end, the 5'-end, or both of the 3' and 5'-ends of the antisense sequence, the siNA optionally further comprising about 1 to about 4 (e.g., about 1, 2, 3, or 4) terminal 2'-deoxynucleotides at the 3'-end of the siNA molecule, wherein the terminal nucleotides can further comprise one or more (e.g., 1, 2, 3, or 4) phosphorothioate internucleotide linkages, and wherein the siNA optionally further comprises a terminal phosphate group, such as a 5'-terminal phosphate group.

In another embodiment, any modified nucleotides present in the single stranded siNA molecules of the invention comprise modified nucleotides having properties or characteristics similar to naturally occurring ribonucleotides. For example, the invention features siNA molecules including modified nucleotides having a Northern conformation (e.g., Northern pseudorotation cycle, see for example Saenger, *Principles of Nucleic Acid Structure*, Springer-Verlag ed., 1984). As such, chemically modified nucleotides present in the single stranded siNA molecules of the invention are preferably resistant to nuclease degradation while at the same time maintaining the capacity to mediate RNAi.

In one embodiment, the invention features a method for modulating the expression of a gene within a cell comprising: (a) synthesizing a siNA molecule of the invention, which can be chemically-modified, wherein one of the siNA strands comprises a sequence complementary to RNA of the gene; and (b) introducing the siNA molecule into a cell under conditions suitable to modulate the expression of the gene in the cell.

In one embodiment, the invention features a method for modulating the expression of a gene within a cell comprising: (a) synthesizing a siNA molecule of the invention, which can be chemically-modified, wherein one of the siNA strands comprises a sequence complementary to RNA of the gene and wherein the sense strand sequence of the siNA comprises a sequence substantially similar to the sequence of the target RNA; and (b) introducing the siNA molecule into a cell under conditions suitable to modulate the expression of the gene in the cell.

In another embodiment, the invention features a method for modulating the expression of more than one gene within a cell comprising: (a) synthesizing siNA molecules of the invention, which can be chemically-modified, wherein one of the siNA strands comprises a sequence complementary to RNA of the genes; and (b) introducing the siNA molecules into a cell under conditions suitable to modulate the expression of the genes in the cell.

In another embodiment, the invention features a method for modulating the expression of more than one gene within a cell comprising: (a) synthesizing a siNA molecule of the invention, which can be chemically-modified, wherein one of the siNA strands comprises a sequence complementary to RNA of the gene and wherein the sense strand sequence of the siNA comprises a sequence substantially similar to the sequence of the target RNA; and (b) introducing the siNA molecules into a cell under conditions suitable to modulate the expression of the genes in the cell.

In one embodiment, siNA molecules of the invention are used as reagents in ex vivo applications. For example, siNA reagents are introduced into tissue or cells that are transplanted into a subject for therapeutic effect. The cells and/or tissue can be derived from an organism or subject that later receives the explant, or can be derived from another organism or subject prior to transplantation. The siNA molecules can be used to modulate the expression of one or more genes in the cells or tissue, such that the cells or tissue obtain a desired phenotype or are able to perform a function when transplanted in vivo. In one embodiment, certain target cells from a patient are extracted. These extracted cells are contacted with siNAs targeting a specific nucleotide sequence within the cells under conditions suitable for uptake of the siNAs by these cells (e.g. using delivery reagents such as cationic lipids, liposomes and the like or using techniques such as electroporation to facilitate the delivery of siNAs into cells). The cells are then reintroduced back into the same patient or other patients. Non-limiting examples of ex vivo applications include use in organ/tissue transplant, tissue grafting, or treatment of pulmonary disease (e.g., restenosis) or prevent neointimal hyperplasia and atherosclerosis in vein grafts. Such ex vivo applications may also used to treat conditions associated with coronary and peripheral bypass graft failure, for example, such methods can be used in conjunction with peripheral vascular bypass graft surgery and coronary artery bypass graft surgery. Additional applications include transplants to treat CNS lesions or injury, including use in treatment of neurodegenerative conditions such as Alzheimer's disease, Parkinson's Disease, Epilepsy, Dementia, Huntington's disease, or amyotrophic lateral sclerosis (ALS).

In one embodiment, the invention features a method of modulating the expression of a gene in a tissue explant comprising: (a) synthesizing a siNA molecule of the invention, which can be chemically-modified, wherein one of the siNA strands comprises a sequence complementary to RNA of the gene; and (b) introducing the siNA molecule into a cell of the tissue explant derived from a particular organism under conditions suitable to modulate the expression of the gene in the tissue explant. In another embodiment, the method further comprises introducing the tissue explant back into the organism the tissue was derived from or into another organism under conditions suitable to modulate the expression of the gene in that organism.

In one embodiment, the invention features a method of modulating the expression of a gene in a tissue explant comprising: (a) synthesizing a siNA molecule of the invention, which can be chemically-modified, wherein one of the siNA strands comprises a sequence complementary to RNA of the gene and wherein the sense strand sequence of the siNA comprises a sequence substantially similar to the sequence of the target RNA; and (b) introducing the siNA molecule into a cell of the tissue explant derived from a particular organism under conditions suitable to modulate the expression of the gene in the tissue explant. In another embodiment, the method further comprises introducing the tissue explant back into the organism the tissue was derived from or into another organism under conditions suitable to modulate the expression of the gene in that organism.

In another embodiment, the invention features a method of modulating the expression of more than one gene in a tissue explant comprising: (a) synthesizing siNA molecules of the invention, which can be chemically-modified, wherein one of the siNA strands comprises a sequence complementary to RNA of the genes; and (b) introducing the siNA molecules into a cell of the tissue explant derived from a particular organism under conditions suitable to modulate the expression of the genes in the tissue explant. In another embodiment, the method further comprises introducing the tissue explant back into the organism the tissue was derived from or into another organism under conditions suitable to modulate the expression of the genes in that organism.

In one embodiment, the invention features a method of modulating the expression of a gene in an organism comprising: (a) synthesizing a siNA molecule of the invention, which can be chemically-modified, wherein one of the siNA strands comprises a sequence complementary to RNA of the gene; and (b) introducing the siNA molecule into the organism under conditions suitable to modulate the expression of the gene in the organism.

In another embodiment, the invention features a method of modulating the expression of more than one gene in an organism comprising: (a) synthesizing siNA molecules of the invention, which can be chemically-modified, wherein one of the siNA strands comprises a sequence complementary to RNA of the genes; and (b) introducing the siNA molecules into the organism under conditions suitable to modulate the expression of the genes in the organism.

In one embodiment, the invention features a method for modulating the expression of a gene within a cell comprising: (a) synthesizing a siNA molecule of the invention, which can be chemically-modified, wherein the siNA comprises a single stranded sequence having complementarity to RNA of the gene; and (b) introducing the siNA molecule into a cell under conditions suitable to modulate the expression of the gene in the cell.

In one embodiment, the invention features a method of modulating the expression of a target gene in an tissue or organ comprising: (a) synthesizing a siNA molecule of the invention, which can be chemically-modified, wherein the siNA comprises a single stranded sequence having complementarity to RNA of the target gene; and (b) introducing the siNA molecule into the tissue or organ under conditions suitable to modulate the expression of the target gene in the organism. In another embodiment, the tissue is ocular tissue and the organ is the eye. In another embodiment, the tissue comprises hepatocytes and/or hepatic tissue and the organ is the liver.

In another embodiment, the invention features a method for modulating the expression of more than one gene within a cell comprising: (a) synthesizing siNA molecules of the invention, which can be chemically-modified, wherein the siNA comprises a single stranded sequence having complementarity to RNA of the gene; and (b) contacting the siNA molecule with a cell in vitro or in vivo under conditions suitable to modulate the expression of the genes in the cell.

In one embodiment, the invention features a method of modulating the expression of a gene in a tissue explant comprising: (a) synthesizing a siNA molecule of the invention, which can be chemically-modified, wherein the siNA comprises a single stranded sequence having complementarity to RNA of the gene; and (b) contacting the siNA molecule with a cell of the tissue explant derived from a particular organism under conditions suitable to modulate the expression of the gene in the tissue explant. In another embodiment, the method further comprises introducing the tissue explant back into the organism the tissue was derived from or into another organism under conditions suitable to modulate the expression of the gene in that organism.

In another embodiment, the invention features a method of modulating the expression of more than one gene in a tissue explant comprising: (a) synthesizing siNA molecules of the invention, which can be chemically-modified, wherein the siNA comprises a single stranded sequence having complementarity to RNA of the gene; and (b) introducing the siNA molecules into a cell of the tissue explant derived from a particular organism under conditions suitable to modulate the expression of the genes in the tissue explant. In another embodiment, the method further comprises introducing the tissue explant back into the organism the tissue was derived from or into another organism under conditions suitable to modulate the expression of the genes in that organism.

In one embodiment, the invention features a method of modulating the expression of a gene in an organism comprising: (a) synthesizing a siNA molecule of the invention, which can be chemically-modified, wherein the siNA comprises a single stranded sequence having complementarity to RNA of the gene; and (b) introducing the siNA molecule into the organism under conditions suitable to modulate the expression of the gene in the organism.

In another embodiment, the invention features a method of modulating the expression of more than one gene in an organism comprising: (a) synthesizing siNA molecules of the invention, which can be chemically-modified, wherein the siNA comprises a single stranded sequence having complementarity to RNA of the gene; and (b) introducing the siNA molecules into the organism under conditions suitable to modulate the expression of the genes in the organism.

In one embodiment, the invention features a method of modulating the expression of a gene in an organism comprising contacting the organism with a siNA molecule of the invention under conditions suitable to modulate the expression of the gene in the organism.

In another embodiment, the invention features a method of modulating the expression of more than one gene in an organism comprising contacting the organism with one or more siNA molecules of the invention under conditions suitable to modulate the expression of the genes in the organism.

The siNA molecules of the invention can be designed to down regulate or inhibit target gene expression through RNAi targeting of a variety of RNA molecules. In one embodiment, the siNA molecules of the invention are used to target various RNAs corresponding to a target gene. Non-limiting examples of such RNAs include messenger RNA (mRNA), alternate RNA splice variants of target gene(s), post-transcriptionally modified RNA of target gene(s), pre-mRNA of target gene(s), and/or RNA templates. If alternate splicing produces a family of transcripts that are distinguished by usage of appropriate exons, the instant invention can be used to inhibit gene expression through the appropriate exons to specifically inhibit or to distinguish among the functions of gene family members. For example, a protein that contains an alternatively spliced transmembrane domain can be expressed in both membrane bound and secreted forms. Use of the invention to target the exon containing the transmembrane domain can be used to determine the functional consequences of pharmaceutical targeting of membrane bound as opposed to the secreted form of the protein. Non-limiting examples of applications of the invention relating to targeting these RNA molecules include therapeutic pharmaceutical applications, pharmaceutical discovery applications, molecular diagnostic and gene function applications, and gene mapping, for example using single nucleotide polymorphism mapping with siNA molecules of the invention. Such applications can be implemented using known gene sequences or from partial sequences available from an expressed sequence tag (EST).

In another embodiment, the siNA molecules of the invention are used to target conserved sequences corresponding to a gene family or gene families. As such, siNA molecules targeting multiple gene targets can provide increased therapeutic effect. In addition, siNA can be used to characterize pathways of gene function in a variety of applications. For example, the present invention can be used to inhibit the activity of target gene(s) in a pathway to determine the function of uncharacterized gene(s) in gene function analysis, mRNA function analysis, or translational analysis. The invention can be used to determine potential target gene pathways involved in various diseases and conditions toward pharmaceutical development. The invention can be used to understand pathways of gene expression involved in, for example, in development, such as prenatal development and postnatal development, and/or the progression and/or maintenance of cancer, infectious disease, autoimmunity, inflammation, endocrine disorders, renal disease, pulmonary disease, cardiovascular disease, birth defects, ageing, any other disease or condition related to gene expression.

In one embodiment, siNA molecule(s) and/or methods of the invention are used to down-regulate or inhibit the expression of gene(s) that encode RNA referred to by Genbank Accession, for example genes encoding RNA sequence(s) referred to herein by Genbank Accession number.

In one embodiment, the invention features a method comprising: (a) generating a library of siNA constructs having a predetermined complexity; and (b) assaying the siNA constructs of (a) above, under conditions suitable to determine RNAi target sites within the target RNA sequence. In one embodiment, the siNA molecules of (a) have strands of a fixed length, for example, about 23 nucleotides in length. In another embodiment, the siNA molecules of (a) are of differing length, for example having strands of about 19 to about 25 (e.g., about 19, 20, 21, 22, 23, 24, or 25) nucleotides in length. In one embodiment, the assay can comprise a reconstituted in vitro siNA assay as described herein. In another embodiment, the assay can comprise a cell culture system in which target RNA is expressed. In another embodiment, fragments of target RNA are analyzed for detectable levels of cleavage, for example by gel electrophoresis, northern blot analysis, or RNAse protection assays, to determine the most suitable target site(s) within the target RNA sequence. The target RNA sequence can be obtained as is known in the art, for example, by cloning and/or transcription for in vitro systems, and by cellular expression in in vivo systems.

In one embodiment, the invention features a method comprising: (a) generating a randomized library of siNA constructs having a predetermined complexity, such as of $4^N$, where N represents the number of base paired nucleotides in each of the siNA construct strands (eg. for a siNA construct having 21 nucleotide sense and antisense strands with 19 base pairs, the complexity would be $4^{19}$); and (b) assaying the siNA constructs of (a) above, under conditions suitable to determine RNAi target sites within the target RNA sequence. In another embodiment, the siNA molecules of (a) have strands of a fixed length, for example about 23 nucleotides in length. In yet another embodiment, the siNA molecules of (a) are of differing length, for example having strands of about 19 to about 25 (e.g., about 19, 20, 21, 22, 23, 24, or 25) nucleotides in length. In one embodiment, the assay can comprise a reconstituted in vitro siNA assay as described in Example 7 herein. In another embodiment, the assay can comprise a cell culture system in which target RNA is expressed. In another embodiment, fragments of target RNA are analyzed for detectable levels of cleavage, for example by gel electrophoresis, northern blot analysis, or RNAse protection assays, to determine the most suitable target site(s) within the target RNA sequence. In another embodiment, the target RNA sequence can be obtained as is known in the art, for example, by cloning and/or transcription for in vitro systems, and by cellular expression in in vivo systems.

In another embodiment, the invention features a method comprising: (a) analyzing the sequence of a RNA target encoded by a target gene; (b) synthesizing one or more sets of siNA molecules having sequence complementary to one or more regions of the RNA of (a); and (c) assaying the siNA molecules of (b) under conditions suitable to determine RNAi targets within the target RNA sequence. In one embodiment, the siNA molecules of (b) have strands of a fixed length, for example about 23 nucleotides in length. In another embodiment, the siNA molecules of (b) are of differing length, for example having strands of about 19 to about 25 (e.g., about 19, 20, 21, 22, 23, 24, or 25) nucleotides in length. In one embodiment, the assay can comprise a reconstituted in vitro siNA assay as described herein. In another embodiment, the assay can comprise a cell culture system in which target RNA is expressed. Fragments of target RNA are analyzed for detectable levels of cleavage, for example by gel electrophoresis, northern blot analysis, or RNAse protection assays, to determine the most suitable target site(s) within the target RNA sequence. The target RNA sequence can be obtained as is known in the art, for example, by cloning and/or transcription for in vitro systems, and by expression in in vivo systems.

By "target site" is meant a sequence within a target RNA that is "targeted" for cleavage mediated by a siNA construct which contains sequences within its antisense region that are complementary to the target sequence.

By "detectable level of cleavage" is meant cleavage of target RNA (and formation of cleaved product RNAs) to an extent sufficient to discern cleavage products above the background of RNAs produced by random degradation of the target RNA. Production of cleavage products from 1-5% of the target RNA is sufficient to detect above the background for most methods of detection.

In one embodiment, the invention features a composition comprising a siNA molecule of the invention, which can be chemically-modified, in a pharmaceutically acceptable carrier or diluent. In another embodiment, the invention features a pharmaceutical composition comprising siNA molecules of the invention, which can be chemically-modified, targeting one or more genes in a pharmaceutically acceptable carrier or diluent. In another embodiment, the invention features a method for diagnosing a disease or condition in a subject comprising administering to the subject a composition of the invention under conditions suitable for the diagnosis of the disease or condition in the subject. In another embodiment, the invention features a method for treating or preventing a disease or condition in a subject, comprising administering to the subject a composition of the invention under conditions suitable for the treatment or prevention of the disease or condition in the subject, alone or in conjunction with one or more other therapeutic compounds. In yet another embodiment, the invention features a method for reducing or preventing tissue rejection in a subject comprising administering to the subject a composition of the invention under conditions suitable for the reduction or prevention of tissue rejection in the subject.

In another embodiment, the invention features a method for validating a gene target, comprising: (a) synthesizing a siNA molecule of the invention, which can be chemically-modified, wherein one of the siNA strands includes a sequence complementary to RNA of a target gene; (b) introducing the siNA molecule into a cell, tissue, or organism under conditions suitable for modulating expression of the target gene in the cell, tissue, or organism; and (c) determining the function of the gene by assaying for any phenotypic change in the cell, tissue, or organism.

In another embodiment, the invention features a method for validating a target gene comprising: (a) synthesizing a siNA molecule of the invention, which can be chemically-modified, wherein one of the siNA strands includes a sequence complementary to RNA of a target gene; (b) introducing the siNA molecule into a biological system under conditions suitable for modulating expression of the target gene in the biological system; and (c) determining the function of the gene by assaying for any phenotypic change in the biological system.

By "biological system" is meant, material, in a purified or unpurified form, from biological sources, including but not limited to human, animal, plant, insect, bacterial, viral or other sources, wherein the system comprises the components required for RNAi activity. The term "biological system" includes, for example, a cell, tissue, or organism, or extract thereof. The term biological system also includes reconstituted RNAi systems that can be used in an in vitro setting.

By "phenotypic change" is meant any detectable change to a cell that occurs in response to contact or treatment with a nucleic acid molecule of the invention (e.g., siNA). Such detectable changes include, but are not limited to, changes in shape, size, proliferation, motility, protein expression or RNA expression or other physical or chemical changes as can be assayed by methods known in the art. The detectable change can also include expression of reporter genes/molecules such as Green Florescent Protein (GFP) or various tags that are used to identify an expressed protein or any other cellular component that can be assayed.

In one embodiment, the invention features a kit containing a siNA molecule of the invention, which can be chemically-modified, that can be used to modulate the expression of a target gene in biological system, including, for example, in a cell, tissue, or organism. In another embodiment, the invention features a kit containing more than one siNA molecule of the invention, which can be chemically-modified, that can be used to modulate the expression of more than one target gene in a biological system, including, for example, in a cell, tissue, or organism.

In one embodiment, the invention features a kit containing a siNA molecule of the invention, which can be chemically-modified, that can be used to modulate the expression of a target gene in a biological system. In another embodiment, the invention features a kit containing more than one siNA molecule of the invention, which can be chemically-modified, that can be used to modulate the expression of more than one target gene in a biological system.

In one embodiment, the invention features a cell containing one or more siNA molecules of the invention, which can be chemically-modified. In another embodiment, the cell containing a siNA molecule of the invention is a mammalian cell. In yet another embodiment, the cell containing a siNA molecule of the invention is a human cell.

In one embodiment, the synthesis of a siNA molecule of the invention, which can be chemically-modified, comprises: (a) synthesis of two complementary strands of the siNA molecule; (b) annealing the two complementary strands together under conditions suitable to obtain a double-stranded siNA molecule. In another embodiment, synthesis of the two complementary strands of the siNA molecule is by solid phase oligonucleotide synthesis. In yet another embodiment, synthesis of the two complementary strands of the siNA molecule is by solid phase tandem oligonucleotide synthesis.

In one embodiment, the invention features a method for synthesizing a siNA duplex molecule comprising: (a) synthesizing a first oligonucleotide sequence strand of the siNA molecule, wherein the first oligonucleotide sequence strand comprises a cleavable linker molecule that can be used as a scaffold for the synthesis of the second oligonucleotide sequence strand of the siNA; (b) synthesizing the second oligonucleotide sequence strand of siNA on the scaffold of the first oligonucleotide sequence strand, wherein the second oligonucleotide sequence strand further comprises a chemical moiety than can be used to purify the siNA duplex; (c) cleaving the linker molecule of (a) under conditions suitable for the two siNA oligonucleotide strands to hybridize and form a stable duplex; and (d) purifying the siNA duplex utilizing the chemical moiety of the second oligonucleotide sequence strand. In one embodiment, cleavage of the linker molecule in (c) above takes place during deprotection of the oligonucleotide, for example, under hydrolysis conditions using an alkylamine base such as methylamine. In one embodiment, the method of synthesis comprises solid phase synthesis on a solid support such as controlled pore glass (CPG) or polystyrene, wherein the first sequence of (a) is synthesized on a cleavable linker, such as a succinyl linker, using the solid support as a scaffold. The cleavable linker in (a) used as a scaffold for synthesizing the second strand can comprise similar reactivity as the solid support derivatized linker, such that cleavage of the solid support derivatized linker and the cleavable linker of (a) takes place concomitantly. In another embodiment, the chemical moiety of (b) that can be used to isolate the attached oligonucleotide sequence comprises a trityl group, for example a dimethoxytrityl group, which can be employed in a trityl-on synthesis strategy as described herein. In yet another embodiment, the chemical moiety, such as a dimethoxytrityl group, is removed during purification, for example, using acidic conditions.

In a further embodiment, the method for siNA synthesis is a solution phase synthesis or hybrid phase synthesis wherein both strands of the siNA duplex are synthesized in tandem using a cleavable linker attached to the first sequence which acts a scaffold for synthesis of the second sequence. Cleavage of the linker under conditions suitable for hybridization of the separate siNA sequence strands results in formation of the double-stranded siNA molecule.

In another embodiment, the invention features a method for synthesizing a siNA duplex molecule comprising: (a) synthesizing one oligonucleotide sequence strand of the siNA molecule, wherein the sequence comprises a cleavable linker molecule that can be used as a scaffold for the synthesis of another oligonucleotide sequence; (b) synthesizing a second oligonucleotide sequence having complementarity to the first sequence strand on the scaffold of (a), wherein the second sequence comprises the other strand of the double-stranded siNA molecule and wherein the second sequence further comprises a chemical moiety than can be used to isolate the attached oligonucleotide sequence; (c) purifying the product of (b) utilizing the chemical moiety of the second oligonucleotide sequence strand under conditions suitable for isolating the full-length sequence comprising both siNA oligonucleotide strands connected by the cleavable linker and under conditions suitable for the two siNA oligonucleotide strands to hybridize and form a stable duplex. In one embodiment, cleavage of the linker molecule in (c) above takes place during deprotection of the oligonucleotide, for example under hydrolysis conditions. In another embodiment, cleavage of the linker molecule in (c) above takes place after deprotection of the oligonucleotide. In another embodiment, the method of synthesis comprises solid phase synthesis on a solid support such as controlled pore glass (CPG) or polystyrene, wherein the first sequence of (a) is synthesized on a cleavable linker, such as a succinyl linker, using the solid support as a scaffold. The cleavable linker in (a) used as a scaffold for synthesizing the second strand can comprise similar reactivity or differing reactivity as the solid support derivatized linker, such that cleavage of the solid support derivatized linker and the cleavable linker of (a) takes place either concomitantly or sequentially. In one embodiment, the chemical moiety of (b) that can be used to isolate the attached oligonucleotide sequence comprises a trityl group, for example a dimethoxytrityl group.

In another embodiment, the invention features a method for making a double-stranded siNA molecule in a single synthetic process comprising: (a) synthesizing an oligonucleotide having a first and a second sequence, wherein the first sequence is complementary to the second sequence, and the first oligonucleotide sequence is linked to the second sequence via a cleavable linker, and wherein a terminal 5'-protecting group, for example, a 5'-O-dimethoxytrityl group (5'-O-DMT) remains on the oligonucleotide having the second sequence; (b) deprotecting the oligonucleotide whereby the deprotection results in the cleavage of the linker joining the two oligonucleotide sequences; and (c) purifying the product of (b) under conditions suitable for isolating the double-stranded siNA molecule, for example using a trityl-on synthesis strategy as described herein.

In another embodiment, the method of synthesis of siNA molecules of the invention comprises the teachings of Scaringe et al., U.S. Pat. Nos. 5,889,136; 6,008,400; and 6,111,086, incorporated by reference herein in their entirety.

In one embodiment, the invention features siNA constructs that mediate RNAi in a cell or reconstituted system, wherein the siNA construct comprises one or more chemical modifications, for example, one or more chemical modifications having any of Formulae I-VII or any combination thereof that increases the nuclease resistance of the siNA construct.

In another embodiment, the invention features a method for generating siNA molecules with increased nuclease resistance comprising (a) introducing nucleotides having any of Formula I-VII or any combination thereof into a siNA molecule, and (b) assaying the siNA molecule of step (a) under conditions suitable for isolating siNA molecules having increased nuclease resistance.

In one embodiment, the invention features siNA constructs that mediate RNAi against a target gene, wherein the siNA construct comprises one or more chemical modifications described herein that modulates the binding affinity between the sense and antisense strands of the siNA construct.

In one embodiment, the binding affinity between the sense and antisense strands of the siNA construct is modulated to increase the activity of the siNA molecule with regard to the ability of the siNA to mediate RNA interference. In another embodiment the binding affinity between the sense and antisense strands of the siNA construct is decreased. The binding affinity between the sense and antisense strands of the siNA construct can be decreased by introducing one or more chemically modified nucleotides in the siNA sequence that disrupts the duplex stability of the siNA (e.g., lowers the Tm of the duplex). The binding affinity between the sense and antisense strands of the siNA construct can be decreased by introducing one or more nucleotides in the siNA sequence that do not form Watson-Crick base pairs. The binding affinity between the sense and antisense strands of the siNA construct can be decreased by introducing one or more wobble base pairs in the siNA sequence. The binding affinity between the sense and antisense strands of the siNA construct can be decreased by modifying the nucleobase composition of the siNA, such as by altering the G-C content of the siNA sequence (e.g., decreasing the number of G-C base pairs in the siNA sequence). These modifications and alterations in sequence can be introduced selectively at pre-determined positions of the siNA sequence to increase siNA mediated RNAi activity. For example, such modifications and sequence alterations can be introduced to disrupt siNA duplex stability between the 5'-end of the antisense strand and the 3'-end of the sense strand, the 3'-end of the antisense strand and the 5'-end of the sense strand, or alternately the middle of the siNA duplex. In another embodiment, siNA molecules are screened for optimized RNAi activity by introducing such modifications and sequence alterations either by rational design based upon observed rules or trends in increasing siNA activity, or randomly via combinatorial selection processes that cover either partial or complete sequence space of the siNA construct.

In another embodiment, the invention features a method for generating siNA molecules with increased binding affinity between the sense and antisense strands of the siNA molecule comprising (a) introducing nucleotides having any of Formula I-VII or any combination thereof into a siNA molecule, and (b) assaying the siNA molecule of step (a) under conditions suitable for isolating siNA molecules having increased binding affinity between the sense and antisense strands of the siNA molecule.

In one embodiment, the invention features siNA constructs that mediate RNAi in a cell or reconstituted system, wherein the siNA construct comprises one or more chemical modifications described herein that modulates the binding affinity between the antisense strand of the siNA construct and a complementary target RNA sequence within a cell.

In one embodiment, the invention features siNA constructs that mediate RNAi in a cell or reconstituted system, wherein the siNA construct comprises one or more chemical modifications described herein that modulates the binding affinity between the antisense strand of the siNA construct and a complementary target DNA sequence within a cell.

In another embodiment, the invention features a method for generating siNA molecules with increased binding affinity between the antisense strand of the siNA molecule and a complementary target RNA sequence comprising (a) introducing nucleotides having any of Formula I-VII or any combination thereof into a siNA molecule, and (b) assaying the siNA molecule of step (a) under conditions suitable for isolating siNA molecules having increased binding affinity between the antisense strand of the siNA molecule and a complementary target RNA sequence.

In another embodiment, the invention features a method for generating siNA molecules with increased binding affinity between the antisense strand of the siNA molecule and a complementary target DNA sequence comprising (a) introducing nucleotides having any of Formula I-VII or any combination thereof into a siNA molecule, and (b) assaying the siNA molecule of step (a) under conditions suitable for isolating siNA molecules having increased binding affinity between the antisense strand of the siNA molecule and a complementary target DNA sequence.

In one embodiment, the invention features siNA constructs that mediate RNAi in a cell or reconstituted system, wherein the siNA construct comprises one or more chemical modifications described herein that modulate the polymerase activity of a cellular polymerase capable of generating additional endogenous siNA molecules having sequence homology to the chemically-modified siNA construct.

In another embodiment, the invention features a method for generating siNA molecules capable of mediating increased polymerase activity of a cellular polymerase capable of generating additional endogenous siNA molecules having sequence homology to a chemically-modified siNA molecule comprising (a) introducing nucleotides having any of Formula I-VII or any combination thereof into a siNA molecule, and (b) assaying the siNA molecule of step (a) under conditions suitable for isolating siNA molecules capable of mediating increased polymerase activity of a cellular polymerase capable of generating additional endogenous siNA molecules having sequence homology to the chemically-modified siNA molecule. In one embodiment, the invention features chemically-modified siNA constructs that mediate RNAi in a cell or reconstituted system, wherein the chemical modifications do not significantly effect the interaction of siNA with a target RNA molecule, DNA molecule and/or proteins or other factors that are essential for RNAi in a manner that would decrease the efficacy of RNAi mediated by such siNA constructs.

In another embodiment, the invention features a method for generating siNA molecules with improved RNAi activity comprising (a) introducing nucleotides having any of Formula I-VII or any combination thereof into a siNA molecule, and (b) assaying the siNA molecule of step (a) under conditions suitable for isolating siNA molecules having improved RNAi activity.

In yet another embodiment, the invention features a method for generating siNA molecules with improved RNAi activity against a target RNA comprising (a) introducing nucleotides having any of Formula I-VII or any combination thereof into a siNA molecule, and (b) assaying the siNA molecule of step (a) under conditions suitable for isolating siNA molecules having improved RNAi activity against the target RNA.

In yet another embodiment, the invention features a method for generating siNA molecules with improved RNAi activity against a DNA target comprising (a) introducing nucleotides having any of Formula I-VII or any combination thereof into a siNA molecule, and (b) assaying the siNA molecule of step (a) under conditions suitable for isolating siNA molecules having improved RNAi activity against the DNA target, such as a gene, chromosome, or portion thereof.

In one embodiment, the invention features siNA constructs that mediate RNAi in a cell or reconstituted system, wherein the siNA construct comprises one or more chemical modifications described herein that modulates the cellular uptake of the siNA construct.

In another embodiment, the invention features a method for generating siNA molecules against a target gene with improved cellular uptake comprising (a) introducing nucleotides having any of Formula I-VII or any combination thereof into a siNA molecule, and (b) assaying the siNA molecule of step (a) under conditions suitable for isolating siNA molecules having improved cellular uptake.

In one embodiment, the invention features siNA constructs that mediate RNAi against a target gene, wherein the siNA construct comprises one or more chemical modifications described herein that increases the bioavailability of the siNA construct, for example, by attaching polymeric conjugates such as polyethyleneglycol or equivalent conjugates that improve the pharmacokinetics of the siNA construct, or by attaching conjugates that target specific tissue types or cell types in vivo. Non-limiting examples of such conjugates are described in Vargeese et al., U.S. Ser. No. 10/201,394 incorporated by reference herein.

In one embodiment, the invention features a method for generating siNA molecules of the invention with improved bioavailability comprising (a) introducing a conjugate into the structure of a siNA molecule, and (b) assaying the siNA molecule of step (a) under conditions suitable for isolating siNA molecules having improved bioavailability. Such conjugates can include ligands for cellular receptors, such as peptides derived from naturally occurring protein ligands; protein localization sequences, including cellular ZIP code sequences; antibodies; nucleic acid aptamers; vitamins and other co-factors, such as folate and N-acetylgalactosamine; polymers, such as polyethyleneglycol (PEG); phospholipids; cholesterol; polyamines, such as spermine or spermidine; and others.

In one embodiment, the invention features a double stranded short interfering nucleic acid (siNA) molecule that comprises a first nucleotide sequence complementary to a target RNA sequence or a portion thereof, and a second sequence having complementarity to said first sequence, wherein said second sequence is chemically modified in a manner that it can no longer act as a guide sequence for efficiently mediating RNA interference and/or is recognized by cellular proteins that facilitate RNAi.

In one embodiment, the invention features a double stranded short interfering nucleic acid (siNA) molecule that comprises a first nucleotide sequence complementary to a target RNA sequence or a portion thereof, and a second sequence having complementarity to said first sequence, wherein the second sequence is designed or modified in a manner that prevents its entry into the RNAi pathway as a guide sequence or as a sequence that is complementary to a target nucleic acid (e.g., RNA) sequence. Such design or modifications are expected to enhance the activity of siNA and/or improve the specificity of siNA molecules of the invention. These modifications are also expected to minimize any off-target effects and/or associated toxicity.

In one embodiment, the invention features a double stranded short interfering nucleic acid (siNA) molecule that comprises a first nucleotide sequence complementary to a target RNA sequence or a portion thereof, and a second sequence having complementarity to said first sequence, wherein said second sequence is incapable of acting as a guide sequence for mediating RNA interference.

In one embodiment, the invention features a double stranded short interfering nucleic acid (siNA) molecule that comprises a first nucleotide sequence complementary to a target RNA sequence or a portion thereof, and a second sequence having complementarity to said first sequence, wherein said second sequence does not have a terminal 5'-hydroxyl (5'-OH) or 5'-phosphate group.

In one embodiment, the invention features a double stranded short interfering nucleic acid (siNA) molecule that comprises a first nucleotide sequence complementary to a target RNA sequence or a portion thereof, and a second sequence having complementarity to said first sequence, wherein said second sequence comprises a terminal cap moiety at the 5'-end of said second sequence. In another embodiment, the terminal cap moiety comprises an inverted abasic, inverted deoxy abasic, inverted nucleotide moiety, a group shown in FIG. 22, an alkyl or cycloalkyl group, a heterocycle, or any other group that prevents RNAi activity in which the second sequence serves as a guide sequence or template for RNAi.

In one embodiment, the invention features a double stranded short interfering nucleic acid (siNA) molecule that comprises a first nucleotide sequence complementary to a target RNA sequence or a portion thereof, and a second sequence having complementarity to said first sequence, wherein said second sequence comprises a terminal cap moiety at the 5'-end and 3'-end of said second sequence. In another embodiment, each terminal cap moiety individually comprises an inverted abasic, inverted deoxy abasic, inverted nucleotide moiety, a group shown in FIG. 22, an alkyl or cycloalkyl group, a heterocycle, or any other group that prevents RNAi activity in which the second sequence serves as a guide sequence or template for RNAi.

In one embodiment, the invention features a method for generating siNA molecules of the invention with improved specificity for down regulating or inhibiting the expression of a target nucleic acid (e.g., a DNA or RNA such as a gene or its corresponding RNA), comprising (a) introducing one or more chemical modifications into the structure of a siNA molecule, and (b) assaying the siNA molecule of step (a) under conditions suitable for isolating siNA molecules having improved specificity. In another embodiment, the chemical modification used to improve specificity comprises terminal cap modifications at the 5'-end, 3'-end, or both 5' and 3'-ends of the siNA molecule. The terminal cap modifications can comprise, for example, structures shown in FIG. 22 (e.g. inverted deoxyabasic moieties) or any other chemical modification that renders a portion of the siNA molecule (e.g. the sense strand) incapable of mediating RNA interference against an off target nucleic acid sequence. In a non-limiting example, a siNA molecule is designed such that only the antisense sequence of the siNA molecule can serve as a guide sequence for RISC mediated degradation of a corresponding target RNA sequence. This can be accomplished by rendering the sense sequence of the siNA inactive by introducing chemical modifications to the sense strand that preclude recognition of the sense strand as a guide sequence by RNAi machinery. In one embodiment, such chemical modifications comprise any chemical group at the 5'-end of the sense strand of the siNA, or any other group that serves to render the sense strand inactive as a guide sequence for mediating RNA interference. These modifications, for example, can result in a molecule where the 5'-end of the sense strand no longer has a free 5'-hydroxyl (5'-OH) or a free 5'-phosphate group (e.g., phosphate, diphosphate, triphosphate, cyclic phosphate etc.). Non-limiting examples of such siNA constructs are described herein, such as "Stab 9/10" and "Stab 7/8" chemistries and variants thereof wherein the 5'-end and 3'-end of the sense strand of the siNA do not comprise a hydroxyl group or phosphate group.

In one embodiment, the invention features a method for generating siNA molecules of the invention with improved specificity for down regulating or inhibiting the expression of a target nucleic acid (e.g., a DNA or RNA such as a gene or its corresponding RNA), comprising (a) introducing one or more chemical modifications into the structure of a siNA molecule that prevent a strand or portion of the siNA molecule from acting as a template or guide sequence for RNAi activity. In another embodiment, the inactive strand or sense region of the siNA molecule is the sense strand or sense region of the siNA molecule, i.e. the strand or region of the siNA that does not have complementarity to the target nucleic acid sequence. In one embodiment, such chemical modifications comprise any chemical group at the 5'-end of the sense strand or region of the siNA that does not comprise a 5'-hydroxyl (5'-OH) or 5'-phosphate group, or any other group that serves to render the sense strand or sense region inactive as a guide sequence for mediating RNA interference. Non-limiting examples of such siNA constructs are described herein, such as "Stab 9/10" and "Stab 7/8" chemistries and variants thereof wherein the 5'-end and 3'-end of the sense strand of the siNA do not comprise a hydroxyl group or phosphate group.

In one embodiment, the invention features a method for screening siNA molecules against a target nucleic acid sequence comprising, (a) generating a plurality of unmodified siNA molecules, (b) assaying the siNA molecules of step (a) under conditions suitable for isolating siNA molecules that are active in mediating RNA interference against the target nucleic acid sequence, (c) introducing chemical modifications (e.g. chemical modifications as described herein or as otherwise known in the art) into the active siNA molecules of (b), and (d) optionally re-screening the chemically modified siNA molecules of (c) under conditions suitable for isolating chemically modified siNA molecules that are active in mediating RNA interference against the target nucleic acid sequence.

In one embodiment, the invention features a method for screening siNA molecules against a target nucleic acid sequence comprising, (a) generating a plurality of chemically modified siNA molecules (e.g. siNA molecules as described herein or as otherwise known in the art), and (b) assaying the siNA molecules of step (a) under conditions suitable for isolating chemically modified siNA molecules that are active in mediating RNA interference against the target nucleic acid sequence.

In another embodiment, the invention features a method for generating siNA molecules of the invention with improved bioavailability comprising (a) introducing an excipient formulation to a siNA molecule, and (b) assaying the siNA molecule of step (a) under conditions suitable for isolating siNA molecules having improved bioavailability. Such excipients include polymers such as cyclodextrins, lipids, cationic lipids, polyamines, phospholipids, nanoparticles, receptors, ligands, and others.

In another embodiment, the invention features a method for generating siNA molecules of the invention with improved bioavailability comprising (a) introducing an excipient formulation to a siNA molecule, and (b) assaying the siNA molecule of step (a) under conditions suitable for isolating siNA molecules having improved bioavailability. Such excipients include polymers such as cyclodextrins, lipids, cationic lipids, polyamines, phospholipids, and others.

In another embodiment, the invention features a method for generating siNA molecules of the invention with improved bioavailability comprising (a) introducing nucleotides having any of Formulae I-VII or any combination thereof into a siNA molecule, and (b) assaying the siNA molecule of step (a) under conditions suitable for isolating siNA molecules having improved bioavailability.

In another embodiment, polyethylene glycol (PEG) can be covalently attached to siNA compounds of the present invention. The attached PEG can be any molecular weight, preferably from about 2,000 to about 50,000 daltons (Da).

The present invention can be used alone or as a component of a kit having at least one of the reagents necessary to carry out the in vitro or in vivo introduction of RNA to test samples and/or subjects. For example, preferred components of the kit include a siNA molecule of the invention and a vehicle that promotes introduction of the siNA into cells of interest as described herein (e.g., using lipids and other methods of transfection known in the art, see for example Beigelman et al, U.S. Pat. No. 6,395,713). The kit can be used for target validation, such as in determining gene function and/or activity, or in drug optimization, and in drug discovery (see for example Usman et al., U.S. Ser. No. 60/402,996). Such a kit can also include instructions to allow a user of the kit to practice the invention.

The term "short interfering nucleic acid", "siNA", "short interfering RNA", "siRNA", "short interfering nucleic acid molecule", "short interfering oligonucleotide molecule", or "chemically-modified short interfering nucleic acid molecule" as used herein refers to any nucleic acid molecule capable of inhibiting or down regulating gene expression or viral replication, for example by mediating RNA interference "RNAi" or gene silencing in a sequence-specific manner; see for example Zamore et al., 2000, Cell, 101, 25-33; Bass, 2001, Nature, 411, 428-429; Elbashir et al., 2001, Nature, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237; Hutvagner and Zamore, 2002, Science, 297, 2056-60; McManus et al., 2002, RNA, 8, 842-850; Reinhart et al., 2002, Gene & Dev., 16, 1616-1626; and Reinhart & Bartel, 2002, Science, 297, 1831). Non limiting examples of siNA molecules of the invention are shown in FIGS. 18A-18F, 19A-19F, and 20, and Table I herein. For example the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double stranded structure, for example wherein the double stranded region is about 19 base pairs); the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof. Alternatively, the siNA is assembled from a single oligonucleotide, where the self-complementary sense and antisense regions of the siNA are linked by means of a nucleic acid based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (for example, where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, *Cell.,* 110, 563-574 and Schwarz et al., 2002, *Molecular Cell,* 10, 537-568), or 5',3'-diphosphate. In certain embodiments, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic intercations, and/or stacking interactions. In certain embodiments, the siNA molecules of the invention comprise nucleotide sequence that is complementary to nucleotide sequence of a target gene. In another embodiment, the siNA molecule of the invention interacts with nucleotide sequence of a target gene in a manner that causes inhibition of expression of the target gene. As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. Applicant describes in certain embodiments short interfering nucleic acids that do not require the presence of nucleotides having a 2'-hydroxy group for mediating RNAi and as such, short interfering nucleic acid molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON." As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siNA molecules of the invention can be used to epigenetically silence genes at both the post-transcriptional level or the pre-transcriptional level. In a non-limiting example, epigenetic regulation of gene expression by siNA molecules of the invention can result from siNA mediated modification of chromatin structure to alter gene expression (see, for example, Allshire, 2002, *Science,* 297, 1818-1819; Volpe et al., 2002, *Science,* 297, 1833-1837; Jenuwein, 2002, *Science,* 297, 2215-2218; and Hall et al., 2002, *Science,* 297, 2232-2237).

By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complimentary nucleotides to base pair with the antisense region and form a duplex with loop. For example, an asymmetric hairpin siNA molecule of the invention can comprise an antisense region having length sufficient to mediate RNAi in a cell or in vitro system (e.g. about 19 to about 22 nucleotides) and a loop region comprising about 4 to about 8 nucleotides, and a sense region having about 3 to about 18 nucleotides that are complementary to the antisense region (see for example FIG. 74). The asymmetric hairpin siNA molecule can also comprise a 5'-terminal phosphate group that can be chemically modified (for example as shown in FIG. 75). The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complimentary nucleotides to base pair with the antisense region and form a duplex. For example, an asymmetric duplex siNA molecule of the invention can comprise an antisense region having length sufficient to mediate RNAi in a cell or in vitro system (e.g. about 19 to about 22 nucleotides) and a sense region having about 3 to about 18 nucleotides that are complementary to the antisense region (see for example FIG. 74).

By "modulate" is meant that the expression of the gene, or level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit," but the use of the word "modulate" is not limited to this definition.

By "inhibit", "down-regulate", or "reduce", it is meant that the expression of the gene, or level of RNA molecules or equivalent RNA molecules encoding one or more proteins or protein subunits, or activity of one or more proteins or protein subunits, is reduced below that observed in the absence of the nucleic acid molecules (e.g., siNA) of the invention. In one embodiment, inhibition, down-regulation or reduction with an siNA molecule is below that level observed in the presence of an inactive or attenuated molecule. In another embodiment, inhibition, down-regulation, or reduction with siNA molecules is below that level observed in the presence of, for example, an siNA molecule with scrambled sequence or with mismatches. In another embodiment, inhibition, down-regulation, or reduction of gene expression with a nucleic acid molecule of the instant invention is greater in the presence of the nucleic acid molecule than in its absence.

By "gene", or "target gene", is meant, a nucleic acid that encodes an RNA, for example, nucleic acid sequences including, but not limited to, structural genes encoding a polypeptide. A gene or target gene can also encode a functional RNA (fRNA) or non-coding RNA (ncRNA), such as small temporal RNA (stRNA), micro RNA (miRNA), small nuclear RNA (snRNA), short interfering RNA (siRNA), small nucleolar RNA (snRNA), ribosomal RNA (rRNA), transfer RNA (tRNA) and precursor RNAs thereof. Such non-coding RNAs can serve as target nucleic acid molecules for siNA mediated RNA interference in modulating the activity of fRNA or ncRNA involved in functional or regulatory cellular processes. Abberant fRNA or ncRNA activity leading to disease can therefore be modulated by siNA molecules of the invention. siNA molecules targeting fRNA and ncRNA can also be used to manipulate or alter the genotype or phenotype of an organism or cell, by intervening in cellular processes such as genetic imprinting, transcription, translation, or nucleic acid processing (e.g., transamination, methylation etc.). The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus. Non-limiting examples of plants include monocots, dicots, or gymnosperms. Non-limiting examples of animals include vertebrates or invertebrates. Non-limiting examples of fungi include molds or yeasts.

By "highly conserved sequence region" is meant, a nucleotide sequence of one or more regions in a target gene does not vary significantly from one generation to the other or from one biological system to the other.

By "cancer" is meant a group of diseases characterized by uncontrolled growth and spread of abnormal cells.

By "sense region" is meant a nucleotide sequence of a siNA molecule having complementarity to an antisense region of the siNA molecule. In addition, the sense region of a siNA molecule can comprise a nucleic acid sequence having homology with a target nucleic acid sequence.

By "antisense region" is meant a nucleotide sequence of a siNA molecule having complementarity to a target nucleic acid sequence. In addition, the antisense region of a siNA molecule can optionally comprise a nucleic acid sequence having complementarity to a sense region of the siNA molecule.

By "target nucleic acid" is meant any nucleic acid sequence whose expression or activity is to be modulated. The target nucleic acid can be DNA or RNA, such as endogenous DNA or RNA, viral DNA or viral RNA, or other RNA encoded by a gene, virus, bacteria, fungus, mammal, or plant.

By "complementarity" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, *CSH Symp. Quant. Biol. LII* pp. 123-133; Frier et al., 1986, *Proc. Nat. Acad. Sci. USA* 83:9373-9377; Turner et al., 1987, *J. Am. Chem. Soc.* 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonuelcotide being based paired to a second nucleic acid sequence having 10 nucleotides represents 50%, 60%, 70%, 80%, 90%, and 100% complementary respectively). "Perfectly complementary" means that all the contiguous residues of a nucleic acid sequence will hydrogen bond with the same number of contiguous residues in a second nucleic acid sequence.

The siNA molecules of the invention represent a novel therapeutic approach to a broad spectrum of diseases and conditions, including cancer or cancerous disease, infectious disease, cardiovascular disease, neurological disease, prion disease, inflammatory disease, autoimmune disease, pulmonary disease, renal disease, liver disease, mitochondrial disease, endocrine disease, reproduction related diseases and conditions, and any other indications that can respond to the level of an expressed gene product in a cell or organism.

In one embodiment of the present invention, each sequence of a siNA molecule of the invention is independently about 18 to about 24 nucleotides in length, in specific embodiments about 18, 19, 20, 21, 22, 23, or 24 nucleotides in length. In another embodiment, the siNA duplexes of the invention independently comprise about 17 to about 23 base pairs (e.g., about 17, 18, 19, 20, 21, 22 or 23). In yet another embodiment, siNA molecules of the invention comprising hairpin or circular structures are about 35 to about 55 (e.g., about 35, 40, 45, 50 or 55) nucleotides in length, or about 38 to about 44 (e.g., 38, 39, 40, 41, 42, 43 or 44) nucleotides in length and comprising about 16 to about 22 (e.g., about 16, 17, 18, 19, 20, 21 or 22) base pairs. Exemplary siNA molecules of the invention are shown in Table I. and/or FIGS. 18A-18F and 19A-19F.

As used herein "cell" is used in its usual biological sense, and does not refer to an entire multicellular organism, e.g., specifically does not refer to a human. The cell can be present in an organism, e.g., birds, plants and mammals such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or pluripotent, dividing or non-dividing. The cell can also be derived from or can comprise a gamete or embryo, a stem cell, or a fully differentiated cell.

The siNA molecules of the invention are added directly, or can be complexed with cationic lipids, packaged within liposomes, or otherwise delivered to target cells or tissues. The nucleic acid or nucleic acid complexes can be locally administered to relevant tissues ex vivo, or in vivo through injection, infusion pump or stent, with or without their incorporation in biopolymers. In particular embodiments, the nucleic acid molecules of the invention comprise sequences shown in Table I and/or FIGS. 18A-18F and 19A-19F. Examples of such nucleic acid molecules consist essentially of sequences defined in these tables and figures. Furthermore, the chemically modified constructs described in Table IV can be applied to any siNA sequence of the invention.

In another aspect, the invention provides mammalian cells containing one or more siNA molecules of this invention. The one or more siNA molecules can independently be targeted to the same or different sites.

By "RNA" is meant a molecule comprising at least one ribonucleotide residue. By "ribonucleotide" is meant a nucleotide with a hydroxyl group at the 2' position of a β-D-ribo-furanose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

By "subject" is meant an organism, which is a donor or recipient of explanted cells or the cells themselves. "Subject" also refers to an organism to which the nucleic acid molecules of the invention can be administered. A subject can be a mammal or mammalian cells, including a human or human cells.

The term "ligand" refers to any compound or molecule, such as a drug, peptide, hormone, or neurotransmitter, that is capable of interacting with another compound, such as a receptor, either directly or indirectly. The receptor that interacts with a ligand can be present on the surface of a cell or can alternately be an intercullular receptor. Interaction of the ligand with the receptor can result in a biochemical reaction, or can simply be a physical interaction or association.

The term "phosphorothioate" as used herein refers to an internucleotide linkage having Formula I, wherein Z and/or W comprise a sulfur atom. Hence, the term phosphorothioate refers to both phosphorothioate and phosphorodithioate internucleotide linkages.

The term "phosphonoacetate" as used herein refers to an internucleotide linkage having Formula I, wherein Z and/or W comprise an acetyl or protected acetyl group.

The term "thiophosphonoacetate" as used herein refers to an internucleotide linkage having Formula I, wherein Z comprises an acetyl or protected acetyl group and W comprises a sulfur atom or alternately W comprises an acetyl or protected acetyl group and Z comprises a sulfur atom.

The term "universal base" as used herein refers to nucleotide base analogs that form base pairs with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see for example Loakes, 2001, *Nucleic Acids Research*, 29, 2437-2447).

The term "acyclic nucleotide" as used herein refers to any nucleotide having an acyclic ribose sugar, for example where any of the ribose carbons (C1, C2, C3, C4, or C5), are independently or in combination absent from the nucleotide.

The nucleic acid molecules of the instant invention, individually, or in combination or in conjunction with other drugs, can be used to treat diseases or conditions discussed herein (e.g., cancers and the proliferative conditions, viral infection, inflammatory disease, autoimmunity, pulmonary disease, renal disease, ocular disease, etc.). For example, to treat a particular disease or condition, the siNA molecules can be administered to a subject or can be administered to other appropriate cells evident to those skilled in the art, individually or in combination with one or more drugs under conditions suitable for the treatment.

In one embodiment, the invention features a method for treating or preventing a disease or condition in a subject, wherein the disease or condition is related to angiogenesis or neovascularization, comprising administering to the subject a siNA molecule of the invention under conditions suitable for the treatment or prevention of the disease or condition in the subject, alone or in conjunction with one or more other therapeutic compounds. In another embodiment, the disease or condition comprises tumor angiogenesis and cancer, including but not limited to breast cancer, lung cancer (including non-small cell lung carcinoma), prostate cancer, colorectal cancer, brain cancer, esophageal cancer, bladder cancer, pancreatic cancer, cervical cancer, head and neck cancer, skin cancers, nasopharyngeal carcinoma, liposarcoma, epithelial carcinoma, renal cell carcinoma, gallbladder adeno carcinoma, parotid adenocarcinoma, ovarian cancer, melanoma, lymphoma, glioma, endometrial sarcoma, multidrug resistant cancers, diabetic retinopathy, macular degeneration, age related macular degeneration, neovascular glaucoma, myopic degeneration, arthritis, psoriasis, endometriosis, female reproduction, verruca vulgaris, angiofibroma of tuberous sclerosis, pot-wine stains, Sturge Weber syndrome, Kippel-Trenaunay-Weber syndrome, Osler-Weber-Rendu syndrome, renal disease such as Autosomal dominant polycystic kidney disease (ADPKD), restenosis, arteriosclerosis, and any other diseases or conditions that are related to gene expression or will respond to RNA interference in a cell or tissue, alone or in combination with other therapies.

In one embodiment, the invention features a method for treating or preventing an ocular disease or condition in a subject, wherein the ocular disease or condition is related to angiogenesis or neovascularization, comprising administering to the subject a siNA molecule of the invention under conditions suitable for the treatment or prevention of the disease or condition in the subject, alone or in conjunction with one or more other therapeutic compounds. In another embodiment, the ocular disease or condition comprises macular degeneration, age related macular degeneration, diabetic retinopathy, neovascular glaucoma, myopic degeneration, trachoma, scarring of the eye, cataract, ocular inflammation and/or ocular infections.

In one embodiment, the invention features a method for treating or preventing tumor angiogenesis in a subject, comprising administering to the subject a siNA molecule of the invention under conditions suitable for the treatment or prevention of tumor angiogenesis in the subject, alone or in conjunction with one or more other therapeutic compounds.

In one embodiment, the invention features a method for treating or preventing viral infection or replication in a subject, comprising administering to the subject a siNA molecule of the invention under conditions suitable for the treatment or prevention of viral infection or replication in the subject, alone or in conjunction with one or more other therapeutic compounds.

In one embodiment, the invention features a method for treating or preventing autoimmune disease in a subject, comprising administering to the subject a siNA molecule of the invention under conditions suitable for the treatment or prevention of autoimmune disease in the subject, alone or in conjunction with one or more other therapeutic compounds.

In one embodiment, the invention features a method for treating or preventing inflammation in a subject, comprising administering to the subject a siNA molecule of the invention under conditions suitable for the treatment or prevention of inflammation in the subject, alone or in conjunction with one or more other therapeutic compounds.

In a further embodiment, the siNA molecules can be used in combination with other known treatments to treat conditions or diseases discussed above. For example, the described molecules could be used in combination with one or more known therapeutic agents to treat a disease or condition. Non-limiting examples of other therapeutic agents that can be readily combined with a siNA molecule of the invention are enzymatic nucleic acid molecules, allosteric nucleic acid molecules, antisense, decoy, or aptamer nucleic acid molecules, antibodies such as monoclonal antibodies, small molecules, and other organic and/or inorganic compounds including metals, salts and ions.

Other features and advantages of the invention will be apparent from the following description of the preferred embodiments thereof, and from the claims.

BRIEF DESCRIPTION OF THE DRAWINGS

FIG. 3 shows the results of a stability assay used to determine the serum stability of chemically modified siNA constructs compared to a siNA control consisting of all RNA with 3'-TT termini. T½ values are shown for duplex stability.

FIGS. 18A-18F shows non-limiting examples of chemically-modified siNA constructs of the present invention. In the figure, N stands for any nucleotide (adenosine, guanosine, cytosine, uridine, or optionally thymidine, for example thymidine can be substituted in the overhanging regions designated by parenthesis (N N). Various modifications are shown for the sense and antisense strands of the siNA constructs. FIG. 18A: The sense strand comprises 21 nucleotides wherein the two terminal 3'-nucleotides are optionally base paired and wherein all nucleotides present are ribonucleotides except for (N N) nucleotides, which can comprise ribonucleotides, deoxynucleotides, universal bases, or other chemical modifications described herein. The antisense strand comprises 21 nucleotides, optionally having a 3'-terminal glyceryl moiety and wherein the two terminal 3'-nucleotides are optionally complementary to the target RNA sequence, and wherein all nucleotides present are ribonucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s" connects the (N N) nucleotides in the antisense strand. FIG. 18B: The sense strand comprises 21 nucleotides wherein the two terminal 3'-nucleotides are optionally base paired and wherein all pyrimidine nucleotides that may be present are 2'-deoxy-2'-fluoro modified nucleotides and all purine nucleotides that may be present are 2'-O-methyl modified nucleotides except for (N N) nucleotides, which can comprise ribonucleotides, deoxynucleotides, universal bases, or other chemical modifications described herein. The antisense strand comprises 21 nucleotides, optionally having a 3'-terminal glyceryl moiety and wherein the two terminal 3'-nucleotides are optionally complementary to the target RNA sequence, and wherein all pyrimidine nucleotides that may be present are 2'-deoxy-2'-fluoro modified nucleotides and all purine nucleotides that may be present are 2'-O-methyl modified nucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s" connects the (N N) nucleotides in the sense and antisense strand. FIG. 18C: The sense strand comprises 21 nucleotides having 5'- and 3'-terminal cap moieties wherein the two terminal 3'-nucleotides are optionally base paired and wherein all pyrimidine nucleotides that may be present are 2'-O-methyl or 2'-deoxy-2'-fluoro modified nucleotides except for (N N) nucleotides, which can comprise ribonucleotides, deoxynucleotides, universal bases, or other chemical modifications described herein. The antisense strand comprises 21 nucleotides, optionally having a 3'-terminal glyceryl moiety and wherein the two terminal 3'-nucleotides are optionally complementary to the target RNA sequence, and wherein all pyrimidine nucleotides that may be present are 2'-deoxy-2'-fluoro modified nucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s" connects the (N N) nucleotides in the antisense strand. FIG. 18D: The sense strand comprises 21 nucleotides having 5'- and 3'-terminal cap moieties wherein the two terminal 3'-nucleotides are optionally base paired and wherein all pyrimidine nucleotides that may be present are 2'-deoxy-2'-fluoro modified nucleotides except for (N N) nucleotides, which can comprise ribonucleotides, deoxynucleotides, universal bases, or other chemical modifications described herein and wherein and all purine nucleotides that may be present are 2'-deoxy nucleotides. The antisense strand comprises 21 nucleotides, optionally having a 3'-terminal glyceryl moiety and wherein the two terminal 3'-nucleotides are optionally complementary to the target RNA sequence, and wherein all pyrimidine nucleotides that may be present are 2'-deoxy-2'-fluoro modified nucleotides and all purine nucleotides that may be present are 2'-O-methyl modified nucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s" connects the (N N) nucleotides in the antisense strand. FIG. 18E: The sense strand comprises 21 nucleotides having 5'- and 3'-terminal cap moieties wherein the two terminal 3'-nucleotides are optionally base paired and wherein all pyrimidine nucleotides that may be present are 2'-deoxy-2'-fluoro modified nucleotides except for (N N) nucleotides, which can comprise ribonucleotides, deoxynucleotides, universal bases, or other chemical modifications described herein. The antisense strand comprises 21 nucleotides, optionally having a 3'-terminal glyceryl moiety and wherein the two terminal 3'-nucleotides are optionally complementary to the target RNA sequence, and wherein all pyrimidine nucleotides that may be present are 2'-deoxy-2'-fluoro modified nucleotides and all purine nucleotides that may be present are 2'-O-methyl modified nucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s" connects the (N N) nucleotides in the antisense strand. FIG. 18F: The sense strand comprises 21 nucleotides having 5'- and 3'-terminal cap moieties wherein the two terminal 3'-nucleotides are optionally base paired and wherein all pyrimidine nucleotides that may be present are 2'-deoxy-2'-fluoro modified nucleotides except for (N N) nucleotides, which can comprise ribonucleotides, deoxynucleotides, universal bases, or other chemical modifications described herein and wherein and all purine nucleotides that may be present are 2'-deoxy nucleotides. The antisense strand comprises 21 nucleotides, optionally having a 3'-terminal glyceryl moiety and wherein the two terminal 3'-nucleotides are optionally complementary to the target RNA sequence, and wherein all pyrimidine nucleotides that may be present are 2'-deoxy-2'-fluoro modified nucleotides and all purine nucleotides that may be present are 2'-deoxy nucleotides except for (N N) nucleotides, which can comprise ribonucleotides, deoxynucleotides, universal bases, or other chemical modifications described herein. A modified internucleotide linkage, such as a phosphorothioate, phosphorodithioate or other modified internucleotide linkage as described herein, shown as "s" connects the (N N) nucleotides in the antisense strand. The antisense strand of constructs A-F comprise sequence complementary to any target nucleic acid sequence of the invention. Furthermore, when a glyceryl moiety (L) is present at the 3'-end of the antisense strand for any construct shown in FIG. 4 A-F, the modified internucleotide linkage is optional.

FIGS. 19A-19F shows non-limiting examples of specific chemically modified siNA sequences of the invention. FIGS. 19A-19F apply the chemical modifications described in FIGS. 18A-18F to a representative siNA sequence targeting the hepatitis C virus (HCV).

(FIG. 21A) A pool of siNA oligonucleotides are synthesized wherein the antisense region of the siNA constructs has complementarity to target sites across the target nucleic acid sequence, and wherein the sense region comprises sequence complementary to the antisense region of the siNA. (FIG. 21B) The sequences are transfected into cells. (FIG. 21C) Cells are selected based on phenotypic change that is associated with modulation of the target nucleic acid sequence. (FIG. 21D) The siNA is isolated from the selected cells and is sequenced to identify efficacious target sites within the target nucleic acid sequence.

FIG. 34 shows a non-limiting example demonstrating the inhibition of viral replication of a HCV/poliovirus chimera by a chemically modified siRNA construct (30051/30053) compared to control construct (30052/30054).

FIG. 37 shows a non-limiting example of several chemically modified siRNA constructs targeting viral replication of a HCV/poliovirus chimera at 25 nM treatment in comparison to a lipid control and an inverse siNA control construct 29593/29600.

FIG. 50 discloses "SGACRGDCLGA" as SEQ ID NO: 684 and "GACRGDCLGA" as SEQ ID NO: 685.

FIG. 53 shows a non-limiting example of a synthetic scheme for preparing a poly-N-acetyl-D-galactosamine nucleic acid conjugate of the invention.

FIG. 61 shows a non-limiting example of various siNA phospholipid conjugates of the invention in which various linker chemistries and/or cleavable linkers can be utilized at different positions of a double stranded siNA molecule.

FIG. 76 shows a non-limiting example of inhibition of VEGF induced neovascularization in the rat corneal model. VEGFr1 site 349 active siNA having "Stab 9/10" chemistry (Sirna #31270/31273) was tested for inhibition of VEGF-induced angiogenesis at three different concentrations (2.0 ug, 1.0 ug, and 0.1 μg dose response) as compared to a matched chemistry inverted control siNA construct (Sirna #31276/31279) at each concentration and a VEGF control in which no siNA was administered. As shown in the figure, the active siNA construct having "Stab 9/10" chemistry (Sirna #31270/31273) is highly effective in inhibiting VEGF-induced angiogenesis in the rat corneal model compared to the matched chemistry inverted control siNA at concentrations from 0.1 μg to 2.0 ug.

FIGS. 77A-77F show activity of modified siNA constructs having stab 4/5 (Sirna 30355/30366), stab 7/8 (Sirna 30612/30620), and stab 7/11 (Sirna 30612/31175) chemistries and an all ribo siNA construct (Sirna 30287/30298) in the reduction of HBsAg levels compared to matched inverted controls at FIG. 77A. 3 days, FIG. 77B. 9 days, and FIG. 77C. 21 days post transfection. Also shown is the corresponding percent inhibition as function of time at siNA concentrations of FIG. 77D. 100 nM, FIG. 77E. 50 nM, and FIG. 77F. 25 nM.

DETAILED DESCRIPTION OF THE INVENTION

Figure 1:
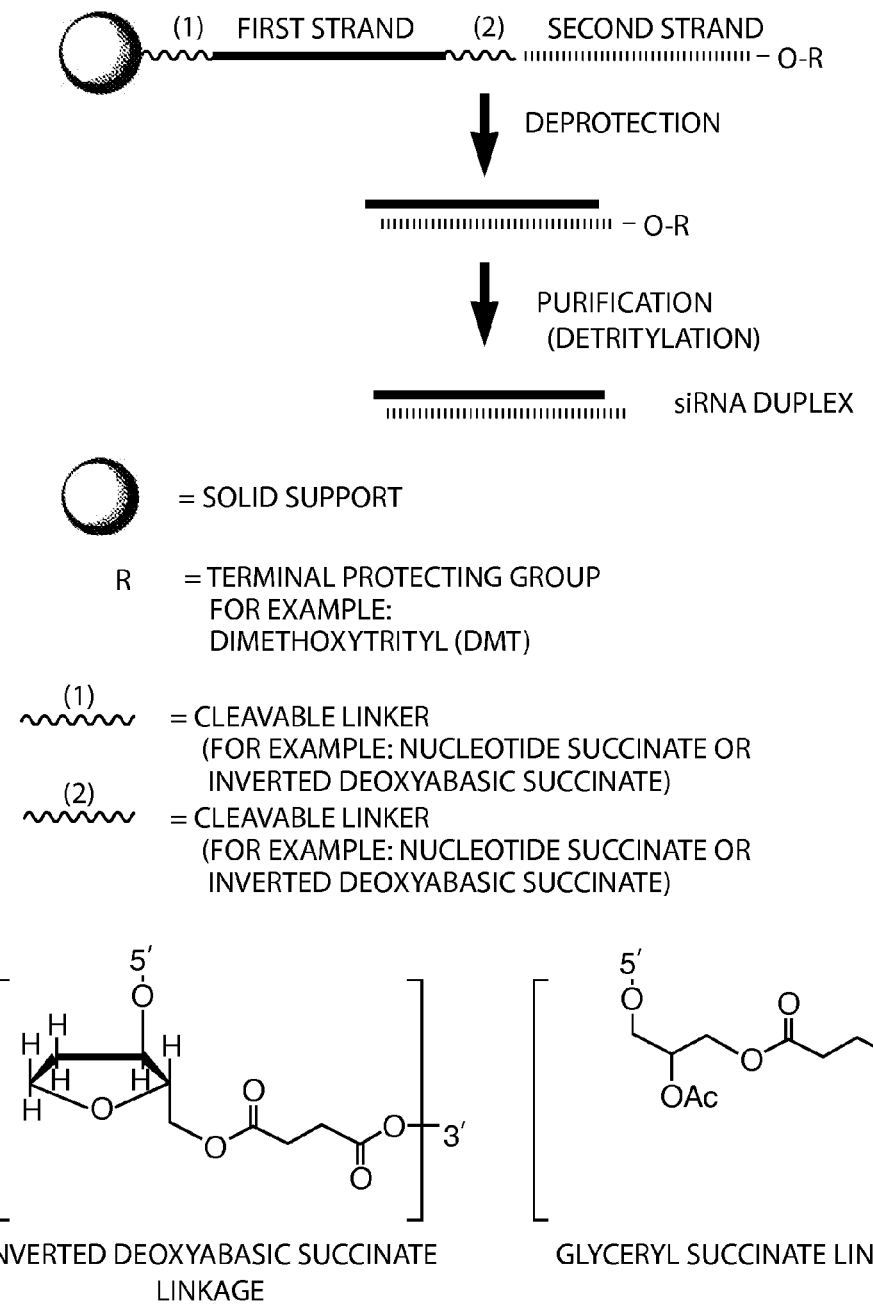
FIG. 1 shows a non-limiting example of a scheme for the synthesis of siNA molecules. The complementary siNA sequence strands, strand 1 and strand 2, are synthesized in tandem and are connected by a cleavable linkage, such as a nucleotide succinate or abasic succinate, which can be the same or different from the cleavable linker used for solid phase synthesis on a solid support. The synthesis can be either solid phase or solution phase, in the example shown, the synthesis is a solid phase synthesis. The synthesis is performed such that a protecting group, such as a dimethoxytrityl group, remains intact on the terminal nucleotide of the tandem oligonucleotide. Upon cleavage and deprotection of the oligonucleotide, the two siNA strands spontaneously hybridize to form a siNA duplex, which allows the purification of the duplex by utilizing the properties of the terminal protecting group, for example by applying a trityl on purification method wherein only duplexes/oligonucleotides with the terminal protecting group are isolated.

Mechanism of Action of Nucleic Acid Molecules of the Invention

The discussion that follows discusses the proposed mechanism of RNA interference mediated by short interfering RNA as is presently known, and is not meant to be limiting and is not an admission of prior art. Applicant demonstrates herein that chemically-modified short interfering nucleic acids possess similar or improved capacity to mediate RNAi as do siRNA molecules and are expected to possess improved stability and activity in vivo; therefore, this discussion is not meant to be limited to siRNA only and can be applied to siNA as a whole. By "improved capacity to mediate RNAi" or "improved RNAi activity" is meant to include RNAi activity measured in vitro and/or in vivo where the RNAi activity is a reflection of both the ability of the siNA to mediate RNAi and the stability of the siNAs of the invention. In this invention, the product of these activities can be increased in vitro and/or in vivo compared to an all RNA siRNA or a siNA containing a plurality of ribonucleotides. In some cases, the activity or stability of the siNA molecule can be decreased (i.e., less than ten-fold), but the overall activity of the siNA molecule is enhanced in vitro and/or in vivo.

RNA interference refers to the process of sequence specific post-transcriptional gene silencing in animals mediated by short interfering RNAs (siRNAs) (Zamore et al., 2000, Cell, 101, 25-33; Fire et al., 1998, Nature, 391, 806). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes which is commonly shared by diverse flora and phyla (Fire et al., 1999, Trends Genet., 15, 358). Such protection from foreign gene expression may have evolved in response to the production of double-stranded RNAs (dsRNAs) derived from viral infection or the random integration of transposon elements into a host genome via a cellular response that specifically destroys homologous single-stranded RNA or viral genomic RNA. The presence of dsRNA in cells triggers the RNAi response though a mechanism that has yet to be fully characterized. This mechanism appears to be different from the interferon response that results from dsRNA-mediated activation of protein kinase PKR and 2', 5'-oligoadenylate synthetase resulting in non-specific cleavage of mRNA by ribonuclease L.

The presence of long dsRNAs in cells stimulates the activity of a ribonuclease III enzyme referred to as Dicer. Dicer is involved in the processing of the dsRNA into short pieces of dsRNA known as short interfering RNAs (siRNAs) (Berstein et al., 2001, Nature, 409, 363). Short interfering RNAs derived from Dicer activity are typically about 21 to about 23 nucleotides in length and comprise about 19 base pair duplexes. Dicer has also been implicated in the excision of 21- and 22-nucleotide small temporal RNAs (stRNAs) from precursor RNA of conserved structure that are implicated in translational control (Hutvagner et al., 2001, Science, 293, 834). The RNAi response also features an endonuclease complex containing a siRNA, commonly referred to as an RNA-induced silencing complex (RISC), which mediates cleavage of single-stranded RNA having sequence homologous to the siRNA. Cleavage of the target RNA takes place in the middle of the region complementary to the guide sequence of the siRNA duplex (Elbashir et al., 2001, Genes Dev., 15, 188). In addition, RNA interference can also involve small RNA (e.g., micro-RNA or miRNA) mediated gene silencing, presumably though cellular mechanisms that regulate chromatin structure and thereby prevent transcription of target gene sequences (see for example Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237). As such, siNA molecules of the invention can be used to mediate gene silencing via interaction with RNA transcripts or alternately by interaction with particular gene sequences, wherein such interaction results in gene silencing either at the transcriptional level or post-transcriptional level.

RNAi has been studied in a variety of systems. Fire et al., 1998, *Nature,* 391, 806, were the first to observe RNAi in *C. elegans.* Wianny and Goetz, 1999, *Nature Cell Biol.,* 2, 70, describe RNAi mediated by dsRNA in mouse embryos. Hammond et al., 2000, *Nature,* 404, 293, describe RNAi in *Drosophila* cells transfected with dsRNA. Elbashir et al., 2001, *Nature,* 411, 494, describe RNAi induced by introduction of duplexes of synthetic 21-nucleotide RNAs in cultured mammalian cells including human embryonic kidney and HeLa cells. Recent work in *Drosophila* embryonic lysates has revealed certain requirements for siRNA length, structure, chemical composition, and sequence that are essential to mediate efficient RNAi activity. These studies have shown that 21 nucleotide siRNA duplexes are most active when containing two 2-nucleotide 3'-terminal nucleotide overhangs. Furthermore, substitution of one or both siRNA strands with 2'-deoxy or 2'-O-methyl nucleotides abolishes RNAi activity, whereas substitution of 3'-terminal siRNA nucleotides with deoxy nucleotides was shown to be tolerated. Mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end (Elbashir et al., 2001, *EMBO J.,* 20, 6877). Other studies have indicated that a 5'-phosphate on the target-complementary strand of a siRNA duplex is required for siRNA activity and that ATP is utilized to maintain the 5'-phosphate moiety on the siRNA (Nykanen et al., 2001, *Cell,* 107, 309); however, siRNA molecules lacking a 5'-phosphate are active when introduced exogenously, suggesting that 5'-phosphorylation of siRNA constructs may occur in vivo.

Synthesis of Nucleic Acid Molecules

Synthesis of nucleic acids greater than 100 nucleotides in length is difficult using automated methods, and the therapeutic cost of such molecules is prohibitive. In this invention, small nucleic acid motifs ("small" refers to nucleic acid motifs no more than 100 nucleotides in length, preferably no more than 80 nucleotides in length, and most preferably no more than 50 nucleotides in length; e.g., individual siNA oligonucleotide sequences or siNA sequences synthesized in tandem) are preferably used for exogenous delivery. The simple structure of these molecules increases the ability of the nucleic acid to invade targeted regions of protein and/or RNA structure. Exemplary molecules of the instant invention are chemically synthesized, and others can similarly be synthesized.

Oligonucleotides (e.g., certain modified oligonucleotides or portions of oligonucleotides lacking ribonucleotides) are synthesized using protocols known in the art, for example as described in Caruthers et al., 1992, *Methods in Enzymology* 211, 3-19, Thompson et al., International PCT Publication No. WO 99/54459, Wincott et al., 1995, *Nucleic Acids Res.* 23, 2677-2684, Wincott et al., 1997, *Methods Mol. Bio.,* 74, 59, Brennan et al., 1998, *Biotechnol Bioeng.,* 61, 33-45, and Brennan, U.S. Pat. No. 6,001,311. All of these references are incorporated herein by reference. The synthesis of oligonucleotides makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 μmol scale protocol with a 2.5 min coupling step for 2'-O-methylated nucleotides and a 45 second coupling step for 2'-deoxy nucleotides or 2'-deoxy-2'-fluoro nucleotides. Table V outlines the amounts and the contact times of the reagents used in the synthesis cycle. Alternatively, syntheses at the 0.2 μmol scale can be performed on a 96-well plate synthesizer, such as the instrument produced by Protogene (Palo Alto, Calif.) with minimal modification to the cycle. A 33-fold excess (60 μL of 0.11 M=6.6 μmol) of 2'-O-methyl phosphoramidite and a 105-fold excess of S-ethyl tetrazole (60 μL of 0.25 M=15 μmol) can be used in each coupling cycle of 2'-O-methyl residues relative to polymer-bound 5'-hydroxyl. A 22-fold excess (40 μL of 0.11 M=4.4 μmol) of deoxy phosphoramidite and a 70-fold excess of S-ethyl tetrazole (40 μL of 0.25 M=10 μmol) can be used in each coupling cycle of deoxy residues relative to polymer-bound 5'-hydroxyl. Average coupling yields on the 394 Applied Biosystems, Inc. synthesizer, determined by colorimetric quantitation of the trityl fractions, are typically 97.5-99%. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/10% 2,6-lutidine in THF (ABI); and oxidation solution is 16.9 mM $I_2$, 49 mM pyridine, 9% water in THF (PERSEPTIVE™). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide, 0.05 M in acetonitrile) is used.

Deprotection of the DNA-based oligonucleotides is performed as follows: the polymer-bound trityl-on oligoribonucleotide is transferred to a 4 mL glass screw top vial and suspended in a solution of 40% aqueous methylamine (1 mL) at 65° C. for 10 minutes. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder.

The method of synthesis used for RNA including certain siNA molecules of the invention follows the procedure as described in Usman et al., 1987, *J. Am. Chem. Soc.,* 109, 7845; Scaringe et al., 1990, *Nucleic Acids Res.,* 18, 5433; and Wincott et al., 1995, *Nucleic Acids Res.* 23, 2677-2684 Wincott et al., 1997, *Methods Mol. Bio.,* 74, 59, and makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 μmol scale protocol with a 7.5 min coupling step for alkylsilyl protected nucleotides and a 2.5 min coupling step for 2'-O-methylated nucleotides. Table V outlines the amounts and the contact times of the reagents used in the synthesis cycle. Alternatively, syntheses at the 0.2 μmol scale can be done on a 96-well plate synthesizer, such as the instrument produced by Protogene (Palo Alto, Calif.) with minimal modification to the cycle. A 33-fold excess (60 µL of 0.11 M=6.6 µmol) of 2'-O-methyl phosphoramidite and a 75-fold excess of S-ethyl tetrazole (60 µL of 0.25 M=15 µmol) can be used in each coupling cycle of 2'-O-methyl residues relative to polymer-bound 5'-hydroxyl. A 66-fold excess (120 µL of 0.11 M=13.2 µmol) of alkylsilyl (ribo) protected phosphoramidite and a 150-fold excess of S-ethyl tetrazole (120 µL of 0.25 M=30 µmol) can be used in each coupling cycle of ribo residues relative to polymer-bound 5'-hydroxyl. Average coupling yields on the 394 Applied Biosystems, Inc. synthesizer, determined by colorimetric quantitation of the trityl fractions, are typically 97.5-99%. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/10% 2,6-lutidine in THF (ABI); oxidation solution is 16.9 mM $I_2$, 49 mM pyridine, 9% water in THF (PERSEPTIVE™). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide 0.05 M in acetonitrile) is used.

Deprotection of the RNA is performed using either a two-pot or one-pot protocol. For the two-pot protocol, the polymer-bound trityl-on oligoribonucleotide is transferred to a 4 mL glass screw top vial and suspended in a solution of 40% aq. methylamine (1 mL) at 65° C. for 10 minutes. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder. The base deprotected oligoribonucleotide is resuspended in anhydrous TEA/HF/NMP solution (300 µL of a solution of 1.5 mL N-methylpyrrolidinone, 750 µL TEA and 1 mL TEA.3HF to provide a 1.4 M HF concentration) and heated to 65° C. After 1.5 h, the oligomer is quenched with 1.5 M $NH_4HCO_3$.

Alternatively, for the one-pot protocol, the polymer-bound trityl-on oligoribonucleotide is transferred to a 4 mL glass screw top vial and suspended in a solution of 33% ethanolic methylamine/DMSO: 1/1 (0.8 mL) at 65° C. for 15 minutes. The vial is brought to room temperature TEA.3HF (0.1 mL) is added and the vial is heated at 65° C. for 15 minutes. The sample is cooled at −20° C. and then quenched with 1.5 M $NH_4HCO_3$.

For purification of the trityl-on oligomers, the quenched $NH_4HCO_3$ solution is loaded onto a C-18 containing cartridge that had been prewashed with acetonitrile followed by 50 mM TEAA. After washing the loaded cartridge with water, the RNA is detritylated with 0.5% TFA for 13 minutes. The cartridge is then washed again with water, salt exchanged with 1 M NaCl and washed with water again. The oligonucleotide is then eluted with 30% acetonitrile.

The average stepwise coupling yields are typically >98% (Wincott et al., 1995 Nucleic Acids Res. 23, 2677-2684). Those of ordinary skill in the art will recognize that the scale of synthesis can be adapted to be larger or smaller than the example described above including but not limited to 96-well format.

Alternatively, the nucleic acid molecules of the present invention can be synthesized separately and joined together post-synthetically, for example, by ligation (Moore et al., 1992, Science 256, 9923; Draper et al., International PCT publication No. WO 93/23569; Shabarova et al., 1991, Nucleic Acids Research 19, 4247; Bellon et al., 1997, Nucleosides & Nucleotides, 16, 951; Bellon et al., 1997, Bioconjugate Chem. 8, 204), or by hybridization following synthesis and/or deprotection.

The siNA molecules of the invention can also be synthesized via a tandem synthesis methodology as described in Example 1 herein, wherein both siNA strands are synthesized as a single contiguous oligonucleotide fragment or strand separated by a cleavable linker which is subsequently cleaved to provide separate siNA fragments or strands that hybridize and permit purification of the siNA duplex. The linker can be a polynucleotide linker or a non-nucleotide linker. The tandem synthesis of siNA as described herein can be readily adapted to both multiwell/multiplate synthesis platforms such as 96 well or similarly larger multi-well platforms. The tandem synthesis of siNA as described herein can also be readily adapted to large scale synthesis platforms employing batch reactors, synthesis columns and the like.

A siNA molecule can also be assembled from two distinct nucleic acid strands or fragments wherein one fragment includes the sense region and the second fragment includes the antisense region of the RNA molecule.

The nucleic acid molecules of the present invention can be modified extensively to enhance stability by modification with nuclease resistant groups, for example, 2'-amino, 2'-C-allyl, 2'-fluoro, 2'-O-methyl, 2'-H (for a review see Usman and Cedergren, 1992, TIBS 17, 34; Usman et al., 1994, Nucleic Acids Symp. Ser. 31, 163). siNA constructs can be purified by gel electrophoresis using general methods or can be purified by high pressure liquid chromatography (HPLC; see Wincott et al., supra, the totality of which is hereby incorporated herein by reference) and re-suspended in water.

In another aspect of the invention, siNA molecules of the invention are expressed from transcription units inserted into DNA or RNA vectors. The recombinant vectors can be DNA plasmids or viral vectors. siNA expressing viral vectors can be constructed based on, but not limited to, adeno-associated virus, retrovirus, adenovirus, or alphavirus. The recombinant vectors capable of expressing the siNA molecules can be delivered as described herein, and persist in target cells. Alternatively, viral vectors can be used that provide for transient expression of siNA molecules.

Optimizing Activity of the Nucleic Acid Molecule of the Invention.

Chemically synthesizing nucleic acid molecules with modifications (base, sugar and/or phosphate) can prevent their degradation by serum ribonucleases, which can increase their potency (see e.g., Eckstein et al., International Publication No. WO 92/07065; Perrault et al., 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; Gold et al., U.S. Pat. No. 6,300,074; and Burgin et al., supra; all of which are incorporated by reference herein). All of the above references describe various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565-568; Pieken et al. Science, 1991, 253, 314-317; Usman and Cedergren, Trends in Biochem. Sci., 1992, 17, 334-339; Usman et al. International Publication PCT No. WO 93/15187; Sproat, U.S. Pat. No. 5,334,711 and Beigelman et al., 1995, J. Biol. Chem., 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, Tetrahedron Lett., 39, 1131; Earnshaw and Gait, 1998, Biopolymers (Nucleic Acid Sciences), 48, 39-55; Verma and Eckstein, 1998, Annu. Rev. Biochem., 67, 99-134; and Burlina et al., 1997, Bioorg. Med. Chem., 5, 1999-2010; all of the references are hereby incorporated in their totality by reference herein). Such publications describe general methods and strategies to determine the location of incorporation of sugar, base and/or phosphate modifications and the like into nucleic acid molecules without modulating catalysis, and are incorporated by reference herein. In view of such teachings, similar modifications can be used as described herein to modify the siNA nucleic acid molecules of the instant invention so long as the ability of siNA to promote RNAi is cells is not significantly inhibited.

While chemical modification of oligonucleotide internucleotide linkages with phosphorothioate, phosphorodithioate, and/or 5'-methylphosphonate linkages improves stability, excessive modifications can cause some toxicity or decreased activity. Therefore, when designing nucleic acid molecules, the amount of these internucleotide linkages should be minimized. The reduction in the concentration of these linkages should lower toxicity, resulting in increased efficacy and higher specificity of these molecules.

Short interfering nucleic acid (siNA) molecules having chemical modifications that maintain or enhance activity are provided. Such a nucleic acid is also generally more resistant to nucleases than an unmodified nucleic acid. Accordingly, the in vitro and/or in vivo activity should not be significantly lowered. In cases in which modulation is the goal, therapeutic nucleic acid molecules delivered exogenously should optimally be stable within cells until translation of the target RNA has been modulated long enough to reduce the levels of the undesirable protein. This period of time varies between hours to days depending upon the disease state. Improvements in the chemical synthesis of RNA and DNA (Wincott et al., 1995, Nucleic Acids Res. 23, 2677; Caruthers et al., 1992, Methods in Enzymology 211, 3-19 (incorporated by reference herein)) have expanded the ability to modify nucleic acid molecules by introducing nucleotide modifications to enhance their nuclease stability, as described above.

In one embodiment, nucleic acid molecules of the invention include one or more (e.g., about 1, 2, 3, 4, 5, 6, 7, 8, 9, 10, or more) G-clamp nucleotides. A G-clamp nucleotide is a modified cytosine analog wherein the modifications confer the ability to hydrogen bond both Watson-Crick and Hoogsteen faces of a complementary guanine within a duplex, see for example Lin and Matteucci, 1998, J. Am. Chem. Soc., 120, 8531-8532. A single G-clamp analog substitution within an oligonucleotide can result in substantially enhanced helical thermal stability and mismatch discrimination when hybridized to complementary oligonucleotides. The inclusion of such nucleotides in nucleic acid molecules of the invention results in both enhanced affinity and specificity to nucleic acid targets, complementary sequences, or template strands. In another embodiment, nucleic acid molecules of the invention include one or more (e.g., about 1, 2, 3, 4, 5, 6, 7, 8, 9, 10, or more) LNA "locked nucleic acid" nucleotides such as a 2', 4'-C methylene bicyclo nucleotide (see for example Wengel et al., International PCT Publication No. WO 00/66604 and WO 99/14226).

In another embodiment, the invention features conjugates and/or complexes of siNA molecules of the invention. Such conjugates and/or complexes can be used to facilitate delivery of siNA molecules into a biological system, such as a cell. The conjugates and complexes provided by the instant invention can impart therapeutic activity by transferring therapeutic compounds across cellular membranes, altering the pharmacokinetics, and/or modulating the localization of nucleic acid molecules of the invention. The present invention encompasses the design and synthesis of novel conjugates and complexes for the delivery of molecules, including, but not limited to, small molecules, lipids, cholesterol, phospholipids, nucleosides, nucleotides, nucleic acids, antibodies, toxins, negatively charged polymers and other polymers, for example, proteins, peptides, hormones, carbohydrates, polyethylene glycols, or polyamines, across cellular membranes. In general, the transporters described are designed to be used either individually or as part of a multi-component system, with or without degradable linkers. These compounds are expected to improve delivery and/or localization of nucleic acid molecules of the invention into a number of cell types originating from different tissues, in the presence or absence of serum (see Sullenger and Cech, U.S. Pat. No. 5,854,038). Conjugates of the molecules described herein can be attached to biologically active molecules via linkers that are biodegradable, such as biodegradable nucleic acid linker molecules.

In one embodiment, the invention features a compound having Formula 1:

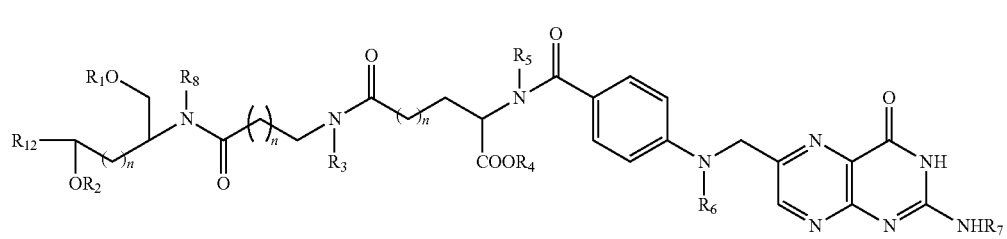

wherein each $R_1$, $R_3$, $R_4$, $R_5$, $R_6$, $R_7$ and $R_8$ is independently hydrogen, alkyl, substituted alkyl, aryl, substituted aryl, or a protecting group, each "n" is independently an integer from 0 to about 200, $R_{12}$ is a straight or branched chain alkyl, substituted alkyl, aryl, or substituted aryl, and $R_2$ is a siNA molecule or a portion thereof.

In one embodiment, the invention features a compound having Formula 2:

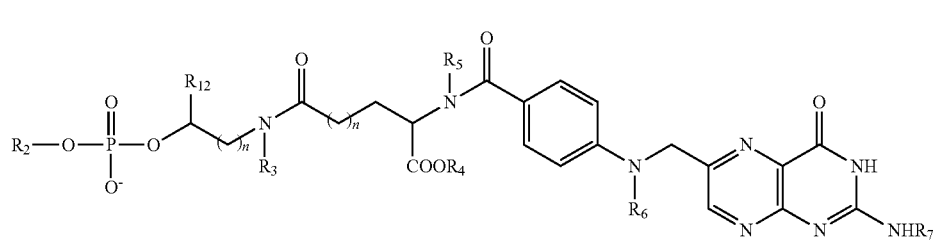

wherein each $R_3$, $R_4$, $R_5$, $R_6$ and $R_7$ is independently hydrogen, alkyl, substituted alkyl, aryl, substituted aryl, or a protecting group, each "n" is independently an integer from 0 to about 200, $R_{12}$ is a straight or branched chain alkyl, substituted alkyl, aryl, or substituted aryl, and $R_2$ is a siNA molecule or a portion thereof.

In one embodiment, the invention features a compound having Formula 3:

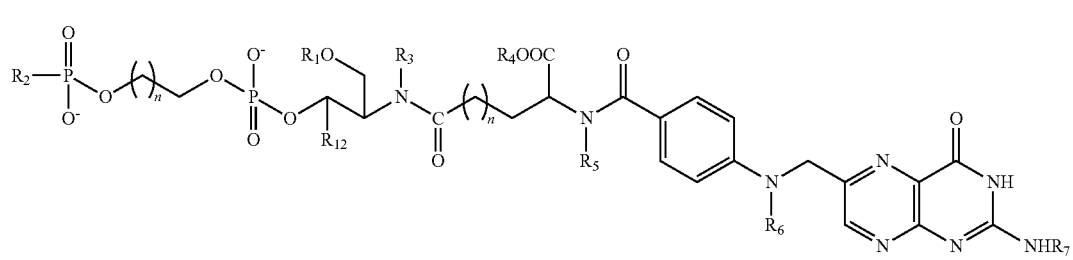

wherein each $R_1$, $R_3$, $R_4$, $R_5$ $R_6$ and $R_7$ is independently hydrogen, alkyl, substituted alkyl, aryl, substituted aryl, or a protecting group, each "n" is independently an integer from 0 to about 200, $R_{12}$ is a straight or branched chain alkyl, substituted alkyl, aryl, or substituted aryl, and $R_2$ is a siNA molecule or a portion thereof.

In one embodiment, the invention features a compound having Formula 4:

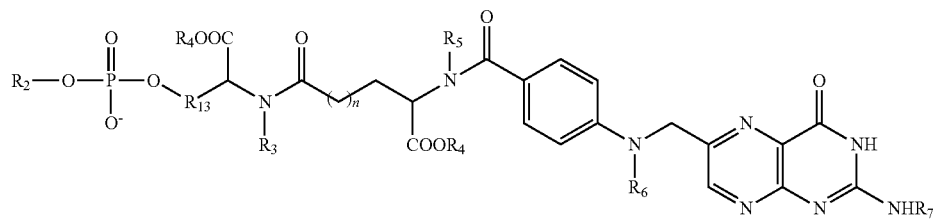

4 wherein each $R_3$, $R_4$, $R_5$, $R_6$ and $R_7$ is independently hydrogen, alkyl, substituted alkyl, aryl, substituted aryl, or a protecting group, each "n" is independently an integer from 0 to about 200, $R_2$ is a siNA molecule or a portion thereof, and $R_{13}$ is an amino acid side chain.

In one embodiment, the invention features a compound having Formula 5:

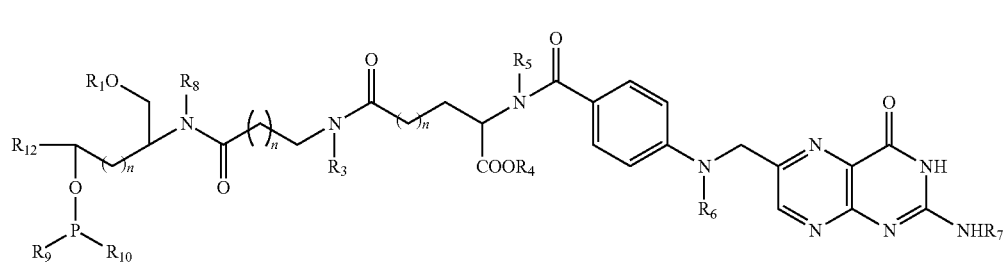

5 wherein each $R_1$ and $R_4$ is independently a protecting group or hydrogen, each $R_3$, $R_5$, $R_6$, $R_7$ and $R_8$ is independently hydrogen, alkyl or nitrogen protecting group, each "n" is independently an integer from 0 to about 200, $R_{12}$ is a straight or branched chain alkyl, substituted alkyl, aryl, or substituted aryl, and each $R_9$ and $R_{10}$ is independently a nitrogen containing group, cyanoalkoxy, alkoxy, aryloxy, or alkyl group.

In one embodiment, the invention features a compound having Formula 6:

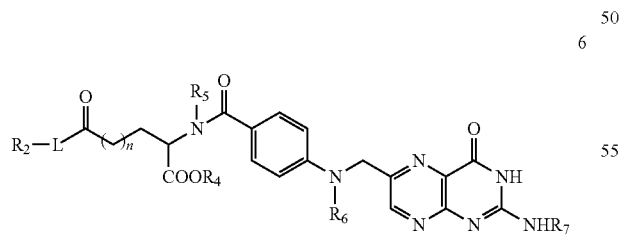

6 wherein each $R_4$, $R_5$, $R_6$ and $R_7$ is independently hydrogen, alkyl, substituted alkyl, aryl, substituted aryl, or a protecting group, $R_2$ is a siNA molecule or a portion thereof, each "n" is independently an integer from 0 to about 200, and L is a degradable linker.

In one embodiment, the invention features a compound having Formula 7:

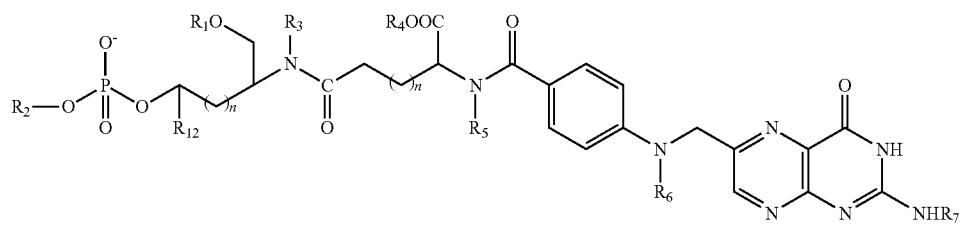

7 wherein each $R_1$, $R_3$, $R_4$, $R_5$, $R_6$ and $R_7$ is independently hydrogen, alkyl, substituted alkyl, aryl, substituted aryl, or a protecting group, each "n" is independently an integer from 0 to about 200, $R_{12}$ is a straight or branched chain alkyl, substituted alkyl, aryl, or substituted aryl, and $R_2$ is a siNA molecule or a portion thereof.

In one embodiment, the invention features a compound having Formula 8:

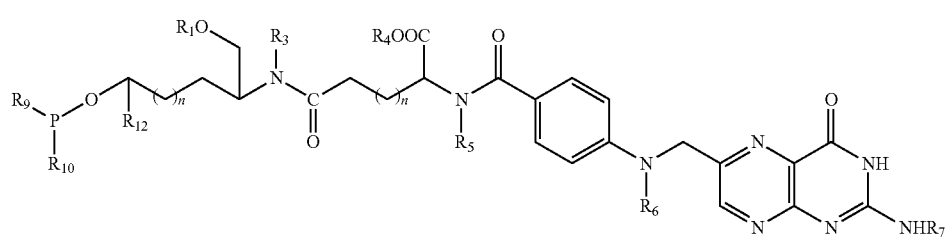

8 wherein each $R_1$ and $R_4$ is independently a protecting group or hydrogen, each $R_3$, $R_5$, $R_6$ and $R_7$ is independently hydrogen, alkyl or nitrogen protecting group, each "n" is independently an integer from 0 to about 200, $R_{12}$ is a straight or branched chain alkyl, substituted alkyl, aryl, or substituted aryl, and each $R_9$ and $R_{10}$ is independently a nitrogen containing group, cyanoalkoxy, alkoxy, aryloxy, or alkyl group.

In one embodiment, $R_{13}$ of a compound of the invention comprises an alkylamino or an alkoxy group, for example, —$CH_2O$— or —$CH(CH_2)CH_2O$—.

In another embodiment, $R_{12}$ of a compound of the invention is an alkylhyrdroxyl, for example, —$(CH_2)_nOH$, where n comprises an integer from about 1 to about 10.

In another embodiment, L of Formula 6 of the invention comprises serine, threonine, or a photolabile linkage.

In one embodiment, $R_9$ of a compound of the invention comprises a phosphorus protecting group, for example —$OCH_2CH_2CN$ (oxyethylcyano).

In one embodiment, $R_{10}$ of a compound of the invention comprises a nitrogen containing group, for example, —$N(R_{14})$ wherein $R_{14}$ is a straight or branched chain alkyl having from about 1 to about 10 carbons.

In another embodiment, $R_{10}$ of a compound of the invention comprises a heterocycloalkyl or heterocycloalkenyl ring containing from about 4 to about 7 atoms, and having from about 1 to about 3 heteroatoms comprising oxygen, nitrogen, or sulfur.

In another embodiment, $R_1$ of a compound of the invention comprises an acid labile protecting group, such as a trityl or substituted trityl group, for example, a dimethoxytrityl or mono-methoxytrityl group.

In another embodiment, $R_4$ of a compound of the invention comprises a tert-butyl, Fm (fluorenyl-methoxy), or allyl group.

In one embodiment, $R_6$ of a compound of the invention comprises a TFA (trifluoracetyl) group.

In another embodiment, $R_3$, $R_5$ $R_7$ and $R_8$ of a compound of the invention are independently hydrogen.

In one embodiment, $R_7$ of a compound of the invention is independently isobutyryl, dimethylformamide, or hydrogen.

In another embodiment, $R_{12}$ of a compound of the invention comprises a methyl group or ethyl group.

In one embodiment, the invention features a compound having Formula 27:

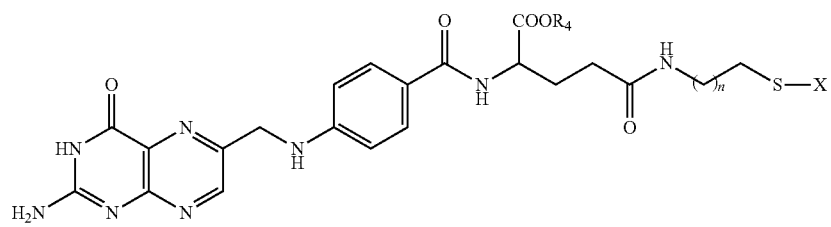

27 wherein "n" is an integer from about 0 to about 20, $R_4$ is H or a cationic salt, X is a siNA molecule or a portion thereof, and $R_{24}$ is a sulfur containing leaving group, for example a group comprising:

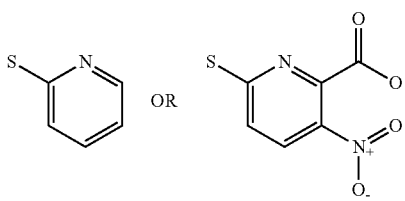

In one embodiment, the invention features a compound having Formula 39:

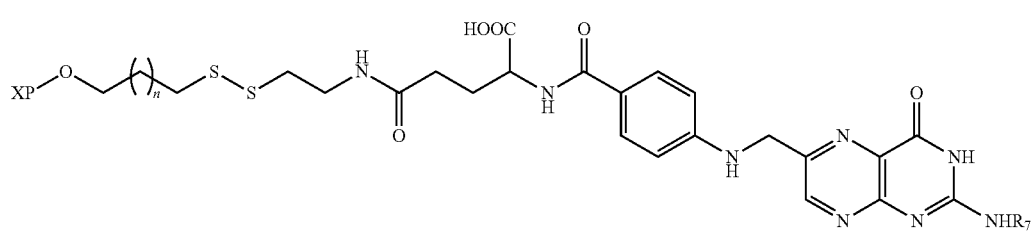

wherein "n" is an integer from about 0 to about 20, X is a siNA molecule or a portion thereof, and P is a phosphorus containing group.

In another embodiment, a thiol containing linker of the invention is a compound having Formula 41:

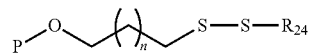

wherein "n" is an integer from about 0 to about 20, P is a phosphorus containing group, for example a phosphine, phosphite, or phosphate, and R24 is any alkyl, substituted alkyl, alkoxy, aryl, substituted aryl, alkenyl, substituted alkenyl, alkynyl, or substituted alkynyl group with or without additional protecting groups.

In one embodiment, the invention features a compound having Formula 43:

wherein X comprises a siNA molecule or portion thereof; W comprises a degradable nucleic acid linker; Y comprises a linker molecule or amino acid that can be present or absent; Z comprises H, OH, O-alkyl, SH, S-alkyl, alkyl, substituted alkyl, aryl, substituted aryl, amino, substituted amino, nucleotide, nucleoside, nucleic acid, oligonucleotide, amino acid, peptide, protein, lipid, phospholipid, or label; n is an integer from about 1 to about 100; and N' is an integer from about 1 to about 20. In another embodiment, W is selected from the group consisting of amide, phosphate, phosphate ester, phosphoramidate, or thiophosphate ester linkage.

In another embodiment, the invention features a compound having Formula 44:

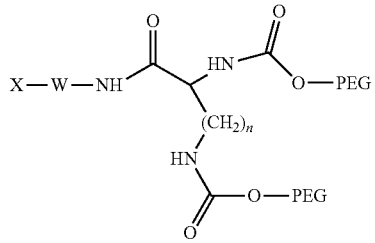

wherein X comprises a siNA molecule or portion thereof; W comprises a linker molecule or chemical linkage that can be present or absent; n is an integer from about 1 to about 50, and PEG represents a compound having Formula 45:

wherein Z comprises H, OH, O-alkyl, SH, S-alkyl, alkyl, substituted alkyl, aryl, substituted aryl, amino, substituted amino, nucleotide, nucleoside, nucleic acid, oligonucleotide, amino acid, peptide, protein, lipid, phospholipid, or label; and n is an integer from about 1 to about 100. In another embodiment, W is selected from the group consisting of amide, phosphate, phosphate ester, phosphoramidate, or thiophosphate ester linkage.

In another embodiment, the invention features a compound having Formula 46:

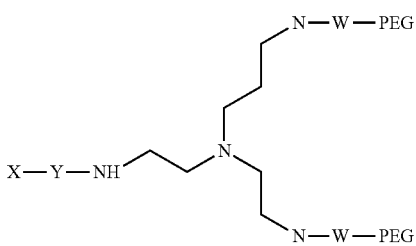

wherein X comprises a siNA molecule or portion thereof; each W independently comprises linker molecule or chemical linkage that can be present or absent, Y comprises a linker molecule or chemical linkage that can be present or absent; and PEG represents a compound having Formula 45:

wherein Z comprises H, OH, O-alkyl, SH, S-alkyl, alkyl, substituted alkyl, aryl, substituted aryl, amino, substituted amino, nucleotide, nucleoside, nucleic acid, oligonucleotide, amino acid, peptide, protein, lipid, phospholipid, or label; and n is an integer from about 1 to about 100. In another embodiment, W is selected from the group consisting of amide, phosphate, phosphate ester, phosphoramidate, or thiophosphate ester linkage.

In one embodiment, the invention features a compound having Formula 47:

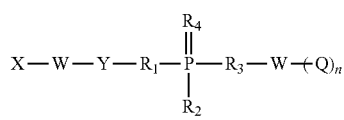

wherein X comprises a siNA molecule or portion thereof; each W independently comprises a linker molecule or chemical linkage that can be the same or different and can be present or absent, Y comprises a linker molecule that can be present or absent; each Q independently comprises a hydrophobic group or phospholipid; each R1, R2, R3, and R4 independently comprises O, OH, H, alkyl, alkylhalo, O-alkyl, O-alkylcyano, S, S-alkyl, S-alkylcyano, N or substituted N, and n is an integer from about 1 to about 10. In another embodiment, W is selected from the group consisting of amide, phosphate, phosphate ester, phosphoramidate, or thiophosphate ester linkage.

In another embodiment, the invention features a compound having Formula 48:

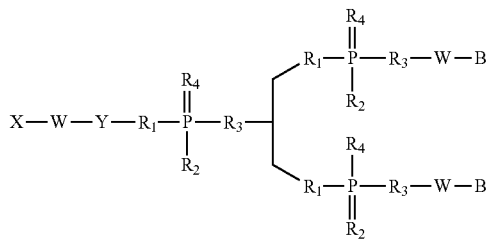

wherein X comprises a siNA molecule or portion thereof; each W independently comprises a linker molecule or chemical linkage that can be present or absent, Y comprises a linker molecule that can be present or absent; each R1, R2, R3, and R4 independently comprises O, OH, H, alkyl, alkylhalo, O-alkyl, O-alkylcyano, S, S-alkyl, S-alkylcyano, N or substituted N, and B represents a lipophilic group, for example a saturated or unsaturated linear, branched, or cyclic alkyl group, cholesterol, or a derivative thereof. In another embodiment, W is selected from the group consisting of amide, phosphate, phosphate ester, phosphoramidate, or thiophosphate ester linkage.

In another embodiment, the invention features a compound having Formula 49:

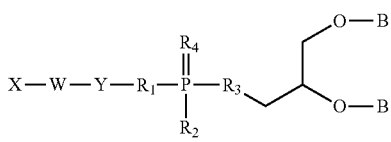

wherein X comprises a siNA molecule or portion thereof; W comprises a linker molecule or chemical linkage that can be present or absent, Y comprises a linker molecule that can be present or absent; each R1, R2, R3, and R4 independently comprises O, OH, H, alkyl, alkylhalo, O-alkyl, O-alkylcyano, S, S-alkyl, S-alkylcyano, N or substituted N, and B represents a lipophilic group, for example a saturated or unsaturated linear, branched, or cyclic alkyl group, cholesterol, or a derivative thereof. In another embodiment, W is selected from the group consisting of amide, phosphate, phosphate ester, phosphoramidate, or thiophosphate ester linkage.

In another embodiment, the invention features a compound having Formula 50:

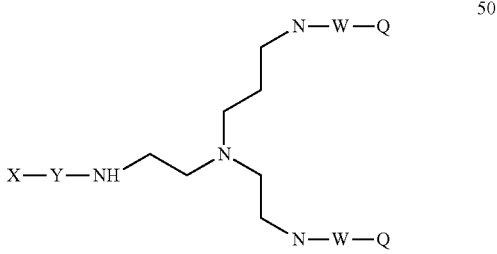

wherein X comprises a siNA molecule or portion thereof; W comprises a linker molecule or chemical linkage that can be present or absent, Y comprises a linker molecule or chemical linkage that can be present or absent; and each Q independently comprises a hydrophobic group or phospholipid. In another embodiment, W is selected from the group consisting of amide, phosphate, phosphate ester, phosphoramidate, or thiophosphate ester linkage.

In one embodiment, the invention features a compound having Formula 51:

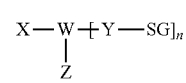

wherein X comprises a siNA molecule or portion thereof; W comprises a linker molecule or chemical linkage that can be present or absent; Y comprises a linker molecule or amino acid that can be present or absent; Z comprises H, OH, O-alkyl, SH, S-alkyl, alkyl, substituted alkyl, aryl, substituted aryl, amino, substituted amino, nucleotide, nucleoside, nucleic acid, oligonucleotide, amino acid, peptide, protein, lipid, phospholipid, or label; SG comprises a sugar, for example galactose, galactosamine, N-acetyl-galactosamine, glucose, mannose, fructose, or fucose and the respective D or L, alpha or beta isomers, and n is an integer from about 1 to about 20. In another embodiment, W is selected from the group consisting of amide, phosphate, phosphate ester, phosphoramidate, or thiophosphate ester linkage.

In another embodiment, the invention features a compound having Formula 52:

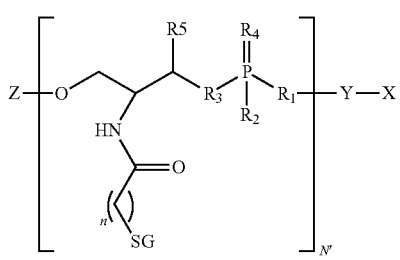

wherein X comprises a siNA molecule or portion thereof; Y comprises a linker molecule or chemical linkage that can be present or absent; each R1, R2, R3, R4, and R5 independently comprises O, OH, H, alkyl, alkylhalo, O-alkyl, O-alkylcyano, S, S-alkyl, S-alkylcyano, N or substituted N; Z comprises H, OH, O-alkyl, SH, S-alkyl, alkyl, substituted alkyl, aryl, substituted aryl, amino, substituted amino, nucleotide, nucleoside, nucleic acid, oligonucleotide, amino acid, peptide, protein, lipid, phospholipid, or label; SG comprises a sugar, for example galactose, galactosamine, N-acetyl-galactosamine, glucose, mannose, fructose, or fucose and the respective D or L, alpha or beta isomers, n is an integer from about 1 to about 20; and N' is an integer from about 1 to about 20. In another embodiment, X comprises a siNA molecule or a portion thereof. In another embodiment, Y is selected from the group consisting of amide, phosphate, phosphate ester, phosphoramidate, or thiophosphate ester linkage.

In another embodiment, the invention features a compound having Formula 53:

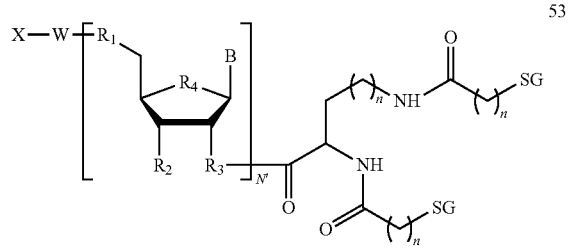

wherein B comprises H, a nucleoside base, or a non-nucleosidic base with or without protecting groups; each R1 independently comprises O, N, S, alkyl, or substituted N; each R2 independently comprises O, OH, H, alkyl, alkylhalo, O-alkyl, O-alkylhalo, S, N, substituted N, or a phosphorus containing group; each R3 independently comprises N or O—N, each R4 independently comprises O, CH2, S, sulfone, or sulfoxy; X comprises H, a removable protecting group, a siNA molecule or a portion thereof; W comprises a linker molecule or chemical linkage that can be present or absent; SG comprises a sugar, for example galactose, galactosamine, N-acetyl-galactosamine, glucose, mannose, fructose, or fucose and the respective D or L, alpha or beta isomers, each n is independently an integer from about 1 to about 50; and N' is an integer from about 1 to about 10. In another embodiment, W is selected from the group consisting of amide, phosphate, phosphate ester, phosphoramidate, or thiophosphate ester linkage.

In another embodiment, the invention features a compound having Formula 54:

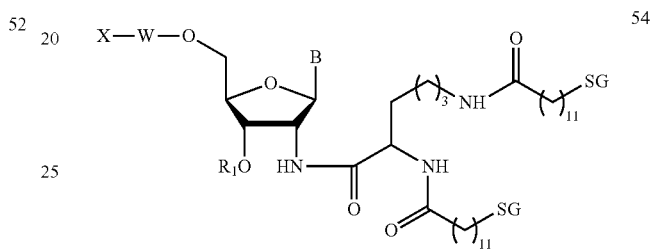

wherein B comprises H, a nucleoside base, or a non-nucleosidic base with or without protecting groups; each R1 independently comprises O, OH, H, alkyl, alkylhalo, O-alkyl, O-alkylhalo, S, N, substituted N, or a phosphorus containing group; X comprises H, a removable protecting group, a siNA molecule or a portion thereof; W comprises a linker molecule or chemical linkage that can be present or absent; and SG comprises a sugar, for example galactose, galactosamine, N-acetyl-galactosamine, glucose, mannose, fructose, or fucose and the respective D or L, alpha or beta isomers. In another embodiment, W is selected from the group consisting of amide, phosphate, phosphate ester, phosphoramidate, or thiophosphate ester linkage.

In one embodiment, the invention features a compound having Formula 55:

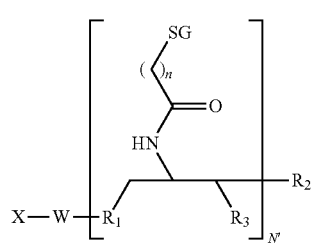

wherein each R1 independently comprises O, N, S, alkyl, or substituted N; each R2 independently comprises O, OH, H, alkyl, alkylhalo, O-alkyl, O-alkylhalo, S, N, substituted N, or a phosphorus containing group; each R3 independently comprises H, OH, alkyl, substituted alkyl, or halo; X comprises H, a removable protecting group, a siNA molecule or a portion thereof; W comprises a linker molecule or chemical linkage that can be present or absent; SG comprises a sugar, for example galactose, galactosamine, N-acetyl-galactosamine, glucose, mannose, fructose, or fucose and the respective D or L, alpha or beta isomers, each n is independently an integer from about 1 to about 50; and N' is an integer from about 1 to about 100. In another embodiment, W is selected from the group consisting of amide, phosphate, phosphate ester, phosphoramidate, or thiophosphate ester linkage.

In another embodiment, the invention features a compound having Formula 56:

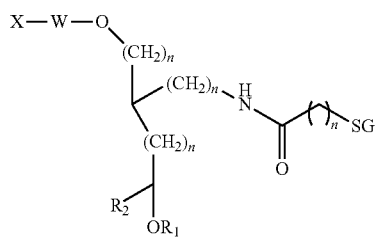

56 wherein R1 comprises H, alkyl, alkylhalo, N, substituted N, or a phosphorus containing group; R2 comprises H, O, OH, alkyl, alkylhalo, halo, S, N, substituted N, or a phosphorus containing group; X comprises H, a removable protecting group, a siNA molecule or a portion thereof; W comprises a linker molecule or chemical linkage that can be present or absent; SG comprises a sugar, for example galactose, galactosamine, N-acetyl-galactosamine, glucose, mannose, fructose, or fucose and the respective D or L, alpha or beta isomers, and each n is independently an integer from about 0 to about 20. In another embodiment, W is selected from the group consisting of amide, phosphate, phosphate ester, phosphoramidate, or thiophosphate ester linkage.

In another embodiment, the invention features a compound having Formula 57:

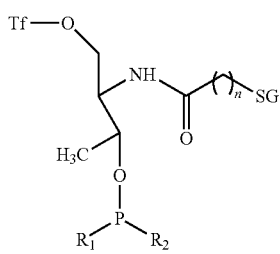

57 wherein R1 can include the groups:

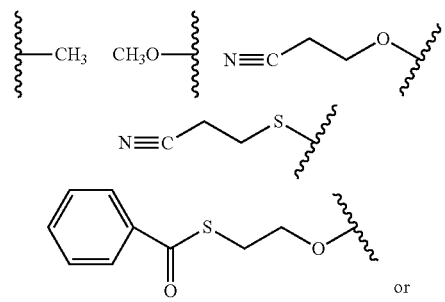

or

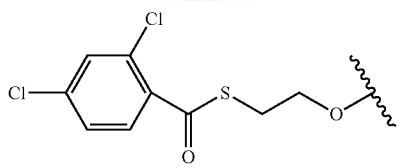

and wherein R2 can include the groups:

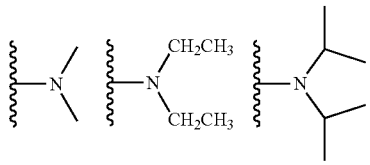

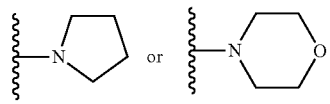

and wherein Tr is a removable protecting group, for example a trityl, monomethoxytrityl, or dimethoxytrityl; SG comprises a sugar, for example galactose, galactosamine, N-acetyl-galactosamine, glucose, mannose, fructose, or fucose and the respective D or L, alpha or beta isomers, and n is an integer from about 1 to about 20.

In one embodiment, compounds having Formula 52, 53, 54, 55, 56, and 57 are featured wherein each nitrogen adjacent to a carbonyl can independently be substituted for a carbonyl adjacent to a nitrogen or each carbonyl adjacent to a nitrogen can be substituted for a nitrogen adjacent to a carbonyl.

In another embodiment, the invention features a compound having Formula 58:

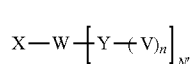

58 wherein X comprises a siNA molecule or portion thereof; W comprises a linker molecule or chemical linkage that can be present or absent; Y comprises a linker molecule or amino acid that can be present or absent; V comprises a signal protein or peptide, for example Human serum albumin protein, Antennapedia peptide, Kaposi fibroblast growth factor peptide, *Caiman crocodylus* Ig(5) light chain peptide, HIV envelope glycoprotein gp41 peptide, HIV-1 Tat peptide, Influenza hemagglutinin envelope glycoprotein peptide, or transportan A peptide; each n is independently an integer from about 1 to about 50; and N' is an integer from about 1 to about 100. In another embodiment, W is selected from the group consisting of amide, phosphate, phosphate ester, phosphoramidate, or thiophosphate ester linkage.

In another embodiment, the invention features a compound having Formula 59:

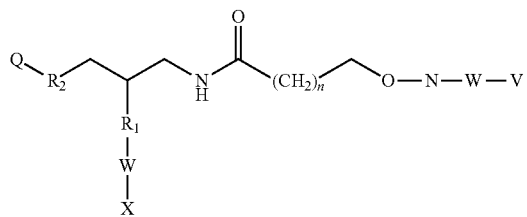

59

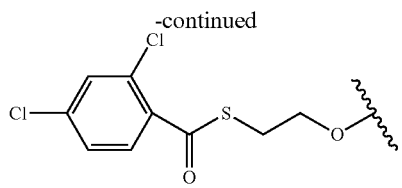

-continued and wherein R2 can include the groups:

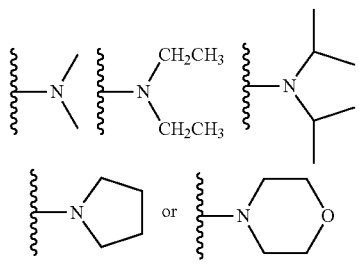

wherein each R1 independently comprises O, S, N, substituted N, or a phosphorus containing group; each R2 independently comprises O, S, or N; X comprises H, amino, substituted amino, nucleotide, nucleoside, nucleic acid, oligonucleotide, or other biologically active molecule; n is an integer from about 1 to about 50, Q comprises H or a removable protecting group which can be optionally absent, each W independently comprises a linker molecule or chemical linkage that can be present or absent, and V comprises a signal protein or peptide, for example Human serum albumin protein, Antennapedia peptide, Kaposi fibroblast growth factor peptide, *Caiman crocodylus* Ig(5) light chain peptide, HIV envelope glycoprotein gp41 peptide, HIV-1 Tat peptide, Influenza hemagglutinin envelope glycoprotein peptide, or transportan A peptide, or a compound having Formula 45

45 wherein Z comprises H, OH, O-alkyl, SH, S-alkyl, alkyl, substituted alkyl, aryl, substituted aryl, amino, substituted amino, a removable protecting group, a siNA molecule or a portion thereof; and n is an integer from about 1 to about 100. In another embodiment, W is selected from the group consisting of amide, phosphate, phosphate ester, phosphoramidate, or thiophosphate ester linkage.

In another embodiment, the invention features a compound having Formula 60:

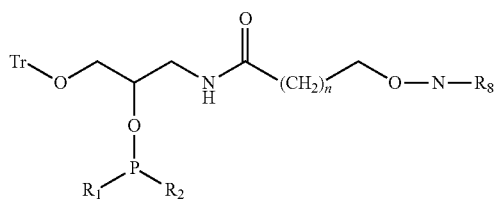

60 wherein R1 can include the groups:

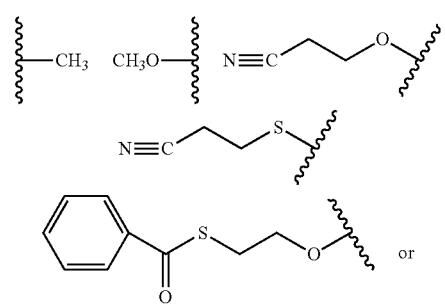

and wherein Tr is a removable protecting group, for example a trityl, monomethoxytrityl, or dimethoxytrityl; n is an integer from about 1 to about 50; and R8 is a nitrogen protecting group, for example a phthaloyl, trifluoroacetyl, FMOC, or monomethoxytrityl group.

In another embodiment, the invention features a compound having Formula 61:

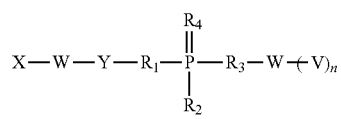

61 wherein X comprises a siNA molecule or portion thereof; each W independently comprises a linker molecule or chemical linkage that can be the same or different and can be present or absent, Y comprises a linker molecule that can be present or absent; each 5 independently comprises a signal protein or peptide, for example Human serum albumin protein, Antennapedia peptide, Kaposi fibroblast growth factor peptide, *Caiman crocodylus* Ig(5) light chain peptide, HIV envelope glycoprotein gp41 peptide, HIV-1 Tat peptide, Influenza hemagglutinin envelope glycoprotein peptide, or transportan A peptide; each R1, R2, R3, and R4 independently comprises O, OH, H, alkyl, alkylhalo, O-alkyl, O-alkylcyano, S, S-alkyl, S-alkylcyano, N or substituted N, and n is an integer from about 1 to about 10. In another embodiment, W is selected from the group consisting of amide, phosphate, phosphate ester, phosphoramidate, or thiophosphate ester linkage.

In another embodiment, the invention features a compound having Formula 62:

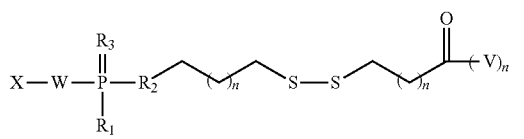

62 wherein X comprises a siNA molecule or portion thereof; each 5 independently comprises a signal protein or peptide, for example Human serum albumin protein, Antennapedia peptide, Kaposi fibroblast growth factor peptide, *Caiman crocodylus* Ig(5) light chain peptide, HIV envelope glycoprotein gp41 peptide, HIV-1 Tat peptide, Influenza hemagglutinin envelope glycoprotein peptide, or transportan A peptide; W comprises a linker molecule or chemical linkage that can be present or absent; each R1, R2, and R3 independently comprises O, OH, H, alkyl, alkylhalo, O-alkyl, O-alkylcyano, S, S-alkyl, S-alkylcyano, N or substituted N, and each n is independently an integer from about 1 to about 10. In another embodiment, W is selected from the group consisting of amide, phosphate, phosphate ester, phosphoramidate, or thiophosphate ester linkage.

In another embodiment, the invention features a compound having Formula 63:

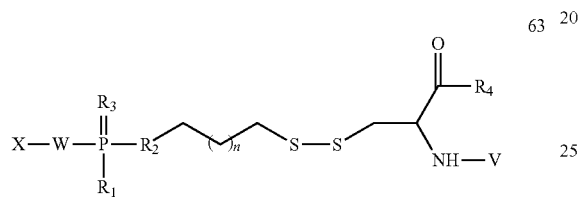

wherein X comprises a siNA molecule or portion thereof; V comprises a signal protein or peptide, for example Human serum albumin protein, Antennapedia peptide, Kaposi fibroblast growth factor peptide, *Caiman crocodylus* Ig(5) light chain peptide, HIV envelope glycoprotein gp41 peptide, HIV-1 Tat peptide, Influenza hemagglutinin envelope glycoprotein peptide, or transportan A peptide; W comprises a linker molecule or chemical linkage that can be present or absent; each R1, R2, R3 independently comprises O, OH, H, alkyl, alkylhalo, O-alkyl, O-alkylcyano, S, S-alkyl, S-alkylcyano, N or substituted N, R4 represents an ester, amide, or protecting group, and each n is independently an integer from about 1 to about 10. In another embodiment, W is selected from the group consisting of amide, phosphate, phosphate ester, phosphoramidate, or thiophosphate ester linkage.

In another embodiment, the invention features a compound having Formula 64:

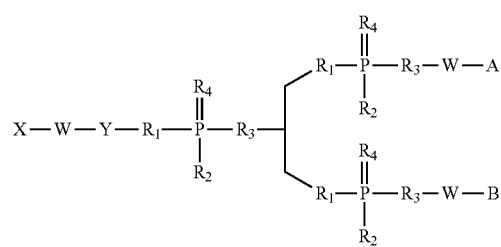

wherein X comprises a siNA molecule or portion thereof; each W independently comprises a linker molecule or chemical linkage that can be present or absent, Y comprises a linker molecule that can be present or absent; each R1, R2, R3, and R4 independently comprises O, OH, H, alkyl, alkylhalo, O-alkyl, O-alkylcyano, S, S-alkyl, S-alkylcyano, N or substituted N, A comprises a nitrogen containing group, and B comprises a lipophilic group. In another embodiment, W is selected from the group consisting of amide, phosphate, phosphate ester, phosphoramidate, or thiophosphate ester linkage.

In another embodiment, the invention features a compound having Formula 65:

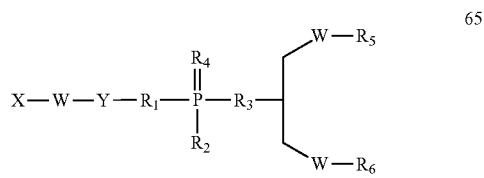

wherein X comprises a siNA molecule or portion thereof; each W independently comprises a linker molecule or chemical linkage that can be present or absent, Y comprises a linker molecule that can be present or absent; each R1, R2, R3, and R4 independently comprises O, OH, H, alkyl, alkylhalo, O-alkyl, O-alkylcyano, S, S-alkyl, S-alkylcyano, N or substituted N, RV comprises the lipid or phospholipid component of any of Formulae 47-50, and R6 comprises a nitrogen containing group. In another embodiment, W is selected from the group consisting of amide, phosphate, phosphate ester, phosphoramidate, or thiophosphate ester linkage.

In another embodiment, the invention features a compound having Formula 92:

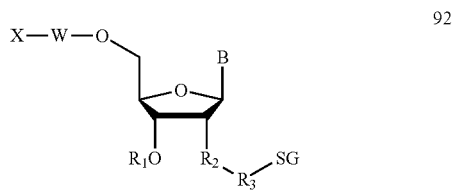

wherein B comprises H, a nucleoside base, or a non-nucleosidic base with or without protecting groups; each R1 independently comprises O, OH, H, alkyl, alkylhalo, O-alkyl, O-alkylhalo, S, N, substituted N, or a phosphorus containing group; X comprises H, a removable protecting group, amino, substituted amino, nucleotide, nucleoside, nucleic acid, oligonucleotide, enzymatic nucleic acid, amino acid, peptide, protein, lipid, phospholipid, biologically active molecule or label; W comprises a linker molecule or chemical linkage that can be present or absent; R2 comprises O, NH, S, CO, COO, ON=C, or alkyl; R3 comprises alkyl, akloxy, or an aminoacyl side chain; and SG comprises a sugar, for example galactose, galactosamine, N-acetyl-galactosamine, glucose, mannose, fructose, or fucose and the respective D or L, alpha or beta isomers. In another embodiment, W is selected from the group consisting of amide, phosphate, phosphate ester, phosphoramidate, or thiophosphate ester linkage.

In another embodiment, the invention features a compound having Formula 86:

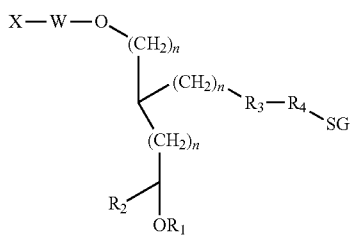

86 wherein R1 comprises H, alkyl, alkylhalo, N, substituted N, or a phosphorus containing group; R2 comprises H, O, OH, alkyl, alkylhalo, halo, S, N, substituted N, or a phosphorus containing group; X comprises H, a removable protecting group, a siNA molecule or a portion thereof; W comprises a linker molecule or chemical linkage that can be present or absent; R3 comprises O, NH, S, CO, COO, ON=C, or alkyl; R4 comprises alkyl, akloxy, or an aminoacyl side chain; and SG comprises a sugar, for example galactose, galactosamine, N-acetyl-galactosamine, glucose, mannose, fructose, or fucose and the respective D or L, alpha or beta isomers, and each n is independently an integer from about 0 to about 20. In another embodiment, W is selected from the group consisting of amide, phosphate, phosphate ester, phosphoramidate, or thiophosphate ester linkage.

In another embodiment, the invention features a compound having Formula 87:

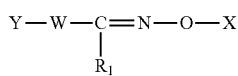

87 wherein X comprises a protein, peptide, antibody, lipid, phospholipid, oligosaccharide, label, biologically active molecule, for example a vitamin such as folate, vitamin A, E, B6, B12, coenzyme, antibiotic, antiviral, nucleic acid, nucleotide, nucleoside, or oligonucleotide such as an enzymatic nucleic acid, allozyme, antisense nucleic acid, siNA, 2,5-A chimera, decoy, aptamer or triplex forming oligonucleotide, or polymers such as polyethylene glycol; W comprises a linker molecule or chemical linkage that can be present or absent; and Y comprises siNA or a portion thereof; R1 comprises H, alkyl, or substituted alkyl. In another embodiment, W is selected from the group consisting of amide, phosphate, phosphate ester, phosphoramidate, or thiophosphate ester linkage.

In another embodiment, the invention features a compound having Formula 88:

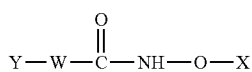

88 wherein X comprises a protein, peptide, antibody, lipid, phospholipid, oligosaccharide, label, biologically active molecule, for example a vitamin such as folate, vitamin A, E, B6, B12, coenzyme, antibiotic, antiviral, nucleic acid, nucleotide, nucleoside, or oligonucleotide such as an enzymatic nucleic acid, allozyme, antisense nucleic acid, siNA, 2,5-A chimera, decoy, aptamer or triplex forming oligonucleotide, or polymers such as polyethylene glycol; W comprises a linker molecule or chemical linkage that can be present or absent, and Y comprises a siNA or a portion thereof. In another embodiment, W is selected from the group consisting of amide, phosphate, phosphate ester, phosphoramidate, or thiophosphate ester linkage.

In another embodiment, the invention features a compound having Formula 99:

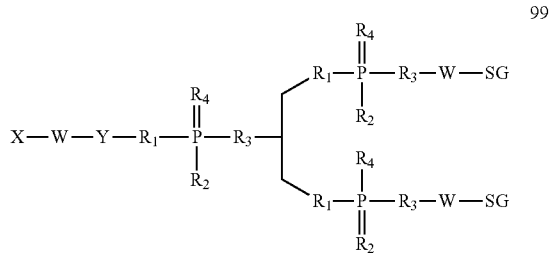

99 wherein X comprises a siNA molecule or portion thereof; each W independently comprises a linker molecule or chemical linkage that can be present or absent, Y comprises a linker molecule that can be present or absent; each R1, R2, R3, and R4 independently comprises O, OH, H, alkyl, alkylhalo, O-alkyl, O-alkylcyano, S, S-alkyl, S-alkylcyano, N or substituted N, and SG comprises a sugar, for example galactose, galactosamine, N-acetyl-galactosamine or branched derivative thereof, glucose, mannose, fructose, or fucose and the respective D or L, alpha or beta isomers. In another embodiment, W is selected from the group consisting of amide, phosphate, phosphate ester, phosphoramidate, or thiophosphate ester linkage.

In another embodiment, the invention features a compound having Formula 100:

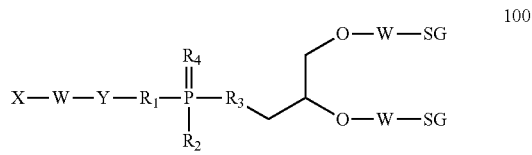

100 wherein X comprises a siNA molecule or portion thereof; W comprises a linker molecule or chemical linkage that can be present or absent, Y comprises a linker molecule that can be present or absent; each R1, R2, R3, and R4 independently comprises O, OH, H, alkyl, alkylhalo, O-alkyl, O-alkylcyano, S, S-alkyl, S-alkylcyano, N or substituted N, and SG comprises a sugar, for example galactose, galactosamine, N-acetyl-galactosamine or branched derivative thereof, glucose, mannose, fructose, or fucose and the respective D or L, alpha or beta isomers. In another embodiment, W is selected from the group consisting of amide, phosphate, phosphate ester, phosphoramidate, or thiophosphate ester linkage.

In one embodiment, the SG component of any compound having Formulae 99 or 100 comprises a compound having Formula 101:

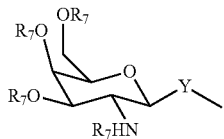

wherein Y comprises a linker molecule or chemical linkage that can be present or absent and each R7 independently comprises an acyl group that can be present or absent, for example a acetyl group.

In one embodiment, the W-SG component of a compound having Formulae 99 comprises a compound having Formula 102:

wherein R2 comprises O, OH, H, alkyl, alkylhalo, O-alkyl, O-alkylhalo, S, N, substituted N, a protecting group, or another compound having Formula 102; R1 independently H, OH, alkyl, substituted alkyl, or halo and each R7 independently comprises an acyl group that can be present or absent, for example a acetyl group, and R3 comprises O or R3 in Formula 99, and n is an integer from about 1 to about 20.

In one embodiment, the W-SG component of a compound having Formulae 99 comprises a compound having Formula 103:

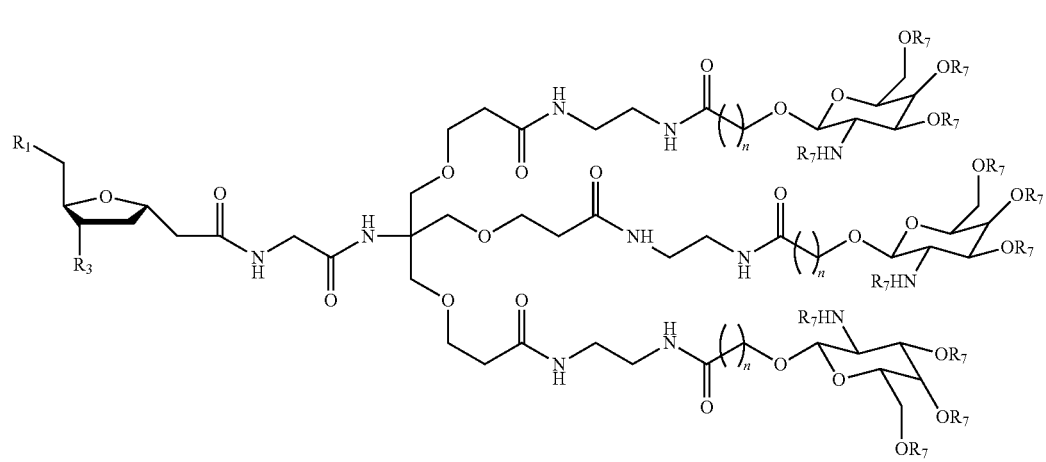

wherein R1 comprises H, alkyl, alkylhalo, O-alkyl, O-alkylhalo, S, N, substituted N, a protecting group, or another compound having Formula 103; each R7 independently comprises an acyl group that can be present or absent, for example a acetyl group, and R3 comprises H or R3 in Formula 99, and each n is independently an integer from about 1 to about 20.

In one embodiment, the invention features a compound having Formula 104:

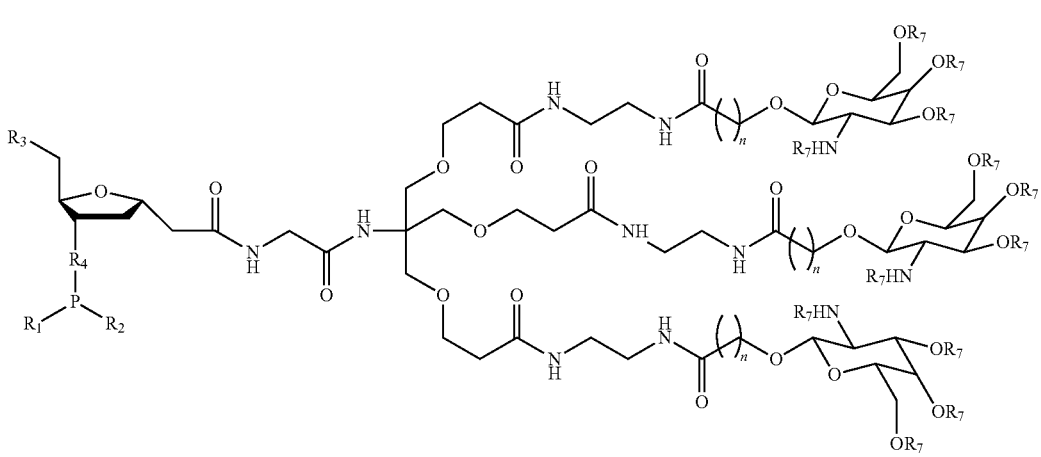

wherein R3 comprises H, OH, amino, substituted amino, nucleotide, nucleoside, nucleic acid, oligonucleotide, amino acid, peptide, protein, lipid, phospholipid, label, or a portion thereof, or OR5 where R5 a removable protecting group, R4 comprises O, alkyl, alkylhalo, O-alkyl, O-alkylcyano, S, S-alkyl, S-alkylcyano, N or substituted N, each R7 independently comprises an acyl group that can be present or absent, for example a acetyl group, and each n is independently an integer from about 1 to about 20, and wherein R1 can include the groups:

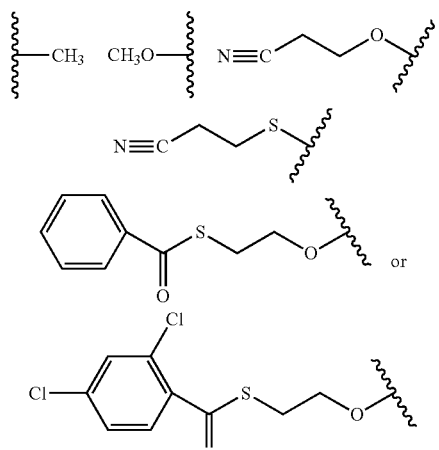

In one embodiment, the invention features a compound having Formula 105:

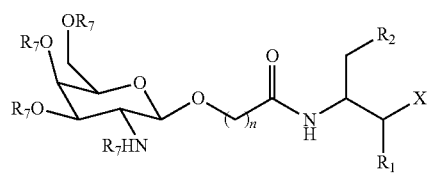

105 wherein X comprises a siNA molecule or a portion thereof, R2 comprises O, OH, H, alkyl, alkylhalo, O-alkyl, O-alkylhalo, S, N, substituted N, a protecting group, or a nucleotide, polynucleotide, or oligonucleotide or a portion thereof; R1 independently H, OH, alkyl, substituted alkyl, or halo and each R7 independently comprises an acyl group that can be present or absent, for example a acetyl group, and n is an integer from about 1 to about 20.

In one embodiment, the invention features a compound having Formula 106:

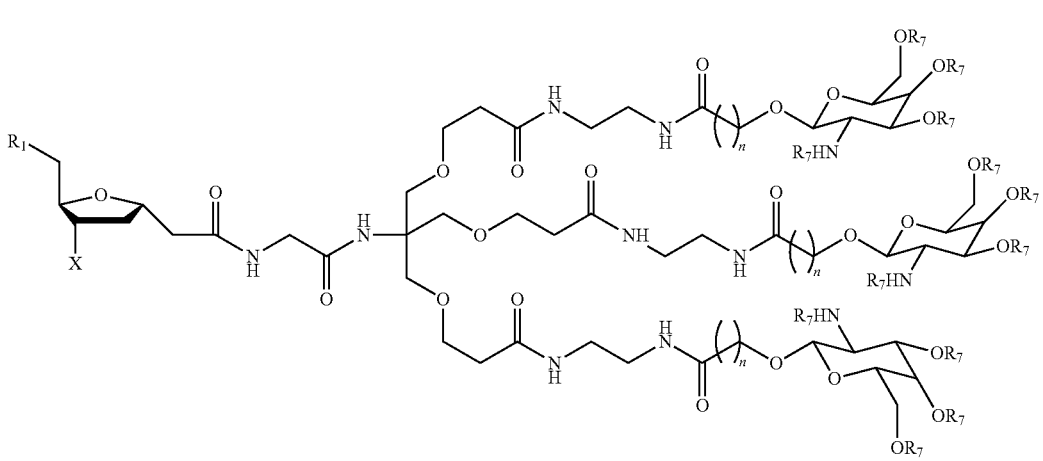

106 and wherein R2 can include the groups:

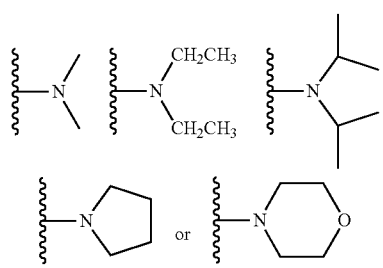

wherein X comprises a siNA molecule or a portion thereof, R1 comprises H, OH, amino, substituted amino, nucleotide, nucleoside, nucleic acid, oligonucleotide, amino acid, peptide, protein, lipid, phospholipid, label, or a portion thereof, or OR5 where R5 a removable protecting group, each R7 independently comprises an acyl group that can be present or absent, for example a acetyl group, and each n is independently an integer from about 1 to about 20

In another embodiment, the invention features a compound having Formula 107:

101

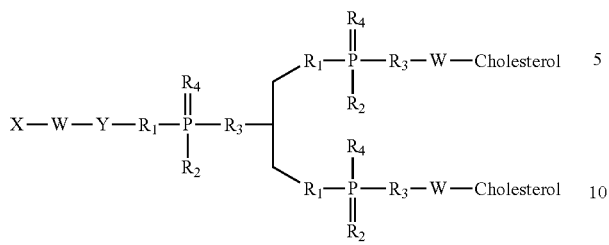

107 wherein X comprises a siNA molecule or portion thereof; each W independently comprises a linker molecule or chemical linkage that can be present or absent, Y comprises a linker molecule that can be present or absent; each R1, R2, R3, and R4 independently comprises O, OH, H, alkyl, alkylhalo, O-alkyl, O-alkylcyano, S, S-alkyl, S-alkylcyano, N or substituted N, and Cholesterol comprises cholesterol or an analog, derivative, or metabolite thereof. In another embodiment, W is selected from the group consisting of amide, phosphate, phosphate ester, phosphoramidate, or thiophosphate ester linkage.

102

In another embodiment, the invention features a compound having Formula 108:

108 wherein X comprises a siNA molecule or portion thereof; W comprises a linker molecule or chemical linkage that can be present or absent, Y comprises a linker molecule that can be present or absent; each R1, R2, R3, and R4 independently comprises O, OH, H, alkyl, alkylhalo, O-alkyl, O-alkylcyano, S, S-alkyl, S-alkylcyano, N or substituted N, and Cholesterol comprises cholesterol or an analog, derivative, or metabolite thereof. In another embodiment, W is selected from the group consisting of amide, phosphate, phosphate ester, phosphoramidate, or thiophosphate ester linkage.

In one embodiment, the W-Cholesterol component of a compound having Formula 107 comprises a compound having Formula 109:

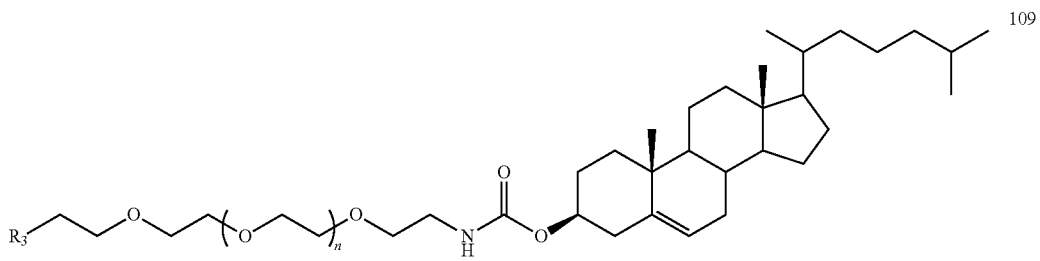

109 wherein R3 comprises R3 as described in Formula 107, and n is independently an integer from about 1 to about 20.

In one embodiment, the invention features a compound having Formula 110:

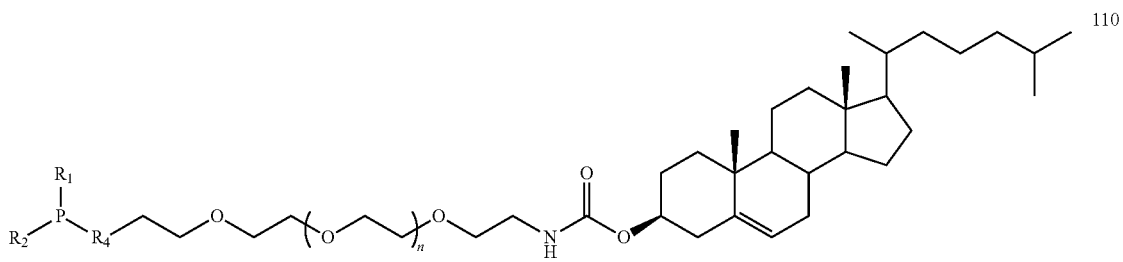

110 wherein R4 comprises O, alkyl, alkylhalo, O-alkyl, O-alkylcyano, S, S-alkyl, S-alkylcyano, N or substituted N, each n is independently an integer from about 1 to about 20, and wherein R1 can include the groups:

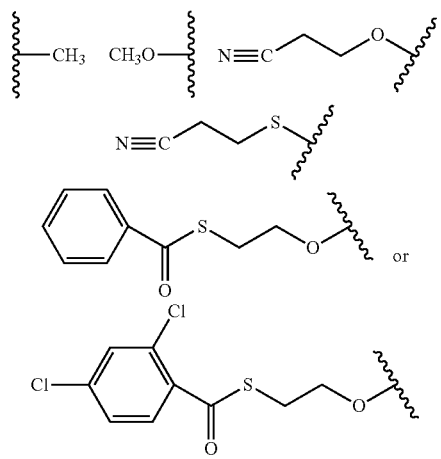

and wherein R2 can include the groups:

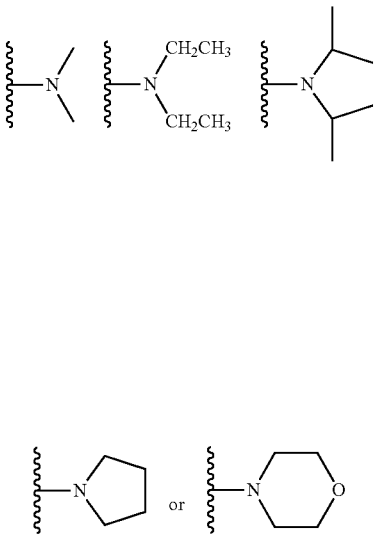

In one embodiment, the invention features a compound having Formula 111:

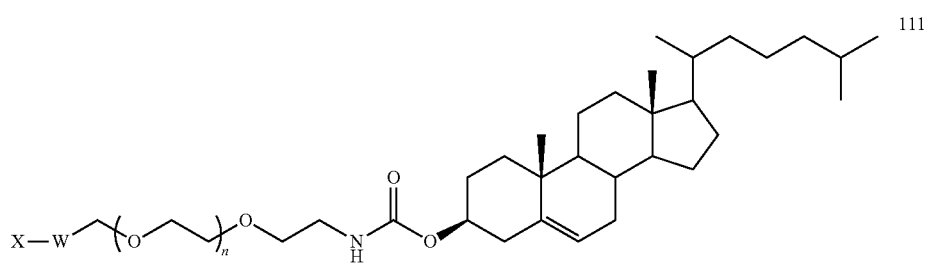

wherein X comprises a siNA molecule or portion thereof; W comprises a linker molecule or chemical linkage that can be present or absent, and n is an integer from about 1 to about 20. In another embodiment, W is selected from the group consisting of amide, phosphate, phosphate ester, phosphoramidate, or thiophosphate ester linkage.

In one embodiment, the invention features a compound having Formula 112:

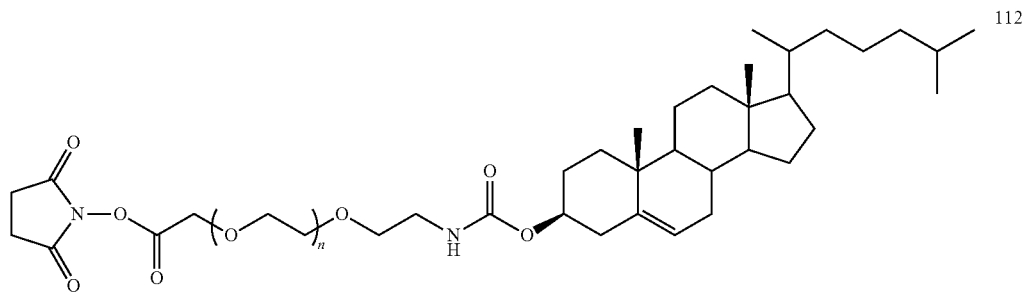

wherein n is an integer from about 1 to about 20. In another embodiment, a compound having Formula 112 is used to generate a compound having Formula 111 via NHS ester mediated coupling with a biologically active molecule, such as a siNA molecule or a portion thereof. In a non-limiting example, the NHS ester coupling can be effectuated via attachment to a free amine present in the siNA molecule, such as an amino linker molecule present on a nucleic acid sugar (e.g. 2'-amino linker) or base (e.g., C5 alkyl amine linker) component of the siNA molecule.

In one embodiment, the invention features a compound having Formula 113:

-continued

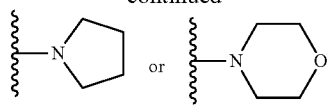

In another embodiment, a compound having Formula 113 is used to generate a compound having Formula 111 via phosphoramidite mediated coupling with a biologically active molecule, such as a siNA molecule or a portion thereof.

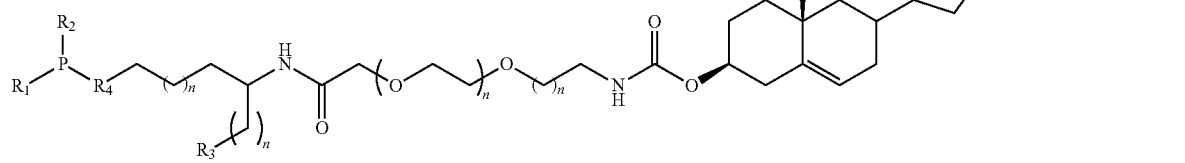

wherein R3 comprises H, OH, amino, substituted amino, nucleotide, nucleoside, nucleic acid, oligonucleotide, amino acid, peptide, protein, lipid, phospholipid, label, or a portion thereof, or OR5 where R5 a removable protecting group, R4 comprises O, alkyl, alkylhalo, O-alkyl, O-alkylcyano, S, S-alkyl, S-alkylcyano, N or substituted N, each n is independently an integer from about 1 to about 20, and wherein R1 can include the groups:

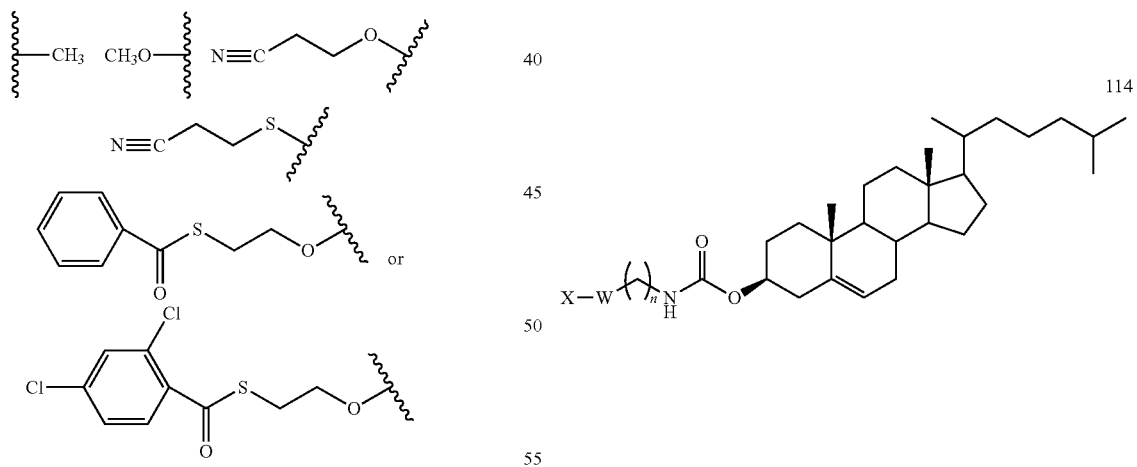

and wherein R2 can include the groups:

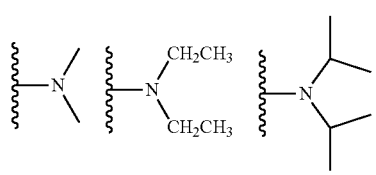

In one embodiment, the invention features a compound having Formula 114:

wherein X comprises a siNA molecule or portion thereof; W comprises a linker molecule or chemical linkage that can be present or absent, and n is an integer from about 1 to about 20. In another embodiment, W is selected from the group consisting of amide, phosphate, phosphate ester, phosphoramidate, or thiophosphate ester linkage.

In one embodiment, the invention features a compound having Formula 115:

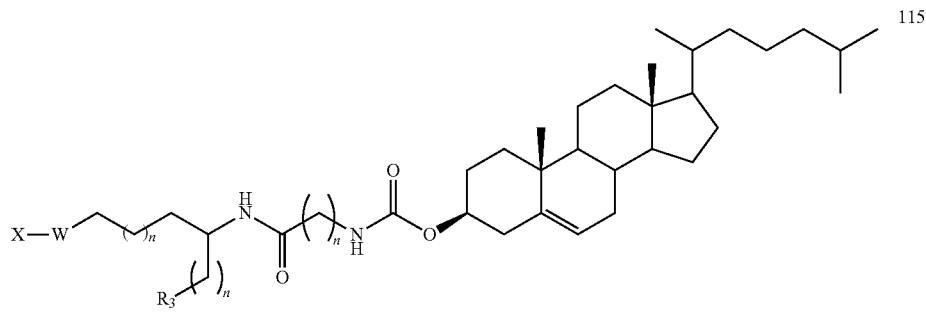

wherein X comprises a siNA molecule or portion thereof; W comprises a linker molecule or chemical linkage that can be present or absent, R3 comprises H, OH, amino, substituted amino, nucleotide, nucleoside, nucleic acid, oligonucleotide, amino acid, peptide, protein, lipid, phospholipid, label, or a portion thereof, or OR5 where R5 a removable protecting group, and each n is independently an integer from about 1 to about 20. In another embodiment, W is selected from the group consisting of amide, phosphate, phosphate ester, phosphoramidate, or thiophosphate ester linkage.

In one embodiment, the invention features a compound having Formula 116:

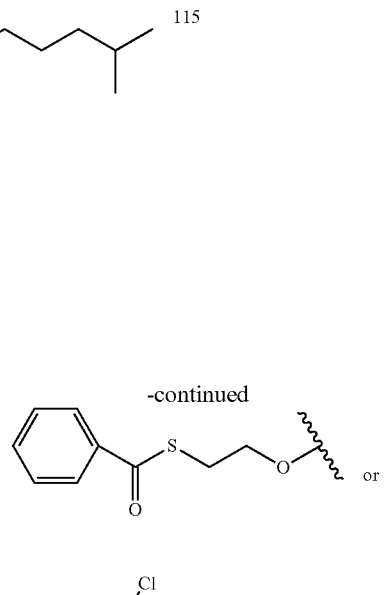

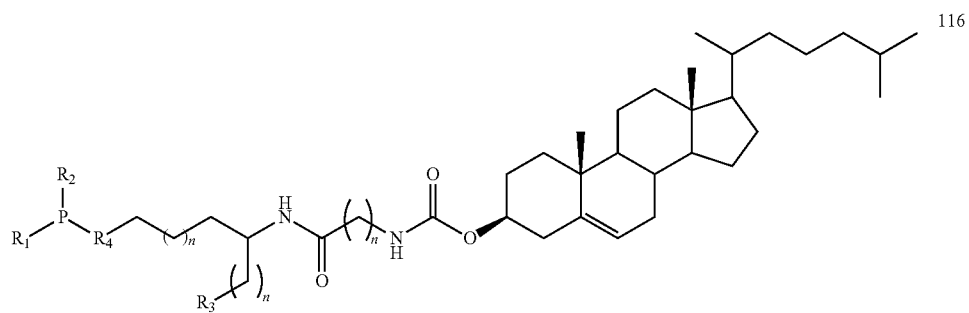

wherein R3 comprises H, OH, amino, substituted amino, nucleotide, nucleoside, nucleic acid, oligonucleotide, amino acid, peptide, protein, lipid, phospholipid, label, or a portion thereof, or OR5 where R5 a removable protecting group, R4 comprises O, alkyl, alkylhalo, O-alkyl, O-alkylcyano, S, S-alkyl, S-alkylcyano, N or substituted N, each n is independently an integer from about 1 to about 20, and wherein R1 can include the groups:

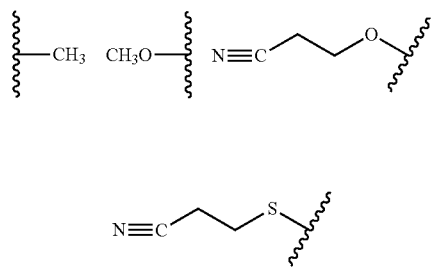

and wherein R2 can include the groups:

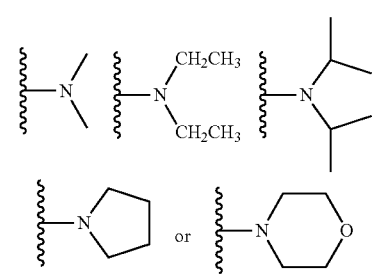

In another embodiment, a compound having Formula 116 is used to generate a compound having Formula 114 or 115 via phosphoramidite mediated coupling with a biologically active molecule, such as a siNA molecule or a portion thereof.

In one embodiment, the invention features a compound having Formula 117:

109

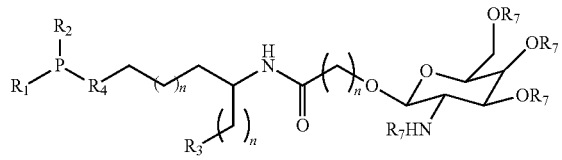

117 wherein R3 comprises H, OH, amino, substituted amino, nucleotide, nucleoside, nucleic acid, oligonucleotide, amino acid, peptide, protein, lipid, phospholipid, label, or a portion thereof, or OR5 where R5 a removable protecting group, R4 comprises O, alkyl, alkylhalo, O-alkyl, O-alkylcyano, S, S-alkyl, S-alkylcyano, N or substituted N, each R7 independently comprises an acyl group that can be present or absent, for example a acetyl group, each n is independently an integer from about 1 to about 20, and wherein R1 can include the groups:

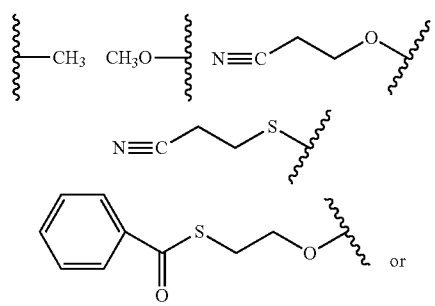

110

-continued

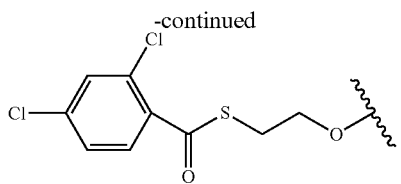

and wherein R2 can include the groups:

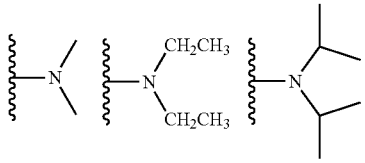

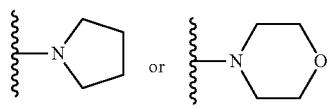

In another embodiment, a compound having Formula 117 is used to generate a compound having Formula 105 via phosphoramidite mediated coupling with a biologically active molecule, such as a siNA molecule or a portion thereof.

In one embodiment, the invention features a compound having Formula 118:

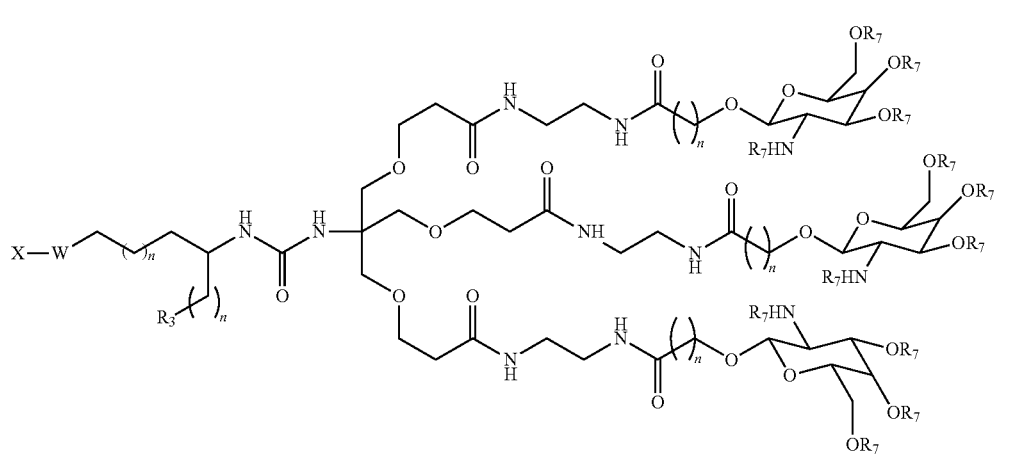

118 wherein X comprises a siNA molecule or portion thereof; W comprises a linker molecule or chemical linkage that can be present or absent, R3 comprises H, OH, amino, substituted amino, nucleotide, nucleoside, nucleic acid, oligonucleotide, amino acid, peptide, protein, lipid, phospholipid, label, or a portion thereof, or OR5 where R5 a removable protecting group, each R7 independently comprises an acyl group that can be present or absent, for example a acetyl group, and each n is independently an integer from about 1 to about 20. In another embodiment, W is selected from the group consisting of amide, phosphate, phosphate ester, phosphoramidate, or thiophosphate ester linkage.

In one embodiment, the invention features a compound having Formula 119:

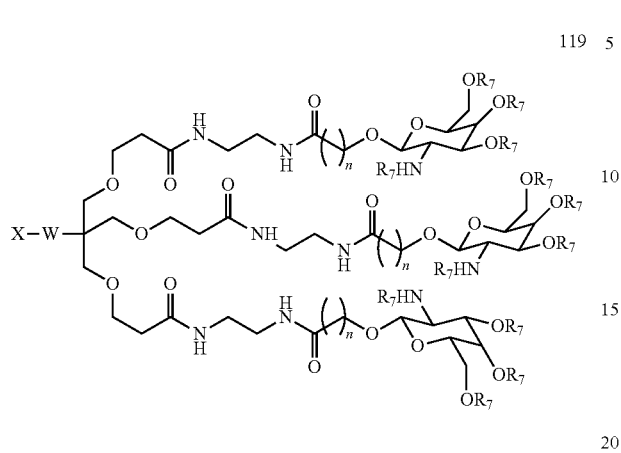

wherein R1 can include the groups:

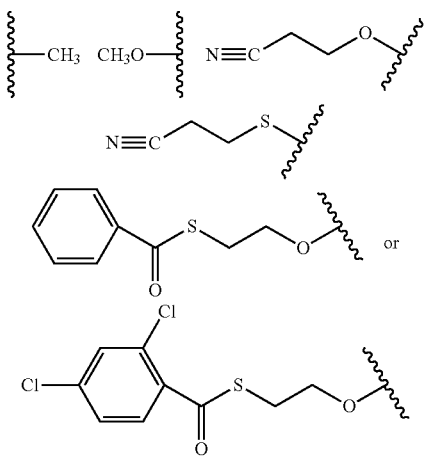

and wherein R2 can include the groups:

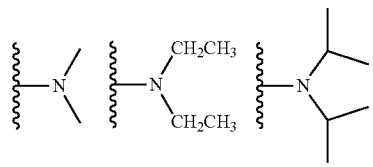

wherein X comprises a siNA molecule or portion thereof; W comprises a linker molecule or chemical linkage that can be present or absent, each R7 independently comprises an acyl group that can be present or absent, for example a acetyl group, and each n is independently an integer from about 1 to about 20. In another embodiment, W is selected from the group consisting of amide, phosphate, phosphate ester, phosphoramidate, or thiophosphate ester linkage.

In one embodiment, the invention features a compound having Formula 120:

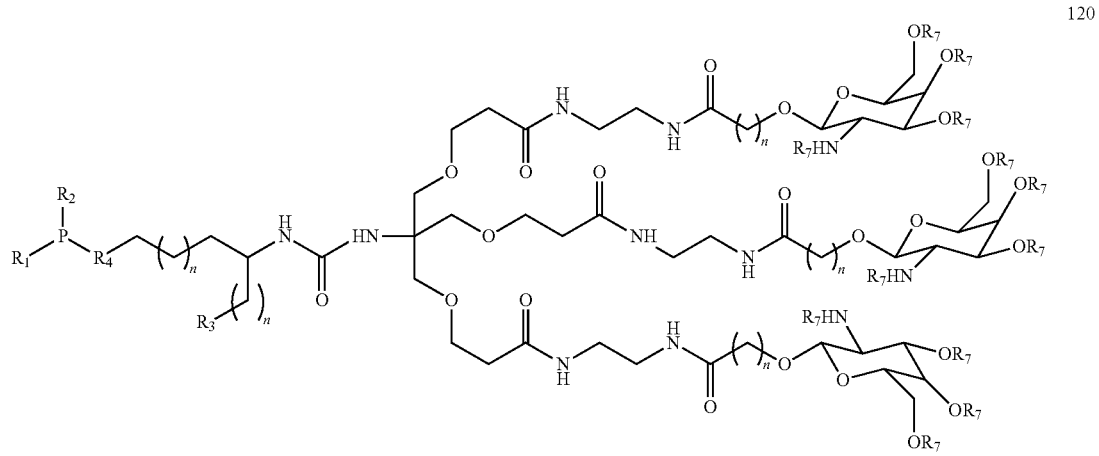

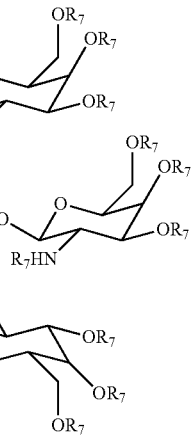

wherein R3 comprises H, OH, amino, substituted amino, nucleotide, nucleoside, nucleic acid, oligonucleotide, amino acid, peptide, protein, lipid, phospholipid, label, or a portion thereof, or OR5 where R5 a removable protecting group, R4 comprises O, alkyl, alkylhalo, O-alkyl, O-alkylcyano, S, S-alkyl, S-alkylcyano, N or substituted N, each R7 independently comprises an acyl group that can be present or absent, for example a acetyl group, each n is independently an integer from about 1 to about 20, and -continued

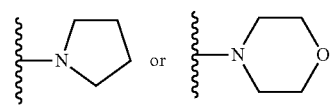

In another embodiment, a compound having Formula 120 is used to generate a compound having Formula 118 or 119 via phosphoramidite mediated coupling with a biologically active molecule, such as a siNA molecule or a portion thereof.

In one embodiment, the invention features a compound having Formula 121:

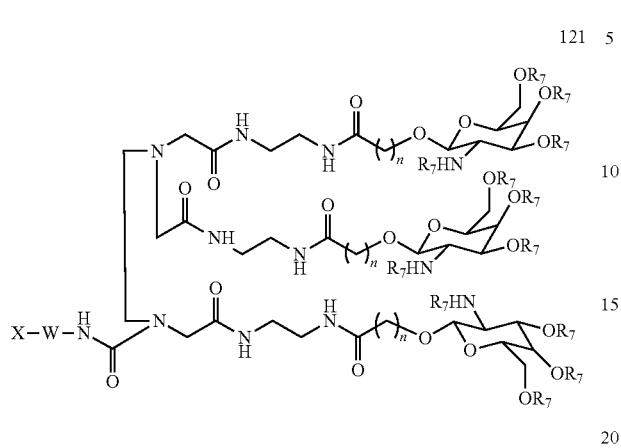

wherein X comprises a siNA molecule or portion thereof; W comprises a linker molecule or chemical linkage that can be present or absent, each R7 independently comprises an acyl group that can be present or absent, for example a acetyl group, and each n is independently an integer from about 1 to about 20. In another embodiment, W is selected from the group consisting of amide, phosphate, phosphate ester, phosphoramidate, or thiophosphate ester linkage.

In one embodiment, the invention features a compound having Formula 122:

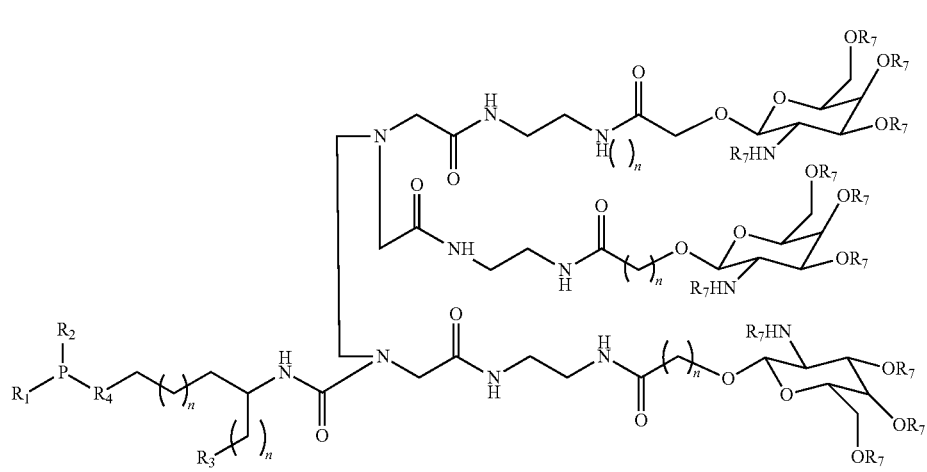

wherein R3 comprises H, OH, amino, substituted amino, nucleotide, nucleoside, nucleic acid, oligonucleotide, amino acid, peptide, protein, lipid, phospholipid, label, or a portion thereof, or OR5 where R5 a removable protecting group, R4 comprises O, alkyl, alkylhalo, O-alkyl, O-alkylcyano, S, S-alkyl, S-alkylcyano, N or substituted N, each R7 independently comprises an acyl group that can be present or absent, for example a acetyl group, each n is independently an integer from about 1 to about 20, and wherein R1 can include the groups:

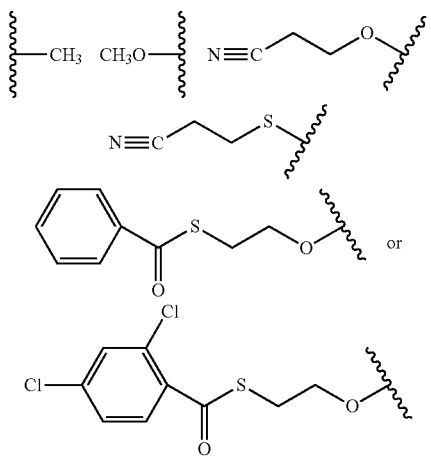

and wherein R2 can include the groups:

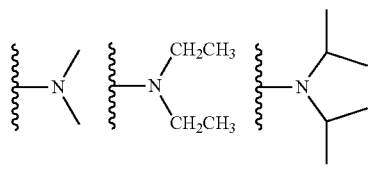

-continued

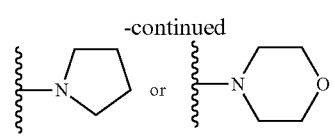

In another embodiment, a compound having Formula 122 is used to generate a compound having Formula 121 via phosphoramidite mediated coupling with a biologically active molecule, such as a siNA molecule or a portion thereof.

In one embodiment, the invention features a compound having Formula 94,

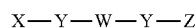
(94)

wherein X comprises a siNA molecule or a portion thereof; each Y independently comprises a linker or chemical linkage that can be present or absent, W comprises a biodegradable nucleic acid linker molecule, and Z comprises a biologically active molecule, for example an enzymatic nucleic acid, allozyme, antisense nucleic acid, siNA, 2,5-A chimera, decoy, aptamer or triplex forming oligonucleotide, peptide, protein, or antibody.

In another embodiment, W of a compound having Formula 94 of the invention comprises 5'-cytidine-deoxythymidine-3',5'-deoxythymidine-cytidine-3',5'-cytidine-deoxyuridine-3',5'-deoxyuridine-cytidine-3',5'-uridine-deoxythymidine-3', or 5'-deoxythymidine-uridine-3'.

In yet another embodiment, W of a compound having Formula 94 of the invention comprises 5'-adenosine-deoxythymidine-3',5'-deoxythymidine-adenosine-3',5'-adenosine-deoxyuridine-3', or 5'-deoxyuridine-adenosine-3'.

In another embodiment, Y of a compound having Formula 94 of the invention comprises a phosphorus containing linkage, phoshoramidate linkage, phosphodiester linkage, phosphorothioate linkage, amide linkage, ester linkage, carbamate linkage, disulfide linkage, oxime linkage, or morpholino linkage.

In another embodiment, compounds having Formula 89 and 91 of the invention are synthesized by periodate oxidation of an N-terminal Serine or Threonine residue of a peptide or protein.

In one embodiment, X of compounds having Formulae 43, 44, 46-52, 58, 61-65, 85-88, 92, 94, 95, 99, 100, 105-108, 111, 114, 115, 118, 119, or 121 of the invention comprises a siNA molecule or a portion thereof. In one embodiment, the siNA molecule can be conjugated at the 5' end, 3'-end, or both 5' and 3' ends of the sense strand or region of the siNA. In one embodiment, the siNA molecule can be conjugated at the 3'-end of the antisense strand or region of the siNA with a compound of the invention. In one embodiment, both the sense strand and antisense strands or regions of the siNA molecule are conjugated with a compound of the invention. In one embodiment, only the sense strand or region of the siNA is conjugated with a compound of the invention. In one embodiment, only the antisense strand or region of the siNA is conjugated with a compound of the invention.

In one embodiment, W and/or Y of compounds having Formulae 43, 44, 46-52, 58, 61-65, 85-88, 92, 94, 95, 99, 100, 101, 107, 108, 111, 114, 115, 118, 119, or 121 of the invention comprises a degradable or cleavable linker, for example a nucleic acid sequence comprising ribonucleotides and/or deoxynucleotides, such as a dimer, trimer, or tetramer. A non limiting example of a nucleic acid cleavable linker is an adenosine-deoxythymidine (A-dT) dimer or a cytidine-deoxythymidine (C-dT) dimer. In yet another embodiment, W and/or V of compounds having Formulae 43, 44, 48-51, 58, 63-65, 96, 99, 100, 107, 108, 111, 114, 115, 118, 119, or 121 of the invention comprises a N-hydroxy succinimide (NHS) ester linkage, oxime linkage, disulfide linkage, phosphoramidate, phosphorothioate, phosphorodithioate, phosphodiester linkage, or NHC(O), $CH_3NC(O)$, CONH, $C(O)NCH_3$, S, SO, $SO_2$, O, NH, $NCH_3$ group. In another embodiment, the degradable linker, W and/or Y, of compounds having Formulae Formulae 43, 44, 46-52, 58, 61-65, 85-88, 92, 94, 95, 99, 100, 101, 107, 108, 111, 114, 115, 118, 119, or 121 of the invention comprises a linker that is susceptible to cleavage by carboxypeptidase activity.

In another embodiment, W and/or Y of Formulae 43, 44, 46-52, 58, 61-65, 85-88, 92, 94, 95, 99, 100, 101, 107, 108, 111, 114, 115, 118, 119, or 121 comprises a polyethylene glycol linker having Formula 45:

(45)

wherein Z comprises H, OH, O-alkyl, SH, S-alkyl, alkyl, substituted alkyl, aryl, substituted aryl, amino, substituted amino, nucleotide, nucleoside, nucleic acid, oligonucleotide, amino acid, peptide, protein, lipid, phospholipid, or label; and n is an integer from about 1 to about 100.

In one embodiment, the nucleic acid conjugates of the instant invention are assembled by solid phase synthesis, for example on an automated peptide synthesizer, for example a Miligen 9050 synthesizer and/or an automated oligonucleotide synthesizer such as an ABI 394, 390Z, or Pharmacia OligoProcess, OligoPilot, OligoMax, or AKTA synthesizer. In another embodiment, the nucleic acid conjugates of the invention are assembled post synthetically, for example, following solid phase oligonucleotide synthesis (see for example FIGS. 45, 50, 53, and 73).

In another embodiment, V of compounds having Formula 58-63 and 96 comprise peptides having SEQ ID NOS: 507-516 (Table V).

In one embodiment, the nucleic acid conjugates of the instant invention are assembled post synthetically, for example, following solid phase oligonucleotide synthesis.

The present invention provides compositions and conjugates comprising nucleosidic and non-nucleosidic derivatives. The present invention also provides nucleic acid, polynucleotide and oligonucleotide derivatives including RNA, DNA, and PNA based conjugates. The attachment of compounds of the invention to nucleosides, nucleotides, non-nucleosides, and nucleic acid molecules is provided at any position within the molecule, for example, at internucleotide linkages, nucleosidic sugar hydroxyl groups such as 5',3', and 2'-hydroxyls, and/or at nucleobase positions such as amino and carbonyl groups.

The exemplary conjugates of the invention are described as compounds of the formulae herein, however, other peptide, protein, phospholipid, and poly-alkyl glycol derivatives are provided by the invention, including various analogs of the compounds of formulae 1-122, including but not limited to different isomers of the compounds described herein.

The exemplary folate conjugates of the invention are described as compounds shown by formulae herein, however, other folate and antifolate derivatives are provided by the invention, including various folate analogs of the formulae of the invention, including dihydrofloates, tetrahydrofolates, tetrahydorpterins, folinic acid, pteropolyglutamic acid, 1-deaza, 3-deaza, 5-deaza, 8-deaza, 10-deaza, 1,5-deaza, 5,10 dideaza, 8,10-dideaza, and 5,8-dideaza folates, antifolates, and pteroic acids. As used herein, the term "folate" is meant to refer to folate and folate derivatives, including pteroic acid derivatives and analogs.

The present invention features compositions and conjugates to facilitate delivery of molecules into a biological system such as cells. The conjugates provided by the instant invention can impart therapeutic activity by transferring therapeutic compounds across cellular membranes. The present invention encompasses the design and synthesis of novel agents for the delivery of molecules, including but not limited to siNA molecules. In general, the transporters described are designed to be used either individually or as part of a multi-component system. The compounds of the invention generally shown in Formulae herein are expected to improve delivery of molecules into a number of cell types originating from different tissues, in the presence or absence of serum.

In another embodiment, the compounds of the invention are provided as a surface component of a lipid aggregate, such as a liposome encapsulated with the predetermined molecule to be delivered. Liposomes, which can be unilamellar or multilamellar, can introduce encapsulated material into a cell by different mechanisms. For example, the liposome can directly introduce its encapsulated material into the cell cytoplasm by fusing with the cell membrane. Alternatively, the liposome can be compartmentalized into an acidic vacuole (i.e., an endosome) and its contents released from the liposome and out of the acidic vacuole into the cellular cytoplasm.

In one embodiment the invention features a lipid aggregate formulation of the compounds described herein, including phosphatidylcholine (of varying chain length; e.g., egg yolk phosphatidylcholine), cholesterol, a cationic lipid, and 1,2-distearoyl-sn-glycero-3-phosphoethanolamine-polythyleneglycol-2000 (DSPE-PEG2000). The cationic lipid component of this lipid aggregate can be any cationic lipid known in the art such as dioleoyl 1,2,-diacyl-3-trimethyl-ammonium-propane (DOTAP). In another embodiment this cationic lipid aggregate comprises a covalently bound compound described in any of the Formulae herein.

In another embodiment, polyethylene glycol (PEG) is covalently attached to the compounds of the present invention. The attached PEG can be any molecular weight but is preferably between 2000-50,000 daltons.

The compounds and methods of the present invention are useful for introducing nucleotides, nucleosides, nucleic acid molecules, lipids, peptides, proteins, and/or non-nucleosidic small molecules into a cell. For example, the invention can be used for nucleotide, nucleoside, nucleic acid, lipids, peptides, proteins, and/or non-nucleosidic small molecule delivery where the corresponding target site of action exists intracellularly.

In one embodiment, the compounds of the instant invention provide conjugates of molecules that can interact with cellular receptors, such as high affinity folate receptors and ASGPr receptors, and provide a number of features that allow the efficient delivery and subsequent release of conjugated compounds across biological membranes. The compounds utilize chemical linkages between the receptor ligand and the compound to be delivered of length that can interact preferentially with cellular receptors. Furthermore, the chemical linkages between the ligand and the compound to be delivered can be designed as degradable linkages, for example by utilizing a phosphate linkage that is proximal to a nucleophile, such as a hydroxyl group. Deprotonation of the hydroxyl group or an equivalent group, as a result of pH or interaction with a nuclease, can result in nucleophilic attack of the phosphate resulting in a cyclic phosphate intermediate that can be hydrolyzed. This cleavage mechanism is analogous RNA cleavage in the presence of a base or RNA nuclease. Alternately, other degradable linkages can be selected that respond to various factors such as UV irradiation, cellular nucleases, pH, temperature etc. The use of degradable linkages allows the delivered compound to be released in a predetermined system, for example in the cytoplasm of a cell, or in a particular cellular organelle.

The present invention also provides ligand derived phosphoramidites that are readily conjugated to compounds and molecules of interest. Phosphoramidite compounds of the invention permit the direct attachment of conjugates to molecules of interest without the need for using nucleic acid phosphoramidite species as scaffolds. As such, the used of phosphoramidite chemistry can be used directly in coupling the compounds of the invention to a compound of interest, without the need for other condensation reactions, such as condensation of the ligand to an amino group on the nucleic acid, for example at the N6 position of adenosine or a 2'-deoxy-2'-amino function. Additionally, compounds of the invention can be used to introduce non-nucleic acid based conjugated linkages into oligonucleotides that can provide more efficient coupling during oligonucleotide synthesis than the use of nucleic acid-based phosphoramidites. This improved coupling can take into account improved steric considerations of abasic or non-nucleosidic scaffolds bearing pendant alkyl linkages.

Compounds of the invention utilizing triphosphate groups can be utilized in the enzymatic incorporation of conjugate molecules into oligonucleotides. Such enzymatic incorporation is useful when conjugates are used in post-synthetic enzymatic conjugation or selection reactions, (see for example Matulic-Adamic et al., 2000, *Bioorg. Med. Chem. Lett.*, 10, 1299-1302; Lee et al., 2001, *NAR.*, 29, 1565-1573; Joyce, 1989, *Gene*, 82, 83-87; Beaudry et al., 1992, *Science* 257, 635-641; Joyce, 1992, *Scientific American* 267, 90-97; Breaker et al., 1994, *TIBTECH* 12, 268; Bartel et al., 1993, *Science* 261:1411-1418; Szostak, 1993, *TIBS* 17, 89-93; Kumar et al., 1995, *FASEB J.*, 9, 1183; Breaker, 1996, *Curr. Op. Biotech.*, 7, 442; Santoro et al., 1997, *Proc. Natl. Acad. Sci.*, 94, 4262; Tang et al., 1997, *RNA* 3, 914; Nakamaye & Eckstein, 1994, supra; Long & Uhlenbeck, 1994, supra; Ishizaka et al., 1995, supra; Vaish et al., 1997, *Biochemistry* 36, 6495; Kuwabara et al., 2000, *Curr. Opin. Chem. Biol.*, 4, 669).

The term "biodegradable linker" as used herein, refers to a nucleic acid or non-nucleic acid linker molecule that is designed as a biodegradable linker to connect one molecule to another molecule, for example, a biologically active molecule to a siNA molecule of the invention or the sense and antisense strands of a siNA molecule of the invention. The biodegradable linker is designed such that its stability can be modulated for a particular purpose, such as delivery to a particular tissue or cell type. The stability of a nucleic acid-based biodegradable linker molecule can be modulated by using various chemistries, for example combinations of ribonucleotides, deoxyribonucleotides, and chemically-modified nucleotides, such as 2'-O-methyl, 2'-fluoro, 2'-amino, 2'-O-amino, 2'-C-allyl, 2'-O-allyl, and other 2'-modified or base modified nucleotides. The biodegradable nucleic acid linker molecule can be a dimer, trimer, tetramer or longer nucleic acid molecule, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus-based linkage, for example, a phosphoramidate or phosphodiester linkage. The biodegradable nucleic acid linker molecule can also comprise nucleic acid backbone, nucleic acid sugar, or nucleic acid base modifications.

The term "biodegradable" as used herein, refers to degradation in a biological system, for example enzymatic degradation or chemical degradation.

The term "biologically active molecule" as used herein, refers to compounds or molecules that are capable of eliciting or modifying a biological response in a system. Non-limiting examples of biologically active siNA molecules either alone or in combination with other molecules contemplated by the instant invention include therapeutically active molecules such as antibodies, cholesterol, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, 2,5-A chimeras, siNA, dsRNA, allozymes, aptamers, decoys and analogs thereof. Biologically active molecules of the invention also include molecules capable of modulating the pharmacokinetics and/or pharmacodynamics of other biologically active molecules, for example, lipids and polymers such as polyamines, polyamides, polyethylene glycol and other polyethers.

The term "phospholipid" as used herein, refers to a hydrophobic molecule comprising at least one phosphorus group. For example, a phospholipid can comprise a phosphorus-containing group and saturated or unsaturated alkyl group, optionally substituted with OH, COOH, oxo, amine, or substituted or unsubstituted aryl groups.

The term "alkyl" as used herein refers to a saturated aliphatic hydrocarbon, including straight-chain, branched-chain "isoalkyl", and cyclic alkyl groups. The term "alkyl" also comprises alkoxy, alkyl-thio, alkyl-thio-alkyl, alkoxyalkyl, alkylamino, alkenyl, alkynyl, alkoxy, cycloalkenyl, cycloalkyl, cycloalkylalkyl, heterocycloalkyl, heteroaryl, C1-C6 hydrocarbyl, aryl or substituted aryl groups. Preferably, the alkyl group has 1 to 12 carbons. More preferably it is a lower alkyl of from about 1 to about 7 carbons, more preferably about 1 to about 4 carbons. The alkyl group can be substituted or unsubstituted. When substituted the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, C1-C6 hydrocarbyl, aryl or substituted aryl groups. The term "alkyl" also includes alkenyl groups containing at least one carbon-carbon double bond, including straight-chain, branched-chain, and cyclic groups. Preferably, the alkenyl group has about 2 to about 12 carbons. More preferably it is a lower alkenyl of from about 2 to about 7 carbons, more preferably about 2 to about 4 carbons. The alkenyl group can be substituted or unsubstituted. When substituted the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, C1-C6 hydrocarbyl, aryl or substituted aryl groups. The term "alkyl" also includes alkynyl groups containing at least one carbon-carbon triple bond, including straight-chain, branched-chain, and cyclic groups. Preferably, the alkynyl group has about 2 to about 12 carbons. More preferably it is a lower alkynyl of from about 2 to about 7 carbons, more preferably about 2 to about 4 carbons. The alkynyl group can be substituted or unsubstituted. When substituted the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, C1-C6 hydrocarbyl, aryl or substituted aryl groups. Alkyl groups or moieties of the invention can also include aryl, alkylaryl, carbocyclic aryl, heterocyclic aryl, amide and ester groups.

The preferred substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from about 1 to about 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted. An "amide" refers to an —C(O)—NH—R, where R is either alkyl, aryl, alkylaryl or hydrogen. An "ester" refers to an —C(O)—OR', where R is either alkyl, aryl, alkylaryl or hydrogen.

The term "alkoxyalkyl" as used herein refers to an alkyl-O-alkyl ether, for example, methoxyethyl or ethoxymethyl.

The term "alkyl-thio-alkyl" as used herein refers to an alkyl-S-alkyl thioether, for example, methylthiomethyl or methylthioethyl.

The term "amino" as used herein refers to a nitrogen containing group as is known in the art derived from ammonia by the replacement of one or more hydrogen radicals by organic radicals. For example, the terms "aminoacyl" and "aminoalkyl" refer to specific N-substituted organic radicals with acyl and alkyl substituent groups respectively.

The term "amination" as used herein refers to a process in which an amino group or substituted amine is introduced into an organic molecule.

The term "exocyclic amine protecting moiety" as used herein refers to a nucleobase amino protecting group compatible with oligonucleotide synthesis, for example, an acyl or amide group.

The term "alkenyl" as used herein refers to a straight or branched hydrocarbon of a designed number of carbon atoms containing at least one carbon-carbon double bond. Examples of "alkenyl" include vinyl, allyl, and 2-methyl-3-heptene.

The term "alkoxy" as used herein refers to an alkyl group of indicated number of carbon atoms attached to the parent molecular moiety through an oxygen bridge. Examples of alkoxy groups include, for example, methoxy, ethoxy, propoxy and isopropoxy.

The term "alkynyl" as used herein refers to a straight or branched hydrocarbon of a designed number of carbon atoms containing at least one carbon-carbon triple bond. Examples of "alkynyl" include propargyl, propyne, and 3-hexyne.

The term "aryl" as used herein refers to an aromatic hydrocarbon ring system containing at least one aromatic ring. The aromatic ring can optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl and naphthyl.

The term "cycloalkenyl" as used herein refers to a C3-C8 cyclic hydrocarbon containing at least one carbon-carbon double bond. Examples of cycloalkenyl include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "cycloalkyl" as used herein refers to a C3-C8 cyclic hydrocarbon. Examples of cycloalkyl include cyclopropyl, cyclobutyl, cyclopentyl, cyclohexyl, cycloheptyl and cyclooctyl.

The term "cycloalkylalkyl," as used herein, refers to a C3-C7 cycloalkyl group attached to the parent molecular moiety through an alkyl group, as defined above. Examples of cycloalkylalkyl groups include cyclopropylmethyl and cyclopentylethyl.

The terms "halogen" or "halo" as used herein refers to indicate fluorine, chlorine, bromine, and iodine.

The term "heterocycloalkyl," as used herein refers to a non-aromatic ring system containing at least one heteroatom selected from nitrogen, oxygen, and sulfur. The heterocycloalkyl ring can be optionally fused to or otherwise attached to other heterocycloalkyl rings and/or non-aromatic hydrocarbon rings. Preferred heterocycloalkyl groups have from 3 to 7 members. Examples of heterocycloalkyl groups include, for example, piperazine, morpholine, piperidine, tetrahydrofuran, pyrrolidine, and pyrazole. Preferred heterocycloalkyl groups include piperidinyl, piperazinyl, morpholinyl, and pyrolidinyl.

The term "heteroaryl" as used herein refers to an aromatic ring system containing at least one heteroatom selected from nitrogen, oxygen, and sulfur. The heteroaryl ring can be fused or otherwise attached to one or more heteroaryl rings, aromatic or non-aromatic hydrocarbon rings or heterocycloalkyl rings. Examples of heteroaryl groups include, for example, pyridine, furan, thiophene, 5,6,7,8-tetrahydroisoquinoline and pyrimidine. Preferred examples of heteroaryl groups include thienyl, benzothienyl, pyridyl, quinolyl, pyrazinyl, pyrimidyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, and benzopyrazolyl.

The term "C1-C6 hydrocarbyl" as used herein refers to straight, branched, or cyclic alkyl groups having 1-6 carbon atoms, optionally containing one or more carbon-carbon double or triple bonds. Examples of hydrocarbyl groups include, for example, methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, vinyl, 2-pentene, cyclopropylmethyl, cyclopropyl, cyclohexylmethyl, cyclohexyl and propargyl. When reference is made herein to C1-C6 hydrocarbyl containing one or two double or triple bonds it is understood that at least two carbons are present in the alkyl for one double or triple bond, and at least four carbons for two double or triple bonds.

The term "protecting group" as used herein, refers to groups known in the art that are readily introduced and removed from an atom, for example O, N, P, or S. Protecting groups are used to prevent undesirable reactions from taking place that can compete with the formation of a specific compound or intermediate of interest. See also "Protective Groups in Organic Synthesis", 3rd Ed., 1999, Greene, T. W. and related publications.

The term "nitrogen protecting group," as used herein, refers to groups known in the art that are readily introduced on to and removed from a nitrogen. Examples of nitrogen protecting groups include Boc, Cbz, benzoyl, and benzyl. See also "Protective Groups in Organic Synthesis", 3rd Ed., 1999, Greene, T. W. and related publications.

The term "hydroxy protecting group," or "hydroxy protection" as used herein, refers to groups known in the art that are readily introduced on to and removed from an oxygen, specifically an —OH group. Examples of hydroxy protecting groups include trityl or substituted trityl groups, such as monomethoxytrityl and dimethoxytrityl, or substituted silyl groups, such as tert-butyldimethyl, trimethylsilyl, or tert-butyldiphenyl silyl groups. See also "Protective Groups in Organic Synthesis", 3rd Ed., 1999, Greene, T. W. and related publications.

The term "acyl" as used herein refers to —C(O)R groups, wherein R is an alkyl or aryl.

The term "phosphorus containing group" as used herein, refers to a chemical group containing a phosphorus atom. The phosphorus atom can be trivalent or pentavalent, and can be substituted with O, H, N, S, C or halogen atoms. Examples of phosphorus containing groups of the instant invention include but are not limited to phosphorus atoms substituted with O, H, N, S, C or halogen atoms, comprising phosphonate, alkylphosphonate, phosphate, diphosphate, triphosphate, pyrophosphate, phosphorothioate, phosphorodithioate, phosphoramidate, phosphoramidite groups, nucleotides and nucleic acid molecules.

The term "phosphine" or "phosphite" as used herein refers to a trivalent phosphorus species, for example compounds having Formula 97:

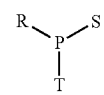

wherein R can include the groups:

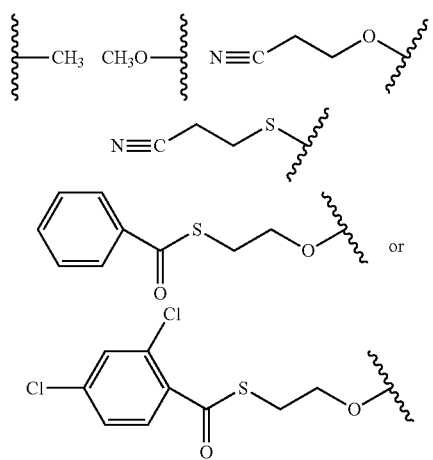

and wherein S and T independently include the groups:

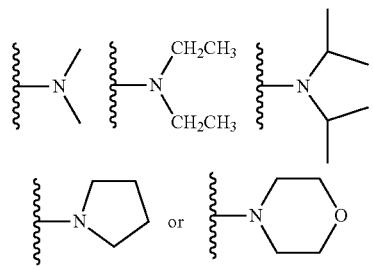

The term "phosphate" as used herein refers to a pentavalent phosphorus species, for example a compound having Formula 98:

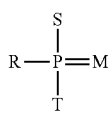

wherein R includes the groups:

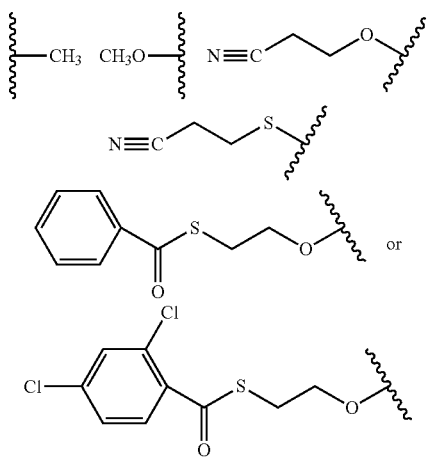

and wherein S and T each independently can be a sulfur or oxygen atom or a group which can include:

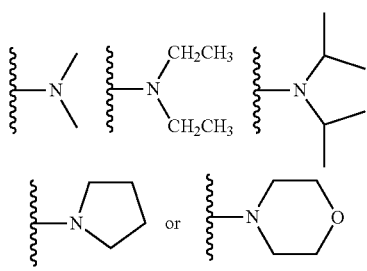

and wherein M comprises a sulfur or oxygen atom. The phosphate of the invention can comprise a nucleotide phosphate, wherein any R, S, or T in Formula 98 comprises a linkage to a nucleic acid or nucleoside.

The term "cationic salt" as used herein refers to any organic or inorganic salt having a net positive charge, for example a triethylammonium (TEA) salt.

The term "degradable linker" as used herein, refers to linker moieties that are capable of cleavage under various conditions. Conditions suitable for cleavage can include but are not limited to pH, UV irradiation, enzymatic activity, temperature, hydrolysis, elimination, and substitution reactions, and thermodynamic properties of the linkage.

The term "photolabile linker" as used herein, refers to linker moieties as are known in the art, that are selectively cleaved under particular UV wavelengths. Compounds of the invention containing photolabile linkers can be used to deliver compounds to a target cell or tissue of interest, and can be subsequently released in the presence of a UV source.

The term "nucleic acid conjugates" as used herein, refers to nucleoside, nucleotide and oligonucleotide conjugates.

The term "lipid" as used herein, refers to any lipophilic compound. Non-limiting examples of lipid compounds include fatty acids and their derivatives, including straight chain, branched chain, saturated and unsaturated fatty acids, carotenoids, terpenes, bile acids, and steroids, including cholesterol and derivatives or analogs thereof.

The term "folate" as used herein, refers to analogs and derivatives of folic acid, for example antifolates, dihydrofloates, tetrahydrofolates, tetrahydorpterins, folinic acid, pteropolyglutamic acid, 1-deaza, 3-deaza, 5-deaza, 8-deaza, 10-deaza, 1,5-deaza, 5,10 dideaza, 8,10-dideaza, and 5,8-dideaza folates, antifolates, and pteroic acid derivatives.

The term "compounds with neutral charge" as used herein, refers to compositions which are neutral or uncharged at neutral or physiological pH. Examples of such compounds are cholesterol and other steroids, cholesteryl hemisuccinate (CHEMS), dioleoyl phosphatidyl choline, distearoylphosphotidyl choline (DSPC), fatty acids such as oleic acid, phosphatidic acid and its derivatives, phosphatidyl serine, polyethylene glycol-conjugated phosphatidylamine, phosphatidylcholine, phosphatidylethanolamine and related variants, prenylated compounds including farnesol, polyprenols, tocopherol, and their modified forms, diacylsuccinyl glycerols, fusogenic or pore forming peptides, dioleoylphosphotidylethanolamine (DOPE), ceramide and the like.

The term "lipid aggregate" as used herein refers to a lipid-containing composition wherein the lipid is in the form of a liposome, micelle (non-lamellar phase) or other aggregates with one or more lipids.

The term "nitrogen containing group" as used herein refers to any chemical group or moiety comprising a nitrogen or substituted nitrogen. Non-limiting examples of nitrogen containing groups include amines, substituted amines, amides, alkylamines, amino acids such as arginine or lysine, polyamines such as spermine or spermidine, cyclic amines such as pyridines, pyrimidines including uracil, thymine, and cytosine, morpholines, phthalimides, and heterocyclic amines such as purines, including guanine and adenine.

Therapeutic nucleic acid molecules (e.g., siNA molecules) delivered exogenously optimally are stable within cells until reverse transcription of the RNA has been modulated long enough to reduce the levels of the RNA transcript. The nucleic acid molecules are resistant to nucleases in order to function as effective intracellular therapeutic agents. Improvements in the chemical synthesis of nucleic acid molecules described in the instant invention and in the art have expanded the ability to modify nucleic acid molecules by introducing nucleotide modifications to enhance their nuclease stability as described above.

In yet another embodiment, siNA molecules having chemical modifications that maintain or enhance enzymatic activity of proteins involved in RNAi are provided. Such nucleic acids are also generally more resistant to nucleases than unmodified nucleic acids. Thus, in vitro and/or in vivo the activity should not be significantly lowered.

Use of the nucleic acid-based molecules of the invention will lead to better treatment of the disease progression by affording the possibility of combination therapies (e.g., multiple siNA molecules targeted to different genes; nucleic acid molecules coupled with known small molecule modulators; or intermittent treatment with combinations of molecules, including different motifs and/or other chemical or biological molecules). The treatment of subjects with siNA molecules can also include combinations of different types of nucleic acid molecules, such as enzymatic nucleic acid molecules (ribozymes), allozymes, antisense, 2,5-A oligoadenylate, decoys, and aptamers.

In another aspect a siNA molecule of the invention comprises one or more 5' and/or a 3'-cap structure, for example on only the sense siNA strand, the antisense siNA strand, or both siNA strands.

By "cap structure" is meant chemical modifications, which have been incorporated at either terminus of the oligonucleotide (see, for example, Adamic et al., U.S. Pat. No. 5,998,203, incorporated by reference herein). These terminal modifications protect the nucleic acid molecule from exonuclease degradation, and can help in delivery and/or localization within a cell. The cap can be present at the 5'-terminus (5'-cap) or at the 3'-terminal (3'-cap) or can be present on both termini. Non-limiting examples of the 5'-cap include, but are not limited to, glyceryl, inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

Non-limiting examples of the 3'-cap include, but are not limited to, glyceryl, inverted deoxy abasic residue (moiety), 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, *Tetrahedron* 49, 1925; incorporated by reference herein).

By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine and therefore lacks a base at the 1'-position.

By "nucleotide" as used herein is as recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see, for example, Usman and McSwiggen, supra; Eckstein et al., International PCT Publication No. WO 92/07065; Usman et al., International PCT Publication No. WO 93/15187; Uhlman & Peyman, supra, all are hereby incorporated by reference herein). There are several examples of modified nucleic acid bases known in the art as summarized by Limbach et al., 1994, *Nucleic Acids Res.* 22, 2183. Some of the non-limiting examples of base modifications that can be introduced into nucleic acid molecules include, inosine, purine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin et al., 1996, *Biochemistry*, 35, 14090; Uhlman & Peyman, supra). By "modified bases" in this aspect is meant nucleotide bases other than adenine, guanine, cytosine and uracil at 1' position or their equivalents.

In one embodiment, the invention features modified siNA molecules, with phosphate backbone modifications comprising one or more phosphorothioate, phosphonoacetate, and/or thiophosphonoacetate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications, see Hunziker and Leumann, 1995, *Nucleic Acid Analogues: Synthesis and Properties*, in *Modern Synthetic Methods*, VCH, 331-417, and Mesmaeker et al., 1994, *Novel Backbone Replacements for Oligonucleotides*, in *Carbohydrate Modifications in Antisense Research*, ACS, 24-39.

By "abasic" is meant sugar moieties lacking a base or having other chemical groups in place of a base at the 1' position, see for example Adamic et al., U.S. Pat. No. 5,998,203.

By "unmodified nucleoside" is meant one of the bases adenine, cytosine, guanine, thymine, or uracil joined to the 1' carbon of β-D-ribo-furanose.

By "modified nucleoside" is meant any nucleotide base which contains a modification in the chemical structure of an unmodified nucleotide base, sugar and/or phosphate. Non-limiting examples of modified nucleotides are shown by Formulae I-VII and/or other modifications described herein.

In connection with 2'-modified nucleotides as described for the present invention, by "amino" is meant 2'-$NH_2$ or 2'-O—$NH_2$, which can be modified or unmodified. Such modified groups are described, for example, in Eckstein et al., U.S. Pat. No. 5,672,695 and Matulic-Adamic et al., U.S. Pat. No. 6,248,878, which are both incorporated by reference in their entireties.

Various modifications to nucleic acid siNA structure can be made to enhance the utility of these molecules. Such modifications will enhance shelf-life, half-life in vitro, stability, and ease of introduction of such oligonucleotides to the target site, e.g., to enhance penetration of cellular membranes, and confer the ability to recognize and bind to targeted cells.

Administration of Nucleic Acid Molecules

A siNA molecule of the invention can be adapted for use to treat any disease, infection or condition associated with gene expression, and other indications that can respond to the level of gene product in a cell or tissue, alone or in combination with other therapies. For example, a siNA molecule can comprise a delivery vehicle, including liposomes, for administration to a subject, carriers and diluents and their salts, and/or can be present in pharmaceutically acceptable formulations. Methods for the delivery of nucleic acid molecules are described in Akhtar et al., 1992, *Trends*

Cell Bio., 2, 139; Delivery Strategies for Antisense Oligonucleotide Therapeutics, ed. Akhtar, 1995, Maurer et al., 1999, Mol. Membr. Biol., 16, 129-140; Hofland and Huang, 1999, Handb. Exp. Pharmacol., 137, 165-192; and Lee et al., 2000, ACS Symp. Ser., 752, 184-192, all of which are incorporated herein by reference. Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example Gonzalez et al., 1999, Bioconjugate Chem., 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and US Patent Application Publication No. US 2002130430), biodegradable nanocapsules, and bioadhesive microspheres, or by proteinaceous vectors (O'Hare and Normand, International PCT Publication No. WO 00/53722). In one embodiment, nucleic acid molecules or the invention are administered via biodegradable implant materials, such as elastic shape memory polymers (see for example Lendelein and Langer, 2002, Science, 296, 1673). Alternatively, the nucleic acid/vehicle combination is locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry et al., 1999, Clin. Cancer Res., 5, 2330-2337 and Barry et al., International PCT Publication No. WO 99/31262. Many examples in the art describe CNS delivery methods of oligonucleotides by osmotic pump, (see Chun et al., 1998, Neuroscience Letters, 257, 135-138, D'Aldin et al., 1998, Mol. Brain Research, 55, 151-164, Dryden et al., 1998, J. Endocrinol., 157, 169-175, Ghirnikar et al., 1998, Neuroscience Letters, 247, 21-24) or direct infusion (Broaddus et al., 1997, Neurosurg. Focus, 3, article 4). Other routes of delivery include, but are not limited to oral (tablet or pill form) and/or intrathecal delivery (Gold, 1997, Neuroscience, 76, 1153-1158). More detailed descriptions of nucleic acid delivery and administration are provided in Sullivan et al., supra, Draper et al., PCT WO93/23569, Beigelman et al., PCT WO99/05094, and Klimuk et al., PCT WO99/04819 all of which have been incorporated by reference herein. The molecules of the instant invention can be used as pharmaceutical agents. Pharmaceutical agents prevent, modulate the occurrence, or treat (alleviate a symptom to some extent, preferably all of the symptoms) of a disease state in a subject.

In addition, the invention features the use of methods to deliver the nucleic acid molecules of the instant invention to hematopoietic cells, including monocytes and lymphocytes. These methods are described in detail by Hartmann et al., 1998, J. Phamacol. Exp. Ther., 285(2), 920-928; Kronenwett et al., 1998, Blood, 91(3), 852-862; Filion and Phillips, 1997, Biochim. Biophys. Acta., 1329(2), 345-356; Ma and Wei, 1996, Leuk. Res., 20(11/12), 925-930; and Bongartz et al., 1994, Nucleic Acids Research, 22(22), 4681-8. Such methods, as described above, include the use of free oligonucleitide, cationic lipid formulations, liposome formulations including pH sensitive liposomes and immunoliposomes, and bioconjugates including oligonucleotides conjugated to fusogenic peptides, for the transfection of hematopoietic cells with oligonucleotides.

In one embodiment, a compound, molecule, or composition for the treatment of ocular conditions (e.g., macular degeneration, diabetic retinopathy etc.) is administered to a subject intraocularly or by intraocular means. In another embodiment, a compound, molecule, or composition for the treatment of ocular conditions (e.g., macular degeneration, diabetic retinopathy etc.) is administered to a subject periocularly or by periocular means (see for example Ahlheim et al., International PCT publication No. WO 03/24420). In one embodiment, a siNA molecule and/or formulation or composition thereof is administered to a subject intraocularly or by intraocular means. In another embodiment, a siNA molecule and/or formulation or composition thereof is administered to a subject periocularly or by periocular means. Periocular administration generally provides a less invasive approach to administering siNA molecules and formulation or composition thereof to a subject (see for example Ahlheim et al., International PCT publication No. WO 03/24420). The use of periocular administration also minimizes the risk of retinal detachment, allows for more frequent dosing or administration, provides a clinically relevant route of administration for macular degeneration and other optic conditions, and also provides the possibility of using reservoirs (e.g., implants, pumps or other devices) for drug delivery.

In one embodiment, a siNA molecule of the invention is complexed with membrane disruptive agents such as those described in U.S. Patent Application Publication No. 20010007666, incorporated by reference herein in its entirety including the drawings. In another embodiment, the membrane disruptive agent or agents and the siNA molecule are also complexed with a cationic lipid or helper lipid molecule, such as those lipids described in U.S. Pat. No. 6,235,310, incorporated by reference herein in its entirety including the drawings.

In one embodiment, siNA molecules of the invention are formulated or complexed with polyethylenimine (e.g., linear or branched PEI) and/or polyethylenimine derivatives, including for example grafted PEIs such as galactose PEI, cholesterol PEI, antibody derivatized PEI, and polyethylene glycol PEI (PEG-PEI) derivatives thereof (see for example Ogris et al., 2001, AAPA PharmSci, 3, 1-11; Furgeson et al., 2003, Bioconjugate Chem., 14, 840-847; Kunath et al., 2002, Phramaceutical Research, 19, 810-817; Choi et al., 2001, Bull. Korean Chem. Soc., 22, 46-52; Bettinger et al., 1999, Bioconjugate Chem., 10, 558-561; Peterson et al., 2002, Bioconjugate Chem., 13, 845-854; Erbacher et al., 1999, Journal of Gene Medicine Preprint, 1, 1-18; Godbey et al., 1999., PNAS USA, 96, 5177-5181; Godbey et al., 1999, Journal of Controlled Release, 60, 149-160; Diebold et al., 1999, Journal of Biological Chemistry, 274, 19087-19094; Thomas and Klibanov, 2002, PNAS USA, 99, 14640-14645; and Sagara, U.S. Pat. No. 6,586,524, incorporated by reference herein.

In one embodiment, a siNA molecule of the invention comprises a bioconjugate, for example a nucleic acid conjugate as described in Vargeese et al., U.S. Ser. No. 10/427,160, filed Apr. 30, 2003; U.S. Pat. No. 6,528,631; U.S. Pat. No. 6,335,434; U.S. Pat. No. 6,235,886; U.S. Pat. No. 6,153,737; U.S. Pat. No. 5,214,136; U.S. Pat. No. 5,138,045, all incorporated by reference herein.

Thus, the invention features a pharmaceutical composition comprising one or more nucleic acid(s) of the invention in an acceptable carrier, such as a stabilizer, buffer, and the like. The polynucleotides of the invention can be administered (e.g., RNA, DNA or protein) and introduced into a subject by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as tablets, capsules or elixirs for oral administration, suppositories for rectal administration, sterile solutions, suspensions for injectable administration, and the other compositions known in the art.

The present invention also includes pharmaceutically acceptable formulations of the compounds described. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g., systemic administration, into a cell or subject, including for example a human. Suitable forms, in part, depend upon the use or the route of entry, for example oral, transdermal, or by injection. Such forms should not prevent the composition or formulation from reaching a target cell (i.e., a cell to which the negatively charged nucleic acid is desirable for delivery). For example, pharmacological compositions injected into the blood stream should be soluble. Other factors are known in the art, and include considerations such as toxicity and forms that prevent the composition or formulation from exerting its effect.

By "systemic administration" is meant in vivo systemic absorption or accumulation of drugs in the blood stream followed by distribution throughout the entire body. Administration routes that lead to systemic absorption include, without limitation: intravenous, subcutaneous, intraperitoneal, inhalation, oral, intrapulmonary and intramuscular. Each of these administration routes exposes the siNA molecules of the invention to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation that can facilitate the association of drug with the surface of cells, such as, lymphocytes and macrophages is also useful. This approach can provide enhanced delivery of the drug to target cells by taking advantage of the specificity of macrophage and lymphocyte immune recognition of abnormal cells, such as cancer cells.

By "pharmaceutically acceptable formulation" is meant a composition or formulation that allows for the effective distribution of the nucleic acid molecules of the instant invention in the physical location most suitable for their desired activity. Non-limiting examples of agents suitable for formulation with the nucleic acid molecules of the instant invention include: P-glycoprotein inhibitors (such as Pluronic P85), which can enhance entry of drugs into the CNS (Jolliet-Riant and Tillement, 1999, *Fundam. Clin. Pharmacol.*, 13, 16-26); biodegradable polymers, such as poly (DL-lactide-coglycolide) microspheres for sustained release delivery after intracerebral implantation (Emerich, D F et al, 1999, *Cell Transplant*, 8, 47-58) (Alkermes, Inc. Cambridge, Mass.); and loaded nanoparticles, such as those made of polybutylcyanoacrylate, which can deliver drugs across the blood brain barrier and can alter neuronal uptake mechanisms (Prog *Neuropsychopharmacol Biol Psychiatry*, 23, 941-949, 1999). Other non-limiting examples of delivery strategies for the nucleic acid molecules of the instant invention include material described in Boado et al., 1998, *J. Pharm. Sci.*, 87, 1308-1315; Tyler et al., 1999, *FEBS Lett.*, 421, 280-284; Pardridge et al., 1995, *PNAS USA.*, 92, 5592-5596; Boado, 1995, *Adv. Drug Delivery Rev.*, 15, 73-107; Aldrian-Herrada et al., 1998, *Nucleic Acids Res.*, 26, 4910-4916; and Tyler et al., 1999, *PNAS USA.*, 96, 7053-7058.

The invention also features the use of the composition comprising surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601-2627; Ishiwata et al., *Chem. Pharm. Bull.* 1995, 43, 1005-1011). Such liposomes have been shown to accumulate selectively in tumors, presumably by extravasation and capture in the neovascularized target tissues (Lasic et al., *Science* 1995, 267, 1275-1276; Oku et al., 1995, *Biochim. Biophys. Acta*, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., *J. Biol. Chem.* 1995, 42, 24864-24870; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro edit. 1985), hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the negatively charged polymer.

The nucleic acid molecules of the invention and formulations thereof can be administered orally, topically, parenterally, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g., intravenous), intramuscular, or intrathecal injection or infusion techniques and the like.

In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions containing nucleic acid molecules of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The nucleic acid molecules of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depending upon the host treated and the particular mode of administration. Dosage unit forms generally contain between from about 1 mg to about 500 mg of an active ingredient.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

In one embodiment, the invention comprises compositions suitable for administering nucleic acid molecules of the invention to specific cell types. For example, the asialoglycoprotein receptor (ASGPr) (Wu and Wu, 1987, J. Biol. Chem. 262, 4429-4432) is unique to hepatocytes and binds branched galactose-terminal glycoproteins, such as asialoorosomucoid (ASOR). In another example, the folate receptor is overexpressed in many cancer cells. Binding of such glycoproteins, synthetic glycoconjugates, or folates to the receptor takes place with an affinity that strongly depends on the degree of branching of the oligosaccharide chain, for example, triatennary structures are bound with greater affinity than biatenarry or monoatennary chains (Baenziger and Fiete, 1980, Cell, 22, 611-620; Connolly et al., 1982, J. Biol. Chem., 257, 939-945). Lee and Lee, 1987, Glycoconjugate J., 4, 317-328, obtained this high specificity through the use of N-acetyl-D-galactosamine as the carbohydrate moiety, which has higher affinity for the receptor, compared to galactose. This "clustering effect" has also been described for the binding and uptake of mannosyl-terminating glycoproteins or glycoconjugates (Ponpipom et al., 1981, J. Med. Chem., 24, 1388-1395). The use of galactose, galactosamine, or folate based conjugates to transport exogenous compounds across cell membranes can provide a targeted delivery approach to, for example, the treatment of liver disease, cancers of the liver, or other cancers. The use of bioconjugates can also provide a reduction in the required dose of therapeutic compounds required for treatment. Furthermore, therapeutic bioavialability, pharmacodynamics, and pharmacokinetic parameters can be modulated through the use of nucleic acid bioconjugates of the invention. Non-limiting examples of such bioconjugates are described in Vargeese et al., U.S. Ser. No. 10/201,394, filed Aug. 13, 2001; and Matulic-Adamic et al., U.S. Ser. No. 10/151,116, filed May 17, 2002. In one embodiment, nucleic acid molecules of the invention are complexed with or covalently attached to nanoparticles, such as Hepatitis B virus S, M, or L evelope proteins (see for example Yamado et al., 2003, Nature Biotechnology, 21, 885). In one embodiment, nucleic acid molecules of the invention are delivered with specificity for human tumor cells, specifically non-apoptotic human tumor cells including for example T-cells, hepatocytes, breast carcinoma cells, ovarian carcinoma cells, melanoma cells, intestinal epithelial cells, prostate cells, testicular cells, non-small cell lung cancers, small cell lung cancers, etc.

EXAMPLES

The following are non-limiting examples showing the selection, isolation, synthesis and activity of nucleic acids of the instant invention.

Example 1: Tandem Synthesis of siNA Constructs

Exemplary siNA molecules of the invention are synthesized in tandem using a cleavable linker, for example, a succinyl-based linker. Tandem synthesis as described herein is followed by a one-step purification process that provides RNAi molecules in high yield. This approach is highly amenable to siNA synthesis in support of high throughput RNAi screening, and can be readily adapted to multi-column or multi-well synthesis platforms.

After completing a tandem synthesis of a siNA oligo and its complement in which the 5'-terminal dimethoxytrityl (5'-O-DMT) group remains intact (trityl on synthesis), the oligonucleotides are deprotected as described above. Following deprotection, the siNA sequence strands are allowed to spontaneously hybridize. This hybridization yields a duplex in which one strand has retained the 5'-O-DMT group while the complementary strand comprises a terminal 5'-hydroxyl. The newly formed duplex behaves as a single molecule during routine solid-phase extraction purification (Trityl-On purification) even though only one molecule has a dimethoxytrityl group. Because the strands form a stable duplex, this dimethoxytrityl group (or an equivalent group, such as other trityl groups or other hydrophobic moieties) is all that is required to purify the pair of oligos, for example, by using a C18 cartridge.

Standard phosphoramidite synthesis chemistry is used up to the point of introducing a tandem linker, such as an inverted deoxy abasic succinate or glyceryl succinate linker (see FIG. 1) or an equivalent cleavable linker. A non-limiting example of linker coupling conditions that can be used includes a hindered base such as diisopropylethylamine (DIPA) and/or DMAP in the presence of an activator reagent such as Bromotripyrrolidinophosphoniumhexafluorophosphate (PyBrOP). After the linker is coupled, standard synthesis chemistry is utilized to complete synthesis of the second sequence leaving the terminal the 5'-O-DMT intact. Following synthesis, the resulting oligonucleotide is deprotected according to the procedures described herein and quenched with a suitable buffer, for example with 50 mM NaOAc or 1.5M NH$_4$H$_2$CO$_3$.

Purification of the siNA duplex can be readily accomplished using solid phase extraction, for example using a Waters C18 SepPak 1 g cartridge conditioned with 1 column volume (CV) of acetonitrile, 2 CV H$_2$O, and 2 CV 50 mM NaOAc. The sample is loaded and then washed with 1 CV H$_2$O or 50 mM NaOAc. Failure sequences are eluted with 1 CV 14% ACN (Aqueous with 50 mM NaOAc and 50 mM NaCl). The column is then washed, for example with 1 CV H$_2$O followed by on-column detritylation, for example by passing 1 CV of 1% aqueous trifluoroacetic acid (TFA) over the column, then adding a second CV of 1% aqueous TFA to the column and allowing to stand for approximately 10 minutes. The remaining TFA solution is removed and the column washed with H$_2$O followed by 1 CV 1M NaCl and additional H$_2$O. The siNA duplex product is then eluted, for example, using 1 CV 20% aqueous CAN.

Figure 2:
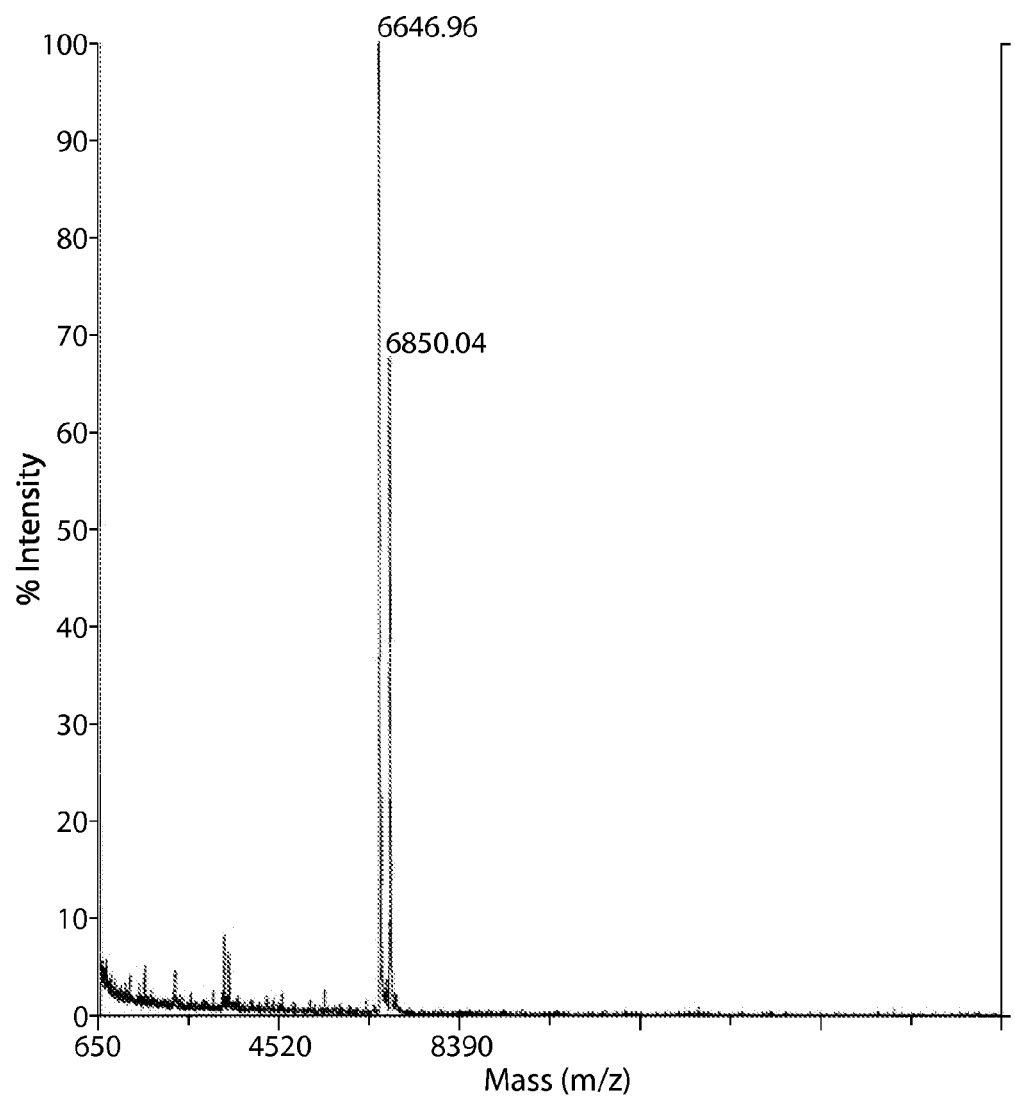
FIG. 2 shows a MALDI-TOF mass spectrum of a purified siNA duplex synthesized by a method of the invention. The two peaks shown correspond to the predicted mass of the separate siNA sequence strands. This result demonstrates that the siNA duplex generated from tandem synthesis can be purified as a single entity using a simple trityl-on purification methodology.

FIG. 2 provides an example of MALDI-TOF mass spectrometry analysis of a purified siNA construct in which each peak corresponds to the calculated mass of an individual siNA strand of the siNA duplex. The same purified siNA provides three peaks when analyzed by capillary gel electrophoresis (CGE), one peak presumably corresponding to the duplex siNA, and two peaks presumably corresponding to the separate siNA sequence strands. Ion exchange HPLC analysis of the same siNA contract only shows a single peak. Testing of the purified siNA construct using a luciferase reporter assay described below demonstrated the same RNAi activity compared to siNA constructs generated from separately synthesized oligonucleotide sequence strands.

Example 2: Serum Stability of Chemically Modified siNA Constructs

Chemical modifications were introduced into siNA constructs to determine the stability of these constructs compared to native siNA oligonucleotides (containing two thymidine nucleotide overhangs) in human serum. An investigation of the serum stability of RNA duplexes revealed that siNA constructs consisting of all RNA nucleotides containing two thymidine nucleotide overhangs have a half-life in serum of 15 seconds, whereas chemically modified siNA constructs remained stable in serum for 1 to 3 days depending on the extent of modification (see FIG. 3). RNAi stability tests were performed by internally labeling one strand (strand 1) of siNA and duplexing with 1.5× the concentration of the complementary siNA strand (strand 2) (to insure all labeled material was in duplex form). Duplexed siNA constructs were then tested for stability by incubating at a final concentration of 2 µM siNA (strand 2 concentration) in 90% mouse or human serum for time-points of 30 sec, 1 min, 5 min, 30 min, 90 min, 4 hrs 10 min, 16 hrs 24 min, and 49 hrs. Time points were run on a 15% denaturing polyacrylamide gels and analyzed on a phosphoimager.

Internal labeling was performed via kinase reactions with polynucleotide kinase (PNK) and $^{32}$P-γ-ATP, with addition of radiolabeled phosphate at nucleotide 13 of strand 2, counting in from the 3' side. Ligation of the remaining 8-mer fragments with T4 RNA ligase resulted in the full length, 21-mer, strand 2. Duplexing of RNAi was done by adding appropriate concentrations of the siNA oligonucleotides and heating to 95° C. for 5 minutes followed by slow cooling to room temperature. Reactions were performed by adding 100% serum to the siNA duplexes and incubating at 37° C., then removing aliquots at desired time-points. Results of this study are summarized in FIG. 3. As shown in the FIG. 3, chemically modified siNA molecules (e.g., SEQ ID NOs: 412/413, 412/414, 412/415, 412/416, and 412/418) have significantly increased serum stability compared to an siNA construct having all ribonucleotides except a 3'-terminal dithymidine (TT) modification (e.g., SEQ ID NOs: 419/420).

Example 3: Identification of Potential siNA Target Sites in any RNA Sequence

The sequence of an RNA target of interest, such as a viral or human mRNA transcript, is screened for target sites, for example by using a computer folding algorithm. In a non-limiting example, the sequence of a gene or RNA gene transcript derived from a database, such as Genbank, is used to generate siNA targets having complementarity to the target. Such sequences can be obtained from a database, or can be determined experimentally as known in the art. Target sites that are known, for example, those target sites determined to be effective target sites based on studies with other nucleic acid molecules, for example ribozymes or antisense, or those targets known to be associated with a disease or condition such as those sites containing mutations or deletions, can be used to design siNA molecules targeting those sites. Various parameters can be used to determine which sites are the most suitable target sites within the target RNA sequence. These parameters include but are not limited to secondary or tertiary RNA structure, the nucleotide base composition of the target sequence, the degree of homology between various regions of the target sequence, or the relative position of the target sequence within the RNA transcript. Based on these determinations, any number of target sites within the RNA transcript can be chosen to screen siNA molecules for efficacy, for example by using in vitro RNA cleavage assays, cell culture, or animal models. In a non-limiting example, anywhere from 1 to 1000 target sites are chosen within the transcript based on the size of the siNA construct to be used. High throughput screening assays can be developed for screening siNA molecules using methods known in the art, such as with multi-well or multi-plate assays or combinatorial/siNA library screening assays to determine efficient reduction in target gene expression.

Example 4: Selection of siNA Molecule Target Sites in a RNA

The following non-limiting steps can be used to carry out the selection of siNAs targeting a given gene sequence or transcript.

The target sequence is parsed in silico into a list of all fragments or subsequences of a particular length, for example 23 nucleotide fragments, contained within the target sequence. This step is typically carried out using a custom Perl script, but commercial sequence analysis programs such as Oligo, MacVector, or the GCG Wisconsin Package can be employed as well.

In some instances the siNAs correspond to more than one target sequence; such would be the case for example in targeting different transcripts of the same gene, targeting different transcripts of more than one gene, or for targeting both the human gene and an animal homolog. In this case, a subsequence list of a particular length is generated for each of the targets, and then the lists are compared to find matching sequences in each list. The subsequences are then ranked according to the number of target sequences that contain the given subsequence; the goal is to find subsequences that are present in most or all of the target sequences. Alternately, the ranking can identify subsequences that are unique to a target sequence, such as a mutant target sequence. Such an approach would enable the use of siNA to target specifically the mutant sequence and not effect the expression of the normal sequence.

In some instances the siNA subsequences are absent in one or more sequences while present in the desired target sequence; such would be the case if the siNA targets a gene with a paralogous family member that is to remain untargeted. As in case 2 above, a subsequence list of a particular length is generated for each of the targets, and then the lists are compared to find sequences that are present in the target gene but are absent in the untargeted paralog.

The ranked siNA subsequences can be further analyzed and ranked according to GC content. A preference can be given to sites containing 30-70% GC, with a further preference to sites containing 40-60% GC.

The ranked siNA subsequences can be further analyzed and ranked according to self-folding and internal hairpins. Weaker internal folds are preferred; strong hairpin structures are to be avoided.

The ranked siNA subsequences can be further analyzed and ranked according to whether they have runs of GGG or CCC in the sequence. GGG (or even more Gs) in either strand can make oligonucleotide synthesis problematic and can potentially interfere with RNAi activity, so it is avoided other appropriately suitable sequences are available. CCC is searched in the target strand because that will place GGG in the antisense strand.

The ranked siNA subsequences can be further analyzed and ranked according to whether they have the dinucleotide UU (uridine dinucleotide) on the 3'-end of the sequence, and/or AA on the 5'-end of the sequence (to yield 3' UU on the antisense sequence). These sequences allow one to design siNA molecules with terminal TT thymidine dinucleotides.

Four or five target sites are chosen from the ranked list of subsequences as described above. For example, in subsequences having 23 nucleotides, the right 21 nucleotides of each chosen 23-mer subsequence are then designed and synthesized for the upper (sense) strand of the siNA duplex, while the reverse complement of the left 21 nucleotides of each chosen 23-mer subsequence are then designed and synthesized for the lower (antisense) strand of the siNA duplex (see Tables I). If terminal TT residues are desired for the sequence (as described in paragraph 7), then the two 3' terminal nucleotides of both the sense and antisense strands are replaced by TT prior to synthesizing the oligos.

The siNA molecules are screened in an in vitro, cell culture or animal model system to identify the most active siNA molecule or the most preferred target site within the target RNA sequence.

In an alternate approach, a pool of siNA constructs specific to a target sequence is used to screen for target sites in cells expressing target RNA, such as human HeLa cells. The general strategy used in this approach is shown in FIGS. 21A-21D. A non-limiting example of such a pool is a pool comprising sequences having antisense sequences complementary to the target RNA sequence and sense sequences complementary to the antisense sequences. Cells (e.g., HeLa cells) expressing the target gene are transfected with the pool of siNA constructs and cells that demonstrate a phenotype associated with gene silencing are sorted. The pool of siNA constructs can be chemically modified as described herein and synthesized, for example, in a high throughput manner. The siNA from cells demonstrating a positive phenotypic change (e.g., decreased target mRNA levels or target protein expression), are identified, for example by positional analysis within the assay, and are used to determine the most suitable target site(s) within the target RNA sequence based upon the complementary sequence to the corresponding siNA antisense strand identified in the assay.

Example 5: RNAi Activity of Chemically Modified siNA Constructs

Short interfering nucleic acid (siNA) is emerging as a powerful tool for gene regulation. All-ribose siNA duplexes activate the RNAi pathway but have limited utility as therapeutic compounds due to their nuclease sensitivity and short half-life in serum, as shown in Example 2 above. To develop nuclease-resistant siNA constructs for in vivo applications, siNAs that target luciferase mRNA and contain stabilizing chemical modifications were tested for activity in HeLa cells. The sequences for the siNA oligonucleotide sequences used in this study are shown in Table I. Modifications included phosphorothioate linkages (P=S), 2'-O-methyl nucleotides, or 2'-fluoro (F) nucleotides in one or both siNA strands and various 3'-end stabilization chemistries, including 3'-glyceryl, 3'-inverted abasic, 3'-inverted Thymidine, and/or Thymidine. The RNAi activity of chemically stabilized siNA constructs was compared with the RNAi activity of control siNA constructs consisting of all ribonucleotides at every position except the 3'-terminus which comprised two thymidine nucleotide overhangs. Active siNA molecules containing stabilizing modifications such as described herein should prove useful for in vivo applications, given their enhanced nuclease-resistance.

A luciferase reporter system was utilized to test RNAi activity of chemically modified siNA constructs compared to siNA constructs consisting of all RNA nucleotides containing two thymidine nucleotide overhangs. Sense and antisense siNA strands (20 uM each) were annealed by incubation in buffer (100 mM potassium acetate, 30 mM HEPES-KOH, pH 7.4, 2 mM magnesium acetate) for 1 min. at 90° C. followed by 1 hour at 37° C. Plasmids encoding firefly luciferase (pGL2) and renilla luciferase (pRLSV40) were purchased from Promega Biotech.

HeLa S3 cells were grown at 37° C. in DMEM with 5% FBS and seeded at 15,300 cells in 100 ul media per well of a 96-well plate 24 hours prior to transfection. For transfection, 4 ul Lipofectamine 2000 (Life Technologies) was added to 96 ul OPTI-MEM, vortexed and incubated at room temperature for 5 minutes. The 100 ul diluted lipid was then added to a microtiter tube containing 5 ul pGL2 (200 ng/ul), 5 ul pRLSV40 (8 ng/ul) 6 ul siNA (25 nM or 10 nM final), and 84 ul OPTI-MEM, vortexed briefly and incubated at room temperature for 20 minutes. The transfection mix was then mixed briefly and 50 ul was added to each of three wells that contained HeLa S3 cells in 100 ul media. Cells were incubated for 20 hours after transfection and analyzed for luciferase expression using the Dual luciferase assay according to the manufacturer's instructions (Promega Biotech). The results of this study are summarized in FIGS. 4-16. The sequences of the siNA strands used in this study are shown in Table I and are referred to by Sirna/RPI # in the figures. Normalized luciferase activity is reported as the ratio of firefly luciferase activity to renilla luciferase activity in the same sample. Error bars represent standard deviation of triplicate transfections. As shown in FIGS. 4-16, the RNAi activity of chemically modified constructs is often comparable to that of unmodified control siNA constructs, which consist of all ribonucleotides at every position except the 3'-terminus which comprises two thymidine nucleotide overhangs. In some instances, the RNAi activity of the chemically modified constructs is greater than the unmodified control siNA construct consisting of all ribonucleotides.

Figure 4:
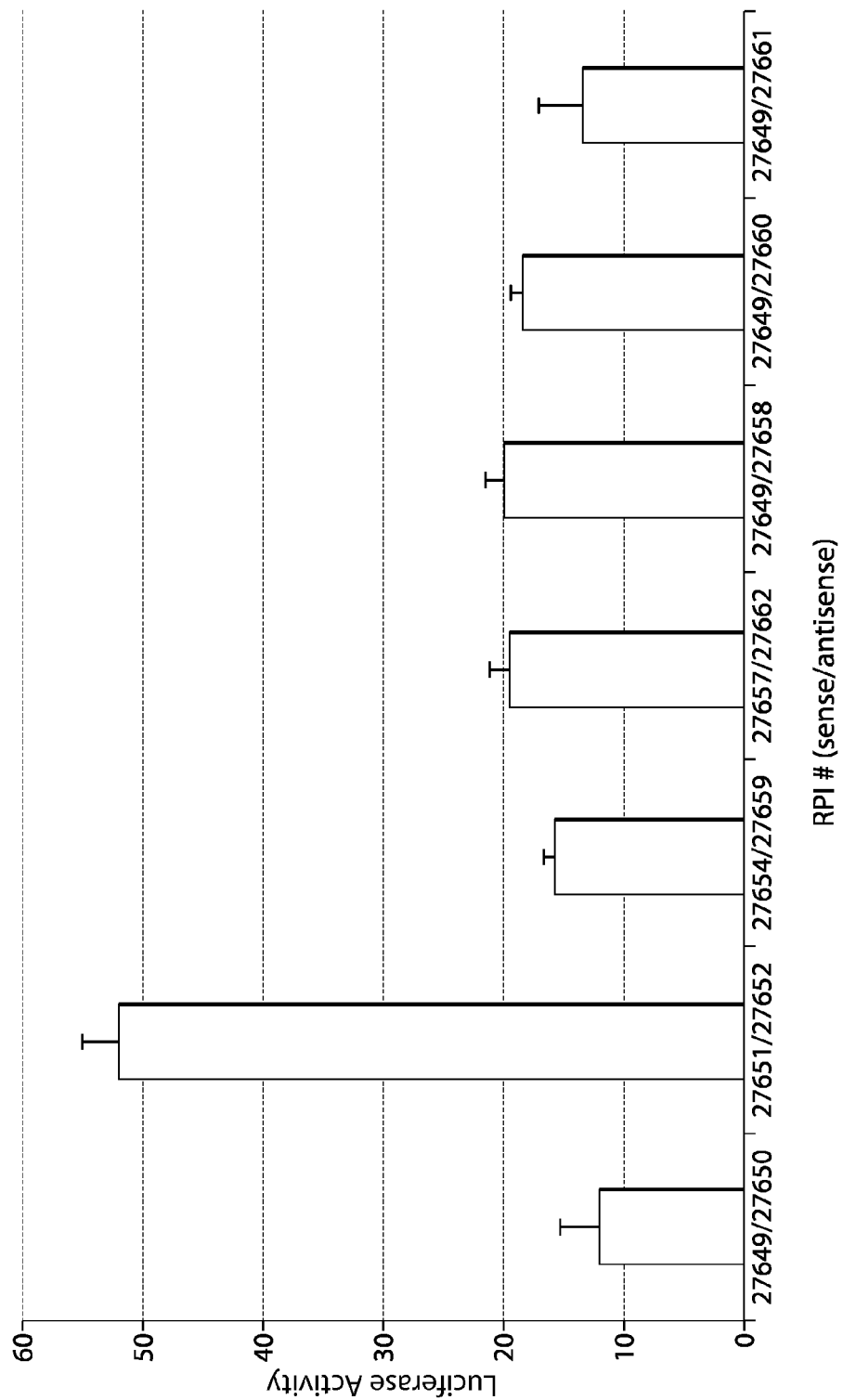
FIG. 4 shows the results of an RNAi activity screen of several phosphorothioate modified siNA constructs using a luciferase reporter system.

For example, FIG. 4 shows results obtained from a screen using phosphorothioate modified siNA constructs. The Sirna/RPI 27654/27659 construct contains phosphorothioate substitutions for every pyrimidine nucleotide in both sequences, the Sirna/RPI 27657/27662 construct contains 5 terminal 3'-phosphorothioate substitutions in each strand, the Sirna/RPI 27649/27658 construct contains all phosphorothioate substitutions only in the antisense strand, whereas the Sirna/RPI 27649/27660 and Sirna/RPI 27649/27661 constructs have unmodified sense strands and varying degrees of phosphorothioate substitutions in the antisense strand. All of these constructs show significant RNAi activity when compared to a scrambled siNA control construct (27651/27652).

Figure 5:
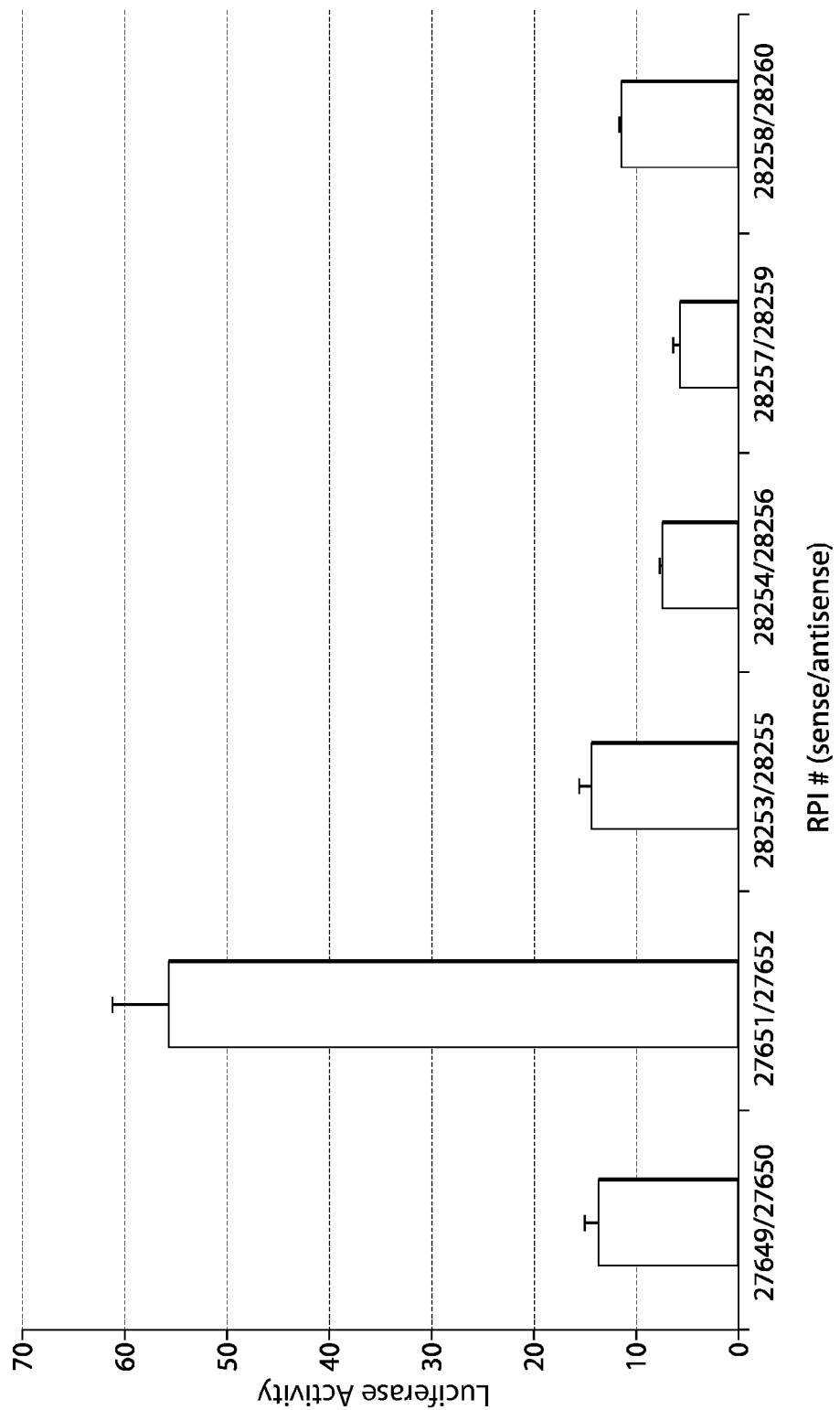
FIG. 5 shows the results of an RNAi activity screen of several phosphorothioate and universal base modified siNA constructs using a luciferase reporter system.

FIG. 5 shows results obtained from a screen using phosphorothioate (Sirna/RPI 28253/28255 and Sirna/RPI 28254/28256) and universal base substitutions (Sirna/RPI 28257/28259 and Sirna/RPI 28258/28260) compared to the same controls described above, these modifications show equivalent or better RNAi activity when compared to the unmodified control siNA construct.

Figure 6:
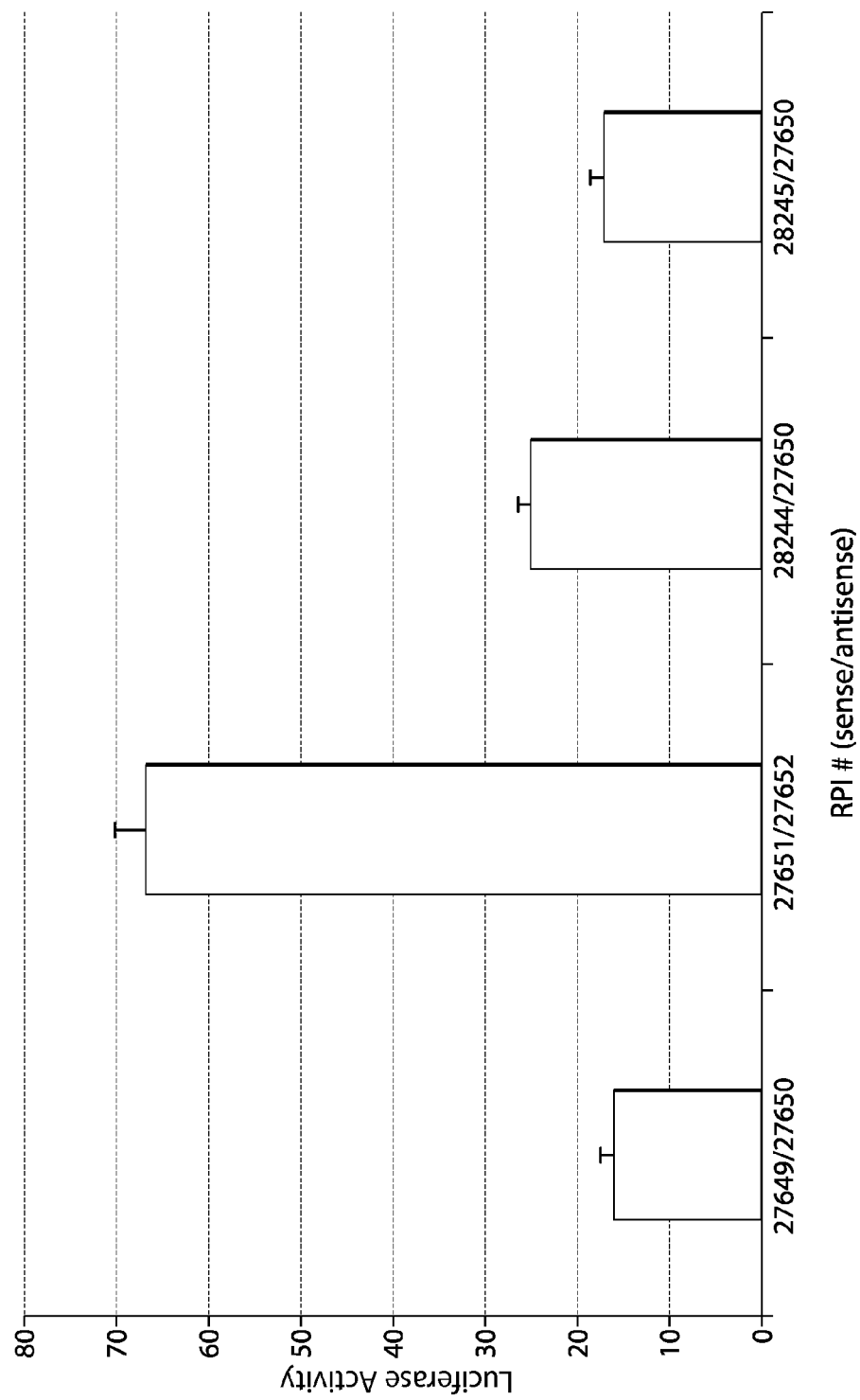
FIG. 6 shows the results of an RNAi activity screen of several 2'-O-methyl modified siNA constructs using a luciferase reporter system.

FIG. 6 shows results obtained from a screen using 2'-O-methyl modified siNA constructs in which the sense strand contains either 10 (Sirna/RPI 28244/27650) or 5 (Sirna/RPI 28245/27650) 2'-O-methyl substitutions, both with comparable activity to the unmodified control siNA construct.

Figure 7:
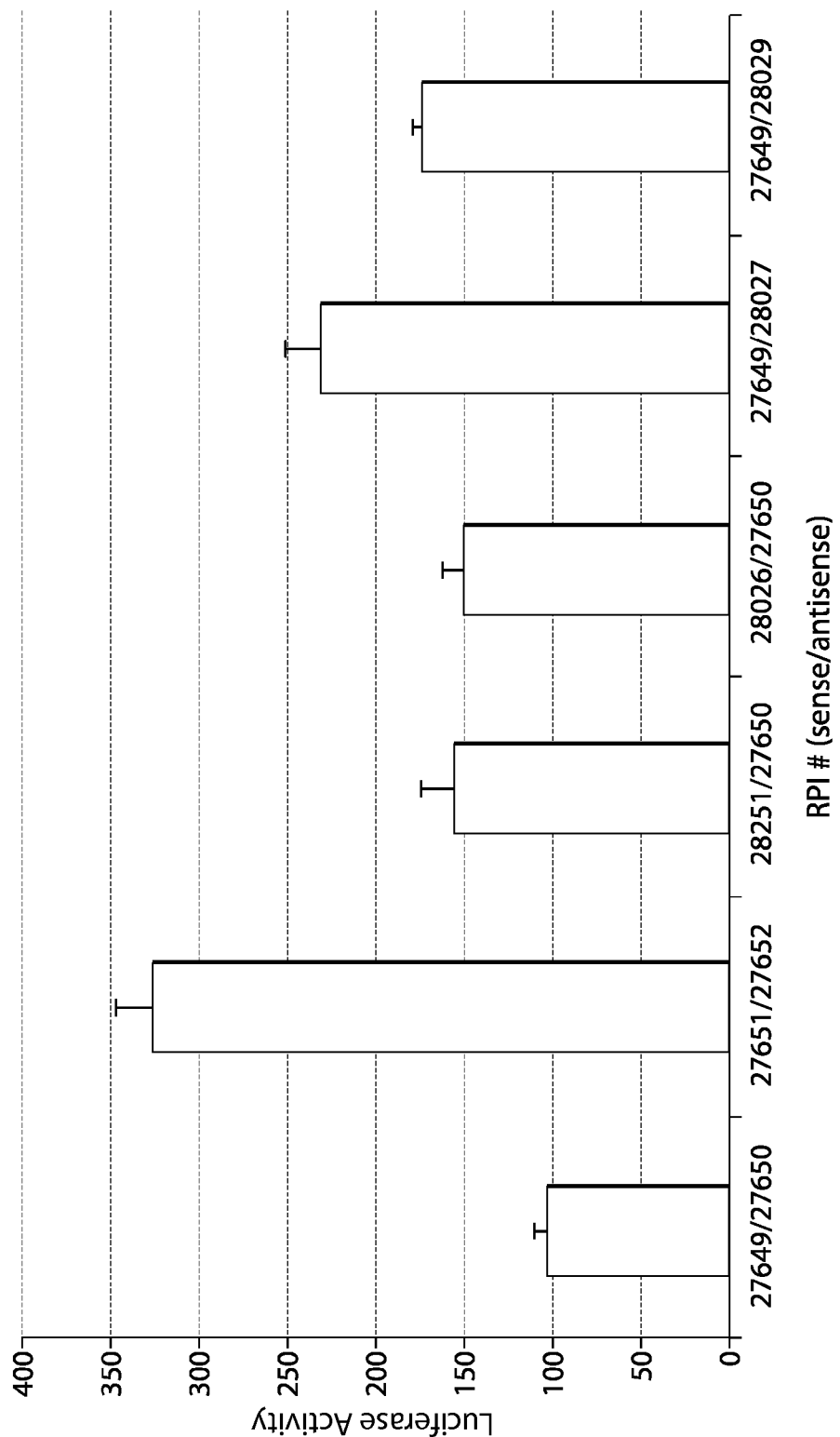
FIG. 7 shows the results of an RNAi activity screen of several 2'-O-methyl and 2'-deoxy-2'-fluoro modified siNA constructs using a luciferase reporter system.

FIG. 7 shows results obtained from a screen using 2'-O-methyl or 2'-deoxy-2'-fluoro modified siNA constructs compared to a control construct consisting of all ribonucleotides at every position except the 3'-terminus which comprises two thymidine nucleotide overhangs.

Figure 8:
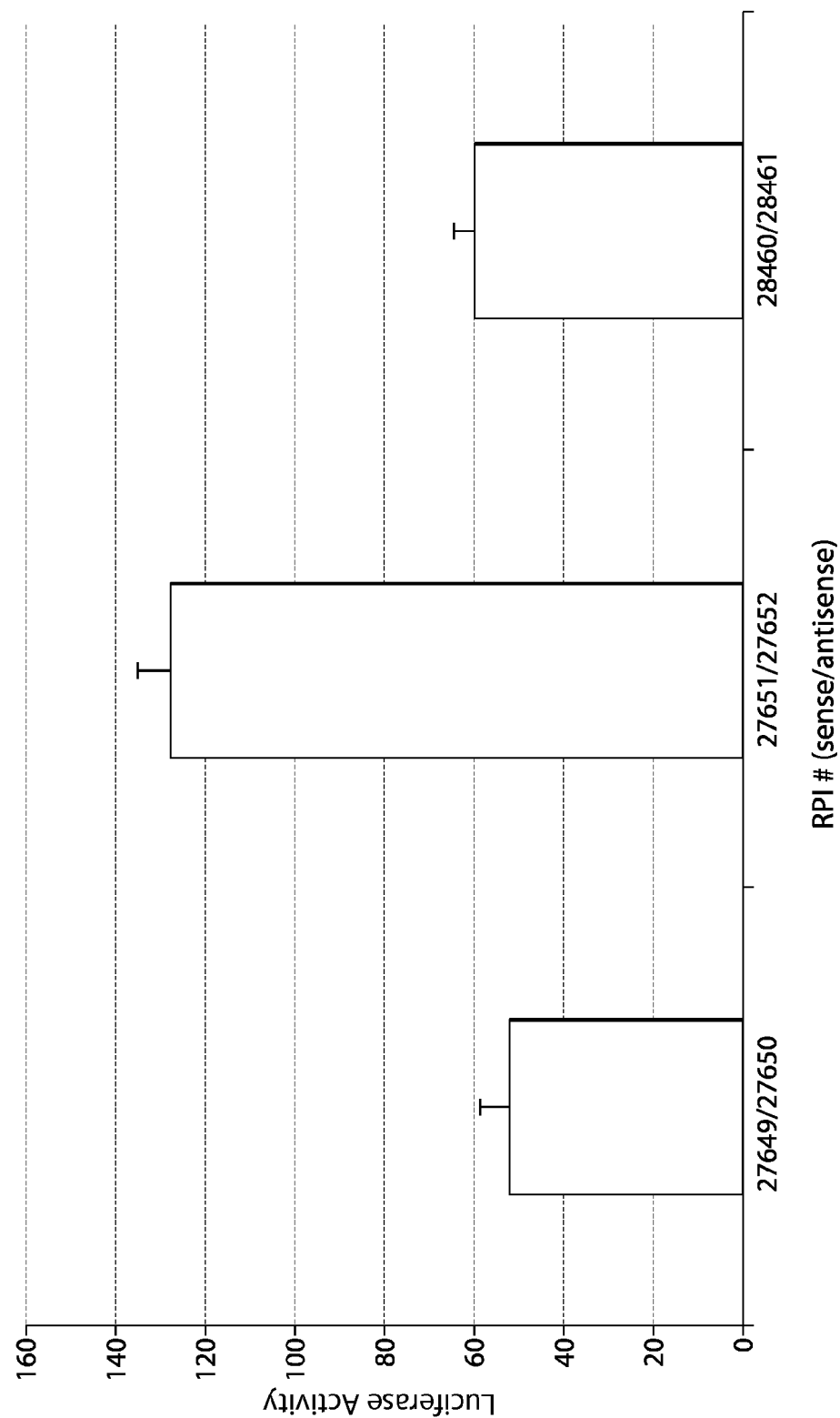
FIG. 8 shows the results of an RNAi activity screen of a phosphorothioate modified siNA construct using a luciferase reporter system.

FIG. 8 compares a siNA construct containing six phosphorothioate substitutions in each strand (Sirna/RPI 28460/28461), where 5 phosphorothioates are present at the 3' end and a single phosphorothioate is present at the 5' end of each strand. This motif shows very similar activity to the control siNA construct consisting of all ribonucleotides at every position except the 3'-terminus, which comprises two thymidine nucleotide overhangs.

Figure 9:
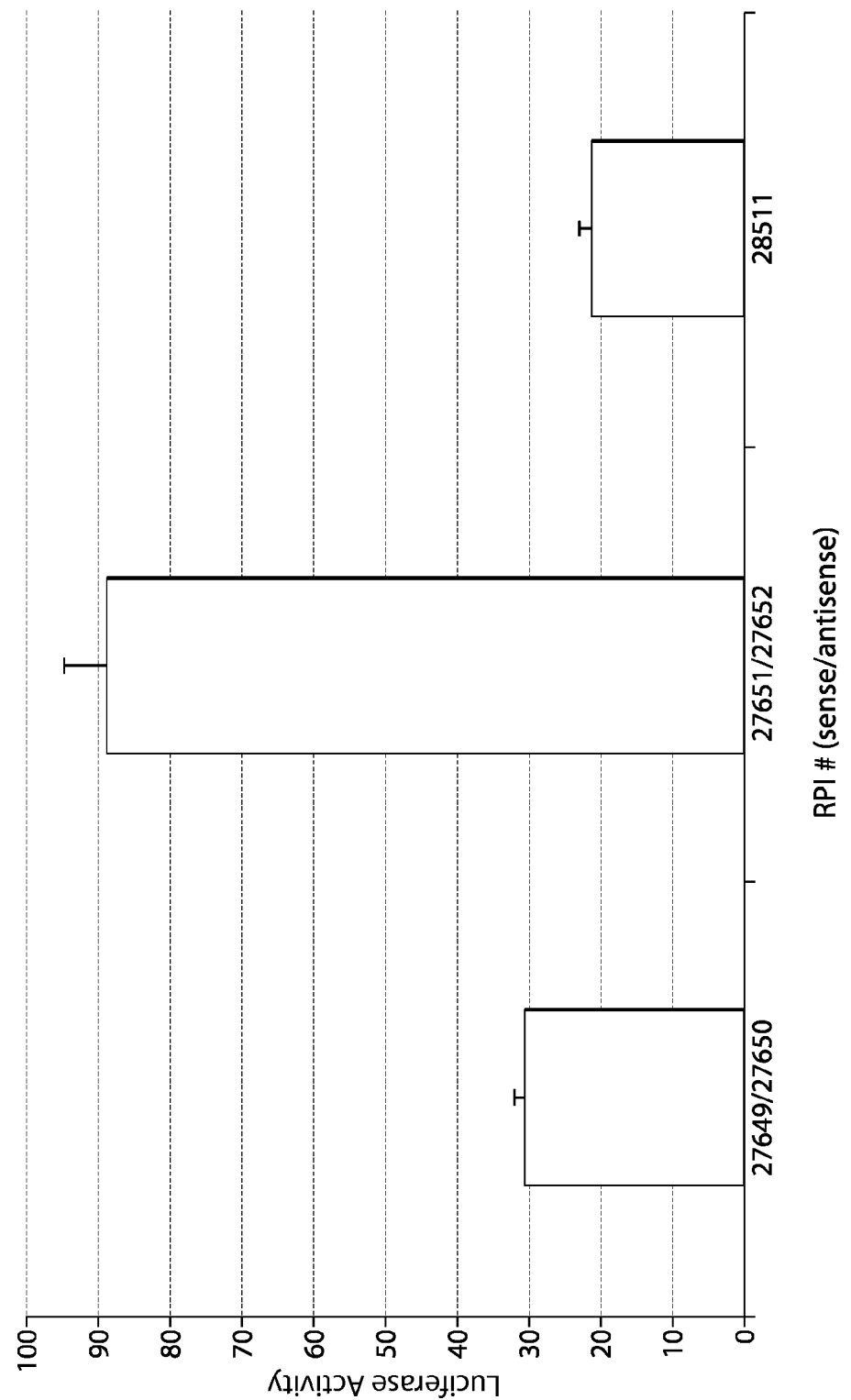
FIG. 9 shows the results of an RNAi activity screen of an inverted deoxyabasic modified siNA construct generated via tandem synthesis using a luciferase reporter system.

FIG. 9 compares a siNA construct synthesized by the method of the invention described in Example 1, wherein an inverted deoxyabasic succinate linker was used to generate a siNA having a 3'-inverted deoxyabasic cap on the antisense strand of the siNA. This construct shows improved activity compared to the control siNA construct consisting of all ribonucleotides at every position except the 3'-terminus which comprises two thymidine nucleotide overhangs.

Figure 10:
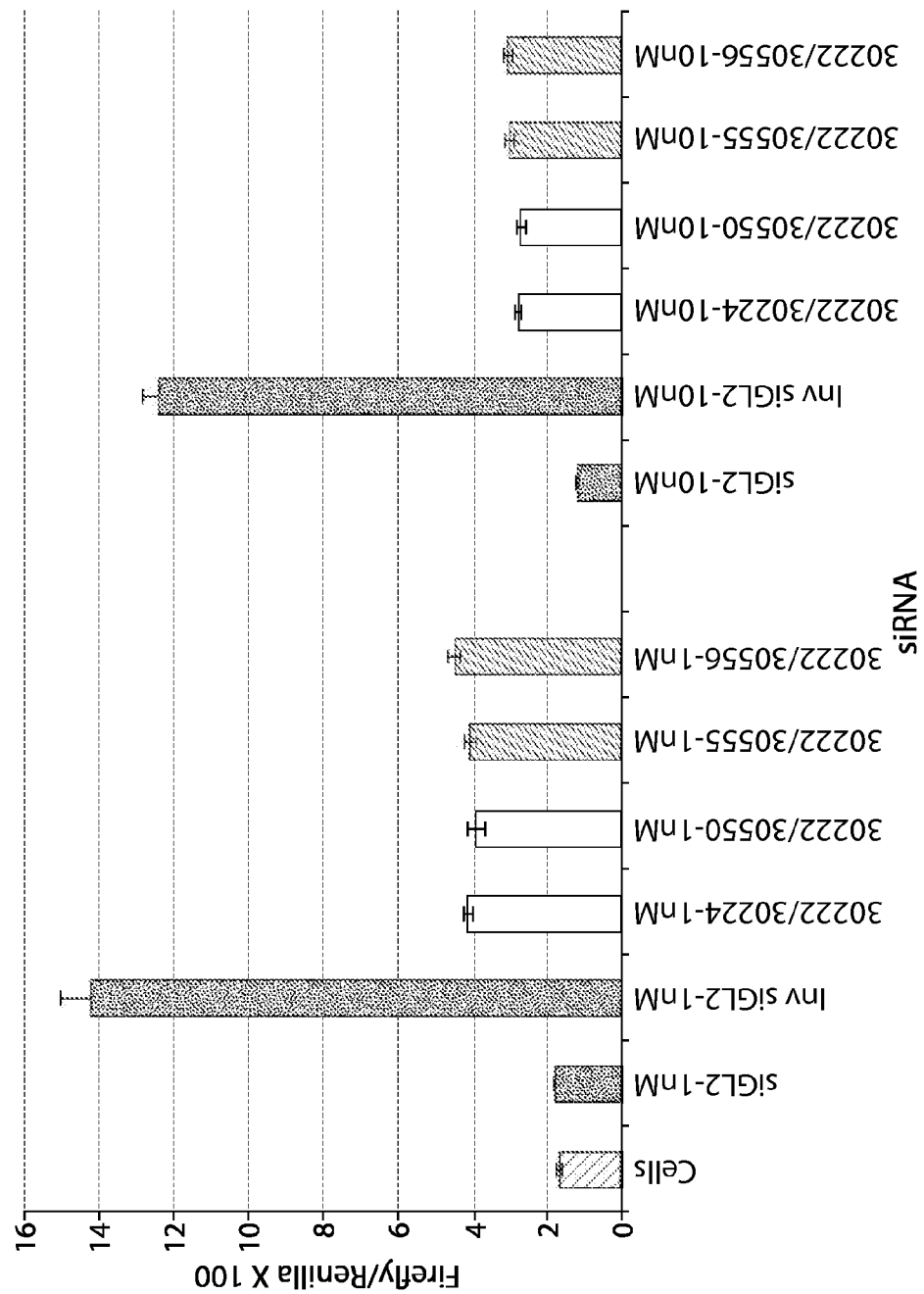
FIG. 10 shows the results of an RNAi activity screen of chemically modified siNA constructs including 3'-glyceryl modified siNA constructs compared to an all RNA control siNA construct using a luciferase reporter system. These chemically modified siNAs were compared in the luciferase assay described herein at 1 nM and 10 nM concentration using an all RNA siNA control (siGL2) having 3'-terminal dithymidine (TT) and its corresponding inverted control (Inv siGL2). The background level of luciferase expression in the HeLa cells is designated by the "cells" column. Sense and antisense strands of chemically modified siNA constructs are shown by Sirna/RPI number (sense strand/antisense strand). Sequences corresponding to these Sirna/RPI numbers are shown in Table I.

FIG. 10 shows the results of an RNAi activity screen of chemically modified siNA constructs including 3'-glyceryl modified siNA constructs compared to an all RNA control siNA construct using a luciferase reporter system. These chemically modified siNAs were compared in the luciferase assay described herein at 1 nM and 10 nM concentration using an all RNA siNA control (siGL2) having 3'-terminal dithymidine (TT) and its corresponding inverted control (Inv siGL2). The background level of luciferase expression in the HeLa cells is designated by the "cells" column. Sense and antisense strands of chemically modified siNA constructs are shown by Sirna/RPI number (sense strand/antisense strand). Sequences corresponding to these Sirna/RPI numbers are shown in Table I. As shown in the Figure, the 3'-terminal modified siNA constructs retain significant RNAi activity compared to the unmodified control siNA (siGL2) construct.

Figure 11:
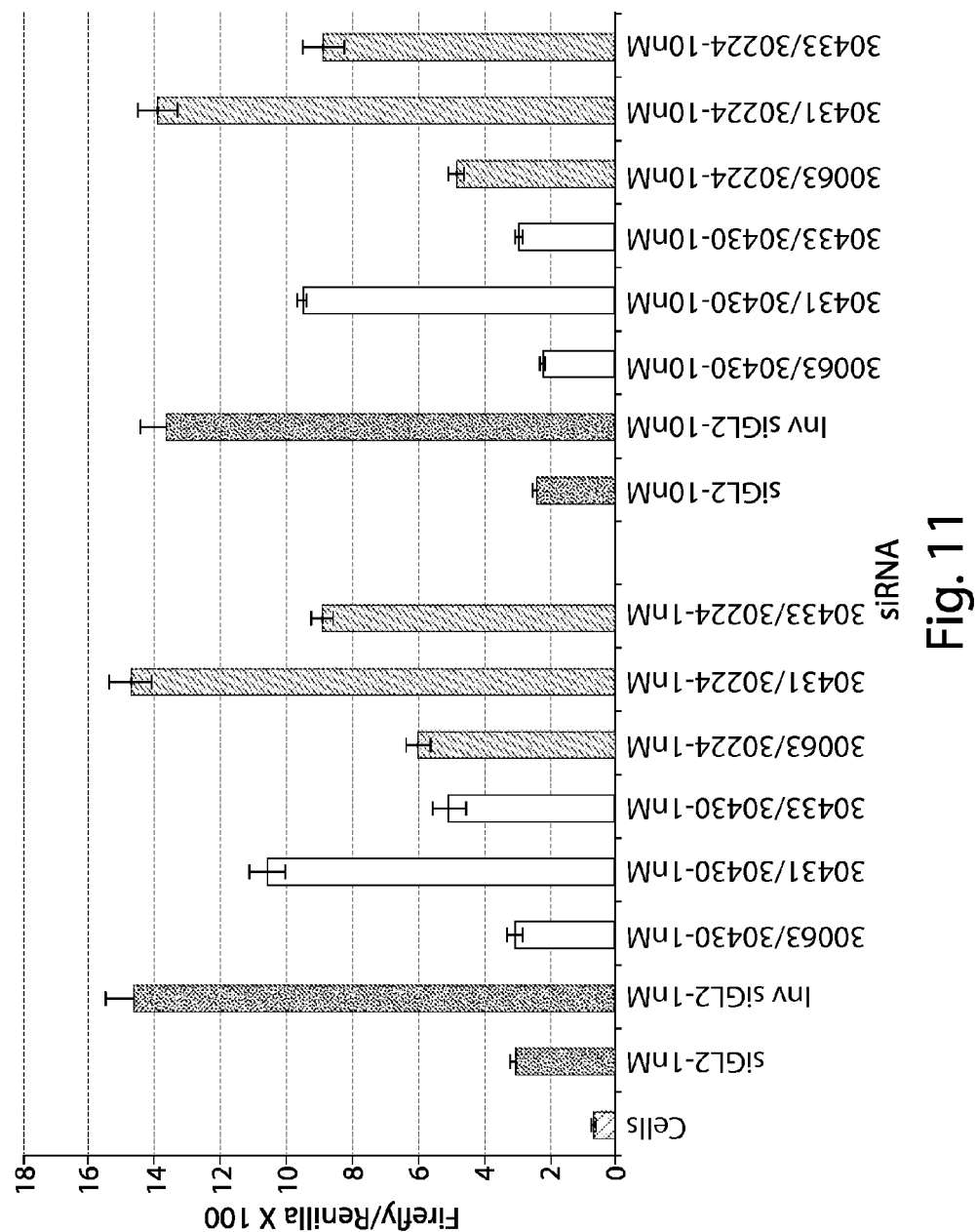
FIG. 11 shows the results of an RNAi activity screen of chemically modified siNA constructs. The screen compared various combinations of sense strand chemical modifications and antisense strand chemical modifications. These chemically modified siNAs were compared in the luciferase assay described herein at 1 nM and 10 nM concentration using an all RNA siNA control (siGL2) having 3'-terminal dithymidine (TT) and its corresponding inverted control (Inv siGL2). The background level of luciferase expression in the HeLa cells is designated by the "cells" column. Sense and antisense strands of chemically modified siNA constructs are shown by Sirna/RPI number (sense strand/antisense strand). Sequences corresponding to these Sirna/RPI numbers are shown in Table I.

FIG. 11 shows the results of an RNAi activity screen of chemically modified siNA constructs. The screen compared various combinations of sense strand chemical modifications and antisense strand chemical modifications. These chemically modified siNAs were compared in the luciferase assay described herein at 1 nM and 10 nM concentration using an all RNA siNA control (siGL2) having 3'-terminal dithymidine (TT) and its corresponding inverted control (Inv siGL2). The background level of luciferase expression in the HeLa cells is designated by the "cells" column. Sense and antisense strands of chemically modified siNA constructs are shown by Sirna/RPI number (sense strand/antisense strand). Sequences corresponding to these Sirna/RPI numbers are shown in Table I. As shown in the figure, the chemically modified Sirna/RPI 30063/30430, Sirna/RPI 30433/30430, and Sirna/RPI 30063/30224 constructs retain significant RNAi activity compared to the unmodified control siNA construct. It should be noted that Sirna/RPI 30433/30430 is a siNA construct having no ribonucleotides which retains significant RNAi activity compared to the unmodified control siGL2 construct in vitro, therefore, this construct is expected to have both similar RNAi activity and improved stability in vivo compared to siNA constructs having ribonucleotides.

Figure 12:
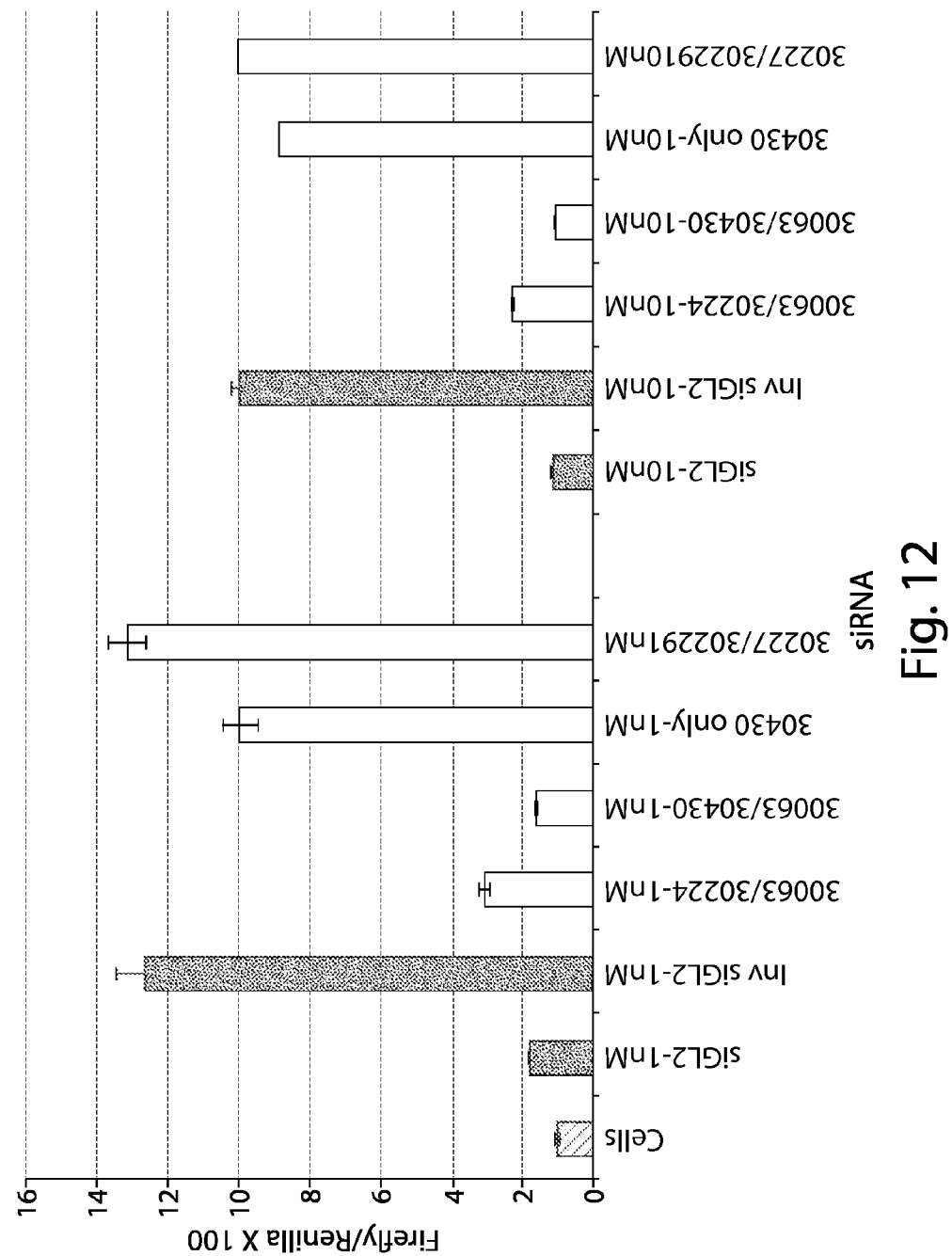
FIG. 12 shows the results of an RNAi activity screen of chemically modified siNA constructs. The screen compared various combinations of sense strand chemical modifications and antisense strand chemical modifications. These chemically modified siNAs were compared in the luciferase assay described herein at 1 nM and 10 nM concentration using an all RNA siNA control (siGL2) having 3'-terminal dithymidine (TT) and its corresponding inverted control (Inv siGL2). The background level of luciferase expression in the HeLa cells is designated by the "cells" column. Sense and antisense strands of chemically modified siNA constructs are shown by Sirna/RPI number (sense strand/antisense strand). Sequences corresponding to these Sirna/RPI numbers are shown in Table I. In addition, the antisense strand alone (Sirna/RPI 30430) and an inverted control (Sirna/RPI 30227/30229, having matched chemistry to Sirna/RPI (30063/30224) was compared to the siNA duplexes described above.

FIG. 12 shows the results of an RNAi activity screen of chemically modified siNA constructs. The screen compared various combinations of sense strand chemical modifications and antisense strand chemical modifications. These chemically modified siNAs were compared in the luciferase assay described herein at 1 nM and 10 nM concentration using an all RNA siNA control (siGL2) having 3'-terminal dithymidine (TT) and its corresponding inverted control (Inv siGL2). The background level of luciferase expression in the HeLa cells is designated by the "cells" column. Sense and antisense strands of chemically modified siNA constructs are shown by Sirna/RPI number (sense strand/antisense strand). Sequences corresponding to these Sirna/RPI numbers are shown in Table I. As shown in the figure, the chemically modified Sirna/RPI 30063/30224 and Sirna/RPI 30063/30430 constructs retain significant RNAi activity compared to the control siNA (siGL2) construct. In addition, the antisense strand alone (Sirna/RPI 30430) and an inverted control (Sirna/RPI 30227/30229), having matched chemistry to Sirna/RPI (30063/30224) were compared to the siNA duplexes described above. The antisense strand (Sirna/RPI 30430) alone provides far less inhibition compared to the siNA duplexes using this sequence.

Figure 13:
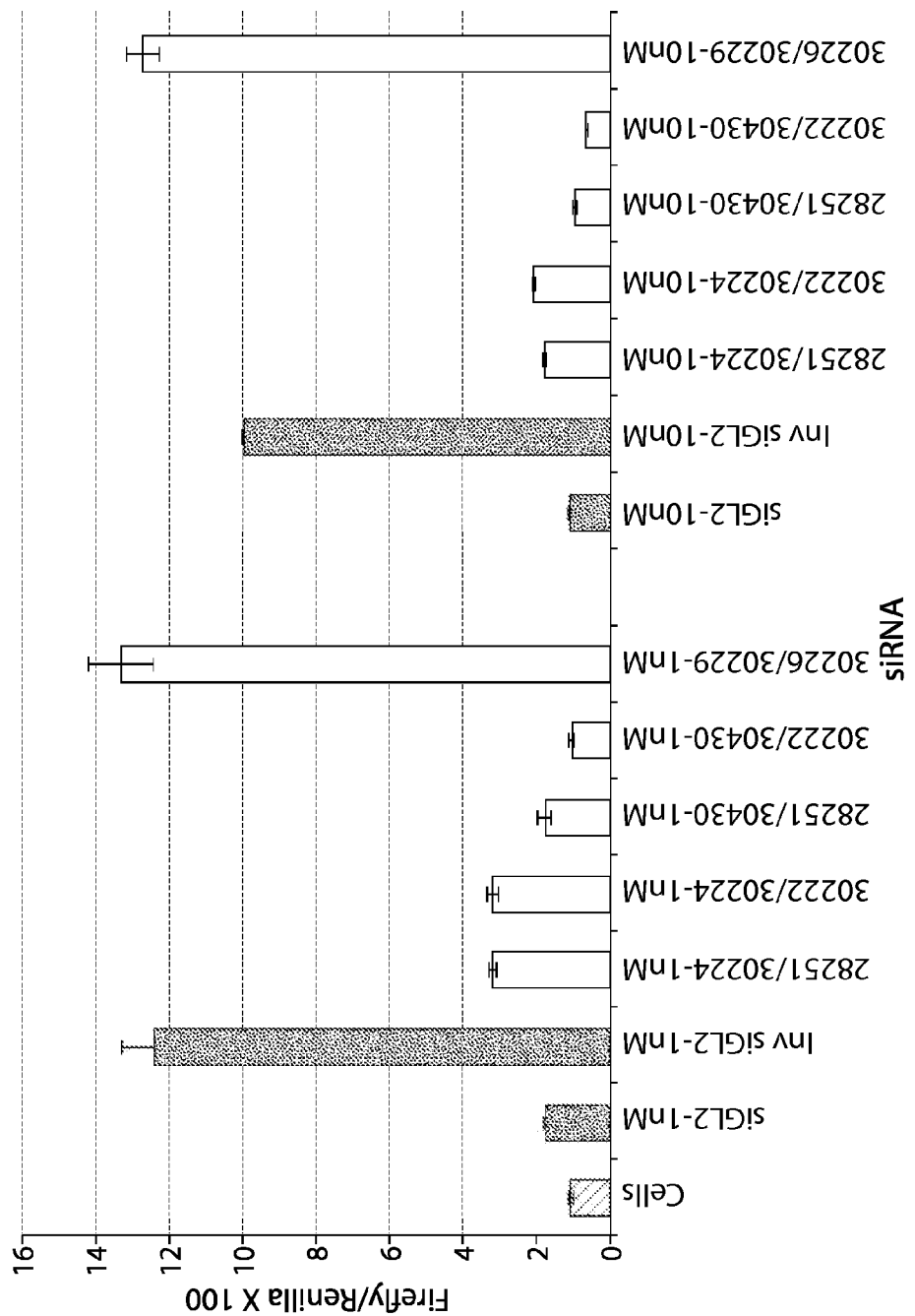
FIG. 13 shows the results of an RNAi activity screen of chemically modified siNA constructs. The screen compared various combinations of sense strand chemical modifications and antisense strand chemical modifications. These chemically modified siNAs were compared in the luciferase assay described herein at 1 nM and 10 nM concentration using an all RNA siNA control (siGL2) having 3'-terminal dithymidine (TT) and its corresponding inverted control (Inv siGL2). The background level of luciferase expression in the HeLa cells is designated by the "cells" column. Sense and antisense strands of chemically modified siNA constructs are shown by Sirna/RPI number (sense strand/antisense strand). Sequences corresponding to these Sirna/RPI numbers are shown in Table I. In addition, an inverted control (Sirna/RPI 30226/30229), having matched chemistry to Sirna/RPI (30222/30224) was compared to the siNA duplexes described above.

FIG. 13 shows the results of an RNAi activity screen of chemically modified siNA constructs. The screen compared various combinations of sense strand chemical modifications and antisense strand chemical modifications. These chemically modified siNAs were compared in the luciferase assay described herein at 1 nM and 10 nM concentration using an all RNA siNA control (siGL2) having 3'-terminal dithymidine (TT) and its corresponding inverted control (Inv siGL2). The background level of luciferase expression in the HeLa cells is designated by the "cells" column. Sense and antisense strands of chemically modified siNA constructs are shown by Sirna/RPI number (sense strand/antisense strand). Sequences corresponding to these Sirna/RPI numbers are shown in Table I. In addition, an inverted control (Sirna/RPI 30226/30229, having matched chemistry to Sirna/RPI 30222/30224) was compared to the siNA duplexes described above. As shown in the figure, the chemically modified Sirna/RPI 28251/30430, Sirna/RPI 28251/30224, and Sirna/RPI 30222/30224 constructs retain significant RNAi activity compared to the control siNA construct, and the chemically modified Sirna/RPI 28251/30430 construct demonstrates improved activity compared to the control siNA (siGL2) construct.

Figure 14:
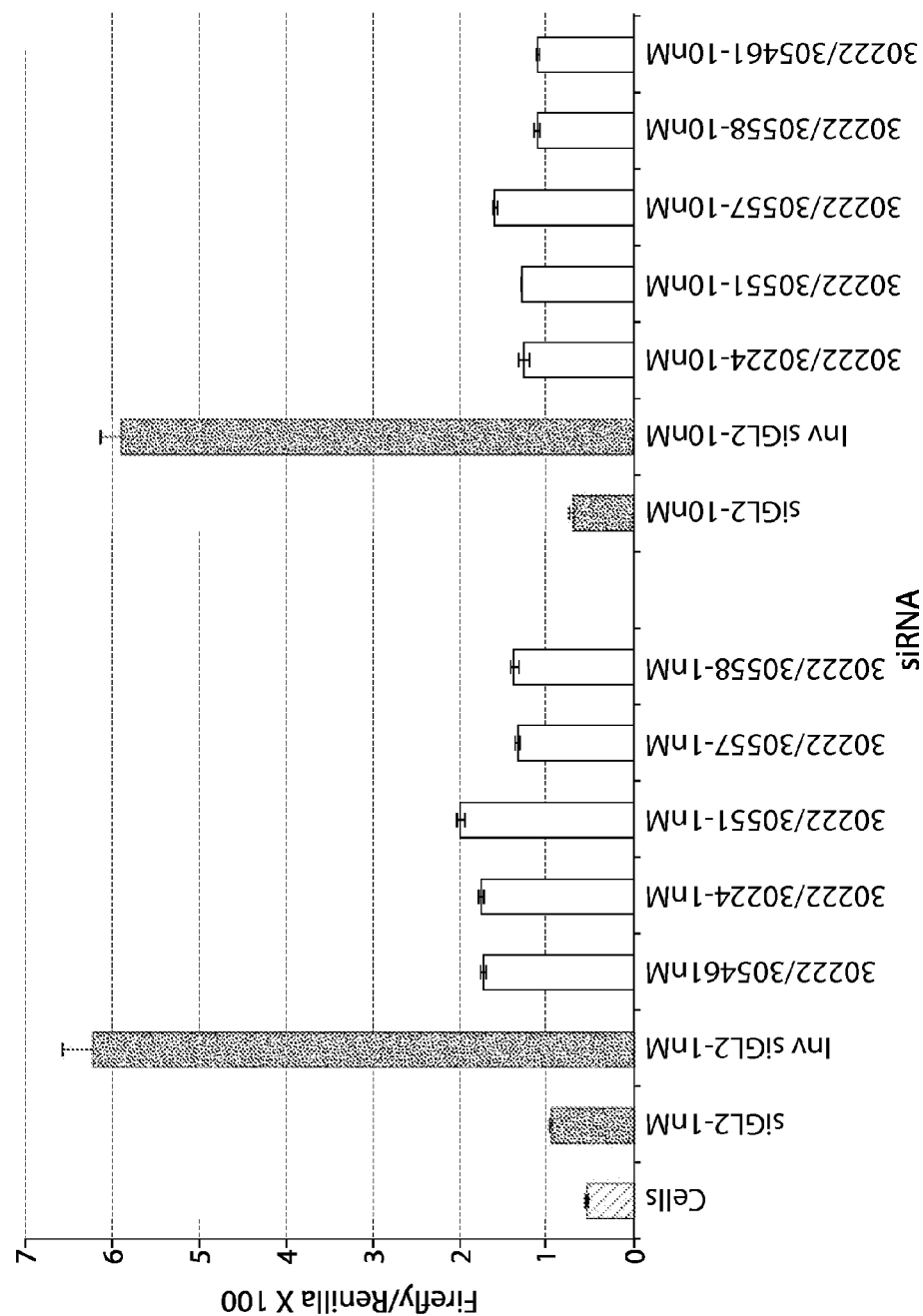
FIG. 14 shows the results of an RNAi activity screen of chemically modified siNA constructs including various 3'-terminal modified siNA constructs compared to an all RNA control siNA construct using a luciferase reporter system. These chemically modified siNAs were compared in the luciferase assay described herein at 1 nM and 10 nM concentration using an all RNA siNA control (siGL2) having 3'-terminal dithymidine (TT) and its corresponding inverted control (Inv siGL2). The background level of luciferase expression in the HeLa cells is designated by the "cells" column. Sense and antisense strands of chemically modified siNA constructs are shown by Sirna/RPI number (sense strand/antisense strand). Sequences corresponding to these Sirna/RPI numbers are shown in Table I.

FIG. 14 shows the results of an RNAi activity screen of chemically modified siNA constructs including various 3'-terminal modified siNA constructs compared to an all RNA control siNA construct using a luciferase reporter system. These chemically modified siNAs were compared in the luciferase assay described herein at 1 nM and 10 nM concentration using an all RNA siNA control (siGL2) having 3'-terminal dithymidine (TT) and its corresponding inverted control (Inv siGL2). The background level of luciferase expression in the HeLa cells is designated by the "cells" column. Sense and antisense strands of chemically modified siNA constructs are shown by Sirna/RPI number (sense strand/antisense strand). Sequences corresponding to these Sirna/RPI numbers are shown in Table I. As shown in the figure, the chemically modified Sirna/RPI 30222/30546, 30222/30224, 30222/30551, 30222/30557 and 30222/30558 constructs retain significant RNAi activity compared to the control siNA construct.

Figure 15:
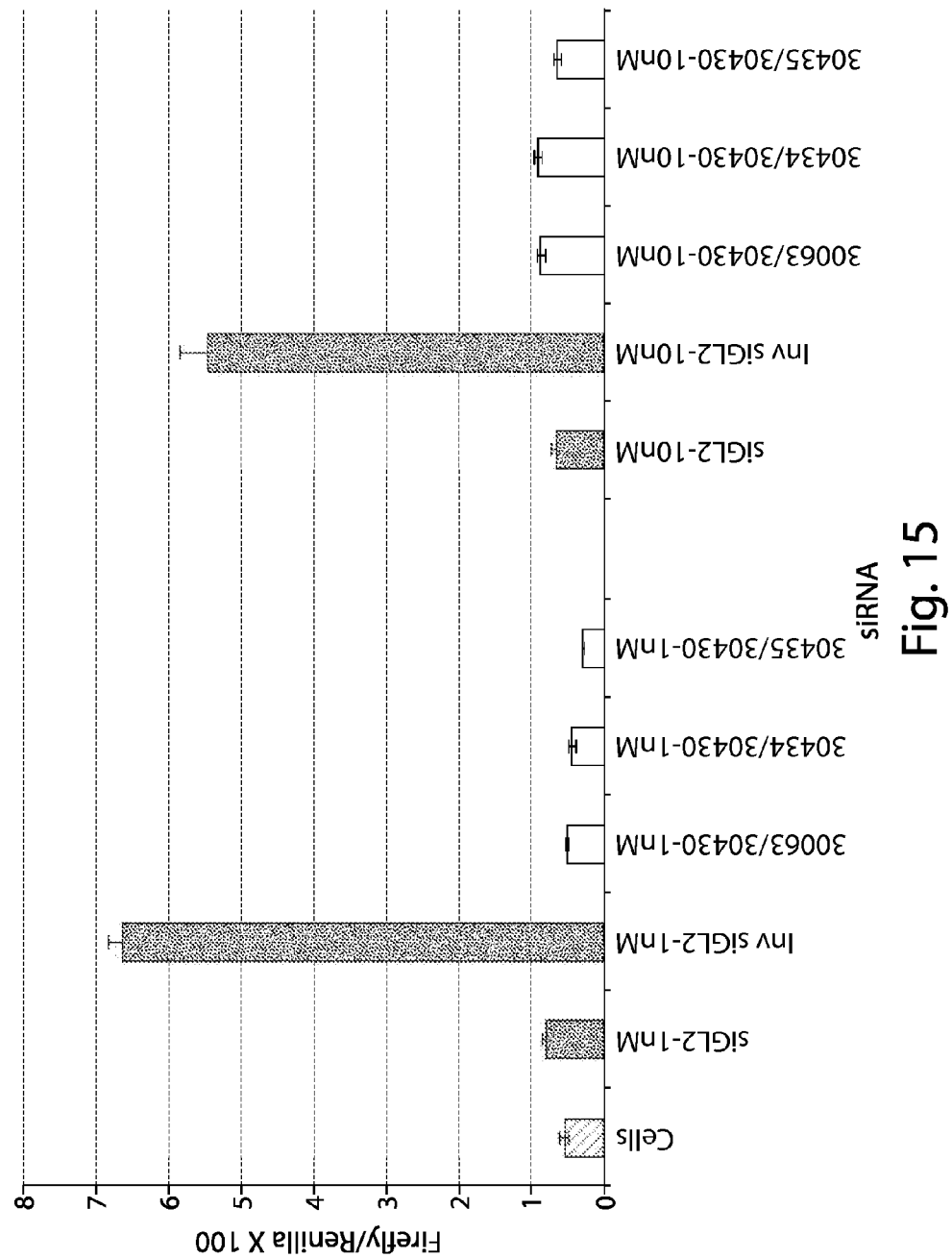
FIG. 15 shows the results of an RNAi activity screen of chemically modified siNA constructs. The screen compared various combinations of sense strand chemistries compared to a fixed antisense strand chemistry. These chemically modified siNAs were compared in the luciferase assay described herein at 1 nM and 10 nM concentration using an all RNA siNA control (siGL2) having 3'-terminal dithymidine (TT) and its corresponding inverted control (Inv siGL2). The background level of luciferase expression in the HeLa cells is designated by the "cells" column. Sense and antisense strands of chemically modified siNA constructs are shown by Sirna/RPI number (sense strand/antisense strand). Sequences corresponding to these Sirna/RPI numbers are shown in Table I.

FIG. 15 shows the results of an RNAi activity screen of chemically modified siNA constructs. The screen compared various combinations of sense strand chemistries compared to a fixed antisense strand chemistry. These chemically modified siNAs were compared in the luciferase assay described herein at 1 nM and 10 nM concentration using an all RNA siNA control (siGL2) having 3'-terminal dithymidine (TT) and its corresponding inverted control (Inv siGL2). The background level of luciferase expression in the HeLa cells is designated by the "cells" column. Sense and antisense strands of chemically modified siNA constructs are shown by Sirna/RPI number (sense strand/antisense strand). Sequences corresponding to these Sirna/RPI numbers are shown in Table I. As shown in the figure, the chemically modified Sirna/RPI 30063/30430, 30434/30430, and 30435/30430 constructs all demonstrate greater activity compared to the control siNA (siGL2) construct.

Example 6: RNAi Activity Titration

Figure 16:
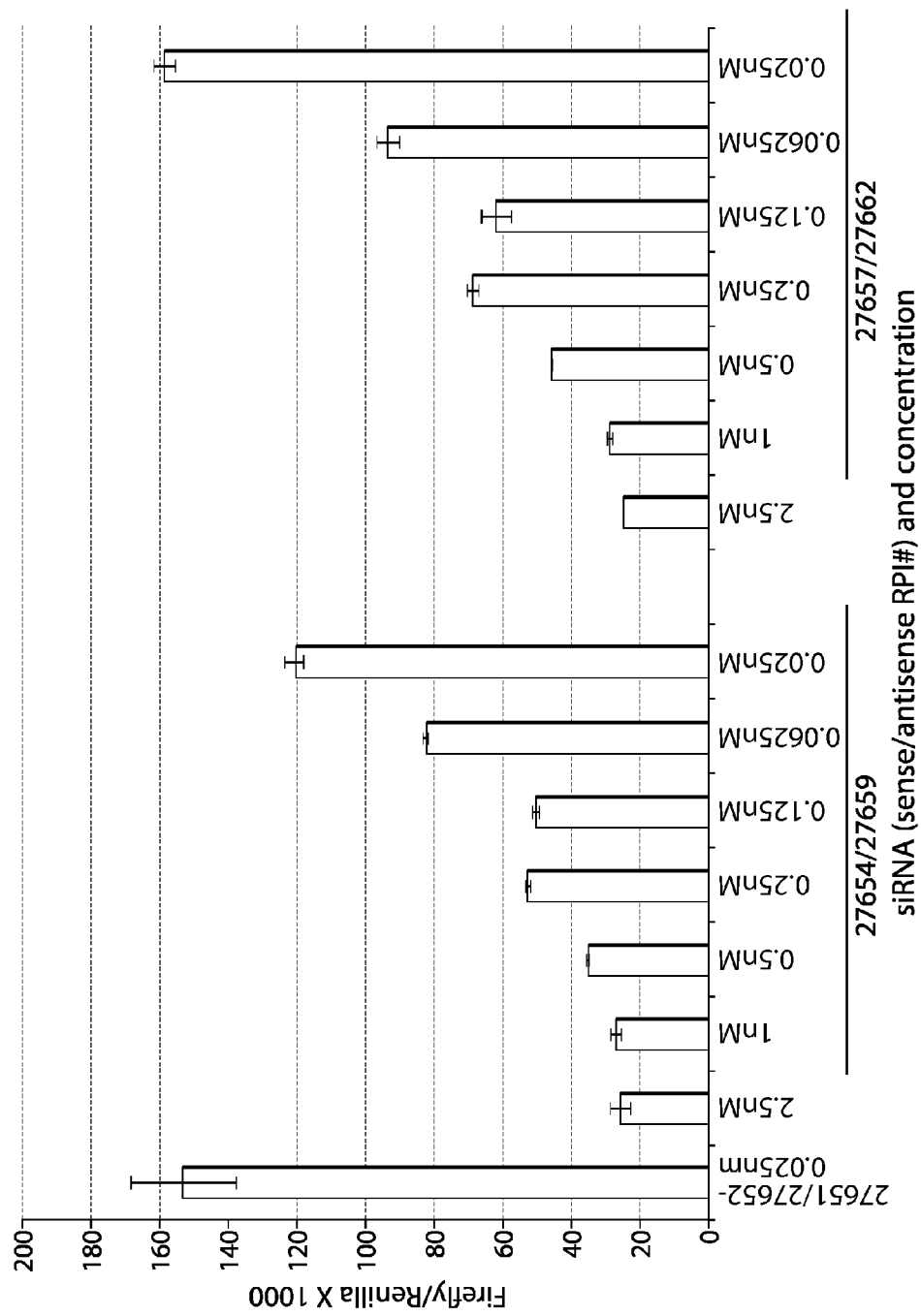
FIG. 16 shows the results of a siNA titration study using a luciferase reporter system, wherein the RNAi activity of a phosphorothioate modified siNA construct is compared to that of a siNA construct consisting of all ribonucleotides except for two terminal thymidine residues.
Figure 17:
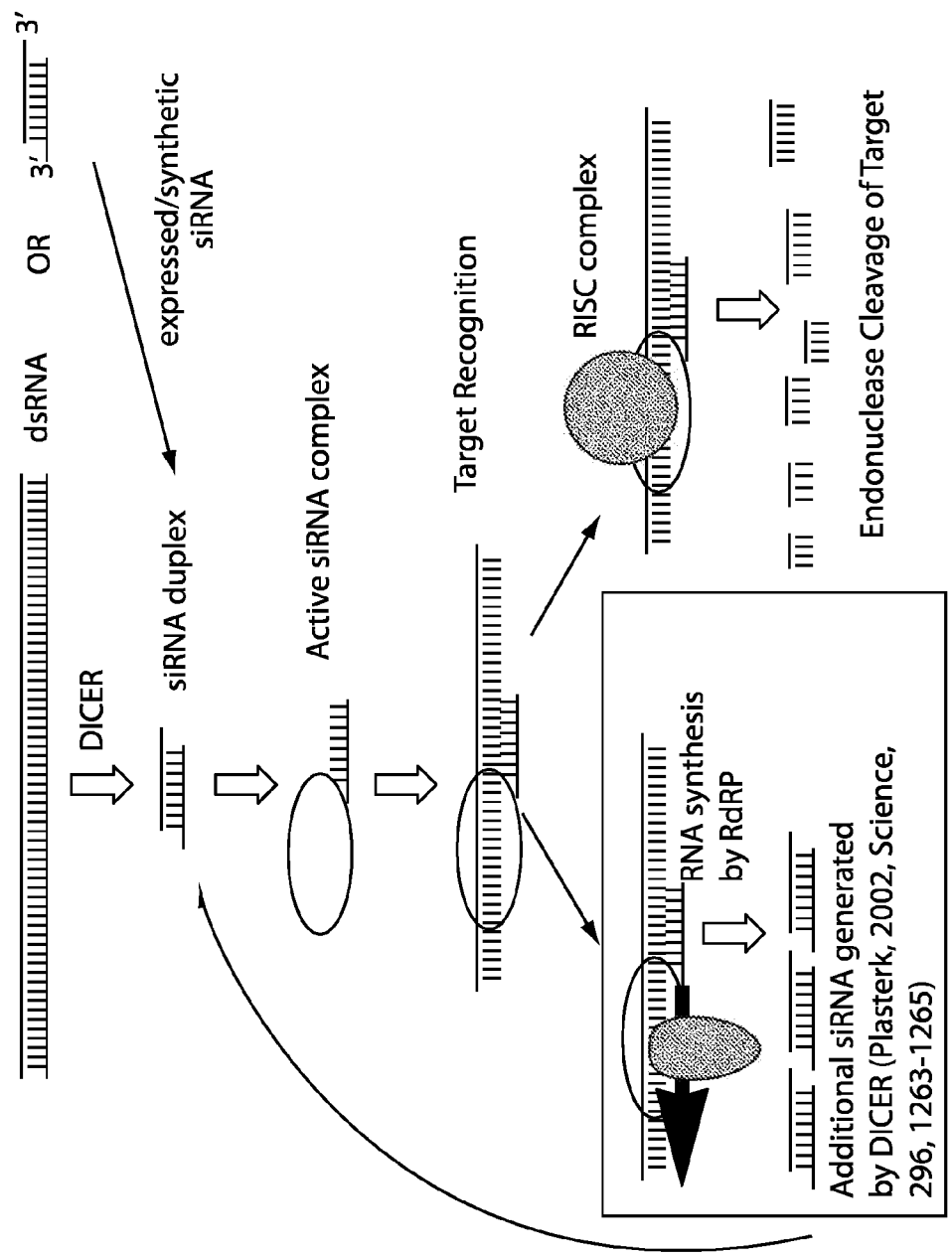
FIG. 17 shows a non-limiting proposed mechanistic representation of target RNA degradation involved in RNAi. Double-stranded RNA (dsRNA), which is generated by RNA-dependent RNA polymerase (RdRP) from foreign single-stranded RNA, for example viral, transposon, or other exogenous RNA, activates the DICER enzyme that in turn generates siNA duplexes. Alternately, synthetic or expressed siNA can be introduced directly into a cell by appropriate means. An active siNA complex forms which recognizes a target RNA, resulting in degradation of the target RNA by the RISC endonuclease complex or in the synthesis of additional RNA by RNA-dependent RNA polymerase (RdRP), which can activate DICER and result in additional siNA molecules, thereby amplifying the RNAi response.
Figure 20:
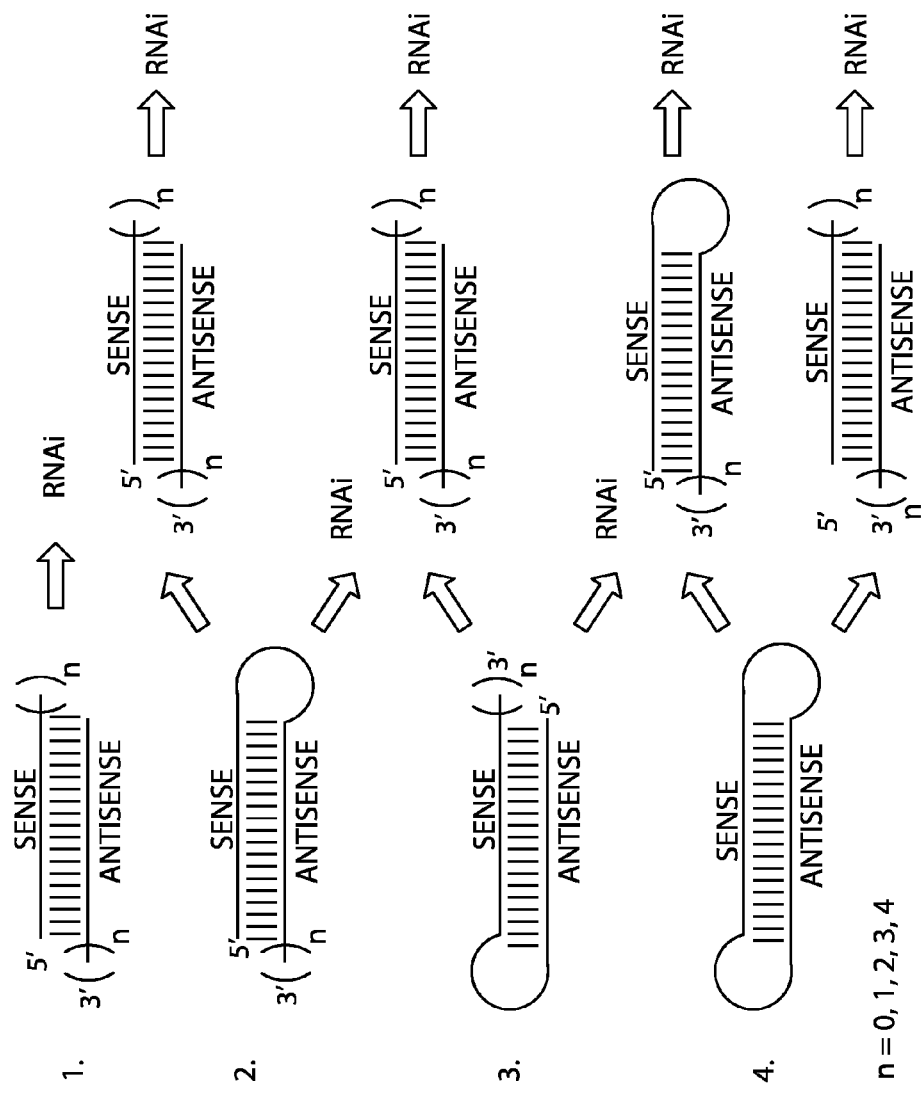
FIG. 20 shows non-limiting examples of different siNA constructs of the invention. The examples shown (constructs 1, 2, and 3) have 19 representative base pairs; however, different embodiments of the invention include any number of base pairs described herein. Bracketed regions represent nucleotide overhangs, for example comprising about 1, 2, 3, or 4 nucleotides in length when present, preferably about 2 nucleotides. Such overhangs can be present or absent (i.e., blunt ends). Such blunt ends can be present on one end or both ends of the siNA molecule, for example where all nucleotides present in a siNA duplex are base paired. Constructs 1 and 2 can be used independently for RNAi activity. Construct 2 can comprise a polynucleotide or non-nucleotide linker, which can optionally be designed as a biodegradable linker. In one embodiment, the loop structure shown in construct 2 can comprise a biodegradable linker that results in the formation of construct 1 in vivo and/or in vitro. In another example, construct 3 can be used to generate construct 2 under the same principle wherein a linker is used to generate the active siNA construct 2 in vivo and/or in vitro, which can optionally utilize another biodegradable linker to generate the active siNA construct 1 in vivo and/or in vitro. As such, the stability and/or activity of the siNA constructs can be modulated based on the design of the siNA construct for use in vivo or in vitro and/or in vitro.
Figure 21A:
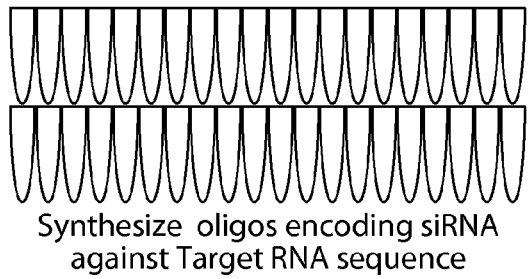
FIGS. 21A-21D are a diagrammatic representation of a method used to determine target sites for siNA mediated RNAi within a particular target nucleic acid sequence, such as messenger RNA.
Figure 21B:
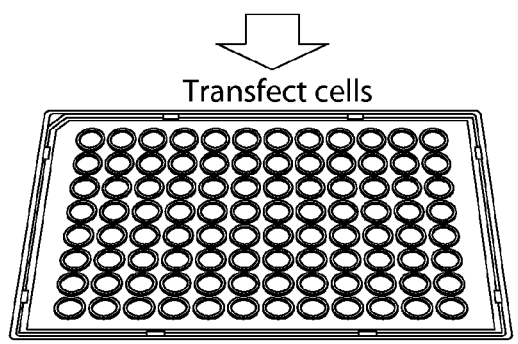
Figure 21C:
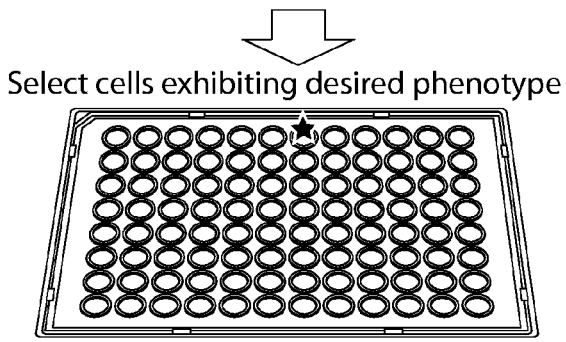
Figure 21D:
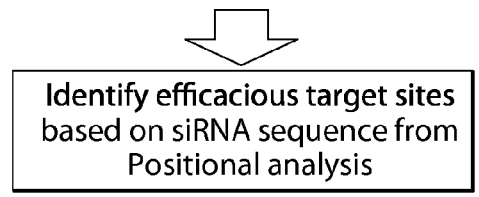

A titration assay was performed to determine the lower range of siNA concentration required for RNAi activity both in a control siNA construct consisting of all RNA nucleotides containing two thymidine nucleotide overhangs and a chemically modified siNA construct comprising five phosphorothioate internucleotide linkages in both the sense and antisense strands. The assay was performed as described above, however, the siNA constructs were diluted to final concentrations between 2.5 nM and 0.025 nM. Results are shown in FIG. 16. As shown in FIG. 16, the chemically modified siNA construct shows a very similar concentration dependent RNAi activity profile to the control siNA construct when compared to an inverted siNA sequence control.

Example 7: siNA Design siNA target sites were chosen by analyzing sequences of the target RNA and optionally prioritizing the target sites on the basis of folding (structure of any given sequence analyzed to determine siNA accessibility to the target), by using a library of siNA molecules as described in Example 4, or alternately by using an in vitro siNA system as described in Example 9 herein. siNA molecules were designed that could bind each target and are optionally individually analyzed by computer folding to assess whether the siNA molecule can interact with the target sequence. Varying the length of the siNA molecules can be chosen to optimize activity. Generally, a sufficient number of complementary nucleotide bases are chosen to bind to, or otherwise interact with, the target RNA, but the degree of complementarity can be modulated to accommodate siNA duplexes or varying length or base composition. By using such methodologies, siNA molecules can be designed to target sites within any known RNA sequence, for example those RNA sequences corresponding to the any gene transcript.

Figure 27:
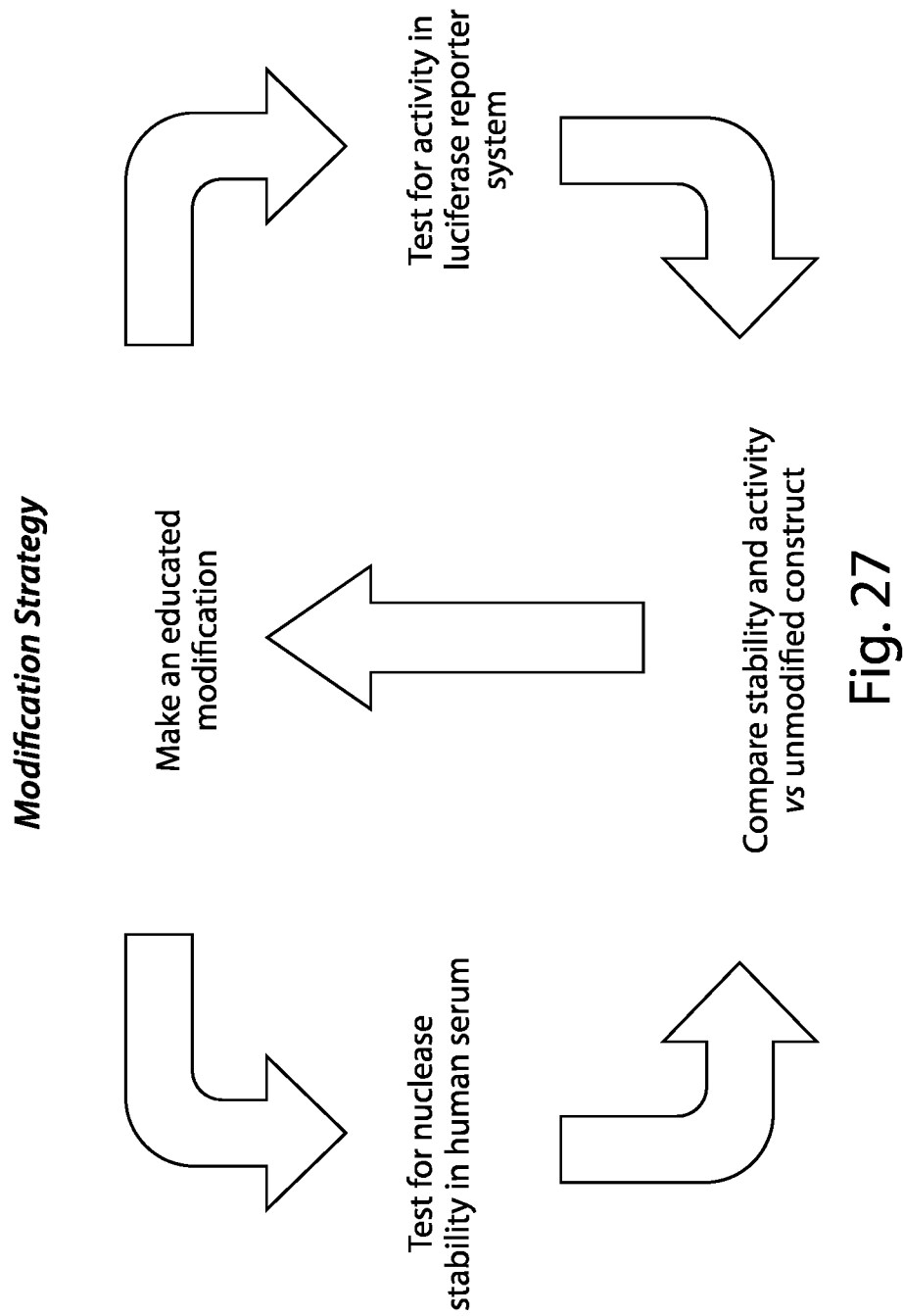
FIG. 27 shows a non-limiting example of a strategy used to identify chemically modified siNA constructs of the invention that are nuclease resistance while preserving the ability to mediate RNAi activity. Chemical modifications are introduced into the siNA construct based on educated design parameters (e.g. introducing 2'-modifications, base modifications, backbone modifications, terminal cap modifications etc). The modified construct in tested in an appropriate system (e.g human serum for nuclease resistance, shown, or an animal model for PK/delivery parameters). In parallel, the siNA construct is tested for RNAi activity, for example in a cell culture system such as a luciferase reporter assay). Lead siNA constructs are then identified which possess a particular characteristic while maintaining RNAi activity, and can be further modified and assayed once again. This same approach can be used to identify siNA-conjugate molecules with improved pharmacokinetic profiles, delivery, and RNAi activity.
Figure 28:
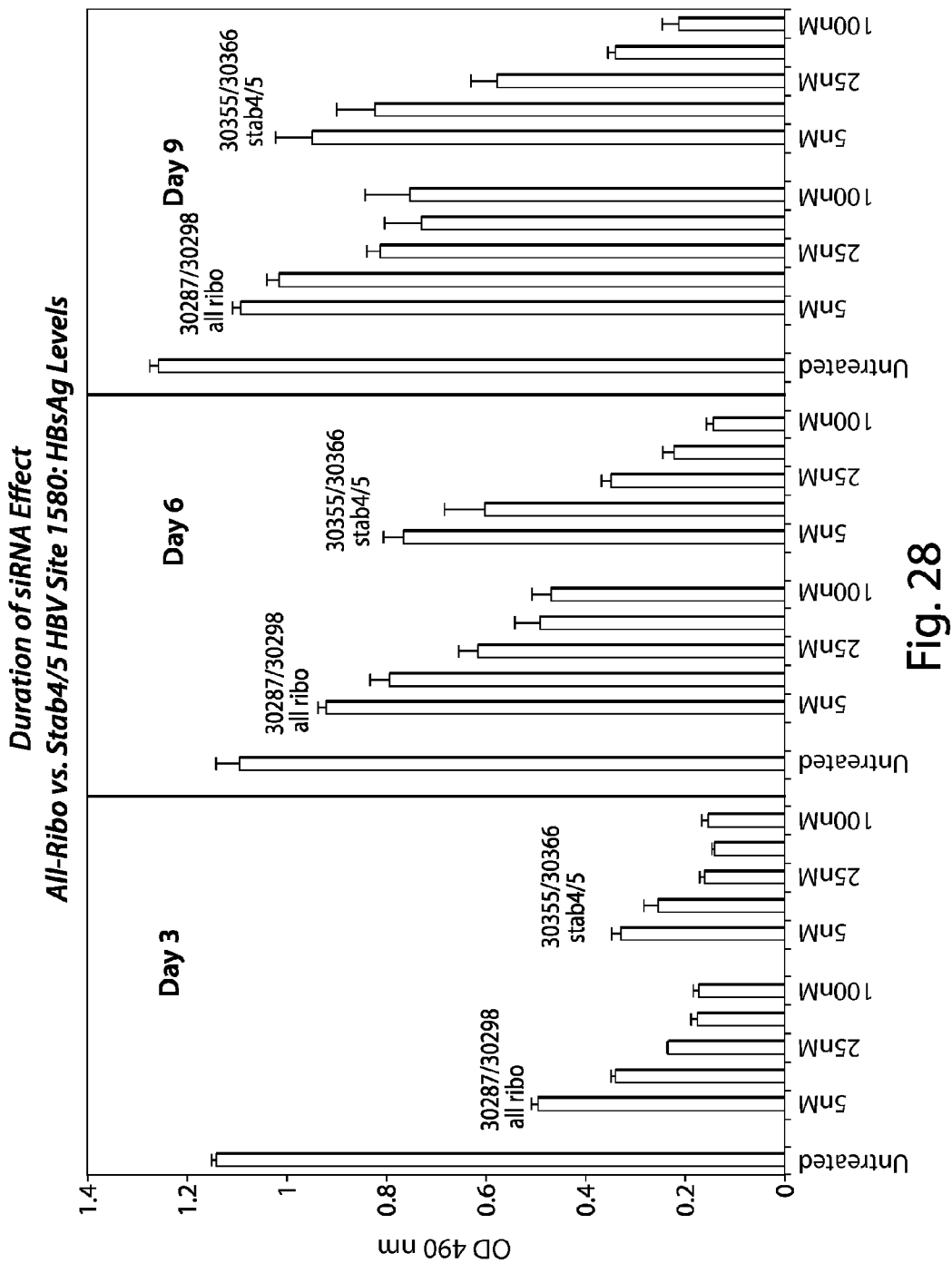
FIG. 28 shows representative data of a chemically modified siNA construct (Stab 4/5, Table IV) targeting HBV site 1580 RNA compared to an unstabilized siRNA construct in a dose response time course HBsAg assay. The constructs were compared at different concentrations (5 nM, 10 nM, 25 nM, 50 nM, and 100 nM) over the course of nine days. Activity based on HBsAg levels was determined at day 3, day 6, and day 9.
Figure 29:
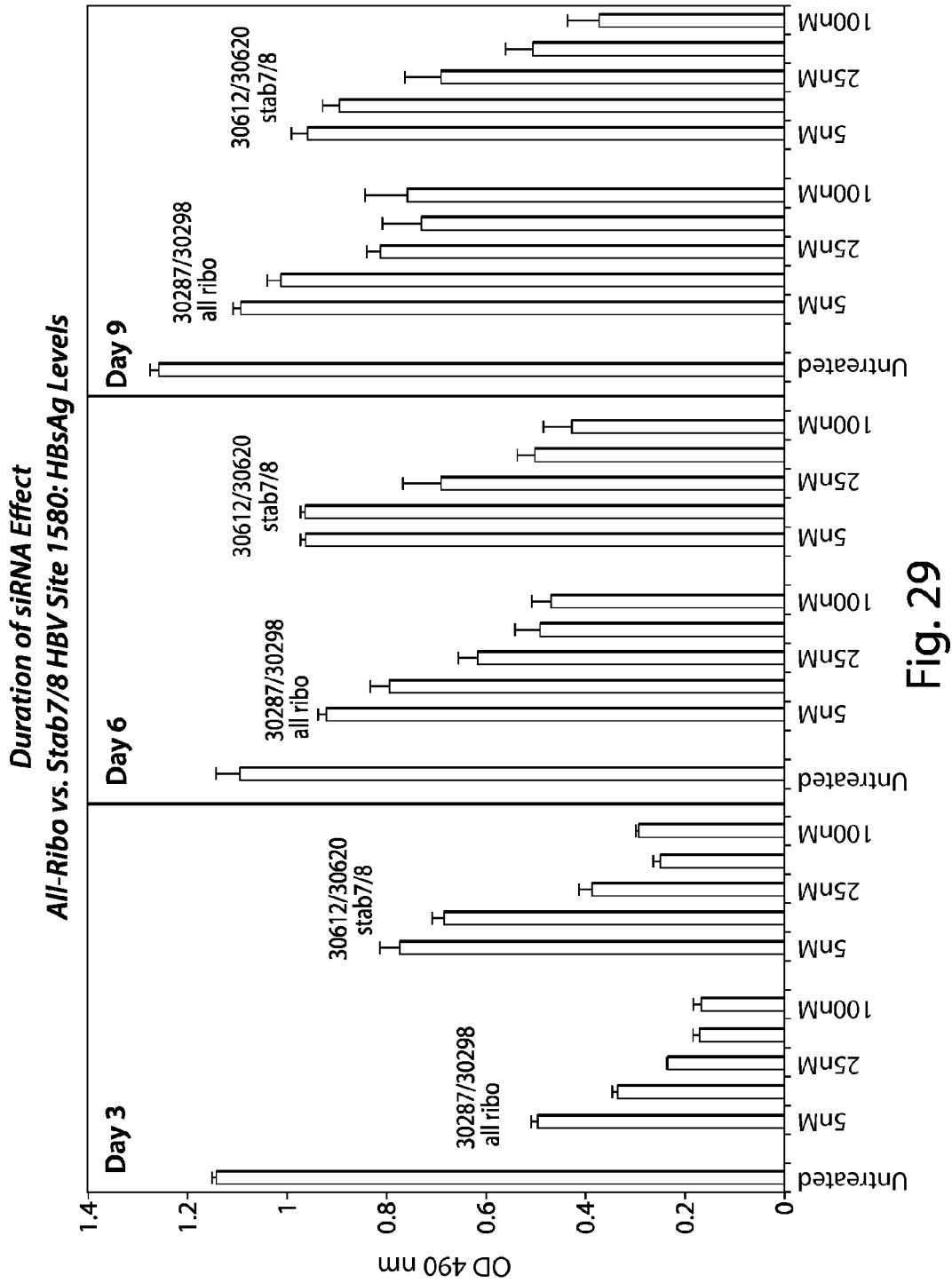
FIG. 29 shows representative data of a chemically modified siNA construct (Stab 7/8, Table IV) targeting HBV site 1580 RNA compared to an unstabilized siRNA construct in a dose response time course HBsAg assay. The constructs were compared at different concentrations (5 nM, 10 nM, 25 nM, 50 nM, and 100 nM) over the course of nine days. SiNA activity based on HBsAg levels was determined at day 3, day 6, and day 9.
Figure 30:
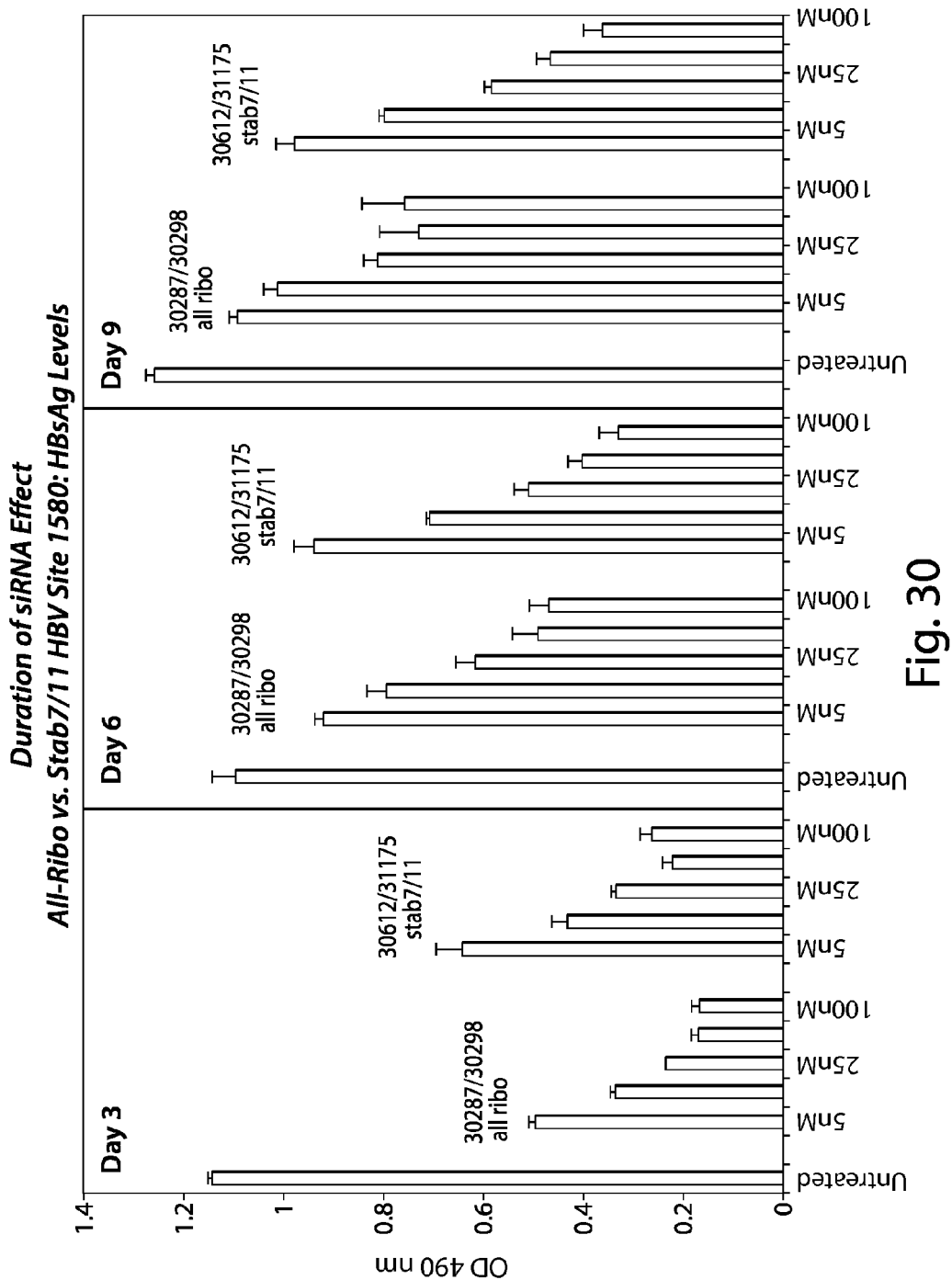
FIG. 30 shows representative data of a chemically modified siNA construct (Stab 7/11, Table IV) targeting HBV site 1580 RNA compared to an unstabilized siRNA construct in a dose response time course HBsAg assay. The constructs were compared at different concentrations (5 nM, 10 nM, 25 nM, 50 nM, and 100 nM) over the course of nine days. SiNA activity based on HBsAg levels was determined at day 3, day 6, and day 9.
Figure 31:
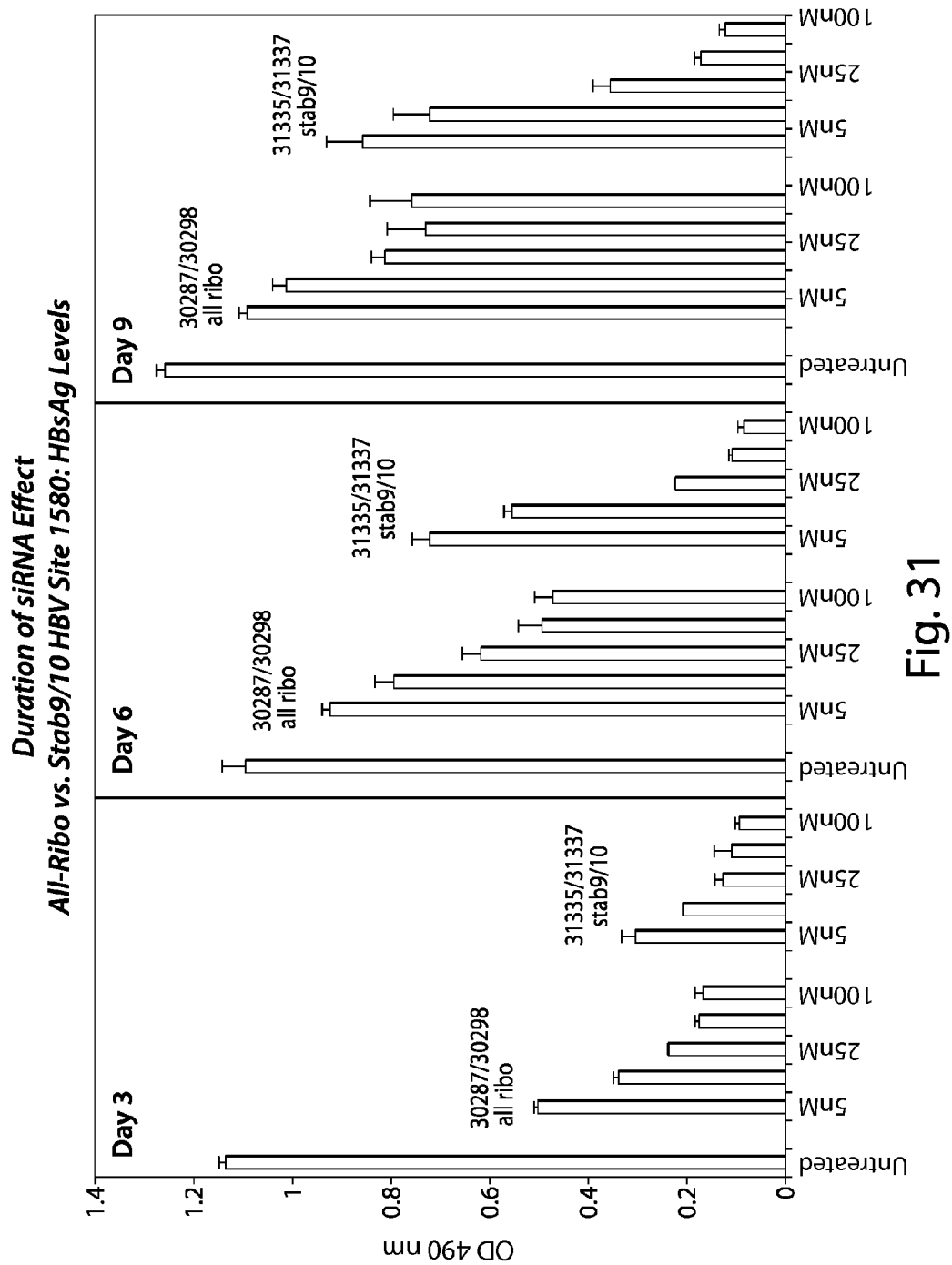
FIG. 31 shows representative data of a chemically modified siNA construct (Stab 9/10, Table IV) targeting HBV site 1580 RNA compared to an unstabilized siRNA construct in a dose response time course HBsAg assay. The constructs were compared at different concentrations (5 nM, 10 nM, 25 nM, 50 nM, and 100 nM) over the course of nine days. SiNA activity based on HBsAg levels was determined at day 3, day 6, and day 9.

Chemically modified siNA constructs are designed to provide nuclease stability for systemic administration in vivo and/or improved pharmacokinetic, localization, and delivery properties while preserving the ability to mediate RNAi activity. Chemical modifications as described herein are introduced synthetically using synthetic methods described herein and those generally known in the art. The synthetic siNA constructs are then assayed for nuclease stability in serum and/or cellular/tissue extracts (e.g. liver extracts). The synthetic siNA constructs are also tested in parallel for RNAi activity using an appropriate assay, such as a luciferase reporter assay as described herein or another suitable assay that can quantity RNAi activity. Synthetic siNA constructs that possess both nuclease stability and RNAi activity can be further modified and re-evaluated in stability and activity assays. The chemical modifications of the stabilized active siNA constructs can then be applied to any siNA sequence targeting any chosen RNA and used, for example, in target screening assays to pick lead siNA compounds for therapeutic development (see for example FIG. 27).

Example 8: Chemical Synthesis and Purification of siNA siNA molecules can be designed to interact with various sites in the RNA message, for example, target sequences within the RNA sequences described herein. The sequence of one strand of the siNA molecule(s) is complementary to the target site sequences described above. The siNA molecules can be chemically synthesized using methods described herein. Inactive siNA molecules that are used as control sequences can be synthesized by scrambling the sequence of the siNA molecules such that it is not complementary to the target sequence. Generally, siNA constructs can by synthesized using solid phase oligonucleotide synthesis methods as described herein (see for example Usman et al., U.S. Pat. Nos. 5,804,683; 5,831,071; 5,998,203; 6,117,657; 6,353,098; 6,362,323; 6,437,117; 6,469,158; Scaringe et al., U.S. Pat. Nos. 6,111,086; 6,008,400; 6,111,086 all incorporated by reference herein in their entirety).

In a non-limiting example, RNA oligonucleotides are synthesized in a stepwise fashion using the phosphoramidite chemistry as is known in the art. Standard phosphoramidite chemistry involves the use of nucleosides comprising any of 5'-O-dimethoxytrityl, 2'-O-tert-butyldimethylsilyl, 3'-O-2-Cyanoethyl N,N-diisopropylphos-phoroamidite groups, and exocyclic amine protecting groups (e.g. N6-benzoyl adenosine, N4 acetyl cytidine, and N2-isobutyryl guanosine). Alternately, 2'-O-Silyl Ethers can be used in conjunction with acid-labile 2'-O-orthoester protecting groups in the synthesis of RNA as described by Scaringe supra. Differing 2' chemistries can require different protecting groups, for example 2'-deoxy-2'-amino nucleosides can utilize N-phthaloyl protection as described by Usman et al., U.S. Pat. No. 5,631,360, incorporated by reference herein in its entirety).

During solid phase synthesis, each nucleotide is added sequentially (3'- to 5'-direction) to the solid support-bound oligonucleotide. The first nucleoside at the 3'-end of the chain is covalently attached to a solid support (e.g., controlled pore glass or polystyrene) using various linkers. The nucleotide precursor, a ribonucleoside phosphoramidite, and activator are combined resulting in the coupling of the second nucleoside phosphoramidite onto the 5'-end of the first nucleoside. The support is then washed and any unreacted 5'-hydroxyl groups are capped with a capping reagent such as acetic anhydride to yield inactive 5'-acetyl moieties. The trivalent phosphorus linkage is then oxidized to a more stable phosphate linkage. At the end of the nucleotide addition cycle, the 5'-O-protecting group is cleaved under suitable conditions (e.g., acidic conditions for trityl-based groups and Fluoride for silyl-based groups). The cycle is repeated for each subsequent nucleotide.

Modification of synthesis conditions can be used to optimize coupling efficiency, for example by using differing coupling times, differing reagent/phosphoramidite concentrations, differing contact times, differing solid supports and solid support linker chemistries depending on the particular chemical composition of the siNA to be synthesized. Deprotection and purification of the siNA can be performed as is generally described in Deprotection and purification of the siNA can be performed as is generally described in Usman et al., U.S. Pat. No. 5,831,071, U.S. Pat. No. 6,353,098, U.S. Pat. No. 6,437,117, and Bellon et al., U.S. Pat. No. 6,054,576, U.S. Pat. No. 6,162,909, U.S. Pat. No. 6,303,773, or Scaringe supra, incorporated by reference herein in their entireties. Additionally, deprotection conditions can be modified to provide the best possible yield and purity of siNA constructs. For example, applicant has observed that oligonucleotides comprising 2'-deoxy-2'-fluoro nucleotides can degrade under inappropriate deprotection conditions. Such oligonucleotides are deprotected using aqueous methylamine at about 35° C. for 30 minutes. If the 2'-deoxy-2'-fluoro containing oligonucleotide also comprises ribonucleotides, after deprotection with aqueous methylamine at about 35° C. for 30 minutes, TEA-HF is added and the reaction maintained at about 65° C. for an additional 15 minutes.

Example 9: RNAi In Vitro Assay to Assess siNA Activity

An in vitro assay that recapitulates RNAi in a cell free system is used to evaluate siNA constructs specific to target RNA. The assay comprises the system described by Tuschl et al., 1999, *Genes and Development*, 13, 3191-3197 and Zamore et al., 2000, *Cell*, 101, 25-33 adapted for use with target RNA. A *Drosophila* extract derived from syncytial blastoderm is used to reconstitute RNAi activity in vitro. Target RNA is generated via in vitro transcription from an appropriate plasmid using T7 RNA polymerase or via chemical synthesis as described herein. Sense and antisense siNA strands (for example 20 uM each) are annealed by incubation in buffer (such as 100 mM potassium acetate, 30 mM HEPES-KOH, pH 7.4, 2 mM magnesium acetate) for 1 minute at 90° C. followed by 1 hour at 37° C., then diluted in lysis buffer (for example 100 mM potassium acetate, 30 mM HEPES-KOH at pH 7.4, 2 mM magnesium acetate). Annealing can be monitored by gel electrophoresis on an agarose gel in TBE buffer and stained with ethidium bromide. The *Drosophila* lysate is prepared using zero to two-hour-old embryos from Oregon R flies collected on yeasted molasses agar that are dechorionated and lysed. The lysate is centrifuged and the supernatant isolated. The assay comprises a reaction mixture containing 50% lysate [vol/vol], RNA (10-50 pM final concentration), and 10% [vol/vol] lysis buffer containing siNA (10 nM final concentration). The reaction mixture also contains 10 mM creatine phosphate, 10 ug·ml creatine phosphokinase, 100 um GTP, 100 uM UTP, 100 uM CTP, 500 uM ATP, 5 mM DTT, 0.1 U/uL RNasin (Promega), and 100 uM of each amino acid. The final concentration of potassium acetate is adjusted to 100 mM. The reactions are pre-assembled on ice and pre-incubated at 25° C. for 10 minutes before adding RNA, then incubated at 25° C. for an additional 60 minutes. Reactions are quenched with 4 volumes of 1.25x Passive Lysis Buffer (Promega). Target RNA cleavage is assayed by RT-PCR analysis or other methods known in the art and are compared to control reactions in which siNA is omitted from the reaction.

Alternately, internally-labeled target RNA for the assay is prepared by in vitro transcription in the presence of [alpha-$^{32}$p] CTP, passed over a G 50 Sephadex column by spin chromatography and used as target RNA without further purification. Optionally, target RNA is 5'-$^{32}$P-end labeled using T4 polynucleotide kinase enzyme. Assays are performed as described above and target RNA and the specific RNA cleavage products generated by RNAi are visualized on an autoradiograph of a gel. The percentage of cleavage is determined by Phosphor Imager® quantitation of bands representing intact control RNA or RNA from control reactions without siNA and the cleavage products generated by the assay.

In one embodiment, this assay is used to determine target sites the RNA target for siNA mediated RNAi cleavage, wherein a plurality of siNA constructs are screened for RNAi mediated cleavage of the RNA target, for example, by analyzing the assay reaction by electrophoresis of labeled target RNA, or by northern blotting, as well as by other methodology well known in the art.

Example 10: Nucleic Acid Inhibition of Target RNA In Vivo siNA molecules targeted to the target RNA are designed and synthesized as described above. These nucleic acid molecules can be tested for cleavage activity in vivo, for example, using the following procedure.

Two formats are used to test the efficacy of siNAs targeting a particular gene transcript. First, the reagents are tested on target expressing cells (e.g., HeLa), to determine the extent of RNA and protein inhibition. siNA reagents are selected against the RNA target. RNA inhibition is measured after delivery of these reagents by a suitable transfection agent to cells. Relative amounts of target RNA are measured versus actin using real-time PCR monitoring of amplification (eg., ABI 7700 Taqman®). A comparison is made to a mixture of oligonucleotide sequences made to unrelated targets or to a randomized siNA control with the same overall length and chemistry, but with randomly substituted nucleotides at each position. Primary and secondary lead reagents are chosen for the target and optimization performed. After an optimal transfection agent concentration is chosen, a RNA time-course of inhibition is performed with the lead siNA molecule. In addition, a cell-plating format can be used to determine RNA inhibition.

Delivery of siNA to Cells

Cells (e.g., HeLa) are seeded, for example, at $1\times10^5$ cells per well of a six-well dish in EGM-2 (BioWhittaker) the day before transfection. siNA (final concentration, for example 20 nM) and cationic lipid (e.g., final concentration 2 µg/ml) are complexed in EGM basal media (Biowhittaker) at 37° C. for 30 mins in polystyrene tubes. Following vortexing, the complexed siNA is added to each well and incubated for the times indicated. For initial optimization experiments, cells are seeded, for example, at $1\times10^3$ in 96 well plates and siNA complex added as described. Efficiency of delivery of siNA to cells is determined using a fluorescent siNA complexed with lipid. Cells in 6-well dishes are incubated with siNA for 24 hours, rinsed with PBS and fixed in 2% paraformaldehyde for 15 minutes at room temperature. Uptake of siNA is visualized using a fluorescent microscope.

Taqman and Lightcycler Quantification of mRNA

Total RNA is prepared from cells following siNA delivery, for example, using Qiagen RNA purification kits for 6-well or Rneasy extraction kits for 96-well assays. For Taqman analysis, dual-labeled probes are synthesized with the reporter dye, FAM or JOE, covalently linked at the 5'-end and the quencher dye TAMRA conjugated to the 3'-end. One-step RT-PCR amplifications are performed on, for example, an ABI PRISM 7700 Sequence Detector using 50 µl reactions consisting of 10 µl total RNA, 100 nM forward primer, 900 nM reverse primer, 100 nM probe, 1x TaqMan PCR reaction buffer (PE-Applied Biosystems), 5.5 mM MgCl$_2$, 300 µM each dATP, dCTP, dGTP, and dTTP, 10 U RNase Inhibitor (Promega), 1.25 U AmpliTaq Gold (PE-Applied Biosystems) and 10 U M-MLV Reverse Transcriptase (Promega). The thermal cycling conditions can consist of 30 min at 48° C., 10 min at 95° C., followed by 40 cycles of 15 sec at 95° C. and 1 min at 60° C. Quantitation of mRNA levels is determined relative to standards generated from serially diluted total cellular RNA (300, 100, 33, 11 ng/rxn) and normalizing to β-actin or GAPDH mRNA in parallel TaqMan reactions. For each gene of interest an upper and lower primer and a fluorescently labeled probe are designed. Real time incorporation of SYBR Green I dye into a specific PCR product can be measured in glass capillary tubes using a lightcyler. A standard curve is generated for each primer pair using control cRNA. Values are represented as relative expression to GAPDH in each sample.

Western Blotting

Nuclear extracts can be prepared using a standard micro preparation technique (see for example Andrews and Faller, 1991, *Nucleic Acids Research*, 19, 2499). Protein extracts from supernatants are prepared, for example using TCA precipitation. An equal volume of 20% TCA is added to the cell supernatant, incubated on ice for 1 hour and pelleted by centrifugation for 5 minutes. Pellets are washed in acetone, dried and resuspended in water. Cellular protein extracts are run on a 10% Bis-Tris NuPage (nuclear extracts) or 4-12% Tris-Glycine (supernatant extracts) polyacrylamide gel and transferred onto nitro-cellulose membranes. Non-specific binding can be blocked by incubation, for example, with 5% non-fat milk for 1 hour followed by primary antibody for 16 hour at 4° C. Following washes, the secondary antibody is applied, for example (1:10,000 dilution) for 1 hour at room temperature and the signal detected with SuperSignal reagent (Pierce).

Example 11: Animal Models

Various animal models can be used to screen siNA constructs in vivo as are known in the art, for example those animal models that are used to evaluate other nucleic acid technologies such as enzymatic nucleic acid molecules (ribozymes) and/or antisense. Such animal models are used to test the efficacy of siNA molecules described herein. In a non-limiting example, siNA molecules that are designed as anti-angiogenic agents can be screened using animal models. There are several animal models available in which to test the anti-angiogenesis effect of nucleic acids of the present invention, such as siNA, directed against genes associated with angiogenesis and/or metastais, such as VEGFR (e.g., VEGFR1, VEGFR2, and VEGFR3) genes. Typically a corneal model has been used to study angiogenesis in rat and rabbit, since recruitment of vessels can easily be followed in this normally avascular tissue (Pandey et al., 1995 *Science* 268: 567-569). In these models, a small Teflon or Hydron disk pretreated with an angiogenesis factor (e.g. bFGF or VEGF) is inserted into a pocket surgically created in the cornea. Angiogenesis is monitored 3 to 5 days later. siNA molecules directed against VEGFR mRNAs would be delivered in the disk as well, or dropwise to the eye over the time course of the experiment. In another eye model, hypoxia has been shown to cause both increased expression of VEGF and neovascularization in the retina (Pierce et al., 1995 *Proc. Natl. Acad. Sci. USA*. 92: 905-909; Shweiki et al., 1992 *J. Clin. Invest.* 91: 2235-2243).

Several animal models exist for screening of anti-angiogenic agents. These include corneal vessel formation following corneal injury (Burger et al., 1985 *Cornea* 4: 35-41; Lepri, et al., 1994 *J. Ocular Pharmacol.* 10: 273-280; Ormerod et al., 1990 *Am. J. Pathol.* 137: 1243-1252) or intracorneal growth factor implant (Grant et al., 1993 *Diabetologia* 36: 282-291; Pandey et al. 1995 supra; Zieche et al., 1992 *Lab. Invest.* 67: 711-715), vessel growth into Matrigel matrix containing growth factors (Passaniti et al., 1992 supra), female reproductive organ neovascularization following hormonal manipulation (Shweiki et al., 1993 *Clin. Invest.* 91: 2235-2243), several models involving inhibition of tumor growth in highly vascularized solid tumors (O'Reilly et al., 1994 *Cell* 79: 315-328; Senger et al., 1993 *Cancer and Metas. Rev.* 12: 303-324; Takahasi et al., 1994 *Cancer Res.* 54: 4233-4237; Kim et al., 1993 supra), and transient hypoxia-induced neovascularization in the mouse retina (Pierce et al., 1995 *Proc. Natl. Acad. Sci. USA*. 92: 905-909). gene The cornea model, described in Pandey et al. supra, is the most common and well characterized anti-angiogenic agent efficacy screening model. This model involves an avascular tissue into which vessels are recruited by a stimulating agent (growth factor, thermal or alkalai burn, endotoxin). The corneal model utilizes the intrastromal corneal implantation of a Teflon pellet soaked in a VEGF-Hydron solution to recruit blood vessels toward the pellet, which can be quantitated using standard microscopic and image analysis techniques. To evaluate their anti-angiogenic efficacy, siNA molecules are applied topically to the eye or bound within Hydron on the Teflon pellet itself. This avascular cornea as well as the Matrigel model (described below) provide for low background assays. While the corneal model has been performed extensively in the rabbit, studies in the rat have also been conducted.

The mouse model (Passaniti et al., supra) is a non-tissue model which utilizes Matrigel, an extract of basement membrane (Kleinman et al., 1986) or Millipore® filter disk, which can be impregnated with growth factors and anti-angiogenic agents in a liquid form prior to injection. Upon subcutaneous administration at body temperature, the Matrigel or Millipore® filter disk forms a solid implant. VEGF embedded in the Matrigel or Millipore® filter disk is used to recruit vessels within the matrix of the Matrigel or Millipore® filter disk which can be processed histologically for endothelial cell specific vWF (factor VIII antigen) immunohistochemistry, Trichrome-Masson stain, or hemoglobin content. Like the cornea, the Matrigel or Millipore® filter disk are avascular; however, it is not tissue. In the Matrigel or Millipore® filter disk model, siNA molecules are administered within the matrix of the Matrigel or Millipore® filter disk to test their anti-angiogenic efficacy. Thus, delivery issues in this model, as with delivery of siNA molecules by Hydron-coated Teflon pellets in the rat cornea model, may be less problematic due to the homogeneous presence of the siNA within the respective matrix.

The Lewis lung carcinoma and B-16 murine melanoma models are well accepted models of primary and metastatic cancer and are used for initial screening of anti-cancer agents. These murine models are not dependent upon the use of immunodeficient mice, are relatively inexpensive, and minimize housing concerns. Both the Lewis lung and B-16 melanoma models involve subcutaneous implantation of approximately $10^6$ tumor cells from metastatically aggressive tumor cell lines (Lewis lung lines 3LL or D122, LLc-LN7; B-16-BL6 melanoma) in C57BL/6J mice. Alternatively, the Lewis lung model can be produced by the surgical implantation of tumor spheres (approximately 0.8 mm in diameter). Metastasis also may be modeled by injecting the tumor cells directly intraveneously. In the Lewis lung model, microscopic metastases can be observed approximately 14 days following implantation with quantifiable macroscopic metastatic tumors developing within 21-25 days. The B-16 melanoma exhibits a similar time course with tumor neovascularization beginning 4 days following implantation. Since both primary and metastatic tumors exist in these models after 21-25 days in the same animal, multiple measurements can be taken as indices of efficacy. Primary tumor volume and growth latency as well as the number of micro- and macroscopic metastatic lung foci or number of animals exhibiting metastases can be quantitated. The percent increase in lifespan can also be measured. Thus, these models would provide suitable primary efficacy assays for screening systemically administered siNA molecules and siNA formulations.

In the Lewis lung and B-16 melanoma models, systemic pharmacotherapy with a wide variety of agents usually begins 1-7 days following tumor implantation/inoculation with either continuous or multiple administration regimens. Concurrent pharmacokinetic studies can be performed to determine whether sufficient tissue levels of siNA can be achieved for pharmacodynamic effect to be expected. Furthermore, primary tumors and secondary lung metastases can be removed and subjected to a variety of in vitro studies (i.e. target RNA reduction).

Ohno-Matsui et al., 2002, *Am. J. Pathology*, 160, 711-719 describe a model of severe proliferative retinopathy and retinal detachment in mice under inducible expression of vascular endothelial growth factor. In this model, expression of a VEGF transgene results in elevated levels of ocular VEGF that is associated with severe proliferative retinopathy and retinal detachment. Furthermore, Mori et al., 2001, *J. Cellular Physiology*, 188, 253-263, describe a model of laser induced choroidal neovascularization that can be used in conjunction with intravitreous or subretianl injection of siNA molecules of the invention to evaluate the efficacy of siNA treatment of severe proliferative retinopathy and retinal detachment.

In utilizing these models to assess siNA activity, VEGFR1, VEGFR2, and/or VEGFR3 protein levels can be measured clinically or experimentally by FACS analysis. VEGFR1, VEGFR2, and/or VEGFR3 encoded mRNA levels can be assessed by Northern analysis, RNase-protection, primer extension analysis and/or quantitative RT-PCR. siNA molecules that block VEGFR1, VEGFR2, and/or VEGFR3 protein encoding mRNAs and therefore result in decreased levels of VEGFR1, VEGFR2, and/or VEGFR3 activity by more than 20% in vitro can be identified using the techniques described herein.

Example 12: siNA-Mediated Inhibition of Angiogenesis In Vivo

The purpose of this study was to assess the anti-angiogenic activity of siNA targeted against VEGFR1, using the rat cornea model of VEGF induced angiogenesis discussed in Example 11 above). The siNA molecules shown in FIG. 23 have matched inverted controls which are inactive since they are not able to interact with the RNA target. The siNA molecules and VEGF were co-delivered using the filter disk method. Nitrocellulose filter disks (Millipore®) of 0.057 diameter were immersed in appropriate solutions and were surgically implanted in rat cornea as described by Pandey et al., supra.

The stimulus for angiogenesis in this study was the treatment of the filter disk with 30 µM VEGF which is implanted within the cornea's stroma. This dose yields reproducible neovascularization stemming from the pericorneal vascular plexus growing toward the disk in a dose-response study 5 days following implant. Filter disks treated only with the vehicle for VEGF show no angiogenic response. The siNA were co-adminstered with VEGF on a disk in three different siNA concentrations. One concern with the simultaneous administration is that the siNA would not be able to inhibit angiogenesis since VEGF receptors can be stimulated. However, Applicant has observed that in low VEGF doses, the neovascular response reverts to normal suggesting that the VEGF stimulus is essential for maintaining the angiogenic response. Blocking the production of VEGF receptors using simultaneous administration of anti-VEGF-R mRNA siNA could attenuate the normal neovascularization induced by the filter disk treated with VEGF.

Materials and Methods:
Test Compounds and Controls
  R&D Systems VEGF, carrier free at 75 µM in 82 mM Tris-Cl, pH 6.9
  siNA, 1.67 µG/µL, SITE 2340 (SIRNA/RPI 29695/29699) sense/antisense
  siNA, 1.67 µG/µL, INVERTED CONTROL FOR SITE 2340 (SIRNA/RPI 29983/29984) sense/antisense
  siNA 1.67 µg/µL, Site 2340 (Sirna/RPI 30196/30416) sense/antisense Animals
Harlan Sprague-Dawley Rats, Approximately 225-250 g
  45 males, 5 animals per group.
Husbandry
  Animals are housed in groups of two. Feed, water, temperature and humidity are determined according to Pharmacology Testing Facility performance standards (SOP's) which are in accordance with the 1996 Guide for the Care and Use of Laboratory Animals (NRC). Animals are acclimated to the facility for at least 7 days prior to experimentation. During this time, animals are observed for overall health and sentinels are bled for baseline serology.
Experimental Groups
  Each solution (VEGF and siNAs) was prepared as a 1× solution for final concentrations shown in the experimental groups described in Table III.
siNA Annealing Conditions
  siNA sense and antisense strands are annealed for 1 minute in H₂O at 1.67 mg/mL/strand followed by a 1 hour incubation at 37° C. producing 3.34 mg/mL of duplexed siNA. For the 20 µg/eye treatment, 6 µLs of the 3.34 mg/mL duplex is injected into the eye (see below). The 3.34 mg/mL duplex siNA can then be serially diluted for dose response assays.
Preparation of VEGF Filter Disk
  For corneal implantation, 0.57 mm diameter nitrocellulose disks, prepared from 0.45 µm pore diameter nitrocellulose filter membranes (Millipore Corporation), were soaked for 30 mM in 1 µL of 75 µM VEGF in 82 mM Tris HCl (pH 6.9) in covered petri dishes on ice. Filter disks soaked only with the vehicle for VEGF (83 mM Tris-Cl pH 6.9) elicit no angiogenic response.
Corneal Surgery
  The rat corneal model used in this study was a modified from Koch et al. Supra and Pandey et al., supra. Briefly, corneas were irrigated with 0.5% povidone iodine solution followed by normal saline and two drops of 2% lidocaine. Under a dissecting microscope (Leica MZ-6), a stromal pocket was created and a presoaked filter disk (see above) was inserted into the pocket such that its edge was 1 mm from the corneal limbus.
Intraconjunctival Injection of Test Solutions Immediately after disk insertion, the tip of a 40-50 μm OD injector (constructed in our laboratory) was inserted within the conjunctival tissue 1 mm away from the edge of the corneal limbus that was directly adjacent to the VEGF-soaked filter disk. Six hundred nanoliters of test solution (siNA, inverted control or sterile water vehicle) were dispensed at a rate of 1.2 μL/min using a syringe pump (Kd Scientific). The injector was then removed, serially rinsed in 70% ethanol and sterile water and immersed in sterile water between each injection. Once the test solution was injected, closure of the eyelid was maintained using microaneurism clips until the animal began to recover gross motor activity. Following treatment, animals were warmed on a heating pad at 37° C.

Quantitation of Angiogenic Response

Five days after disk implantation, animals were euthanized following administration of 0.4 mg/kg atropine and corneas were digitally imaged. The neovascular surface area (NSA, expressed in pixels) was measured postmortem from blood-filled corneal vessels using computerized morphometry (Image Pro Plus, Media Cybernetics, v2.0). The individual mean NSA was determined in triplicate from three regions of identical size in the area of maximal neovascularization between the filter disk and the limbus. The number of pixels corresponding to the blood-filled corneal vessels in these regions was summated to produce an index of NSA. A group mean NSA was then calculated. Data from each treatment group were normalized to VEGF/siNA vehicle-treated control NSA and finally expressed as percent inhibition of VEGF-induced angiogenesis.

Statistics

After determining the normality of treatment group means, group mean percent inhibition of VEGF-induced angiogenesis was subjected to a one-way analysis of variance. This was followed by two post-hoc tests for significance including Dunnett's (comparison to VEGF control) and Tukey-Kramer (all other group mean comparisons) at alpha=0.05. Statistical analyses were performed using JMP v.3.1.6 (SAS Institute).

Figure 23:
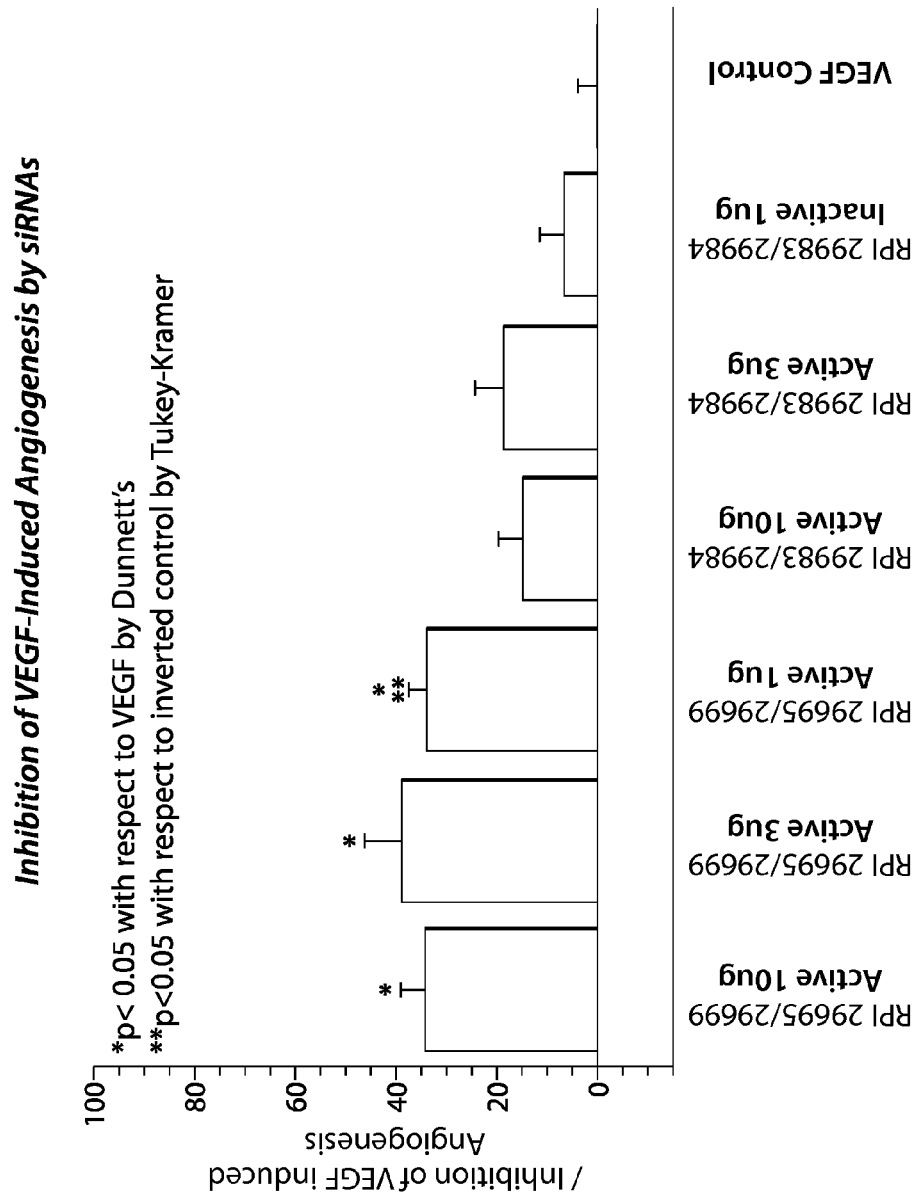
FIG. 23 shows a non-limiting example of siNA mediated inhibition of VEGF-induced angiogenesis using the rat corneal model of angiogenesis. siNA targeting site 2340 of VEGFR1 RNA (shown as Sirna/RPI No. 29695/29699) were compared to inverted controls (shown as Sirna/RPI No. 29983/29984) at three different concentrations and compared to a VEGF control in which no siNA was administered.

Results of the study are graphically represented in FIGS. 23 and 76. As shown in FIG. 23, VEGFr1 site 4229 active siNA (Sirna/RPI 29695/29699) at three concentrations were effective at inhibiting angiogenesis compared to the inverted siNA control (Sirna/RPI 29983/29984) and the VEGF control. A chemically modified version of the VEGFr1 site 4229 active siNA comprising a sense strand having 2'-deoxy-2'-fluoro pyrimidines and ribo purines with 5' and 3' terminal inverted deoxyabasic residues and an antisense strand having 2'-deoxy-2'-fluoro pyrimidines and ribo purines with a terminal 3'-phosphorothioate internucleotide linkage (Sirna/RPI 30196/30416), showed similar inhibition. Furthermore, VEGFr1 site 349 active siNA having "Stab 9/10" chemistry (Sirna #31270/31273) was tested for inhibition of VEGF-induced angiogenesis at three different concentrations (2.0 ug, 1.0 ug, and 0.1 μg dose response) as compared to a matched chemistry inverted control siNA construct (Sirna #31276/31279) at each concentration and a VEGF control in which no siNA was administered. As shown in FIG. 76, the active siNA construct having "Stab 9/10" chemistry (Sirna #31270/31273) is highly effective in inhibiting VEGF-induced angiogenesis in the rat corneal model compared to the matched chemistry inverted control siNA at concentrations from 0.1 μg to 2.0 ug. These results demonstrate that siNA molecules having different chemically modified composi-tions, such as the modifications described herein, are capable of significantly inhibiting angiogenesis in vivo.

Example 13: Inhibition of HBV Using siNA Molecules of the Invention

Transfection of HepG2 Cells with psHBV-1 and siNA The human hepatocellular carcinoma cell line Hep G2 was grown in Dulbecco's modified Eagle media supplemented with 10% fetal calf serum, 2 mM glutamine, 0.1 mM nonessential amino acids, 1 mM sodium pyruvate, 25 mM Hepes, 100 units penicillin, and 100 μg/ml streptomycin. To generate a replication competent cDNA, prior to transfection the HBV genomic sequences are excised from the bacterial plasmid sequence contained in the psHBV-1 vector. Other methods known in the art can be used to generate a replication competent cDNA. This was done with an EcoRI and Hind III restriction digest. Following completion of the digest, a ligation was performed under dilute conditions (20 μg/ml) to favor intermolecular ligation. The total ligation mixture was then concentrated using Qiagen spin columns.

siNA Activity Screen and Dose Response Assay

Figure 24:
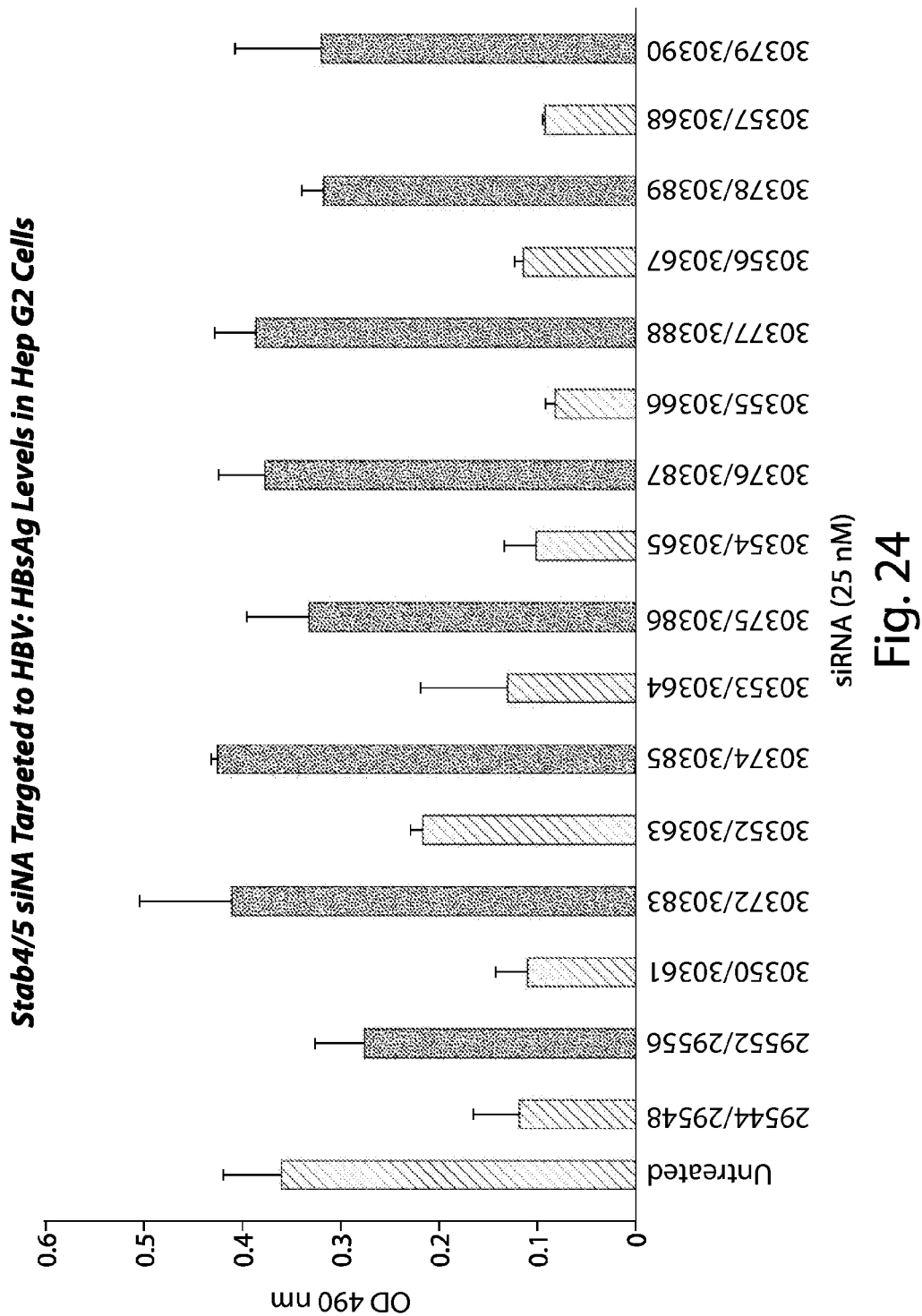
FIG. 24 is a non-limiting example of a HBsAg screen of stabilized siNA constructs ("stab 4/5", see Table IV) targeting HBV pregenomic RNA in HepG2 cells at 25 nM compared to untreated and matched chemistry inverted sequence controls. The siNA sense and antisense strands are shown by Sirna/RPI number (sense/antisense).

Transfection of the human hepatocellular carcinoma cell line, Hep G2, with replication-competent HBV DNA results in the expression of HBV proteins and the production of virions. To test the efficacy of siNAs targeted against HBV RNA, several siNA duplexes targeting different sites within HBV pregenomic RNA were co-transfected with HBV genomic DNA once at 25 nM with lipid at 12.5 ug/ml into Hep G2 cells, and the subsequent levels of secreted HBV surface antigen (HBsAg) were analyzed by ELISA (see FIG. 24). Inverted sequence duplexes were used as negative controls. Subsequently, dose response studies were performed in which the siNA duplexes were co-transfected with HBV genomic DNA at 0.5, 5, 10 and 25 nM with lipid at 12.5 ug/ml into Hep G2 cells, and the subsequent levels of secreted HBV surface antigen (HBsAg) were analyzed by ELISA (see FIG. 25).

Analysis of HBsAg Levels Following siNA Treatment

Figure 25:
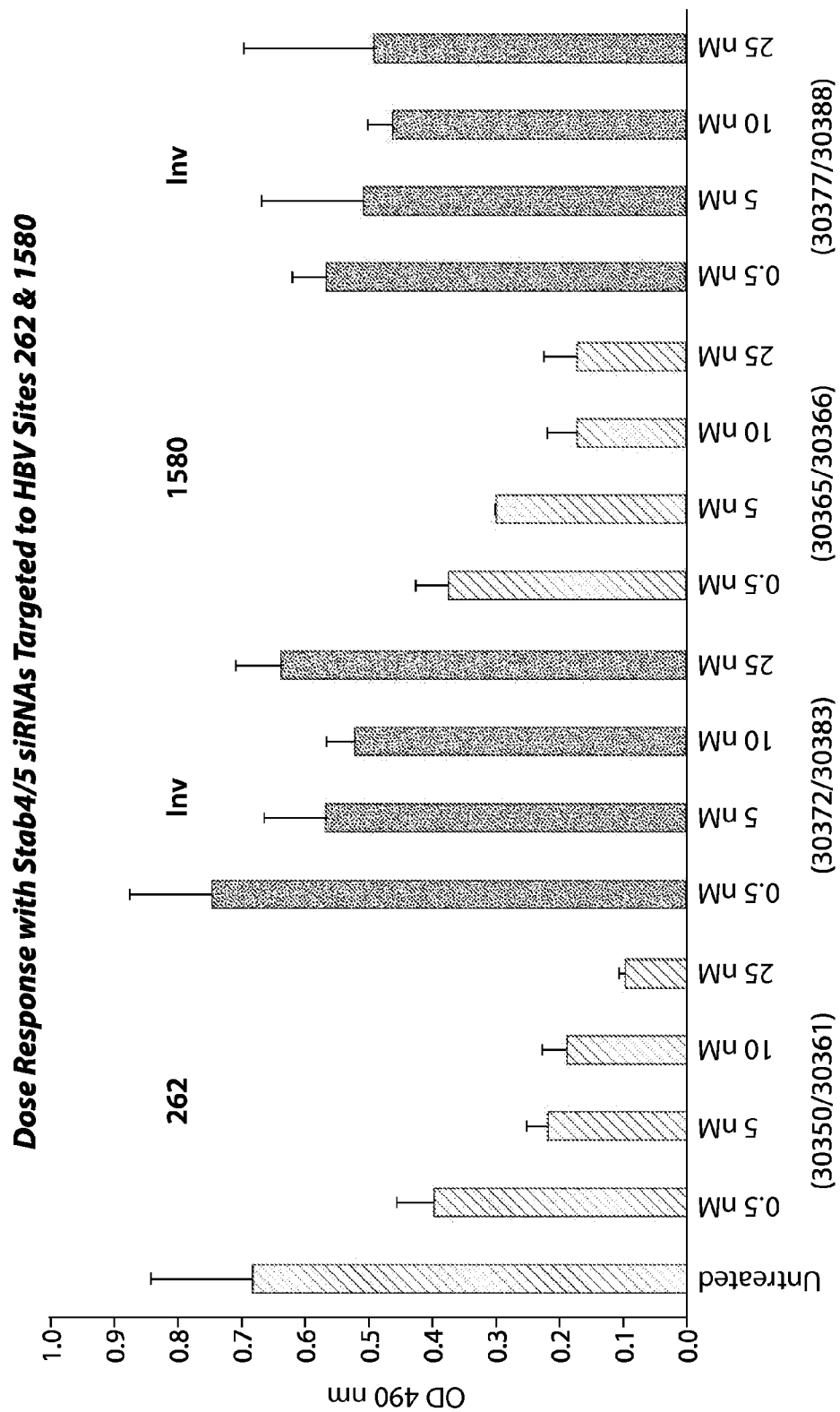
FIG. 25 is a non-limiting example of a dose response HBsAg screen of stabilized siNA constructs ("stab 4/5", see Table IV) targeting sites 262 and 1580 of the HBV pregenomic RNA in HepG2 cells at 0.5, 5, 10 and 25 nM compared to untreated and matched chemistry inverted sequence controls. The siNA sense and antisense strands are shown by Sirna/RPI number (sense/antisense).

To determine siNA activity, HbsAg levels were measured following transfection with siNA Immulon 4 (Dynax) microtiter wells were coated overnight at 4° C. with anti-HBsAg Mab (Biostride B88-95-31ad,ay) at 1 μg/ml in Carbonate Buffer (Na2CO3 15 mM, NaHCO3 35 mM, pH 9.5). The wells were then washed 4× with PBST (PBS, 0.05% Tween® 20) and blocked for 1 hr at 37° C. with PBST, 1% BSA. Following washing as above, the wells were dried at 37° C. for 30 mM. Biotinylated goat ant-HBsAg (Accurate YVS1807) was diluted 1:1000 in PBST and incubated in the wells for 1 hr. at 37° C. The wells were washed 4× with PB ST. Streptavidin/Alkaline Phosphatase Conjugate (Pierce 21324) was diluted to 250 ng/ml in PBST, and incubated in the wells for 1 hr. at 37° C. After washing as above, p-nitrophenyl phosphate substrate (Pierce 37620) was added to the wells, which were then incubated for 1 hour at 37° C. The optical density at 405 nm was then determined Results of the HBV screen study are summarized in FIG. 24, whereas the results of a dose response assay using lead siNA constructs targeting sites 262 and 1580 of the HBV pregenomic RNA are shown in FIG. 25. As shown in FIG. 25, the siNA constructs targeting sites 262 and 1580 of HBV RNA provides significant dose response inhibition of viral replication/activity when compared to inverted siNA controls.

Comparison of Different Chemically Stabilized siNA Motifs Targeting HBV RNA Site 1580

Figure 26:
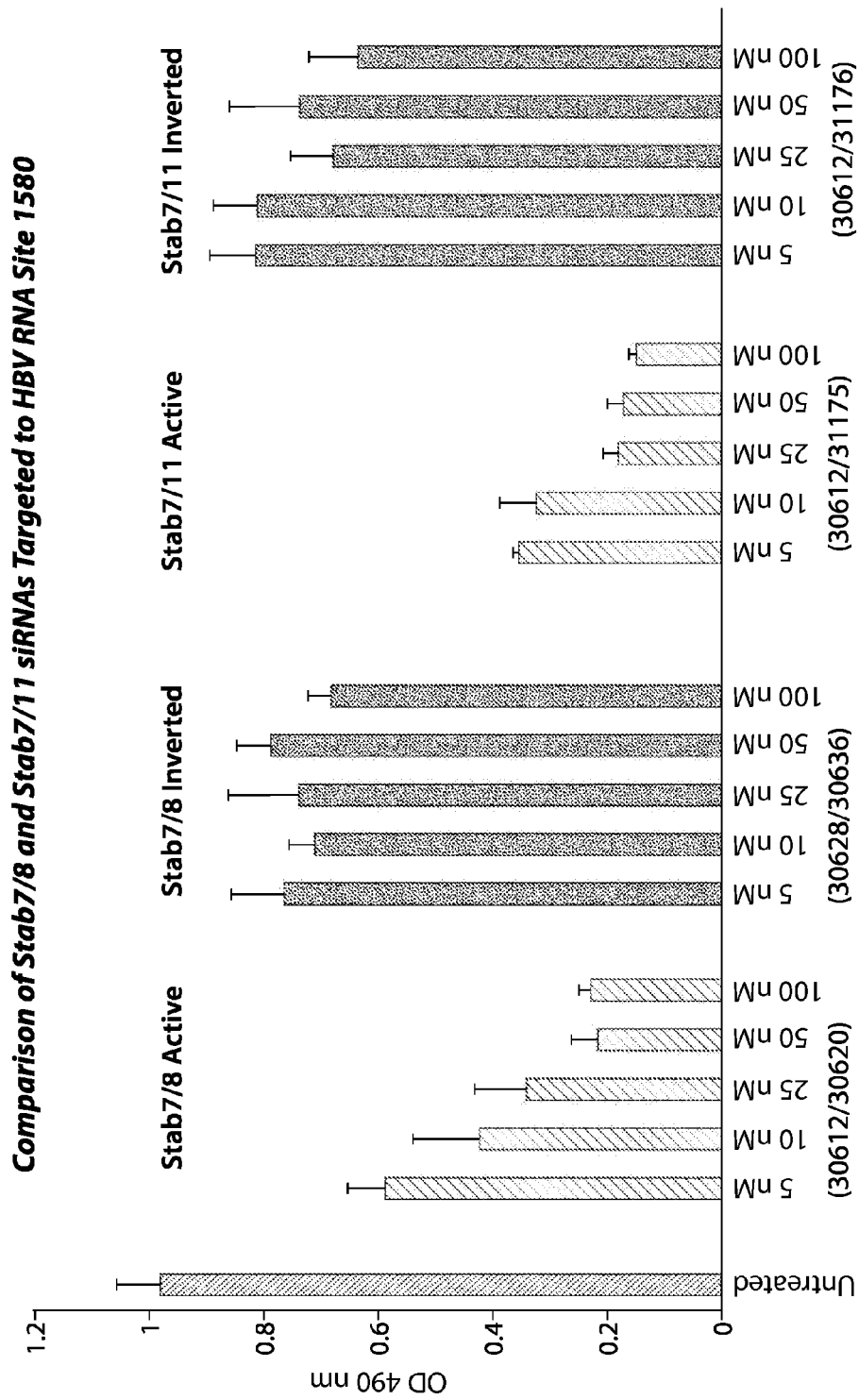
FIG. 26 shows a dose response comparison of two different stabilization chemistries ("stab 7/8" and "stab 7/11", see Table IV) targeting site 1580 of the HBV pregenomic RNA in HepG2 cells at 5, 10, 25, 50 and 100 nM compared to untreated and matched chemistry inverted sequence controls. The siNA sense and antisense strands are shown by Sirna/RPI number (sense/antisense).
Figure 87:
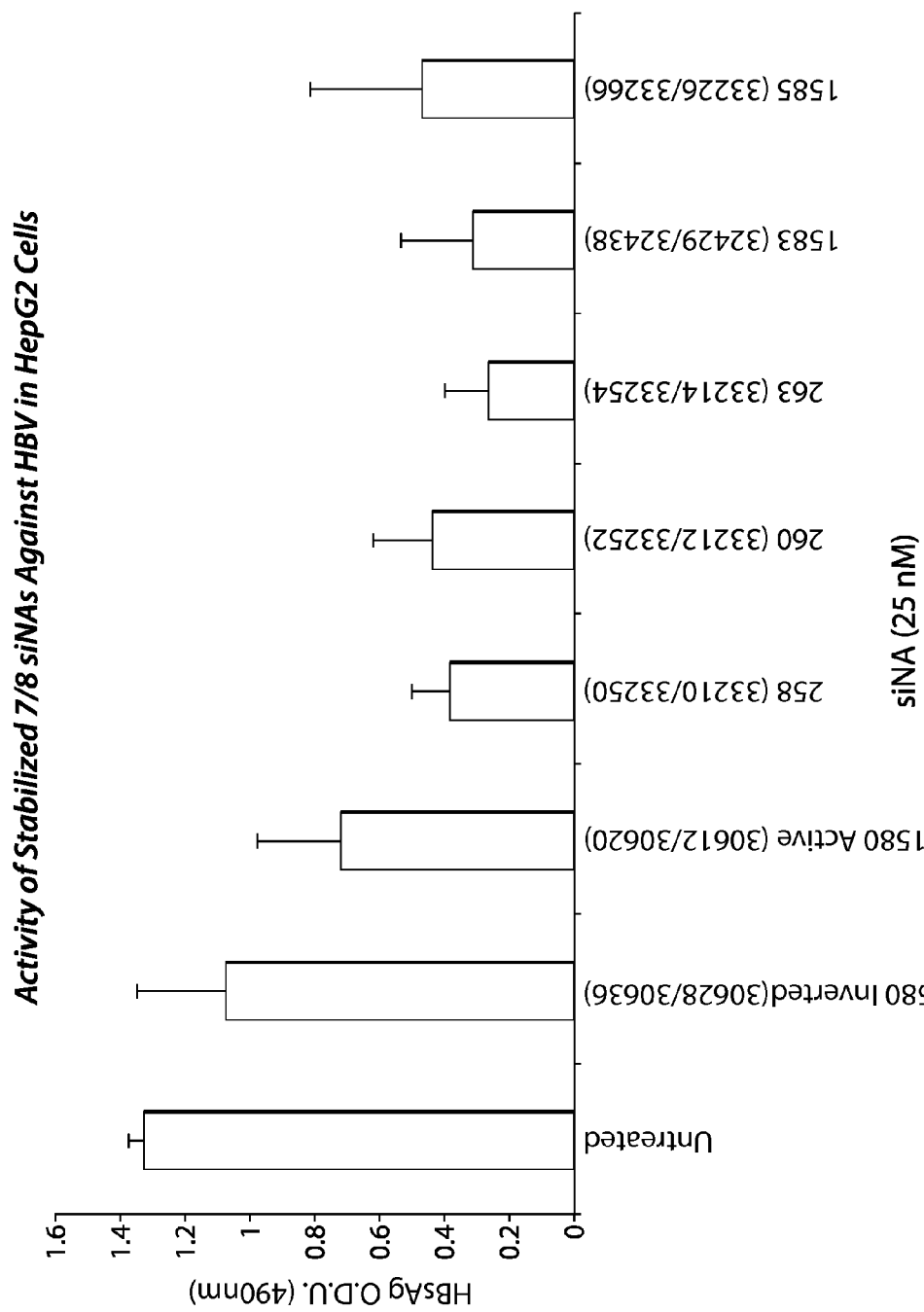
FIG. 87 shows a non-limiting example of an assay screen of Stab 7/8 siNA constructs targeting various sites of HBV RNA in HEpG2 cells compared to untreated cells and an inverted control. As shown in the figure, several Stab 7/8 constructs were identified with potent anti-HBV activity as shown by reduction in HBV S antigen levels.

Two different siNA stabilization chemistries were compared in a dose response HBsAg assay using inverted matched chemistry controls. The "Stab7/8" (Table IV) constructs comprise a sense strand having 2'-deoxy-2'-fluoro pyrimidine nucleotides and 2'-deoxy purine nucleotides with 5' and 3' terminal inverted deoxyabasic residues and an antisense strand having 2'-deoxy-2'-fluoro pyrimidine nucleotides and 2'-O-methyl purine nucleotides with a terminal 3' phosphorothioate linkage. The "Stab7/11 (Table IV) constructs comprise a sense strand having 2'-deoxy-2'-fluoro pyrimidine nucleotides and 2'-deoxy purine nucleotides with 5' and 3' terminal inverted deoxyabasic residues and an antisense strand having 2'-deoxy-2'-fluoro pyrimidine nucleotides and 2'-deoxy purine nucleotides with a terminal 3' phosphorothioate linkage (see for example Table I). As shown in FIG. 26, the chemically stabilized siNA constructs both show significant inhibition of HBV antigen in a dose dependent manner compared to matched inverted controls. A separate direct screen of Stab 7/8 constructs targeting HBV RNA in HepG2 cells that identified stabilized siNA constructs with potent activity is shown in FIG. 87.

Time Course Evaluation of Different Chemically Stabilized siNA Motifs Targeting HBV RNA Site 1580

Four different siNA constructs having different stabilization chemistries were compared to an unstabilized siRNA construct in a dose response time course HBsAg assay, the results of which are shown in FIGS. 28-31. The different constructs were compared to an unstabilized ribonucleotide control siRNA construct (Sirna/RPI#30287/30298) at different concentrations (5 nM, 10 nM, 25 nM, 50 nM, and 100 nM) over the course of nine days. Activity based on HBsAg levels was determined at day 3, day 6, and day 9. The "Stab 4/5" (Table IV) constructs comprise a sense strand (Sirna/RPI#30355) having 2'-deoxy-2'-fluoro pyrimidine nucleotides and purine ribonucleotides with 5' and 3' terminal inverted deoxyabasic residues and an antisense strand (Sirna/RPI#30366) having 2'-deoxy-2'-fluoro pyrimidine nucleotides and purine ribonucleotides with a terminal 3' phosphorothioate linkage (data shown in FIG. 28). The "Stab7/8" (Table IV) constructs comprise a sense strand (Sirna/RPI#30612) having 2'-deoxy-2'-fluoro pyrimidine nucleotides and 2'-deoxy purine nucleotides with 5' and 3' terminal inverted deoxyabasic residues and an antisense strand (Sirna/RPI#30620) having 2'-deoxy-2'-fluoro pyrimidine nucleotides and 2'-O-methyl purine nucleotides with a terminal 3' phosphorothioate linkage (data shown in FIG. 29). The "Stab7/11 (Table IV) constructs comprise a sense (Sirna/RPI#30612) strand having 2'-deoxy-2'-fluoro pyrimidine nucleotides and 2'-deoxy purine nucleotides with 5' and 3' terminal inverted deoxyabasic residues and an antisense strand (Sirna/RPI#31175) having 2'-deoxy-2'-fluoro pyrimidine nucleotides and 2'-deoxy purine nucleotides with a terminal 3' phosphorothioate linkage (data shown in FIG. 30). The "Stab9/10 (Table IV) constructs comprise a sense (Sirna/RPI#31335) strand having ribonucleotides with 5' and 3' terminal inverted deoxyabasic residues and an antisense strand (Sirna/RPI#31337) having ribonucleotides with a terminal 3' phosphorothioate linkage (data shown in FIG. 31). As shown in FIGS. 28-31, the chemically stabilized siNA constructs all show significantly greater inhibition of HBV antigen in a dose dependent manner over the time course experiment compared to the unstabilized siRNA construct.

A second study was performed using the stab 4/5 (Sirna 30355/30366), stab 7/8 (Sirna 30612/30620), and stab 7/11 (Sirna 30612/31175) siNA constructs described above to examine the duration of effect of the modified siNA constructs out to 21 days post transfection compared to an all RNA control siNA (Sirna 30287/30298). A single transfection was performed with siRNAs targeted to HBV site 1580 and the culture media was subsequently replaced every three days. Secreted HBsAg levels were monitored for at 3, 6, 9, 12, 15, 18 and 21 days post-transfection. FIGS. 77A-77F show activity of siNAs in reduction of HBsAg levels compared to matched inverted controls at FIG. 77A. 3 days, FIG. 77B. 9 days, and FIG. 77C. 21 days post transfection. Also shown is the corresponding percent inhibition as function of time at siNA concentrations of FIG. 77D. 100 nM, FIG. 77E. 50 nM, and FIG. 77F. 25 nM.

Figure 32:
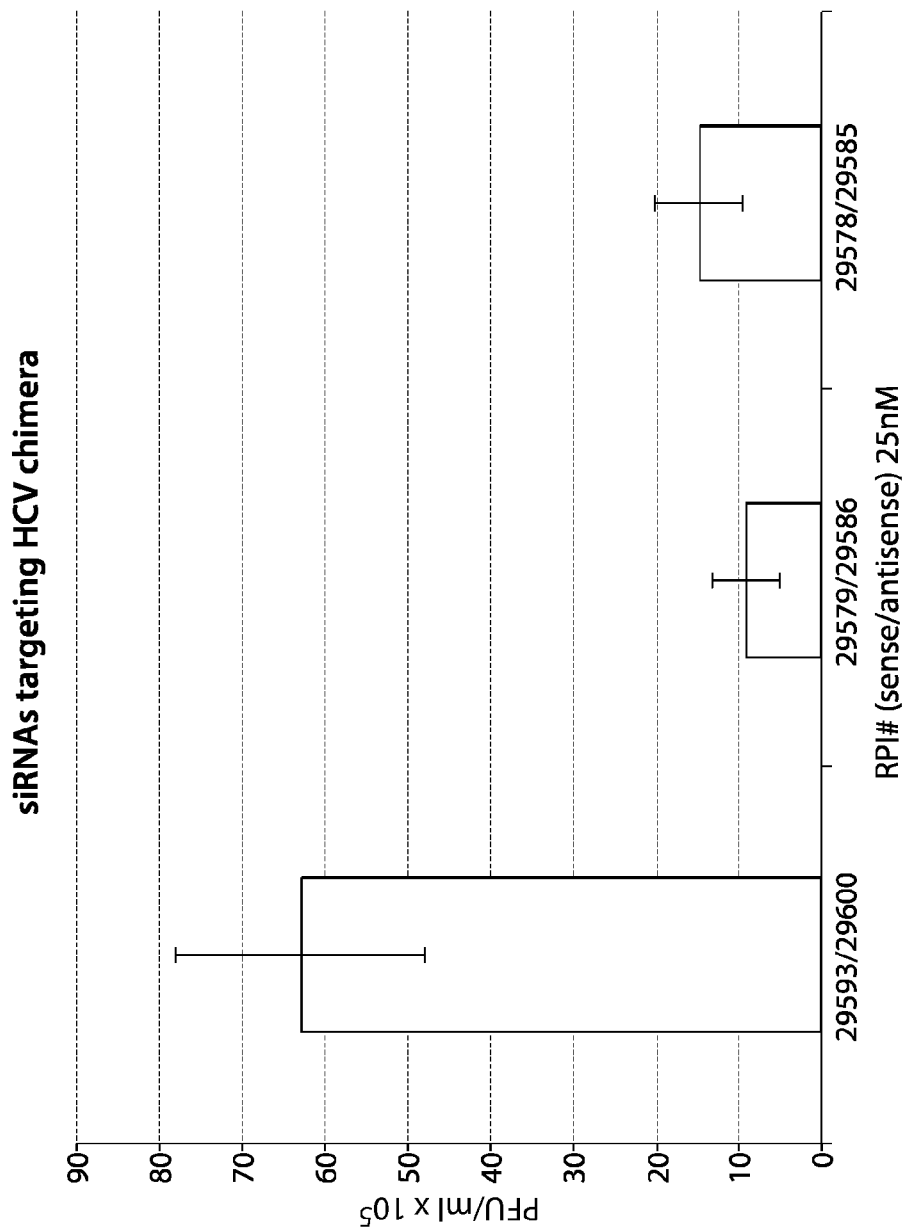
FIG. 32 shows non-limiting examples of inhibition of viral replication of a HCV/poliovirus chimera by siNA constructs targeted to HCV chimera (29579/29586; 29578/29585) compared to control (29593/29600).
Figure 33:
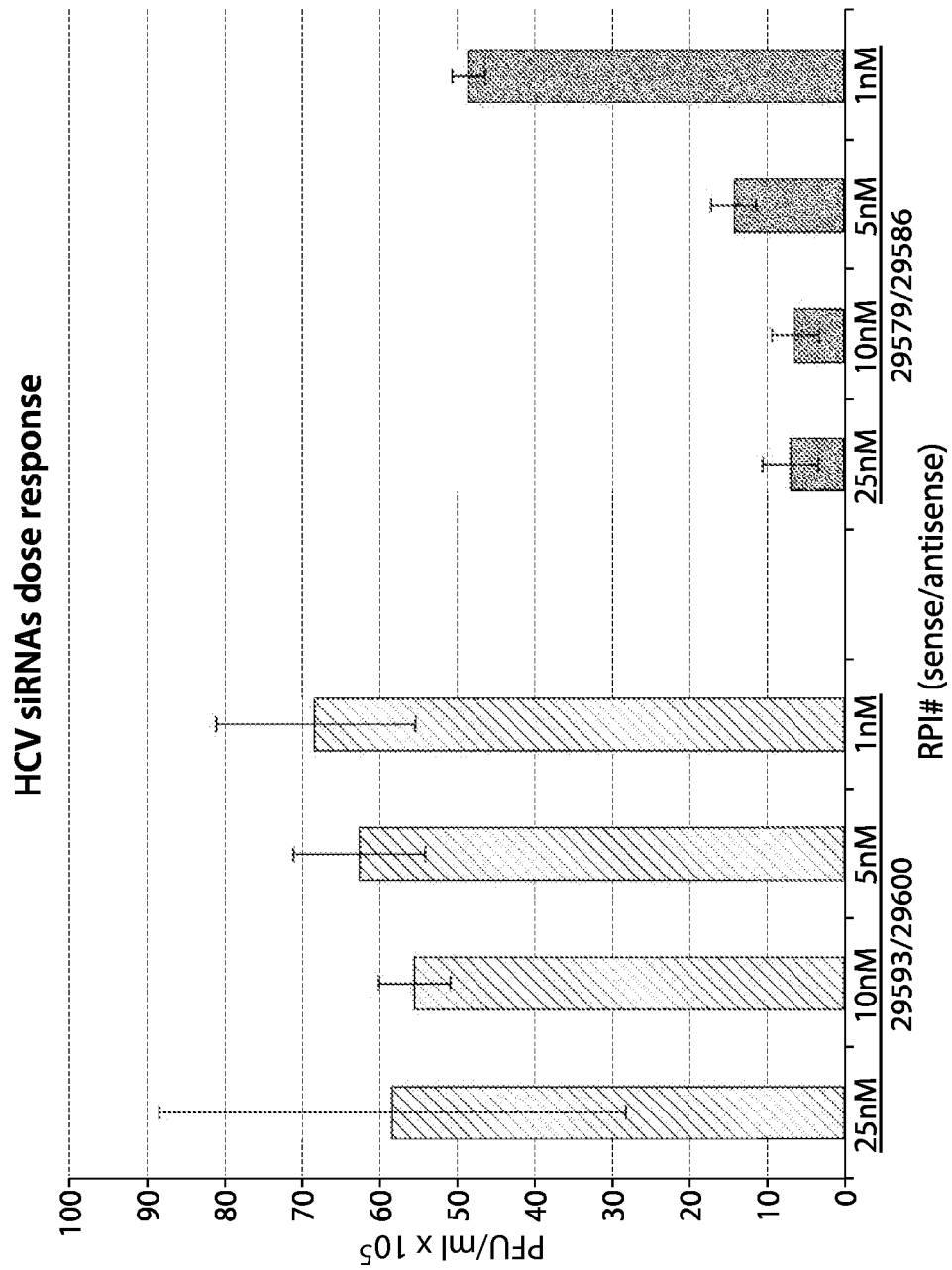
FIG. 33 shows a non-limiting example of a dose response study demonstrating the inhibition of viral replication of a HCV/poliovirus chimera by siNA construct (29579/29586) at various concentrations (1 nM, 5 nM, 10 nM, and 25 nM) compared to control (29593/29600).
Figure 34:
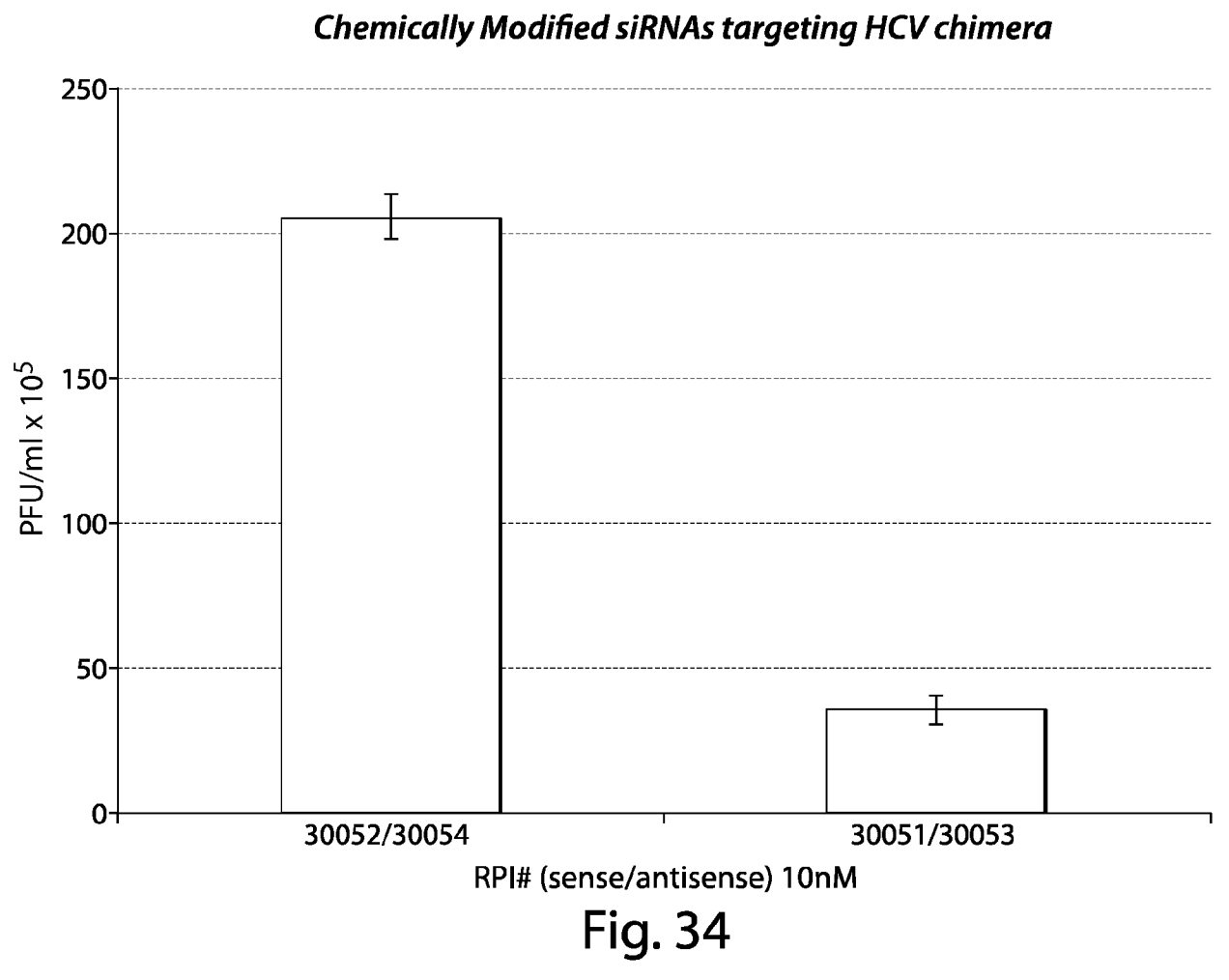
Figure 35:
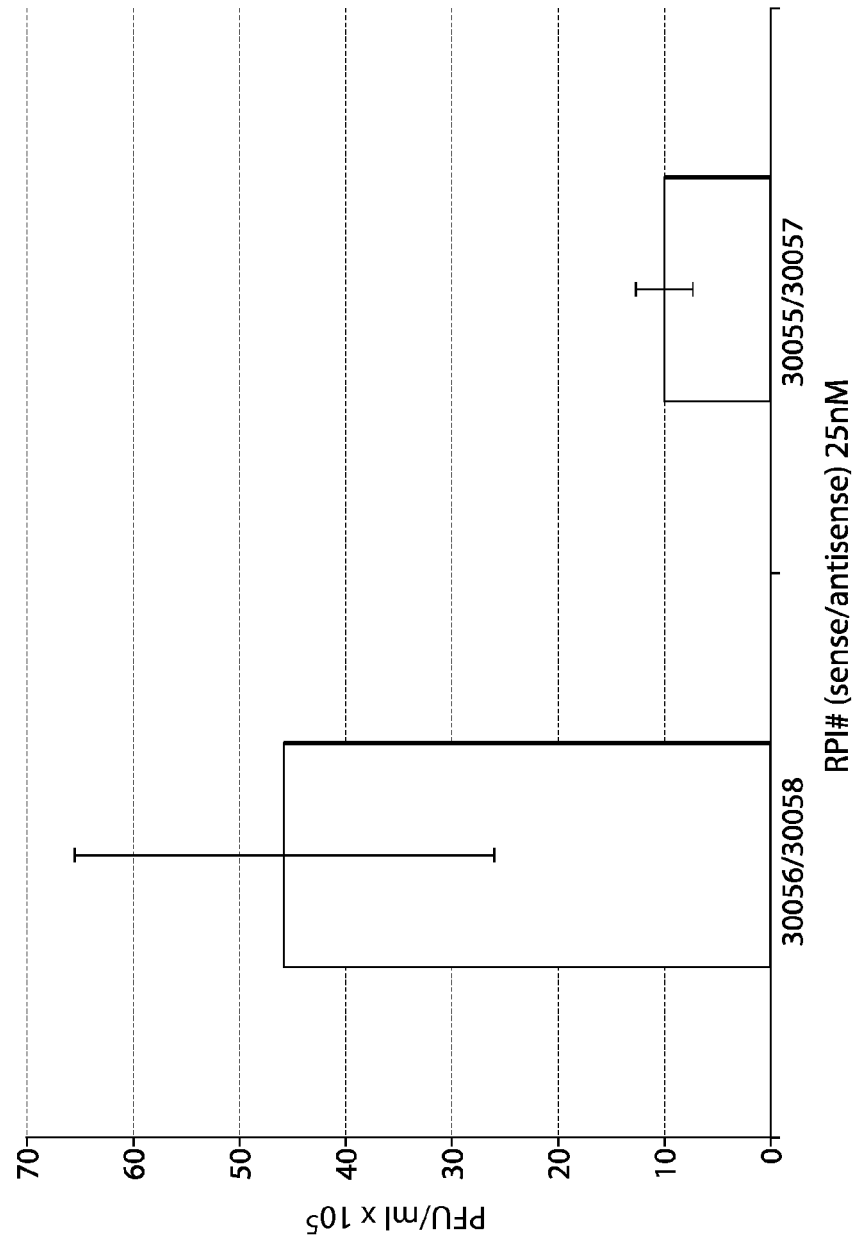
FIG. 35 shows a non-limiting example demonstrating the inhibition of viral replication of a HCV/poliovirus chimera by a chemically modified siRNA construct (30055/30057) compared to control construct (30056/30058).
Figure 36:
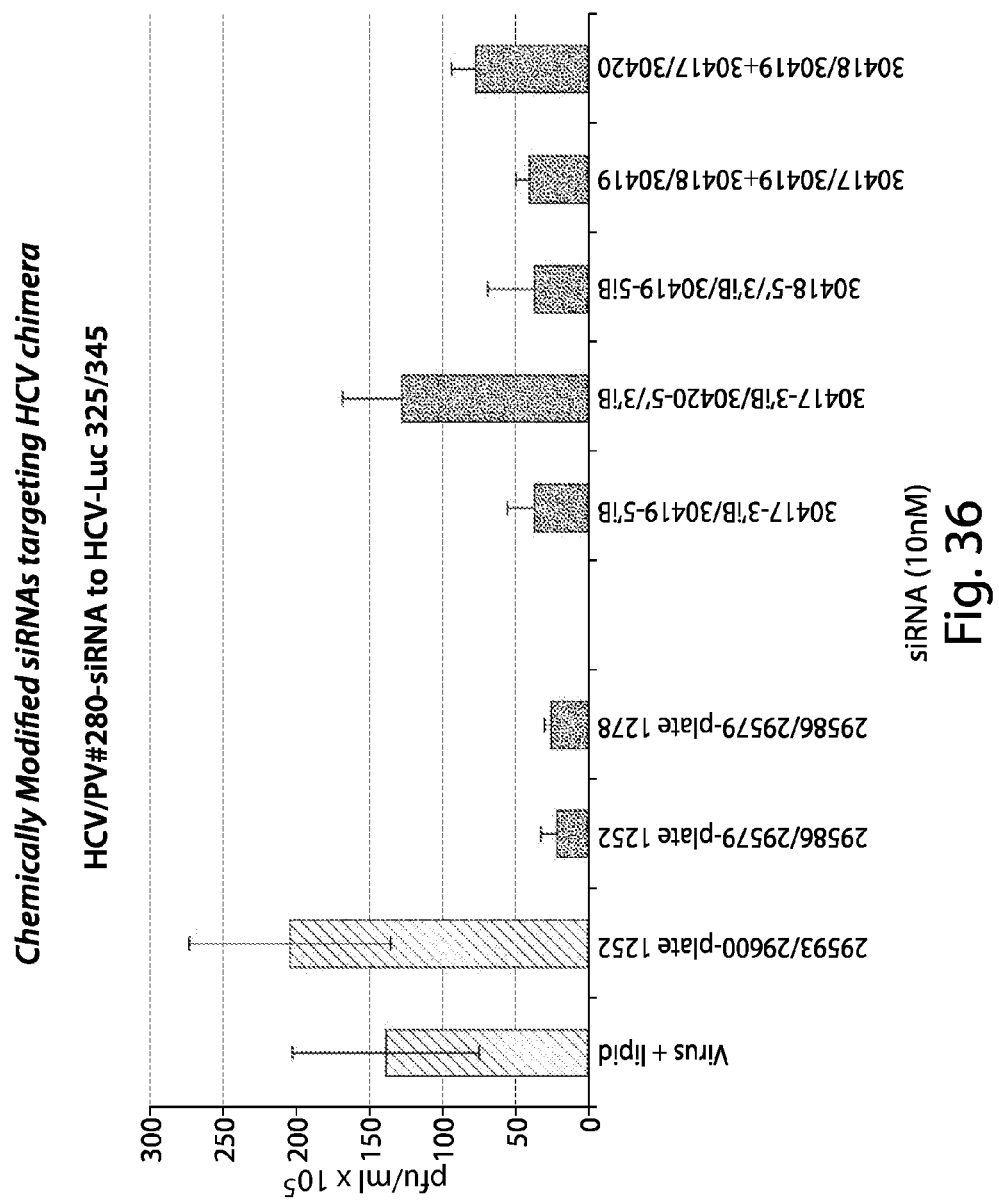
FIG. 36 shows a non-limiting example of several chemically modified siRNA constructs targeting viral replication of an HCV/poliovirus chimera at 10 nM treatment in comparison to a lipid control and an inverse siNA control construct 29593/29600.

Example 14: Inhibition of HCV Using siNA Molecules of the Invention siNA Inhibition of a Chimeric HCV/Poliovirus in HeLa Cells Inhibition of a chimeric HCV/Poliovirus was investigated using 21 nucleotide siNA duplexes in HeLa cells. Seven siNA constructs were designed that target three regions in the highly conserved 5' untranslated region (UTR) of HCV RNA. The siNAs were screened in two cell culture systems dependent upon the 5'-UTR of HCV; one requires translation of an HCV/luciferase gene, while the other involves replication of a chimeric HCV/poliovirus (PV) (see Blatt et al., U.S. Ser. No. 09/740,332, filed Dec. 18, 2000, incorporated by reference herein). Two siNAs (29579/29586; 29578/29585) targeting the same region (shifted by one nucleotide) are active in both systems (see FIG. 32) as compared with inverse control siNA (29593/29600). For example, a >85% reduction in HCVPV replication was observed in siNA-treated cells compared to an inverse siNA control (FIG. 32) with an IC50=~2.5 nM (FIG. 33). To develop nuclease-resistant siNA for in vivo applications, siNAs can be modified to contain stabilizing chemical modifications. Such modifications include phosphorothioate linkages (P=S), 2'-O-methyl nucleotides, 2'-fluoro (F) nucleotides, 2'-deoxy nucleotides, universal base nucleotides, 5' and/or 3' end modifications and a variety of other nucleotide and non-nucleotide modifications, in one or both siNA strands. Several of these constructs were tested in the HCV/poliovirus chimera system, demonstrating significant reduction in viral replication (FIGS. 34-37). siNA constructs shown in FIGS. 34-37 are referred to by Sirna/RPI#s that are cross referenced to Table III, which shows the sequence and chemical modifications of the constructs. siNA activity is compared to relevant controls (untreated cells, scrambled/inactive control sequences, or transfection controls). As shown in the Figures, siNA constructs of the invention provide potent inhibition of HCV RNA in the HCV/poliovirus chimera system. As such, siNA constructs, including chemically modified, nuclease resistant siNA molecules, represent an important class of therapeutic agents for treating chronic HCV infection.

siNA Inhibition of a HCV RNA Expression in a HCV Replicon System

Figure 38:
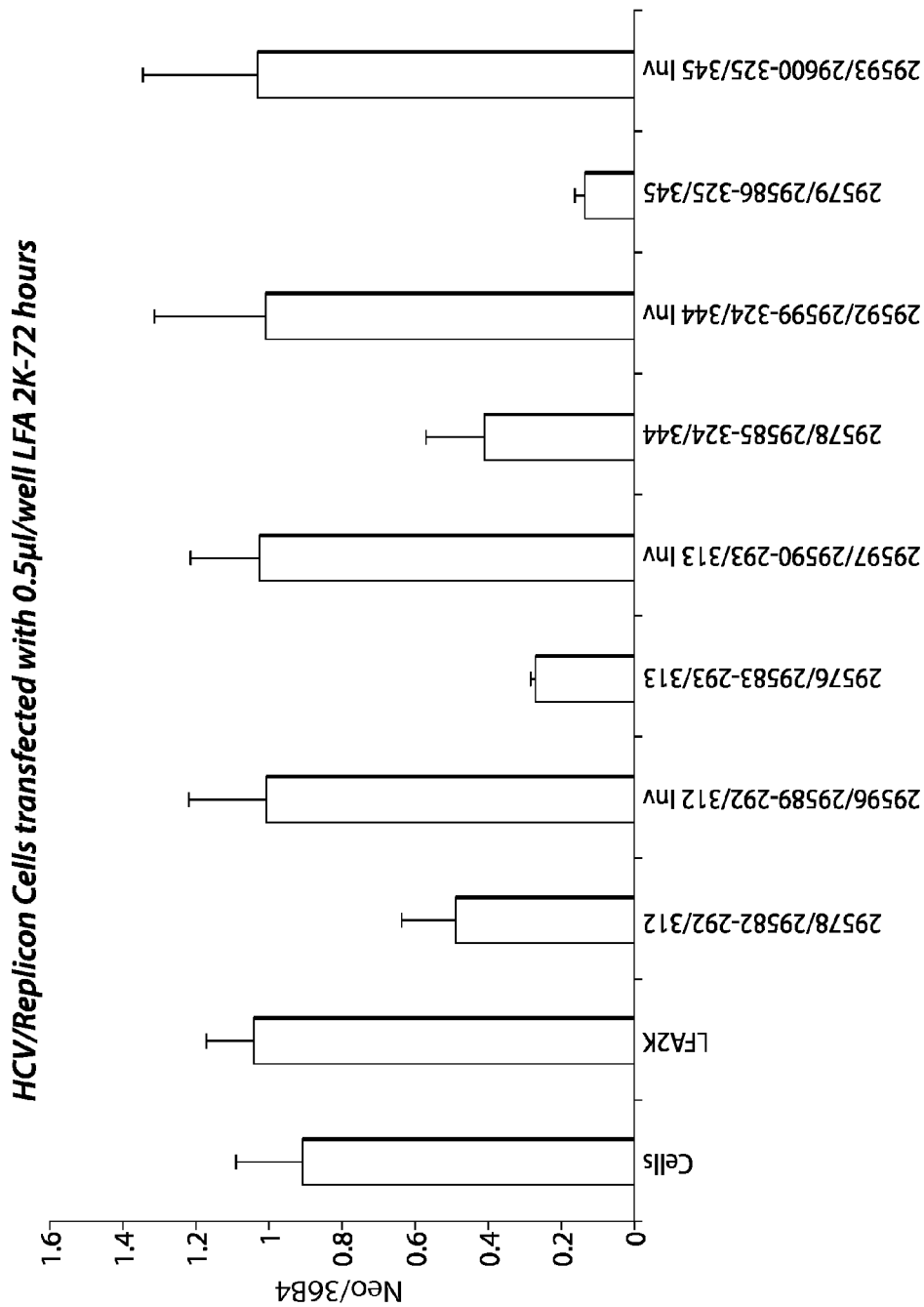
FIG. 38 shows a non-limiting example of several chemically modified siRNA constructs targeting viral replication of a Huh7 HCV replicon system at 25 nM treatment in comparison to untreated cells ("cells"), cells transfected with lipofectamine ("LFA2K") and inverse siNA control constructs.
Figure 39:
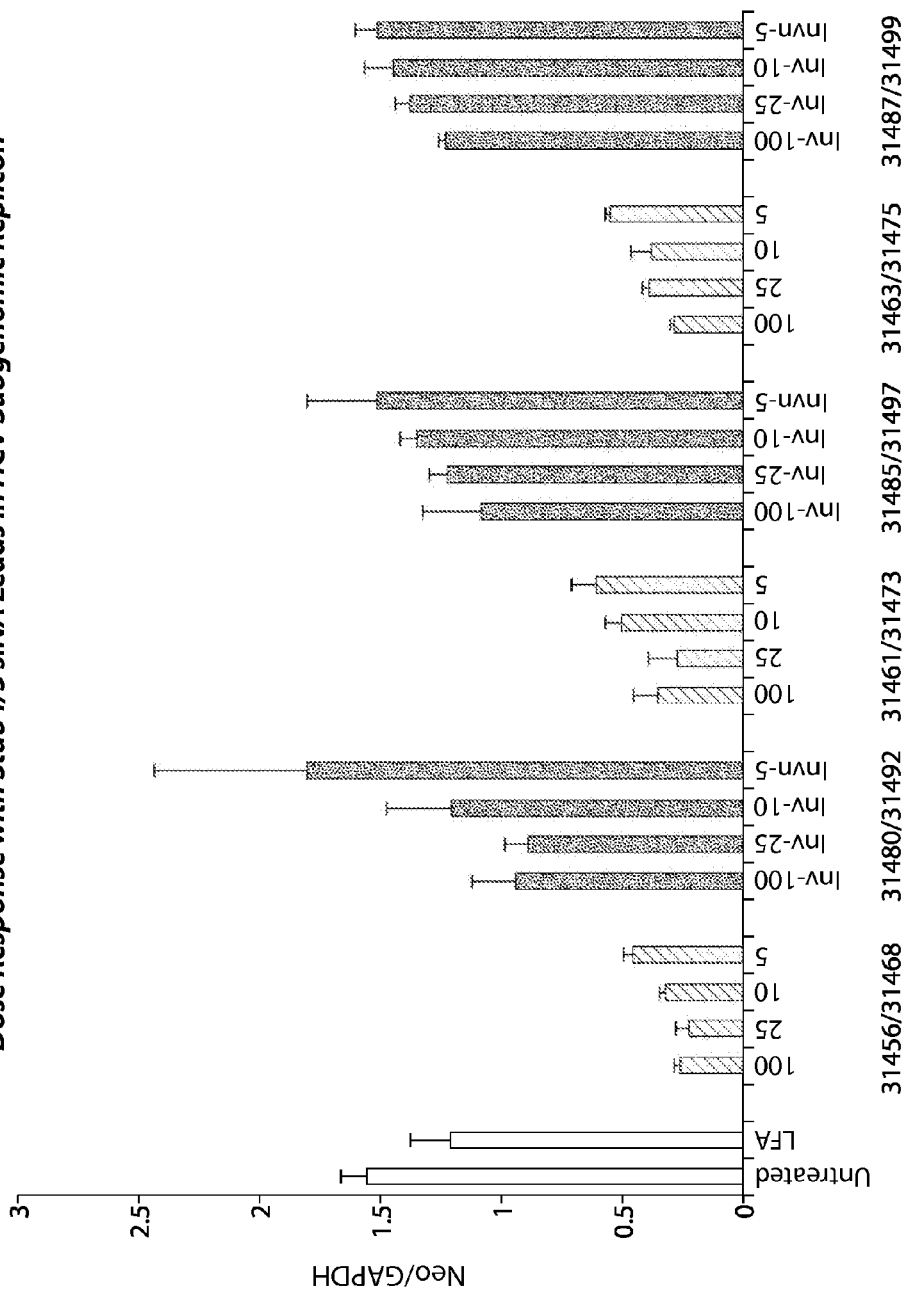
FIG. 39 shows a non-limiting example of a dose response study using chemically modified siNA molecules (Stab 4/5, see Table IV) targeting HCV RNA sites 291, 300, and 303 in a Huh7 HCV replicon system at 5, 10, 25, and 100 nM treatment comparison to untreated cells ("cells"), cells transfected with lipofectamine ("LFA") and inverse siNA control constructs.
Figure 40:
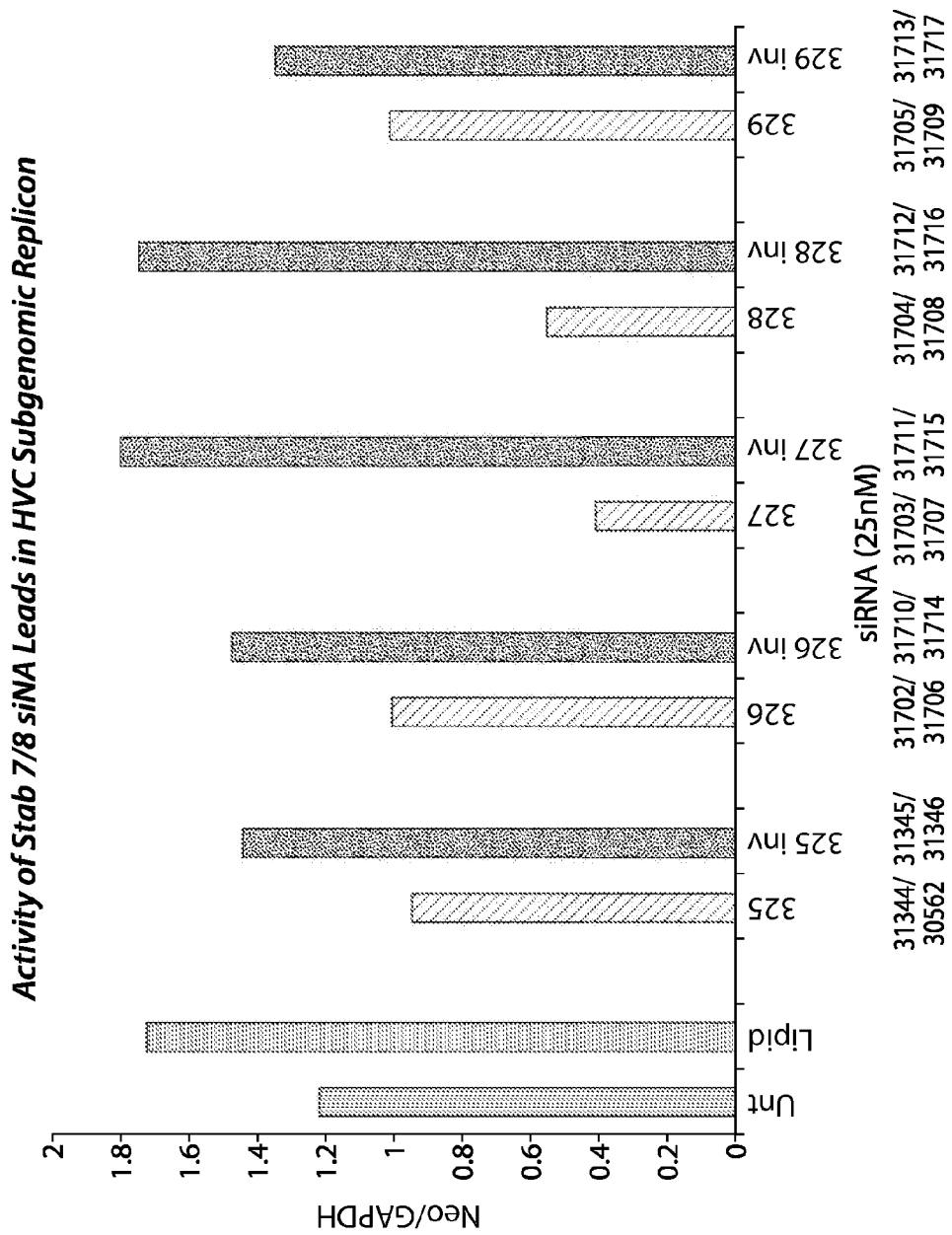
FIG. 40 shows a non-limiting example of several chemically modified siNA constructs (Stab 7/8, see Table IV) targeting viral replication in a Huh7 HCV replicon system at 25 nM treatment in comparison to untreated cells ("cells"), cells transfected with lipofectamine ("Lipid") and inverse siNA control constructs.
Figure 41:
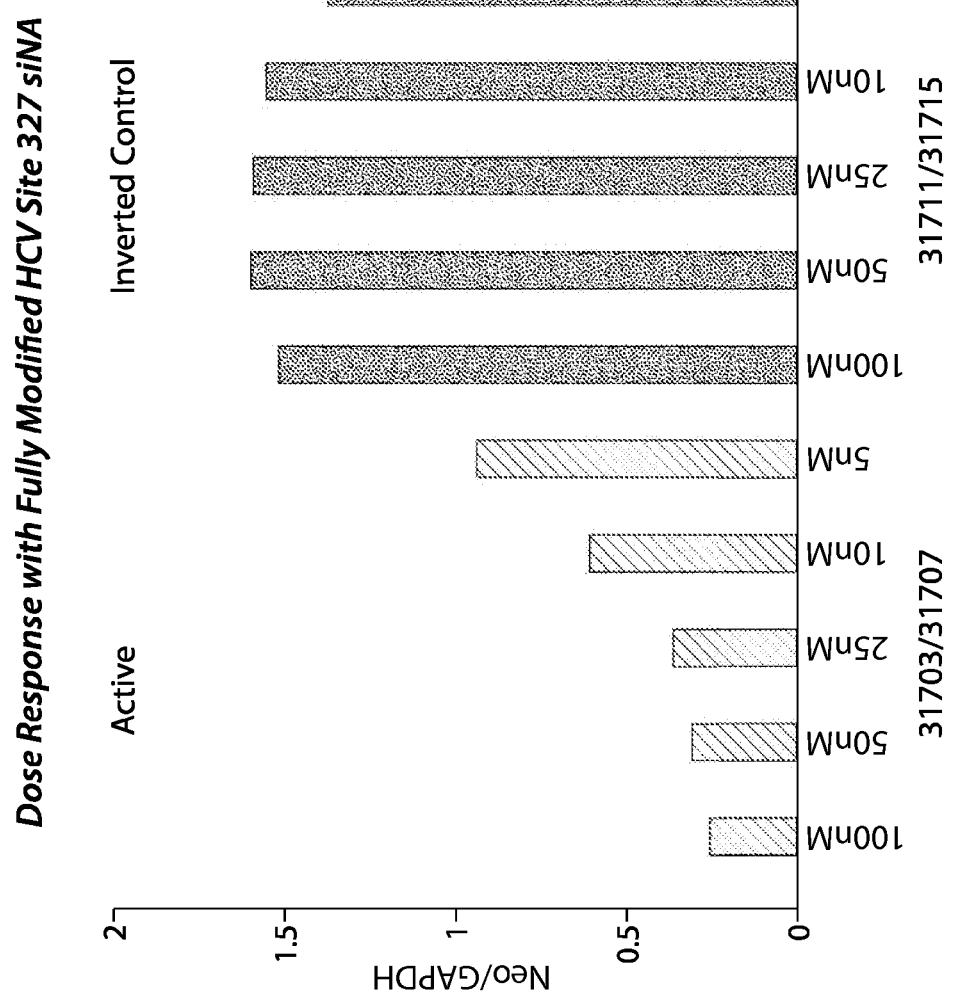
FIG. 41 shows a non-limiting example of a dose response study using chemically modified siNA molecules (Stab 7/8, see Table IV) targeting HCV site 327 in a Huh7 HCV replicon system at 5, 10, 25, 50, and 100 nM treatment in comparison to inverse siNA control constructs.
Figure 42:
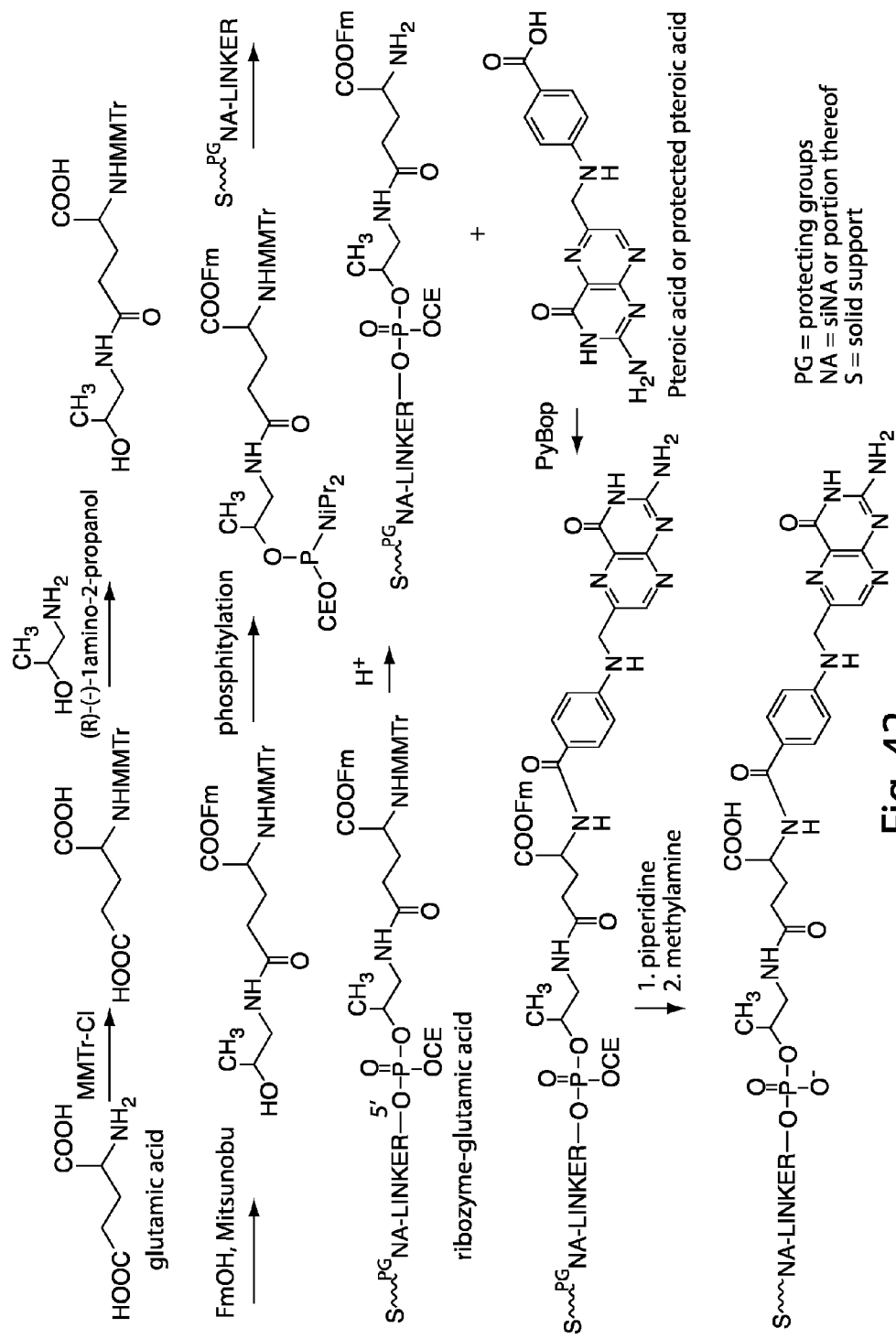
FIG. 42 shows a synthetic scheme for post-synthetic modification of a nucleic acid molecule to produce a folate conjugate.
Figure 86:
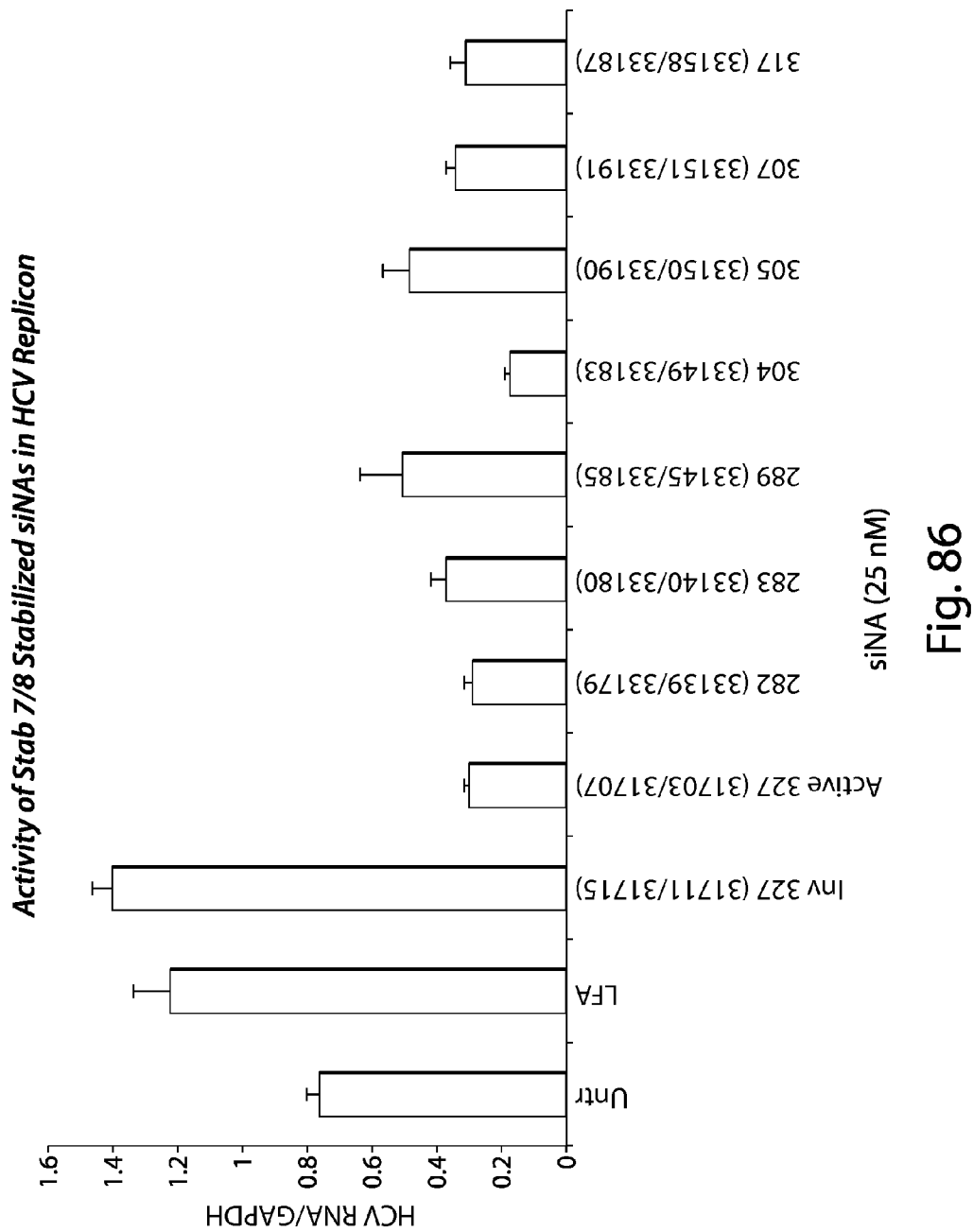
FIG. 86 shows a non-limiting example of an assay screen of Stab 7/8 siNA constructs targeting various sites of HCV RNA in a replicon system compared to untreated, lipid, and an inverted control. As shown in the figure, several Stab 7/8 constructs were identified with potent anti-HCV activity as shown by reduction in HCV RNA levels.

In addition, a HCV replicon system was used to test the efficacy of siNAs targeting HCV RNA. The reagents are tested in cell culture using Huh7 cells (see for example Randall et al., 2003, *PNAS USA,* 100, 235-240) to determine the extent of RNA and protein inhibition. siNA were selected against the HCV target as described herein. RNA inhibition was measured after delivery of these reagents by a suitable transfection agent to Huh7 cells. Relative amounts of target RNA are measured versus actin using real-time PCR monitoring of amplification (eg., ABI 7700 Taqman®). A comparison is made to a mixture of oligonucleotide sequences designed to target unrelated targets or to a randomized siNA control with the same overall length and chemistry, but with randomly substituted nucleotides at each position. Primary and secondary lead reagents were chosen for the target and optimization performed. After an optimal transfection agent concentration is chosen, a RNA time-course of inhibition is performed with the lead siNA molecule. In addition, a cell-plating format can be used to determine RNA inhibition. A non-limiting example of a multiple target screen to assay siNA mediated inhibition of HCV RNA is shown in FIG. 38. siNA reagents (Table I) were transfected at 25 nM into Huh7 cells and HCV RNA quantitated compared to untreated cells ("cells" column in the figure) and cells transfected with lipofectamine ("LFA2K" column in the figure). As shown in the Figure, several siNA constructs show significant inhibition of HCV RNA expression in the Huh7 replicon system. Chemically modified siNA constructs were then screened as described above, with a non-limiting example of a Stab 7/8 (see Table IV) chemistry siNA construct screen shown in FIG. 40. A follow up dose response study using chemically modified siNA constructs (Stab 4/5, see Table IV) at concentrations of 5 nM, 10 nM, 25 nM and 100 nM compared to matched chemistry inverted controls is shown in FIG. 39, whereas a dose response study for Stab 7/8 constructs at concentrations of 5 nM, 10 nM, 25 nM, 50 nM and 100 nM compared to matched chemistry inverted controls is shown in FIG. 41. A separate direct screen of Stab 7/8 constructs targeting HCV RNA that identified stabilized siNA constructs with potent activity is shown in FIG. 86.

Example 15: Target Discovery in Mammalian Cells Using siNA Molecules

In a non-limiting example, compositions and methods of the invention are used to discover genes involved in a process of interest within mammalian cells, such as cell growth, proliferation, apoptosis, morphology, angiogenesis, differentiation, migration, viral multiplication, drug resistance, signal transduction, cell cycle regulation, or temperature sensitivity or other process. First, a randomized siNA library is generated. These constructs are inserted into a vector capable of expressing a siNA from the library inside mammalian cells. Alternately, a pool of synthetic siNA molecules is generated.

Reporter System

In order to discover genes playing a role in the expression of certain proteins, such as proteins involved in a cellular process described herein, a readily assayable reporter system is constructed in which a reporter molecule is co-expressed when a particular protein of interest is expressed. The reporter system consists of a plasmid construct bearing a gene coding for a reporter gene, such as Green Fluorescent Protein (GFP) or other reporter proteins known and readily available in the art. The promoter region of the GFP gene is replaced by a portion of a promoter for the protein of interest sufficient to direct efficient transcription of the GFP gene. The plasmid can also contain a drug resistance gene, such as neomycin resistance, in order to select cells containing the plasmid.

Host Cell Lines for Target Discovery

A cell line is selected as host for target discovery. The cell line is preferably known to express the protein of interest, such that upstream genes controlling the expression of the protein can be identified when modulated by a siNA construct expressed therein. The cells preferably retain protein expression characteristics in culture. The reporter plasmid is transfected into cells, for example, using a cationic lipid formulation. Following transfection, the cells are subjected to limiting dilution cloning, for example, under selection by 600 μg/mL Geneticin. Cells retaining the plasmid survive the Geneticin treatment and form colonies derived from single surviving cells. The resulting clonal cell lines are screened by flow cytometry for the capacity to upregulate GFP production. Treating the cells with, for example, sterilized M9 bacterial medium in which *Pseudomonas aeruginosa* had been cultured (*Pseudomonas* conditioned medium, PCM) is used to induce the promoter. The PCM is supplemented with phorbol myristate acetate (PMA). A clonal cell line highly responsive to promoter induction is selected as the reporter line for subsequent studies.

siNA Library Construction

A siNA library was constructed with oligonucletides containing hairpin siNA constructs having randomized antisense regions and self complementary sense regions. The library is generated synthesizing siNA constructs having randomized sequence. Alternately, the siNA libraries are constructed as described in Usman et al., U.S. Ser. No. 60/402,996 (incorporated by reference herein) Oligo sequence 5' and 3' of the siNA contains restriction endonuclease cleavage sites for cloning. The 3' trailing sequence forms a stem-loop for priming DNA polymerase extension to form a hairpin structure. The hairpin DNA construct is melted at 90° C. allowing DNA polymerase to generate a dsDNA construct. The double-stranded siNA library is cloned into, for example, a U6+27 transcription unit located in the 5' LTR region of a retroviral vector containing the human nerve growth factor receptor (hNGFr) reporter gene. Positioning the U6+27/siNA transcription unit in the 5' LTR results in a duplication of the transcription unit when the vector integrates into the host cell genome. As a result, the siNA is transcribed by RNA polymerase III from U6+27 and by RNA polymerase II activity directed by the 5' LTR. The siNA library is packaged into retroviral particles that are used to infect and transduce clonal cells selected above. Assays of the hNGFr reporter are used to indicate the percentage of cells that incorporated the siNA construct. By randomized region is meant a region of completely random sequence and/or partially random sequence. By completely random sequence is meant a sequence wherein theoretically there is equal representation of A, T, G and C nucleotides or modified derivatives thereof, at each position in the sequence. By partially random sequence is meant a sequence wherein there is an unequal representation of A, T, G and C nucleotides or modified derivatives thereof, at each position in the sequence. A partially random sequence can therefore have one or more positions of complete randomness and one or more positions with defined nucleotides.

Enriching for Non-Responders to Induction

Sorting of siNA library-containing cells is performed to enrich for cells that produce less reporter GFP after treatment with the promoter inducers PCM and PMA. Lower GFP production cancan be due to RNAi activity against genes involved in the activation of the mucin promoter. Alternatively, siNA can directly target the mucin/GFP transcript resulting in reduced GFP expression.

Cells are seeded at a certain density, such as $1 \times 10^6$ per 150 $cm^2$ style cell culture flasks and grown in the appropriate cell culture medium with fetal bovine serum. After 72 hours, the cell culture medium is replaced with serum-free medium. After 24 hours of serum deprivation, the cells are treated with serum-containing medium supplemented with PCM (to 40%) and PMA (to 50 nM) to induced GFP production. After 20 to 22 hours, cells are monitored for GFP level on, for example, a FACStar Plus cell sorter. Sorting is performed if ≥90% of siNA library cells from an unsorted control sample were induced to produce GFP above background levels. Two cell fractions are collected in each round of sorting. Following the appropriate round of sorting, the M1 fraction is selected to generate a database of siNA molecules present in the sorted cells.

Recovery of siNA Sequence from Sorted Cells

Genomic DNA is obtained from sorted siNA library cells by standard methods. Nested polymerase chain reaction (PCR) primers that hybridized to the retroviral vector 5' and 3' of the siNA are used to recover and amplify the siNA sequences from the particular clone of library cell DNA. The PCR product is ligated into a bacterial cloning vector. The recovered siNA library in plasmid form can be used to generate a database of siNA sequences. For example, the library is cloned into E. coli. DNA is prepared by plasmid isolation from bacterial colonies or by direct colony PCR and siNA sequence is determined. A second method can use the siNA library to transfect cloned cells. Clonal lines of stably transfected cells are established and induced with, for example, PCM and PMA. Those lines which fail to respond to GFP induction are probed by PCR for single siNA integration events. The unique siNA sequences obtained by both methods are added to a Target Sequence Tag (TST) database.

Bioinformatics

The antisense region sequences of the isolated siNA constructs are compared to public and private gene data banks. Gene matches are compiled according to perfect and imperfect matches. Potential gene targets are categorized by the number of different siNA sequences matching each gene. Genes with more than one perfect siNA match are selected for Target Validation studies.

Validation of the Target Gene

To validate a target as a regulator of protein expression, siNA reagents are designed to the target gene cDNA sequence from Genbank. The siNA reagents are complexed with a cationic lipid formulation prior to administration to cloned cells at appropriate concentrations (e.g. 5-50 nM or less). Cells are treated with siNA reagents, for example from 72 to 96 hours. Before the termination of siNA treatment, PCM (to 40%) and PMA (to 50 nM), for example, are added to induce the promoter. After twenty hours of induction the cells are harvested and assayed for phenotypic and molecular parameters. Reduced GFP expression in siNA treated cells (measured by flow cytometry) is taken as evidence for validation of the target gene. Knockdown of target RNA in siNA treated cells can correlate with reduced endogenous RNA and reduced GFP RNA to complete validation of the target.

Example 16: Screening siNA Constructs for Improved Pharmacokinetics

In a non-limiting example, siNA constructs are screened in vivo for improved pharmacokinetic properties compared to all RNA or unmodified siNA constructs. Chemical modifications are introduced into the siNA construct based on educated design parameters (e.g. introducing 2'-modifications, base modifications, backbone modifications, terminal cap modifications, or covalently attached conjugates etc). The modified construct in tested in an appropriate system (e.g human serum for nuclease resistance, shown, or an animal model for PK/delivery parameters). In parallel, the siNA construct is tested for RNAi activity, for example in a cell culture system such as a luciferase reporter assay). Lead siNA constructs are then identified which possess a particular characteristic while maintaining RNAi activity, and can be further modified and assayed once again. This same approach can be used to identify siNA-conjugate molecules with improved pharmacokinetic profiles, delivery, localized delivery, cellular uptake, and RNAi activity.

Example 17: Indications

The siNA molecules of the invention can be used to treat a variety of diseases and conditions through modulation of gene expression. Using the methods described herein, chemically modified siNA molecules can be designed to modulate the expression any number of target genes, including but not limited to genes associated with cancer, metabolic diseases, infectious diseases such as viral, bacterial or fungal infections, neurologic diseases, musculoskeletal diseases, diseases of the immune system, diseases associated with signaling pathways and cellular messengers, and diseases associated with transport systems including molecular pumps and channels.

Non-limiting examples of various viral genes that can be targeted using siNA molecules of the invention include Hepatitis C Virus (HCV, for example Genbank Accession Nos: D11168, D50483.1, L38318 and S82227), Hepatitis B Virus (HBV, for example GenBank Accession No. AF100308.1), Human Immunodeficiency Virus type 1 (HIV-1, for example GenBank Accession No. U51188), Human Immunodeficiency Virus type 2 (HIV-2, for example GenBank Accession No. X60667), West Nile Virus (WNV for example GenBank accession No. NC_001563), cytomegalovirus (CMV for example GenBank Accession No. NC_001347), respiratory syncytial virus (RSV for example GenBank Accession No. NC_001781), influenza virus (for example GenBank Accession No. AF037412, rhinovirus (for example, GenBank accession numbers: D00239, X02316, X01087, L24917, M16248, K02121, X01087), papillomavirus (for example GenBank Accession No. NC_001353), Herpes Simplex Virus (HSV for example GenBank Accession No. NC_001345), and other viruses such as HTLV (for example GenBank Accession No. AJ430458). Due to the high sequence variability of many viral genomes, selection of siNA molecules for broad therapeutic applications would likely involve the conserved regions of the viral genome. Nonlimiting examples of conserved regions of the viral genomes include but are not limited to 5'-Non Coding Regions (NCR), 3'-Non Coding Regions (NCR) LTR regions and/or internal ribosome entry sites (IRES). siNA molecules designed against conserved regions of various viral genomes will enable efficient inhibition of viral replication in diverse patient populations and may ensure the effectiveness of the siNA molecules against viral quasi species which evolve due to mutations in the non-conserved regions of the viral genome.

Non-limiting examples of human genes that can be targeted using siNA molecules of the invention using methods described herein include any human RNA sequence, for example those commonly referred to by Genbank Accession Number. These RNA sequences can be used to design siNA molecules that inhibit gene expression and therefore abrogate diseases, conditions, or infections associated with expression of those genes. Such non-limiting examples of human genes that can be targeted using siNA molecules of the invention include VEGF (for example GenBank Accession No. NM_003376.3), VEGFr (VEGFR1 for example GenBank Accession No. XM_067723, VEGFR2 for example GenBank Accession No. AF063658), HER1, HER2, HER3, and HER4 (for example Genbank Accession Nos: NM_005228, NM_004448, NM_001982, and NM_005235 respectively), telomerase (TERT, for example GenBank Accession No. NM_003219), telomerase RNA (for example GenBank Accession No. U86046), NFkappaB, Rel-A (for example GenBank Accession No. NM_005228), NOGO (for example GenBank Accession No. AB020693), NOGOr (for example GenBank Accession No. XM_015620), RAS (for example GenBank Accession No. NM_004283), RAF (for example GenBank Accession No. XM_033884), CD20 (for example GenBank Accession No. X07203), METAP2 (for example GenBank Accession No. NM_003219), CLCA1 (for example GenBank Accession No. NM_001285), phospholamban (for example GenBank Accession No. NM_002667), PTP1B (for example GenBank Accession No. M31724), PCNA (for example GenBank Accession No. NM_002592.1), PKC-alpha (for example GenBank Accession No. NM_002737) and others. The genes described herein are provided as non-limiting examples of genes that can be targeted using siNA molecules of the invention. Additional examples of such genes are described by accession number in Beigelman et al., U.S. Ser. No. 60/363,124, filed Mar. 11, 2002 and incorporated by reference herein in its entirety.

The siNA molecule of the invention can also be used in a variety of agricultural applications involving modulation of endogenous or exogenous gene expression in plants using siNA, including use as insecticidal, antiviral and anti-fungal agents or modulate plant traits such as oil and starch profiles and stress resistance.

Example 18: Diagnostic Uses

The siNA molecules of the invention can be used in a variety of diagnostic applications, such as in the identification of molecular targets (e.g., RNA) in a variety of applications, for example, in clinical, industrial, environmental, agricultural and/or research settings. Such diagnostic use of siNA molecules involves utilizing reconstituted RNAi systems, for example, using cellular lysates or partially purified cellular lysates. siNA molecules of this invention can be used as diagnostic tools to examine genetic drift and mutations within diseased cells or to detect the presence of endogenous or exogenous, for example viral, RNA in a cell. The close relationship between siNA activity and the structure of the target RNA allows the detection of mutations in any region of the molecule, which alters the base-pairing and three-dimensional structure of the target RNA. By using multiple siNA molecules described in this invention, one can map nucleotide changes, which are important to RNA structure and function in vitro, as well as in cells and tissues. Cleavage of target RNAs with siNA molecules can be used to inhibit gene expression and define the role of specified gene products in the progression of disease or infection. In this manner, other genetic targets can be defined as important mediators of the disease. These experiments will lead to better treatment of the disease progression by affording the possibility of combination therapies (e.g., multiple siNA molecules targeted to different genes, siNA molecules coupled with known small molecule inhibitors, or intermittent treatment with combinations siNA molecules and/or other chemical or biological molecules). Other in vitro uses of siNA molecules of this invention are well known in the art, and include detection of the presence of mRNAs associated with a disease, infection, or related condition. Such RNA is detected by determining the presence of a cleavage product after treatment with a siNA using standard methodologies, for example, fluorescence resonance emission transfer (FRET).

In a specific example, siNA molecules that cleave only wild-type or mutant forms of the target RNA are used for the assay. The first siNA molecules (i.e., those that cleave only wild-type forms of target RNA) are used to identify wild-type RNA present in the sample and the second siNA molecules (i.e., those that cleave only mutant forms of target RNA) are used to identify mutant RNA in the sample. As reaction controls, synthetic substrates of both wild-type and mutant RNA are cleaved by both siNA molecules to demonstrate the relative siNA efficiencies in the reactions and the absence of cleavage of the "non-targeted" RNA species. The cleavage products from the synthetic substrates also serve to generate size markers for the analysis of wild-type and mutant RNAs in the sample population. Thus, each analysis requires two siNA molecules, two substrates and one unknown sample, which is combined into six reactions. The presence of cleavage products is determined using an RNase protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., disease related or infection related) is adequate to establish risk. If probes of comparable specific activity are used for both transcripts, then a qualitative comparison of RNA levels is adequate and decreases the cost of the initial diagnosis. Higher mutant form to wild-type ratios are correlated with higher risk whether RNA levels are compared qualitatively or quantitatively.

Example 19: Synthesis of siNA Conjugates

Figure 65:
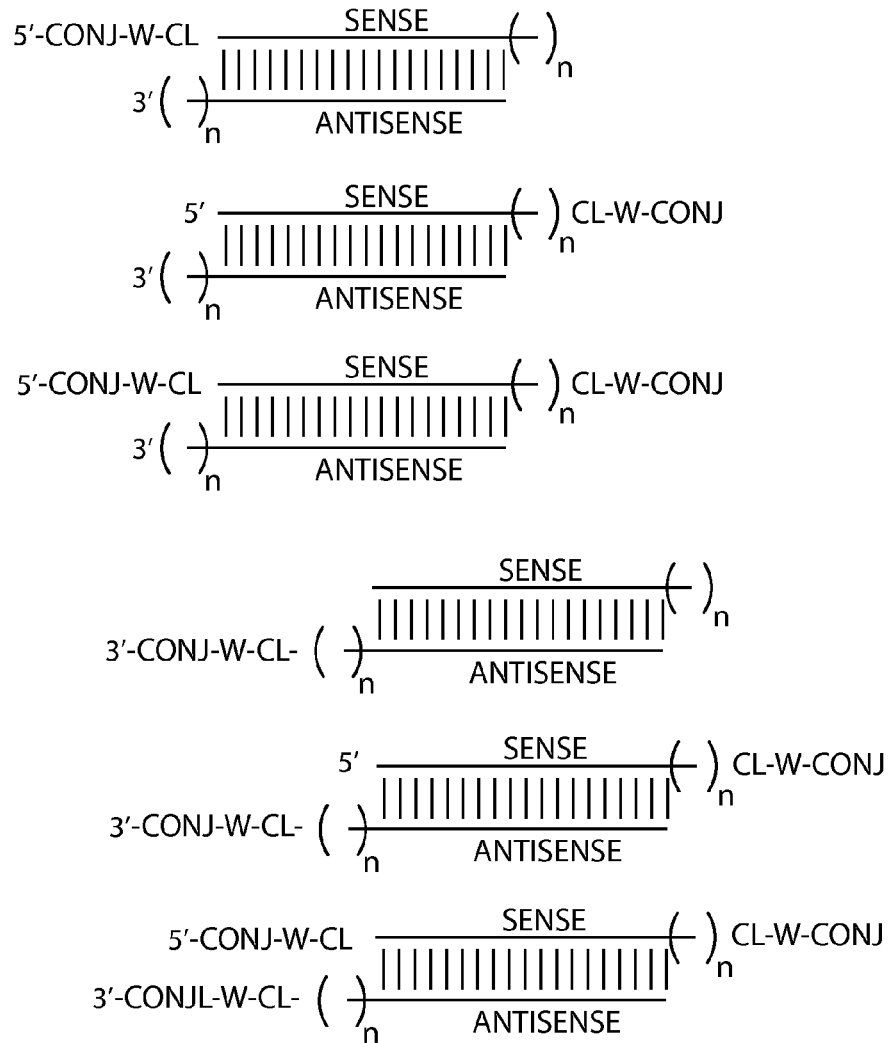
FIG. 65 shows a non-limiting example of various generalized siNA conjugates of the invention in which various linker chemistries and/or cleavable linkers can be utilized at different positions of a double stranded siNA molecule. CONJ in the figure refers to any biologically active compound or any other conjugate compound as described herein and in the Formulae herein.

The introduction of conjugate moieties to siNA molecules of the invention is accomplished either during solid phase synthesis using phosphoramidite chemistry described above, or post-synthetically using, for example, N-hydroxysuccinimide (NHS) ester coupling to an amino linker present in the siNA. Typically, a conjugate introduced during solid phase synthesis will be added to the 5'-end of a nucleic acid sequence as the final coupling reaction in the synthesis cycle using the phosphoramidite approach. Coupling conditions can be optimized for high yield coupling, for example by modification of coupling times and reagent concentrations to effectuate efficient coupling. As such, the 5'-end of the sense strand of a siNA molecule is readily conjugated with a conjugate moiety having a reactive phosphorus group available for coupling (e.g., a compound having Formulae 1, 5, 8, 55, 56, 57, 60, 86, 92, 104, 110, 113, 115, 116, 117, 118, 120, or 122) using the phosphoramidite approach, providing a 5'-terminal conjugate (see for example FIG. 65).

Figure 66:
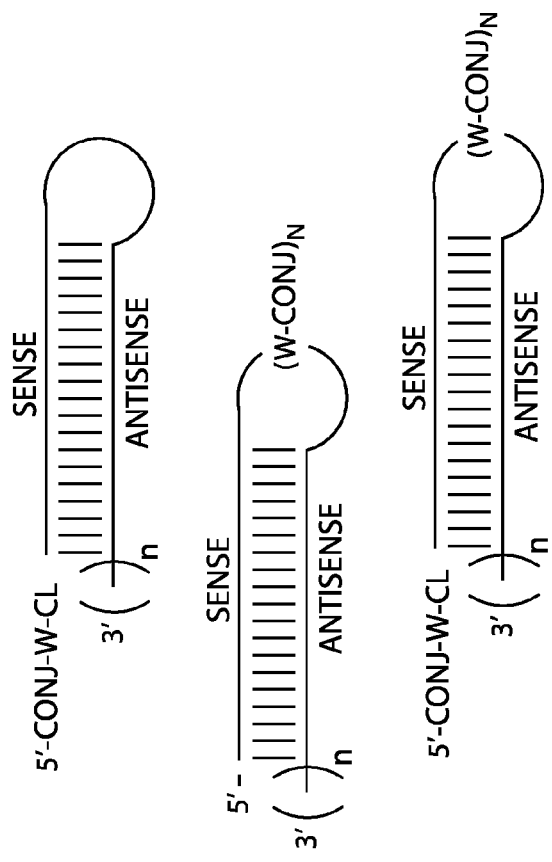
FIG. 66 shows a non-limiting example of various generalized siNA conjugates of the invention in which various linker chemistries and/or cleavable linkers can be utilized at different positions of a single stranded siNA molecule. CONJ in the figure refers to any biologically active compound or any other conjugate compound as described herein and in the Formulae herein.

Conjugate precursors having a reactive phosphorus group and a protected hydroxyl group can be used to incorporate a conjugate moiety anywhere in the siNA sequence, such as in the loop portion of a single stranded hairpin siNA construct (see for example FIG. 66). For example, using the phosphoramidite approach, a conjugate moiety comprising a phosphoramidite and protected hydroxyl (e.g., a compound having Formulae 86, 92, 104, 113, 115, 116, 117, 118, 120, or 122 herein) is first coupled at the desired position within the siNA sequence using solid phase synthesis phosphoramidite coupling. Second, removal of the protecting group (e.g., dimethoxytrityl) allows coupling of additional nucleotides to the siNA sequence. This approach allows the conjugate moiety to be positioned anywhere within the siNA molecule.

Conjugate derivatives can also be introduced to a siNA molecule post synthetically. Post synthetic conjugation allows a conjugate moiety to be introduced at any position within the siNA molecule where an appropriate functional group is present (e.g., a C5 alkylamine linker present on a nucleotide base or a 2'-alkylamine linker present on a nucleotide sugar can provide a point of attachment for an NHS-conjugate moiety). Generally, a reactive chemical group present in the siNA molecule is unmasked following synthesis, thus allowing post-synthetic coupling of the conjugate to occur. In a non-limiting example, an protected amino linker containing nucleotide (e.g., TFA protected C5 propylamino thymidine) is introduced at a desired position of the siNA during solid phase synthesis. Following cleavage and deprotection of the siNA, the free amine is made available for NHS ester coupling of the conjugate at the desired position within the siNA sequence, such as at the 3'-end of the sense and/or antisense strands, the 3' and/or 5'-end of the sense strand, or within the siNA sequence, such as in the loop portion of a single stranded hairpin siNA sequence.

A conjugate moiety can be introduced at different locations within a siNA molecule using both solid phase synthesis and post-synthetic coupling approaches. For example, solid phase synthesis can be used to introduce a conjugate moiety at the 5'-end of the siNA (e.g. sense strand) and post-synthetic coupling can be used to introduce a conjugate moiety at the 3'-end of the siNA (e.g. sense strand and/or antisense strand). As such, a siNA sense strand having 3' and 5' end conjugates can be synthesized (see for example FIG. 65). Conjugate moieties can also be introduced in other combinations, such as at the 5'-end, 3'-end and/or loop portions of a siNA molecule (see for example FIG. 66).

Figure 67:
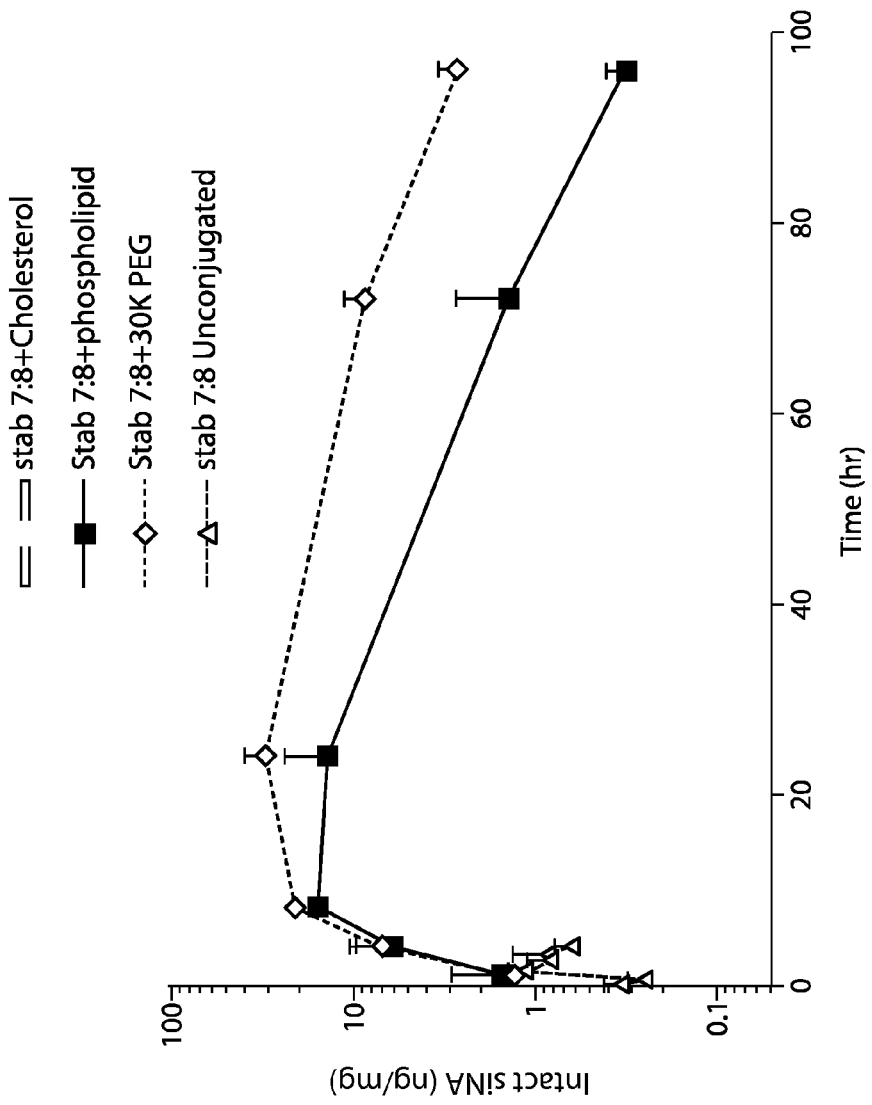
FIG. 67 shows a non-limiting example of the pharmacokinetic distribution of intact siNA in liver after administration of conjugated or unconjugated siNA molecules in mice.

Example 20: Phamacokinetics of siNA Conjugates
(FIG. 67)

Three nuclease resistant siNA molecule targeting site 1580 of hepatitis B virus (HBV) RNA were designed using Stab 7/8 chemistry (see Table IV) and a 5'-terminal conjugate moiety.

One siNA conjugate comprises a branched cholesterol conjugate linked to the sense strand of the siNA. The "cholesterol" siNA conjugate molecule has the structure shown below:

where T stands for thymidine, B stands for inverted deoxyabasic, G stands for 2'-deoxy guanosine, A stands for 2'-deoxy adenosine, G stands for 2'-O-methyl guanosine, A stands for 2'-O-methyl adenosine, u stands for 2'-fluoro uridine, c stands for 2'-fluoro cytidine, a stands for adenosine, and s stands for phosphorothioate linkage.

Another siNA conjugate comprises a branched phospholipid conjugate linked to the sense strand of the siNA. The "phospholipid" siNA conjugate molecule has the structure shown below:

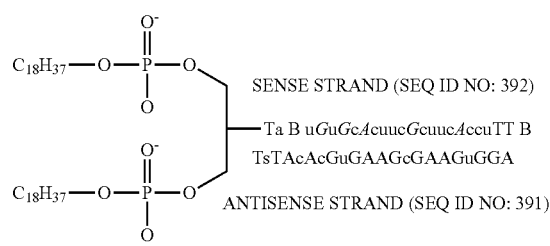

SENSE STRAND (SEQ ID NO: 392)

—Ta B u*GuGcA*cuuc*Gc*uuc*A*ccuTT B
TsTAcAcGuGAAGcGAAGuGGA

ANTISENSE STRAND (SEQ ID NO: 391)

where T stands for thymidine, B stands for inverted deoxyabasic, G stands for 2'-deoxy guanosine, A stands for 2'-deoxy adenosine, G stands for 2'-O-methyl guanosine, A stands for 2'-O-methyl adenosine, u stands for 2'-fluoro uridine, c stands for 2'-fluoro cytidine, a stands for adenosine, and s stands for phosphorothioate linkage.

Another siNA conjugate comprises a polyethylene glycol (PEG) conjugate linked to the sense strand of the siNA. The "PEG" siNA conjugate molecule has the structure shown below:

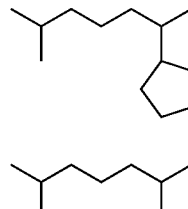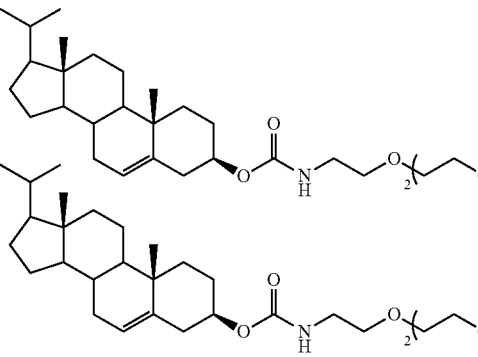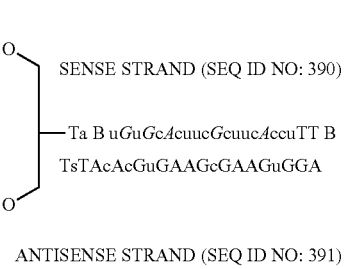

SENSE STRAND (SEQ ID NO: 390)

—Ta B u*GuGcA*cuuc*Gc*uuc*A*ccuTT B
TsTAcAcGuGAAGcGAAGuGGA

ANTISENSE STRAND (SEQ ID NO: 391)

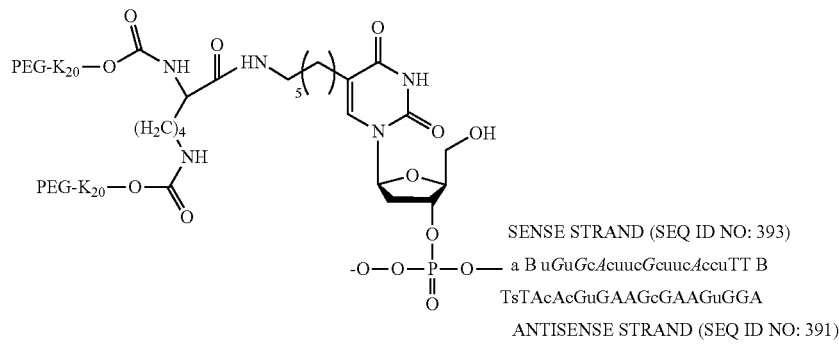

SENSE STRAND (SEQ ID NO: 393)
-O—O—P(=O)—O— a B u*GuGc*Acuuc*Gc*uuc*A*ccuTT B
TsTAcAcGuGAAGcGAAGuGGA
ANTISENSE STRAND (SEQ ID NO: 391)

where T stands for thymidine, B stands for inverted deoxyabasic, G stands for 2'-deoxy guanosine, A stands for 2'-deoxy adenosine, G stands for 2'-O-methyl guanosine, A stands for 2'-O-methyl adenosine, u stands for 2'-fluoro uridine, c stands for 2'-fluoro cytidine, a stands for adenosine, and s stands for phosphorothioate linkage.

The Cholesterol, Phospholipid, and PEG conjugates were evaluated for pharmakokinetic properties in mice compared to a non-conjugated siNA construct having matched chemistry and sequence. This study was conducted in female CD-1 mice approximately 26 g (6-7 weeks of age). Animals were housed in groups of 3. Food and water were provided ad libitum. Temperature and humidity were according to Pharmacology Testing Facility performance standards (SOP's) which are in accordance with the 1996 Guide for the Care and Use of Laboratory Animals (NRC). Animals were acclimated to the facility for at least 3 days prior to experimentation.

Absorbance at 260 nm was used to determine the actual concentration of the stock solution of pre-annealed HBV siNA. An appropriate amount of HBV siNA was diluted in sterile veterinary grade normal saline (0.9%) based on the average body weight of the mice. A small amount of the antisense (Stab 7) strand was internally labeled with gamma 32P-ATP. The 32P-labeled stock was combined with excess sense strand (Stab 8) and annealed. Annealing was confirmed prior to combination with unlabled drug. Each mouse received a subcutaneous bolus of 30 mg/kg (based on duplex) and approximately 10 million cpm (specific activity of approximately 15 cpm/ng).

Three animals per timepoint (1, 4, 8, 24, 72, 96 h) were euthanized by CO2 inhalation followed immediately by exsanguination. Blood was sampled from the heart and collected in heparinized tubes. After exsanguination, animals were perfused with 10-15 mL of sterile veterinary grade saline via the heart. Samples of liver were then collected and frozen.

Figure 43:
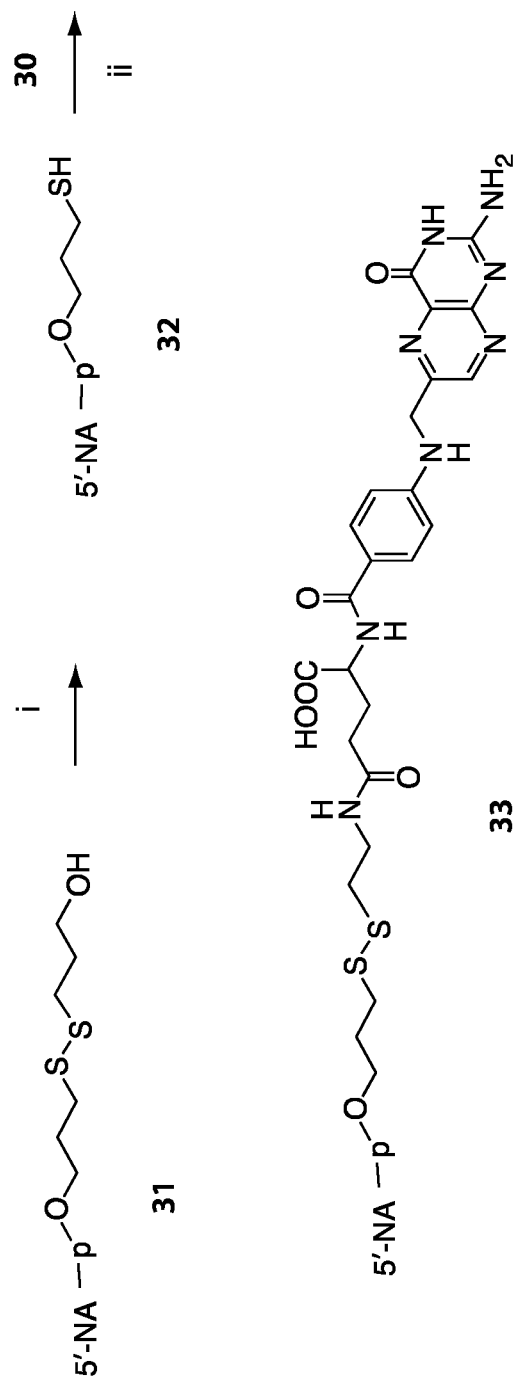
FIG. 43 shows a synthetic scheme for generating an oligonucleotide or nucleic acid-folate conjugate.

Tissue samples were homogenized in a digestion buffer prior to compound quantitation. Quantitation of intact compound was determined by scintillation counting followed by PAGE and phosphorimage analysis. Results are shown in FIG. 43. As shown in the figure, the conjugated siNA constructs shown vastly improved liver PK compared to the unconjugated siNA construct.

Figure 68:
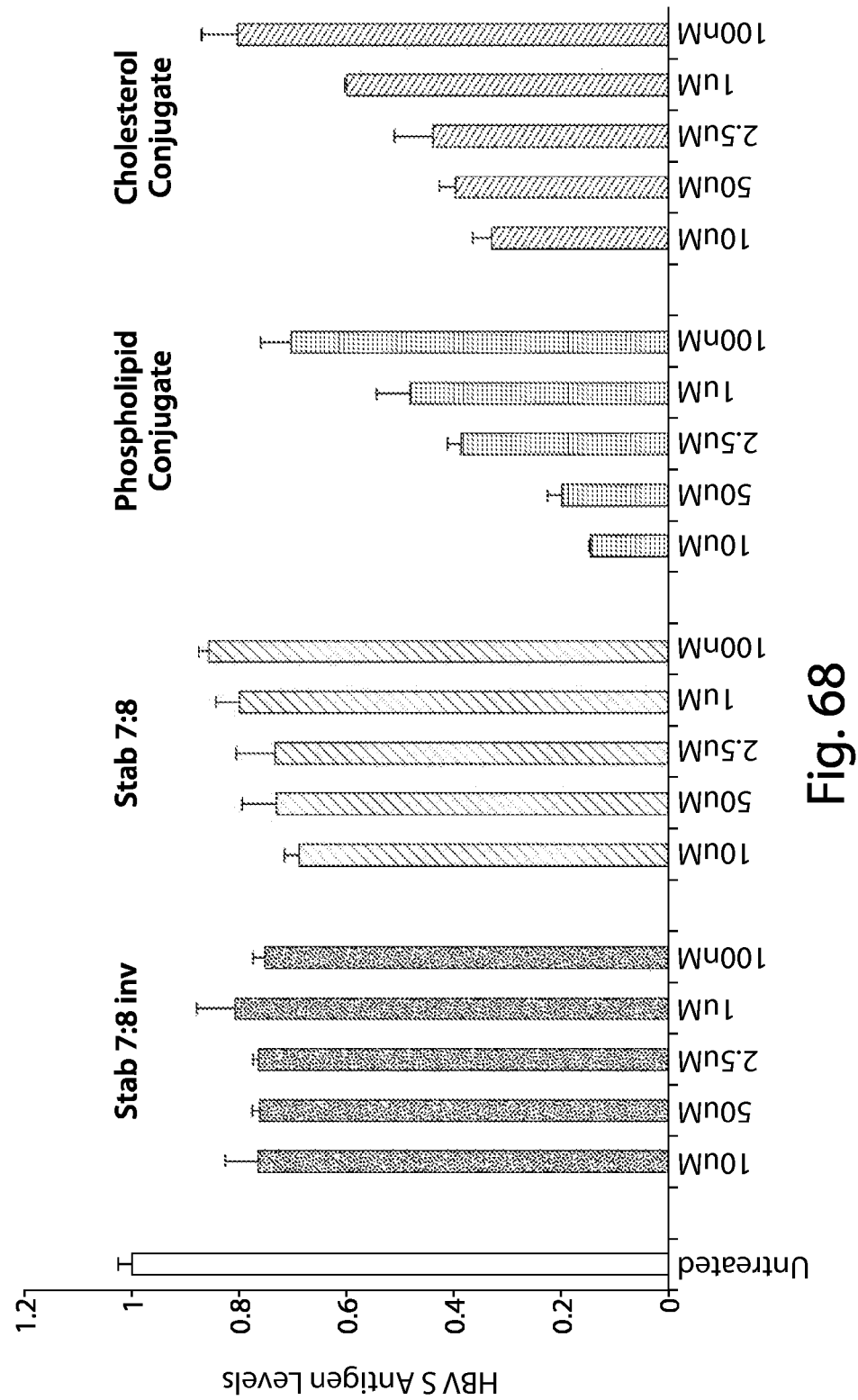
FIG. 68 shows a non-limiting example of the activity of conjugated siNA constructs compared to matched chemistry unconjugated siNA constructs in an HBV cell culture system without the use of transfection lipid. As shown in the Figure, siNA conjugates provide efficacy in cell culture without the need for transfection reagent.
Figure 69:
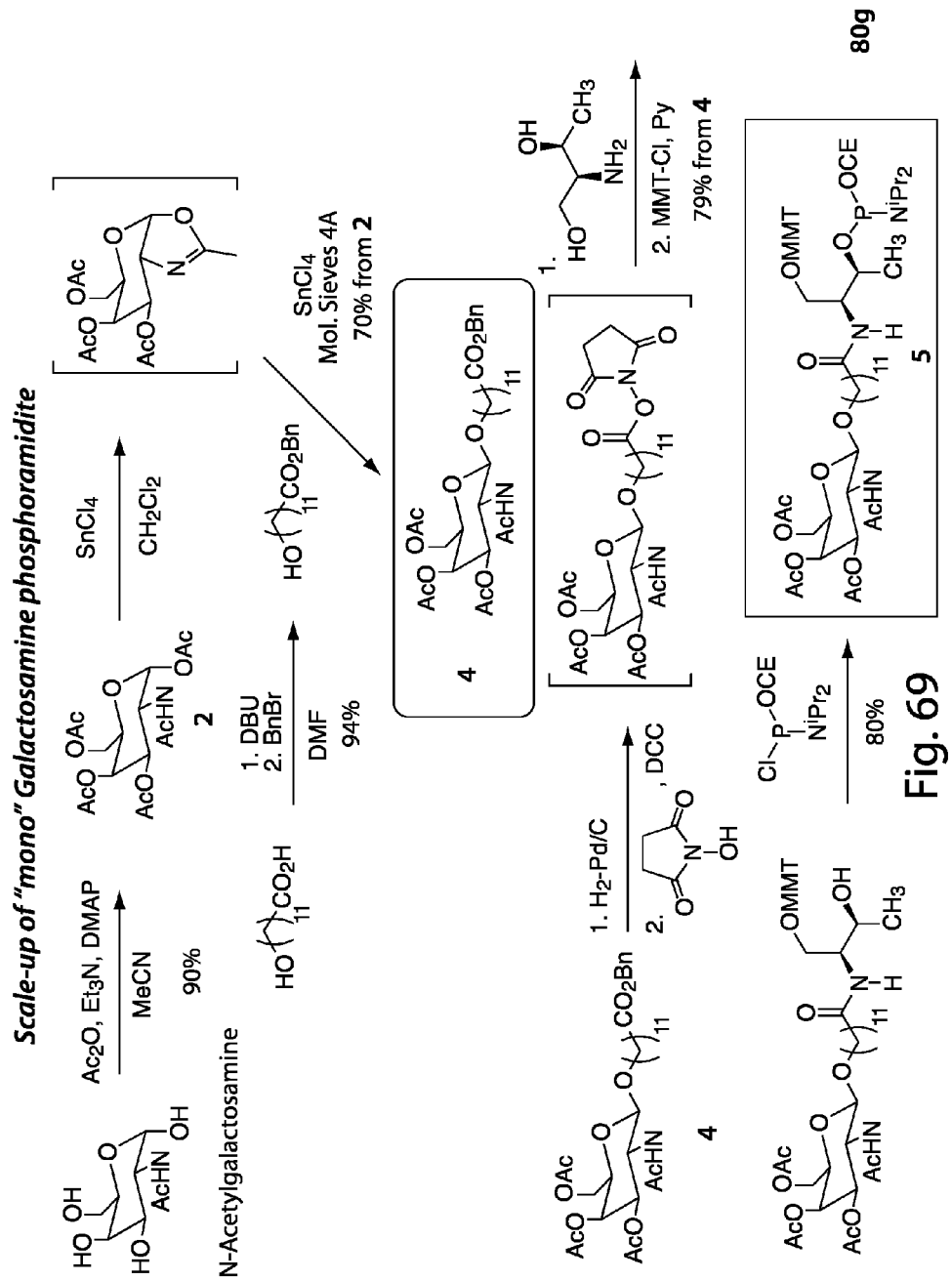
FIG. 69 shows a non-limiting example of a scheme for the synthesis of a mono-galactosamine phosphoramidite of the invention that can be used to generate galactosamine conjugated nucleic acid molecules.
Figure 70:
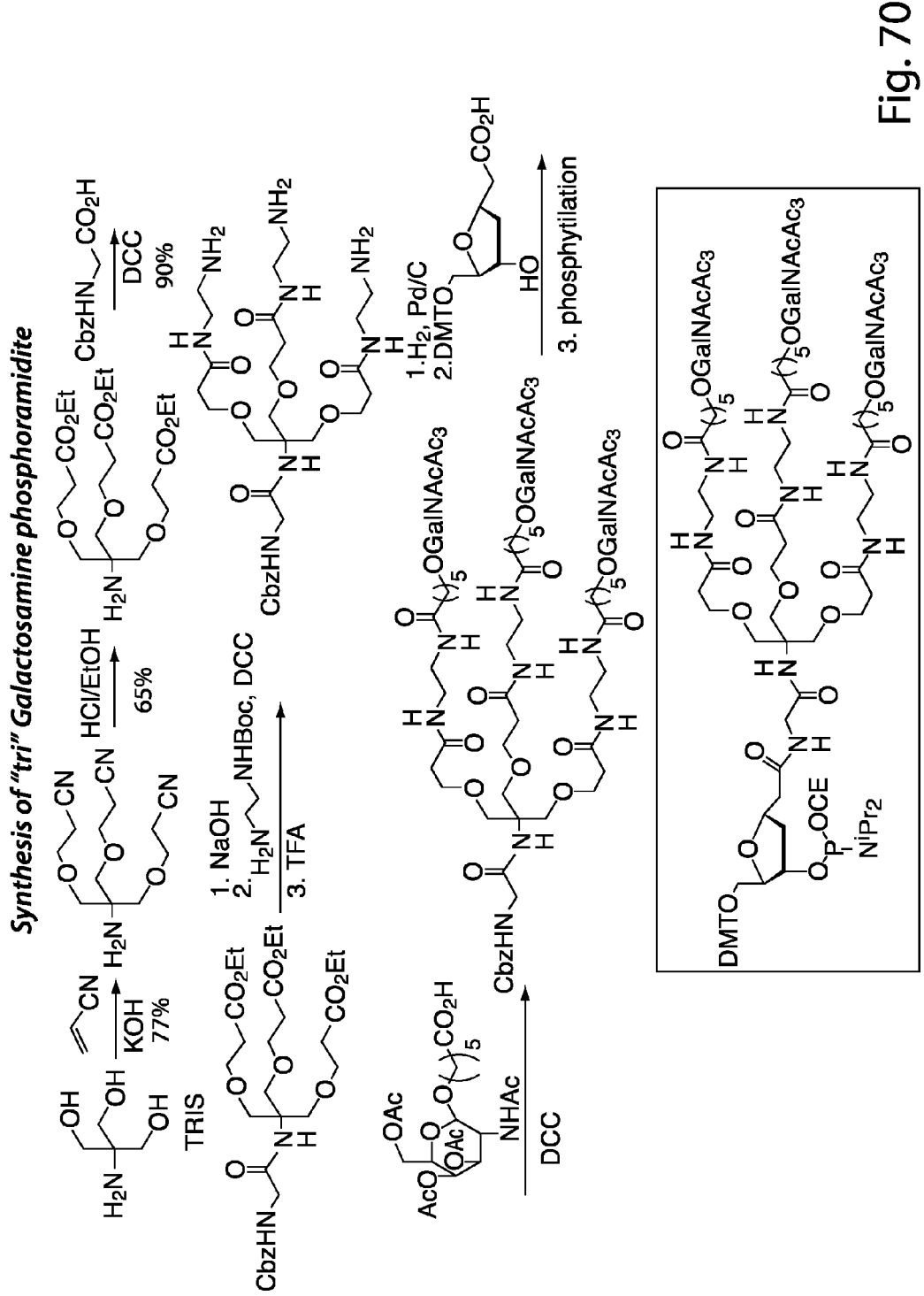
FIG. 70 shows a non-limiting example of a scheme for the synthesis of a tri-galactosamine phosphoramidite of the invention that can be used to generate tri-galactosamine conjugated nucleic acid molecules.
Figure 71:
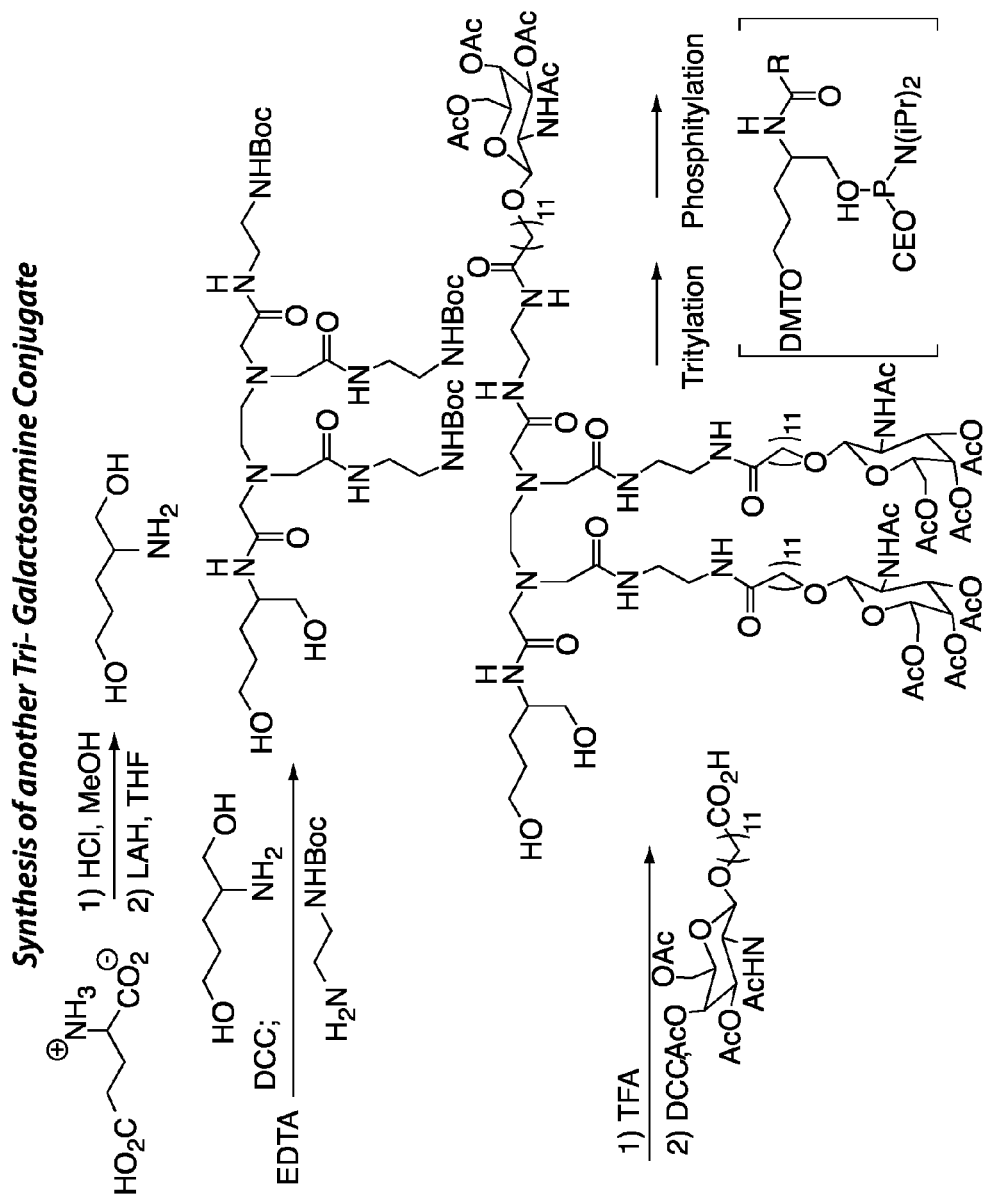
FIG. 71 shows a non-limiting example of a scheme for the synthesis of another tri-galactosamine phosphoramidite of the invention that can be used to generate tri-galactosamine conjugated nucleic acid molecules.
Figure 72:
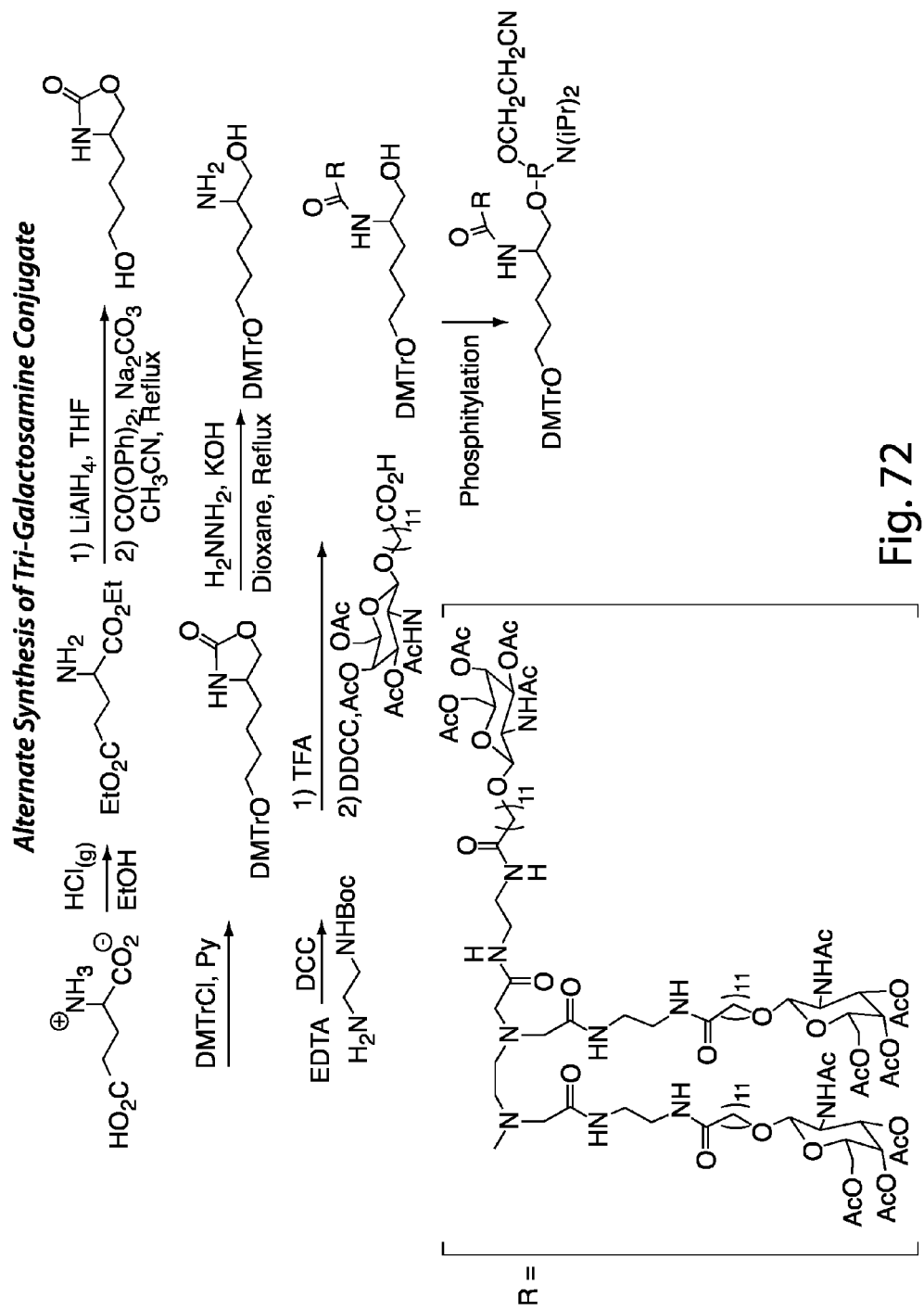
FIG. 72 shows a non-limiting example of an alternate scheme for the synthesis of a tri-galactosamine phosphoramidite of the invention that can be used to generate tri-galactosamine conjugated nucleic acid molecules.
Figure 73:
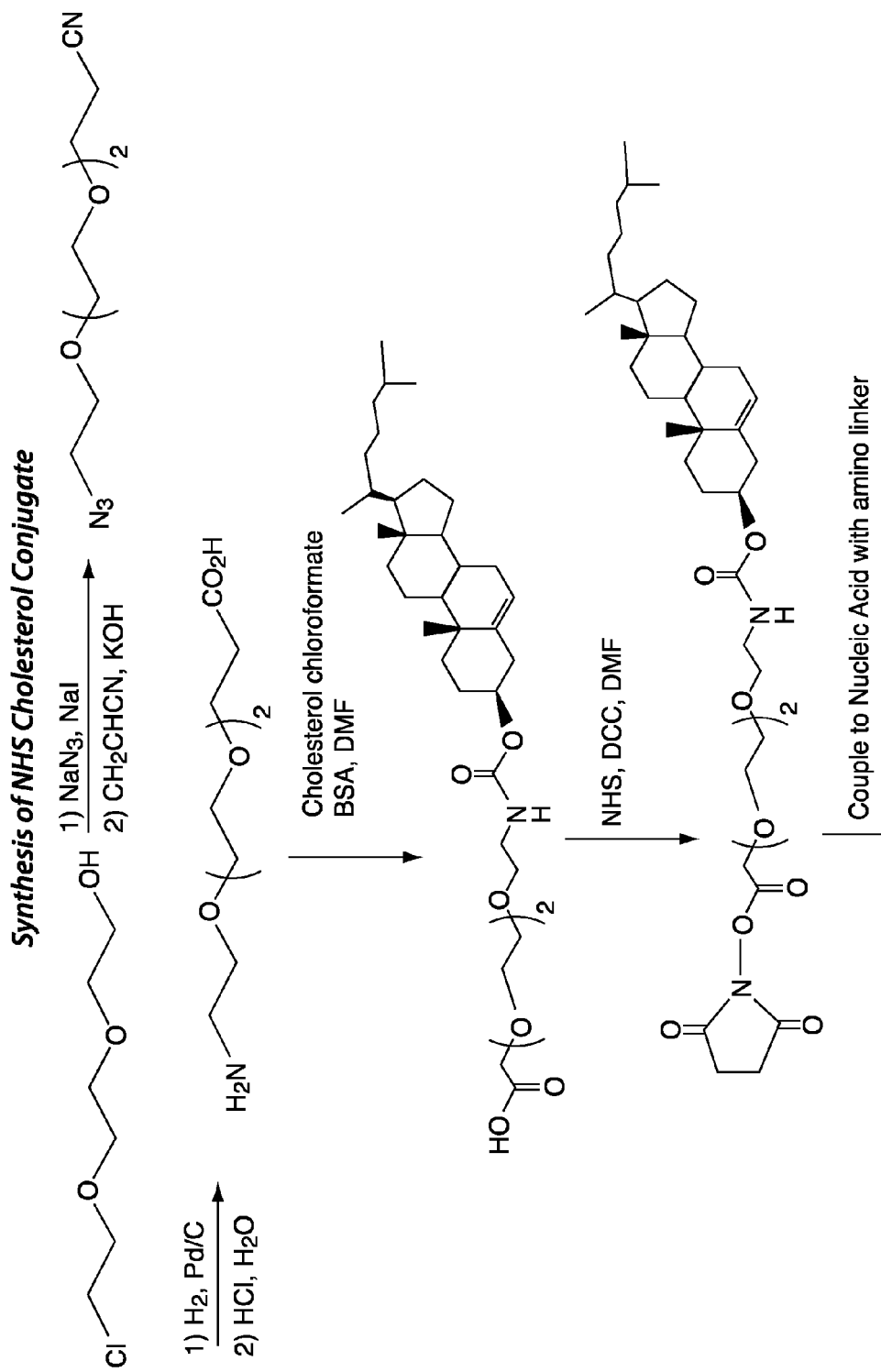
FIG. 73 shows a non-limiting example of a scheme for the synthesis of a cholesterol NHS ester of the invention that can be used to generate cholesterol conjugated nucleic acid molecules.
Figure 74:
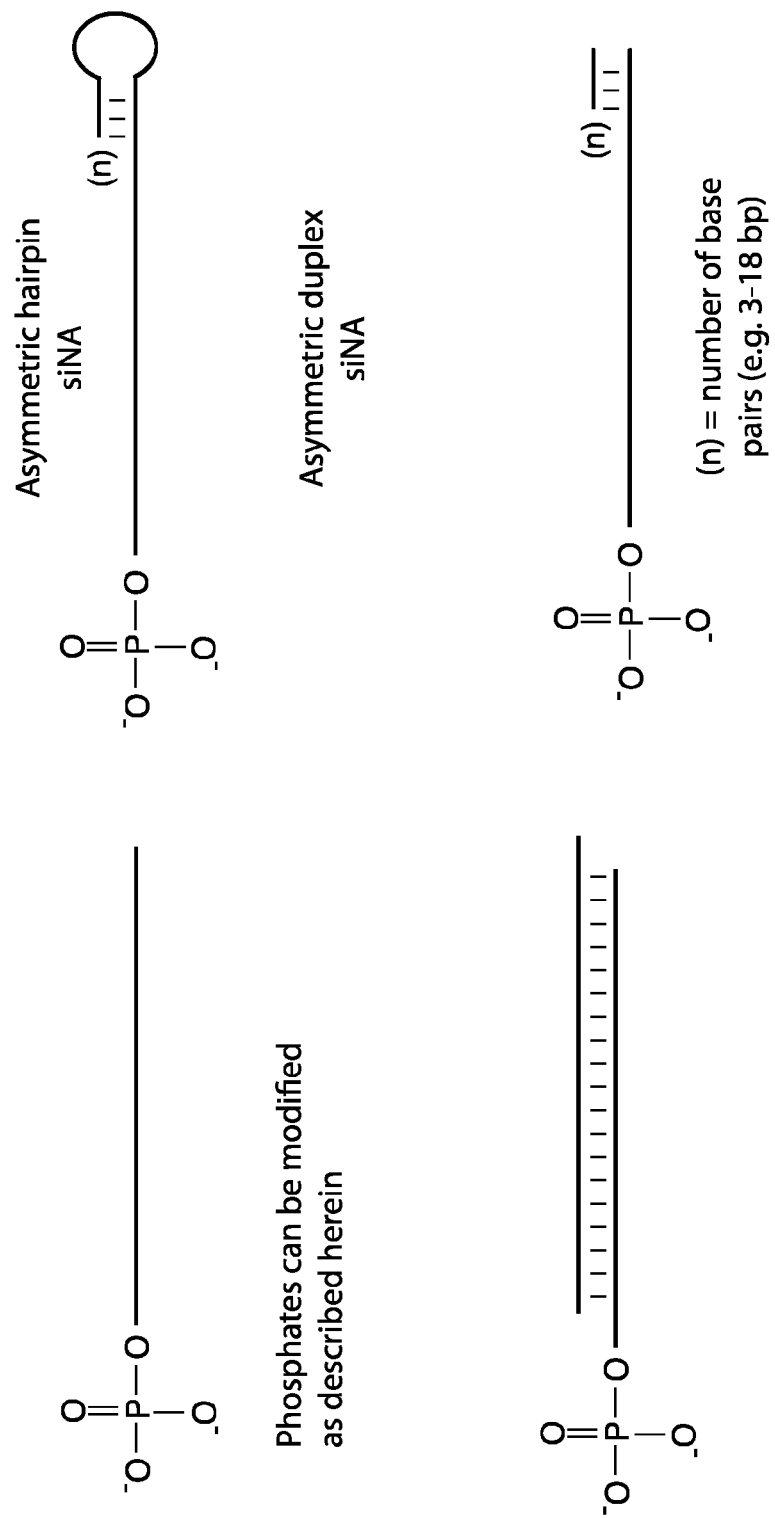
FIG. 74 shows non-limiting examples of phosphorylated siNA molecules of the invention, including linear and duplex constructs and asymmetric derivatives thereof.
Figure 75:
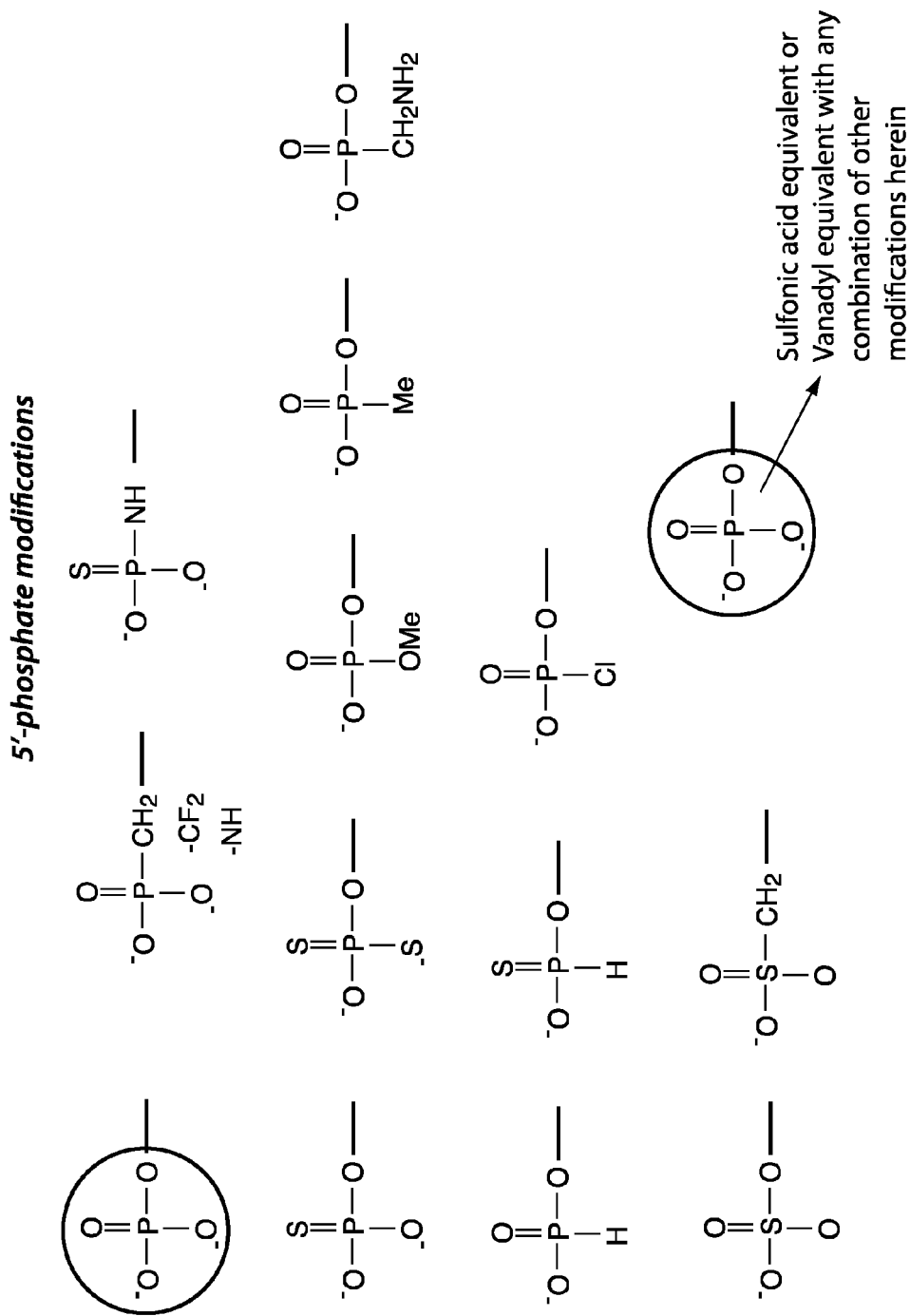
FIG. 75 shows non-limiting examples of a chemically modified terminal phosphate groups of the invention.
Figure 77B:
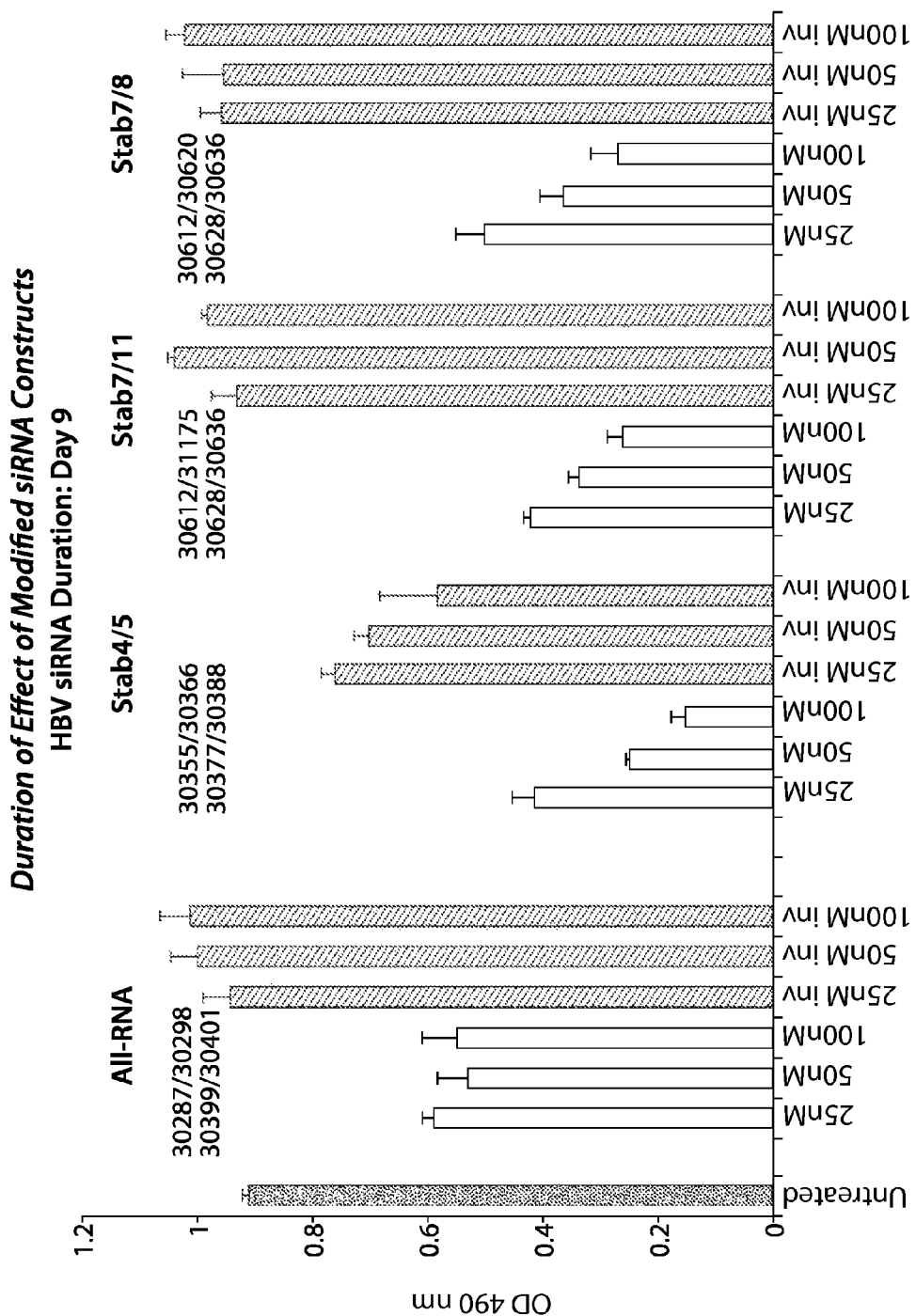
Figure 77D:
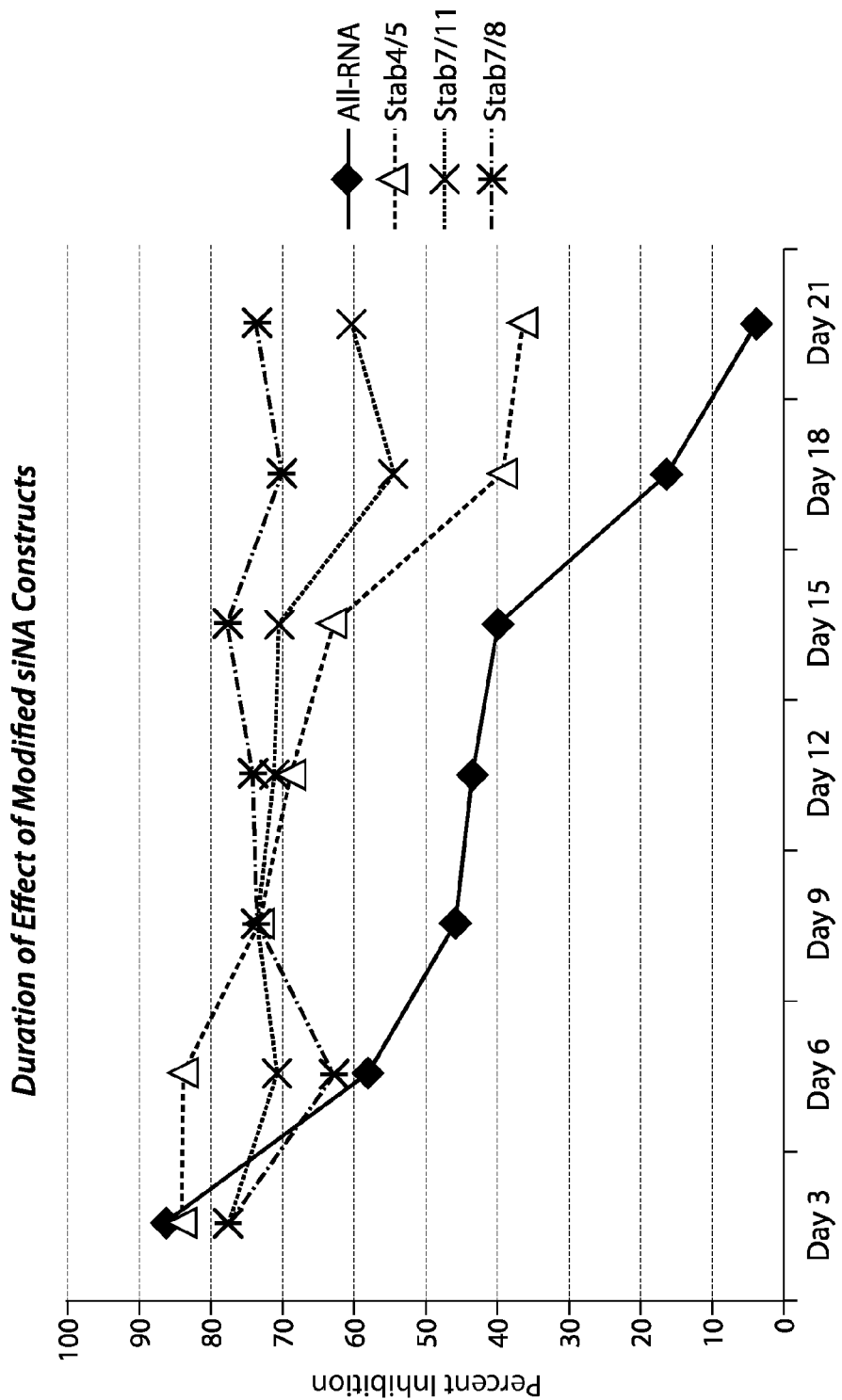
Figure 77E:
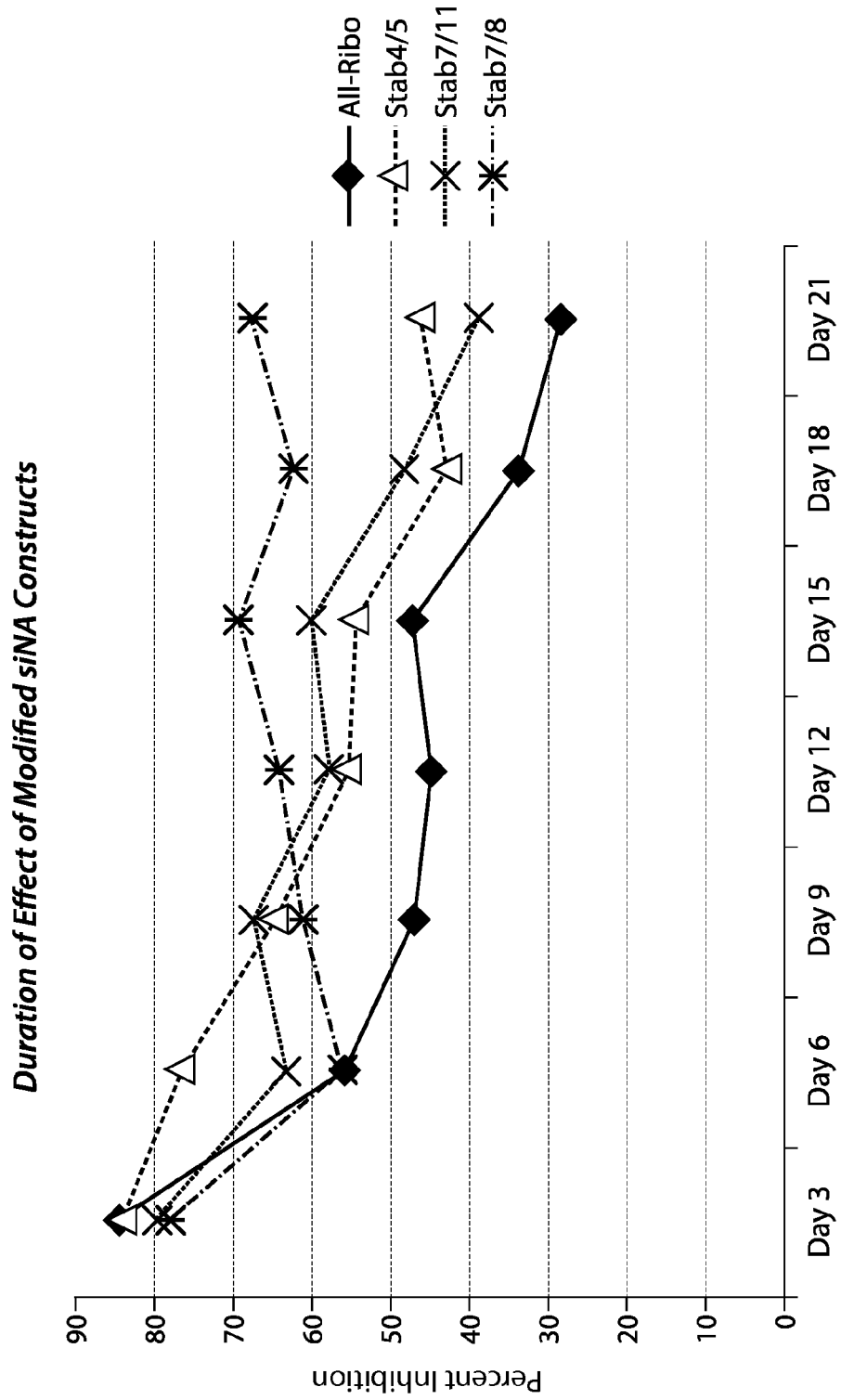
Figure 77F:
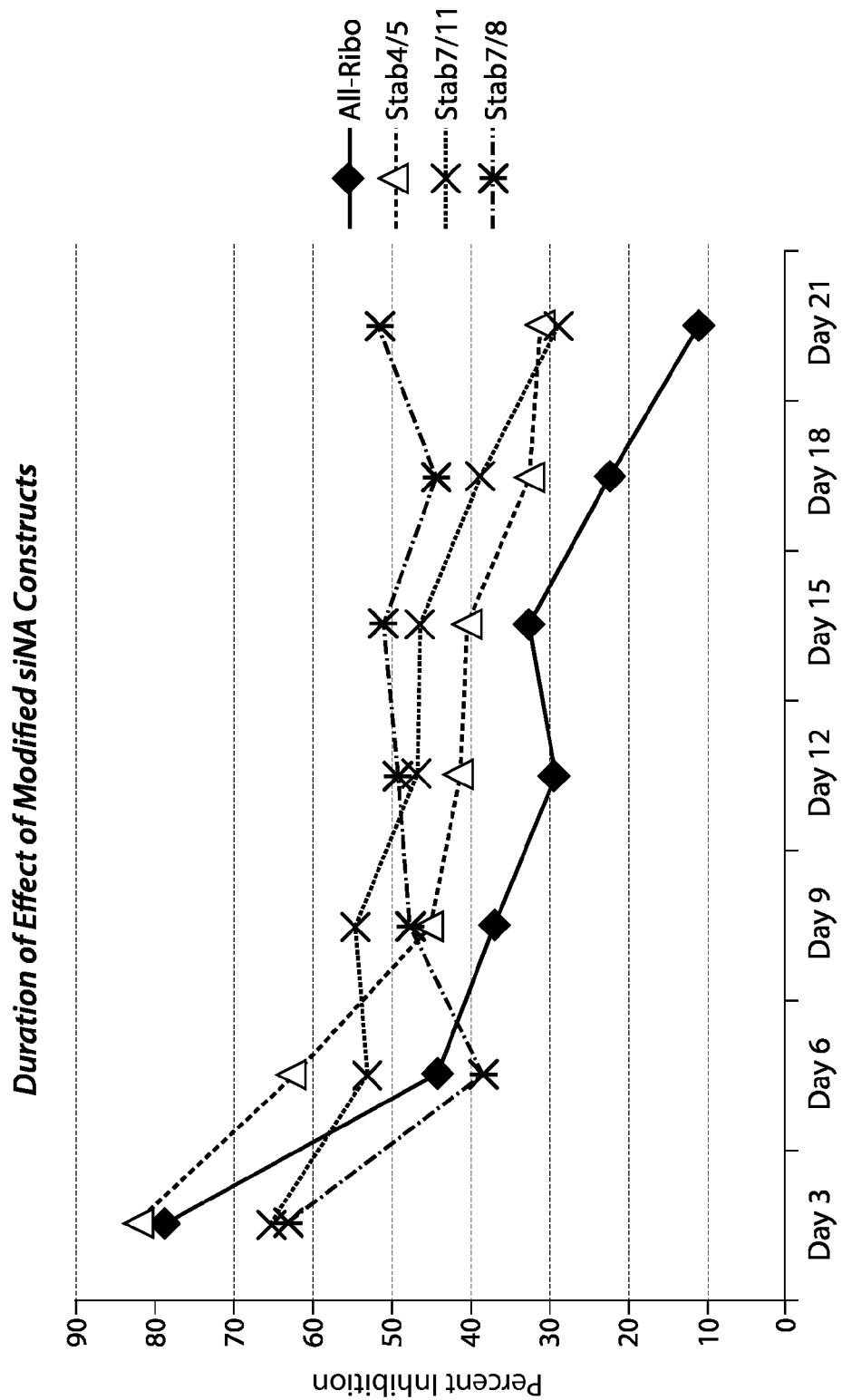
Figure 78:
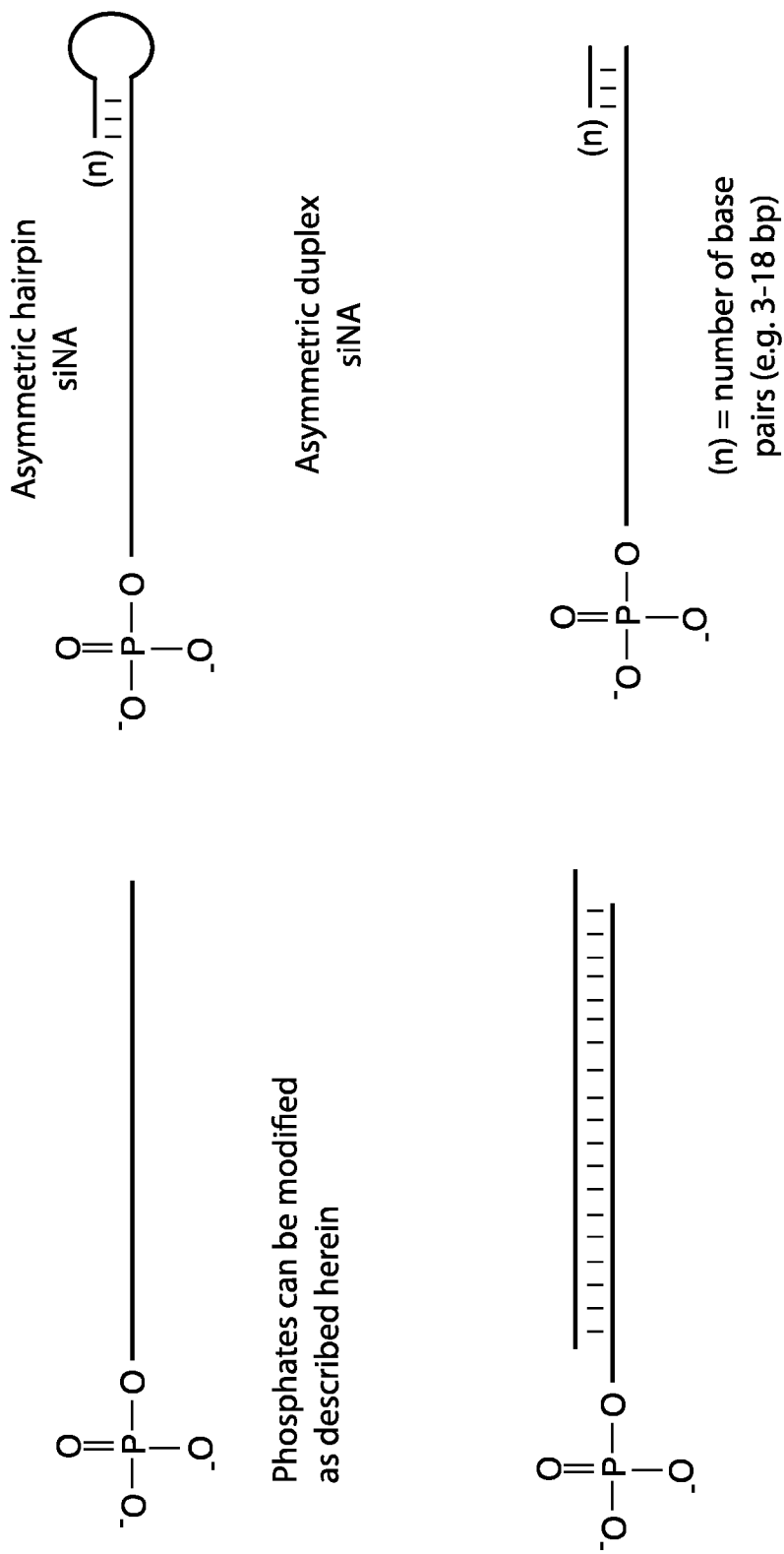
FIG. 78 shows non-limiting examples of phosphorylated siNA molecules of the invention, including linear and duplex constructs and asymmetric derivatives thereof.
Figure 79:
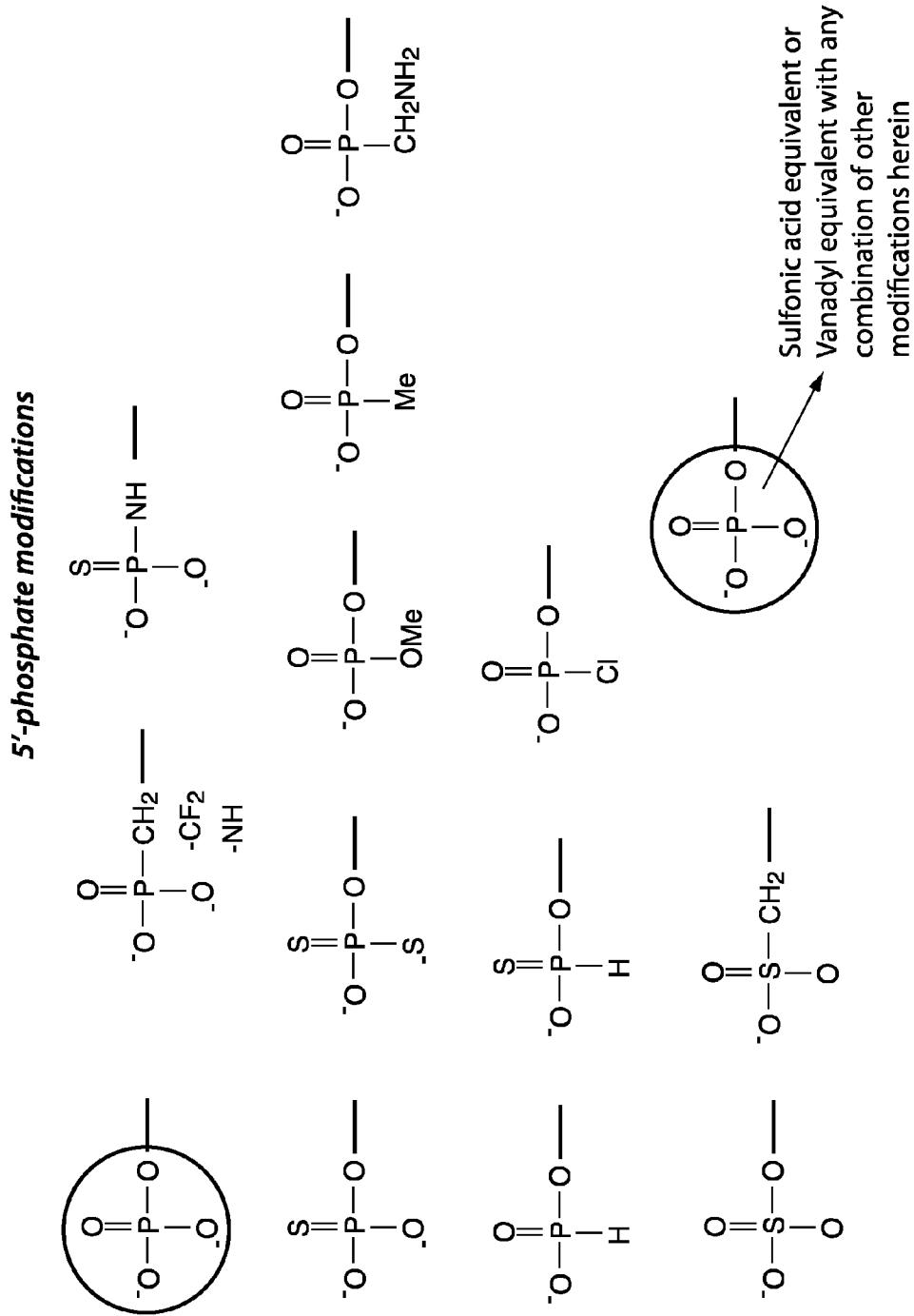
FIG. 79 shows non-limiting examples of chemically modified terminal phosphate groups of the invention.

Example 21: Cell Culture of siNA Conjugates
(FIG. 68)

The Cholesterol conjugates and Phospholipid conjugated siNA constructs described in Example 20 above were evaluated for cell culture efficacy in a HBV cell culture system.

Transfection of HepG2 Cells with psHBV-1 and siNA

The human hepatocellular carcinoma cell line Hep G2 was grown in Dulbecco's modified Eagle media supplemented with 10% fetal calf serum, 2 mM glutamine, 0.1 mM nonessential amino acids, 1 mM sodium pyruvate, 25 mM Hepes, 100 units penicillin, and 100 µg/ml streptomycin. To generate a replication competent cDNA, prior to transfection the HBV genomic sequences are excised from the bacterial plasmid sequence contained in the psHBV-1 vector. Other methods known in the art can be used to generate a replication competent cDNA. This was done with an EcoRI and Hind III restriction digest. Following completion of the digest, a ligation was performed under dilute conditions (20 µg/ml) to favor intermolecular ligation. The total ligation mixture was then concentrated using Qiagen spin columns.

siNA Activity Screen and Dose Response Assay

Figure 44:
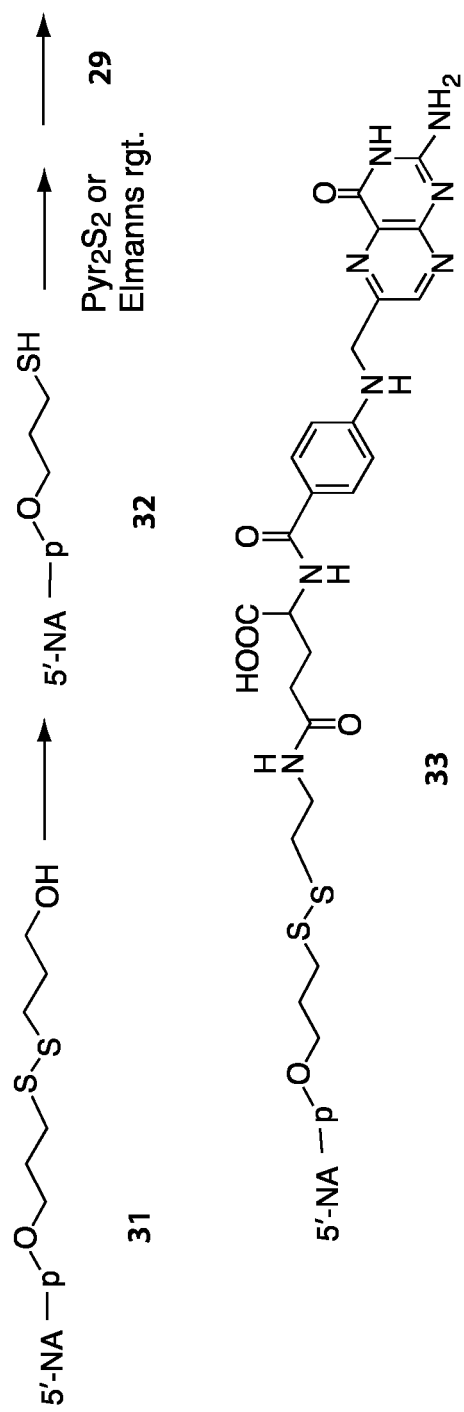
FIG. 44 shows an alternative synthetic scheme for generating an oligonucleotide or nucleic acid-folate conjugate.
Figure 45:
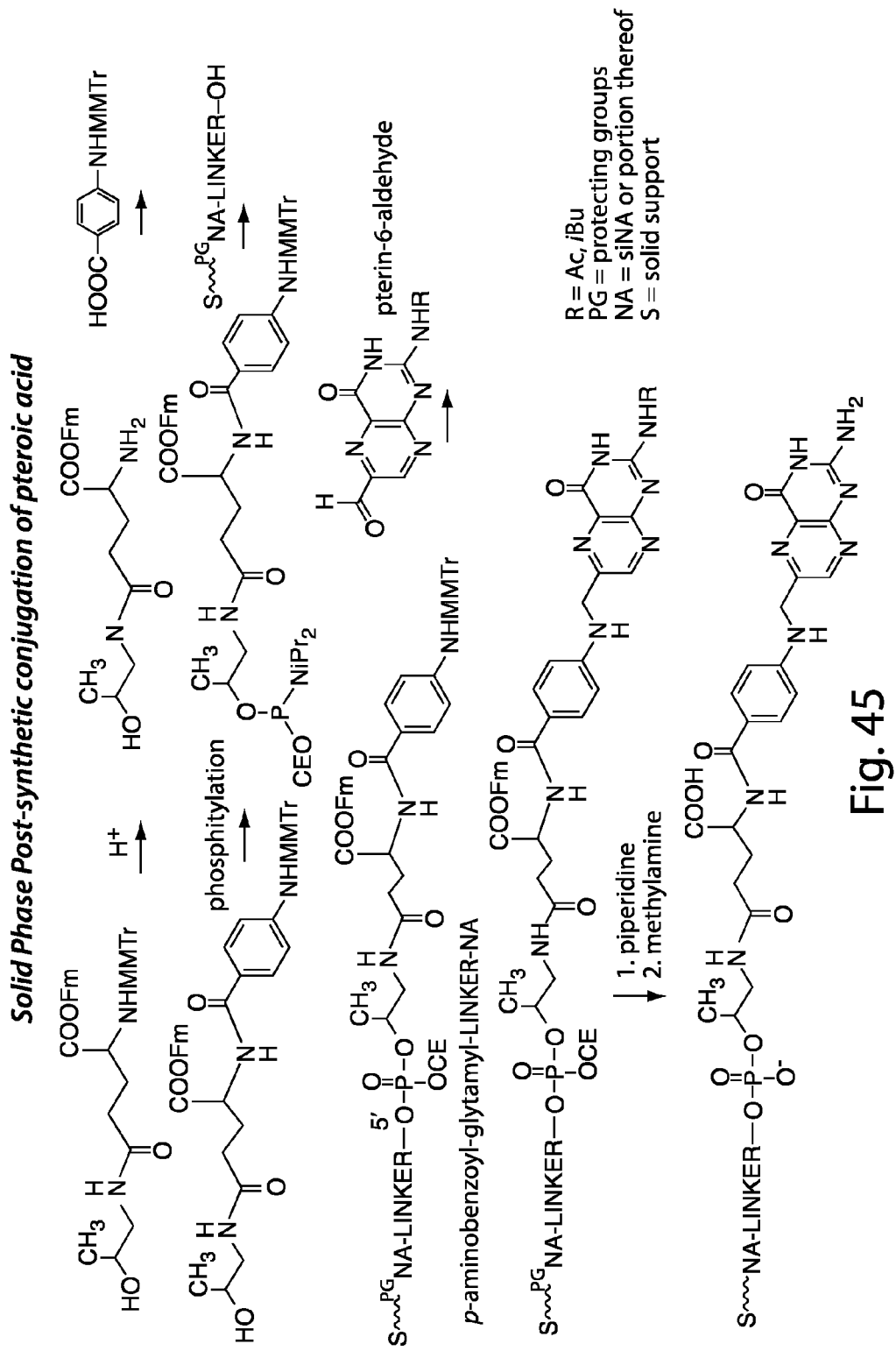
FIG. 45 shows an alternative synthetic scheme for post-synthetic modification of a nucleic acid molecule to produce a folate conjugate.
Figure 46:
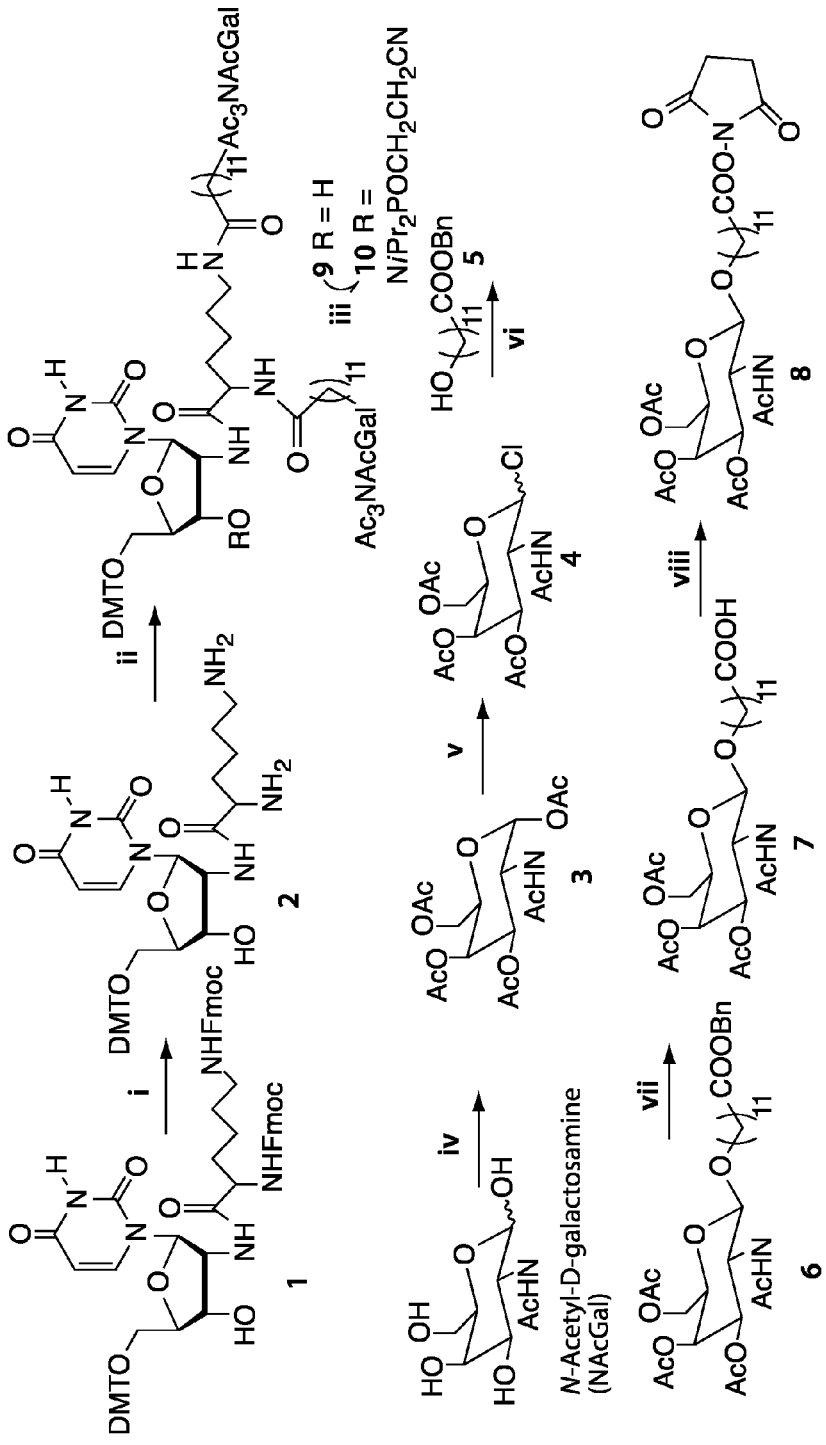
FIG. 46 shows a non-limiting example of a synthetic scheme for the synthesis of a N-acetyl-D-galactosamine-2'-aminouridine phosphoramidite conjugate of the invention.
Figure 47:
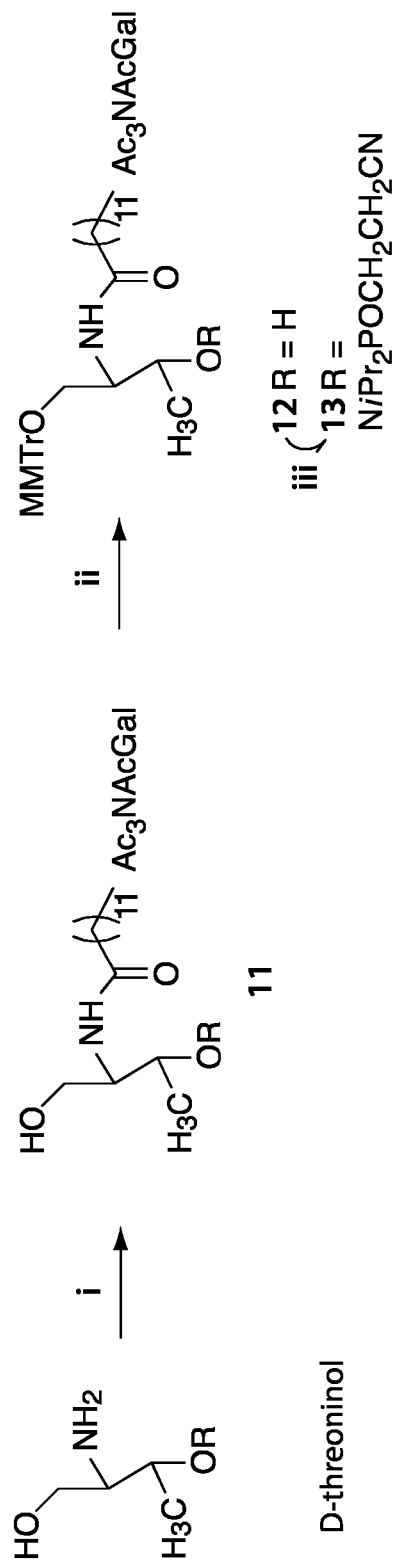
FIG. 47 shows a non-limiting example of a synthetic scheme for the synthesis of a N-acetyl-D-galactosamine-D-threoninol phosphoramidite conjugate of the invention.
Figure 48:
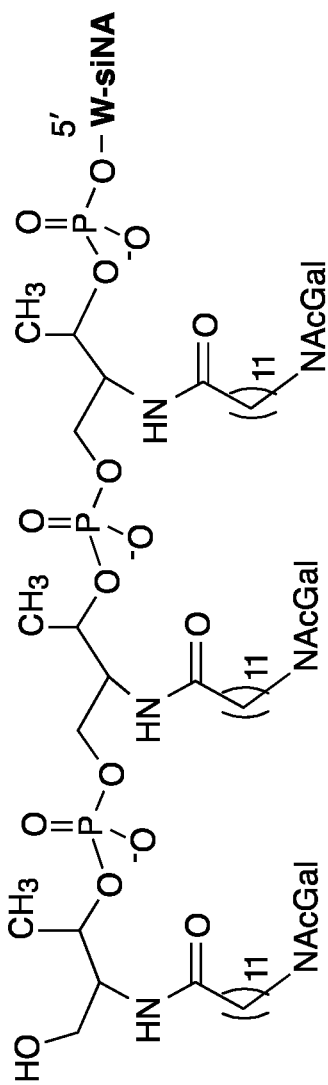
FIG. 48 shows a non-limiting example of a N-acetyl-D-galactosamine siNA nucleic acid conjugate of the invention. W shown in the example refers to a biodegradable linker, for example a nucleic acid dimer, trimer, or tetramer comprising ribonucleotides and/or deoxyribonucleotides. The siNA can be conjugated at the 3', 5' or both 3' and 5' ends of the sense strand of a double stranded siNA and/or the 3'-end of the antisense strand of the siNA. A single stranded siNA molecule can be conjugated at the 3'-end of the siNA.
Figure 49:
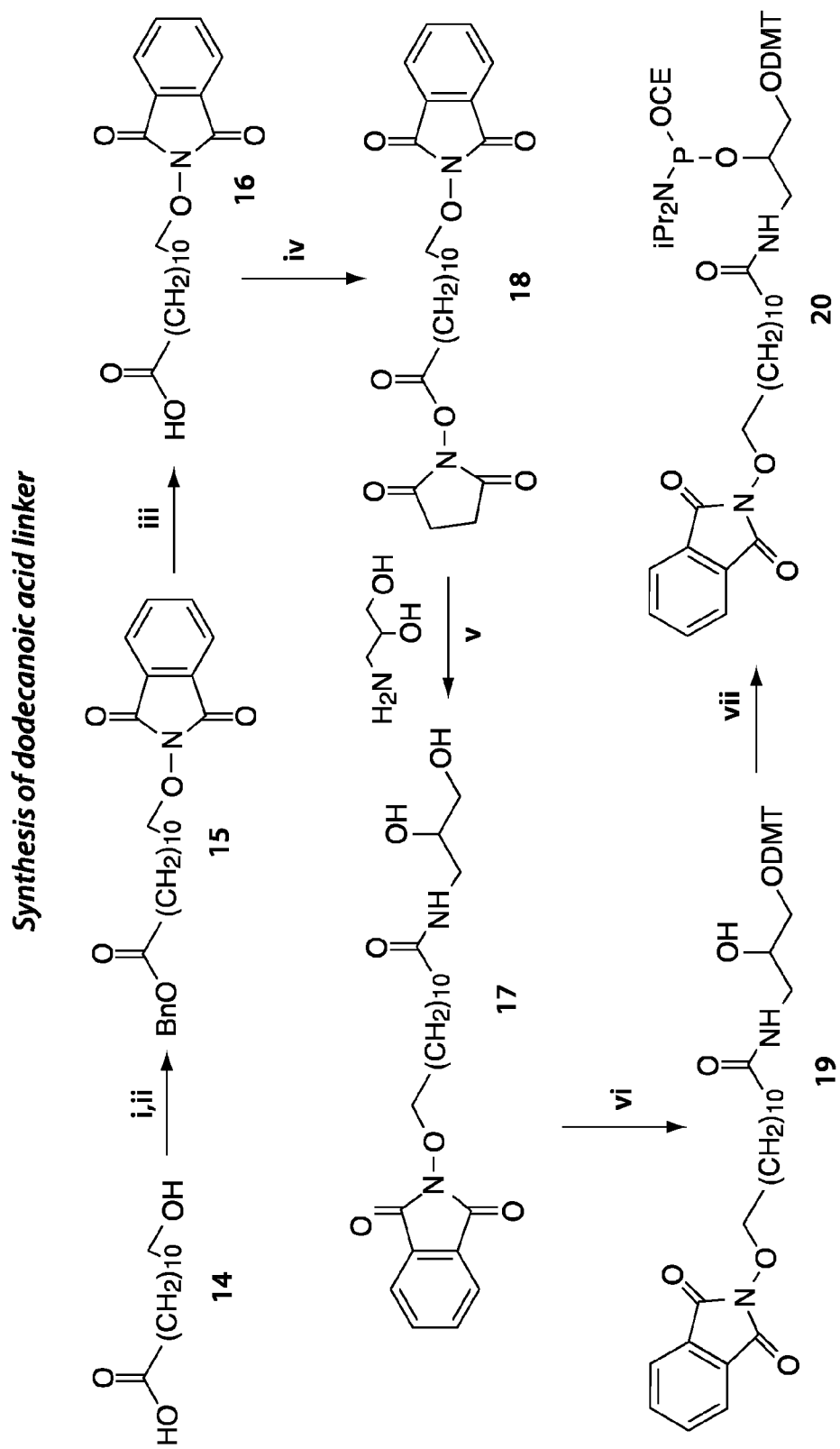
FIG. 49 shows a non-limiting example of a synthetic scheme for the synthesis of a dodecanoic acid derived conjugate linker of the invention.
Figure 50:
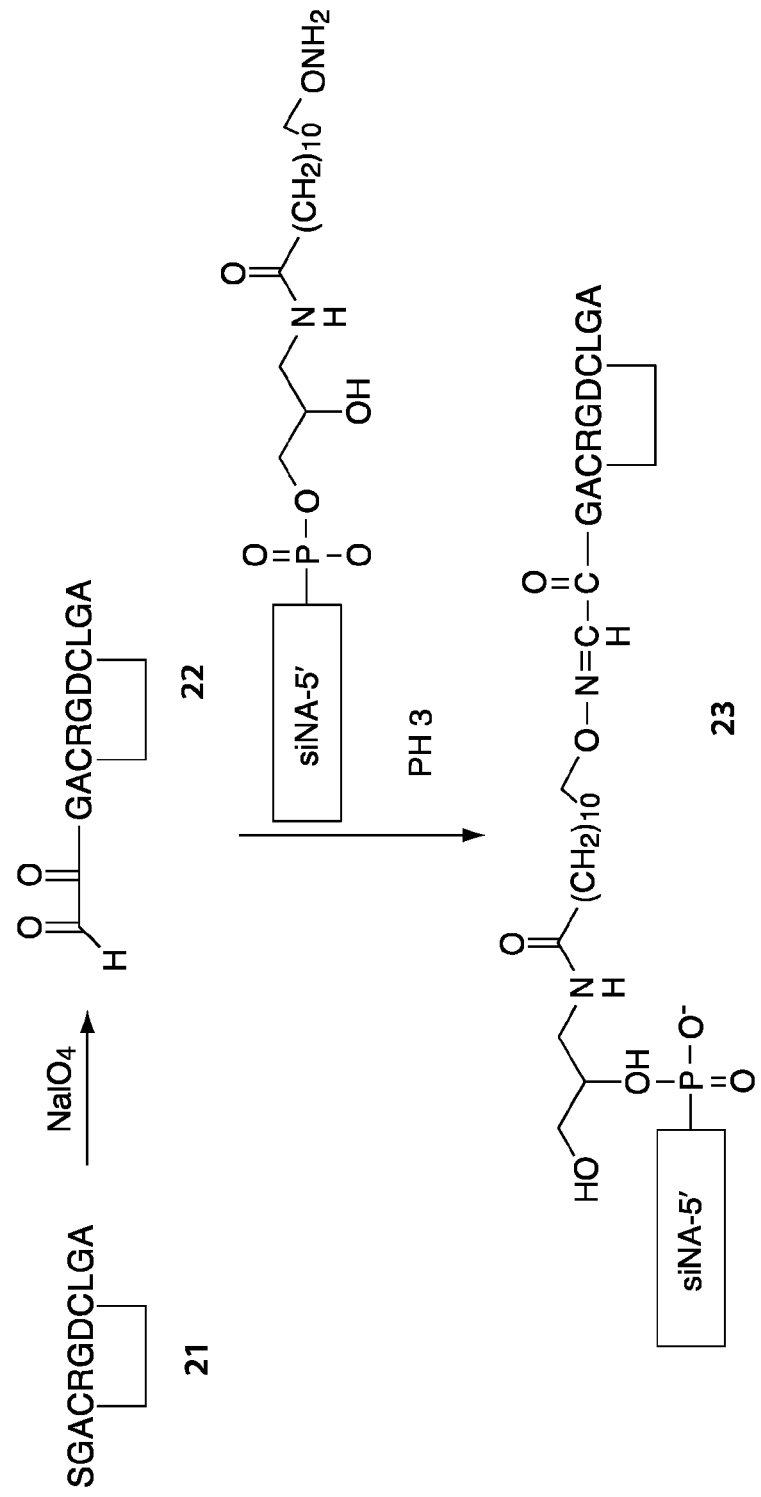
FIG. 50 shows a non-limiting example of a synthetic scheme for the synthesis of an oxime linked nucleic acid/peptide conjugate of the invention.
Figure 51:
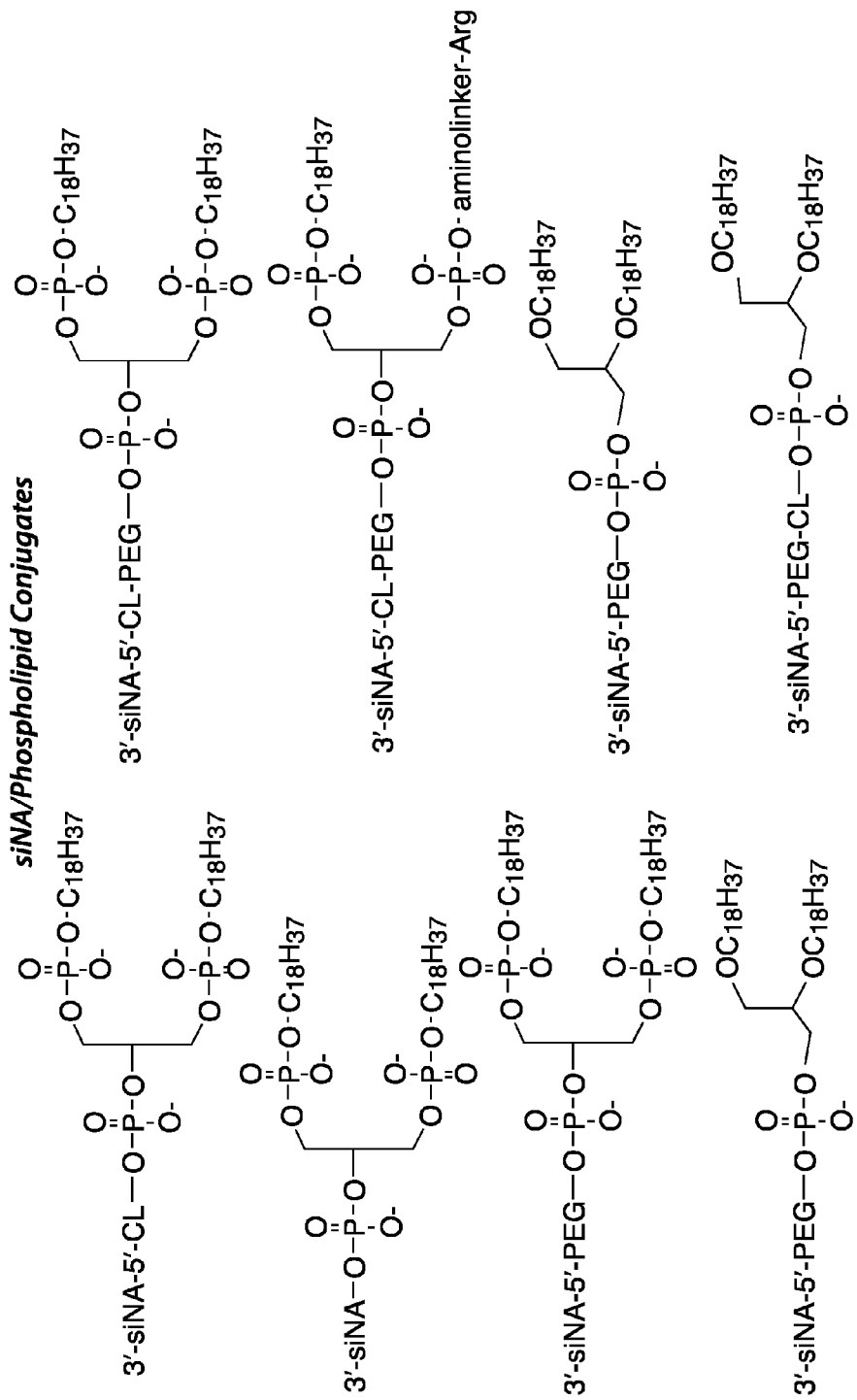
FIG. 51 shows non-limiting examples of phospholipid derived siNA conjugates of the invention. CL shown in the examples refers to a biodegradable linker, for example a nucleic acid dimer, trimer, or tetramer comprising ribonucleotides and/or deoxyribonucleotides. The siNA can be conjugated at the 3', 5' or both 3' and 5' ends of the sense strand of a double stranded siNA and/or the 3'-end of the antisense strand of the siNA. A single stranded siNA molecule can be conjugated at the 3'-end of the siNA.
Figure 52:
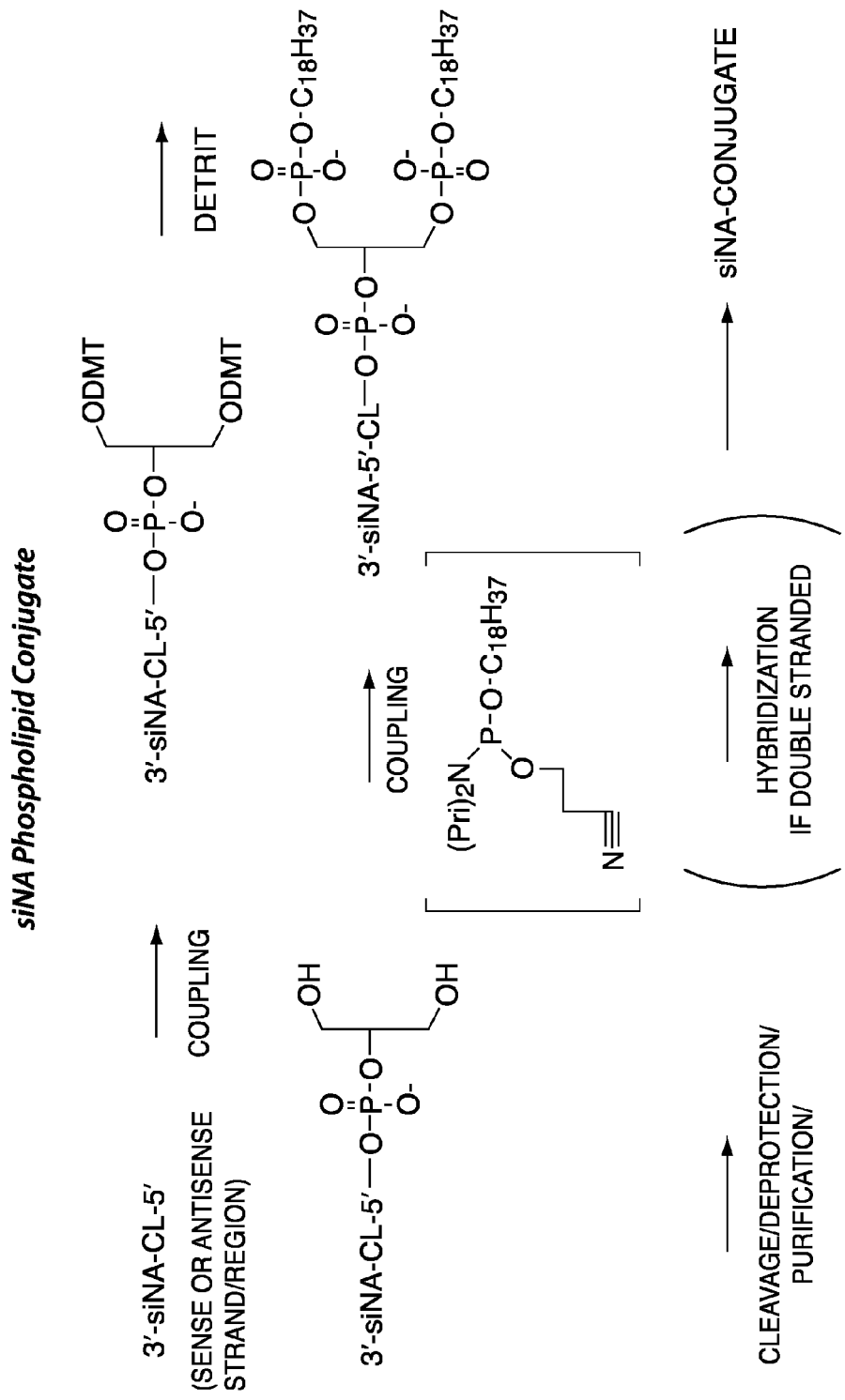
FIG. 52 shows a non-limiting example of a synthetic scheme for preparing a phospholipid derived siNA conjugates of the invention.
Figure 54:
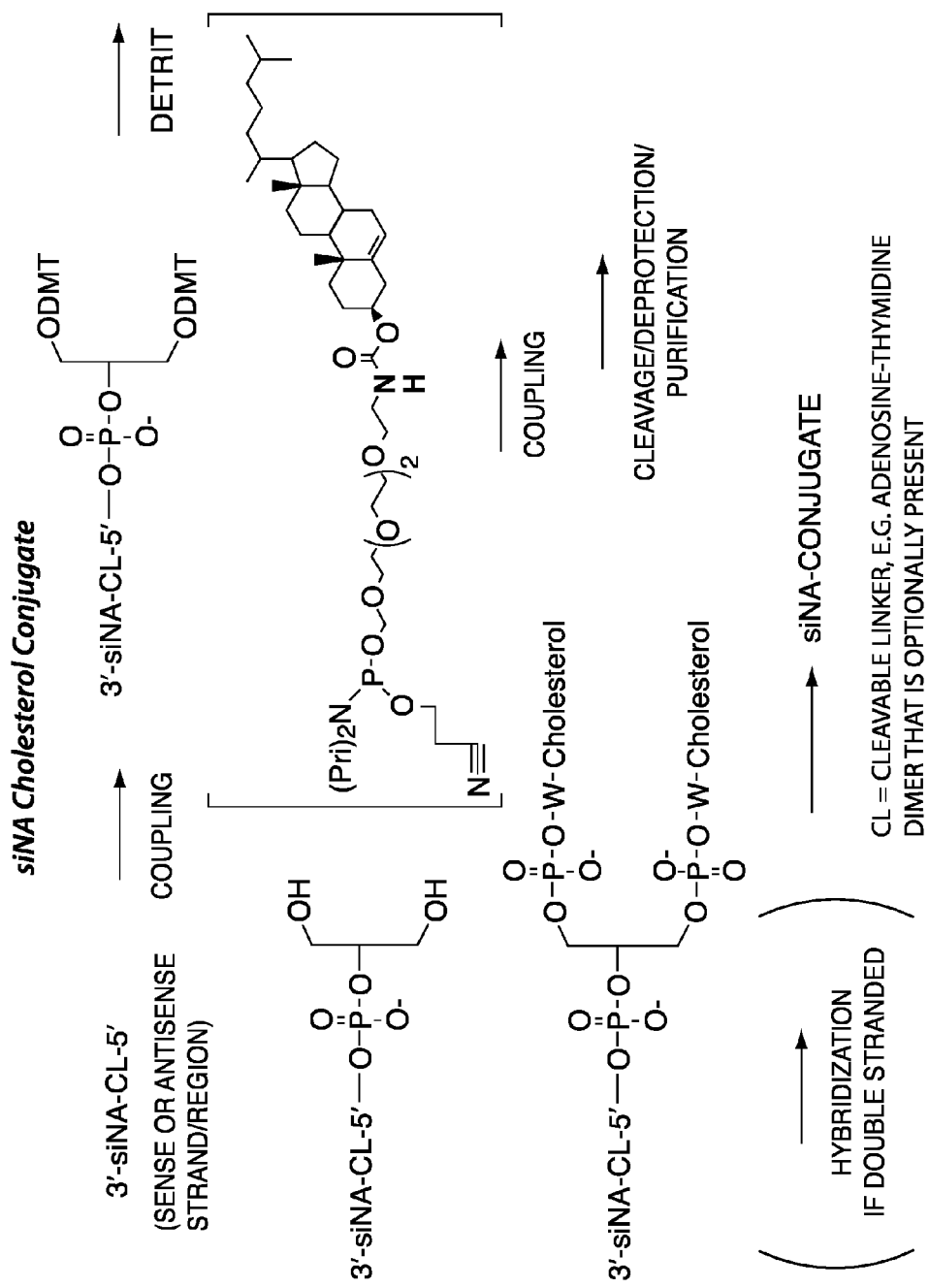
FIG. 54 shows a non-limiting example of the synthesis of siNA cholesterol conjugates of the invention using a phosphoramidite approach.
Figure 55:
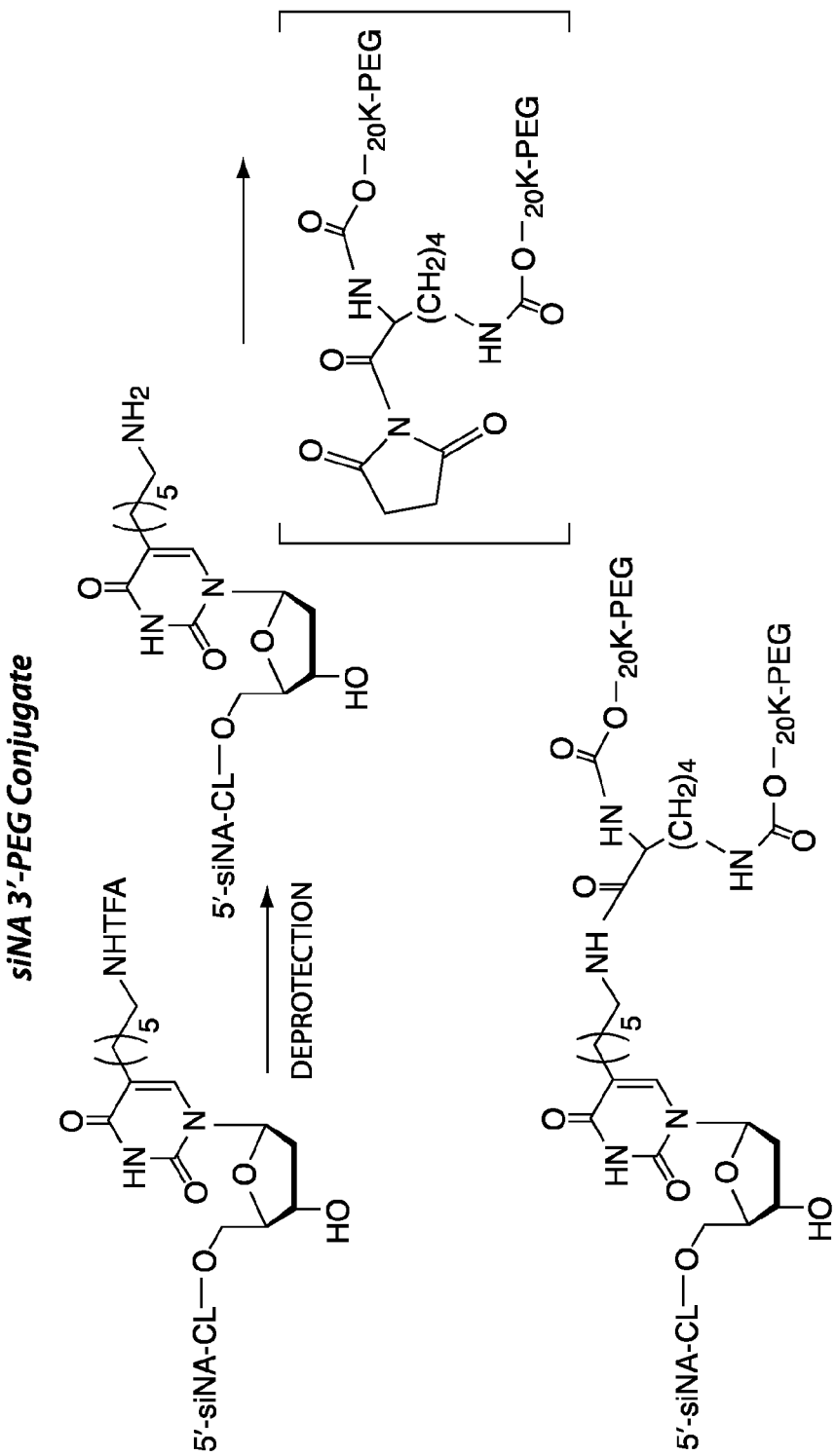
FIG. 55 shows a non-limiting example of the synthesis of siNA PEG conjugates of the invention using NHS ester coupling.
Figure 56:
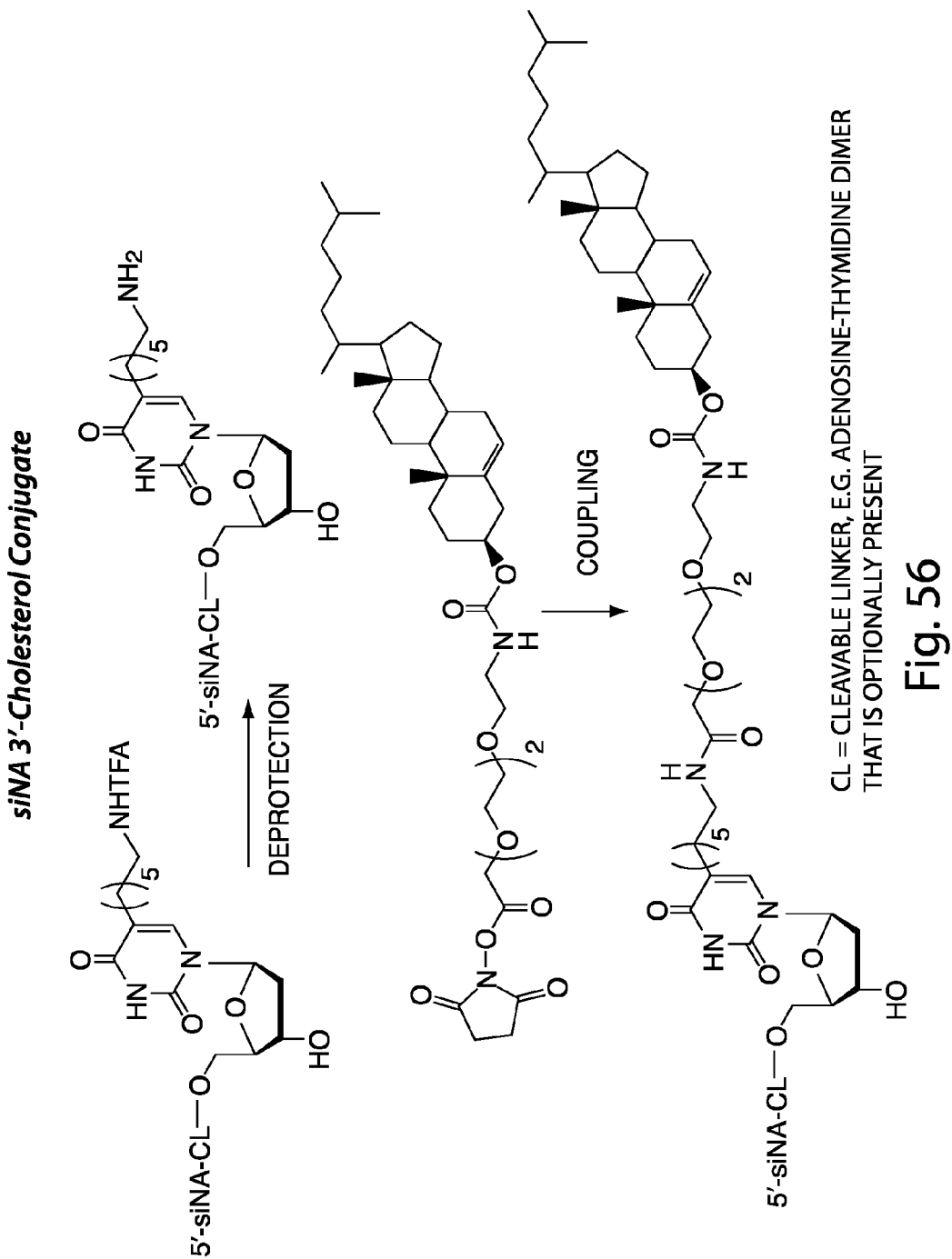
FIG. 56 shows a non-limiting example of the synthesis of siNA cholesterol conjugates of the invention using NHS ester coupling.
Figure 57:
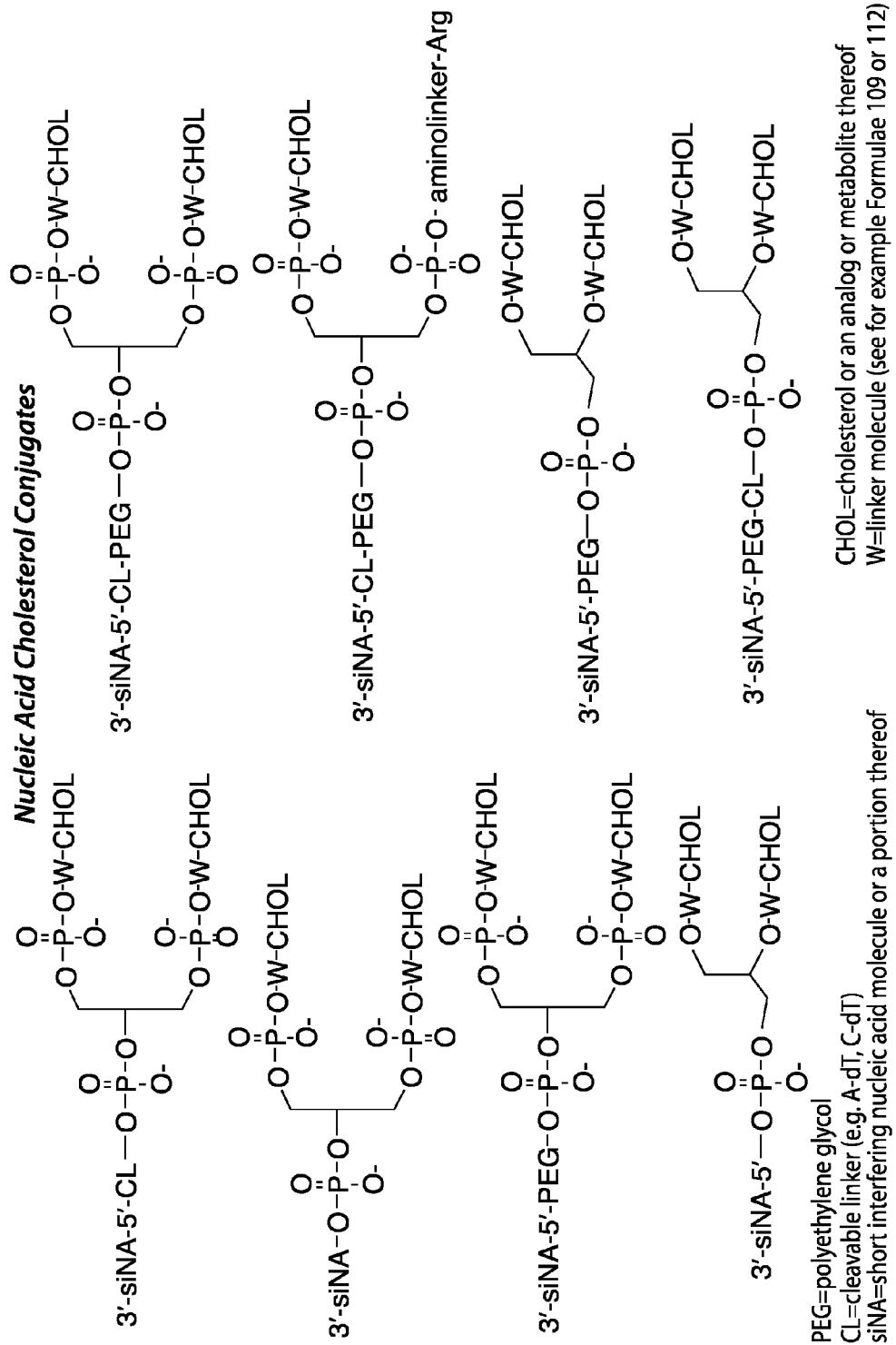
FIG. 57 shows a non-limiting example of various siNA cholesterol conjugates of the invention.
Figure 58:
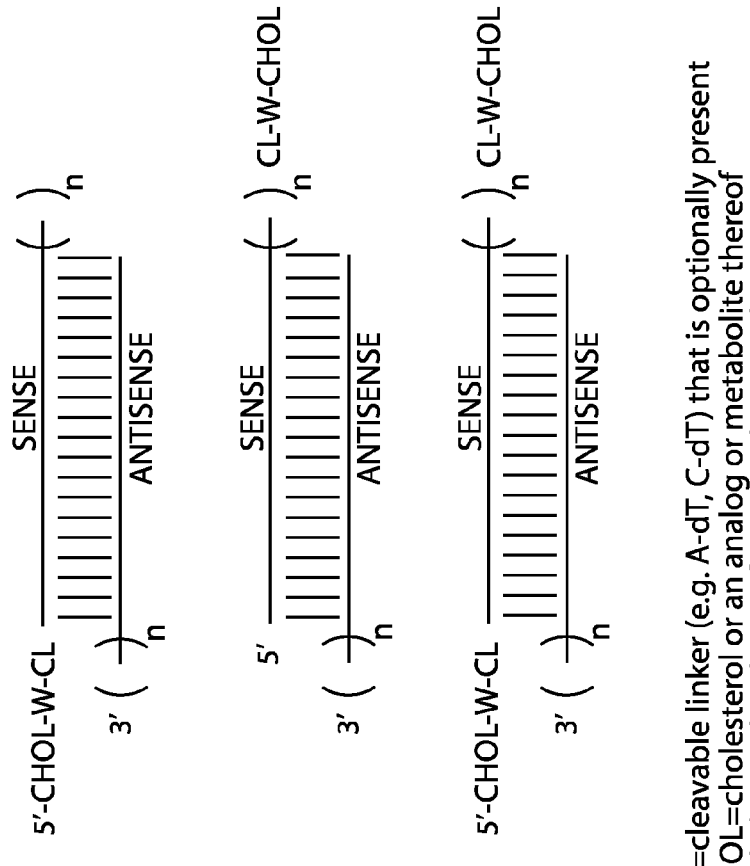
FIG. 58 shows a non-limiting example of various siNA cholesterol conjugates of the invention in which various linker chemistries and/or cleavable linkers can be utilized at different positions of a double stranded siNA molecule.
Figure 59:
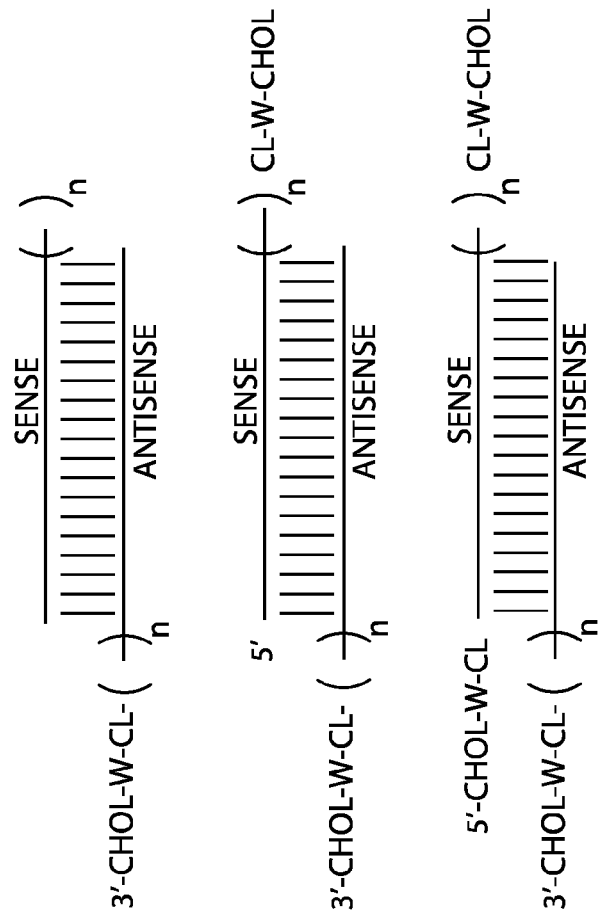
FIG. 59 shows a non-limiting example of various siNA cholesterol conjugates of the invention in which various linker chemistries and/or cleavable linkers can be utilized at different positions of a double stranded siNA molecule.
Figure 60:
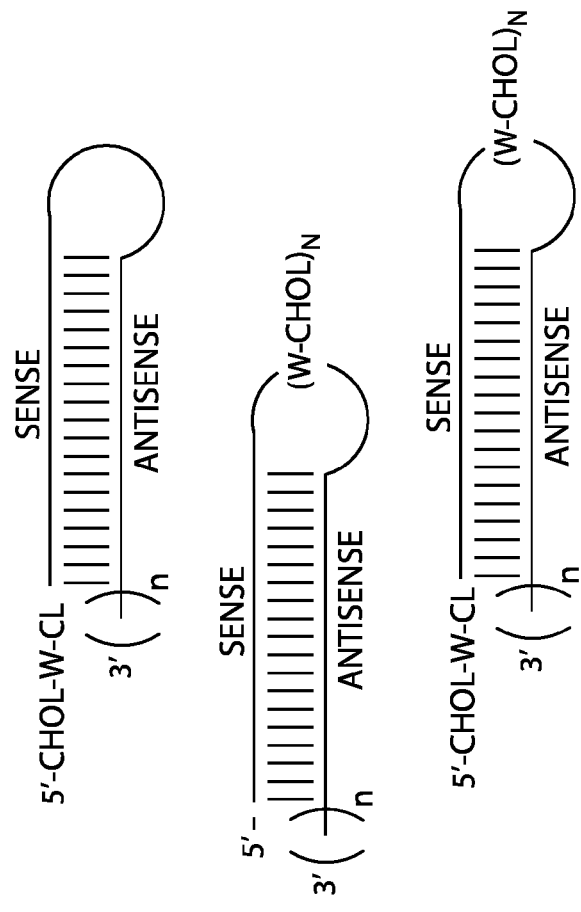
FIG. 60 shows a non-limiting example of various siNA cholesterol conjugates of the invention in which various linker chemistries and/or cleavable linkers can be utilized at different positions of a single stranded siNA molecule.
Figure 62:
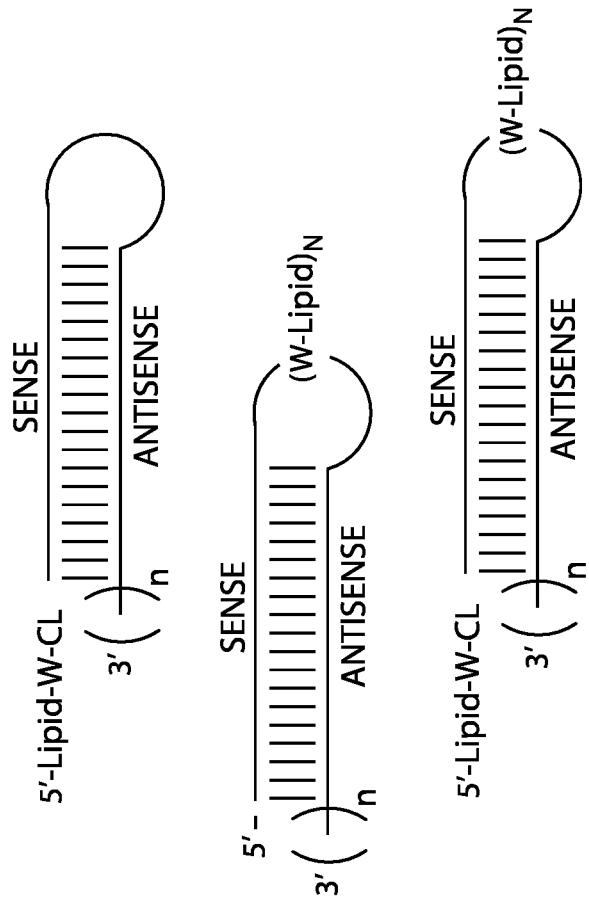
FIG. 62 shows a non-limiting example of various siNA phospholipid conjugates of the invention in which various linker chemistries and/or cleavable linkers can be utilized at different positions of a single stranded siNA molecule.
Figure 63:
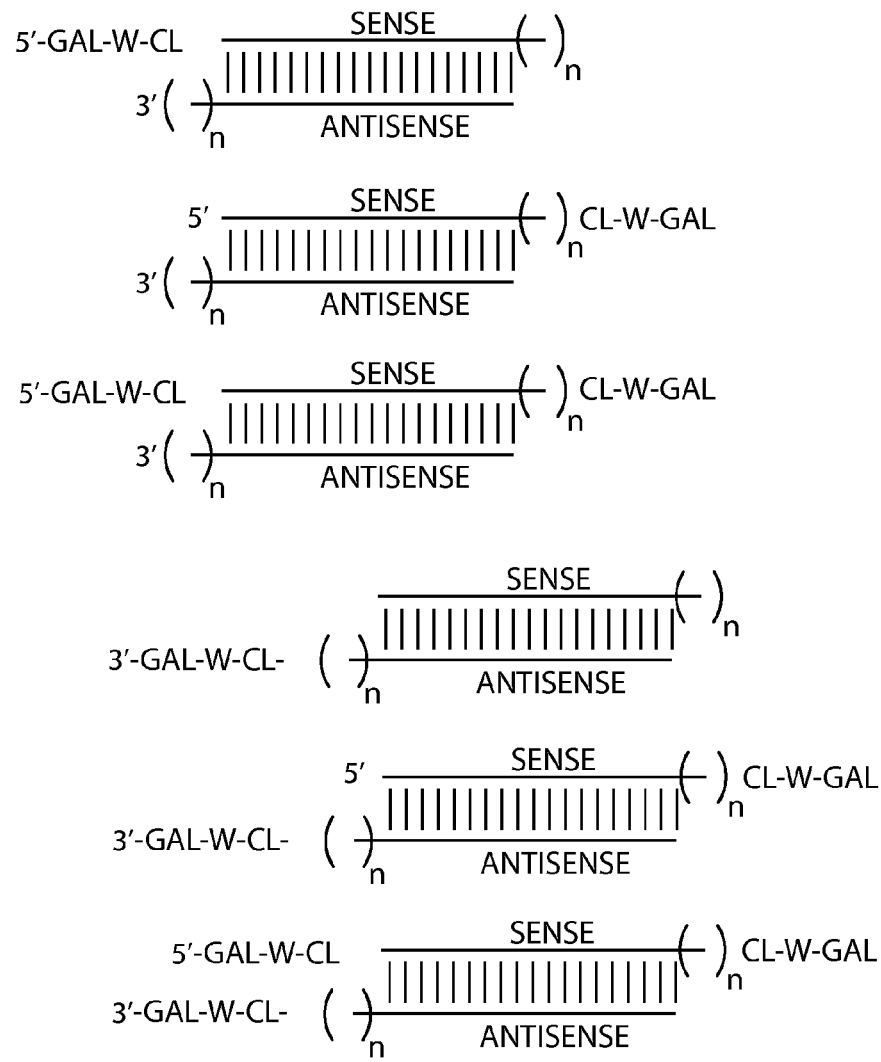
FIG. 63 shows a non-limiting example of various siNA galactosamine conjugates of the invention in which various linker chemistries and/or cleavable linkers can be utilized at different positions of a double stranded siNA molecule.
Figure 64:
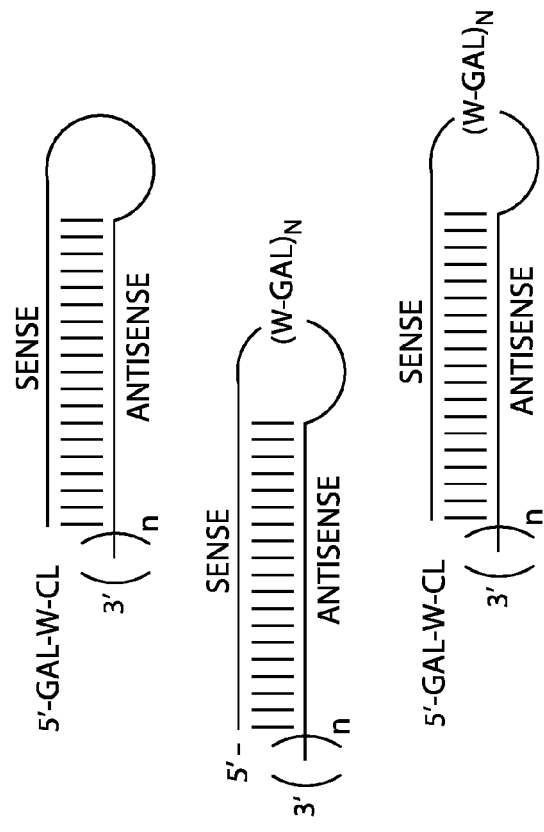
FIG. 64 shows a non-limiting example of various siNA galactosamine conjugates of the invention in which various linker chemistries and/or cleavable linkers can be utilized at different positions of a single stranded siNA molecule.

Transfection of the human hepatocellular carcinoma cell line, Hep G2, with replication-competent HBV DNA results in the expression of HBV proteins and the production of virions. To test the efficacy of siNA conjugates targeted against HBV RNA, the Cholesterol siNA conjugate and Phospholipid siNA conjugate described in Example 12 were compared to a non-conjugated control siNA (see FIG. 68). An inverted sequence duplex was used as a negative control for the unconjugated siNA. Dose response studies were performed in which HBV genomic DNA was transfected with HBV genomic DNA with lipid at 12.5 ug/ml into Hep G2 cells. 24 hours after transfection with HBV DNA, cell culture media was removed and siNA duplexes were added to cells without lipid at 10 uM, 5, uM, 2.5 uM, 1 uM, and 100 nm and the subsequent levels of secreted HBV surface antigen (HBsAg) were analyzed by ELISA 72 hours post treatment (see FIG. 44). To determine siNA activity, HbsAg levels were measured following transfection with siNA Immulon 4 (Dynax) microtiter wells were coated overnight at 4° C. with anti-HBsAg Mab (Biostride B88-95-31ad,ay) at 1 µg/ml in Carbonate Buffer (Na2CO3 15 mM, NaHCO3 35 mM, pH 9.5). The wells were then washed 4× with PBST (PBS, 0.05% Tween® 20) and blocked for 1 hr at 37° C. with PBST, 1% BSA. Following washing as above, the wells were dried at 37° C. for 30 min. Biotinylated goat ant-HBsAg (Accurate YVS1807) was diluted 1:1000 in PBST and incubated in the wells for 1 hr. at 37° C. The wells were washed 4× with PBST. Streptavidin/Alkaline Phosphatase Conjugate (Pierce 21324) was diluted to 250 ng/ml in PBST, and incubated in the wells for 1 hr. at 37° C. After washing as above, p-nitrophenyl phosphate substrate (Pierce 37620) was added to the wells, which were then incubated for 1 hour at 37° C. The optical density at 405 nm was then determined. As shown in FIG. 68, the phospholipid and cholesterol conjugates demonstrate marked dose dependent inhibition of HBsAg expression compared to the unconjugated siNA construct when delivered to cells without any transfection agent (lipid).

Example 22: Ex Vivo Stability of siNA Constructs

Chemically modified siNA constructs were designed and synthesized in order to improve resistance to nucleases while maintaining silencing in cell culture systems. Modified strands, designated Stab 4, Stab 5, Stab 7, Stab 8, and Stab 11 (Table IV), were tested in three sets of duplexes that demonstrated a range of stability and activity. These duplexes contained differentially modified sense and antisense strands. All modified sense strands contain terminal 5' and 3' inverted abasic caps, while antisense strands possess a 3' terminal phosphorothioate linkage. The results characterize the impact of chemical modifications on nuclease resistance in ex vivo models of the environments sampled by drugs.

Active siNAs were assessed for their resistance to degradation in serum and liver extracts. Stability in blood will be a requirement for a systemically administered siNA, and an anti-HBV or anti-HCV siNA would require stability and activity in the hepatic intracellular environment. Liver extracts potentially provide an extreme nuclease model where many catabolic enzymes are present. Both mouse and human systems were assessed.

Individual strands of siNA duplexes were internally labeled with 32P and incubated as single strands or as duplex siRNAs in human or mouse serum and liver extracts. Representative data is shown in Table VI. Throughout the course of the experiments, constant levels of ribonuclease activity were verified. The extent and pattern of all-RNA siNA degradation (3 minute time point) did not change following preincubation of serum or liver extract at 37° C. for up to 24 hours.

The biological activity of siRNAs containing all-ribose residues has been well established. The extreme instability (t½=0.017 hours) of these compounds in serum underscores the need for chemical modification for use in systemic therapeutic applications. The Stab 4/5 duplex modifications provide significant stability in human and mouse serum (t½'s=10-408 hours) and human liver extract (t½'s=28-43 hours). In human serum the Stab 4 strand chemistry in the context of the Stab 4/5 duplex, possesses greater stability than the Stab 5 strand chemistry (t ½=408 vs. 39 hours). This result highlights the impact terminal modifications have on stability. A fully-modified Stab 7/11 construct (no ribonucleotides present) was generated from the Stab 4/5 constructs by substituting the ribonucleotides in all purine positions with deoxyribonucleotides. Another fully modified construct, Stab 7/8, was generated by replacing all purine positions in the antisense strand with 2'-O-methyl nucleotides. This proved to be the most stable antisense strand chemistry observed, with t½=816 hours in human liver extract.

The dramatic stability of Stab 8 modifications was also observed when non-duplexed single strands were incubated in human serum and liver extract, as shown in Table VII. An approximate five-fold increase in serum stability is seen for the double stranded constructs, compared to that observed for the individual strands. In liver extract, the siNA duplex provides even greater stability compared to the single strands. For example, the Stab 5 chemistry is greater than 100-fold more stable in the Stab 4/5 duplex relative to its stability alone.

Figure 22:
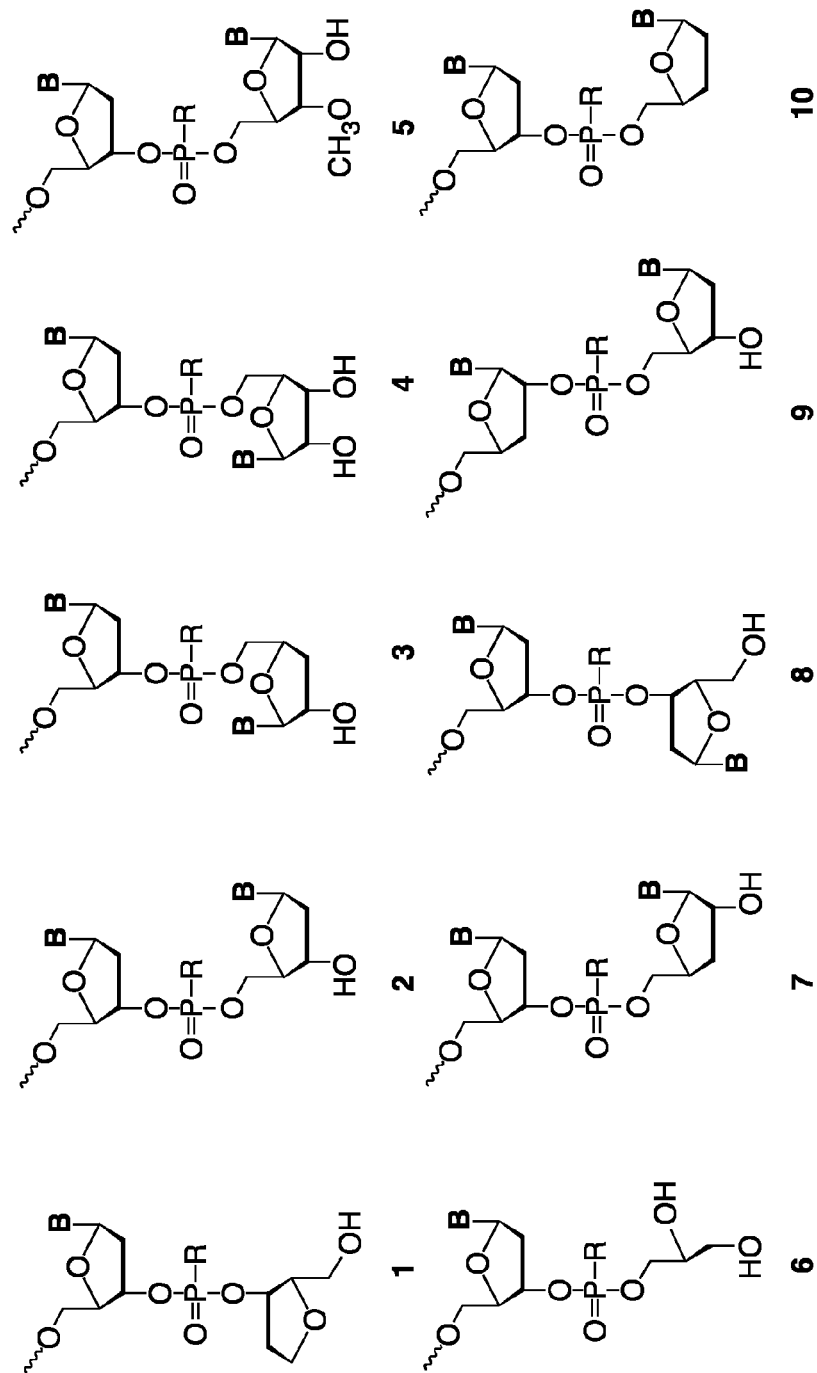
FIG. 22 shows non-limiting examples of different stabilization chemistries (1-10) that can be used, for example, to stabilize the 3'-end of siNA sequences of the invention, including (1) [3-3']-inverted deoxyribose; (2) deoxyribonucleotide; (3) [5'-3']-3'-deoxyribonucleotide; (4) [5'-3']-ribonucleotide; (5) [5'-3']-3'-O-methyl ribonucleotide; (6) 3'-glyceryl; (7) [3'-5']-3'-deoxyribonucleotide; (8) [3'-3']-deoxyribonucleotide; (9) [5'-2']-deoxyribonucleotide; and (10) [5-3']-dideoxyribonucleotide. In addition to modified and unmodified backbone chemistries indicated in the figure, these chemistries can be combined with different backbone modifications as described herein, for example, backbone modifications having Formula I. In addition, the 2'-deoxy nucleotide shown 5' to the terminal modifications shown can be another modified or unmodified nucleotide or non-nucleotide described herein, for example modifications having any of Formulae I-VII or any combination thereof.

Terminal modifications have a large impact on stability in human serum, as can be seen from a comparison of sense verses antisense stabilities in duplex form, and the Stab 4 and Stab 5 single-strand stabilities. Therefore, a number of 3' antisense capping moieties on Stab 4/5 chemistry duplexes were assessed for their contribution to stability in human serum. The structures of these modifications are shown in FIG. 22, and resultant half-lives are shown in Table VIII. A wide range of different stabilities were observed, from half-lives as short as one hour to greater than 770 hours. Thus, in the context of 2'-fluoro modified pyrimidines, 3'-exonuclease becomes the primary mode of attack on duplexes in human serum; a number of chemistries minimize this site of attack. These results suggest that susceptibility to 3' exonucleases is a major path to degradation in the serum.

Example 23: Activity of siNA Molecules Delivered Via Hydrodynamic Injection

An in vivo mouse model that utilizes hydrodynamic tail vein injection of a replication competent HBV vector has been used to assess the activity of chemically stabilized siRNA targeted to HBV RNA. The hydrodynamic delivery of nucleic acids in the mouse has been described by Liu et al., 1999, *Gene Therapy*, 6, 1258-1266, who showed that the vast majority of the nucleic acid is delivered to the liver by this technique. The use of the hydrodynamic technology to develop an HBV mouse model has been described by Yang et al., 2002, *PNAS*, 99, 13825-13830. In the vector-based model, HBV replicates in the liver for approximately 10 days, resulting in detectable levels of HBV RNA and antigens in the liver and HBV DNA and antigens in the serum.

Figure 80:
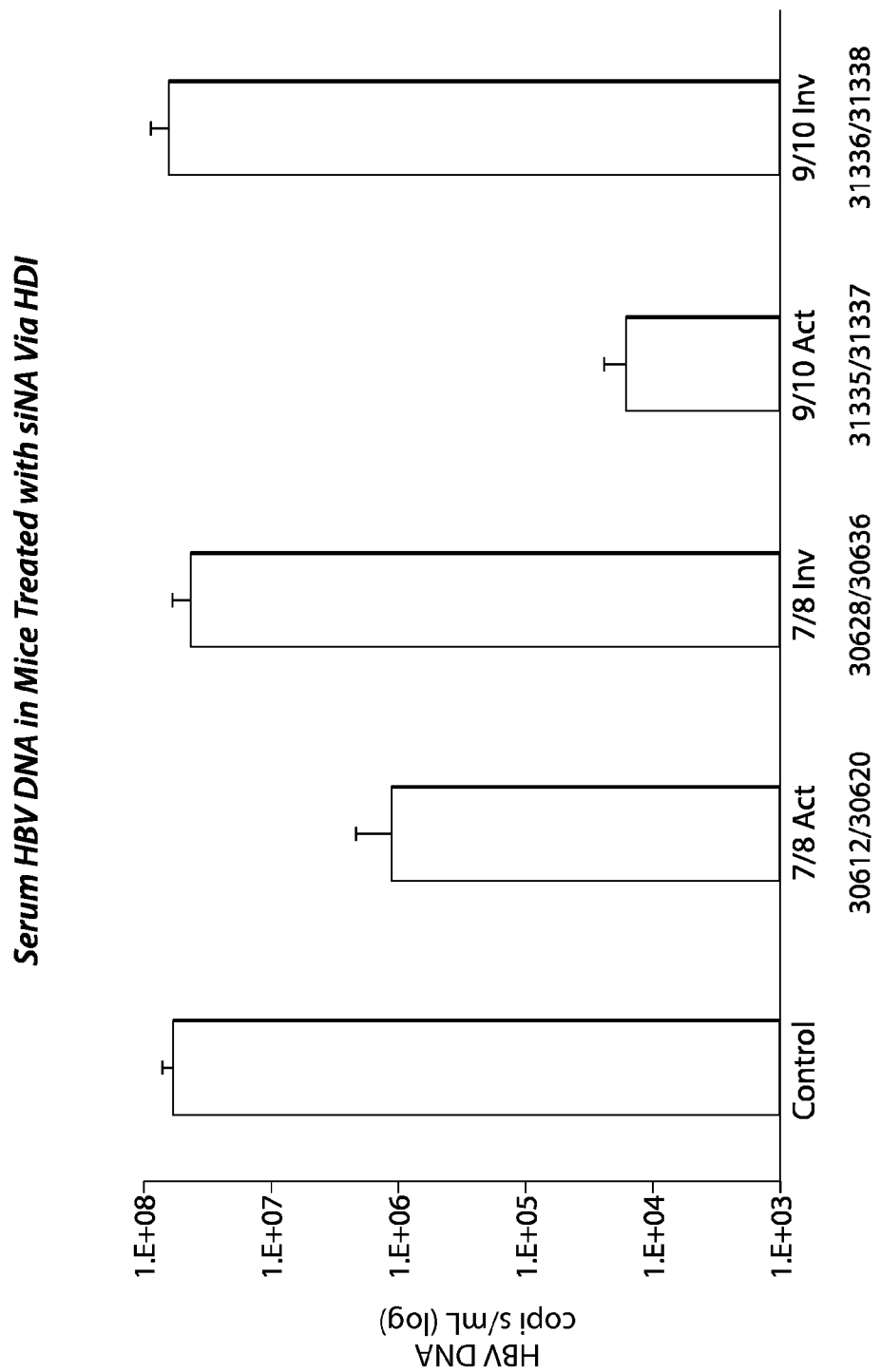
FIG. 80 shows a non-limiting example of reduction of serum HBV DNA in mice treated with hydrodynamically administered chemically modified siNA (Stab 7/8 and Stab 9/10) targeting HBV RNA compared to matched chemistry inverted controls and a saline control.
Figure 81:
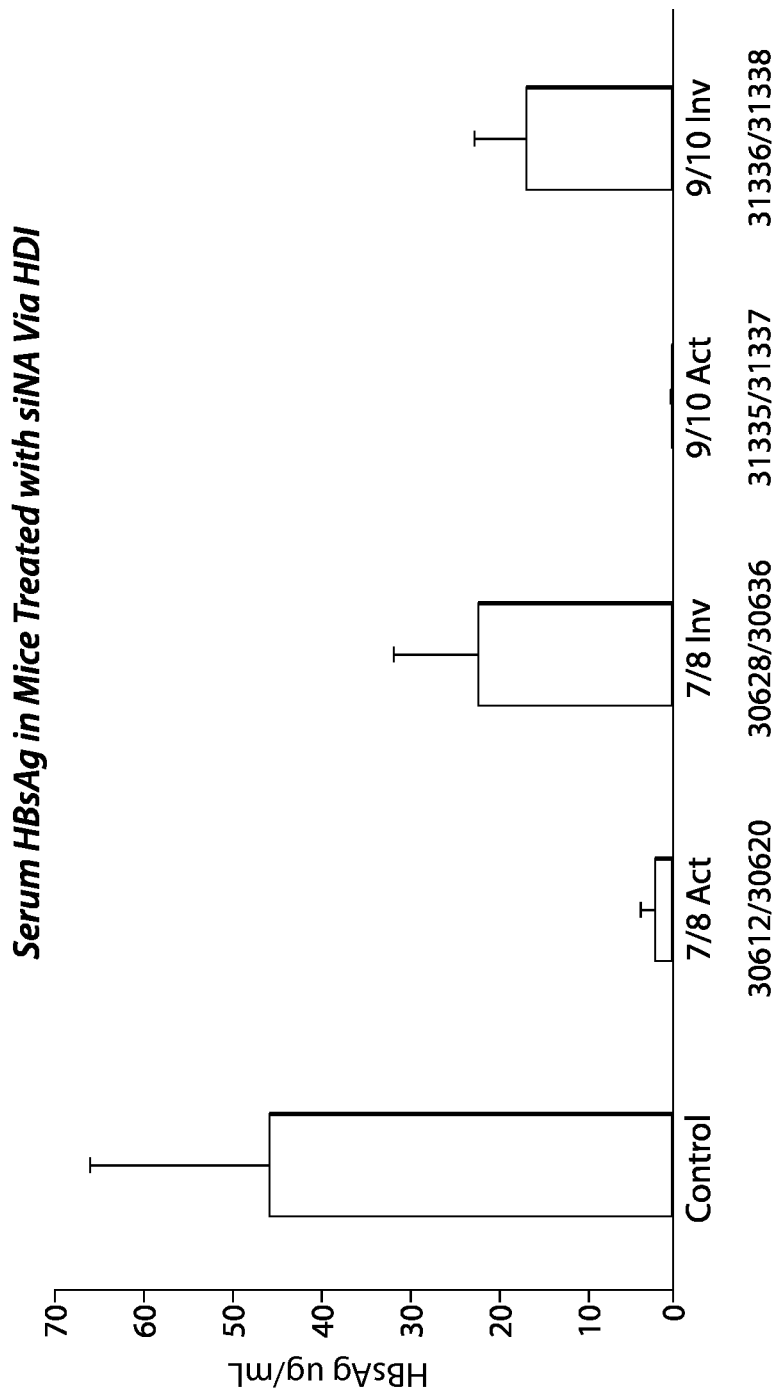
FIG. 81 shows a non-limiting example of reduction of serum HBV S antigen (HBsAg) in mice treated with hydrodynamically administered chemically modified siNA (Stab 7/8 and Stab 9/10) targeting HBV RNA compared to matched chemistry inverted controls and a saline control.
Figure 82:
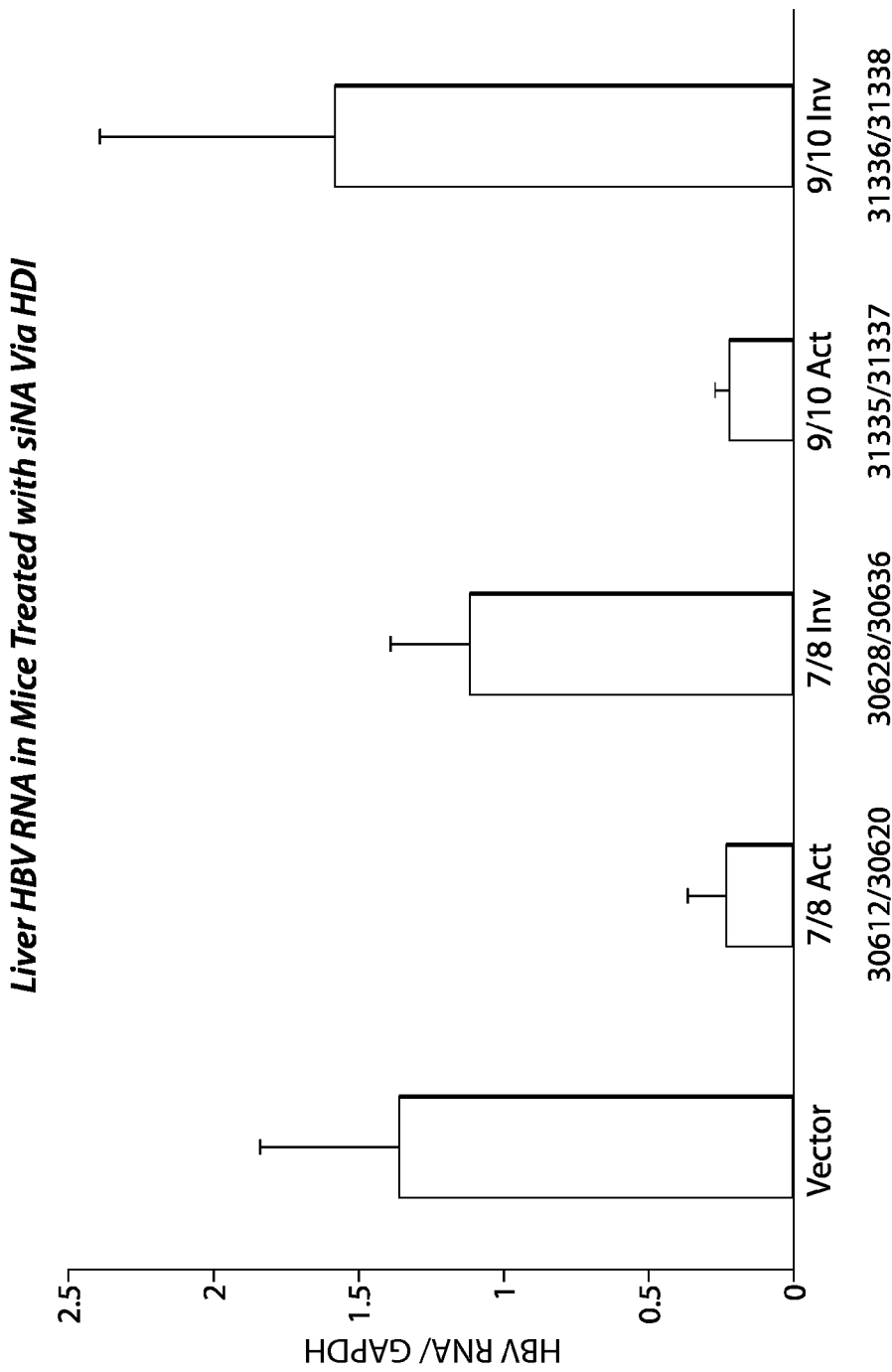
FIG. 82 shows a non-limiting example of reduction of serum HBV RNA in mice treated with hydrodynamically administered chemically modified siNA (Stab 7/8 and Stab 9/10) targeting HBV RNA compared to matched chemistry inverted controls and a saline control.
Figure 83:
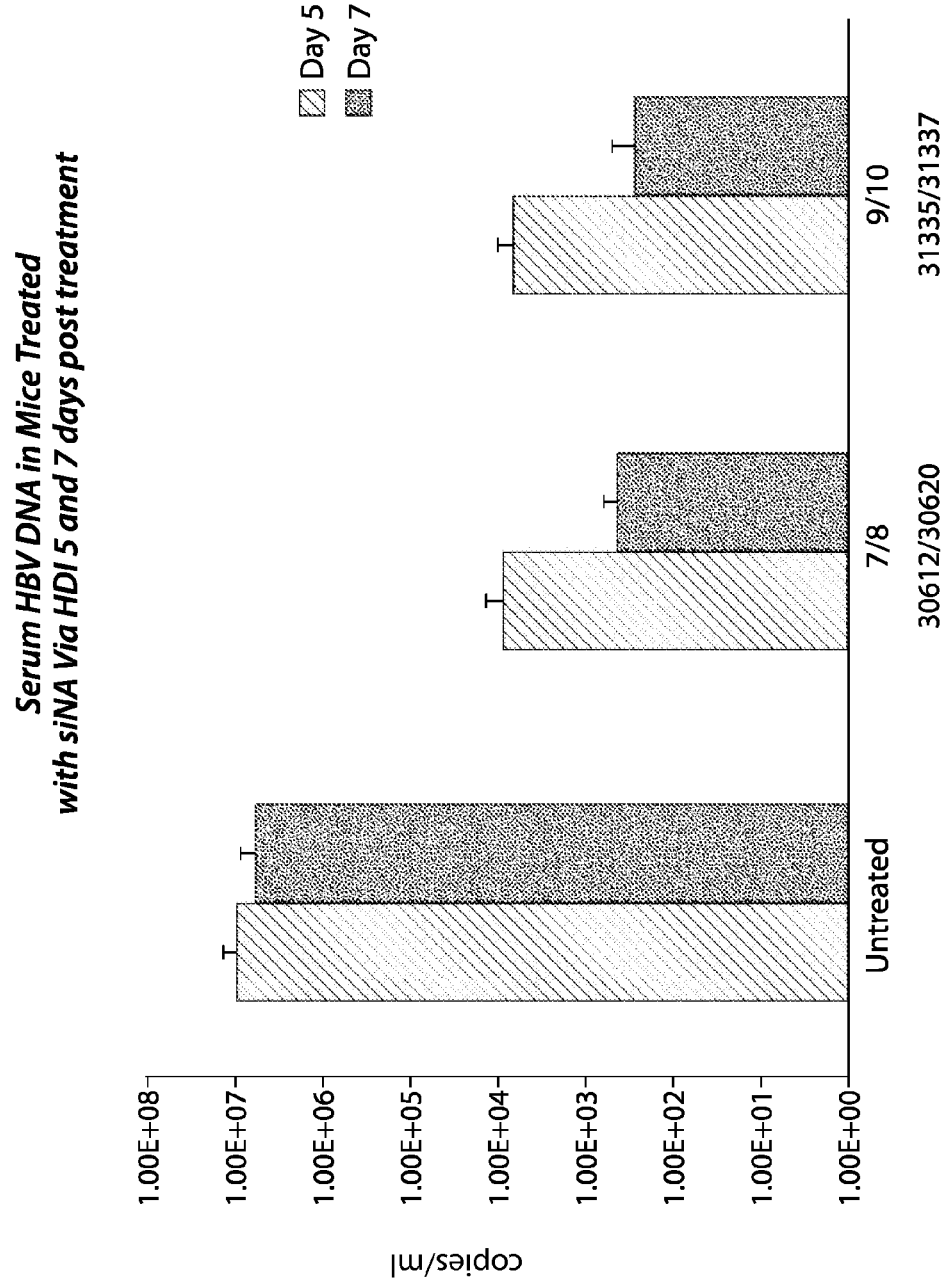
FIG. 83 shows a non-limiting example of reduction of serum HBV DNA in mice treated with hydrodynamically administered chemically modified siNA (Stab 7/8 and Stab 9/10) targeting HBV RNA at 5 days and 7 days post administration.

To assess the activity of chemically stabilized siNAs against HBV, co-injection of the siNAs along with the HBV vector was done in mouse strain C57BL/J6. The HBV vector used, pWTD, is a head-to-tail dimer of the complete HBV genome (see for example Buckwold et al., 1996, *J. Virology*, 70, 5845-5851). For a 20 gram mouse, a total injection of 1.6 ml containing 10 µg or 1 µg of pWTD and 100 µg of siNA duplex in saline, was injected into the tail vein within 5 seconds. For a larger mouse, the volume is scaled to maintain a level of 140% of the blood volume of the mouse. The injection is done using a 3 cc syringe and 27 g1/2 needle. The animals were sacrificed at 72 hrs post-injection. Animals were treated with siNA constructs and matched chemistry inverted controls. Analysis of the HBV DNA (FIG. 80) and HBsAg (FIG. 81) levels in serum was conducted by real-time PCR and ELISA respectively. The levels of HBV RNA in the liver (FIG. 82) were analyzed by real-time RT-PCR. In a separate experiment, analysis of HBV DNA levels in serum was carried out at 5 days and 7 days (FIG. 83) after co-injection of siNA and the HBV vector.

Example 24: Activity Screens Using Chemically Modified siNA

Two formats can be used to identify active chemically modified siNA molecules against target nucleic acid molecules (e.g., RNA). One format involves screening unmodified siNA constructs in an appropriate system (e.g., cell culture or animal models) then applying chemical modifications to the sequence of identified leads and rescreening the modified constructs. Another format involves direct screening of chemically modified constructs to identify chemically modified leads (see for example the Stab 7/8 HCV screen shown in FIG. 86 and the Stab 7/8 HBV screen shown FIG. 87, as described above). The latter approach can be useful in identifying active constructs that are specific to various combinations of chemical modifications (e.g., Stab 1-18 chemistries shown in Table V herein). Additionally, different iterations of such chemical modifications can be assessed using active chemically modified leads and appropriate rules for selective active constructs given a particular chemistry can be established using this approach. Non-limiting examples of such activity screen are described below.

Activity Screen of Stab 7/8 Constructs Targeting Luciferase RNA

Figure 84:
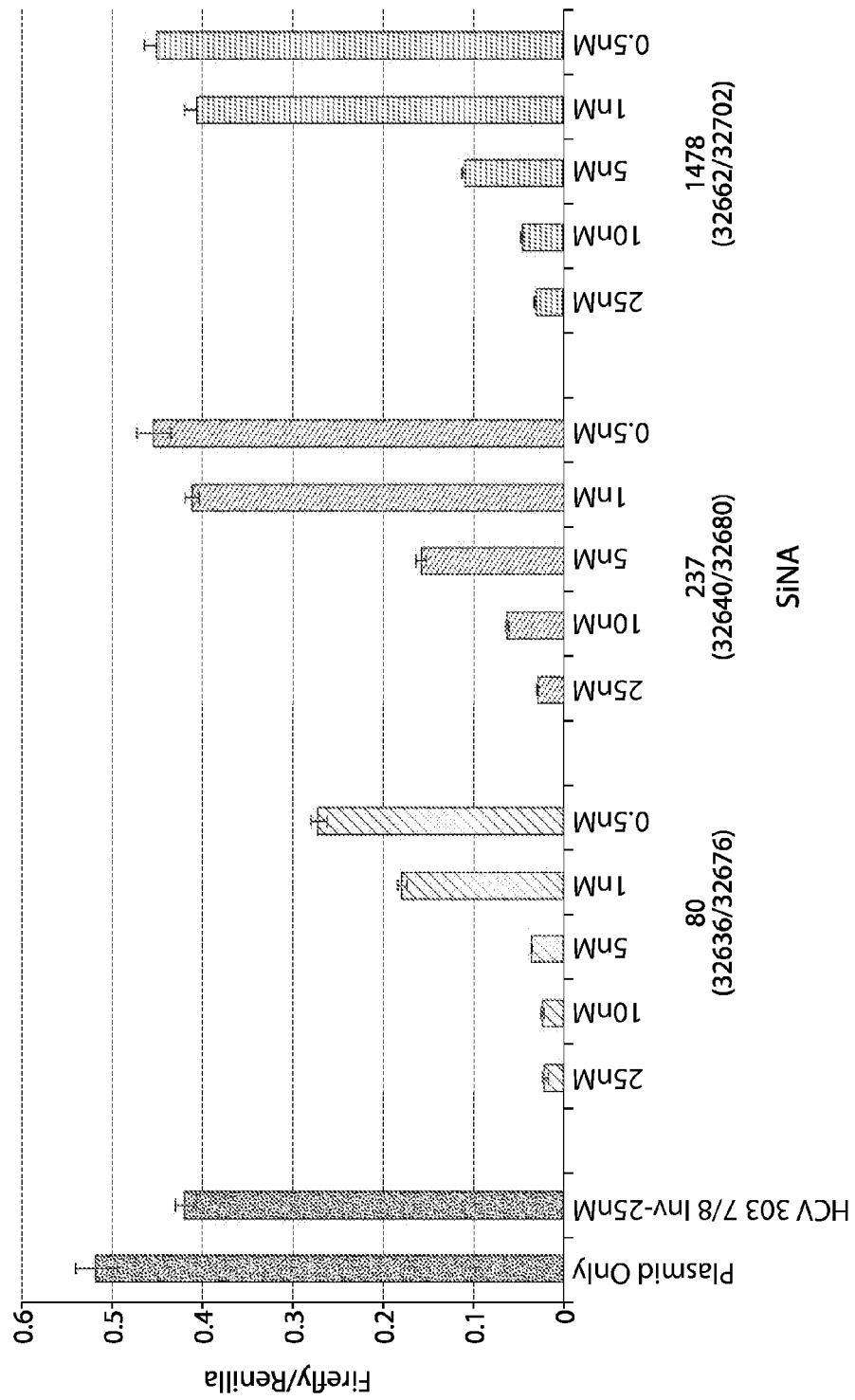
FIG. 84 shows a non-limiting example of an assay for dose dependent reduction of Luciferase expression utilizing Stab 7/8 chemically modified siNA constructs targeting luciferase RNA sites 80, 237, and 1478 that were selected from a screen using all Stab 7/8 chemically modified siNA constructs.
Figure 85:
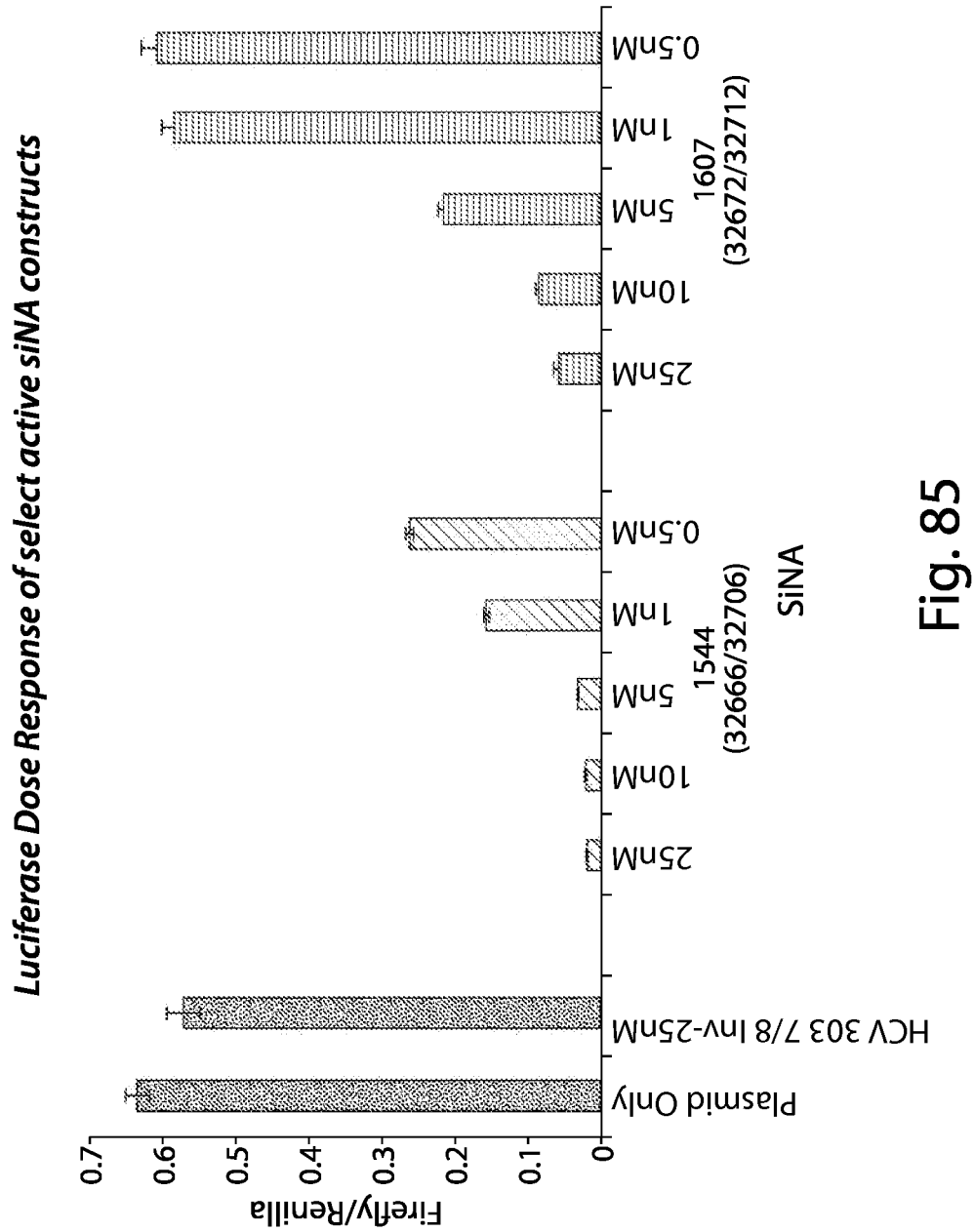
FIG. 85 shows a non-limiting example of an assay for dose dependent reduction of Luciferase expression utilizing Stab 7/8 chemically modified siNA constructs targeting luciferase RNA sites 1544 and 1607 that were selected from a screen using all Stab 7/8 chemically modified siNA constructs.

HeLa cells were co-transfected with pGF3 vector (250 ng/well), renilla luciferase vector (10 ng/well) and siNA (0.5-25 nM) using 0.5 ul lipofectamine 2000 per well. Twenty-four hours post-transfection, the cells were assayed for luciferase activity using the Promega Dual Luciferase Assay Kit per the manufacturer's instruction. siNA constructs having high levels of activity were identified and tested in a dose response assay with concentrations ranging from 0.5 to 25 nM. Results for siNA constructs targeting sites 80, 237, and 1478 are shown in FIG. 84 and sites 1544 and 1607 are shown in FIG. 85. As shown in the Figures, several active Stab 7/8 constructs were identified that demonstrate potent dose related inhibition of luciferase expression.

Activity Screen of Combination siNA Constructs Targeting HBV RNA in HepG2 Cells

Figure 88:
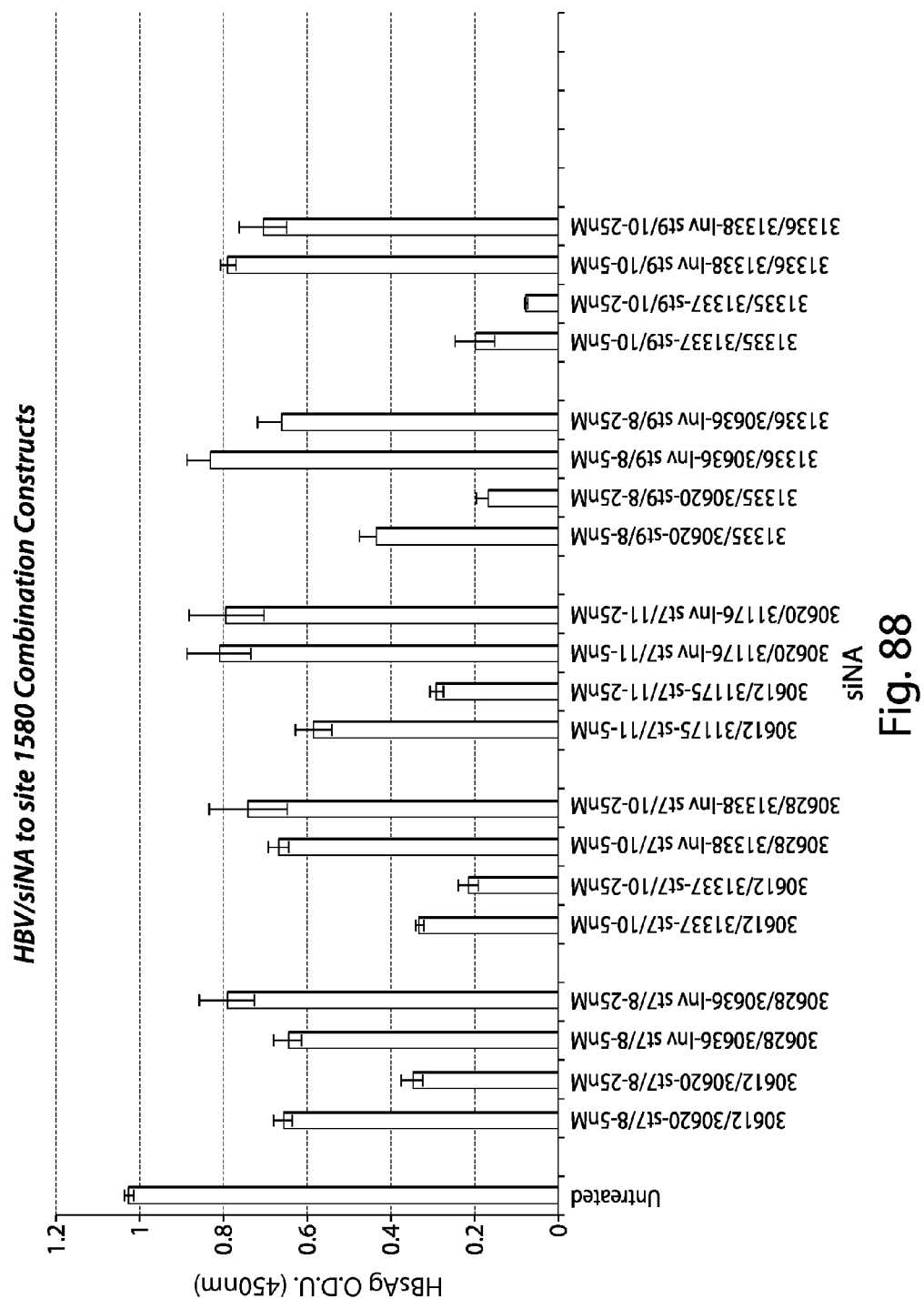
FIG. 88 shows a non-limiting example of an assay screen of various combinations of chemically modified siNA constructs (e.g., Stab 7/8, 7/10, 7/11, 9/8, and 9/10) targeting site 1580 of HBV RNA in HEpG2 cells compared to untreated cells and an matched chemistry inverted controls. As shown in the figure, the combination chemistries tested demonstrated potent anti-HBV activity as shown by reduction in HBV S antigen levels.
Figure 89:
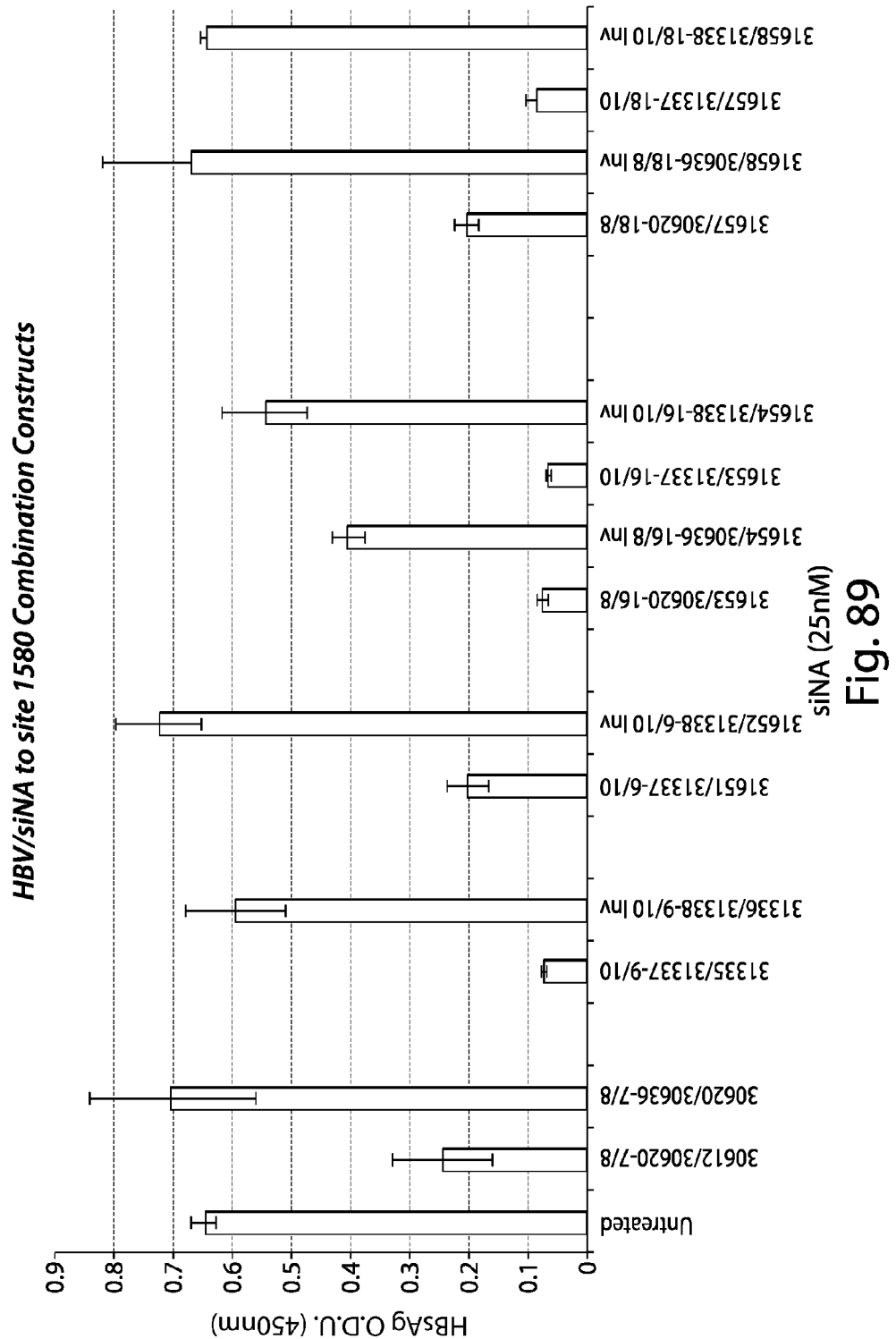
FIG. 89 shows a non-limiting example of an assay screen of various combinations of chemically modified siNA constructs (e.g., Stab 7/8, 9/10, 6/10, 16/8, 16/10, 18/8, and 18/10) targeting site 1580 of HBV RNA in HEpG2 cells compared to untreated cells and an matched chemistry inverted controls. As shown in the figure, the combination chemistries tested demonstrated potent anti-HBV activity as shown by reduction in HBV S antigen levels.
Figure 90:
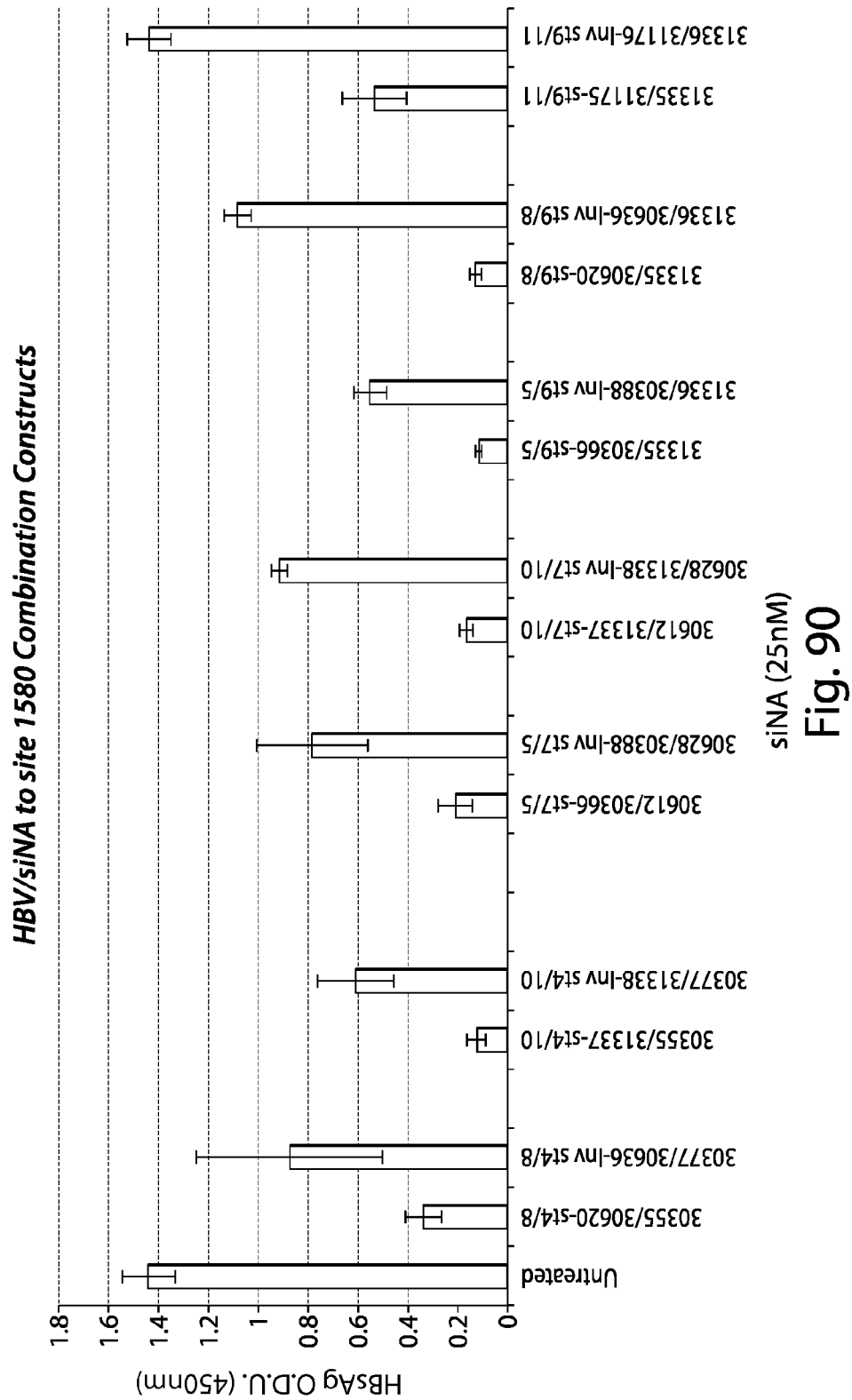
FIG. 90 shows a non-limiting example of an assay screen of various combinations of chemically modified siNA constructs (e.g., Stab 4/8, 4/10, 7/5, 7/10, 9/5, 9/8, and 9/11) targeting site 1580 of HBV RNA in HEpG2 cells compared to untreated cells and an matched chemistry inverted controls. As shown in the figure, the combination chemistries tested demonstrated potent anti-HBV activity as shown by reduction in HBV S antigen levels.

The HBV HepG2 cell culture system described in Example 13 above was utilized to evaluate the efficacy of various combinations of chemical modifications (Table V) in the sense strand and antisense strand of siNA molecules as compared to matched chemistry inverted controls. To determine siNA activity, HbsAg levels were measured following transfection with siNA Immulon 4 (Dynax) microtiter wells were coated overnight at 4° C. with anti-HBsAg Mab (Biostride B88-95-31ad,ay) at 1 µg/ml in Carbonate Buffer (Na2CO3 15 mM, NaHCO3 35 mM, pH 9.5). The wells were then washed 4× with PBST (PBS, 0.05% Tween® 20) and blocked for 1 hr at 37° C. with PBST, 1% BSA. Following washing as above, the wells were dried at 37° C. for 30 min. Biotinylated goat ant-HBsAg (Accurate YVS1807) was diluted 1:1000 in PBST and incubated in the wells for 1 hr. at 37° C. The wells were washed 4× with PBST. Streptavidin/Alkaline Phosphatase Conjugate (Pierce 21324) was diluted to 250 ng/ml in PB ST, and incubated in the wells for 1 hr. at 37° C. After washing as above, p-nitrophenyl phosphate substrate (Pierce 37620) was added to the wells, which were then incubated for 1 hour at 37° C. The optical density at 450 nm was then determined Results of the combination HBV siNA screen are shown in FIGS. 88-90. As shown in the Figures, the various combinations of differing sense and antisense chemistries (e.g., sense/antisense constructs having Stab 7/8, 7/10, 7/11, 9/8, 9/10, 6/10, 16/8, 16/10, 18/8, 18/10, 4/8, 4/10, 7/5, 9/5, and 9/11 chemistry) result in active siNA constructs.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims. The present invention teaches one skilled in the art to test various combinations and/or substitutions of chemical modifications described herein toward generating nucleic acid constructs with improved activity for mediating RNAi activity. Such improved activity can comprise improved stability, improved bioavailability, and/or improved activation of cellular responses mediating RNAi. Therefore, the specific embodiments described herein are not limiting and one skilled in the art can readily appreciate that specific combinations of the modifications described herein can be tested without undue experimentation toward identifying siNA molecules with improved RNAi activity.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

TABLE I

| Sirna/RPI# | Aliases | Sequence | SEQ ID# |
| --- | --- | --- | --- |
| 28443 | Sirna/RPI GL2 Str1 (sense) 2'-amino U C | cGuAcGcGGAAuAcuucGATT | 349 |

TABLE I-continued

| Sirna/RPI# | Aliases | Sequence | SEQ ID# |
|---|---|---|---|
| 28444 | Sirna/RPI GL2 Str2 (antisense) 2'-amino U C | ucGAAGuAuuccGcGuAcGTT | 350 |
| 28445 | Sirna/RPI GL2 Str1 (sense) 2'-amino U C uT 3'end | cGuAcGcGGAAuAcuucGAuT | 351 |
| 28446 | Sirna/RPI GL2 Str2 (antisense) 2'-amino U C uT 3'end | ucGAAGuAuuccGcGuAcGuT | 352 |
| 30051 | HCV-Luc:325U21 siNA 5 5' P = S + 3' univ. base 2 + 5'/3' invAba (antisense) | BC$_S$C$_S$C$_S$G$_S$GGAGGUCUCGUAGAXXB | 353 |
| 30052 | HCV-Luc:325U21 siNA rev 5 5' P = S + 3' univ. base 2 + 5'/3' invAba (antisense) | BA$_S$G$_S$A$_S$U$_S$G$_S$CUCUGGAGGGCCCCXXB | 354 |
| 30053 | HCV-Luc:345L21 siNA (325C) (antisense) 5 5' P = S + 3' univ. base 2 + 3' invAba (sense) | U$_S$C$_S$U$_S$A$_S$C$_S$GAGACCUCCCGGGGXXB | 355 |
| 30054 | HCV-Luc:345L21 siNA (325C) (antisense) rev 5 5' P = S + 3' univ. base 2 + 3' invAba (sense) | G$_S$G$_S$G$_S$G$_S$C$_S$CCUCCAGAGCAUCUXXB | 356 |
| 30055 | HCV-Luc:325U21 siNA all Y P = S + 3' univ. base 2 + 5'/3' invAba (antisense) | BC$_S$C$_S$C$_S$C$_S$GGGAGGU$_S$C$_S$U$_S$C$_S$GU$_S$AGAXXB | 357 |
| 30056 | HCV-Luc:325U21 siNA rev all Y P = S + 3' univ. base 2 + 5'/3' invAba (antisense) | BAGAU$_S$GC$_S$U$_S$C$_S$U$_S$GGAGGGC$_S$C$_S$C$_S$C$_S$XXB | 358 |
| 30057 | HCV-Luc:345L21 siNA (325C) (antisense) all Y P = S + 3' univ. base 2 + 3' invAba (sense) | U$_S$C$_S$U$_S$AC$_S$GAGAC$_S$C$_S$U$_S$C$_S$C$_S$C$_S$GGGGXXB | 359 |
| 30058 | HCV-Luc:345L21 siNA (325C) (antisense) rev all Y P = S + 3' univ. base 2 + 3' invAba (sense) | GGGGC$_S$C$_S$C$_S$U$_S$C$_S$C$_S$AGAGC$_S$AU$_S$C$_S$U$_S$XXB | 360 |
| 30059 | HCV-Luc:325U21 siNA 4/3 P = S ends + all Y - 2'F + 3' univ. base 2 + 5'/3' invAba (antisense) | Bc$_S$c$_S$c$_S$c$_S$GGGAGGucucGuA$_S$G$_S$A$_S$XXB | 361 |
| 30060 | HCV-Luc:325U21 siNA rev 4/3 P = S ends + all Y - 2'F + 3' univ. base 2 + 5'/3' invAba (antisense) | BA$_S$G$_S$A$_S$u$_S$GcucuGGAGGGcc$_S$c$_S$c$_S$c$_S$XXB | 362 |
| 30170 | HCV-Luc:325U21 siNA all Y - 2'F + 3' univ. base 2 + 5'/3' invAba (antisense) | B ccccGGGAGGucucGuAGAXX B | 363 |
| 30171 | HCV-Luc:325U21 siNA rev all Y - 2'F + 3' univ. base 2 + 5'/3' invAba (antisense) | B AGAuGcucuGGAGGGccccXX B | 364 |
| 30172 | HCV-Luc:345L21 siNA (325C) (antisense) all Y P+32S +3' univ. base 2 + 5'/3' invAba (antisense) | B U$_S$C$_S$U$_S$AC$_S$GAGAC$_S$C$_S$U$_S$C$_S$C$_S$C$_S$GGGGXX B | 365 |
| 30173 | HCV-Luc:345L21 siNA (325C) (antisense) all Y - 2'F | ucuAcGAGAccucccGGGG | 366 |
| 30174 | HCV-Luc:345L21 siNA (325C) (antisense) rev all Y - 2'F | GGGGcccuccAGAGcAucu | 367 |
| 30175 | HCV-Luc:345L21 siNA (325C) (antisense) all Y - 2'F + 3' univ. base 2 | ucuAcGAGAccucccGGGGXX | 368 |
| 30176 | HCV-Luc:345L21 siNA (325C) (antisense) rev all Y - 2'F + 3' univ. base 2 | GGGGcccuccAGAGcAucuXX | 369 |
| 30177 | HCV-Luc:345L21 siNA (325C) (antisense) all Y - 2'F + 3' univ. base 2 + 5'/3' iB | B ucuAcGAGAccucccGGGGXX B | 370 |
| 30178 | HCV-Luc:325U21 siNA all Y P+32S + 3' univ. base 2 +3' invAba (sense) | CCCC$_S$GGGAGGU$_S$C$_S$U$_S$C$_S$GU$_S$AGAXX B | 371 |
| 30063 | Sirna/RPI GL2 Str1 (sense) 2'-F U,C + 3', 5' abasic | BcGuAcGcGGAAuAcuucGATTB | 372 |

TABLE I-continued

| Sirna/RPI# | Aliases | Sequence | SEQ ID# |
|---|---|---|---|
| 30222 | Sirna/RPI GL2 Str1 (sense) Y 2'-O-Me with 3'-TT & 5'/3' iB | B cGuAcGcGGAAuAcuucGATT B | 373 |
| 30224 | Sirna/RPI GL2 Str2 (antisense) Y 2'-F & 3' TsT | ucGAAGuAuuccGcGuAcGT$_S$T | 374 |
| 30430 | Sirna/RPI GL2 Str2 (antisense) 2'-F U, C + 5,3' abasic, A,G = 2'-O-Me | ucgaaguauuccgcguacgT$_S$T | 375 |
| 30431 | Sirna/RPI GL2 Str1 (sense) 2'-F U,C + 3', 5' abasic,TT; 2'-O-Me-A,G | Bcguacgcggaauacuucga TTB | 376 |
| 30433 | Sirna/RPI GL2 Str1 (sense) 2'-F U,C + 3', 5' abasic,TT; 2'-deoxy-A,G | BcGuAcGcGGAAuAcuucGATTB | 377 |
| 30550 | Sirna/RPI GL2 Str2 (antisense) 2'-F U, C 3'-dTsT | ucGAAGuAuuccGcGuAcGTSt | 378 |
| 30555 | Sirna/RPI GL2 Str2 (antisense) 2'-F U,C 3'-glycerol,T | ucGAAGuAuuccGcGuAcGTL | 379 |
| 30556 | Sirna/RPI GL2 Str2 (antisense) 2'-F U,C 3'-glycerol,2T | ucGAAGuAuuccGcGuAcGTTL | 380 |
| 30226 | rev Sirna/RPI GL2 Str1 (sense) Y 2'-O-Me with 3'-TT & 5'/3' iB | B AGcuucAuAAGGcGcAuGcTT B | 381 |
| 30227 | rev Sirna/RPI GL2 Str1 (sense) Y 2'-F with 5-TT & 5'/3' iB | B AGcuucAuAAGGcGcAuGcTT B | 382 |
| 30229 | rev Sirna/RPI GL2 Str2 (antisense) Y 2'-F & 3' TsT | GcAuGcGccuuAuGAAGcuTST | 383 |
| 30434 | Sirna/RPI GL2 Str1 (sense) 2'-F U,C + 3', 5' Abasic,TT; 2'-O-Me-A,G;ribo core | BcguacgcGGAAuAcuucgaTTB | 384 |
| 30435 | Sirna/RPI GL2 Str1 (sense) 2'-F U,C + 3', 5' Abasic,TT; 2'-deoxyA,G;ribo core | BcGuAcGcGGAAuAcuucGATTB | 385 |
| 30546 | Sirna/RPI GL2 Str2 (antisense) 2'-F U,C 3'-dTT | ucGAAGuAuuccGcGuAcG3T | 386 |
| 30551 | Sirna/RPI GL2 Str2 (antisense) 2'-F U,C dTddC | ucGAAGuAuuccGcGuAcGTddC | 387 |
| 30557 | Sirna/RPI GL2 Str2 (antisense) 2'-F U,C 3'-invertedT,T | ucGAAGuAuuccGcGuAcGT | 388 |
| 30558 | Sirna/RPI GL2 Str2 (antisense) 2'-F U,C 3'-invertedT,TT | ucGAAGuAuuccGcGuAcGTT | 389 |
| 30196 | FLT1:2340U21 siRNA sense iB caps w/2'FY's | B cAAccAcAAAAuAcAAcAATT B | 419 |
| 30416 | FLT1:2358L21 siRNA (2340C) (antisense) TsT | uuGuuGuAuuuuGuGGuuGTST | 420 |
| 29548 | HBV:394L21 siRNA (414C) (antisense) | GAUGAGGCAUAGCAGCAGGTT | 421 |
| 29544 | HBV:414U21 siRNA pos (sense) | CCUGCUGCUAUGCCUCAUCUU | 422 |
| 29556 | HBV:394L21 siRNA neg (414C) (antisense) inv | GGACGACGAUACGGAGUAGTT | 423 |
| 29552 | HBV:414U21 siRNA pos (sense) inv | CUACUCCGUAUCGUCGUCCTT | 424 |
| 30350 | HBV:262U21 siRNA stab04 (sense) | B uGGAcuucucucAAuuuucuA B | 425 |
| 30361 | HBV:280L21 siRNA (262C) (antisense) stab05 | GAAAuuGAGAGAAGuccATST | 426 |
| 30372 | HBV:262U21 siRNA inv stab04 (sense) | B AucuuuuAAcucucuucAGGu B | 427 |
| 30383 | HBV:280L21 siRNA (262C) (antisense) inv stab05 | AccuGAAGAGAGuuAAAAGT$_S$T | 428 |

TABLE I-continued

| Sirna/RPI# | Aliases | Sequence | SEQ ID# |
|---|---|---|---|
| 30352 | HBV:380U21 siRNA stab04 (sense) | B uGuGucuGcGGcGuuuuAucA B | 429 |
| 30363 | HBV:398L21 siRNA (380C) (antisense) stab05 | AuAAAAcGccGcAGAcAcAT$_S$T | 430 |
| 30374 | HBV:380U21 siRNA inv stab04 (sense) | B AcuAuuuuGcGGcGucuGuGu B | 431 |
| 30385 | HBV:398L21 siRNA (380C) (antisense) inv stab05 | AcAcAGAcGccGcAAAAuATST | 432 |
| 30353 | HBV:413U21 siRNA stab04 (sense) | B uccuGcuGcuAuGccucAucu B | 433 |
| 30364 | HBV:431L21 siRNA (413C) (antisense) stab05 | AuGAGGcAuAGcAGcAGGAT$_S$T | 434 |
| 30375 | HBV:413U21 siRNA inv stab04 (sense) | B ucuAcuccGuAucGucGuccu B | 435 |
| 30386 | HBV:431L21 siRNA (413C) (antisense) inv stab05 | AGGAcGAcGAuAcGGAGuAT$_S$T | 436 |
| 30354 | HBV:462U21 siRNA stab04 (sense) | B uAuGuuGcccGuuuGuccucu B | 437 |
| 30365 | HBV:480L21 siRNA (462C) (antisense) stab05 | AGGAcAAAcGGGcAAcAuAT$_S$T | 438 |
| 30376 | HBV:462U21 siRNA inv stab04 (sense) | B ucuccuGuuuGcccGuuGuAu B | 439 |
| 30387 | HBV:480L21 siRNA (462C) (antisense) inv stab05 | AuAcAAcGGGcAAAcAGGATST | 440 |
| 30355 | HBV:1580U21 siRNA stab04 (sense) | B uGuGcAcuucGcuucAccucu B | 441 |
| 30366 | HBV:1598L21 siRNA (1580C) (antisense) stab05 | AGGuGAAGcGAAGuGcAcAT$_S$T | 442 |
| 30377 | HBV:1580U21 siRNA inv stab04 (sense) | B ucuccAcuucGcuucAcGuGu B | 443 |
| 30388 | HBV:1598L21 siRNA (1580C) (antisense) inv stab05 | AcAcGuGAAGcGAAGuGGAT$_S$T | 444 |
| 30356 | HBV:1586U21 siRNA stab04 (sense) | B cuucGcuucAccucuGcAcGu B | 445 |
| 30367 | HBV:1604L21 siRNA (1586C) (antisense) stab05 | GuGcAGAGGuGAAGcGAAGT$_S$T | 446 |
| 30378 | HBV:1586U21 siRNA inv stab04 (sense) | B uGcAcGucuccAcuucGcuuc B | 447 |
| 30389 | HBV:1604L21 siRNA (1586C) (antisense) inv stab05 | GAAGcGAAGuGGAGAcGuGT$_S$T | 448 |
| 30357 | HBV:1780U21 siRNA stab04 (sense) | B AGGcuGuAGGcAuAAAuuGGu B | 449 |
| 30368 | HBV:1798L21 siRNA (1780C) (antisense) stab05 | cAAuuuAuGccuAcAGccuT$_S$T | 450 |
| 30379 | HBV:1780U21 siRNA inv stab04 (sense) | B uGGuuAAAuAcGGAuGcGGA B | 451 |
| 30390 | HBV:1798L21 siRNA (1780C) (antisense) inv stab05 | uccGAcAuccGuAuuuAAcT$_S$T | 452 |
| 30612 | HBV:1580U21 siRNA stab07 (sense) | B uGuGcAcuucGcuucAccuTT B | 453 |
| 30620 | HBV:1598L21 siRNA (1580C) (antisense) stab08 | aggugaagcgaagugcacaT$_S$T | 454 |
| 30628 | HBV:1582U21 siRNA inv stab07 (sense) | B ucuccAcuucGcuucAcGuTT B | 455 |
| 30636 | HBV:1596L21 siRNA (1578C) (antisense) inv stab08 | gcacacgugaagcgaagugT$_S$T | 456 |
| 30612 | HBV:1580U21 siRNA stab07 (sense) | B uGuGcAcuucGcuucAccuTT B | 457 |
| 31175 | HBV:1598L21 siRNA (1580C) stabil (antisense) | AGGuGAAGcGAAGuGcAcAT$_S$T | 458 |
| 30612 | HBV:1580U21 siRNA stab07 (sense) | B uGuGcAcuucGcuucAccuTT B | 459 |

TABLE I-continued

| Sirna/RPI# | Aliases | Sequence | SEQ ID# |
|---|---|---|---|
| 31176 | HBV:1596L21 siRNA (1578C) (antisense) inv stabil (antisense) | GcAcAcGuGAAGcGAAGuGT$_S$T | 460 |
| 30287 | HBV:1580U21 siRNA (sense) | UGUGCACUUCGCUUCACCUCU | 461 |
| 30298 | HBV:1598L21 siRNA (1580C) (antisense) | AGGUGAAGCGAAGUGCACACG | 462 |
| 30355 | HBV:1580U21 siRNA stab04 (sense) | B uGuGcAcuucGcuucAccucu B | 463 |
| 30366 | HBV:1598L21 siRNA (1580C) (antisense) stab05 | AGGuGAAGcGAAGuGcAcAT$_S$T | 464 |
| 30612 | HBV:1580U21 siRNA stab07 (sense) | B uGuGcAcuucGcuucAccuTT B | 465 |
| 31175 | HBV:1598L21 siRNA (1580C) stabi11 (antisense) | AGGuGAAGcGAAGuGcAcAT$_S$T | 466 |
| 30612 | HBV:1580U21 siRNA stab07 (sense) | B uGuGcAcuucGcuucAccuTT B | 467 |
| 30620 | HBV:1598L21 siRNA (1580C) (antisense) stab08 | AGGuGAAGcGAAGuGcAcATsT | 468 |
| 31335 | HBV:1580U21 siRNA stab09 (sense) | B UGUGCACUUCGCUUCACCUTT B | 469 |
| 31337 | HBV:1598L21 siRNA (1580C) stab10 (antisense) | AGGUGAAGCGAAGUGCACATsT | 470 |
| 31456 | HCVa:291U21 siRNA stab04 | B cuuGuGGuAcuGccuGAuATT B | 471 |
| 31468 | HCVa:309L21 siRNA (291C) stab05 | uAucAGGcAGuAccAcAAGTsT | 472 |
| 31480 | HCVa:291U21 siRNA inv stab04 | B AuAGuccGucAuGGuGuucTT B | 473 |
| 31492 | HCVa:309L21 siRNA (291C) inv stab05 | GAAcAccAuGAcGGAcuAuTsT | 474 |
| 31461 | HCVa:300U21 siRNA stab04 | B cuGccuGAuAGGGuGcuuGTT B | 475 |
| 31473 | HCVa:318L21 siRNA (300C) stab05 | cAAGcAcccuAucAGGcAGTsT | 476 |
| 31485 | HCVa:300U21 siRNA inv stab04 | B GuucGuGGGAuAGuccGucTT B | 477 |
| 31497 | HCVa:318L21 siRNA (300C) inv stab05 | GAcGGAcuAucccAcGAAcTsT | 478 |
| 31463 | HCVa:303U21 siRNA stab04 | B ccuGAuAGGGuGcuuGcGATT B | 479 |
| 31475 | HCVa:321L21 siRNA (303C) stab05 | ucGcAAGcAcccuAucAGGTsT | 480 |
| 31487 | HCVa:303U21 siRNA inv stab04 | B AGcGuucGuGGGAuAGuccTT B | 481 |
| 31499 | HCVa:321L21 siRNA (303C) inv stab05 | GGAcuAucccAcGAAcGcuTsT | 482 |
| 31344 | HCVa:325U21 siRNA stab07 | B ccccGGGAGGucucGuAGATT B | 483 |
| 30562 | HCVa:345L21 siRNA (325C) Y-2'F, R-2'OMe + TsT | ucuAcGAGAccucccGGGGTsT | 484 |
| 31345 | HCVa:325U21 siRNA inv stab07 | B AGAuGcucuGGAGGGccccTT B | 485 |
| 31346 | HCVa:343L21 siRNA (325C) inv stab08 | GGGGcccuccAGAGcAucuTsT | 486 |
| 31702 | HCVa:326U21 siRNA stab07 | B cccGGGAGGucucGuAGAcTT B | 487 |
| 31706 | HCVa:344L21 siRNA (326C) stab08 | GucuAcGAGAccucccGGGTsT | 488 |
| 31710 | HCVa:326U21 siRNA inv stab07 | B cAGAuGcucuGGAGGGcccTT B | 489 |
| 31714 | HCVa:344L21 siRNA (326C) inv stab08 | GGGcccuccAGAGcAucuGTsT | 490 |
| 31703 | HCVa:327U21 siRNA stab07 | B ccGGGAGGucucGuAGAccTT B | 491 |
| 31707 | HCVa:345L21 siRNA (327C) stab08 | GGucuAcGAGAccucccGGTsT | 492 |
| 31711 | HCVa:327U21 siRNA inv stab07 | B ccAGAuGcucuGGAGGGccTT B | 493 |
| 31715 | HCVa:345L21 siRNA (327C) inv stab08 | GGcccuccAGAGcAucuGGTsT | 494 |
| 31704 | HCVa:328U21 siRNA stab07 | B cGGGAGGucucGuAGAccGTT B | 495 |

TABLE I-continued

| Sirna/RPI# | Aliases | Sequence | SEQ ID# |
|---|---|---|---|
| 31708 | HCVa:346L21 siRNA (328C) stab08 | cGGucuAcGAGAccucccGTsT | 496 |
| 31712 | HCVa:328U21 siRNA inv stab07 | B GccAGAuGcucuGGAGGGcTT B | 497 |
| 31716 | HCVa:346L21 siRNA (328C) inv stab08 | GcccuccAGAGcAucuGGcTsT | 498 |
| 31705 | HCVa:329U21 siRNA stab07 | B GGGAGGucucGuAGAccGuTT B | 499 |
| 31709 | HCVa:347L21 siRNA (329C) stab08 | AcGGucuAcGAGAccucccTsT | 500 |
| 31713 | HCVa:329U21 siRNA inv stab07 | B uGccAGAuGcucuGGAGGGTT B | 501 |
| 31717 | HCVa:347L21 siRNA (329C) inv stab08 | cccuccAGAGcAucuGGcATsT | 502 |
| 31703 | HCVa:327U21 siRNA stab07 | B ccGGGAGGucucGuAGAccTT B | 503 |
| 31707 | HCVa:345L21 siRNA (327C) stab08 | GGucuAcGAGAccucccGGTsT | 504 |
| 31711 | HCVa:327U21 siRNA inv stab07 | B ccAGAuGcucuGGAGGGccTT B | 505 |
| 31715 | HCVa:345L21 siRNA (327C) inv stab08 | GGcccuccAGAGcAucuGGTsT | 506 |
| 29579 | HCVa:325U21 siRNA | CCCCGGGAGGUCUCGUAGACCGU | 543 |
|  | HCVa:327 siRNA 3'-class1 10 bp | UCUCGUAGACCUUGGUCUACGAGACCUCCCGGTT | 544 |
|  | HCVa:327 siRNA 3'-class1 8 bp | UCGUAGACCUUGGUCUACGAGACCUCCCGGTT | 545 |
|  | HCVa:327 siRNA 3'-class1 6 bp | GUAGACCUUGGUCUACGAGACCUCCCGGTT | 546 |
|  | HCVa:327 siRNA 3'-class1 4 bp | AGACCUUGGUCUACGAGACCUCCCGGTT | 547 |
|  | HCVa:327 siRNA 5'-class1 10 bp | GGUCUACGAGACCUCCCGGUUCCGGGAGGUCU | 548 |
|  | HCVa:327 siRNA 5'-class1 8 bp | GGUCUACGAGACCUCCCGGUUCCGGGAGGU | 549 |
|  | HCVa:327 siRNA 5'-class1 6 bp | GGUCUACGAGACCUCCCGGUUCCGGGAG | 550 |
|  | HCVa:327 siRNA 5'-class1 4 bp | GGUCUACGAGACCUCCCGGUUCCGGG | 551 |
|  | HCVa:327 siRNA 3'-gaaa 10 bp | CUCGUAGACCGAAAGGUCUACGAGACCUCCCGGTT | 552 |
|  | HCVa:327 siRNA 3'-gaaa 8 bp | CGUAGACCGAAAGGUCUACGAGACCUCCCGGTT | 553 |
|  | HCVa:327 siRNA 3'-gaaa 6 bp | UAGACCGAAAGGUCUACGAGACCUCCCGGTT | 554 |
|  | HCVa:327 siRNA 3'-gaaa 4 bp | GACCGAAAGGUCUACGAGACCUCCCGGTT | 555 |
|  | HCVa:327 siRNA 5'-gaaa 10 bp | GGUCUACGAGACCUCCCGGUUGAAACCGGAGGUC | 556 |
|  | HCVa:327 siRNA 5'-gaaa 8 bp | GGUCUACGAGACCUCCCGGUUGAAACCGGAGG | 557 |
|  | HCVa:327 siRNA 5'-gaaa 6 bp | GGUCUACGAGACCUCCCGGUUGAAACCGGGA | 558 |
|  | HCVa:327 siRNA 5'-gaaa 4 bp | GGUCUACGAGACCUCCCGGUUGAAACCGG | 559 |
|  | HCVa:327 siRNA 3'-uuuguguag 10 bp | CGUAGACCUUUUGUGUAGGGUCUACGAGACCUCCCGGTT | 560 |
|  | HCVa:327 siRNA 3'-uuuguguag 8 bp | UAGACCUUUUGUGUAGGGUCUACGAGACCUCCCGGTT | 561 |
|  | HCVa:327 siRNA 3'-uuuguguag 6 bp | GACCUUUUGUGUAGGGUCUACGAGACCUCCCGGTT | 562 |
|  | HCVa:327 siRNA 3'-uuuguguag 4 bp | CCUUUUGUGUAGGGUCUACGAGACCUCCCGGTT | 563 |

TABLE I-continued

| Sirna/RPI# | Aliases | Sequence | SEQ ID# |
|---|---|---|---|
| | HCVa:327 siRNA 5'-uuuguguag 10 bp | GGUCUACGAGACCUCCCGGUUUUUGUGUAGC CGGGAGGUC | 564 |
| | HCVa:327 siRNA 5'-uuuguguag 8 bp | GGUCUACGAGACCUCCCGGUUUUUGUGUAG CCGGGAGG | 565 |
| | HCVa:327 siRNA 5'-uuuguguag 6 bp | GGUCUACGAGACCUCCCGGUUUUUGUGUAG CCGGGA | 566 |
| | HCVa:327 siRNA 5'-uuuguguag 4 bp | GGUCUACGAGACCUCCCGGUUUUUGUGUAGC CGG | 567 |
| | HCVa:327 siRNA 3'-class1 10 bp stab08 | ucucGuAGAccuuGGucuAcGAGAccuccc GGTsT | 568 |
| | HCVa:327 siRNA 3'-class1 8 bp stab08 | ucGuAGAccuuGGucuAcGAGAccucccGGT sT | 569 |
| | HCVa:327 siRNA 3'-class1 6 bp stab08 | GuAGAccuuGGucuAcGAGAccucccGGTsT | 570 |
| | HCVa:327 siRNA 3'-class1 4 bp stab08 | AGAccuuGGucuAcGAGAccucccGGTsT | 571 |
| | HCVa:327 siRNA 5'-class1 10 bp stab08 | GGucuAcGAGAccucccGGuuccGGGAGGu cu | 572 |
| | HCVa:327 siRNA 5'-class1 8 bp stab08 | GGucuAcGAGAccucccGGuuccGGGAGGu | 573 |
| | HCVa:327 siRNA 5'-class1 6 bp stab08 | GGucuAcGAGAccucccGGuuccGGGAG | 574 |
| | HCVa:327 siRNA 5'-class1 4 bp stab08 | GGucuAcGAGAccucccGGuuccGGG | 575 |
| | HCVa:327 siRNA 3'-gaaa 10 bp stab08 | cucGuAGAccGAAAGGucuAcGAGAccuccc GGTsT | 576 |
| | HCVa:327 siRNA 3'-gaaa 8 bp stab08 | cGuAGAccGAAAGGucuAcGAGAccuccc GGTsT | 577 |
| | HCVa:327 siRNA 3'-gaaa 6 bp stab08 | uAGAccGAAAGGucuAcGAGAccucccGGTsT | 578 |
| | HCVa:327 siRNA 3'-gaaa 4 bp stab08 | GAccGAAAGGucuAcGAGAccucccGGTsT | 579 |
| | HCVa:327 siRNA 5'-gaaa 10 bp stab08 | GGucuAcGAGAccucccGGuuGAAAccGGG AGGuc | 580 |
| | HCVa:327 siRNA 5'-gaaa 8 bp stab08 | GGucuAcGAGAccucccGGuuGAAAccGGGA GG | 581 |
| | HCVa:327 siRNA 5'-gaaa 6 bp stab08 | GGucuAcGAGAccucccGGuuGAAAccGGGA | 582 |
| | HCVa:327 siRNA 5'-gaaa 4 bp stab08 | GGucuAcGAGAccucccGGuuGAAAccGG | 583 |
| | HCVa:327 siRNA 3'-uuuguguag 10 bp stab08 | cGuAGAccuuuuuGuGuAGGGucuAcGAGAc cucccGGTsT | 584 |
| | HCVa:327 siRNA 3'-uuuguguag 8 bp stab08 | uAGAccuuuuuGuGuAGGGucuAcGAGAccu cccGGTsT | 585 |
| | HCVa:327 siRNA 3'-uuuguguag 6 bp stab08 | GAccuuuuuGuGuAGGGucuAcGAGAccucc cGGTsT | 586 |
| | HCVa:327 siRNA 3'-uuuguguag 4 bp stab08 | ccuuuuuGuGuAGGGucuAcGAGAccuccc GGTsT | 587 |
| | HCVa:327 siRNA 5'-uuuguguag 10 bp stab08 | GGucuAcGAGAccucccGGuuuuuGuGuAGc cGGGAGGuc | 588 |
| | HCVa:327 siRNA 5'-uuuguguag 8 bp stab08 | GGucuAcGAGAccucccGGuuuuuGuGuAGc cGGGAGG | 589 |
| | HCVa:327 siRNA 5'-uuuguguag 6 bp stab08 | GGucuAcGAGAccucccGGuuuuuGuGuAG ccGGGA | 590 |
| | HCVa:327 siRNA 5'-uuuguguag 4 bp stab08 | GGucuAcGAGAccucccGGuuuuuGuGuAGc cGG | 591 |
| | HCVa:347L23 siRNA (327C) stab08 | AcGGucuAcGAGAccucccGGTsT | 592 |

TABLE I-continued

| Sirna/RPI# | Aliases | Sequence | SEQ ID# |
|---|---|---|---|
|  | HCVa:346L22 siRNA (327C) stab08 | cGGucuAcGAGAccucccGGTsT | 593 |
|  | HCVa:345L21 siRNA (327C) stab08 | GGucuAcGAGAccucccGGTsT | 594 |
|  | HCVa:344L20 siRNA (327C) stab08 | GucuAcGAGAccucccGGTsT | 595 |
|  | HCVa:343L19 siRNA (327C) stab08 | ucuAcGAGAccucccGGTsT | 596 |
|  | HCVa:342L18 siRNA (327C) stab08 | cuAcGAGAccucccGGTsT | 597 |
|  | HCVa:341L17 siRNA (327C) stab08 | uAcGAGAccucccGGTsT | 598 |
|  | HCVa:340L16 siRNA (327C) stab08 | AcGAGAccucccGGTsT | 599 |
|  | HCVa:339L15 siRNA (327C) stab08 | cGAGAccucccGGTsT | 600 |
|  | HCVa:345L21 siRNA (327C) stab08 GG | GGucuAcGAGAccucccGGGsG | 601 |
|  | HCVa:345L20 siRNA (327C) stab08 G | GGucuAcGAGAccucccGGsG | 602 |
|  | HCVa:345L20 siRNA (327C) stab08 | GGucuAcGAGAccucccGGsT | 603 |
|  | HCVa:345L19 siRNA (327C) stab08 | GGucuAcGAGAccucccGsG | 604 |
|  | HCVa:345L18 siRNA (327C) stab08 | GGucuAcGAGAccucccsG | 605 |
|  | HCVa:345L17 siRNA (327C) stab08 | GGucuAcGAGAccuccsc | 606 |
|  | HCVa:345L16 siRNA (327C) stab08 | GGucuAcGAGAccucsc | 607 |
|  | HCVa:345L15 siRNA (327C) stab08 | GGucuAcGAGAccusc | 608 |
|  | HCVa:327U21 siRNA stab07 | B ccGGGAGGucucGuAGAccTT B | 609 |
|  | HCVa:327U21 siRNA stab07 GT | B ccGGGAGGucucGuAGAccGT B | 610 |
|  | HCVa:327U21 siRNA stab07 | B cGGGAGGucucGuAGAccTT B | 611 |
|  | HCVa:328U20 siRNA stab07 | B GGGAGGucucGuAGAccTT B | 612 |
|  | HCVa:329U 19 siRNA stab07 | B GGAGGucucGuAGAccTT B | 613 |
|  | HCVa:330U 18 siRNA stab07 | B GAGGucucGuAGAccTT B | 614 |
|  | HCVa:331U 17 siRNA stab07 | B AGGucucGuAGAccTT B | 615 |
|  | HCVa:332U 16 siRNA stab07 | B ccGGGAGGucucGuAGAccT B | 616 |
|  | HCVa:327U21 siRNA stab07 | B ccGGGAGGucucGuAGAcc B | 617 |
|  | HCVa:327U21 siRNA stab07 | B ccGGGAGGucucGuAGAc B | 618 |
|  | HCVa:327U21 siRNA stab07 | B ccGGGAGGucucGuAGA B | 619 |
|  | HCVa:327U21 siRNA stab07 | B ccGGGAGGucucGuAG B | 620 |
| 31270 | FLT1:349U21 siRNA stab09 sense | B CUGAGUUUAAAAGGCACCCTT B | 621 |
| 31273 | FLT1:367L21 siRNA (349C) stab10 antisense | GGGUGCCUUUUAAACUCAGTsT | 622 |
| 31276 | FLT1:349U21 siRNA stab09 inv sense | B CCCACGGAAAAUUUGAGUCTT B | 623 |
| 31279 | FLT1:367L21 siRNA (349C) stab10 inv antisense | GACUCAAAUUUUCCGUGGGTsT | 624 |
| 31679 | HBV1598 all RNA sense | AGGUGAAGCGAAGUGCACAUU | 625 |
| 30287 | HBV1598 all RNA antisense | UGUGCACUUCGCUUCACCUCU | 626 |
| 31336 | HBV:1580U21 siRNA inv stab09 sense | B UCCACUUCGCUUCACGUGUTT B | 627 |
| 31338 | HBV:1598L21 siRNA (1580C) inv stab10 antisense | ACACGUGAAGCGAAGUGGATsT | 629 |
| 32636 | Luc3:80U21 siRNA stab07 sense | B AuAAGGcuAuGAAGAGAuATT B | 630 |

TABLE I-continued

| Sirna/RPI# | Aliases | Sequence | SEQ ID# |
|---|---|---|---|
| 32676 | Luc3:98L21 siRNA (80C) stab08 antisense | uAucucuucAuAGccuuAuTsT | 631 |
| 32640 | Luc3:237U21 siRNA stab07 sense | B cGuAuGcAGuGAAAAcucuTT B | 632 |
| 32680 | Luc3:255L21 siRNA (237C) stab08 antisense | AGAGuuuucAcuGcAuAcGTsT | 633 |
| 32662 | Luc3:1478U21 siRNA stab07 sense | B uGAcGGAAAAAGAGAucGuTT B | 634 |
| 32702 | Luc3:1496L21 siRNA (1478C) stab08 antisense | AcGAucucuuuuccGucATsT | 635 |
| 32666 | Luc3:1544U21 siRNA stab07 sense | B GAGuuGuGuuuGuGGAcGATT B | 636 |
| 32706 | Luc3:1562L21 siRNA (1544C) stab08 antisense | ucGuccAcAAAcAcAAcucTsT | 637 |
| 32672 | Luc3:1607U21 siRNA stab07 sense | B GAGAGAuccucAuAAAGGcTT B | 638 |
| 32712 | Luc3:1625L21 siRNA (1607C) stab08 antisense | GccuuuAuGAGGAucucucTsT | 639 |
| 33139 | HCVa:282U21 siRNA stab07 sense | B GcGAAAGGccuuGuGGuAcTT B | 640 |
| 33179 | HCVa:300L21 siRNA (282C) stab08 antisense | GuAccAcAAGGccuuucGcTsT | 641 |
| 33140 | HCVa:283U21 siRNA stab07 sense | B cGAAAGGccuuGuGGuAcuTT B | 642 |
| 33180 | HCVa:301L21 siRNA (283C) stab08 antisense | AGuAccAcAAGGccuuucGTsT | 643 |
| 33145 | HCVa:289U21 siRNA stab07 sense | B GccuuGuGGuAcuGccuGATT B | 644 |
| 33185 | HCVa:307L21 siRNA (289C) stab08 antisense | ucAGGcAGuAccAcAAGGcTsT | 645 |
| 33149 | HCVa:304U21 siRNA stab07 sense | B cuGAuAGGGuGcuuGcGAGTT B | 646 |
| 33183 | HCVa:304L21 siRNA (286C) stab08 antisense | GGcAGuAccAcAAGGccuuTsT | 647 |
| 33150 | HCVa:305U21 siRNA stab07 sense | B uGAuAGGGuGcuuGcGAGuTT B | 648 |
| 33190 | HCVa:323L21 siRNA (305C) stab08 antisense | AcucGcAAGcAcccuAucATsT | 649 |
| 33151 | HCVa:307U21 siRNA stab07 sense | B AuAGGGuGcuuGcGAGuGcTT B | 650 |
| 33191 | HCVa:325L21 siRNA (307C) stab08 antisense | GcAcucGcAAGcAcccuAuTsT | 651 |
| 33158 | HCVa:317U21 siRNA stab07 sense | B uGcGAGuGccccGGGAGGuTT B | 652 |
| 33187 | HCVa:317L21 siRNA (299C) stab08 antisense | AAGcAcccuAucAGGcAGuTsT | 653 |
| 33210 | HBV:258U21 siRNA stab07 sense | B GuGGuGGAcuucucucAAuTT B | 654 |
| 33250 | HBV:276L21 siRNA (258C) stab08 antisense | Au uGAGAGAAG uccAccAcTsT | 655 |
| 33212 | HBV:260U21 siRNA stab07 sense | B GGuGGAcuucucucAAuuTT B | 656 |
| 33252 | HBV:278L21 siRNA (260C) stab08 antisense | AAAuuGAGAGAAGuccAccTsT | 657 |
| 33214 | HBV:263U21 siRNA stab07 sense | B GGAcuucucucAAuuuucuTT B | 658 |
| 33254 | HBV:281L21 siRNA (263C) stab08 antisense | AGAAAAuuGAGAGAAGuccTsT | 659 |
| 32429 | H BV:1583 U21 siRNA stab07 sense | B GcAcuucGcuucAccucuGTT B | 660 |
| 32438 | HBV:1601L21 siRNA (1583C) stab08 | cAGAGGuGAAGcGAAGuGcTsT | 661 |

TABLE I-continued

| Sirna/RPI# | Aliases | Sequence | SEQ ID# |
|---|---|---|---|
| | antisense | | |
| 33226 | H BV:1585 U21 siRNA stab07 sense | B AcuuGcuucAccucuGcATT B | 662 |
| 33266 | HBV:1603L21 siRNA (1585C) stab08 antisense | uGcAGAGGuGAAGcGAAGuTsT | 663 |
| 31651 | HBV:1580U21 siRNA stab06 sense | B U<u>G</u>UGC<u>A</u>CUUC<u>G</u>CUUC<u>A</u>CCUTT B | 664 |
| 31652 | HBV:1580U21 siRNA inv stab06 sense | B UCC<u>A</u>CUUC<u>G</u>CUUC<u>A</u>C<u>G</u>UGUTT B | 665 |
| 31653 | HBV:1580U21 siRNA stab16 sense | B U<u>G</u>U<u>G</u>C<u>A</u>CUUC<u>G</u>CUUC<u>A</u>CCUTT B | 666 |
| 31654 | HBV:1580U21 siRNA inv stab16 sense | B UCC<u>A</u>CUUC<u>G</u>CUUC<u>A</u>C<u>G</u>UGUTT B | 667 |
| 31657 | HBV:1580U21 siRNA stab18 sense | B u<u>G</u>u<u>G</u>c<u>A</u>cuuc<u>G</u>cuuc<u>A</u>ccuTT B | 668 |
| 31658 | HBV:1580U21 siRNA inv stab18 sense | B ucc<u>A</u>cuuc<u>G</u>cuuc<u>A</u>c<u>G</u>u<u>G</u>uTT B | 669 |

UPPER CASE = ribonucleotide
UPPER CASE UNDERLINE = 2'-O-methyl nucleotide
Lowercase = 2'-deoxy-2'-fluoro nucleotide
T = thymidine
T = inverted thymidine
t = 3'-deoxy thymidine
<u>B</u> = inverted deoxyabasic succinate linker
B = inverted deoxyabasic
X = universal base (5-nitroindole)
Z = universal base (3-nitropyrrole)
S = phosphorothioate internucleotide linkage
U = 5-bromodeoxyuridine
A = deoxyadenosine
G = deoxyguanosine
L = glyceryl moiety
ddC = dideoxy Cytidine
p = phosphate

TABLE II

| Reagent | Equivalents | Amount | Wait Time* DNA | Wait Time* 2'-O-methyl | Wait Time*RNA |
|---|---|---|---|---|---|
| A. 2.5 µmol Synthesis Cycle ABI 394 Instrument ||||||
| Phosphoramidites | 6.5 | 163 µL | 45 sec | 2.5 min | 7.5 min |
| S-Ethyl Tetrazole | 23.8 | 238 µL | 45 sec | 2.5 min | 7.5 min |
| Acetic Anhydride | 100 | 233 µL | 5 sec | 5 sec | 5 sec |
| N-Methyl Imidazole | 186 | 233 µL | 5 sec | 5 sec | 5 sec |
| TCA | 176 | 2.3 mL | 21 sec | 21 sec | 21 sec |
| Iodine | 11.2 | 1.7 mL | 45 sec | 45 sec | 45 sec |
| Beaucage | 12.9 | 645 µL | 100 sec | 300 sec | 300 sec |
| Acetonitrile | NA | 2.64 mL | NA | NA | NA |
| B. 0.2 µmol Synthesis Cycle ABI 394 Instrument ||||||
| Phosphoramidites | 15 | 31 µL | 45 sec | 233 sec | 465 sec |
| S-Ethyl Tetrazole | 38.7 | 31 µL | 45 sec | 233 min | 465 sec |
| Acetic Anhydride | 655 | 124 µL | 5 sec | 5 sec | 5 sec |
| N-Methyl Imidazole | 1245 | 124 µL | 5 sec | 5 sec | 5 sec |
| TCA | 700 | 732 µL | 10 sec | 10 sec | 10 sec |
| Iodine | 20.6 | 244 µL | 15 sec | 15 sec | 15 sec |
| Beaucage | 7.7 | 232 µL | 100 sec | 300 sec | 300 sec |
| Acetonitrile | NA | 2.64 mL | NA | NA | NA |

| Reagent | Equivalents: DNA/2'-O-methyl/Ribo | Amount: DNA/2'-O-methyl/Ribo | Wait Time* DNA | Wait Time* 2'-O-methyl | Wait Time* Ribo |
|---|---|---|---|---|---|
| C. 0.2 µmol Synthesis Cycle 96 well Instrument ||||||
| Phosphoramidites | 22/33/66 | 40/60/120 µL | 60 sec | 180 sec | 360 sec |
| S-Ethyl Tetrazole | 70/105/210 | 40/60/120 µL | 60 sec | 180 min | 360 sec |
| Acetic Anhydride | 265/265/265 | 50/50/50 µL | 10 sec | 10 sec | 10 sec |
| N-Methyl | 502/502/502 | 50/50/50 µL | 10 sec | 10 sec | 10 sec |

TABLE II-continued

| | | | | | |
|---|---|---|---|---|---|
| Imidazole | | | | | |
| TCA | 238/475/475 | 250/500/500 μL | 15 sec | 15 sec | 15 sec |
| Iodine | 6.8/6.8/6.8 | 80/80/80 μL | 30 sec | 30 sec | 30 sec |
| Beaucage | 34/51/51 | 80/120/120 | 100 sec | 200 sec | 200 sec |
| Acetonitrile | NA | 1150/1150/1150 μL | NA | NA | NA |

• Wait time does not include contact time during delivery.
• Tandem synthesis utilizes double coupling of linker molecule

TABLE III

| Group | Solution on Filter (1.0 μL) | Stock VEGF concentration | Number of Animals | Injectate (6.0 μL) | Dose | Conc. injectate |
|---|---|---|---|---|---|---|
| 1 | Tris-Cl pH 6.9 | NA | 5 | water | NA | NA |
| 2 | R&D Systems VEGF-carrier free 75 μM | 3.53 μg/μL | 5 | water | NA | NA |
| 3 | R&D Systems VEGF-carrier free 75 μM | 3.53 μg/μL | 5 | Site 2340 Stab1 siRNA | 10 μg/eye | 1.67 μg/μL |
| 4 | R&D Systems VEGF-carrier free 75 μM | 3.53 μg/μL | 5 | Site 2340 Stab1 siRNA | 3 μg/eye | 0.5 μg/μL |
| 5 | R&D Systems VEGF-carrier free 75 μM | 3.53 μg/μL | 5 | Site 2340 Stab1 siRNA | 1 μg/eye | 0.167 μg/μL |
| 6 | R&D Systems VEGF-carrier free 75 μM | 3.53 μg/μL | 5 | Inactive Site 2340 Stab1 siRNA | 10 μg/eye | 1.67 μg/μL |
| 7 | R&D Systems VEGF-carrier free 75 μM | 3.53 μg/μL | 5 | Inactive Site 2340 Stab1 siRNA | 3 μg/eye | 0.5 μg/μL |
| 8 | R&D Systems VEGF-carrier free 75 μM | 3.53 μg/μL | 5 | Inactive Site 2340 Stab1 siRNA | 1 μg/eye | 0.167 μg/μL |

TABLE IV

Non-limiting examples of Stabilization Chemistries for chemically modified siNA constructs

| Chemistry | pyrimidine | Purine | cap | p = S | Strand |
|---|---|---|---|---|---|
| "Stab 1" | Ribo | Ribo | — | 5 at 5'-end 1 at 3'-end | S/AS |
| "Stab 2" | Ribo | Ribo | — | All linkages | Usually AS |
| "Stab 3" | 2'-fluoro | Ribo | — | 4 at 5'-end 4 at 3'-end | Usually S |
| "Stab 4" | 2'-fluoro | Ribo | 5' and 3'-ends | — | Usually S |
| "Stab 5" | 2'-fluoro | Ribo | — | 1 at 3'-end | Usually AS |
| "Stab 6" | 2'-O-Methyl | Ribo | 5' and 3'-ends | — | Usually S |
| "Stab 7" | 2'-fluoro | 2'-deoxy | 5' and 3'-ends | — | Usually S |
| "Stab 8" | 2'-fluoro | 2'-O-Methyl | — | 1 at 3'-end | S or AS |
| "Stab 9" | Ribo | Ribo | 5' and 3'-ends | — | Usually S |
| "Stab 10" | Ribo | Ribo | — | 1 at 3'-end | Usually AS |
| "Stab 11" | 2'-fluoro | 2'-deoxy | — | 1 at 3'-end | Usually AS |
| Stab 12 | 2'-fluoro | LNA | 5' and 3'-ends | | Usually S |
| "Stab 13" | 2'-fluoro | LNA | | 1 at 3'-end | Usually AS |
| "Stab 14" | 2'-fluoro | 2'-deoxy | | 2 at 5'-end 1 at 3'-end | Usually AS |
| "Stab 15" | 2'-deoxy | 2'-deoxy | | 2 at 5'-end 1 at 3'-end | Usually AS |
| "Stab 16" | Ribo | 2'-O-Methyl | 5' and 3'-ends | | Usually S |

TABLE IV-continued

Non-limiting examples of Stabilization Chemistries for chemically modified siNA constructs

| Chemistry | pyrimidine | Purine | cap | p = S | Strand |
|---|---|---|---|---|---|
| "Stab 17" | 2'-O-Methyl | 2'-O-Methyl | 5' and 3'-ends | | Usually S |
| "Stab 18" | 2'-fluoro | 2'-O-Methyl | | 1 at 3'-end | Usually AS |

CAP = any terminal cap, see for example FIG. 22.
All Stab 1-18 chemistries can comprise 3'-terminal thymidine (TT) residues
All Stab 1-18 chemistries typically comprise 21 nucleotides, but can vary as described herein.
S = sense strand
AS = antisense strand

TABLE V

Peptides for Conjugation

| Peptide | Sequence | SEQ ID NO |
|---|---|---|
| ANTENNAPEDIA | RQI KIW FQN RRM KWK K amide | 507 |
| Kaposi fibroblast growth factor | AAV ALL PAV LLA LLA P + VQR KRQ KLMP | 508 |
| caiman crocodylus Ig(5) light chain | MGL GLH LLV LAA ALQ GA | 509 |
| HIVenvelope glycoprotein gp41 | GAL FLG FLG AAG STM GA + PKS KRK 5 (NLS of the SV40) | 510 |
| HIV-1 Tat | RKK RRQ RRR | 511 |
| Influenza hemagglutinin envelop glycoprotein | GLFEAIAGFIENGWEGMIDGGGYC | 512 |
| RGD peptide | X-RGD-X where X is any amino acid or peptide | 513 |
| transportan A | GWT LNS AGY LLG KIN LKA LAA LAK KIL | 514 |
| Somatostatin (tyr-3-octreotate) | (S)FC YWK TCT | 515 |
| Pre-S-peptide | (S)DH QLN PAF | 516 |

(S) optional Serine for coupling
Italic = optional D isomer for stability

TABLE VI

Duplex half-lives in human and mouse serum and liver extracts

| Stability S/AS Sirna # | All RNA 47715/47933 | 4*/5 30355/30366 | 4/5* 30355/30366 | 7/11* 30612/31175 | 7*/8 30612/30620 | 7/8* 30612/30620 |
|---|---|---|---|---|---|---|
| Human Serum $t_{1/2}$ hours | 0.017 | 408 (0.96) † | 39 (0.65) | 54 (0.76) | 130 (0.88) | 94 (0.86) |
| Human Liver $t_{1/2}$ hours | 2.5 | 28.6 (0.40) | 43.5 (0.66) | 0.78/2.9‡ (0.45) | 9 (0.39) | 816 (0.99) |
| Mouse Serum $t_{1/2}$ hours | 1.17 | 16.7 (0.9) | 10 (0.81) | 2.3 | 16.6 (0.46) | 35.7 (0.69) |

TABLE VI-continued

Duplex half-lives in human and mouse serum and liver extracts

| Stability S/AS Sirna # | All RNA 47715/47933 | 4*/5 30355/30366 | 4/5* 30355/30366 | 7/11* 30612/31175 | 7*/8 30612/30620 | 7/8* 30612/30620 |
|---|---|---|---|---|---|---|
| Mouse Liver $t_{1/2}$ hours | 6 | 1.08 | 0.80 | 0.20 | 0.22 | 120 (0.89) |

*The asterisk designates the strand carrying the radiolabel in the duplex.
† For longer half-lives the fraction full-length at the 18 hours is presented as the parenthetic lower number in each cell.
‡A biphasic curve was observed, half-lives for both phases are shown.

TABLE VII

Single strand half-lives in human serum

| | Stability | | | | |
|---|---|---|---|---|---|
| | 4 | 5 | 7 | 11 | 8 |
| | | | Sirna # | | |
| | 30355 | 30366 | 30612 | 31175 | 30620 |
| Human serum $t_{1/2}$ hours | 22 | 16 | 13 | 19 | 28 |
| Human liver $t_{1/2}$ hours | 0.92 | 0.40 | 0.43 | 0.27 | 192 |

TABLE VIII

Human serum half-lives for Stab 4/5 duplex chemistry with terminus chemistries of figure 22

| | 2 | 7 | 9 | 2 | 8 | 1 | 3 | 6 |
|---|---|---|---|---|---|---|---|---|
| Cap | (R = O) | (R = O) | (R = O) | (R = S) | (R = O) | (R = O) | (R = O) | (R = O) |
| Chemistry | (B = T) | (B = T) | (B = T) | (B = T) | (B = T) | (B = T) | (B = T) | (B = T) |
| Human Serum $t_{1/2}$ hours | 1 | 1.2 | 2.3 | 39 | 96 (0.69)‡ | 460 (0.95) | 770 (0.94) | 770 (0.95) |

The capping structures were in the following position of the 4:5 chemistry formatted sequence:
antisense strand -5'-uuGuuGuAuuuuGuGGuuG-CAP-3' where CAP is 1, 2, 3, 6, 7, 8, or 9 from FIG. 22. (SEQ ID NO: 670)
sense strand 5'-CAP-cAAccAcAAAAuAcAAcAATT-CAP-3' where CAP is 1 from FIG. 22. (SEQ ID NO: 671)
‡For half-lives that extend beyond the time course sampled the fraction full-length is presented in parentheses.

---

What we claim is:

1. A compound comprising:
   (I) a short interfering nucleic acid (siNA) molecule capable of inhibiting expression of a human coagulation factor VII gene, said siNA molecule consisting of a single-stranded polynucleotide comprising a nucleotide sequence complementary to a Factor VII RNA, wherein said single-stranded polynucleotide:
      i) is about 18 to 20 nucleotides in length;
      ii) comprises 10 or more phosphorothioate internucleotide linkages;
      iii) comprises 10 or more modified pyrimidines chosen from 2' deoxy pyrimidine, 2'-O-methyl pyrimidine, 2'-deoxy-2'-fluoro pyrimidine, locked nucleic acid (LNA) pyrimidine, 2'-methoxyethoxy (MOE) pyrimidine, or a combination thereof; and
   (II) a galactosamine.

2. The compound of claim 1, wherein the single-stranded polynucleotide comprises 10 or more 2'-deoxy nucleotides.

3. The compound of claim 1, wherein the single-stranded polynucleotide comprises one or more 2'-methoxyethoxy (MOE) nucleotides.

4. The compound of claim 1, wherein the single-stranded polynucleotide comprises 1, 2, 3, 4, 5 or more locked nucleic acid (LNA) nucleotides, which is/are located at the 5'-end, the 3'-end, or both of the 5' and 3'-ends, of the single-stranded polynucleotide.

5. The compound of claim 1, wherein the single-stranded polynucleotide comprises 10 or more 2' deoxy pyrimidines, 2'-O-methyl pyrimidines, or 2'-deoxy-2'-fluoro pyrimidines.

6. The compound of claim 1, wherein the galactosamine comprises N-acetylgalactosamine which is a mono-antennary galactosamine, bi-antennary galactosamine or a tri-antennary galactosamine.

7. The compound of claim 1, wherein the galactosamine is attached at the 5'-end or the 3'-end of the single-stranded polynucleotide.

8. A conjugate comprising:
   (I) a short interfering nucleic acid (siNA) molecule capable of inhibiting expression of a human coagulation factor VII gene, said siNA molecule consisting of a single-stranded polynucleotide comprising a nucleotide sequence complementary to a human Factor VII RNA, wherein said single-stranded polynucleotide:
      i) is about 18 to 20 nucleotides in length;
      ii) comprises 10 or more phosphorothioate internucleotide linkages;
      iii) comprises 10 or more modified pyrimidines chosen from 2' deoxy pyrimidine, 2'-O-methyl pyrimidine, 2'-deoxy-2'-fluoro pyrimidine, locked nucleic acid (LNA) pyrimidine, 2'-methoxyethoxy (MOE) pyrimidine, or a combination thereof; and
   (II) a galactosamine attached at the 5'-end or the 3'-end of the single-stranded polynucleotide.

9. The conjugate of claim 8, wherein the single-stranded polynucleotide comprises 10 or more 2'-deoxy nucleotides.

10. The conjugate of claim 9, wherein the single-stranded polynucleotide comprises one or more 2'-methoxyethoxy (MOE) nucleotides.

11. The conjugate of claim 9, which comprises 1, 2, 3, 4, 5 or more locked nucleic acid molecules located at the 5'-end, the 3'-end, or both of the 5' and 3'-ends, of the single-stranded polynucleotide.

12. The conjugate of claim 8, wherein the single-stranded polynucleotide comprises 5 or more 2' deoxy pyrimidines.

13. The conjugate of claim 12, wherein the galactosamine is a mono-antennary galactosamine, bi-antennary galactosamine or a tri-antennary galactosamine.

14. A short interfering nucleic acid (siNA) molecule capable of inhibiting expression of a human coagulation factor VII gene, said siNA molecule consisting of a single-stranded polynucleotide comprising a nucleotide sequence complementary to a human Factor VII RNA, wherein said single-stranded polynucleotide:
   i) is 20 nucleotides in length;
   ii) comprises 10 or more phosphorothioate internucleotide linkages; and
   iii) comprises 10 or more modified pyrimidines chosen from 2' deoxy pyrimidine, 2'-O-methyl pyrimidine, 2'-deoxy-2'-fluoro pyrimidine, 2'-methoxyethoxy (MOE) pyrimidine or a combination thereof.

15. The siNA molecule of claim 14, wherein the single-stranded polynucleotide further comprises a ligand chosen from a galactosamine or a cholesterol.

16. The siNA molecule of claim 14, wherein the single-stranded polynucleotide comprises one or more 2'-methoxyethoxy (MOE) nucleotides.

17. The siNA molecule of claim 14, wherein the single-stranded polynucleotide comprises 1, 2, 3, 4, 5 or more locked nucleic acid (LNA) nucleotides, wherein said LNA nucleotides is/are located at the 5'-end, the 3'-end, both of the 5' and 3'-ends, of the single-stranded polynucleotide.

18. The conjugate of claim 8, wherein the single-stranded polynucleotide comprises 10 or more modified pyrimidines chosen from 2' deoxy pyrimidines, 2'-O-methyl pyrimidines, or 2'-deoxy-2'-fluoro pyrimidines.

19. The conjugate of claim 8, wherein the single-stranded polynucleotide comprises 1, 2, 3, 4, 5 or more locked nucleic acid (LNA) nucleotides, wherein said LNA nucleotides is/are located at the 5'-end, the 3'-end, both of the 5' and 3'-ends, of the single-stranded polynucleotide.

20. The compound of claim 1, wherein the single-stranded polynucleotide comprises 5 or more 2' deoxy pyrimidines.

21. The siNA molecule of claim 14, wherein the single-stranded polynucleotide comprises 5 or more 2' deoxy pyrimidines.

22. The compound of claim 1, wherein the single-stranded polynucleotide is 20 nucleotides long.

23. The conjugate of claim 8, wherein the single-stranded polynucleotide is 20 nucleotides long.

* * * * *